US011180557B2

(12) United States Patent
Noelle

(10) Patent No.: US 11,180,557 B2
(45) Date of Patent: Nov. 23, 2021

(54) VISTA MODULATORS FOR DIAGNOSIS AND TREATMENT OF CANCER

(71) Applicants: KING'S COLLEGE LONDON, London (GB); THE TRUSTEES OF DARTMOUTH COLLEGE, Hanover, NH (US)

(72) Inventor: Randolph J. Noelle, Plainfield, NH (US)

(73) Assignees: KING'S COLLEGE LONDON, London (GB); THE TRUSTEES OF DARTMOUTH COLLEGE, Hanover, NH (US)

( * ) Notice: Subject to any disclaimer, the term of this patent is extended or adjusted under 35 U.S.C. 154(b) by 245 days.

(21) Appl. No.: 15/847,132

(22) Filed: Dec. 19, 2017

(65) Prior Publication Data

US 2018/0215826 A1 Aug. 2, 2018

Related U.S. Application Data

(60) Division of application No. 14/158,531, filed on Jan. 17, 2014, now Pat. No. 9,890,215, which is a continuation-in-part of application No. PCT/US2013/058785, filed on Sep. 9, 2013, which is a continuation-in-part of application No. PCT/US2013/047009, filed on Jun. 21, 2013.

(60) Provisional application No. 61/753,682, filed on Jan. 17, 2013, provisional application No. 61/698,003, filed on Sep. 7, 2012, provisional application No. 61/663,431, filed on Jun. 22, 2012, provisional application No. 61/663,969, filed on Jun. 25, 2012, provisional application No. 61/735,799, filed on Dec. 11, 2012, provisional application No. 61/776,234, filed on Mar. 11, 2013, provisional application No. 61/807,135, filed on Apr. 1, 2013.

(51) Int. Cl.

| | |
|---|---|
| ***C07K 14/705*** | (2006.01) |
| ***C12N 15/113*** | (2010.01) |
| ***C12N 5/10*** | (2006.01) |
| ***C07K 16/28*** | (2006.01) |
| *A61K 39/00* | (2006.01) |

(52) U.S. Cl.
CPC .... *C07K 16/2827* (2013.01); *C07K 14/70532* (2013.01); *C07K 16/2803* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,517,288 | A | 5/1985 | Giegel et al. |
| 4,522,811 | A | 6/1985 | Eppstein et al. |
| 4,596,556 | A | 6/1986 | Morrow et al. |
| 4,676,980 | A | 6/1987 | Segal et al. |
| 4,683,195 | A | 7/1987 | Mullis et al. |
| 4,683,202 | A | 7/1987 | Mullis |
| 4,699,880 | A | 10/1987 | Goldstein |
| 4,736,866 | A | 4/1988 | Leder et al. |
| 4,790,824 | A | 12/1988 | Morrow et al. |
| 4,816,567 | A | 3/1989 | Cabilly et al. |
| 4,837,168 | A | 6/1989 | de Jaeger et al. |
| 4,870,009 | A | 9/1989 | Evans et al. |
| 4,873,191 | A | 10/1989 | Wagner et al. |

(Continued)

FOREIGN PATENT DOCUMENTS

| | | |
|---|---|---|
| CA | 2383456 | 3/2001 |
| CN | 1753912 | 3/2006 |

(Continued)

OTHER PUBLICATIONS

Warrington et al. 2011 Allergy, Asthma & Clinical Immunology 7(Suppl 1): S1, 8 pages.*

(Continued)

*Primary Examiner* — Ilia I Ouspenski

(74) *Attorney, Agent, or Firm* — Robin L. Teskin; Baker, Donelson, Bearman, Caldwell & Berkowitz PC

(57) ABSTRACT

The present disclosure relates to compositions and therapeutic methods for activating an immune response in a patient in need thereof. In a preferred embodiment, the subject methods and compositions are able to antagonize the activity of VISTA, a naturally occurring "checkpoint" protein which contributes to immune tolerance, optionally in combination with an antagonist of a second checkpoint pathway such as PD-1. For example, such methods and compositions may be suitable for preventing and treating colon cancer or another cancer. An exemplary VISTA antagonist, specifically, an anti-VISTA antibody, is demonstrated herein to activate an immune response against cancer cells in vitro and in vivo, thereby conferring protective anti-tumor immunity which decreased tumor burden. Additionally, an additive benefit was observed when a VISTA antagonist was used in combination with a second checkpoint protein antagonist, specifically, an antibody against PD-1 ligand (PD-L1).

10 Claims, 67 Drawing Sheets

Specification includes a Sequence Listing.

(56) References Cited

U.S. PATENT DOCUMENTS 4,873,316 A 10/1989 Meade et al.
4,881,175 A 11/1989 Ladner
4,941,880 A 7/1990 Burns
4,946,778 A 8/1990 Ladner et al.
4,954,617 A 9/1990 Fanger et al.
4,987,071 A 1/1991 Cech et al.
5,013,653 A 5/1991 Huston et al.
5,064,413 A 11/1991 McKinnon et al.
5,091,513 A 2/1992 Huston et al.
5,116,742 A 5/1992 Cech et al.
5,116,964 A 5/1992 Capon et al.
5,132,405 A 7/1992 Huston et al.
5,139,941 A 8/1992 Muzyczka et al.
5,190,878 A 3/1993 Wilhelm
5,223,409 A 6/1993 Ladner et al.
5,225,539 A 7/1993 Winter
5,258,498 A 11/1993 Huston et al.
5,260,203 A 11/1993 Ladner et al.
5,272,071 A 12/1993 Chappel
5,283,173 A 2/1994 Fields et al.
5,283,317 A 2/1994 Saifer et al.
5,288,641 A 2/1994 Roizman
5,312,335 A 5/1994 McKinnon et al.
5,328,470 A 7/1994 Nabel et al.
5,374,548 A 12/1994 Caras
5,383,851 A 1/1995 McKinnon, Jr. et al.
5,399,163 A 3/1995 Peterson et al.
5,399,331 A 3/1995 Loughrey et al.
5,403,484 A 4/1995 Ladner et al.
5,416,016 A 5/1995 Low et al.
5,427,908 A 6/1995 Dower et al.
5,455,030 A 10/1995 Ladner et al.
5,476,786 A 12/1995 Huston
5,476,996 A 12/1995 Wilson et al.
5,478,925 A 12/1995 Wallach et al.
5,482,858 A 1/1996 Huston et al.
5,530,101 A 6/1996 Queen et al.
5,545,806 A 8/1996 Lonberg et al.
5,545,807 A 8/1996 Surani et al.
5,547,853 A 8/1996 Wallner et al.
5,569,825 A 10/1996 Lonberg et al.
5,571,698 A 11/1996 Ladner et al.
5,580,717 A 12/1996 Dower et al.
5,580,756 A 12/1996 Linsley et al.
5,585,089 A 12/1996 Queen et al.
5,624,659 A 4/1997 Bigner et al.
5,624,821 A 4/1997 Winter et al.
5,625,126 A 4/1997 Lonberg et al.
5,633,425 A 5/1997 Lonberg et al.
5,648,260 A 7/1997 Winter et al.
5,661,016 A 8/1997 Lonberg et al.
5,677,425 A 10/1997 Bodmer et al.
5,693,762 A 12/1997 Queen et al.
5,698,767 A 12/1997 Wilson et al.
5,714,350 A 2/1998 Co et al.
5,723,125 A 3/1998 Chang et al.
5,731,168 A 3/1998 Carter et al.
5,770,429 A 6/1998 Lonberg et al.
5,776,427 A 7/1998 Thorpe et al.
5,789,650 A 8/1998 Lonberg et al.
5,811,097 A 9/1998 Allison et al.
5,814,318 A 9/1998 Lonberg et al.
5,821,333 A 10/1998 Carter et al.
5,837,243 A 11/1998 Deo et al.
5,844,095 A 12/1998 Linsley et al.
5,851,795 A 12/1998 Linsley et al.
5,869,046 A 2/1999 Presta et al.
5,874,299 A 2/1999 Lonberg et al.
5,877,397 A 3/1999 Lonberg et al.
5,885,793 A 3/1999 Griffiths et al.
5,888,807 A 3/1999 Palsson et al.
5,922,845 A 7/1999 Deo et al.
5,932,448 A 8/1999 Tso et al.
5,939,598 A 8/1999 Kucherlapati et al.
5,969,108 A 10/1999 McCafferty et al.
5,985,653 A 11/1999 Armstrong et al.
6,054,297 A 4/2000 Carter et al.
6,069,134 A 5/2000 Roth et al.
6,075,181 A 6/2000 Kucherlapati et al.
6,096,532 A 8/2000 Armstrong et al.
6,114,598 A 9/2000 Kucherlapati et al.
6,121,022 A 9/2000 Presta et al.
6,150,584 A 11/2000 Kucherlapati et al.
6,153,737 A 11/2000 Manoharan et al.
6,162,963 A 12/2000 Kucherlapati et al.
6,165,745 A 12/2000 Ward et al.
6,172,197 B1 1/2001 McCafferty et al.
6,172,208 B1 1/2001 Cook
6,180,370 B1 1/2001 Queen et al.
6,187,287 B1 2/2001 Leung et al.
6,194,551 B1 2/2001 Idusogie et al.
6,277,375 B1 8/2001 Ward
6,300,319 B1 10/2001 Manoharan
6,335,434 B1 1/2002 Guzaev et al.
6,335,437 B1 1/2002 Manoharan
6,350,861 B1 2/2002 Co et al.
6,395,437 B1 5/2002 Wollesen
6,407,213 B1 6/2002 Carter et al.
6,444,806 B1 9/2002 Veerapanani et al.
6,486,308 B2 11/2002 Kutyavin et al.
6,492,123 B1 12/2002 Holliger et al.
6,521,404 B1 2/2003 Griffiths et al.
6,525,031 B2 2/2003 Manoharan
6,528,631 B1 3/2003 Cook et al.
6,544,731 B1 4/2003 Griffiths et al.
6,545,170 B2 4/2003 Pitzele et al.
6,548,640 B1 4/2003 Winter
6,555,313 B1 4/2003 Griffiths et al.
6,559,279 B1 5/2003 Manoharan et al.
6,562,576 B2 5/2003 Manfredi
6,582,915 B1 6/2003 Griffiths et al.
6,586,474 B2 7/2003 Webber et al.
6,591,889 B2 7/2003 Bettio et al.
6,593,081 B1 7/2003 Griffiths et al.
6,593,372 B2 7/2003 Enikolopov et al.
6,632,927 B2 10/2003 Adair et al.
6,639,055 B1 10/2003 Carter et al.
6,653,104 B2 11/2003 Goldenberg
6,696,686 B1 2/2004 Wainer et al.
6,790,624 B2 9/2004 Mayer
6,809,117 B2 10/2004 Enikolopov et al.
6,818,418 B1 11/2004 Lipovsek et al.
6,924,355 B2 8/2005 Baker et al.
6,936,436 B2 8/2005 Baker et al.
6,936,697 B2 8/2005 Desnoyers et al.
6,982,323 B1 1/2006 Wang et al.
7,026,448 B2 4/2006 Baker et al.
7,049,058 B2 5/2006 Singh
7,196,118 B2 3/2007 Webber et al.
7,226,759 B2 6/2007 Sun
7,250,297 B1 7/2007 Beste et al.
7,488,802 B2 2/2009 Collins et al.
7,595,048 B2 9/2009 Honjo
7,655,778 B2 2/2010 Yang
7,919,585 B2 4/2011 Chen
8,193,162 B2 * 6/2012 Zhao ...................... C07K 14/47
514/44 A
8,202,849 B2 * 6/2012 Nevalainen ........ A61K 38/1709
514/44 A
8,231,872 B2 7/2012 Noelle et al.
8,236,304 B2 8/2012 Noelle et al.
8,268,795 B2 * 9/2012 Wellman ................ A61K 31/00
514/44 A
8,309,532 B2 * 11/2012 Feinstein ............. A61K 31/713
514/44 A
8,334,275 B2 * 12/2012 Finkel ................ C07K 14/4747
514/44 A
8,465,740 B2 6/2013 Noelle et al.
8,501,915 B2 8/2013 Noelle et al.
8,652,465 B2 2/2014 Freeman
9,217,035 B2 12/2015 Noelle et al.
9,381,244 B2 * 7/2016 Noelle .................... A61P 35/00
9,631,018 B2 4/2017 Noelle et al.
9,890,215 B2 2/2018 Noelle et al.

(56) References Cited

U.S. PATENT DOCUMENTS

2003/0031671 A1 2/2003 Welt et al.
2003/0054406 A1 3/2003 Baker et al.
2004/0110704 A1 6/2004 Yamane et al.
2004/0132028 A1 7/2004 Stumpp et al.
2004/0259209 A1 12/2004 Sun et al.
2005/0043519 A1 2/2005 Dooley et al.
2005/0063948 A1 3/2005 Dickerson et al.
2006/0025576 A1 2/2006 Miller et al.
2006/0034852 A1 2/2006 Rixon et al.
2006/0084082 A1 4/2006 Ruben et al.
2007/0092512 A1 4/2007 Daaka et al.
2007/0122378 A1 5/2007 Freeman et al.
2007/0148167 A1 6/2007 Stohl
2007/0224633 A1 9/2007 Skerra et al.
2008/0069820 A1 3/2008 Fuh et al.
2008/0139791 A1 6/2008 Lipovsek et al.
2008/0166353 A1 7/2008 Cherwinski
2008/0226553 A1* 9/2008 Lowe .................... C12N 15/111 424/9.1
2008/0248007 A1 10/2008 Chen
2008/0287358 A1* 11/2008 Noelle ............... A61K 38/1709 514/1.1
2009/0215991 A1 8/2009 Lazar et al.
2010/0260808 A1* 10/2010 Baier ................... C12N 5/0636 424/277.1
2010/0316639 A1 12/2010 Lackner
2010/0317834 A1 12/2010 Lazar et al.
2011/0027278 A1* 2/2011 Noelle ............... C07K 16/2827 424/134.1
2011/0158995 A1 6/2011 Tan et al.
2011/0206699 A1 8/2011 Hossain et al.
2011/0223188 A1 9/2011 Langermann
2011/0243942 A1 10/2011 Wang
2011/0262408 A1* 10/2011 Nemunaitis ........ A61K 39/0011 424/93.21
2012/0195894 A1 8/2012 Noelle et al.
2013/0177557 A1 7/2013 Noelle et al.
2014/0037634 A1 2/2014 Noelle et al.
2014/0056890 A1 2/2014 Gurney et al.
2014/0056892 A1 2/2014 Noelle et al.
2014/0079706 A1* 3/2014 Cannarile ............ A61K 31/337 424/139.1
2014/0105912 A1 4/2014 Noelle et al.
2014/0220012 A1 8/2014 Noelle et al.
2014/0241983 A1* 8/2014 Hu ........................... A61N 5/10 424/1.11
2014/0294765 A1* 10/2014 Cojocaru ................ A61P 29/00 424/85.2
2014/0341920 A1 11/2014 Noelle et al.
2015/0231215 A1 8/2015 Noelle et al.
2016/0008316 A1 1/2016 Bacha et al.
2016/0083472 A1 3/2016 Noelle et al.
2016/0159927 A1 6/2016 Molloy et al.
2016/0168248 A1 6/2016 Noelle et al.
2016/0318999 A9 11/2016 Noelle et al.
2016/0331803 A1 11/2016 Noelle et al.
2017/0119877 A1 5/2017 Green et al.
2017/0334990 A1 11/2017 Noelle et al.
2018/0051070 A1 2/2018 Noelle et al.

FOREIGN PATENT DOCUMENTS

EP 0 045 665 2/1982
EP 0 125 023 11/1984
EP 0 154 316 9/1985
EP 0 171 496 2/1986
EP 0 173 494 3/1986
EP 0 184 187 6/1986
EP 0 264 166 4/1988
EP 0 401 384 12/1990
EP 1 176 195 1/2002
EP 1 641 818 4/2006
JP 08-506635 3/2008
WO WO 00/045665 2/1982
WO WO 86/001533 3/1986
WO WO 87/002671 5/1987
WO WO 87/005330 9/1987
WO WO 88/000052 1/1988
WO WO 88/009810 12/1988
WO WO 89/010134 11/1989
WO WO 91/006667 5/1991
WO WO 92/003918 3/1992
WO WO 93/008829 5/1993
WO WO 93/012227 6/1993
WO WO 94/010300 5/1994
WO WO 94/010332 5/1994
WO WO 94/025585 11/1994
WO WO 94/029351 12/1994
WO WO 94/029436 12/1994
WO WO 97/007668 3/1997
WO WO 97/007669 3/1997
WO WO 97/013852 4/1997
WO WO 97/028267 8/1997
WO WO 98/024884 6/1998
WO WO 99/045962 9/1999
WO WO 99/054342 10/1999
WO WO 00/006593 2/2000
WO WO 00/029004 5/2000
WO WO 00/031113 6/2000
WO WO 00/042072 7/2000
WO WO 01/000814 1/2001
WO WO 01/003737 1/2001
WO WO 01/014424 3/2001
WO WO 02/029072 4/2002
WO WO 02/043478 6/2002
WO WO 02/079449 10/2002
WO WO 02/092780 11/2002
WO WO 03/035835 5/2003
WO WO 03/074679 9/2003
WO WO 04/018520 3/2004
WO WO 04/037999 5/2004
WO WO 05/056764 6/2005
WO WO 05/112834 12/2005
WO WO 05/113606 12/2005
WO WO 06/012232 2/2006
WO WO 06/050247 5/2006
WO WO 06/050262 5/2006
WO WO 06/116181 11/2006
WO WO 07/030198 3/2007
WO WO 08/098796 8/2008
WO WO 09/089004 7/2009
WO WO 10/027827 3/2010
WO WO 13/184912 12/2013
WO WO 15/109340 7/2015
WO WO 15/191881 12/2015
WO WO 16/090347 6/2016
WO WO 17/181109 10/2017
WO WO 17/181139 10/2017
WO WO 18/027042 2/2018

OTHER PUBLICATIONS

Platt et al., 2014 J Allergy Clin Immunol 134: 262-268.*
Bikoff et al. 1993 J Exp Med; 177: 1699-1712.*
Elliott et al. 1994 J Exp Med; 179: 681-694.*
Watts et al. 2012 J Pathol; 226(2): 365-379.*
Wang et al. 2011 J. Exp. Med. 208: 577-592.*
Norde et al. (2012) Blood 120(4): 728-736.*
Lee et al. 2013 Br J Clin Pharmacol 76: 233-247.*
Gao et al. 2013 Trends in Immunology 34: 90-98.*
Lines et al. (2014) Cancer Immunol Res 2: 510-517.*
Le Mericer et al. (2014) Cancer Res 74(7): 1933-1944.*
Flies et al. 2014 J Clin Invest. 124(5): 1966-1975.*
Liu et al. (2015) PNAS 112: 6682-6687.*
Kondo et al. 2016 Oral Oncology 57: 54-60.*
Powderly et al. 2017 Annals of Oncology 28(Supplement 5): 405-406.*
Lee et al. 2017 Journal of Clinical Oncology 35, No. 15(Suppl.), Abstract TPS3099, 4 pages.*
Antonarakis ES. "Combining active immunotherapy with immune checkpoint blockade for the treatment of advanced prostate cancer," Asian J Androl. Jul. 2012; 14(4):520-1.

(56) References Cited

OTHER PUBLICATIONS

Brahmer JR, et al. "Safety and activity of anti-PD-L1 antibody in patients with advanced cancer," N Engl J Med. Jun. 28, 2012; 366(26):2455-65.
Brahmer, et al. Supplementary Appendix, Jun. 28, 2012, 26 pages.
Brahmer, et al. Supplementary Protocol, Jun. 28, 2012, 700 pages.
Curran MA, et al. "PD-1 and CTLA-4 combination blockade expands infiltrating T cells and reduces regulatory T and myeloid cells within B16 melanoma tumors," Proc Natl Acad Sci U S A. Mar. 2, 2010; 107(9):4275-80.
Nang, Li PhD—Dartmouth Medical School Presentation at the SITC (Society for Immunotherapy of Cancer) 26th Annual Meeting Dec. 2011.
Martinez Forero I, et al. "Workshop on immunotherapy combinations. Society for Immunotherapy of Cancer annual meeting Bethesda, Nov. 3, 2011," J Transl Med. May 28, 2012; 10:108.
Pilon-Thomas S, et al. "Blockade of programmed death ligand 1 enhances the therapeutic efficacy of combination immunotherapy against melanoma," J Immunol. Apr. 1, 2010; 184(7):3442-9.
Program of the SITC (Society for Immunotherapy of Cancer) 26th Annual Meeting Nov. 2011.
Quah BJ, et al. "The use of carboxyfluorescein diacetate succinimidyl ester (CFSE) to monitor lymphocyte proliferation," J Vis Exp. Oct. 12, 2010; (44). pii: 2259.
Topalian SL, et al. "Targeting the PD-1/B7-H1(PD-L1) pathway to activate anti-tumor immunity," Curr Opin Immunol. Apr. 2012; 24(2):207-12.
Wang, L. et al. "Immune Checkpoint Protein Vista as a Novel Target for Cancer Immunotherapy," Abstracts for the 27th Annual Scientific Meeting of the Society for Immunotherapy of Cancer (SITC), J Immunother. Nov.-Dec. 2012; 35(9):721, 781.
Yu P, et al. "Simultaneous blockade of multiple immune system inhibitory checkpoints enhances antitumor activity mediated by interleukin-15 in a murine metastatic colon carcinoma model," Clin Cancer Res. Dec. 15, 2010; 16(24):6019-28.
Yu P, et al. "Simultaneous inhibition of two regulatory T-cell subsets enhanced Interleukin-15 efficacy in a prostate tumor model," Proc Natl Acad Sci U S A. Apr. 17, 2012; 109(16):6187-92.
Zitvogel L, et al. "Targeting PD-1/PD-L1 interactions for cancer immunotherapy," Oncoimmunology. Nov. 1, 2012; 1(8):1223-1225.
Linsley PS, et al. " The clinical utility of inhibiting CD28-mediated costimulation," Immunol Rev. May 2009; 229(1):307-21.
Aalberse RC, et al. "IgG4 breaking the rules," Immunology. Jan. 2002; 105(1):9-19.
Adriouch S, et al. "Improved Immunological Tolerance Following Combination Therapy with CTLA-4/Ig and AAV-Mediated PD-L1/2 Muscle Gene Transfer," Front Microbiol. Sep. 29, 2011; 2:199.
Allen, et al., (2009), "Interchain disulfide bonding in human IgG2 antibodies probed by site-directed mutagenesis", Biochemistry, 48(17), 3755-3766.
Allen, T. M. "Ligand-targeted therapeutics in anticancer therapy," Nat Rev Cancer. Oct. 2002; 2(10):750-63.
Almquist RG, et al. "Synthesis and biological activity of a ketomethylene analogue of a tripeptide inhibitor of angiotensin converting enzyme," J Med Chern. Dec. 1980; 23(12):1392-8.
Al-Obeidi F, et al. "Peptide and peptidomimetic libraries. Molecular diversity and drug design," Mol Biotechnol. Jun. 1998; 9(3):205-23.
Altman JD, et al. "Phenotypic analysis of antigen-specific T lymphocytes," Science. Oct. 4, 1996; 274(5284):94-6.
Altschul SF, et al. "Basic local alignment search tool," J Mol Biol. Oct. 5, 1990; 215(3):403-10.
Altschul SF, et al. "Gapped BLAST and PSI-BLAST: a new generation of protein database search programs," Nucleic Acids Res. Sep. 1, 1997; 25(17):3389-402.
Amancha PK, et al. "In vivo blockade of the programmed cell death-1 pathway using soluble recombinant PD-1-Fc enhances CD4+ and CD8+ T cell responses but has limited clinical benefit," J Immunol. Dec. 15, 2013; 191(12):6060-70.
Ansari MJ, et al. "The programmed death-1 (PD-1) pathway regulates autoimmune diabetes in nonobese diabetic (NOD) mice," J Exp Med. Jul. 7, 2003; 198(1):63-9.
Arkin AP, et al. "An algorithm for protein engineering: simulations of recursive ensemble mutagenesis," Proc Natl Acad Sci U S A. Aug. 15, 1992; 89(16):7811-5.
Attia, P., et al., Autoimmunity correlates with tumor regression in patients with metastatic melanoma treated with anti-cytotoxic T-lymphocyte antigen-4. J Clin Oncol, 2005. 23(25): p. 6043-53.
Auffray, C et al. "Blood monocytes: development, heterogeneity, and relationship with dendritic cells," Annu Rev Immunol, 2009. 27: p. 669-92.
Bagley RG, et al. "sFLT01: a novel fusion protein with antiangiogenic activity," Mol Cancer Ther. Mar. 2011; 10(3):404-15.
Bak, S. P., et al., Murine ovarian cancer vascular leukocytes require arginase-1 activity for T cell suppression. Mol Immunol, 2008. 46(2): p. 258-68.
Baldari C, et al. "A novel leader peptide which allows efficient secretion of a fragment of human interleukin 1 beta in *Saccharomyces cerevisiae*," EMBO J. Jan. 1987; 6(1):229-34.
Banerji J, et al. "A lymphocyte-specific cellular enhancer is located downstream of the joining region in immunoglobulin heavy chain genes," Cell. Jul. 1983; 33(3):729-40.
Barringer KJ, et al. "Blunt-end and single-strand ligations by *Escherichia coli* ligase: influence on an in vitro amplification scheme," Gene. Apr. 30, 1990; 89(1):117-22.
Bartel DP, et al. "Isolation of new ribozymes from a large pool of random sequences," Science. Sep. 10, 1993; 261(5127):1411-8.
Baskar S, et al. "Constitutive expression of B7 restores immunogenicity of tumor cells expressing truncated major histocompatibility complex class II molecules," Proc Natl Acad Sci U S A. Jun. 15, 1993; 90(12):5687-90.
Batzer MA, et al. "Enhanced evolutionary PCR using oligonucleotides with inosine at the 3'-terminus," Nucleic Acids Res. Sep. 25, 1991; 19(18):5081.
Bauer S, et al. "Immunotherapy of human tumors with T-cell-activating bispecific antibodies: stimulation of cytotoxic pathways in vivo," Cancer Res. Apr. 15, 1999; 59(8):1961-5.
Beidler CB, et al. "Cloning and high level expression of a chimeric antibody with specificity for human carcinoembryonic antigen," J Immunol. Dec. 1, 1988; 141(11):4053-60.
Beilharz MW, et al. "Timed ablation of regulatory CD4+ T cells can prevent murine AIDS progression," J Immunol. Apr. 15, 2004; 172(8):4917-25.
Belousov ES, et al. "Sequence-specific targeting and covalent modification of human genomic DNA," Nucleic Acids Res. Sep. 1, 1997; 25(17):3440-4.
Béranger F, et al. "Getting more from the two-hybrid system: N-terminal fusions to LexA are efficient and sensitive baits for two-hybrid studies," Nucleic Acids Res. May 15, 1997; 25(10):2035-6.
Berge SM, et al. "Pharmaceutical salts," J Pharm Sci. Jan. 1977; 66(1):1-19.
Berney C, et al. "A member of the dendritic cell family that enters B cell follicles and stimulates primary antibody responses identified by a mannose receptor fusion protein," J Exp Med. Sep. 20, 1999; 190(6):851-60.
Better M, et al. "*Escherichia coli* secretion of an active chimeric antibody fragment," Science. May 20, 1988; 240(4855):1041-3.
Bird RE, et al. "Single-chain antigen-binding proteins," Science. Oct. 21, 1988; 242(4877):423-6.
Blank C, et al. "Interaction of PD-L1 on tumor cells with PD-1 on tumor-specific T cells as a mechanism of immune evasion: implications for tumor immunotherapy," Cancer Immunol Immunother. Apr. 2005; 54(4):307-14.
Blank, C., et al., "PD-L1/B7H-1 inhibits the effector phase of tumor rejection by T cell receptor (TCR) transgenic CD8+ T cells," Cancer Res, 2004. 64(3): p. 1140-45.
Blazar et al., "Infusion of anti-B7.1 (CD80) and anti-B7.2 (CD86) monoclonal antibodies inhibits murine graft-versus-host disease lethality in part via direct effects on CD4+ and CD8+ T cells." The Journal of Immunology 157.8 (1996): 3250-3259.

(56) References Cited

OTHER PUBLICATIONS

Bloemen PG, et al. "Adhesion molecules: a new target for immunoliposome-mediated drug delivery," FEBS Lett. Jan. 3, 1995; 357(2):140-4.
Blommers MJ, et al. "Effects of the introduction of L-nucleotides into DNA. Solution structure of the heterochiral duplex d(G-C-G-(L)T-G-C-G).d(C-G-C-A-C-G-C) studied by NMR spectroscopy," Biochemistry. Jun. 28, 1994; 33(25):7886-96.
Bluestone JA, et al. "Natural versus adaptive regulatory T cells," Nat Rev Immunol. Mar. 2003; 3(3):253-7.
Bogdan C. "Nitric oxide and the immune response," Nat Immunol. Oct. 2001; 2(10):907-16.
Bolhassani, A. et al., "Improvement of different vacine delivery systems for cancer therapy", Molecular Cancer, 2011, vol. 10, No. 1, Article No. 3.
Boon T, et al. "Human T cell responses against melanoma," Annu. Rev. Immunol.. Apr. 23, 2006; 24:175-208.
Borriello F, et al. "B7-1 and B7-2 have overlapping, critical roles in immunoglobulin class switching and germinal center formation," Immunity. Mar. 1997; 6(3):303-13.
Borrok MJ, "pH-dependent Binding Engineering Reveals an FcRn Affinity Threshold That Governs IgG Recycling," The Journal of Biological Chemistry. 2015; 290(7):4282-90.
Boulianne GL, et al. "Production of functional chimaeric mouse/human antibody," Nature. Dec. 13-19, 1984; 312(5995):643-6.
Bowen JL, et al. "Innate immune CD11b+Gr-1+ cells, suppressor cells, affect the immune response during Theiler's virus-induced demyelinating disease," J Immunol. Dec. 1, 2009; 183(11):6971-80.
Brahmer, J. R., et al., Phase I study of single-agent anti-programmed death-1 (MDX-1106) in refractory solid tumors: safety, clinical activity, pharmacodynamics, and immunologic correlates. J Clin Oncol, 2010. 28(19): p. 3167-75.
Brandt C, et al. "The B7 family member B7-H6 is a tumor cell ligand for the activating natural killer cell receptor NKp30 in humans," J Exp Med. Jul. 6, 2009; 206(7):1495-503.
Brennan M, et al. "Preparation of bispecific antibodies by chemical recombination of monoclonal immunoglobulin G1 fragments," Science. Jul. 5, 1985; 229(4708):81-3.
Briscoe P, et al. "Delivery of superoxide dismutase to pulmonary epithelium via pH-sensitive liposomes," Am J Physiol. Mar. 1995; 268(3 Pt 1):L374-80.
Brisson, et al. "Expression of a bacterial gene in plants by using a viral vector," Nature vol. 310 Aug. 1984, 511-14.
Broglie R, et al. "Light-regulated expression of a pea ribulose-1,5-bisphosphate carboxylase small subunit gene in transformed plant cells," Science. May 25, 1984; 224(4651):838-43.
Brown JP, et al. "Protein antigens of normal and malignant human cells identified by immunoprecipitation with monoclonal antibodies," J Biol Chern. Jun. 10, 1980; 255(11):4980-3.
Brown JP, et al. "Structural characterization of human melanoma-associated antigen p97 with monoclonal antibodies," J Immunol. Aug. 1981; 127(2):539-46.
Brys L, et al. "Reactive oxygen species and 12/15-lipoxygenase contribute to the antiproliferative capacity of alternatively activated myeloid cells elicited during helminth infection," J Immunol. May 15, 2005; 174(10):6095-104.
Burg JL, et al. "Single molecule detection of RNA reporter probes by amplification with Q beta replicase," Mol Cell Probes. Aug. 1996; 10(4):257-71.
Butte MJ, et al. "Programmed death-1 ligand 1 interacts specifically with the B7-1 costimulatory molecule to inhibit T cell responses," Immunity. Jul. 2007; 27(1):111-22.
Byrne GW, et al. "Multiplex gene regulation: a two-tiered approach to transgene regulation in transgenic mice," Proc Natl Acad Sci U S A. Jul. 1989; 86(14):5473-7.
Cabilly S, et al. "Generation of antibody activity from immunoglobulin polypeptide chains produced in *Escherichia coli*," Proc Natl Acad Sci U S A. Jun. 1984; 81(11):3273-7.
Cabilly S, et al. "Immunoglobulin transcripts and molecular history of a hybridoma that produces antibody to carcinoembryonic antigen," Gene. 1985; 40(1):157-61.
Calabro, L., et al., "Clinical studies with anti-CTLA-4 antibodies in non-melanoma indications," Semin Oncol, 2010. 37(5): p. 460-7.
Calame K, et al. "Transcriptional controlling elements in the immunoglobulin and T cell receptor loci," Adv Immunol. 1988; 43:235-75.
Camper SA, et al. "Postnatal repression of the alpha-fetoprotein gene is enhancer independent," Genes Dev. Apr. 1989; 3(4):537-46.
Cancer Prevention Overview (PDQ®), PDQ Cancer Information Summaries [Internet]. 2017, 14 pages.
Carell, et al. "A Solution-Phase Screening Procedure for the Isolation of Active Compounds from a Library of Molecules," Angew. Chern. Int. Ed. Engl. 1994, 33. No. 20, 2061-64.
Carter L, et al. "PD-1:PD-L inhibitory pathway affects both CD4(+) and CD8(+) T cells and is overcome by IL-2," Eur J Immunol. Mar. 2002; 32(3):634-43.
Ceeraz S, et al. "VISTA Deficiency Accelerates the Development of Fatal Murine Lupus Nephritis," Arthritis Rheumatol. Apr. 2017; 69(4):814-825.
Chambers CA, et al. "Lymphoproliferation in CTLA-4-deficient mice is mediated by costimulation-dependent activation of CD4+ T cells," Immunity. Dec. 1997; 7(6):885-95.
Chan AC, et al. "Therapeutic antibodies for autoimmunity and inflammation," Nat Rev Immunol. May 2010; 10(5):301-16.
Chen J, et al. "B cell development in mice that lack one or both immunoglobulin kappa light chain genes," EMBO J. Mar. 1993; 12(3):821-30.
Chen J, et al. "Immunoglobulin gene rearrangement in B cell deficient mice generated by targeted deletion of the JH locus," Int Immunol. Jun. 1993; 5(6):647-56.
Chen L, et al. "Costimulation of antitumor immunity by the B7 counterreceptor for the T lymphocyte molecules CD28 and CTLA-4," Cell. Dec. 24, 1992; 71(7):1093-102.
Chen S, et al. "Immunosuppressive functions of hepatic myeloid-derived suppressor cells of normal mice and in a murine model of chronic hepatitis B virus," Clin Exp Immunol. Oct. 2011; 166(1):134-42.
Chen SH, et al. "Gene therapy for brain tumors: regression of experimental gliomas by adenovirus-mediated gene transfer in vivo," Proc Natl Acad Sci U S A. Apr. 12, 1994; 91(8):3054-7.
Chen, Y., "Development of a sandwich ELISA for evaluating soluble PD-LI (CD274) in human sera of different ages as well as supernatants of PD-L1(+) cell lines," Cytokine 2011.
Cho CY, et al. "An unnatural biopolymer," Science. Sep. 3, 1993; 261(5126):1303-5.
Choi TK, et al. "Transgenic mice containing a human heavy chain immunoglobulin gene fragment cloned in a yeast artificial chromosome," Nat Genet. Jun. 1993; 4(2):117-23.
Chothia C, et al. "Canonical structures for the hypervariable regions of immunoglobulins," J Mol Biol. Aug. 20, 1987; 196(4):901-17.
Church GM, et al. "Genomic sequencing," Proc Natl Acad Sci U S A. Apr. 1984; 81(7):1991-5.
Clark KL, et al. "Association of the Arabidopsis CTR1 Raf-like kinase with the ETR1 and ERS ethylene receptors," Proc Natl Acad Sci U S A. Apr. 28, 1998; 95(9):5401-6.
Cohen AA, et al. "Structure design: an artificial intelligence-based method for the design of molecules under geometrical constraints," J Mol Graph. Sep. 1993; 11(3):166-73.
Cole SP, et al. "Human monoclonal antibodies," Mol Cell Biochem. Jun. 1984; 62(2):109-20.
Colman PM. "Effects of amino acid sequence changes on antibody-antigen interactions," Res Immunol. Jan. 1994; 145(1):33-6.
Conejo-Garcia, J. R., et al., "Tumor-infiltrating dendritic cell precursors recruited by a beta-defensin contribute to vasculogenesis under the influence of Vegf-A," Nat Med, 2004. 10(9): p. 950-8.
Copin, R., et al., "MyD88-dependent activation of B220-CD11b+ LY-6C+ dendritic cells during *Brucella melitensis* infection," J Immunol, 2007. 178(8): p. 5182-91.
Coruzzi G, et al. "Tissue-specific and light-regulated expression of a pea nuclear gene encoding the small subunit of ribulose-1,5-bisphosphate carboxylase," EMBO J. Aug. 1984; 3(8):1671-9.

(56) References Cited

OTHER PUBLICATIONS

Corzo, C. A., et al., "HIF-1alpha regulates function and differentiation of myeloid-derived suppressor cells in the tumor microenvironment," J Exp Med, 2010. 207(11): p. 2439-53.
Cote RJ, et al. "Generation of human monoclonal antibodies reactive with cellular antigens," Proc Natl Acad Sci U S A. Apr. 1983; 80(7):2026-30.
Cox JP, et al. "A directory of human germ-line V kappa segments reveals a strong bias in their usage," Eur J Immunol. Apr. 1994; 24(4):827-36.
Cubillos-Ruiz, J. R., et al., "Polyethylenimine-based siRNA nanocomplexes reprogram tumor-associated dendritic cells via TLR5 to elicit therapeutic antitumor immunity," J Clin Invest, 2009. 119(8): p. 2231-44.
Cull MG, et al. "Screening for receptor ligands using large libraries of peptides linked to the C terminus of the lac repressor," Proc Natl Acad Sci U S A. Mar. 1, 1992; 89(5):1865-9.
Cunningham BC, et al. "High-resolution epitope mapping of hGH-receptor interactions by alanine-scanning mutagenesis," Science. Jun. 2, 1989; 244(4908):1081-5.
Curiel, T. J., et al., "Blockade of B7-H1 improves myeloid dendritic cell-mediated antitumor immunity," Nat Med, 2003. 9(5): p. 562-7.
Curiel, T. J., et al., "Specific recruitment of regulatory T cells in ovarian carcinoma fosters immune privilege and predicts reduced survival," Nat Med, 2004. 10(9): p. 942-9.
Curis, Inc. "A Study of CA-170 (Oral PD-L1, PD-L2 and VISTA Checkpoint Antagonist) in Patients With Advanced Tumors and Lymphomas," U.S. National Library of Medicine, ClinicalTrials.gov; (https://clinicaltrials.gov) 2018. 8 pages.
Cwirla SE, et al. "Peptides on phage: a vast library of peptides for identifying ligands," Proc Natl Acad Sci U S A. Aug. 1990; 87(16):6378-82.
Dal Porto J, et al. "A soluble divalent class I major histocompatibility complex molecule inhibits alloreactive T cells at nanomolar concentrations," Proc Natl Acad Sci U S A. Jul. 15, 1993; 90(14):6671-5.
David GS, et al. "Protein iodination with solid state lactoperoxidase," Biochemistry. Feb. 26, 1974; 13(5):1014-21.
De Vos AM, et al. "Human growth hormone and extracellular domain of its receptor: crystal structure of the complex," Science. Jan. 17, 1992; 255(5042):306-12.
Dean PM. "Recent advances in drug design methods: where will they lead?" Bioessays. Sep. 1994; 16(9):683-7.
Delagrave S, et al. "Recursive ensemble mutagenesis," Protein Eng. Apr. 1993; 6(3):327-31.
Dellinger et al. "International Guidelines for Management of Severe Sepsis and Septic Shock" (2013 Intensive Care Med 39: 165-228).
Deng J, et al. "A New VISTA on combination therapy for negative checkpoint regulator blockade," J Immunother Cancer. Dec. 20, 2016; 4:86.
Deshayes S, et al. "Insight into the mechanism of internalization of the cell-penetrating carrier peptide Pep-1 through conformational analysis," Biochemistry. Feb. 17, 2004; 43(6):1449-57.
D'Eustachio P, et al. "Somatic cell genetics and gene families," Science. May 27, 1983; 220(4600):919-24.
Devlin JJ, et al. "Random peptide libraries: a source of specific protein binding molecules," Science. Jul. 27, 1990; 249(4967):404-6.
DeWitt SH, et al. "'Diversomers': an approach to nonpeptide, nonoligomeric chemical diversity," Proc Natl Acad Sci U S A. Aug. 1, 1993; 90(15):6909-13.
Di Maro, Antimo, et al. "Isolation and characterization of four type-1 ribosome-inactivating proteins, with polynucleotide: adenosine glycosidase activity, from leaves of Phytolacca dioica L." Planta 208.1 (1999): 125-131.
DiLillo DJ, et al. "Fc-Receptor Interactions Regulate Both Cytotoxic and Immunomodulatory Therapeutic Antibody Effector Functions," Cancer Immunology Research. 2015; 3(7):704-13.
Dillon et al., "Optimization of a reversed-phase high-performance liquid chromatography/mass spectrometry method for characterizing recombinant antibody heterogeneity and stability," J Chromatogr A. Jul. 7, 2006; 1120(1-2):112-20.
Dong C, et al. "ICOS co-stimulatory receptor is essential for T-cell activation and function," Nature. Jan. 4, 2001; 409(6816):97-101.
Dong H, et al. "B7-H1 pathway and its role in the evasion of tumor immunity," J Mol Med (Berl). May 2003; 81(5):281-7.
Dong H, et al. "Tumor-associated B7-H1 promotes T-cell apoptosis: a potential mechanism of immune evasion," Nat Med. Aug. 2002; 8(8):793-800.
Dubey AK, et al. "Belimumab: First targeted biological treatment for systemic lupus erythematosus," J Pharmacol Pharmacother. 2011; 2(4):317-9.
Duttagupta et al., "Costimulation signals for memory CD8+ T cells during viral infections." Critical Reviews™ in Immunology 29.6 (2009).
Edlund T, et al. "Cell-specific expression of the rat insulin gene: evidence for role of two distinct 5' flanking elements," Science. Nov. 22, 1985; 230(4728):912-6.
Ehst BD, et al. "Development of a novel transgenic mouse for the study of interactions between CD4 and CD8 T cells during graft rejection," American Journal of Transplantation: 2003; 3(11):1355-62.
Elbashir SM, et al. "Duplexes of 21-nucleotide RNAs mediate RNA interference in cultured mammalian cells," Nature. May 24, 2001; 411(6836):494-8.
Ellenberger TE, et al. "The GCN4 basic region leucine zipper binds DNA as a dimer of uninterrupted alpha helices: crystal structure of the protein-DNA complex," Cell. Dec. 24, 1992; 71(7):1223-37.
Erb E, et al. "Recursive deconvolution of combinatorial chemical libraries," Proc Natl Acad Sci U S A. Nov. 22, 1994; 91(24):11422-6.
Evans BE, et al. "Design of nonpeptidal ligands for a peptide receptor: cholecystokinin antagonists," J Med Chem. Jul. 1987; 30(7):1229-39.
Fallarino F, et al. "B7-1 engagement of cytotoxic T lymphocyte antigen 4 inhibits T cell activation in the absence of CD28," J Exp Med. Jul. 6, 1998; 188(1):205-10.
Fan YS, et al. "Mapping small DNA sequences by fluorescence in situ hybridization directly on banded metaphase chromosomes," Proc Natl Acad Sci U S A. Aug. 1990; 87(16):6223-7.
Felici F, et al. "Selection of antibody ligands from a large library of oligopeptides expressed on a multivalent exposition vector," J Mol Biol. Nov. 20, 1991; 222(2):301-10.
Finn PJ, et al. "Synthesis and properties of DNA-PNA chimeric oligomers," Nucleic Acids Res. Sep. 1, 1996; 24(17):3357-63.
Fishwild DM, et al. "High-avidity human IgG kappa monoclonal antibodies from a novel strain of minilocus transgenic mice," Nat Biotechnol. Jul. 1996; 14(7):845-51.
Flicek P, et al. "Ensembl 2008," Nucleic Acids Res. Jan. 2008; 36(Database issue):D707-14.
Flies DB, et al. "Coinhibitory receptor PD-1H preferentially suppresses $CD4^+$ T cell-mediated immunity," J Clin Invest. May 2014; 124(5):1966-75.
Flies DB, et al. "Cutting edge: A monoclonal antibody specific for the programmed death-1 homolog prevents graft-versus-host disease in mouse models," J Immunol. Aug. 15, 2011; 187(4):1537-41.
Flies DB, et al. "Mechanistic Assessment of PD-1H Coinhibitory Receptor-Induced T Cell Tolerance to Allogeneic Antigens," J Immunol. Jun. 1, 2015; 194(11):5294-304.
Fodor SP, et al. "Multiplexed biochemical assays with biological chips," Nature. Aug. 5, 1993; 364(6437):555-6.
Fontenot JD, et al. "Regulatory T cell lineage specification by the forkhead transcription factor foxp3," Immunity. Mar. 2005; 22(3):329-41.
Formstecher E, et al. "Protein interaction mapping: a Drosophila case study," Genome Res. Mar. 2005; 15(3):376-84.
Franklin, et al. "Immunologic differences between the 19 S and 7 S components of normal human gamma-globulin," J Immunol. Jan. 1957; 78(1):11-8.
Freeman GJ, et al. "Engagement of the PD-1 immunoinhibitory receptor by a novel B7 family member leads to negative regulation of lymphocyte activation," J Exp Med. Oct. 2, 2000; 192(7):1027-34.

(56) References Cited

OTHER PUBLICATIONS

Freeman GJ, et al. "Uncovering of functional alternative CTLA-4 counter-receptor in B7-deficient mice," Science. Nov. 5, 1993; 262(5135):907-9.
Freeman GJ. "Structures of PD-1 with its ligands: sideways and dancing cheek to cheek," Proc Natl Acad Sci U S A. Jul. 29, 2008; 105(30):10275-6.
Freier SM, et al. "Improved free-energy parameters for predictions of RNA duplex stability," Proc Natl Acad Sci U S A. Dec. 1986; 83(24):9373-7.
Frenkel K, et al. "7,12-dimethylbenz[a]anthracene induces oxidative DNA modification in vivo," Free Radic Biol Med. Sep. 1995; 19(3):373-80.
Fromont-Racine M, et al. "Toward a functional analysis of the yeast genome through exhaustive two-hybrid screens," Nat Genet. Jul. 1997; 16(3):277-82.
Futaki S. "Arginine-rich peptides: potential for intracellular delivery of macromolecules and the mystery of the translocation mechanisms," Int J Pharm. Oct. 1, 2002; 245(1-2):1-7.
Gabrilovich D. "Mechanisms and functional significance of tumour-induced dendritic-cell defects," Nat Rev Immunol. Dec. 2004; 4(12):941-52.
Gabrilovich DI, et al. "Myeloid-derived suppressor cells as regulators of the immune system," Nat Rev Immunol. Mar. 2009; 9(3):162-74.
Galfre, G. et al. "Antibodies to major histocompatibility anitigens produced by hybrid cell lines," Nature, vol. 266, Apr. 1977, 550-52.
Gallop MA, et al. "Applications of combinatorial technologies to drug discovery. 1. Background and peptide combinatorial libraries," J Med Chem. Apr. 29, 1994; 37(9):1233-51.
Gao J, et al. "VISTA is an inhibitory immune checkpoint that is increased after ipilimumab therapy in patients with prostate cancer," Nat Med. May 2017; 23(5):551-555.
Gao, Q., et al., "Overexpression of PD-L1 significantly associates with tumor aggressiveness and postoperative recurrence in human hepatocellular carcinoma," Clin Cancer Res, 2009. 15(3): p. 971-9.
Garg A, et al. "HIV type 1 gp120-induced expansion of myeloid derived suppressor cells is dependent on interleukin 6 and suppresses immunity," J Infect Dis. Feb. 1, 2014; 209(3):441-51.
Gautier C, et al. "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids Res. Aug. 25, 1987; 15(16):6625-41.
Gavin MA, et al. " Homeostasis and anergy of CD4(+)CD25(+) suppressor T cells in vivo," Nat Immunol. Jan. 2002; 3(1):33-41.
Gefter ML, et al. "A simple method for polyethylene glycol-promoted hybridization of mouse myeloma cells," Somatic Cell Genet. Mar. 1977; 3(2):231-6.
Geissmann, F., et al. "Blood monocytes consist of two principal subsets with distinct migratory properties," Immunity, 2003. 19(1): p. 71-82.
Geissmann, F., et al., "Blood monocytes: distinct subsets, how they relate to dendritic cells, and their possible roles in the regulation of T-cell responses," Immunol Cell Biol, 2008. 86(5): p. 398-408.
Geissmann, F., et al., "Development of monocytes, macrophages, and dendritic cells," Science, 2010. 327(5966): p. 656-61.
GenBank Accession No. NP.sub.--071436 (Sep. 3, 2009), platelet receptor Gi24 precursor [*Homo spaiens*].
GenBank Accession No. NP.sub.--083008 (Mar. 3, 3010) platelet receptor Gi24 isoform 1 precursor [Mus musculus].
Genbank entry EGW09616.1 (Mar. 14, 2015) [retrieved on Jun. 22, 2015 from http://www.ncbi.nlm.nih.gov/protein/EGW09616.1] 1 page.
Geng H, et al. "HSP70 vaccine in combination with gene therapy with plasmid DNA encoding sPD-1 overcomes immune resistance and suppresses the progression of pulmonary metastatic melanoma," Int J Cancer. Jun. 1, 2006; 118(11):2657-64.
Ghiringhelli, F., et al., "Tumor cells convert immature myeloid dendritic cells into TGF-beta-secreting cells inducing CD4+CD25+ regulatory T cell proliferation," J Exp Med, 2005. 202(7): p. 919-29.
Gilliland DG, et al. "Antibody-directed cytotoxic agents: use of monoclonal antibody to direct the action of toxin A chains to colorectal carcinoma cells," Proc Natl Acad Sci U S A. Aug. 1980; 77(8):4539-43.
Glennie MJ, et al. "Preparation and performance of bispecific F(ab' gamma)2 antibody containing thioether-linked Fab' gamma fragments," J Immunol. Oct. 1, 1987; 139(7):2367-75.
Gluzman Y, et al. "SV40 early mutants that are defective for viral DNA synthesis but competent for transformation of cultured rat and simian cells," Virology. Nov. 1982; 123(1):78-92.
Goeddel DV. "Systems for heterologous gene expression," Methods Enzymol. 1990; 185:3-7.
Gorczynski RM, et al. "Checkpoint blockade in solid tumors and B-cell malignancies, with special consideration of the role of CD200," Cancer Manag Res. Nov. 13, 2017; 9:601-609.
Grabie N, et al. "Endothelial programmed death-1 ligand 1 (PD-L1) regulates CD8+ T-cell mediated injury in the heart," Circulation. Oct. 30, 2007; 116(18):2062-71.
Graziano RF, et al. "Construction and characterization of a humanized anti-gamma-Ig receptor type I (Fc gamma RI) monoclonal antibody," J Immunol. Nov. 15, 1995; 155(10):4996-5002.
Green KA, et al. "Antibody to the ligand for CD40 (gp39) inhibits murine AIDS-associated splenomegaly, hypergammaglobulinemia, and immunodeficiency in disease-susceptible C57BL/6 mice," J Virol. Apr. 1996; 70(4):2569-75.
Green KA, et al. "Myeloid-derived suppressor cells in murine retrovirus-induced AIDS inhibit T- and B-cell responses in vitro that are used to define the immunodeficiency," J Virol. Feb. 2013; 87(4):2058-71.
Greenwald RJ, et al. " The B7 family revisited," Annu Rev Immunol. 2005; 23:515-48.
Groux H, et al. "A CD4+ T-cell subset inhibits antigen-specific T-cell responses and prevents colitis," Nature. Oct. 16, 1997; 389(6652):737-42.
Gruber M, et al. "Efficient tumor cell lysis mediated by a bispecific single chain antibody expressed in *Escherichia coli*," J Immunol. Jun. 1, 1994; 152(11):5368-74.
Guatelli JC, et al. "Isothermal, in vitro amplification of nucleic acids by a multienzyme reaction modeled after retroviral replication," Proc Natl Acad Sci U S A. Mar. 1990; 87(5):1874-8.
Guindon S, et al. "A simple, fast, and accurate algorithm to estimate large phylogenies by maximum likelihood," Syst Biol. Oct. 2003; 52(5):696-704.
Guleria I, et al. "A critical role for the programmed death ligand 1 in fetomaternal tolerance," J Exp Med. Jul. 18, 2005; 202(2):231-7.
Gurley WB, et al. "Upstream sequences required for efficient expression of a soybean heat shock gene," Mol Cell Biol. Feb. 1986; 6(2):559-65.
Hamilton AJ, et al. "A species of small antisense RNA in post-transcriptional gene silencing in plants," Science. Oct. 29, 1999; 286(5441):950-2.
Hann M "On the Double Bond Isostere of the Peptide Bond: Preparation of an Enkephalin Analogue," Journal of the Chemical Society, Perkin Transactions 1982 (1), 307-14.
Hara M, et al. "IL-10 is required for regulatory T cells to mediate tolerance to alloantigens in vivo," J Immunol. Mar. 15, 2001; 166(6):3789-96.
Harding FA, et al. "Class switching in human immunoglobulin transgenic mice," nn N Y Acad Sci. Sep. 29, 1995; 764:536-46.
Haseloff J, et al. "Simple RNA enzymes with new and highly specific endoribonuclease activities," Nature. Aug. 18, 1988; 334(6183):585-91.
Hashida H, et al. "Fusion of HIV-1 Tat protein transduction domain to poly-lysine as a new DNA delivery tool," Br J Cancer. Mar. 22, 2004; 90(6):1252-8.
Haskins K, et al. "The major histocompatibility complex-restricted antigen receptor on T cells. I. Isolation with a monoclonal antibody," The Journal of Experimental Medicine. 1983; 157(4):1149-69.

(56) References Cited

OTHER PUBLICATIONS

Hauser N, et al. "Interaction of cartilage matrix protein with aggrecan. Increased covalent cross-linking with tissue maturation," J Biol Chem. Dec. 13, 1996; 271(50):32247-52.
Hauser N, et al. "Native cartilage matrix protein (CMP). A compact trimer of subunits assembled via a coiled-coil alpha-helix," J Biol Chem. Oct. 14, 1994; 269(41):25747-53.
Haynes JR, et al. "Particle-mediated nucleic acid immunization," J Biotechnol. Jan. 26, 1996; 44(1-3):37-42.
Hedbom E, et al. "Cartilage matrix proteins. An acidic oligomeric protein (COMP) detected only in cartilage," J Biol Chem. Mar. 25, 1992; 267(9):6132-6.
Helene C, et al. "Control of gene expression by triple helix-forming oligonucleotides. The antigene strategy," Ann N Y Acad Sci. Oct. 28, 1992; 660:27-36.
Hellstrom I, et al. "CD3-mediated activation of tumor-reactive lymphocytes from patients with advanced cancer," Proc Natl Acad Sci U S A. Jun. 5, 2001; 98(12):6783-8.
Hinton PR, et al. "Engineered human IgG antibodies with longer serum half-lives in primates," J Biol Chem. Feb. 20, 2004; 279(8):6213-6.
Hirano, F., et al., Blockade of B7-H1 and PD-1 by monoclonal antibodies potentiates cancer therapeutic immunity Cancer Res, 2005. 65(3): p. 1089-96.
Ho SN, et al. "Site-directed mutagenesis by overlap extension using the polymerase chain reaction," Gene. Apr. 15, 1989; 77(1):51-9.
Ho VT, et al. "The history and future of T-cell depletion as graft-versus-host disease prophylaxis for allogeneic hematopoietic stem cell transplantation," Blood. Dec. 1, 2001; 98(12):3192-204.
Hodi, F. S., Overcoming immunological tolerance to melanoma: Targeting CTLA-4. Asia Pac J Clin Oncol, 2010. 6 Suppl 1: p. S16-23.
Hogg N. "The structure and function of Fc receptors," Immunol Today. Jul.-Aug. 1988; 9(7-8):185-7.
Holladay, M. W., et al. (1983). "Synthesis of hydroxyethylene and ketomethylene dipeptide isosteres," Tetrahedron Letters 1983 24(41), 4401-4404.
Hollenbaugh D, et al. "Cleavable CD40Ig fusion proteins and the binding to sgp39," J Immunol Methods. Dec. 15, 1995; 188(1):1-7.
Holliger P, et al. ""Diabodies": small bivalent and bispecific antibody fragments," Proc Natl Acad Sci U S A. Jul. 15, 1993; 90(14):6444-8.
Holm L, et al. "DaliLite workbench for protein structure comparison," Bioinformatics. Jun. 2000; 16(6):566-7.
Hoos, A., et al., "Development of ipilimumab: contribution to a new paradigm for cancer immunotherapy," Semin Oncol, 2010. 37(5): p. 533-46.
Hopp TP, et al. "Prediction of protein antigenic determinants from amino acid sequences," Proc Natl Acad Sci U S A. Jun. 1981; 78(6):3824-8.
Horn JR, et al. "The role of protein dynamics in increasing binding affinity for an engineered protein-protein interaction established by H/D exchange mass spectrometry," Biochemistry. Jul. 18, 2006; 45(28):8488-98.
Hotchkiss RS, et al. "Immunosuppression in sepsis: a novel understanding of the disorder and a new therapeutic approach," Lancet Infect Dis. Mar. 2013; 13(3):260-8.
Houghten RA, et al. "The use of synthetic peptide combinatorial libraries for the identification of bioactive peptides," Bioorganic & Medicianl Chemistry Letters, vol. 3, No. 3, 1993. pp. 405-412.
Hruby VJ, et al. "Conformational and topographical considerations in the design of biologically active peptides," Biopolymers. Jul. 1993; 33(7):1073-82.
Hruby VJ, et al. "Synthesis of oligopeptide and peptidomimetic libraries," Curr Opin Chem Biol. Jun. 1997; 1(1):114-9.
Hruby VJ. "Conformational restrictions of biologically active peptides via amino acid side chain groups," Life Sci. Jul. 19, 1982; 31(3):189-99.
Huarte, E., et al., "Depletion of dendritic cells delays ovarian cancer progression by boosting antitumor immunity," Cancer Res, 2008. 68(18): p. 7684-91.
Hudson D, et al. "Methionine enkephalin and isosteric analogues. I. Synthesis on a phenolic resin support," Int J Pept Protein Res. 1979; 14(3):177-85.
Huston JS, et al. "Protein engineering of antibody binding sites: recovery of specific activity in an anti-digoxin single-chain Fv analogue produced in *Escherichia coli*," Proc Natl Acad Sci U S A. Aug. 1988; 85(16):5879-83.
Hutloff A, et al. "ICOS is an inducible T-cell co-stimulator structurally and functionally related to CD28," Nature. Jan. 21, 1999; 397(6716):263-6.
Hyrup B, e al. "Peptide nucleic acids (PNA): synthesis, properties and potential applications," Bioorg Med Chem. Jan. 1996; 4(1):5-23.
Ike Y, et al. "Solid phase synthesis of polynucleotides. VIII. Synthesis of mixed oligodeoxyribonucleotides by the phosphotriester solid phase method," Nucleic Acids Res. Jan. 25, 1983; 11(2):477-88.
Iliopoulos D, et al. "The negative costimulatory molecule PD-1 modulates the balance between immunity and tolerance via miR-21," Eur J Immunol. Jun. 2011; 41(6):1754-63.
Inoue H, et al. "Sequence-dependent hydrolysis of RNA using modified oligonucleotide splints and RNase H," FEBS Lett. May 11, 1987; 215(2):327-30.
Inoue H, et al. "Synthesis and hybridization studies on two complementary nona(2'-O-methyl)ribonucleotides," Nucleic Acids Res. Aug. 11, 1987; 15(15):6131-48.
Invitrogen (2002) "Guide to Baculovirus Expression Vector Systems (BEVs) and Insect Culture Techniques" Instruction Manual. 30 pages.
Itakura K, et al. "Expression in *Escherichia coli* of a chemically synthesized gene for the hormone somatostatin," Science. Dec. 9, 1977; 198(4321):1056-63.
Itakura K, et al. "Synthesis and use of synthetic oligonucleotides," Annu Rev Biochem. 1984; 53:323-56.
Iwai, Y., et al., "Involvement of PD-L1 on tumor cells in the escape from host immune system and tumor immunotherapy by PD-L1 blockade," Proc Natl Acad Sci USA, 2002. 99(19): p. 12293-7.
Janssen Clinical Trials "A Study of Safety, Pharmacokinetics, Pharmacodynamics of JNJ-61610588 in Participants With Advanced Cancer," U.S. National Library of Medicine, ClinicalTrials.gov; (https://clinicaltrials.gov) 2017. 9 pages.
Jarvinen LZ, et al. "CD154 on the surface of CD4+CD25+ regulatory T cells contributes to skin transplant tolerance," Transplantation. Nov. 15, 2003; 76(9):1375-9.
Jeisy-Scott V, et al. "Increased MDSC accumulation and Th2 biased response to influenza A virus infection in the absence of TLR7 in mice," PLoS One. 2011; 6(9):e25242.
Jennings-White, C. et al. (1982). "Synthesis of ketomethylene analogs of dipeptides," Tetrahedron Letters 1982 23(25), 2533-2534.
Jones E, et al. "Depletion of CD25+ regulatory cells results in suppression of melanoma growth and induction of autoreactivity in mice," Cancer Immun. Feb. 22, 2002; 2:1.
Jones PT, et al. "Replacing the complementarity-determining regions in a human antibody with those from a mouse," Nature. May 29-Jun. 4, 1986; 321(6069):522-5.
Jones TD, et al. "The development of a modified human IFN-alpha2b linked to the Fc portion of human IgG1 as a novel potential therapeutic for the treatment of hepatitis C virus infection," J Interferon Cytokine Res. Sep. 2004; 24(9):560-72.
Kaehler, K. C., et al., "Update on immunologic therapy with anti-CTLA-4 antibodies in melanoma: identification of clinical and biological response patterns, immune-related adverse events, and their management," Semin Oncol, 2010. 37(5): p. 485-98.
Kang SM, et al. "Transactivation by AP-1 is a molecular target of T cell clonal anergy," Science. Aug. 21, 1992; 257(5073):1134-8.
Karpovsky B, et al. "Production of target-specific effector cells using hetero-cross-linked aggregates containing anti-target cell and anti-Fc gamma receptor antibodies," J Exp Med. Dec. 1, 1984; 160(6):1686-701.

(56) References Cited

OTHER PUBLICATIONS

Kashmiri SV, et al. "SDR grafting—a new approach to antibody humanization," Methods. May 2005; 36(1):25-34.
Kaufman RJ, et al. "Translational efficiency of polycistronic mRNAs and their utilization to express heterologous genes in mammalian cells," EMBO J. Jan. 1987; 6(1):187-93.
Kay MA, et al. "Transient immunomodulation with anti-CD40 ligand antibody and CTLA4Ig enhances persistence and secondary adenovirus-mediated gene transfer into mouse liver," Proc Natl Acad Sci U S A. Apr. 29, 1997; 94(9):4686-91.
Keinänen K, et al. "Biosynthetic lipid-tagging of antibodies," FEBS Lett. Jun. 6, 1994; 346(1):123-6.
Keir ME, et al. "PD-1 and its ligands in tolerance and immunity," Annu Rev Immunol. 2008; 26:677-704.
Keir ME, et al. "PD-1 regulates self-reactive CD8+ T cell responses to antigen in lymph nodes and tissues," mmunol. Oct. 15, 2007; 179(8):5064-70.
Kessel M, et al. "Murine developmental control genes," Science. Jul. 27, 1990; 249(4967):374-9.
Killion JJ, et al. "Systemic targeting of liposome-encapsulated immunomodulators to macrophages for treatment of cancer metastasis," Immunomethods. Jun. 1994; 4(3):273-9.
Kimmel AR, et al. "Preparation of cDNA and the generation of cDNA libraries: overview," Methods Enzymol. 1987; 152:307-16.
Kipriyanov SM, et al. "Recombinant single-chain Fv fragments carrying C-terminal cysteine residues: production of bivalent and biotinylated miniantibodies," Mol Immunol. Oct. 1994; 31(14):1047-58.
Kipriyanov SM, et al. "Single-chain antibody streptavidin fusions: tetrameric bifunctional scFv-complexes with biotin binding activity and enhanced affinity to antigen," Hum Antibodies Hybridomas. 1995; 6(3):93-101.
Kiss I, et al. "Structure of the gene for cartilage matrix protein, a modular protein of the extracellular matrix. Exon/intron organization, unusual splice sites, and relation to alpha chains of beta 2 integrins, von Willebrand factor, complement factors B and C2, and epidermal growth factor," J Biol Chem. May 15, 1989; 264(14):8126-34.
Klinken SP, et al. "Evolution of B cell lineage lymphomas in mice with a retrovirus-induced immunodeficiency syndrome, MAIDS," J Immunol. Feb. 15, 1988; 140(4):1123-31.
Kohl S, et al. "Human antibody-dependent cellular cytotoxicity and natural killer cytotoxicity to herpes simplex virus-infected autologous and allogeneic cells," Immunology. Jan. 1983; 48(1):187-93.
Köhler G, et al. "Continuous cultures of fused cells secreting antibody of predefined specificity," Nature. Aug. 7, 1975; 256(5517):495-7.
Kolaskar AS, et al. "A semi-empirical method for prediction of antigenic determinants on protein antigens," FEBS Lett. Dec. 10, 1990; 276(1-2):172-4.
Kostelny SA, et al. "Formation of a bispecific antibody by the use of leucine zippers," J Immunol. Mar. 1, 1992; 148(5):1547-53.
Kozbor D, et al. "Specific immunoglobulin production and enhanced tumorigenicity following ascites growth of human hybridomas," J Immunol Methods. Jul. 16, 1985; 81(1):31-42.
Kozbor D, et al. "The production of monoclonal antibodies from human lymphocytes," Immunol Today. Mar. 1983; 4(3):72-9.
Krishnamurthy S, et al. "Molecular and biologic markers of premalignant lesions of human breast," Adv Anat Pathol. May 2002; 9(3):185-97.
Krolick KA, et al. "Selective killing of normal or neoplastic B cells by antibodies coupled to the A chain of ricin," Proc Natl Acad Sci U S A. Sep. 1980; 77(9):5419-23.
Kroll DJ, et al. "A multifunctional prokaryotic protein expression system: overproduction, affinity purification, and selective detection," DNA Cell Biol. Jun. 1993; 12(5):441-53.
Krutzik, S. R., et al., "TLR activation triggers the rapid differentiation of monocytes into macrophages and dendritic cells," Nat Med, 2005. 11(6): p. 653-60.
Kryczek, I., et al., "B7-H4 expression identifies a novel suppressive macrophage population in human ovarian carcinoma," J Exp Med, 2006. 203(4): p. 871-81.
Kryczek, I., et al., "Cutting edge: induction of B7-H4 on APCs through IL-10: novel suppressive mode for regulatory T cells," J Immunol, 2006. 177(1): p. 40-4.
Kurjan J, et al. "Structure of a yeast pheromone gene (MF alpha): a putative alpha-factor precursor contains four tandem copies of mature alpha-factor," Cell. Oct. 1982; 30(3):933-43.
Kuroiwa Y, et al. "Cloned transchromosomic calves producing human immunoglobulin," Nat Biotechnol. Sep. 2002; 20(9):889-94.
Kwoh DY, et al. "Transcription-based amplification system and detection of amplified human immunodeficiency virus type 1 with a bead-based sandwich hybridization format," Proc Natl Acad Sci U S A. Feb. 1989; 86(4):1173-7.
Labrijn AF, et al. "Efficient generation of stable bispecific IgG1 by controlled Fab-arm exchange," Proc Natl Acad Sci U S A. Mar. 26, 2013; 110(13):5145-50.
LaFace D, et al. "Meeting report: regulatory myeloid cells," Int Immunopharmacol. Jul. 2011; 11(7):780-2.
Lakso M, et al. "Targeted oncogene activation by site-specific recombination in transgenic mice," Proc Natl Acad Sci U S A. Jul. 15, 1992; 89(14):6232-6.
Lam KS, et al. "A new type of synthetic peptide library for identifying ligand-binding activity," Nature. Nov. 7, 1991; 354(6348):82-4.
Lam KS. "Application of combinatorial library methods in cancer research and drug discovery," Anticancer Drug Des. Apr. 1997; 12(3):145-67. [Abstract Only].
Landegren U, et al. "A ligase-mediated gene detection technique," Science. Aug. 26, 1988; 241(4869):1077-80.
Landt O, et al. "A general method for rapid site-directed mutagenesis using the polymerase chain reaction," Gene. Nov. 30, 1990; 96(1):125-8.
Latchman Y, et al. "PD-L2 is a second ligand for PD-1 and inhibits T cell activation," Nat Immunol. Mar. 2001; 2(3):261-8.
Latchman YE, et al. "PD-L1-deficient mice show that PD-L1 on T cells, antigen-presenting cells, and host tissues negatively regulates T cells," Proc Natl Acad Sci U S A. Jul. 20, 2004; 101(29):10691-6.
Lathe R. "Synthetic oligonucleotide probes deduced from amino acid sequence data. Theoretical and practical considerations," J Mol Biol. May 5, 1985; 183(1):1-12.
Laubach VE, et al. "Mice lacking inducible nitric oxide synthase are not resistant to lipopolysaccharide-induced death," Proc Natl Acad Sci U S A. Nov. 7, 1995; 92(23):10688-92.
Lázár-Molnár E, et al. "Crystal structure of the complex between programmed death-1 (PD-1) and its ligand PD-L2," Proc Natl Acad Sci U S A. Jul. 29, 2008; 105(30):10483-8.
Le Borgne, M., et al., "Dendritic cells rapidly recruited into epithelial tissues via CCR6/CCL20 are responsible for CD8+ T cell crosspriming in vivo," Immunity, 2006. 24(2): p. 191-201.
Le Mercier I, et al. "Beyond CTLA-4 and PD-1, the Generation Z of Negative Checkpoint Regulators," Front Immunol. Aug. 21, 2015; 6:418.
Lederman, Seth, et al. "A single amino acid substitution in a common African allele of the CD4 molecule ablates binding of the monoclonal antibody, OKT4." Molecular immunology 28.11 (1991): 1171-1181.
Lee et al., "Increased vaccine-specific T cell frequency after peptide-based vaccination correlates with increased susceptibility to in vitro stimulation but does not lead to tumor regression." The Journal of Immunology 163.11 (1999): 6292-6300.
Lemaitre M, et al." Specific antiviral activity of a poly(L-lysine)-conjugated oligodeoxyribonucleotide sequence complementary to vesicular stomatitis virus N protein mRNA initiation site," Proc Natl Acad Sci U S A. Feb. 1987; 84(3):648-52.
Leng et al., "Potential roles of IL-9 in the pathogenesis of systemic lupus erythematosus", American Journal of Clinical and Experimental Immunology 2012; I(I):28-32.
León B, et al. "Monocyte-derived dendritic cells formed at the infection site control the induction of protective T helper 1 responses against Leishmania," Immunity. Apr. 2007; 26(4):519-31.

(56) References Cited

OTHER PUBLICATIONS

León B, et al. "Monocyte-derived dendritic cells in innate and adaptive immunity," Immunol Cell Biol. May-Jun. 2008; 86(4):320-4.
Lerner EA. "How to make a hybridoma," Yale J Biol Med. Sep.-Oct. 1981; 54(5):387-402.
Letsinger RL, et al. "Cholesteryl-conjugated oligonucleotides: synthesis, properties, and activity as inhibitors of replication of human immunodeficiency virus in cell culture," Proc Natl Acad Sci U S A. Sep. 1989; 86(17):6553-6.
Li CH, et al. "beta-Endorphin omission analogs: dissociation of immunoreactivity from other biological activities," Proc Natl Acad Sci U S A. Jun. 1980; 77(6):3211-4.
Li F, et al. "Inhibitory Fcγ receptor is required for the maintenance of tolerance through distinct mechanisms," J Immunol. Apr. 1, 2014; 192(7):3021-8.
Li W, et al. "Immunotherapy of murine retrovirus-induced acquired immunodeficiency by CD4 T regulatory cell depletion and PD-1 blockade," J Virol. Dec. 2011; 85(24):13342-53.
Li W, et al. "The role of CD4 T cells in the pathogenesis of murine AIDS," J Virol. Jun. 2006; 80(12):5777-89.
Lin DY, et al. "The PD-1/PD-L1 complex resembles the antigen-binding Fv domains of antibodies and T cell receptors," Proc Natl Acad Sci U S A. Feb. 26, 2008; 105(8):3011-6.
Lines JL, et al. "VISTA is a novel broad-spectrum negative checkpoint regulator for cancer immunotherapy," Cancer Immunol Res. Jun. 2014; 2(6):510-7.
Lines JL, et al. "VISTA is an immune checkpoint molecule for human T cells," Cancer Res. Apr. 1, 2014; 74(7):1924-32.
Liu AY, et al. "Chimeric mouse-human IgG1 antibody that can mediate lysis of cancer cells," Proc Natl Acad Sci U S A. May 1987; 84(10):3439-43.
Liu J, et al. "Immune-checkpoint proteins VISTA and PD-1 nonredundantly regulate murine T-cell responses," Proc Natl Acad Sci U S A. May 26, 2015; 112(21):6682-7.
Liu MA, et al. "Heteroantibody duplexes target cells for lysis by cytotoxic T lymphocytes," Proc Natl Acad Sci U S A. Dec. 1985; 82(24):8648-52.
Lobley A, et al. "pGenTHREADER and pDomTHREADER: new methods for improved protein fold recognition and superfamily discrimination," Bioinformatics. Jul. 15, 2009; 25(14):1761-7.
Lonberg N, et al. "Antigen-specific human antibodies from mice comprising four distinct genetic modifications," Nature. Apr. 28, 1994; 368(6474):856-9.
Lonberg N, et al. "Human antibodies from transgenic mice," Int Rev Immunol. 1995; 13(1):65-93.
Lopez-Pedrera et al., "Accelerated atherosclerosis in systemic lupus erythematosus: role of proinflammatory cytokines and therapeutic approaches", Journal of Biomedicine & Biotechnology, 2010 Article ID 607084.
Lorain S, et al. "Transient immunomodulation allows repeated injections of AAV1 and correction of muscular dystrophy in multiple muscles," Mol Ther. Mar. 2008; 16(3):541-7.
Luckow VA, et al. "High level expression of nonfused foreign genes with Autographa californica nuclear polyhedrosis virus expression vectors," Virology. May 1989; 170(1):31-9.
Lutz MB, et al. "An advanced culture method for generating large quantities of highly pure dendritic cells from mouse bone marrow," J Immunol Methods. Feb. 1, 1999; 223(1):77-92.
Macatangay BJ, et al. "MDSC: a new player in HIV immunopathogenesis," AIDS. Jul. 31, 2012; 26(12):1567-9.
Maher LJ. "DNA triple-helix formation: an approach to artificial gene repressors?" Bioessays. Dec. 1992; 14(12):807-15.
Mahnke K, et al. "The dendritic cell receptor for endocytosis, DEC-205, can recycle and enhance antigen presentation via major histocompatibility complex class II-positive lysosomal compartments," J Cell Biol. Oct. 30, 2000; 151(3):673-84.
Malashkevich VN, et al. "The crystal structure of a five-stranded coiled coil in COMP: a prototype ion channel?" Science. Nov. 1, 1996; 274(5288):761-5.
Marigo, I., et al. "Tumor-induced tolerance and immune suppression by myeloid derived suppressor cells," Immunol Rev, 2008. 222: p. 162-79.
Martinez T, et al. "Disulfide connectivity of human immunoglobulin G2 structural isoforms," Biochemistry. Jul. 15, 2008; 47(28):7496-508.
McCafferty J, et al. "Phage antibodies: filamentous phage displaying antibody variable domains," Nature. Dec. 6, 1990; 348(6301):552-4.
McConnell HM, et al. "The cytosensor microphysiometer: biological applications of silicon technology," Science. Sep. 25, 1992; 257(5078):1906-12.
McHugh RS, et al. "CD4(+)CD25(+) immunoregulatory T cells: gene expression analysis reveals a functional role for the glucocorticoid-induced TNF receptor," Immunity. Feb. 2002; 16(2):311-23.
McIvor RS, et al. "Isolation and characterization of a variant dihydrofolate reductase cDNA from methotrexate-resistant murine L5178Y cells," Nucleic Acids Res. Dec. 11, 1990; 18(23):7025-32.
Medina D. "The preneoplastic phenotype in murine mammary tumorigenesis," J Mammary Gland Biol Neoplasia. Oct. 2000; 5(4):393-407.
Melief CJ. "Cancer immunotherapy by dendritic cells," Immunity. Sep. 19, 2008; 29(3):372-83.
Mencacci A, et al. "CD80+Gr-1+ myeloid cells inhibit development of antifungal Th1 immunity in mice with candidiasis," J Immunol. Sep. 15, 2002; 169(6):3180-90.
Merrifield B. "Concept and early development of solid-phase peptide synthesis," Methods Enzymol. 1997; 289:3-13.
Mezo AR, et al. "Atrial natriuretic peptide-Fc, ANP-Fc, fusion proteins: semisynthesis, in vitro activity and pharmacokinetics in rats," Bioconjug Chem. Mar. 21, 2012; 23(3):518-26.
Milstein C, et al. "Hybrid hybridomas and their use in immunohistochemistry," Nature. Oct. 6-12, 1983; 305(5934):537-40.
Mingozzi F, et al. "Immune responses to AAV vectors: overcoming barriers to successful gene therapy," Blood. Jul. 4, 2013; 122(1):23-36.
Monteiro RC, et al. "Molecular heterogeneity of Fc alpha receptors detected by receptor-specific monoclonal antibodies," J Immunol. Mar. 15, 1992; 148(6):1764-70.
Moore GJ. "Designing peptide mimetics," Trends Pharmacol Sci. Apr. 1994; 15(4):124-9.
Morrison SL, et al. "Chimeric human antibody molecules: mouse antigen-binding domains with human constant region domains," Proc Natl Acad Sci U S A. Nov. 1984; 81(21):6851-5.
Morrison SL. "Transfectomas provide novel chimeric antibodies," Science. Sep. 20, 1985; 229(4719):1202-7.
Muller PY, et al. "Safety assessment and dose selection for first-in-human clinical trials with immunomodulatory monoclonal antibodies," Clin Pharmacol Ther. Mar. 2009; 85(3):247-58.
Nakano H, et al. "Blood-derived inflammatory dendritic cells in lymph nodes stimulate acute T helper type 1 immune responses," Nat Immunol. Apr. 2009; 10(4):394-402.
Nalbandian A, et al. "Interleukin-17 and systemic lupus erythematosus: current concepts," Clin Exp Immunol. Aug. 2009; 157(2):209-15.
Nathwani AC, et al. "Adenovirus-associated virus vector-mediated gene transfer in hemophilia B," N Engl J Med. Dec. 22, 2011; 365(25):2357-65.
NCBI Accession No. AAH89443 [gi:59807841] with Revision History—Feb. 16, 2005-Jun. 6, 2006.
NCBI Accession No. AK004116 [gi:12835174] with Revision History—Feb. 8, 2001-Sep. 2, 2005.
NCBI Accession No. BC089443 [gi:59807840] with Revision History—Feb. 15, 2005-Jun. 6, 2006.
NCBI Accession No. NM.sub.—022153 [gi:62339431] with Revision History—Apr. 7, 2005-Jun. 26, 2007.
NCBI Accession No. NM.sub.—026125 [gi:13385631] with Revision History—Mar. 20, 2001-May 7, 2006. 142365660 which replaced 13385631 is provided.
NCBI Accession No. NM.sub.—028732 [gi:31980769] with Revision History—Mar. 20, 2001-May 7, 2006. 143249860 which replaced 31980769 is provided.

(56) References Cited

OTHER PUBLICATIONS

NCBI Accession No. NM.sub.—138530 [gi:51491892] with Revision History—Apr. 4, 2002-Nov. 18, 2006.
NCBI Accession No. NP.sub.—071436 [gi:62339432] with Revision History—Apr. 7, 2005-Aug. 13, 2006.
NCBI Accession No. NP.sub.—080401 [gi:13385632] with Revision History—Mar. 20, 2001-May 7, 2006.
NCBI Accession No. XM.sub.—233720 [gi:109475938] with Revision History—Jan. 13, 2003-Jun. 22, 2006.
Nesbeth YC, et al. "CD4+ T cells elicit host immune responses to MHC class II-negative ovarian cancer through CCL5 secretion and CD40-mediated licensing of dendritic cells," J Immunol. May 15, 2010; 184(10):5654-62.
Neuberger MS, et al. "A hapten-specific chimaeric IgE antibody with human physiological effector function," Nature. Mar. 21-27, 1985; 314(6008):268-70.
Neuberger MS, et al. "Recombinant antibodies possessing novel effector functions," Nature. Dec. 13-19, 1984; 312(5995):604-8.
Nielsen MB, et al. "Melanoma vaccines: the paradox of T cell activation without clinical response," Cancer Chemother Pharmacol. 2000; 46 Suppl:S62-6.
Niklinski J, et al. "Molecular genetic abnormalities in premalignant lung lesions: biological and clinical implications," Eur J Cancer Prev. Jun. 2001; 10(3):213-26.
Nishikawa H, et al. "Regulatory T cells in tumor immunity," Int J Cancer. Aug. 15, 2010; 127(4):759-67.
Nishimura H, et al. "Autoimmune dilated cardiomyopathy in PD-1 receptor-deficient mice," Science. Jan. 12, 2001; 291(5502):319-22.
Nishimura H, et al. "Development of lupus-like autoimmune diseases by disruption of the PD-1 gene encoding an ITIM motif-carrying immunoreceptor," Immunity. Aug. 1999; 11(2):141-51.
Nomi, T. et al., Clinical significance and therapeutic potential of the programmed death-1 ligand/programmed death-1 pathway in human pancreatic cancer. Clin. Cancer Res. 2007, vol. 13, pp. 2152-2157.
Norde, W.J. et al., "Coinhibitory molecules in hematologic malignancies: targets for therapeutic intervention", Blood, Jul. 2012, vol. 120, No. 4, pp. 728-736.
Nowak EC, et al. "Immunoregulatory functions of VISTA," Immunol Rev. Mar. 2017; 276(1):66-79.
Nygren H. "Conjugation of horseradish peroxidase to Fab fragments with different homobifunctional and heterobifunctional cross-linking reagents. A comparative study," J Histochem Cytochem. May 1982; 30(5):407-12.
O'Gorman S, et al. "Recombinase-mediated gene activation and site-specific integration in mammalian cells," Science. Mar. 15, 1991; 251(4999):1351-5.
Ohtsuka E, et al. "An alternative approach to deoxyoligonucleotides as hybridization probes by insertion of deoxyinosine at ambiguous codon positions," J Biol Chem. Mar. 10, 1985; 260(5):2605-8.
Okazaki T, et al. "The PD-1-PD-L pathway in immunological tolerance," Trends Immunol. Apr. 2006; 27(4):195-201.
Orlandi R, et al. "Cloning immunoglobulin variable domains for expression by the polymerase chain reaction," Proc Natl Acad Sci U S A. May 1989; 86(10):3833-7.
Ortler S, et al. "B7-H1 restricts neuroantigen-specific T cell responses and confines inflammatory CNS damage: implications for the lesion pathogenesis of multiple sclerosis," Eur J Immunol. Jun. 2008; 38(6):1734-44.
Ostergaard S, et al. "Peptomers: a versatile approach for the preparation of diverse combinatorial peptidomimetic bead libraries," Mol Divers. 1997; 3(1):17-27.
Ostrand-Rosenberg S, et al. "Myeloid-derived suppressor cells: linking inflammation and cancer," J Immunol. Apr. 15, 2009; 182(8):4499-506.
Ostrand-Rosenberg S. "Myeloid-derived suppressor cells: more mechanisms for inhibiting antitumor immunity," Cancer Immunol Immunother. Oct. 2010; 59(10):1593-600.
Ostresh JM, et al. "Generation and use of nonsupport-bound peptide and peptidomimetic combinatorial libraries," Methods Enzymol. 1996; 267:220-34.
Ottavi A, et al. "An improved method to obtain a single recombinant vasoactive intestinal peptide (VIP) analog," Biochimie. Apr. 1998; 80(4):289-93.
Owais M, et al. "Chloroquine encapsulated in malaria-infected erythrocyte-specific antibody-bearing liposomes effectively controls chloroquine-resistant Plasmodium berghei infections in mice," Antimicrob Agents Chemother. Jan. 1995; 39(1):180-4.
Oyarzun P, et al. "A bioinformatics tool for epitope-based vaccine design that accounts for human ethnic diversity: Application to emerging infectious diseases," Vaccine. 2015; 33(10):1267-73.
Ozkaynak, E., et al. "Programmed death-1 targeting can promote al lograft survival," J Immunol 2002. 169: 6546-6553.
Pain D, et al. "Preparation of protein A-peroxidase monoconjugate using a heterobifunctional reagent, and its use in enzyme immunoassays," J Immunol Methods. 1981; 40(2):219-30.
Parisi, S., et al. "A regulatory loop involving Diesl and miR-125a controls BMP4 signaling in mouse embryonic stem cells," FASEB J 2012. 26: 3957-3968.
Paulsson M, et al. "Purification and structural characterization of a cartilage matrix protein," Biochem J. Aug. 1, 1981; 197(2):367-75.
Payne G. "Progress in immunoconjugate cancer therapeutics," Cancer Cell. Mar. 2003; 3(3):207-12.
Peranzoni E, et al. "Myeloid-derived suppressor cell heterogeneity and subset definition," Curr Opin Immunol. Apr. 2010; 22(2):238-44.
Perry-O'Keefe H, et al. "Peptide nucleic acid pre-gel hybridization: an alternative to southern hybridization," Proc Natl Acad Sci U S A. Dec. 10, 1996; 93(25):14670-5.
Piccirillo CA, et al. "Naturally-occurring CD4+CD25+ immunoregulatory T cells: central players in the arena of peripheral tolerance," Semin Immunol. Apr. 2004; 16(2):81-8.
Piccotti JR, et al. "T-cell-dependent antibody response: assay development in cynomolgus monkeys," J Immunotoxicol. Oct. 1, 2005; 2(4):191-6.
Picha, Kristen M. et al., "Protein Engineering Strategies for Sustained Glucagon-Like Peptide-1 Receptor-Dependent Control of Glucose Homeostasis", Diabetes, 2008. vol. 57, pp. 1926-1934.
Pilat N, et al. "Costimulatory pathways in transplantation," Semin Immunol. Aug. 2011; 23(4):293-303.
Pinkert CA, et al. "An albumin enhancer located 10 kb upstream functions along with its promoter to direct efficient, liver-specific expression in transgenic mice," Genes Dev. May 1987; 1(3):268-76.
Platt et al., "Gene hunting in the genomic era: approaches to diagnostic dilemmas in patients with primary immunodeficiencies," J Allergy Clin Immunol 2014, 134: 262-268.
Podojil JR, et al. "B7-H4Ig inhibits mouse and human T-cell function and treats EAE via IL-10/Treg-dependent mechanisms," J Autoimmun. Aug. 2013; 44:71-81.
Polyak SW, et al. "Introduction of spacer peptides N-terminal to a cleavage recognition motif in recombinant fusion proteins can improve site-specific cleavage," Protein Eng. Jun. 1997; 10(6):615-9.
Pontén J. "Cell biology of precancer," Eur J Cancer. Oct. 2001; 37 Suppl 8:S97-113.
Powell et al. "Peptide stability in drug development. II. Effect of single amino acid substitution and glycosylation on peptide reactivity in human serum," Pharm Res. Sep. 1993; 10(9):1268-73.
Prasad, D. V., et al. "B7S1, a novel B7 family member that negatively regulates T cell activation," Immunity, 2003. 18(6): p. 863-73.
Prokunina, L., A regulatory polymorphism in PDCD1 is associated with susceptibility to systemic lupus erythematosus in humans. Nat Genet 2002. 32: 666-669.
Qin A, et al. "Expansion of monocytic myeloid-derived suppressor cells dampens T cell function in HIV-1-seropositive individuals," J Virol. Feb. 2013; 87(3):1477-90.
Qin W, et al. "Fusion protein of CDR mimetic peptide with Fc inhibit TNF-alpha induced cytotoxicity," Mol Immunol. Feb. 2006; 43(6):660-6.
Qu, C., et al., Role of CCR8 and other chemokine pathways in the migration of monocyte-derived dendritic cells to lymph nodes. J Exp Med, 2004. 200(10): p. 1231-41.

(56) References Cited

OTHER PUBLICATIONS

Queen C, et al. "Immunoglobulin gene transcription is activated by downstream sequence elements," Cell. Jul. 1983; 33(3):741-8.
Queen, et al. "A humanized antibody that binds to the interleukin 2 receptor," Proc Natl Acad Sci U S A. Dec. 1989; 86(24):10029-33.
Rabinovich, G. A., D. Gabrilovich, and E. M. Sotomayor, Immunosuppressive strategies that are mediated by tumor cells. Annu Rev Immunol, 2007. 25: p. 267-96.
Rai BK, et al. "MMM: a sequence-to-structure alignment protocol," Bioinformatics. Nov. 1, 2006; 22(21):2691-2.
Rain J.C. et al. (2001) The protein-protein interaction map of Helicobacter pylori. Nature 409: 211-15.
Ranade VV. "Drug delivery systems. 1. site-specific drug delivery using liposomes as carriers," J Clin Pharmacol. Aug. 1989; 29(8):685-94.
Randolph, G. J., et al. "Differentiation of phagocytic monocytes into lymph node dendritic cells in vivo," Immunity, 1999. 11(6): p. 753-61.
Rathore R, et al. "Current State of Tolerance: The Holy Grail," Arch Clin Nephrol 3(2): 057-063.
Rattan SI, et al. "Protein synthesis, posttranslational modifications, and aging," Ann N Y Acad Sci. Nov. 21, 1992; 663:48-62.
Ravetch JV, et al. "IgG Fc receptors," Annu Rev Immunol. 2001; 19:275-90.
Rice RH, et al. "Localization of hair shaft protein VSIG8 in the hair follicle, nail unit, and oral cavity," J Invest Dermatol. Sep. 2011; 131(9):1936-8.
Rizo J, et al. "Constrained peptides: models of bioactive peptides and protein substructures," Annu Rev Biochem. 1992; 61:387-418.
Robben, P. M., et al., Recruitment of Gr-1+ monocytes is essential for control of acute toxoplasmosis. J Exp Med, 2005. 201(11): p. 1761-9.
Roberge JY, et al. "A strategy for a convergent synthesis of N-linked glycopeptides on a solid support," Science. Jul. 14, 1995; 269(5221):202-4.
Robertson JM, Jensen PE, Evavold BD. DO11.10 and OT-II T Cells Recognize a C-Terminal Ovalbumin 323-339 Epitope. The Journal of Immunology. 2000; 164(9):4706-12. doi: 10.4049/jimmunol.164.9.4706.
Roda G, Jharap B, Neeraj N, Colombel J-F. Loss of Response to Anti-TNFs: Definition, Epidemiology, and Ma nagement. Clin Trans Gastroenterol. 2016; 7:el35. doi: 10.1038/ctg.2015.63.
Rose TM, et al. "Consensus-degenerate hybrid oligonucleotide primers for amplification of distantly related sequences," Nucleic Acids Res. Apr. 1, 1998; 26(7):1628-35.
Rossolini GM, et al. "Use of deoxyinosine-containing primers vs degenerate primers for polymerase chain reaction based on ambiguous sequence information," Mol Cell Probes. Apr. 1994; 8(2):91-8.
Rowe WP, et al. "Plaque assay techniques for murine leukemia viruses," Virology. Dec. 1970; 42(4):1136-9.
Saito G, et al. "Drug delivery strategy utilizing conjugation via reversible disulfide linkages: role and site of cellular reducing activities," Adv Drug Deliv Rev. Feb. 10, 2003; 55(2):199-215.
Sakaguchi S, et al. "Immunologic self-tolerance maintained by activated T cells expressing IL-2 receptor alpha-chains (CD25). Breakdown of a single mechanism of self-tolerance causes various autoimmune diseases," J Immunol. Aug. 1, 1995; 155(3):1151-64.
Sakaguchi S, et al. "Immunologic tolerance maintained by CD25+ CD4+ regulatory T cells: their common role in controlling autoimmunity, tumor immunity, and transplantation tolerance," Immunol Rev. Aug. 2001; 182:18-32.
Sakaguchi S, et al. "Organ-specific autoimmune diseases induced in mice by elimination of T cell subset. I. Evidence for the active participation of T cells in natural self-tolerance; deficit of a T cell subset as a possible cause of autoimmune disease," J Exp Med. Jan. 1, 1985; 161(1):72-87.
Sakaguchi S, et al. "Regulatory T cells: key controllers of immunologic self-tolerance," Cell. May 26, 2000; 101(5):455-8.
Salama AD, et al. "Critical role of the programmed death-1 (PD-1) pathway in regulation of experimental autoimmune encephalomyelitis," J Exp Med. Jul. 7, 2003; 198(1):71-8.
Sasikumar P, et al. "Abstact B006: Functional antagonism of VISG8-mediated immune suppression by oral VISTA agents, Abstacts" AACR-NCI-EORTC International Conference: Molecular Targets and Cancer Therapeutics; Oct. 2017. 5 pages.
Scaria A, et al. "Antibody to CD40 ligand inhibits both humoral and cellular immune responses to adenoviral vectors and facilitates repeated administration to mouse airway," Gene Ther. Jun. 1997; 4(6):611-7.
Scarlett, U. K., et al., In situ stimulation of CD40 and Toll-like receptor 3 transforms ovarian cancerinfiltrating dendritic cells from immunosuppressive to immunostimulatory cells. Cancer Res, 2009. 69(18): p. 7329-37.
Schreier et al. "Targeting of liposomes to cells expressing CD4 using glycosylphosphatidylinositol-anchored gp120. Influence of liposome composition on intracellular trafficking," J Biol Chem. Mar. 25, 1994; 269(12):9090-8.
Schubbert R, et al. "Foreign (M13) DNA ingested by mice reaches peripheral leukocytes, spleen, and liver via the intestinal wall mucosa and can be covalently linked to mouse DNA," Proc Natl Acad Sci U S A. Feb. 4, 1997; 94(3):961-6.
Schultz LD, et al. "Expression and secretion in yeast of a 400-kDa envelope glycoprotein derived from Epstein-Barr virus," Gene. 1987; 54(1):113-23.
Scott JK, et al. "Searching for peptide ligands withan epitope library," Science. Jul. 27, 1990; 249(4967):386-90.
Sedy, J. R., "B and T lymphocyte attenuator regulates T cell activation through interaction with herpesvirus entry mediator," Nat Immunol 2005. 6: 90-98.
Seed B. "An LFA-3 cDNA encodes a phospholipid-linked membrane protein homologous to its receptor CD2," Nature. Oct. 29-Nov. 4, 1987; 329(6142):840-2.
Seifter S, et al. "Analysis for protein modifications and nonprotein cofactors," Methods Enzymol. 1990; 182:626-46.
Senter PD, et al. "Selective activation of anticancer prodrugs by monoclonal antibody-enzyme conjugates," Adv Drug Deliv Rev. Dec. 31, 2001; 53(3):247-64.
Sequence Alignment, 2010, 1 page. U.S. Pat. No. 8,236,304 (U.S. Appl. No. 11/912,397) dated May 14, 2010.
Sequence alignment, 2014, 2 pages. U.S. Pat. No. 9,631,018 (U.S. Appl. No. 13/637,381) dated Oct. 29, 2014.
Sequence alignment, 2015, 3 pages. U.S. Appl. No. 13/925,034 dated Oct. 16, 2015.
Serbina, N. V., et al., TNF/iNOS-producing dendritic cells mediate innate immune defense against bacterial infection. Immunity, 2003. 19(1): p. 59-70.
Seregin SS, et al. "Improving adenovirus based gene transfer: strategies to accomplish immune evasion," Viruses. Sep. 2010; 2(9):2013-36.
Sharma, M. D., et al., "Plasmacytoid dendritic cells from mouse tumor-draining lymph nodes directly activate mature Tregs via indoleamine 2,3-dioxygenase," J Clin Invest, 2007. 117(9): p. 2570-82.
Sharma, P. et al., "Novel cancer immunotherapy agents with survival benefit: recent successes and next steps", Nature Reviews Cancer, 2011, vol. 11, pp. 805-812.
Sharpe AH, et al. "The B7-CD28 superfamily," Nat Rev Immunol. Feb. 2002; 2(2):116-26.
Shaw DR, et al. "Mouse/human chimeric antibodies to a tumor-associated antigen: biologic activity of the four human IgG subclasses," J Natl Cancer Inst. Dec. 7, 1988; 80(19):1553-9.
Sheehan, K, et al. "The relationship between cyclooxygenase-2 expression and colorectal cancer," JAMA, 1999. 282: p. 1254-7.
Shevach EM. "Regulatory T cells in autoimmmunity," Annu Rev Immunol. 2000; 18:423-49.
Shevach, E. M., CD4+ CD25+ suppressor T cells: more questions than answers. Nat Rev Immunol, 2002. 2(6): p. 389-400.
Shields RL, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001; 276(9):6591-604.

(56) References Cited

OTHER PUBLICATIONS

Shields RL, et al. "Lack of fucose on human IgG1 N-linked oligosaccharide improves binding to human Fcgamma RIII and antibody-dependent cellular toxicity," J Biol Chem. Jul. 26, 2002; 277(30):26733-40.
Shimizu J, et al. "Stimulation of CD25(+)CD4(+) regulatory T cells through GITR breaks immunological self-tolerance," Nat Immunol. Feb. 2002; 3(2):135-42.
Shortman, K. et al. "Steady-state and inflammatory dendritic-cell development," Nat Rev Immunol, 2007. 7(1): p. 19-30.
Shulman M, et al. "A better cell line for making hybridomas secreting specific antibodies," Nature. Nov. 16, 1978; 276(5685):269-70.
Sica GL, et al. "B7-H4, a molecule of the B7 family, negatively regulates T cell immunity," Immunity. Jun. 2003; 18(6):849-61.
Simard C, et al. " Studies of the susceptibility of nude, CD4 knockout, and SCID mutant mice to the disease induced by the murine AIDS defective virus," J Virol. Apr. 1997; 71(4):3013-22.
Sizemore DR, et al. "Attenuated Shigella as a DNA delivery vehicle for DNA-mediated immunization," Science. Oct. 13, 1995; 270(5234):299-302.
Skehel JJ, et al. "Coiled coils in both intracellular vesicle and viral membrane fusion," Cell. Dec. 23, 1998; 95(7):871-4.
Smith DB, et al. "Single-step purification of polypeptides expressed in *Escherichia coli* as fusions with glutathione S-transferase," Gene. Jul. 15, 1988; 67(1):31-40.
Smith GE, et al. "Production of human beta interferon in insect cells infected with a baculovirus expression vector," Mol Cell Biol. Dec. 1983; 3(12):2156-65.
Smith JH, et al. "Detection of *Mycobacterium tuberculosis* directly from sputum by using a prototype automated Q-beta replicase assay," J Clin Microbiol. Jun. 1997; 35(6):1477-83.
Smith JH, et al. "Performance of an automated Q-beta replicase amplification assay for *Mycobacterium tuberculosis* in a clinical trial," J Clin Microbiol. Jun. 1997; 35(6):1484-91.
Smith LJ, et al. "Human interleukin 4. The solution structure of a four-helix bundle protein," J Mol Biol. Apr. 20, 1992; 224(4):899-904.
Son YI, et al. "A novel bulk-culture method for generating mature dendritic cells from mouse bone marrow cells," J Immunol Methods. Apr. 1, 2002; 262(1-2):145-57.
Spatola AF, et al. "Structure-activity relationships of enkephalins containing serially replaced thiomethylene amide bond surrogates," Life Sci. Apr. 7, 1986; 38(14):1243-9.
Steinman, R. M. et al. "Tolerogenic dendritic cells," Annu Rev Immunol, 2003. 21: p. 685-711.
Stewart MJ, et al. "Gene transfer in vivo with DNA-liposome complexes: safety and acute toxicity in mice," Hum Gene Ther. Jun. 1992; 3(3):267-75.
Studier FW, et al. "Use of T7 RNA polymerase to direct expression of cloned genes," Methods Enzymol. 1990; 185:60-89.
Su AI, et al. "Large-scale analysis of the human and mouse transcriptomes," Proc Natl Acad Sci U S A. Apr. 2, 2002; 99(7):4465-70.
Suh, W. K., et al. "The B7 family member B7-H3 preferentially down-regulates T helper type 1-mediated immune responses," Nat Immunol 2003. 4: 899-906.
Sun LK, et al. "Chimeric antibody with human constant regions and mouse variable regions directed against carcinoma-associated antigen 17-1A," Proc Natl Acad Sci U S A. Jan. 1987; 84(1):214-8.
Sunderkotter, C., et al., "Subpopulations of mouse blood monocytes differ in maturation stage and inflammatory response," J Immunol, 2004. 172(7): p. 4410-7.
Tacke, F. et al. "Migratory fate and differentiation of blood monocyte subsets," Immunobiology, 2006. 211(6-8): p. 609-18.
Tafuri A, et al. "ICOS is essential for effective T-helper-cell responses," Nature. Jan. 4, 2001; 409(6816):105-9.
Takamatsu N, et al. "Expression of bacterial chloramphenicol acetyltransferase gene in tobacco plants mediated by TMV-RNA," EMBO J. Feb. 1987; 6(2):307-11.
Takamura S, et al. "Premature terminal exhaustion of Friend virus-specific effector CD8+ T cells by rapid induction of multiple inhibitory receptors," J Immunol. May 1, 2010; 184(9):4696-707.
Takeda S, et al. "Construction of chimaeric processed immunoglobulin genes containing mouse variable and human constant region sequences," Nature. Apr. 4-10, 1985; 314(6010):452-4.
Tarhini, A., E. Lo, and D. R. Minor, Releasing the brake on the immune system: ipilimumab in melanoma and other tumors. Cancer Biother Radiopharm, 2010. 25(6): p. 601-13.
Taylor LD, et al. "A transgenic mouse that expresses a diversity of human sequence heavy and light chain immunoglobulins," Nucleic Acids Res. Dec. 11, 1992; 20(23):6287-95.
Taylor LD, et al. "Human immunoglobulin transgenes undergo rearrangement, somatic mutation and class switching in mice that lack endogenous IgM," Int Immunol. Apr. 1994; 6(4):579-91.
Taylor WR. "The classification of amino acid conservation," J Theor Biol. Mar. 21, 1986; 119(2):205-18.
Teft WA, et al. "A molecular perspective of CTLA-4 function," Annu Rev Immunol. 2006; 24:65-97.
Terawaki, S., "Specific and high-affinity binding of tetramerized PD-LI extracellular domain to PD-I-expressing cells: possible application to enhance T cell function," Int Immunol 2007. 19: 881-890.
Thompson JA, et al. "A phase I trial of CD3/CD28-activated T cells (Xcellerated T cells) and interleukin-2 in patients with metastatic renal cell carcinoma," Clin Cancer Res. Sep. 1, 2003; 9(10 Pt 1):3562-70.
Thompson JD, et al. "Clustal W: improving the sensitivity of progressive multiple sequence alignment through sequence weighting, position-specific gap penalties and weight matrix choice," Nucleic Acids Res. Nov. 11, 1994; 22(22):4673-80.
Thorpe et al., "The Preparation And Cytotoxic Properties Of Antibody-Toxin Conjugates", Immunol. Rev., 62: 119-58 (1982).
Tivol EA, et al. "Loss of CTLA-4 leads to massive lymphoproliferation and fatal multiorgan tissue destruction, revealing a critical negative regulatory role of CTLA-4," Immunity. Nov. 1995; 3(5):541-7.
Tomizuka K, et al. "Double trans-chromosomic mice: maintenance of two individual human chromosome fragments containing Ig heavy and kappa loci and expression of fully human antibodies," Proc Natl Acad Sci U S A. Jan. 18, 2000; 97(2):722-7.
Tomlinson, et al. (1992) "The Repertoire of Human Germline VH Sequences Reveals about Fifty Groups of VH Segments with Different Hypervariable Loops" J. Mol. Biol. 227: 776-798.
Townsend SE, et al. "Tumor rejection after direct costimulation of CD8+ T cells by B7-transfected melanoma cells," Science. Jan. 15, 1993; 259(5093):368-70.
Trail PA, et al. "Monoclonal antibody drug immunoconjugates for targeted treatment of cancer," Cancer Immunol Immunother. May 2003; 52(5):328-37.
Transmembrane Region Prediction, "SACS MEMSAT2" 2018, 16 pages.
Traunecker A, et al. "Bispecific single chain molecules (Janusins) target cytotoxic lymphocytes on HIV infected cells," EMBO J. Dec. 1991; 10(12):3655-9.
Tuaillon N, et al." Human immunoglobulin heavy-chain minilocus recombination in transgenic mice: gene-segment use in mu and gamma transcripts," Proc Natl Acad Sci U S A. Apr. 15, 1993; 90(8):3720-4.
Tuaillon N, et al. "Biased utilization of DHQ52 and JH4 gene segments in a human Ig transgenic minilocus is independent of antigenic selection," J Immunol. Mar. 15, 1994; 152(6):2912-20.
Tuladhar et al., "Role of Co-stimulation in Leishmaniasis." Int J Biol Sci. 2011; 7(9):1382-90.
Tutt A, et al. "Trispecific F(ab')3 derivatives that use cooperative signaling via the TCR/CD3 complex and CD2 to activate and redirect resting cytotoxic T cells," J Immunol. Jul. 1, 1991; 147(1):60-9.
Umaña P, et al. "Engineered glycoforms of an antineuroblastoma IgG1 with optimized antibody-dependent cellular cytotoxic activity," Nat Biotechnol. Feb. 1999; 17(2):176-80.
Umezawa F, et al. "Liposome targeting to mouse brain: mannose as a recognition marker," Biochem Biophys Res Commun. Jun. 30, 1988; 153(3):1038-44.

(56) References Cited

OTHER PUBLICATIONS

Uy R, et al. "Posttranslational covalent modification of proteins," Science. Dec. 2, 1977; 198(4320):890-6.
Vaccaro C, et al. "Engineering the Fc region of immunoglobulin G to modulate in vivo antibody levels," Nature Biotechnology. 2005; 23(10):1283-8.
Van Elsas A, et al. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," J Exp Med. Aug. 2, 1999; 190(3):355-66.
Van Wauwe JP, et al. "OKT3: a monoclonal anti-human T lymphocyte antibody with potent mitogenic properties," The Journal of Immunology. 1980; 124(6):2708-13.
Velu V, et al. "Enhancing SIV-specific immunity in vivo by PD-1 blockade," Nature. Mar. 12, 2009; 458(7235):206-10.
Verhoeyen M, et al. "Reshaping human antibodies: grafting an antilysozyme activity," Science. Mar. 25, 1988; 239(4847):1534-6.
Via CS. "Advances in lupus stemming from the parent-into-FI model". Trends Immunol., Jun. 2010. 31(6):236-45).
Wada K, et al. "Codon usage tabulated from the GenBank genetic sequence data," Nucleic Acids Res. May 11, 1992; 20 Suppl:2111-8.
Wadia JS, et al. "Protein transduction technology," Curr Opin Biotechnol. Feb. 2002; 13(1):52-6.
Walch A, et al. "Microdissection of tissue sections: application to the molecular genetic characterisation of premalignant lesions," Pathobiology. Jan.-Feb. 2000; 68(1):9-17.
Walker JD, et al. "Oncolytic herpes simplex virus 1 encoding 15-prostaglandin dehydrogenase mitigates immune suppression and reduces ectopic primary and metastatic breast cancer in mice," J Virol. Jul. 2011; 85(14):7363-71.
Wallace DJ, et al. "Long-Term Safety and Efficacy of Epratuzumab in the Treatment of Moderate-to-Severe Systemic Lupus Erythematosus: Results From an Open-Label Extension Study," Arthritis Care Res (Hoboken). Apr. 2016; 68(4):534-43.
Wang et al. "Immune checkpoint protein VISTA regulate autoimmunity and anti-tumor immunity" J Immunol (May 2013) vol. 190 (Meeting Abstract Supplement) No. 53.35, abstract. 2 pages.
Wang G, et al. "The effects of PDL-Ig on collagen-induced arthritis," Rheumatol Int. Apr. 2011; 31(4):513-9.
Wang HC, et al. "Maximum immunobioactivity of murine small intestinal intraepithelial lymphocytes resides in a subpopulation of CD43+ T cells," J Immunol. Nov. 15, 2004; 173(10):6294-302.
Wang H-X, "Immune mechanisms of Concanavalin A model of autoimmune hepatitis," World Journal of Gastroenterology: WJG. 2012; 18(2):119-25.
Wang L, et al. "Disruption of the immune-checkpoint VISTA gene imparts a proinflammatory phenotype with predisposition to the development of autoimmunity," Proc Natl Acad Sci U S A. Oct. 14, 2014; 111(41):14846-51.
Wang, L., et al., "Programmed death 1 ligand signaling regulates the generation of adaptive Foxp3+CD4+ regulatory T cells," Proc Natl Acad Sci USA, 2008. 105(27): p. 9331-6.
Wang, X., "B7-H4 induces donor-specific tolerance in mouse islet allografts," Cell Transplant 2012. 21:99-111.
Wang, X., "B7-H4Treatment of T Cells Inhibits ERK, JN K, p38, and AKT Activation," PLoS One 2012. 7:e28232.
Ward ES, et al. "Binding activities of a repertoire of single immunoglobulin variable domains secreted from *Escherichia coli*," Nature. Oct. 12, 1989; 341(6242):544-6.
Warrington et al. Allergy, Asthma & Clinical Immunology 2011, 7(Suppl 1):S1, 8 pages.
Waterhouse P, et al. "Lymphoproliferative disorders with early lethality in mice deficient in Ctla-4," Science. Nov. 10, 1995; 270(5238):985-8.
Weber, J., "Immune checkpoint proteins: a new therapeutic paradigm for cancer—preclinical background: CTLA-4 and PD-1 blockade," Semin Oncol, 2010. 37(5): p. 430-9.
Weiner GJ. "Building better monoclonal antibody-based therapeutics," Nat Rev Cancer. 2015; 15(6):361-70.
Weintraub H., et al. "Anti-sense RNA as a molecular tool for] genetic analysis," Trends in Genetics, 1985, pp. 22-25.
Weissmuller S, "TGN1412 Induces Lymphopenia and Human Cytokine Release in a Humanized Mouse Model," PloS One. 2016; II(3):e0149093.
Welling GW, et al. "Prediction of sequential antigenic regions in proteins," FEBS Lett. Sep. 2, 1985; 188(2):215-8.
Wetmur JG. "DNA probes: applications of the principles of nucleic acid hybridization," Crit Rev Biochem Mol Biol. 1991; 26(3-4):227-59.
White et al., (2015), "Conformation of the human immunoglobulin G2 hinge imparts superagonistic properties to immunostimulatory anticancer antibodies", Cancer Cell, 27(1), 138-148.
Wilcox, R. A., "Cancer-associated myeloproliferation: old association, new therapeutic target," Mayo Clin Proc, 2010. 85(7): p. 656-63.
Wiley RA, et al. "Peptidomimetics derived from natural products," Med Res Rev. May 1993; 13(3):327-84.
Williams G, et al. "Dissection of the extracellular human interferon gamma receptor alpha-chain into two immunoglobulin-like domains. Production in an *Escherichia coli* thioredoxin gene fusion expression system and recognition by neutralizing antibodies," Biochemistry. Feb. 7, 1995; 34(5):1787-97.
Willmon C, et al. "Vesicular stomatitis virus-induced immune suppressor cells generate antagonism between intratumoral oncolytic virus and cyclophosphamide," Mol Ther. Jan. 2011; 19(1):140-9.
Wilmut I, et al. "Viable offspring derived from fetal and adult mammalian cells," Nature. Feb. 27, 1997; 385(6619):810-3.
Wing, K., et al., "CTLA-4 control over Foxp3—regulatory T cell function," Science, 2008. 322(5899): p. 271-5.
Winoto A, et al. "A novel, inducible and T cell-specific enhancer located at the 3' end of the T cell receptor alpha locus," EMBO J. Mar. 1989; 8(3):729-33.
Winter G, et al. "Man-made antibodies," Nature. Jan. 24, 1991; 349(6307):293-9.
Wojcik J, et al. "Prediction, assessment and validation of protein interaction maps in bacteria," J Mol Biol. Nov. 1, 2002; 323(4):763-70.
Wolchok JD, et al. "Nivolumab plus ipilimumab in advanced melanoma," N Engl J Med. Jul. 11, 2013; 369(2):122-33.
Wood CR, et al. "The synthesis and in vivo assembly of functional antibodies in yeast," Nature. Apr. 4-10, 1985; 314(6010):446-9.
Wood KJ, et al. "Regulatory T cells in transplantation tolerance," Nat Rev Immunol. Mar. 2003; 3(3):199-210.
Wu DY, et al. "The ligation amplification reaction (LAR)—amplification of specific DNA sequences using sequential rounds of template-dependent ligation," Genomics. May 1989; 4(4):560-9.
Wu S, et al. "Development and application of 'phosphoflow' as a tool for immunomonitoring," Expert Rev Vaccines. 2010; 9(6):631-43.
Xu X, et al. "The genomic sequence of the Chinese hamster ovary (CHO)-K1 cell line," Nat Biotechnol. Jul. 31, 2011; 29(8):735-41.
Yamaguchi, T et al. "Regulatory T cells in immune surveillance and treatment of cancer," Semin Cancer Biol, 2006. 16(2): p. 115-23.
Yamane-Ohnuki N, et al. "Establishment of FUT8 knockout Chinese hamster ovary cells: an ideal host cell line for producing completely defucosylated antibodies with enhanced antibody-dependent cellular cytotoxicity," Biotechnol Bioeng. Sep. 5, 2004; 87(5):614-22.
Yamaura, K., "In vivo function of immune inhibitory molecule B7-H4 in alloimmune responses," Am J Transplant 2010. 10: 2355-2362.
Yeh MY, et al. "A cell-surface antigen which is present in the ganglioside fraction and shared by human melanomas," Int J Cancer. Mar. 15, 1982; 29(3):269-75.
Yeh MY, et al. "Cell surface antigens of human melanoma identified by monoclonal antibody," Proc Natl Acad Sci U S A. Jun. 1979; 76(6):2927-31.
Yetter RA, et al. "CD4+ T cells are required for development of a murine retrovirus-induced immunodeficiency syndrome (MAIDS)," J Exp Med. Aug. 1, 1988; 168(2):623-35.

(56) References Cited

OTHER PUBLICATIONS

Yi, K. H., et al. "Fine tuning the immune response through B7-H3 and B7-H4," Immunol Rev, 2009. 229(1): p. 145-51.
Yoon KW, et al. "Control of signaling-mediated clearance of apoptotic cells by the tumor suppressor p53," Science. 2015; 349(6247):1261669.
Yoshinaga SK, et al. "T-cell co-stimulation through B7RP-1 and ICOS," Nature. Dec. 16, 1999; 402(6763):827-32.
Youle RJ, et al. "Anti-Thy 1.2 monoclonal antibody linked to ricin is a potent cell-type-specific toxin," Proc Natl Acad Sci U S A. Sep. 1980; 77(9):5483-6.
Youn JI, et al. "The biology of myeloid-derived suppressor cells: the blessing and the curse of morphological and functional heterogeneity," Eur J Immunol. Nov. 2010; 40(11):2969-75.
Youngnak, P., "Differential binding properties of B7-H1 and B7-DC to programmed death-1," Biochem Biophys Res Commun 2003. 307: 672-677.
Zelinskyy G, et al. "The regulatory T-cell response during acute retroviral infection is locally defined and controls the magnitude and duration of the virus-specific cytotoxic T-cell response," Blood. Oct. 8, 2009; 114(15):3199-207.
Zenewicz, et al. "CD4 T-cell differentiation and inflammatory bowel disease," Trends Mol Med. May 2009; 15(5):199-207.
Zervos AS, et al. "Mxi1, a protein that specifically interacts with Max to bind Myc-Max recognition sites," Cell. Jan. 29, 1993; 72(2):223-32.
Zhang X, et al. "Bcr-Abl efficiently induces a myeloproliferative disease and production of excess interleukin-3 and granulocyte-macrophage colony-stimulating factor in mice: a novel model for chronic myelogenous leukemia," Blood. Nov. 15, 1998; 92(10):3829-40.
Zhang, A., (2015), "Conformational difference in human IgG2 disulfide isoforms revealed by hydrogen/deuterium exchange mass spectrometry", Biochemistry, 54(10), 1956-1962.
Zheng, S. G., et al., "TGF-beta requires CTLA-4 early after T cell activation to induce FoxP3 and generate adaptive CD4+CD25+ regulatory cells," J Immunol, 2006. 176(6): p. 3321-9.
Zhu N, et al. "Systemic gene expression after intravenous DNA delivery into adult mice," Science. Jul. 9, 1993; 261(5118):209-11.
Zhu Y, et al. "B7-H5 costimulates human T cells via CD28H," Nat Commun. 2013; 4:2043.
Zhu Z, et al. "High level secretion of a humanized bispecific diabody from *Escherichia coli*," Biotechnology (N Y). Feb. 1996; 14(2):192-6.
Zhu, G., "B7-H4-deficient mice display augmented neutrophil-mediated innate immunity," Blood 2009. 113: 1759-1767.
Zon G. "Oligonucleotide analogues as potential chemotherapeutic agents," Pharm Res. Sep. 1988; 5(9):539-49.
Zou, W, et al. "Inhibitory B7-family molecules in the tumour microenvironment," Nat Rev Immunol, 2008. 8(6): p. 467-77.
Zou, W., "Regulatory T cells, tumour immunity and immunotherapy," Nat Rev Immunol, 2006. 6(4): p. 295-307.
Zuckermann RN, et al. "Discovery of nanomolar ligands for 7-transmembrane G-protein-coupled receptors from a diverse N-(substituted)glycine peptoid library," J Med Chem. Aug. 19, 1994; 37(17):2678-85.

* cited by examiner

```
MGVPAVPEASSPRWGTLLLAIFLAASRGLVAAFKVTTPYSLYVCPEGQNA 50
TLTCRILGPVSKGHDVTIYKTWYLSSRGEVQMCKEHRPIRNFTLQHLQHH 100
GSHLKANASHDQPQKHGLELASDHHGNFSITLRNVTPRDSGLYCCLVIEL 150
KNHHPEQRFYGSMELQVQAGKGSGSTCMASNEQDSDSITAAALATGACIV 200
GILCLPLILLLVYKQRQVASHRRAQELVRMDSSNTQGIENPGFETTPPFQ 250
GMPEAKTRPPLSYVAQRQPSESGRYLLSDPSTPLSPPGPGDVFFPSLDPV 300
PDSPNSEAI*
```

FIG. 1A

```
                     *********************************************************
VISTA                ----FKVTTPYSLYVC-------PEGQNATLTCRILGPVSKGHDVTIYKTWYLSSRGEVQM
B7-H1_(PD-L1)        ----FTITAPKDLYVV-------EYGSNVTMECRF--PVERELDLLALVVYWEKE-DEQ--
B7-DC_(PD-L2)        L---FTVTAPKEVYTV-------DVGSSVSLECDF-----------------------DRRE
B7-H3_(CD276)        ----VEVQVSEDPVVA-------LVDTDATLFCSF--SPEPGFSLAQLNLIWQLT-DTKQL
B7-H4_(B7S1)         LIIGFGISGKHFITVTTFTSAGNIGEDGTLSCTF----EPDIKLNGIVIQWLKE-GIKGL
                     *************************************************************

VISTA                CKEHRPIRN-FTLQHLQHHGSHLKANASHDQPQKHGLELASDHHGNFSITLRNVTPRDSG
B7-H1_(PD-L1)        VIQFVAGEEDLKPQHSNFRG---RASLPKDQLLK-----------GNAALQITDVKLQDAG
B7-DC_(PD-L2)        CTELEGIRASLQKVENDTSLQSERATLLEEQLPL-----------GKALFHIPSVQVRDSG
B7-H3_(CD276)        VHSFTEGRD----QGSAYSN---RTALFPDLLVQ-----------GNASLRLQRVRVTDEG
B7-H4_(B7S1)         VHEFKEGKDDLSQQMEMFAG---RTAVFADQVVV-----------GNASLRLKNVQLTDAG
                     ******************************

VISTA                LYCCLV-----------IELKNHHPEQRF---------------YGSMELQVQAGKG-----
B7-H1_(PD-L1         VYCCIISYGGA-DYKRITLKVNAPYRKINQRISVDPA------TSEHELICQA-EGYPEAE
B7-DC_(PD-L2)        QYRCLVICGAAWDYKYLTVKVKASYMRIDTRILEVPG------TGEVQLTCQA-RGYPLAE
B7-H3_(CD276)        SYTCTVSIQDF-DSAAVSLQVAAPYSK--PSMTLEPNKDLRPGNMVTITCSSYQGYPEAE
B7-H4_(B7S1)         TYTCYIRTSKGKGNANLEYKTGAFSM---PEINVDYN------ASSESLRCEAPRWFPQPT

VISTA                -------------SGST-----------------------------CMASNEQDSDSITA
B7-H1_(PD-L1)        VIWTN--SDHQPVSGKRSVTTSRTEGMLLNVTSSLRVNATANDVFYCTFWRSQPGQNHTA
B7-DC_(PD-L2)        VSWQN-------VSVPANTSHIRTPEGLYQVTSVLRLKPQPSRNFSCMFWNAHMKELTSA
B7-H3_(CD276)        VFWKD--GQGVPLTGNVTTSQMANERGLFDVHSVLRVVLGANGTYSCLVRNPVLQQDAHG
B7-H4_(B7S1)         VAWASQVDQGANFSEVSNTSFELNSENVTMKVVSVLYNVTINNTYSCMIENDIAK--ATG

VISTA                A------------
B7-H1_(PD-L1)        ELIIPELPATHPPQNRTH---
B7-DC_(PD-L2)        IIDPLSRMEPKVPRTW-----
B7-H3_(CD276)        SVTITGQPLTFPPEA------
B7-H4_(B7S1)         DIKVTDSEVKRRSQLQLLNSG
```

FIG. 1B

```
          *********************************************************
VISTA     ---FKVTTPY----------SLYVCPEGQNATLTCRILGPVSKGHDVTIYKTWYLSSRGE
PD-1      -SGWLLEVPNGPWRSLTFYPAWLTVSEGANATFTCSLS---------------NWSEDLM
CTLA-4    -EAIQVTQPS----------VVLASSHG-VASFPCEYS---------------PSHNTDE
CD28      ---------------------------RSNAEFNCD------------------------
BTLA      EKATKRNDEECPVQLTITRNSKQSARTGELFKIQCPVK---------------YCVHRPN
ICOS      --EINGSADH----------RMFSFHNG-GVQISCKYP---------------ETVQQLK
          ************************************************************
VISTA     VQMCKEHRPIR---NFTLQHLQHHGSHLKANASHDQPQKHGLELASDHHGNFSITLRNVT
PD-1      LNWNRLSPSNQ------TEKQAAFCNGLSQPVQDARFQIIQLPN----RHDFHMNILDTR
CTLA-4    VRVTVLRQTND---QMTEVCATTFTEKNTVGFLDYPFCSGTFNE-----SRVNLTIQGLR
CD28      ---------------------------------------GDFDN-----ETVTFRLWNLH
BTLA      VTWCKHNGTICVPLEVSPQLYTSWEENQSVPVFVLHFKPIHLSDNGSYSCSTNFNSQVIN
ICOS      MRLFREREVLC---ELT----KTKGSGNAVSIKNPMLCLYMLSN-----NSVSFFLNNPD
          **************************
VISTA     PRDSGLYCCLVIELKNHHPEQRFYGSMELQVQAGKCSGSTCMASNEQDSDSITAA-----
PD-1      RNDSGIYLC---GAISLMPKAKIEES----------PGAELVVTERILETSTRYPSPSPK
CTLA-4    AVDTGLYLC---KVELMYPPPYFVGM---------GNGTQIYVIDPEPCPDSD-------
CD28      VNHTDIYFC---KIEFMYPPPYLDNE--------RSNGTITHIKEKHLCHTQSSPKL---
BTLA      SHSVTIHVRERTQNSSEHPLITVSDI---------PDATNASGPSTMEERPGRTWLLY--
ICOS      SSQGSYYFC---SLSIFDPPPFQERN---------LSGGYLHIYESQLCCQLKLWL----
VISTA     --------
PD-1      PEERFQGM
CTLA-4    --------
CD28      --------
BTLA      --------
ICOS      --------
```

FIG. 1C

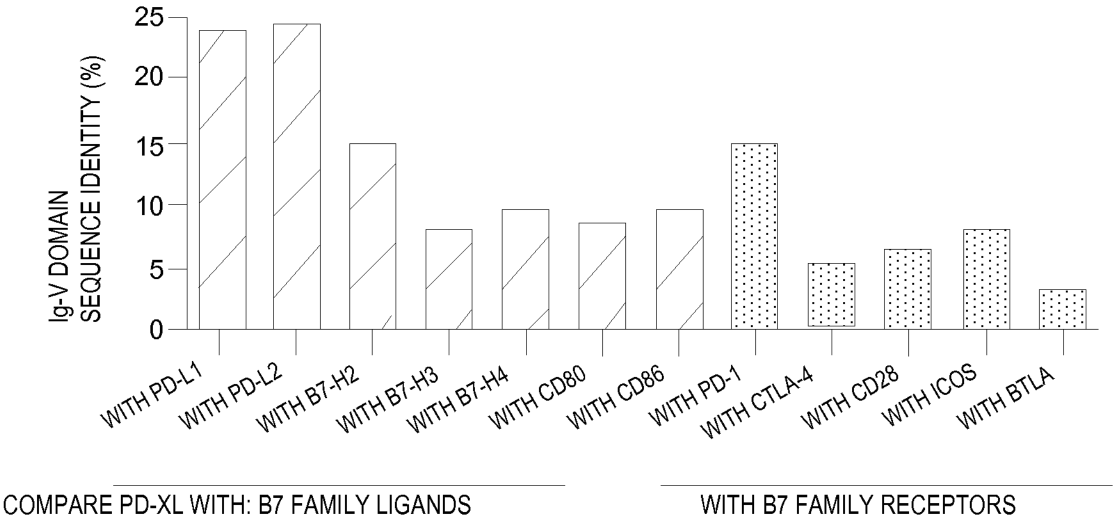

FIG. 1D

```
VISTA_MOUSE  MGVPNVPEASSPRWGTLLLLADFLAASRGLVAAFKVTTPYSLYVCPEGQNATLTCRILGPV 60
VISTA_HUMAN  MGVPTAIEASSWRWGSLIFALFLAASLGPVAAFKVATPYSLYVCPEGQNVTLTCRLLGPV 60
             ****:. ** * ***:**:*:***** * ******:***** ******* *****:****

VISTA_MOUSE  SKGHDVTIYKTWYLSSRGEVQMCKEERPIRNFILQHLQHHG-SHLKANASHDQPQKHGLE 119
VISTA_HUMAN  DKGHDVTFYKTWYRSSRGEVQTCSERRPIRNLTFQDLHLHHGGHQAANTSHDLAQRHGLE 120
             .******:***** ******* *.*:*****:*:*.*:  *  .*  **:***  .*:****

VISTA_MOUSE  TASDHHGNFSITLRNVTPRDSGLYCCLVIELKNHHPKQRFYGSMELQVQAGKGSG T NA 179
VISTA_HUMAN  SASDHHGNFSITNRNLTLLDSGLYCCLVVEIRHHHSKHRVHGAMELQVQTGKDAP N VV 180
             ***********:**:*  *********:*::**.*:* .*:*******:**.:  *  *:.

VISTA_MOUSE  S--NEQDSDSITAAALATGACIVGILCLPLILLLVYKQRQVASHRRAQELVRMDSSNTQG 237
VISTA_HUMAN  YPSSSQDSENITAAALATGACIVGILCLPLILLLVYKQRQAASNRRAQELVRMDS-NIQG 239
               ::***:.****************************.**:***********  *  **

VISTA_MOUSE  IKNPGFETTPPFQGMPEAKTRPPLSYVAQRQPSESGRYLLSDPSTPLSPPGPGDVFFPSL 297
VISTA_HUMAN  IKNPGFEASPPAQGIPEAKVRHPLSYVAQRQPSESGRHLLSEPSTPLSPPGPGDVFFPSL 299
             *******::** **:****.* ***************:***:*****************

VISTA_MOUSE  DPVPDSNSEAI 309
VISTA_HUMAN  DPVPDSNFEVI 311
             ******* *.*
```

FIG. 1E

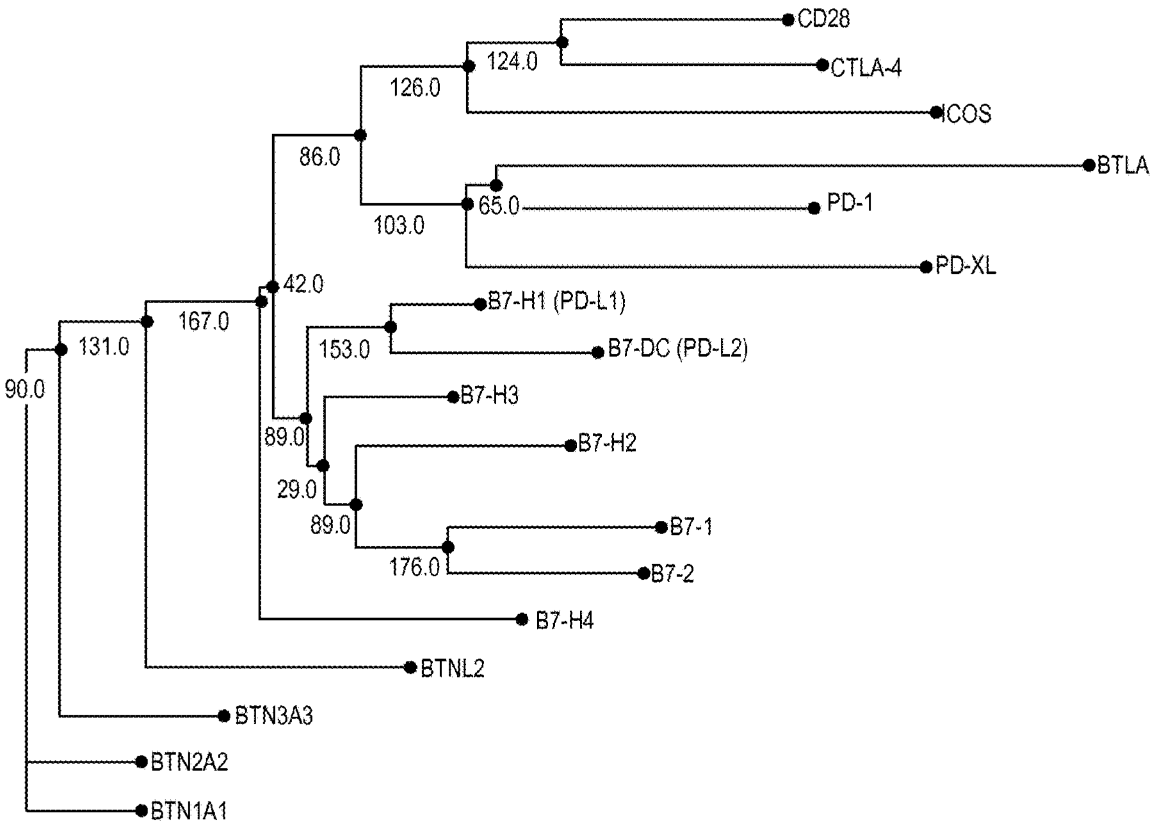

FIG. 2

FIG. 18
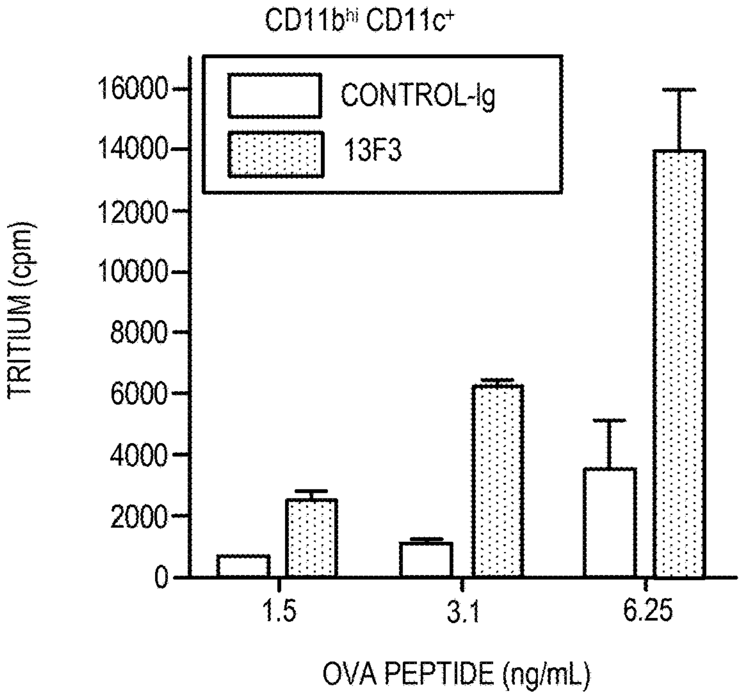
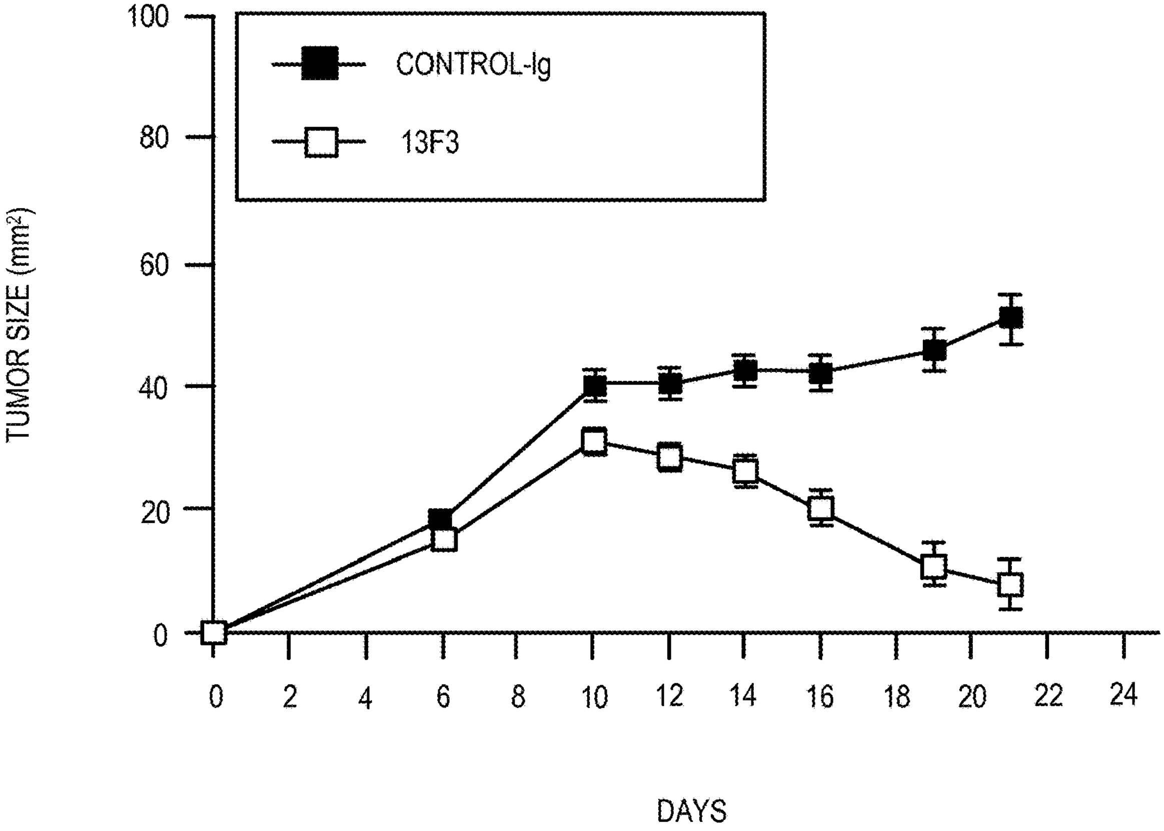
FIG. 19

E. MDSC

MGVPAVPEASSPRWGTLLLAIFLAASRGLVAAFKVTTPYSLYVCPEGQNATLTC
RILGPVSKGHDVTIYKTWYLSSRGEVQMCKEHRPIRNFTLQHLQHHGSHLKAN
ASHDQPQKHGLELASDHHGNFSITLRNVTPRDSGLYCCLVIELKNHHPEQRFYG
SMELQVQ*AGKGSGSTCMASNEQDSDSITAA*ALATGACIVGILCLPLILLLVYKQRQ
VASHRRAQELVRMDSSNTQGIENPGFETTPPFQGMPEAKTRPPLSYVAQRQPS
ESGRYLLSDPSTPLSPPGPGDVFFPSLDPVPDSPNSEAI
(SEQ ID NO: 17)

FIG. 23A

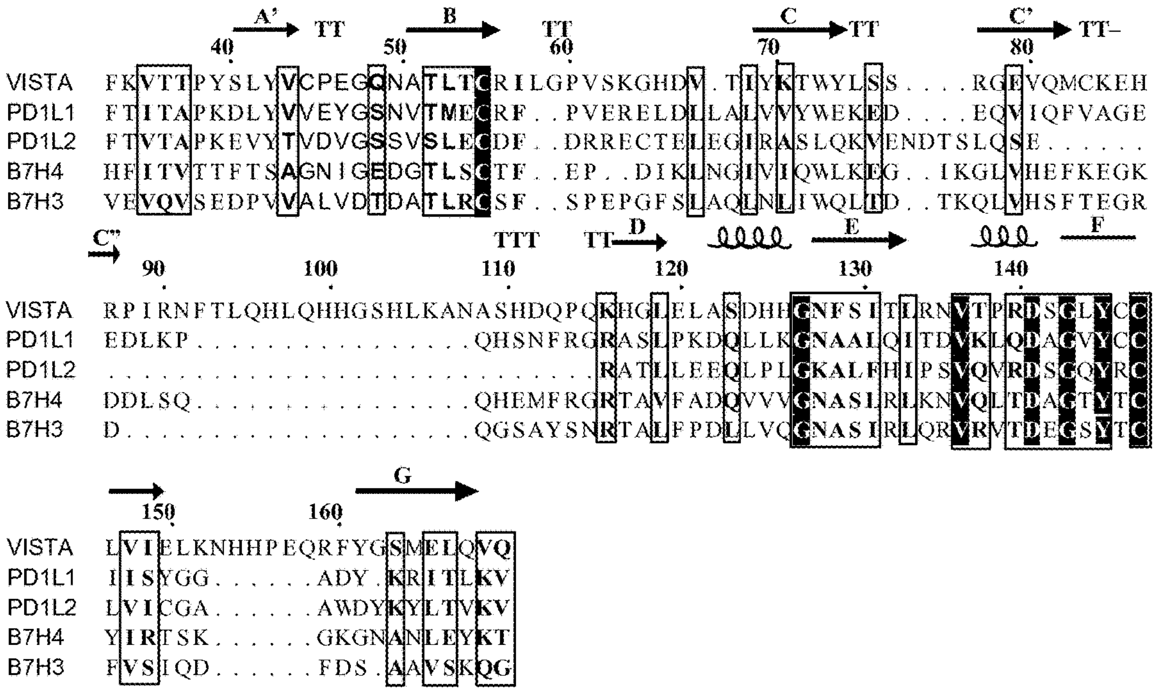

FIG. 23B (SEQ ID NO: 17)

```
              A'      TT      B           TT            C     →TT           C'    →TT–
              40              50              60              70              80
VISTA    FK VTT PYSLY V CPEG Q NA T LT C R ILGPVSKGHD V . T I Y K TWYL S S . . . . RG E VQMCKEH
PD1L1    FT I TA PKDLY V VEYG S NV T ME C RF . . PVERELD L LA L VV Y WEK E D . . . . EQ V IQFVAGE
PD1L2    FT VTA PKEVY T VDVG S SV S LE C DF . . DRRECTE L EGI R A SLQK V ENDTSLQ S E . . . . . .
B7H4     HF I TV TTFTS A GN I GE D G T LS C TF . . EP . . DIK L NGI V I QWLK E G . . IKGL V HEFKEGK
B7H3     VE VQV SEDPV V A LVD T DA T LR C SF . . SPEPGFS L AQ L NL I WQL I D . . TKQL V HSFTEGR
         C"                            TTT    TT–→ D                 E              F
              90              100              110              120              130             140
VISTA    RPIRNFTLQHLQHHGSHLKANASHDQPQ K HG L ELA S DH H GNFSI T L RN V TPR D SGLY CC
PD1L1    EDLKP . . . . . . . . . . . . . QHSNFRG R AS L PKD Q LLK G NAAI Q ITD V KL Q AGVY CC
PD1L2    . . . . . . . . . . . . . . . . . . . RAT L LEE Q LPL G KALF H IP S VQM R DSGQVR C
B7H4     DDLSQ . . . . . . . . . . . . . QHEMFRG R TA V FAD Q VVV G NASI R L KN V QL T DACTY T C
B7H3     D . . . . . . . . . . . . . . . . . QGSAYSN R TA L FPD L LVQ G NASI R L QR V RV T L EGSY T C

              G
              150              160
VISTA    L V I E LKNHHPEQRFYG S ME L Q V Q
PD1L1    I I S YGG . . . . . ADY . K R I T L KV
PD1L2    L V I CGA . . . . . AWDY K Y L T V KV
B7H4     Y I R T SK . . . . . GKGN A N L E Y KT
B7H3     F VS I QD . . . . . FDS . A A VSK Q G
```

```
                      Signal Peptide
                 1         10         20         3
Mouse        MGVPA.VPEASS..PRWGTLLLAIFLAASR.GLVAAFKVITEYSLYVCPEGQNATLTCRLLGPVSKGHDV
Human        MGVPT.ALEAGS..WRWGSLLFALFLAASL.GPVAAFKVATEYSLYVCPEGQNVTLTCRLLGPVDKGHDV
Kangaroo     MNVPTSVLESGG..RRWGPLLLAFFLAASL.GLVAAFKVATEYSLYVCPEGENITLACQLLGPVPKGHDV
Dolphin      MGVPP.VPEAGS..WRRGPVLLAFFLAASR.GLVAAFKVATEYSLYVCPEGQNVTLTCRLLGPLAKGHDV
Chicken      ..........................GGTAAFLVTVEYTLCICPEGQNVTLSCRVSGPPADHHDL
Xenopus      ..........................DAITAFSVSALYSHITCPEGQNVLTCTVSGHVADKHDV
Zebra-finch  GHPAT....MGTASPRPGLLLAALCLLASH.GGADAFLISTEYSLCVCPEGQNVTLSCRISGALAERHDL
Zebrafish    .........MDV..FRAVLLCFHVFTAIQASGDHHSLRVSVEHRTYECPEGADVILKCVPSGTKAYPQDT
Fugu         LEKFT.SAHHTKQTLEKGLNLLCLTKSNAH.HGHEAMSVSAHLYYTCPEGANATLVCNQRGGALHPNDS

                                      Lg-V domain
             70        80        90        100       110       120
Mouse        TIMKTWYISSRGEVQMCKEHRFIRNFTIQH.LQ.HHGSHL..KANASHDQP.....QKHGLELASDHHGN
Human        TFMKTWYRSSRGEVQICSERRFIRNLTFQD.LHLHHGGHQ..AANTSHDLA.....QRHGLESASDHHGN
Kangaroo     SFMKTWFRSSRGEVQVCSEHRFIRNVTIQN.LHPYHGGHQ..ASNTSHNLL.....QSHGLETASDHHGN
Dolphin      TFMKTWYRSSRGEVQACSERRFIRNLTFQD.LHLHHGGHQ..ANSSQDLA.....QRHGLESASDHHGN
Chicken      .IEKTWYFSNNGD.QSCSEKRHVRNLTEKE.LRHDPGRHHSTAANSTARSPHGSLASHHGVEFVPDHHGA
Xenopus      .LFSLWHESKDKN.SECLERRHIQNTTERDHLHKEHLSHS.................MHNGA
Zebra-finch  .LYKTWYFSSTGD.QSCSDKRHIRNVTDKE.LRHDLGRHHELPGNASQKPPFGWQSGHHGVELVLDHHGA
Zebrafish    .FWTTWLYTERSQ.DHCQKGAHPRKANHTN.............RSLGVVYSSGDKV.
Fugu         .LWRLWFFTEHKD.QHCTKHGPLRNVTEKH.SKLSSG..................LHFGATQEN...L.

                                                            Stalk region
             130       140       150       160       170       180
Mouse        FSITLRNVTPRDSGLYCCLVIELKNH.HP....EQRFYGSMELQVQAGKG....SGSTCMASNE...QDS
Human        FSITMRNLTLLDSGLYCCLVVEIRHH.HS....EHRVHGAMELQVQTGKD....APSNCVVYPSSS.QDS
Kangaroo     FSITMRNLTVQDGGLYCCLVVEMRHR.HS....EHRVHAAMELQVQKGKD....APSKCITYPSSP.EES
Dolphin      FTITMRNLTLLDGGLYCCLVVEIRHR.HS....EQRLYGAMELQVQRGEE....APSKCTVYPPSS.KES
Chicken      FHIVVMNLTLQDSGNYCCYAMETRRD.HGKAHTLHIAHGFVELQIQRGRG....SLQNCTFHTATS.KD.
Xenopus      FQITLTNVSQDSGGYCCYVIEASKK.H.....HTRHYSYIEFQVKTDDL....NLYTCMFHSPT..EGD
Zebra-finch  FHLVVMNLTLQDSGNYCCYAVEVRREGHSKPHTVQAAHGFVELQIQRGEP........CSHARAQSQRAA
Zebrafish    ESVSLKNVKHTDQGKYCCWLLDLHGR.HK....EQEAHDFMYLSVMPTPKDAHNGSLKCLEYSHTASDDS
Fugu         BWVQLQNVTHADQGRYCCAALEIESI.HHEA..VQRTHSHMFLNIIPRGT....GSPNCTVSAPSAPEGN

             Transmembrane          Cytoplasmic region
             190       200       210       220       230       240       250
Mouse        DSI...TAAAIATGACIVGILCIPLIILLVYKQRQVA.SHRRAQEIVRMDSSNTQGIENPCFETTPPFQGM
Human        ENI...TAAAIATGACIVGILCIPLIILLVYKQRQAA.SNRRAQEIVRMDSNI.QGIENPCFEASPPAQGI
Kangaroo     DNI...TAAAIATGACIVGILCIPLIILLVYKQRQVA.SHRRAQEIVRMDSSP.QGIENPCFEAPPSSQGL
Dolphin      ESI...TAAAIATSACIVGILCIPLIILLVYKQRQVA.SNRRAQEIVRMDSNT.QGIENPCFETSPPSHGM
Chicken      ..I...TAAAIATGACIVGILCIPLIILLIYKQRQAV.SHRRAHEIVRMESSA.QGIENPVFEALP..AGS
Xenopus      NSS...TAAAIAIVSCVIGILCMPLIIFLVYKQRRAI.SHRRSYHFVFIDFSEAQGIENPVFDDPPPANVV
Zebra-finch  DDI...TAAVIATGACIVGILCIPLIILLIYKQRQAA.SSRRAHEIVRMDSGA.QGIENPVFEAVPSAG..
Zebrafish    ....VAEGIAIAACVAFVLCIPLILMLVYRQRQTVRHRRAHEIVRMDSEA.QGHENPVF.....LGDS
Fugu         ATLCTVPVAIAMGACIILAILSIPLIILLVYRDRQSACSHRRAQEIVRMDSEA.HGHENPVF.....LGGS

             260       270       280       290       300
Mouse        PEAKIRPELSYVAQRQFSESGRYLLSDESTPLSPPGPGDV PSLDPVPDSPNSEAI
Human        PEAKVRHELSYVAQRQFSESGRHLLSEESTPLSPPGPGDV PSLDPVPDSPNFEVI
Kangaroo     PEAKVRPELSYMAQRQFSESGRHLLSEENTPLSPPGPGDV PSLDPVPDSPNSEFN
Dolphin      PETKERPELTYMARROFSESGRHLLSEENTPLSPPGPGDV PSLDPVPDSPNSEAI
Chicken      TEORRRPCLSYLGGRQLSESGRHLLSEENTPLSPPAPGEC PTLDPVPDSPNSLKA
Zenopus      EQ...RPRLAFMASRQCSESDRHLLSEENTPLSPSCPNEC PSL.PVPDSPDPGNV
Zebra-finch  AEPRFRACLSYVASRLESESGRHLLSEESTPLSPPGPGDC PTLDPVPDSPNSLKA
Zebrafish    PEPKMR.TVSQIMMRQESETGHHLLSEEGTPFSPNIQGEL .SAQGLPES....NI
Fugu         PQIKNR.TVSQIMARQESETGRHLLSEEGTPLSPAHGDV PAEDTIFETEELRQV
```

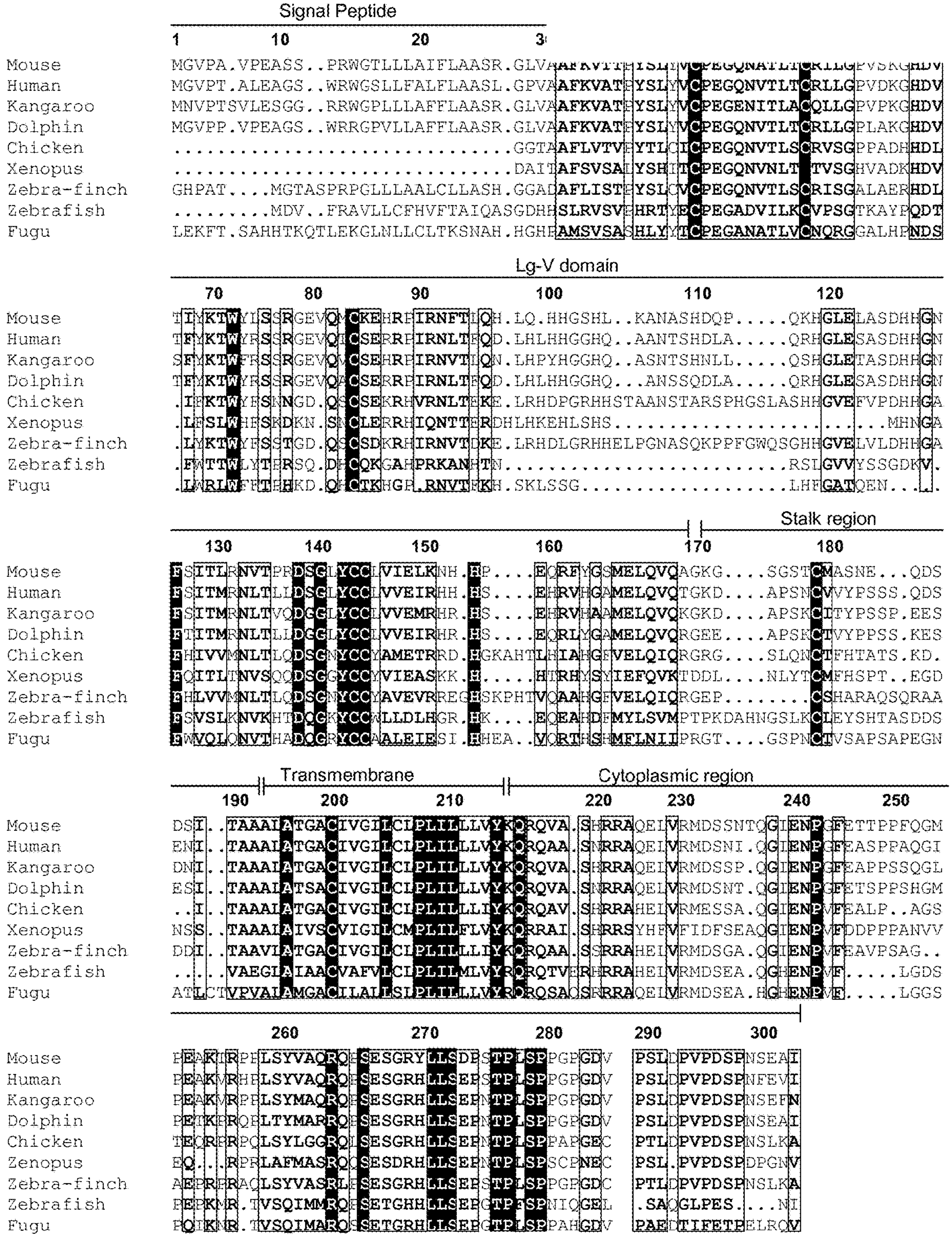

FIG. 23C

Therapeutic effect of VISTA-IgG2a on EAE progression

Control IgG2a (100 µg) vs VISTA-IgG2a (100 µg) p = 0.0051
Control IgG2a (300 µg vs VISTA-IgG2a (300 µg) p = 0.0043
VISTA-IgG2a (100 µg) vs VISTA-IgG2a (300 µg) p = ns VISTA versus PD-L1 in normal tissues – qRT-PCR Titration of human versus mouse vista on human CD4

VISTA treated cells do not express markers of activation

VISTA effect is stable

Cells cultured on anti-CD3/VISTA-Ig
and then moved to CD3 alone
A)3 days CD3/VISTA then 2 days CD3
B)2 days CD3/VISTA then 3 days CD3

VISTA reduces cytokine production

FIG. 40A
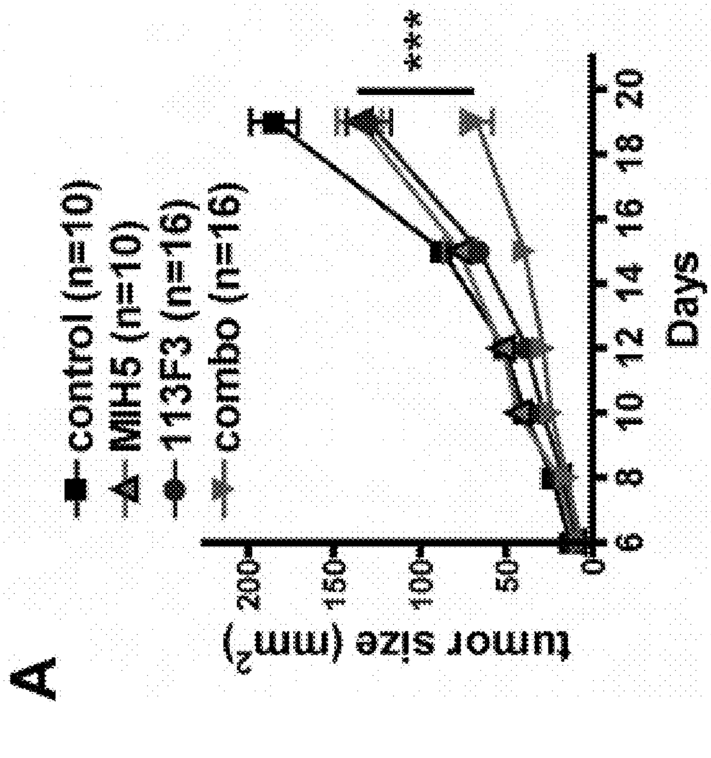
FIG. 40B
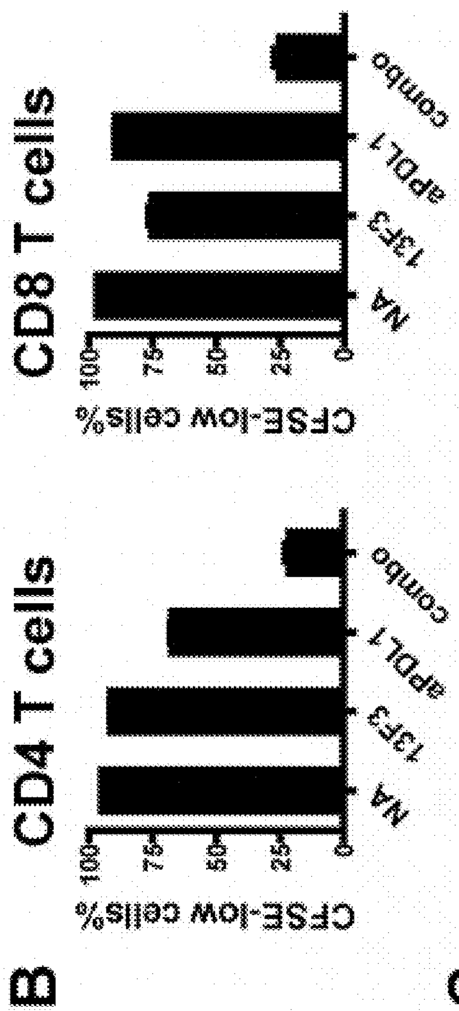
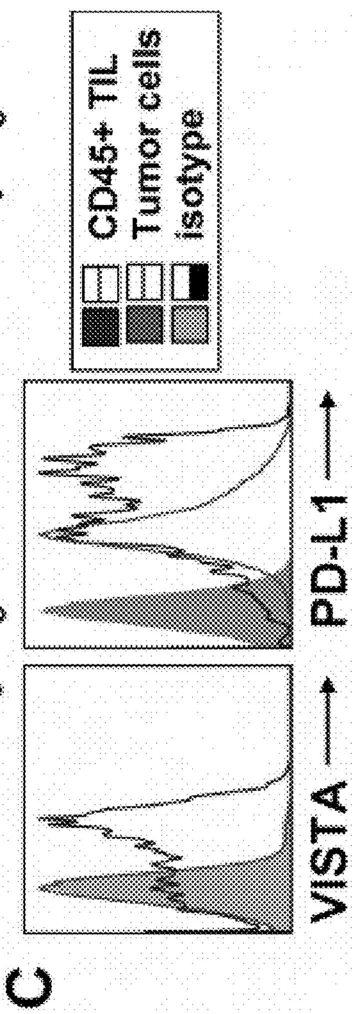
FIG. 40C

SEQUENCE LISTING

<160> NUMBER OF SEQ ID NOS: 75

<210> SEQ ID NO 1
<211> LENGTH: 4795
<212> TYPE: DNA
<213> ORGANISM: Mus musculus

<400> SEQUENCE: 1
gagcattcac tctagcgagc gagcggcgtg tacagccggc tccctgggct cctggagtcc 60
cgcttgctcc aagcgcactc cagcagtctc tttctgctct tgcccggctc gacggcgaca 120
tgggtgtccc cgcggtccca gaggccagca gcccgcgctg gggaaccctg ctccttgcta 180
ttttcctggc tgcatccaga ggtctggtag cagccttcaa ggtcaccact ccatattctc 240
tctatgtgtg tcccgaggga cagaatgcca ccctcacctg caggattctg ggccccgtgt 300
ccaaagggca cgatgtgacc atctacaaga cgtggtacct cagctcacga ggcgaggtcc 360
agatgtgcaa agaacaccgg cccatacgca acttcacatt gcagcacctt cagcaccacg 420
gaagccacct gaaagccaac gccagccatg accagcccca gaagcatggg ctagagctag 480
cttctgacca ccacggtaac ttctctatca ccctgcgcaa tgtgacccca agggacagcg 540
gcctctactg ctgtctagtg atagaattaa aaaaccacca cccagaacaa cggttctacg 600
ggtccatgga gctacaggta caggcaggca aaggctcggg gtccacatgc atggcgtcta 660
atgagcagga cagtgacagc atcacggctg cggccctggc caccggcgcc tgcatcgtgg 720
gaatcctctg cctcccccctt atcctgctgc tggtctataa gcagagacag gtggcctctc 780
accgccgtgc ccaggagttg gtgaggatgg acagcagcaa cacccaagga atcgaaaacc 840
caggcttcga gaccactcca cccttccagg ggatgcctga ggccaagacc aggccgccac 900
tgtcctatgt ggcccagcgg caaccttcgg agtcaggacg gtacctgctc tctgacccca 960
gcacacctct gtcgcctcca ggccctgggg acgtcttttt cccatcccta gatccagtcc 1020
ctgactcccc taactctgaa gccatctaaa ccagctgggg aaccatgaac catggtacct 1080
gggtcaggga tatgtgcact tgatctatgg ctggcccttg gacagtcttt taggcactga 1140
ctccagcttc cttgctcctg ctctgagcct agactctgct tttacaagat gcacagaccc 1200
tcccctatct ctttcagacg ctacttgggg ggcagggaga agatgttgga ttgctcatgg 1260
ctgttctcaa gatcttggga tgctgagttc tccctagaga cttgacttcg acagccacag 1320
atgtcagatg acctgcatcc tatgaacgtc cggcttggca agagcctttc ttcatggaaa 1380
ccagtagccc ggaggggatg aggtaggcac cttgccaccc tcccgggaga gagacacaag 1440
atgtgagaga ctcctgctca ctgtggggggt gtggctggcc tgcttgtttg cctgaggatg 1500
ctcctctgtt ggactgactc tatccccctg gattctggag cttggctggc ctatgtccca 1560
ccagaggagc atctcagcag ccttccacca gcaacctgag ggcctgccag cttcgtggct 1620
ctgggctctc attacctgta tggccgtcca cagagctcag tggccagagg ctttgaaaca 1680
ggaagtacat gtcaggttca ggaaccactg tgagctcatt agtgtcttga gcaatgtgag 1740
gcctggacca gtggacacgg agggagggtg gcgagaggat gatggggatg atgaggggaa 1800
cacgctccct tcctgtcctt gtcatccacc actaccacta ttcagtgtgg agcagtggca 1860
aaggtgaccg acctccacaa tgtcctagtg atgctggacc atttctaagt gtgaaagaga 1920
tgctattaaa aacagtatgt ggcaatggct gccaacagct gagtggactg gaggcactgg 1980
ctttaaggcc ctggaggtgc agggcccggt atggggatag ggatgggagt ttcagtgagg 2040
gcctagggat cactccgctt ctgaccactc ttcttctgag cctcacctca gggtgacctt 2100
caggcacaca gaagagcttg cccctggtcc gatactactc ttggctctca tctccagggt 2160
ttggcatgac ctgggcacac agggggagtc ttcagaaagg attttaaagc atgaaaagaa 2220
agggtagttc ttgtgaggta gggatgggca gctgatgttt gagagtgagg agggatacgg 2280
ctgggcagat cactctccag tctctagagg gaaagtagct ctaagtctgg gagagcagca 2340
gcccagtggt accatatgtc ttcttgcagc ttccactggc tgggctgaac tgggcatggg 2400
taggaaagct cctgttctgg gcctgcagcc agggagaacc ccattcattc cctgaggaca 2460
gatgggtggg gagagaagag agagtttcag gccgggaagc agcaataagc tatctgctgg 2520
ggacccagac aagttgtctg atgaggtcca agatgtggga tgccagttat acctggggct 2580
tggggatcct tagaggcttt gtatcatcat cataggagtg tcggggtggc cagggcatca 2640
aagccatgac ccctgtttta tcctcagggt ccactcttct gcaccatcca ttgctctaga 2700
tctatgcagt tactatagac agaatgtgtt gttctgtttg gctttgggga taatggcctg 2760
gcgaactgcc agctgttcag tggcagggct gtgaggccag tcaaagacta gaacccacag 2820
accagctgaa cgatgagtat agcctgtccc ctgggggagc ctgacctgtc tccagcccta 2880
agcttcagac ctcaccactc agatgacttc taagaatttg cctgtgggga cccctgcatg 2940
gctgcagctc cgtggaaagg agaggaggcc cccagcagaa gaaccactcg cttcctgccc 3000
agcttcctcc tgtagggctc taagtctctt cttcttggga ccctgcaagc aaaggcatgt 3060
cagcttggtg gtttcctgtt ttgggtgaag ttttgtgtgg tccgggttct gtctacatcc 3120
atgaacttgg ggtgctacca ccttgctgct gctgtagaga cagctgcagg atcttagggt 3180
ggaaaatgga ggtgccctga ggtgctagcc cttggggcaa aagatggggt ggcaatgaga 3240
cacagtgggg aactgagttc cccaagagga gggaggagcc ctgtagcctc aagggccata 3300
ttgggttcct ggtaccagca aaagcctaga gagcgaagtc tgtattttga ggaggtaatt 3360
gatccttacg gaatccatca gaaatttgga gcgggtgctt tatctatctc tggagggtct 3420
ctacctatct ccgatgaagc tctccctggg cctgggatgg gagaaaccag gaggaaaggt 3480
gtctgataaa gcaggggctt cttgacaagc caaagggcca ctggtagctg ttgtggaccg 3540
agctgaccct gctgaagtat tgtagtgtgc cttggaccaa cttctcaaaa gagcaacccc 3600
ggggctaccc tacttctgcc aggaagaggc ggagaagggg ctgagaggcc tggaaggggc 3660
tagctccttc tttgagaact gctccccgga ggacttggag gaggcggcta ggctacgggc 3720
tgctgagggc cctttgtctt tcctaacctg ggcactgtta ggatgctccc tcctggaaaa 3780
ggctttcctg ggtgtgagct agagcagtgt ccatgccagc gctgaacctg ccatggtggg 3840
agctgaacta aaaatttctc agggaactaa aataggcaaa agaggaactg ggggaggagg 3900
gtgccaggca ggatgggggg aagggagggc agtgcaaaag tctcttgaaa cacagacagc 3960
ccagctgagt gccagtccca gatcacagag aatacggctc atctggctca tgttctgcat 4020
gcttgctgct ttaccctggc actttccttc tccaccatga gtgcgagtcc tgggagtcct 4080
gggagggtga ggattaatgc cagcctgggg agcagatagc tgacagagtc cttgggtaac 4140
tggcttgaac caggacctca ggattccact ctggggatct agctttgtct gggccagtga 4200
agatctctat aatggcatta ttgccagggg ataaacattt cactgggttc tgatctgttg 4260
ggtgtggctt cctggaaaat atggtgagag gaattctgct aaggatacag ttgataagaa 4320
agttctgaga ttgattagta atgcctgcct tggactcagg aagggaagtg gcagtatgaa 4380
tgccatgtct taatcatttt ggttaaaata tgcttcccaa aagatttcca cgtgtgttct 4440

-continued

```
tgtttatttg acatctgtct ccatatcagt cttgaaagcc tttctgtgtg tatatatatg   4500

atgtttgcgt gtatatatgt ttttgtgtgt gcatatggaa gtcagaaatc actgggtgtc   4560

ttcctccatt cctttgcaat gtatgttttt ttttttttta cgatttattt actatatgaa   4620

tgttttgcct gaatacatgc ataggtgtca cgtacatgcc tgctggaacg cttggaactg   4680

gagttacagg tggctatgag ctacagtgtg agcactggga atcaaacctg ggtcttctgc   4740

aagagcaaca aattaaaagt cagctcttaa ctacttgagc tatttttcca actcc        4795


<210> SEQ ID NO 2
<211> LENGTH: 309
<212> TYPE: PRT
<213> ORGANISM: Mus musculus

<400> SEQUENCE: 2

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
            100                 105                 110

Pro Gln Lys His Gly Leu Glu Leu Ala Ser Asp His His Gly Asn Phe
        115                 120                 125

Ser Ile Thr Leu Arg Asn Val Thr Pro Arg Asp Ser Gly Leu Tyr Cys
    130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
            180                 185                 190

Leu Ala Thr Gly Ala Cys Ile Val Gly Ile Leu Cys Leu Pro Leu Ile
        195                 200                 205

Leu Leu Leu Val Tyr Lys Gln Arg Gln Val Ala Ser His Arg Arg Ala
    210                 215                 220

Gln Glu Leu Val Arg Met Asp Ser Ser Asn Thr Gln Gly Ile Glu Asn
225                 230                 235                 240

Pro Gly Phe Glu Thr Thr Pro Pro Phe Gln Gly Met Pro Glu Ala Lys
                245                 250                 255

Thr Arg Pro Pro Leu Ser Tyr Val Ala Gln Arg Gln Pro Ser Glu Ser
            260                 265                 270

Gly Arg Tyr Leu Leu Ser Asp Pro Ser Thr Pro Leu Ser Pro Pro Gly
        275                 280                 285

Pro Gly Asp Val Phe Phe Pro Ser Leu Asp Pro Val Pro Asp Ser Pro
    290                 295                 300

Asn Ser Glu Ala Ile
305
```

<210> SEQ ID NO 3
<211> LENGTH: 4714
<212> TYPE: DNA
<213> ORGANISM: Homo sapiens

<400> SEQUENCE: 3

```
gggggcgggt gcctggagca cggcgctggg gccgcccgca gcgctcactc gctcgcactc     60
agtcgcggga ggcttccccg cgccggccgc gtcccgcccg ctccccggca ccagaagttc    120
ctctgcgcgt ccgacggcga catgggcgtc cccacggccc tggaggccgg cagctggcgc    180
tggggatccc tgctcttcgc tctcttcctg gctgcgtccc taggtccggt ggcagccttc    240
aaggtcgcca cgccgtattc cctgtatgtc tgtcccgagg ggcagaacgt caccctcacc    300
tgcaggctct tgggccctgt ggacaaaggg cacgatgtga ccttctacaa gacgtggtac    360
cgcagctcga ggggcgaggt gcagacctgc tcagagcgcc ggcccatccg caacctcacg    420
ttccaggacc ttcacctgca ccatggaggc caccaggctg ccaacaccag ccacgacctg    480
gctcagcgcc acgggctgga gtcggcctcc gaccaccatg gcaacttctc catcaccatg    540
cgcaacctga ccctgctgga tagcggcctc tactgctgcc tggtggtgga gatcaggcac    600
caccactcgg agcacagggt ccatggtgcc atgagctgtc aggtgcagac aggcaaagat    660
gcaccatcca actgtgtggt gtacccatcc tcctcccagg atagtgaaaa catcacggct    720
gcagccctgg ctacgggtgc ctgcatcgta ggaatcctct gcctccccct catcctgctc    780
ctggtctaca agcaaaggca ggcagcctcc aaccgccgtg cccaggagct ggtgcggatg    840
gacagcaaca ttcaagggat tgaaaacccc ggctttgaag cctcaccacc tgcccagggg    900
atacccgagg ccaaagtcag gcaccccctg tcctatgtgg cccagcggca gccttctgag    960
tctgggcggc atctgctttc ggagcccagc accccccctgt ctcctccagg ccccggagac   1020
gtcttcttcc catccctgga ccctgtccct gactctccaa actttgaggt catctagccc   1080
agctggggga cagtgggctg ttgtggctgg gtctggggca ggtgcatttg agccagggct   1140
ggctctgtga gtggcctcct tggcctcggc cctggttccc tccctcctgc tctgggctca   1200
gatactgtga catcccagaa gcccagcccc tcaacccctc tggatgctac atggggatgc   1260
tggacggctc agcccctgtt ccaaggattt tggggtgctg agattctccc ctagagacct   1320
gaaattcacc agctacagat gccaaatgac ttacatctta agaagtctca gaacgtccag   1380
cccttcagca gctctcgttc tgagacatga gccttgggat gtggcagcat cagtgggaca   1440
agatggacac tgggccaccc tcccaggcac cagacacagg gcacggtgga gagacttctc   1500
ccccgtggcc gccttggctc ccccgttttg cccgaggctg ctcttctgtc agacttcctc   1560
tttgtaccac agtggctctg gggccaggcc tgcctgccca ctggccatcg ccaccttccc   1620
cagctgcctc ctaccagcag tttctctgaa gatctgtcaa caggttaagt caatctgggg   1680
cttccactgc ctgcattcca gtccccagag cttggtggtc ccgaaacggg aagtacatat   1740
tggggcatgg tggcctccgt gagcaaatgg tgtcttgggc aatctgaggc caggacagat   1800
gttgccccac ccactggaga tggtgctgag ggaggtgggt ggggccttct gggaaggtga   1860
gtggagaggg gcacctgccc cccgccctcc ccatccccta ctcccactgc tcagcgcggg   1920
ccattgcaag ggtgccacac aatgtcttgt ccaccctggg acacttctga gtatgaagcg   1980
ggatgctatt aaaaactaca tggggaaaca ggtgcaaacc ctggagatgg attgtaagag   2040
ccagtttaaa tctgcactct gctgctcctc ccccaccccc accttccact ccatacaatc   2100
```

-continued

```
tgggcctggt ggagtcttcg cttcagagcc attcggccag gtgcgggtga tgttcccatc   2160
tcctgcttgt gggcatgccc tggctttgtt tttatacaca taggcaaggt gagtcctctg   2220
tggaattgtg attgaaggat tttaaagcag gggaggagag tagggggcat ctctgtacac   2280
tctgggggta aaacagggaa ggcagtgcct gagcatgggg acaggtgagg tggggctggg   2340
cagacccccct gtagcgttta gcaggatggg ggccccaggt actgtggaga gcatagtcca   2400
gcctgggcat ttgtctccta gcagcctaca ctggctctgc tgagctgggc ctgggtgctg   2460
aaagccagga tttggggcta ggcgggaaga tgttcgccca attgcttggg gggttggggg   2520
gatggaaaag gggagcacct ctaggctgcc tggcagcagt gagccctggg cctgtggcta   2580
cagccaggga accccacctg gacacatggc cctgcttcta agccccccag ttaggcccaa   2640
aggaatggtc cactgagggc ctcctgctct gcctgggctg ggccaggggc tttgaggaga   2700
gggtaaacat aggcccggag atggggctga cacctcgagt ggccagaata tgcccaaacc   2760
ccggcttctc ccttgtccct aggcagaggg gggtcccttc ttttgttccc tctggtcacc   2820
acaatgcttg atgccagctg ccataggaag agggtgctgg ctggccatgg tggcacacac   2880
ctgtcctccc agcactttgc agggctgagg tggaaggacc gcttaagccc aggtgttcaa   2940
ggctgctgtg agctgtgttc gagccactac actccagcct ggggacggag caaaactttg   3000
cctcaaaaca aattttaaaa agaaagaaag aaggaaagag ggtatgtttt tcacaattca   3060
tgggggcctg catggcagga gtggggacag gacacctgct gttcctggag tcgaaggaca   3120
agcccacagc ccagattccg gttctcccaa ctcaggaaga gcatgccctg ccctctgggg   3180
aggctggcct ggccccagcc ctcagctgct gaccttgagg cagagacaac ttctaagaat   3240
ttggctgcca gaccccaggc ctggctgctg ctgtgtggag agggaggcgg cccgcagcag   3300
aacagccacc gcacttcctc ctcagcttcc tctggtgcgg ccctgccctc tcttctctgg   3360
acccttttac aactgaacgc atctgggctt cgtggtttcc tgttttcagc gaaatttact   3420
ctgagctccc agttccatct tcatccatgg ccacaggccc tgcctacaac gcactaggga   3480
cgtccctccc tgctgctgct ggggaggggc aggctgctgg agccgccctc tgagttgccc   3540
tgggtgcgag aacatggcgc ctccaggggg cgggaggagc actaggggct ggggcaggag   3600
gctcctggag cgctggattc ctggcacagt ctgaggccct gagagggaaa tccatgcttt   3660
taagaactaa ttcattgtta ggagatcaat caggaattag ggccatcttt acctatctcc   3720
tgacattcac agtttaatag agacttcctg cctttattcc ctcccaggga gaggctgaag   3780
gaatggaatt gaaagcacca tttggagggt tttgctgaca cagcggggac tgctcagcac   3840
tccctaaaaa cacaccatgg aggccactgg tgactgctgg tgggcaggct ggccctgcct   3900
gggggagtcc gtggcgatgg gcgctggggt ggaggtgcag gagccccagg acctgctttt   3960
caaaagactt ctgcctgacc agagctccca ctacatgcag tggcccaggg cagaggggct   4020
gatacatggc ctttttcagg gggtgctcct cgcggggtgg acttgggagt gtgcagtggg   4080
acagggggct gcaggggtcc tgccaccacc gagcaccaac ttggccccctg gggtcctgcc   4140
tcatgaatga ggccttcccc agggctggcc tgactgtgct gggggctggg ttaacgtttt   4200
ctcagggaac cacaatgcac gaaagaggaa ctggggttgc taaccaggat gctgggaaca   4260
aaggcctctt gaagcccagc cacagcccag ctgagcatga ggcccagccc atagacggca   4320
caggccacct ggcccattcc ctgggcattc cctgctttgc attgctgctt ctcttcaccc   4380
catggaggct atgtcaccct aactatcctg gaatgtgttg agagggattc tgaatgatca   4440
atatagcttg gtgagacagt gccgagatag atagccatgt ctgccttggg cacgggagag   4500
```

```
ggaagtggca gcatgcatgc tgtttcttgg ccttttctgt tagaatactt ggtgctttcc   4560

aacacacttt cacatgtgtt gtaacttgtt tgatccaccc ccttccctga aaatcctggg   4620

aggttttatt gctgccattt aacacagagg gcaatagagg ttctgaaagg tctgtgtctt   4680

gtcaaaacaa gtaaacggtg gaactacgac taaa                               4714


<210> SEQ ID NO 4
<211> LENGTH: 311
<212> TYPE: PRT
<213> ORGANISM: Homo sapiens

<400> SEQUENCE: 4

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310


<210> SEQ ID NO 5
```

<211> LENGTH: 30
<212> TYPE: PRT
<213> ORGANISM: Artificial Sequence
<220> FEATURE:
<223> OTHER INFORMATION: Consensus sequence for PD-L3

<400> SEQUENCE: 5

Ile Thr Ala Ala Ala Leu Ala Thr Gly Ala Cys Ile Val Gly Ile Leu
1 5 10 15

Cys Leu Pro Leu Ile Leu Leu Leu Val Tyr Lys Gln Arg Gln
20 25 30

<210> SEQ ID NO 6
<211> LENGTH: 1316
<212> TYPE: DNA
<213> ORGANISM: Mus musculus

<400> SEQUENCE: 6
ggagtcctcc ccttggagcc tgggaggcct agggagaaag tagttctctt tcggtggcag 60
ggttgctgtc gagggcaccg agcaggagga taggtcgaca gagacgagga gttctggctc 120
ctcctgcaga catgcaccag cggctgctgg gctcgtccct gggrctcgcc cccgcgcggg 180
ggctctgaat gcctgccgcc gcccccatga gagcaccggc ctgggctccc gcccctaagc 240
ctctgctcgc ggagactgag ccatgtgggc ctggggctgg gccgctgcag cgctcctctg 300
gctacagact gcaggagccg ggcccggca ggagctcaag aagtctcggc agctgtttgc 360
gcgtgtggat tcccccaata ttaccacgtc caaccgtgag ggattcccag gctccgtcaa 420
gcccccggaa gcctctggac ctgagctctc agatgcccac atgacgtggt tgaactttgt 480
ccgacggcca gatgatgggt cctctagaaa acggtgtcgt ggccgggaca agaagtcgcg 540
aggcctctca ggtctcccag ggcccccagg acctcctggc cctcctggtc cccctggctc 600
ccctggtgtg ggcgttaccc cagaggcctt actgcaggaa tttcaggaga tactgaaaga 660
ggccacagaa cttcgattcc cagggctacc agacacattg ttaccccagg aacccagcca 720
acggctggtg gttgaggcct tctactgccg tttgaaaggc cctgtgctgg tggacaagaa 780
gactctggtg gaactgcaag gattccaagc tcctactact cagggcgcct tcctgcgggg 840
atctggcctg agcctgtcct tgggccgatt cacagcccca gtctctgcca tcttccagtt 900
ttctgccagc ctgcacgtgg accacagtga actgcagggc agaggccggt tgcgtacccg 960
ggatatggtc cgtgttctca tctgtattga gtccttgtgt catcgtcata cgtccctgga 1020
ggctgtatca ggtctggaga gcaacagcag ggtcttcaca gtgcaggttc aggggctgct 1080
gcatctacag tctggacagt atgtctctgt gttcgtggac aacagttctg ggcagtcct 1140 caccatccag aacacttcca gcttctcggg aatgcttttg ggtacctagc ggagctgaag 1200
aaacgattgt ggattgagga accaacacct tgcttcttag aggagctgaa aaggactact 1260
cactcccctt ttaatagttt tcatagcaat aaagaactcc aaacttcttc atcgct 1316

<210> SEQ ID NO 7
<211> LENGTH: 308
<212> TYPE: PRT
<213> ORGANISM: Mus musculus

<400> SEQUENCE: 7

Met Trp Ala Trp Gly Trp Ala Ala Ala Ala Leu Leu Trp Leu Gln Thr
1 5 10 15

Ala Gly Ala Gly Ala Arg Gln Glu Leu Lys Lys Ser Arg Gln Leu Phe
20 25 30

```
Ala Arg Val Asp Ser Pro Asn Ile Thr Thr Ser Asn Arg Glu Gly Phe
        35                  40                  45

Pro Gly Ser Val Lys Pro Pro Glu Ala Ser Gly Pro Glu Leu Ser Asp
    50                  55                  60

Ala His Met Thr Trp Leu Asn Phe Val Arg Arg Pro Asp Asp Gly Ser
65                  70                  75                  80

Ser Arg Lys Arg Cys Arg Gly Arg Asp Lys Lys Ser Arg Gly Leu Ser
                85                  90                  95

Gly Leu Pro Gly Pro Pro Gly Pro Pro Gly Pro Pro Gly Pro Pro Gly
            100                 105                 110

Ser Pro Gly Val Gly Val Thr Pro Glu Ala Leu Leu Gln Glu Phe Gln
        115                 120                 125

Glu Ile Leu Lys Glu Ala Thr Glu Leu Arg Phe Ser Gly Leu Pro Asp
    130                 135                 140

Thr Leu Leu Pro Gln Glu Pro Ser Gln Arg Leu Val Val Glu Ala Phe
145                 150                 155                 160

Tyr Cys Arg Leu Lys Gly Pro Val Leu Val Asp Lys Lys Thr Leu Val
                165                 170                 175

Glu Leu Gln Gly Phe Gln Ala Pro Thr Thr Gln Gly Ala Phe Leu Arg
            180                 185                 190

Gly Ser Gly Leu Ser Leu Ser Leu Gly Arg Phe Thr Ala Pro Val Ser
        195                 200                 205

Ala Ile Phe Gln Phe Ser Ala Ser Leu His Val Asp His Ser Glu Leu
    210                 215                 220

Gln Gly Arg Gly Arg Leu Arg Thr Arg Asp Met Val Arg Val Leu Ile
225                 230                 235                 240

Cys Ile Glu Ser Leu Cys His Arg His Thr Ser Leu Glu Ala Val Ser
                245                 250                 255

Gly Leu Glu Ser Asn Ser Arg Val Phe Thr Val Gln Val Gln Gly Leu
            260                 265                 270

Leu His Leu Gln Ser Gly Gln Tyr Val Ser Val Phe Val Asp Asn Ser
        275                 280                 285

Ser Gly Ala Val Leu Thr Ile Gln Asn Thr Ser Ser Phe Ser Gly Met
    290                 295                 300

Leu Leu Gly Thr
305
```

```
<210> SEQ ID NO 8
<211> LENGTH: 1055
<212> TYPE: DNA
<213> ORGANISM: Homo sapiens

<400> SEQUENCE: 8

ctcgccgcgc tgagccgcct cgggacggag ccatgcggcg ctgggcctgg gccgcggtcg      60

tggtcccccct cgggccgcag ctcgtgctcc tcgggggcgt cggggcccgg cgggaggcac     120

agaggacgca gcagcctggc cagcgcgcag atccccccaa cgccaccgcc agcgcgtcct     180

cccgcgaggg gctgcccgag gcccccaagc catcccaggc ctcaggacct gagttctccg     240

acgcccacat gacatggctg aactttgtcc ggcggccgga cgacggcgcc ttaaggaagc     300

ggtgcggaag cagggacaag aagccgcggg atctcttcgg tcccccagga cctccaggtg     360

cagaagtgac cgcggagact ctgcttcacg agtttcagga gctgctgaaa gaggccacgg     420

agcgccggtt ctcagggctt ctggacccgc tgctgcccca gggggcgggc ctgcggctgg     480
```

```
tgggcgaggc ctttcactgc cggctgcagg gtccccgccg ggtggacaag cggacgctgg    540

tggagctgca tggtttccag gctcctgctg cccaaggtgc cttcctgcga ggctccggtc    600

tgagcctggc ctcgggtcgg ttcacggccc ccgtgtccgg catcttccag ttctctgcca    660

gtctgcacgt ggaccacagt gagctgcagg gcaaggcccg gctgcgggcc cgggacgtgg    720

tgtgtgttct catctgtatt gagtccctgt gccagcgcca cacgtgcctg gaggccgtct    780

caggcctgga gagcaacagc agggtcttca cgctacaggt gcaggggctg ctgcagctgc    840

aggctggaca gtacgcttct gtgtttgtgg acaatggctc cggggccgtc ctcaccatcc    900

aggcgggctc cagcttctcc gggctgctcc tgggcacgtg agggcgccca ggggggctgg    960

cgaggagctg ccgccggatc ccggggaccc tcctactgat gcccgtggtc accacaataa   1020

agagccctcc accctcaaaa aaaaaaaaaa aaaaa                              1055
```

<210> SEQ ID NO 9
<211> LENGTH: 302
<212> TYPE: PRT
<213> ORGANISM: Homo sapiens

<400> SEQUENCE: 9

```
Met Arg Arg Trp Ala Trp Ala Ala Val Val Val Leu Leu Gly Pro Gln
1               5                   10                  15

Leu Val Leu Leu Gly Gly Val Gly Ala Arg Arg Glu Ala Gln Arg Thr
            20                  25                  30

Gln Gln Pro Gly Gln Arg Ala Asp Pro Pro Asn Ala Thr Ala Ser Ala
        35                  40                  45

Ser Ser Arg Glu Gly Leu Pro Glu Ala Pro Lys Pro Ser Gln Ala Ser
    50                  55                  60

Gly Pro Glu Phe Ser Asp Ala His Met Thr Trp Leu Asn Phe Val Arg
65                  70                  75                  80

Arg Pro Asp Asp Gly Ala Leu Arg Lys Arg Cys Gly Ser Arg Asp Lys
                85                  90                  95

Lys Pro Arg Asp Leu Phe Gly Pro Pro Gly Pro Pro Gly Ala Glu Val
            100                 105                 110

Thr Ala Glu Thr Leu Leu His Glu Phe Gln Glu Leu Leu Lys Glu Ala
        115                 120                 125

Thr Glu Arg Arg Phe Ser Gly Leu Leu Asp Pro Leu Leu Pro Gln Gly
    130                 135                 140

Ala Gly Leu Arg Leu Val Gly Glu Ala Phe His Cys Arg Leu Gln Gly
145                 150                 155                 160

Pro Arg Arg Val Asp Lys Arg Thr Leu Val Glu Leu His Gly Phe Gln
                165                 170                 175

Ala Pro Ala Ala Gln Gly Ala Phe Leu Arg Gly Ser Gly Leu Ser Leu
            180                 185                 190

Ala Ser Gly Arg Phe Thr Ala Pro Val Ser Gly Ile Phe Gln Phe Ser
        195                 200                 205

Ala Ser Leu His Val Asp His Ser Glu Leu Gln Gly Lys Ala Arg Leu
    210                 215                 220

Arg Ala Arg Asp Val Val Cys Val Leu Ile Cys Ile Glu Ser Leu Cys
225                 230                 235                 240

Gln Arg His Thr Cys Leu Glu Ala Val Ser Gly Leu Glu Ser Asn Ser
                245                 250                 255

Arg Val Phe Thr Leu Gln Val Gln Gly Leu Leu Gln Leu Gln Ala Gly
            260                 265                 270
```

```
Gln Tyr Ala Ser Val Phe Val Asp Asn Gly Ser Gly Ala Val Leu Thr
        275                 280                 285

Ile Gln Ala Gly Ser Ser Phe Ser Gly Leu Leu Leu Gly Thr
    290                 295                 300


<210> SEQ ID NO 10
<211> LENGTH: 17
<212> TYPE: PRT
<213> ORGANISM: Artificial Sequence
<220> FEATURE:
<223> OTHER INFORMATION: Consensus sequence for Treg-sTNF

<400> SEQUENCE: 10

Ile Phe Gln Phe Ser Ala Ser Leu His Val Asp His Ser Glu Leu Gln
1               5                   10                  15

Gly


<210> SEQ ID NO 11
<211> LENGTH: 112
<212> TYPE: PRT
<213> ORGANISM: Homo sapien
<220> FEATURE:
<221> NAME/KEY: MISC_FEATURE
<222> LOCATION: (1)..(112)
<223> OTHER INFORMATION: PD1L1 Ig-V domain

<400> SEQUENCE: 11

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110


<210> SEQ ID NO 12
<211> LENGTH: 99
<212> TYPE: PRT
<213> ORGANISM: Homo sapien
<220> FEATURE:
<221> NAME/KEY: MISC_FEATURE
<222> LOCATION: (1)..(99)
<223> OTHER INFORMATION: PD1L2 Ig-V domain

<400> SEQUENCE: 12

Phe Thr Val Thr Ala Pro Lys Glu Val Tyr Thr Val Asp Val Gly Ser
1               5                   10                  15

Ser Val Ser Leu Glu Cys Asp Phe Asp Arg Arg Glu Cys Thr Glu Leu
            20                  25                  30

Glu Gly Ile Arg Ala Ser Leu Gln Lys Val Glu Asn Asp Thr Ser Leu
        35                  40                  45

Gln Ser Glu Arg Ala Thr Leu Leu Glu Glu Gln Leu Pro Leu Gly Lys
    50                  55                  60

Ala Leu Phe His Ile Pro Ser Val Gln Val Arg Asp Ser Gly Gln Tyr
```

```
65                  70                  75                  80

Arg Cys Leu Val Ile Cys Gly Ala Ala Trp Asp Tyr Lys Tyr Leu Thr
                85                  90                  95

Val Lys Val


<210> SEQ ID NO 13
<211> LENGTH: 113
<212> TYPE: PRT
<213> ORGANISM: Homo sapien
<220> FEATURE:
<221> NAME/KEY: MISC_FEATURE
<222> LOCATION: (1)..(113)
<223> OTHER INFORMATION: B7H4 Ig-V domain

<400> SEQUENCE: 13

His Phe Ile Thr Val Thr Thr Phe Thr Ser Ala Gly Asn Ile Gly Glu
1               5                   10                  15

Asp Gly Thr Leu Ser Cys Thr Phe Glu Pro Asp Ile Lys Leu Asn Gly
            20                  25                  30

Ile Val Ile Gln Trp Leu Lys Glu Gly Ile Lys Gly Leu Val His Glu
        35                  40                  45

Phe Lys Glu Gly Lys Asp Asp Leu Ser Gln Gln His Glu Met Phe Arg
    50                  55                  60

Gly Arg Thr Ala Val Phe Ala Asp Gln Val Val Val Gly Asn Ala Ser
65                  70                  75                  80

Leu Arg Leu Lys Asn Val Gln Leu Thr Asp Ala Gly Thr Tyr Thr Cys
                85                  90                  95

Tyr Ile Arg Thr Ser Lys Gly Lys Gly Asn Ala Asn Leu Glu Tyr Lys
            100                 105                 110

Thr


<210> SEQ ID NO 14
<211> LENGTH: 110
<212> TYPE: PRT
<213> ORGANISM: Homo sapien
<220> FEATURE:
<221> NAME/KEY: MISC_FEATURE
<222> LOCATION: (1)..(110)
<223> OTHER INFORMATION: B7H3 Ig-V domain

<400> SEQUENCE: 14

Val Glu Val Gln Val Ser Glu Asp Pro Val Val Ala Leu Val Asp Thr
1               5                   10                  15

Asp Ala Thr Leu Arg Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Thr Glu Gly Arg Asp Gln Gly Ser Ala Tyr Ser Asn Arg
    50                  55                  60

Thr Ala Leu Phe Pro Asp Leu Leu Val Gln Gly Asn Ala Ser Leu Arg
65                  70                  75                  80

Leu Gln Arg Val Arg Val Thr Asp Glu Gly Ser Tyr Thr Cys Phe Val
                85                  90                  95

Ser Ile Gln Asp Phe Asp Ser Ala Ala Val Ser Leu Gln Val
            100                 105                 110


<210> SEQ ID NO 15
<211> LENGTH: 136
<212> TYPE: PRT
```

<213> ORGANISM: Homo sapien
<220> FEATURE:
<221> NAME/KEY: MISC_FEATURE
<222> LOCATION: (1)..(136)
<223> OTHER INFORMATION: VISTA Ig-V domain

<400> SEQUENCE: 15

```
Phe Lys Val Thr Thr Pro Tyr Ser Leu Tyr Val Cys Pro Glu Gly Gln
1               5                   10                  15

Asn Ala Thr Leu Thr Cys Arg Ile Leu Gly Pro Val Ser Lys Gly His
            20                  25                  30

Asp Val Thr Ile Tyr Lys Thr Trp Tyr Leu Ser Ser Arg Gly Glu Val
        35                  40                  45

Gln Met Cys Lys Glu His Arg Pro Ile Arg Asn Phe Thr Leu Gln His
    50                  55                  60

Leu Gln His His Gly Ser His Leu Lys Ala Asn Ala Ser His Asp Gln
65                  70                  75                  80

Pro Gln Lys His Gly Leu Glu Leu Ala Ser Asp His His Gly Asn Phe
                85                  90                  95

Ser Leu Thr Leu Arg Asn Val Thr Pro Arg Asp Ser Gly Leu Tyr Cys
            100                 105                 110

Cys Leu Val Ile Glu Leu Lys Asn His His Pro Glu Gln Arg Phe Tyr
        115                 120                 125

Gly Ser Met Glu Leu Gln Val Gln
    130                 135
```

<210> SEQ ID NO 16
<211> LENGTH: 311
<212> TYPE: PRT
<213> ORGANISM: Homo sapiens

<400> SEQUENCE: 16

```
Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190
```

-continued

Ala Ala Ala Leu Ala Thr Gly Ala Cys Ile Val Gly Ile Leu Cys Leu
195 200 205

Pro Leu Ile Leu Leu Leu Val Tyr Lys Gln Arg Gln Ala Ala Ser Asn
210 215 220

Arg Arg Ala Gln Glu Leu Val Arg Met Asp Ser Asn Ile Gln Gly Ile
225 230 235 240

Glu Asn Pro Gly Phe Glu Ala Ser Pro Pro Ala Gln Gly Ile Pro Glu
245 250 255

Ala Lys Val Arg His Pro Leu Ser Tyr Val Ala Gln Arg Gln Pro Ser
260 265 270

Glu Ser Gly Arg His Leu Leu Ser Glu Pro Ser Thr Pro Leu Ser Pro
275 280 285

Pro Gly Pro Gly Asp Val Phe Phe Pro Ser Leu Asp Pro Val Pro Asp
290 295 300

Ser Pro Asn Phe Glu Val Ile
305 310

<210> SEQ ID NO 17
<211> LENGTH: 309
<212> TYPE: PRT
<213> ORGANISM: Mus musculus
<220> FEATURE:
<221> NAME/KEY: misc-feature
<222> LOCATION: (1)..(309)
<223> OTHER INFORMATION: VISTA orthologue

<400> SEQUENCE: 17

Met Gly Val Pro Ala Val Pro Glu Ala Ser Ser Pro Arg Trp Gly Thr
1 5 10 15

Leu Leu Leu Ala Ile Phe Leu Ala Ala Ser Arg Gly Leu Val Ala Ala
20 25 30

Phe Lys Val Thr Thr Pro Tyr Ser Leu Tyr Val Cys Pro Glu Gly Gln
35 40 45

Asn Ala Thr Leu Thr Cys Arg Ile Leu Gly Pro Val Ser Lys Gly His
50 55 60

Asp Val Thr Ile Tyr Lys Thr Trp Tyr Leu Ser Ser Arg Gly Glu Val
65 70 75 80

Gln Met Cys Lys Glu His Arg Pro Ile Arg Asn Phe Thr Leu Gln His
85 90 95

Leu Gln His His Gly Ser His Leu Lys Ala Asn Ala Ser His Asp Gln
100 105 110

Pro Gln Lys His Gly Leu Glu Leu Ala Ser Asp His His Gly Asn Phe
115 120 125

Ser Ile Thr Leu Arg Asn Val Thr Pro Arg Asp Ser Gly Leu Tyr Cys
130 135 140

Cys Leu Val Ile Glu Leu Lys Asn His His Pro Glu Gln Arg Phe Tyr
145 150 155 160

Gly Ser Met Glu Leu Gln Val Gln Ala Gly Lys Gly Ser Gly Ser Thr
165 170 175

Cys Met Ala Ser Asn Glu Gln Asp Ser Asp Ser Ile Thr Ala Ala Ala
180 185 190

Leu Ala Thr Gly Ala Cys Ile Val Gly Ile Leu Cys Leu Pro Leu Ile
195 200 205

Leu Leu Leu Val Tyr Lys Gln Arg Gln Val Ala Ser His Arg Arg Ala
210 215 220

Gln Glu Leu Val Arg Met Asp Ser Ser Asn Thr Gln Gly Ile Glu Asn

```
225                 230                 235                 240

Pro Gly Phe Glu Thr Thr Pro Pro Phe Gln Gly Met Pro Glu Ala Lys
                245                 250                 255

Thr Arg Pro Pro Leu Ser Tyr Val Ala Gln Arg Gln Pro Ser Glu Ser
            260                 265                 270

Gly Arg Tyr Leu Leu Ser Asp Pro Ser Thr Pro Leu Ser Pro Pro Gly
        275                 280                 285

Pro Gly Asp Val Phe Phe Pro Ser Leu Asp Pro Val Pro Asp Ser Pro
    290                 295                 300

Asn Ser Glu Ala Ile
305


<210> SEQ ID NO 18
<211> LENGTH: 312
<212> TYPE: PRT
<213> ORGANISM: Kangaroo
<220> FEATURE:
<221> NAME/KEY: misc_feature
<222> LOCATION: (1)..(312)
<223> OTHER INFORMATION: VISTA orthlogue

<400> SEQUENCE: 18

Met Asn Val Pro Thr Ser Val Leu Glu Ser Gly Gly Arg Arg Trp Gly
1               5                   10                  15

Pro Leu Leu Leu Ala Phe Phe Leu Ala Ala Ser Arg Gly Leu Val Ala
            20                  25                  30

Ala Phe Lys Val Ala Thr Pro Tyr Ser Leu Tyr Val Cys Pro Glu Gly
        35                  40                  45

Glu Asn Ile Thr Leu Ala Cys Gln Leu Leu Gly Pro Val Pro Lys Gly
    50                  55                  60

His Asp Val Ser Phe Tyr Lys Thr Trp Phe Arg Ser Ser Arg Gly Glu
65                  70                  75                  80

Val Gln Val Cys Ser Glu His Arg Pro Ile Arg Asn Val Thr Leu Gln
                85                  90                  95

Asn Leu His Pro Tyr His Gly Gly His Gln Ala Ser Asn Thr Ser His
            100                 105                 110

Asn Leu Leu Gln Ser His Gly Leu Glu Thr Ala Ser Asp His His Gly
        115                 120                 125

Asn Phe Ser Ile Thr Met Arg Asn Leu Thr Val Gln Asp Gly Gly Leu
    130                 135                 140

Tyr Cys Cys Leu Val Val Glu Met Arg His Arg His Ser Glu His Arg
145                 150                 155                 160

Val His Ala Ala Met Glu Leu Gln Val Gln Lys Gly Lys Asp Ala Pro
                165                 170                 175

Ser Lys Cys Ile Thr Tyr Pro Ser Ser Pro Glu Glu Ser Asp Asn Ile
            180                 185                 190

Thr Ala Ala Ala Leu Ala Thr Gly Ala Cys Ile Val Gly Ile Leu Cys
        195                 200                 205

Leu Pro Leu Ile Leu Leu Leu Val Tyr Lys Gln Arg Gln Val Ala Ser
    210                 215                 220

His Arg Arg Ala Gln Glu Leu Val Arg Met Asp Ser Ser Pro Gln Gly
225                 230                 235                 240

Ile Glu Asn Pro Gly Phe Glu Ala Pro Pro Ser Ser Gln Gly Leu Pro
                245                 250                 255

Glu Ala Lys Val Arg Pro Pro Leu Ser Tyr Met Ala Gln Arg Gln Pro
            260                 265                 270
```

```
Ser Glu Ser Gly Arg His Leu Leu Ser Glu Pro Asn Thr Pro Leu Ser
        275                 280                 285

Pro Pro Gly Pro Gly Asp Val Phe Phe Pro Ser Leu Asp Pro Val Pro
    290                 295                 300

Asp Ser Pro Asn Ser Glu Phe Asn
305                 310


<210> SEQ ID NO 19
<211> LENGTH: 310
<212> TYPE: PRT
<213> ORGANISM: Dolphin
<220> FEATURE:
<221> NAME/KEY: misc_feature
<222> LOCATION: (1)..(310)
<223> OTHER INFORMATION: VISTA orthologue

<400> SEQUENCE: 19

Met Gly Val Pro Pro Val Pro Glu Ala Gly Ser Trp Arg Arg Gly Pro
1               5                   10                  15

Val Leu Leu Ala Phe Phe Leu Ala Ala Ser Arg Gly Leu Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Leu Ala Lys Gly His
    50                  55                  60

Asp Val Thr Phe Tyr Lys Thr Trp Tyr Arg Ser Ser Arg Gly Glu Val
65                  70                  75                  80

Gln Ala Cys Ser Glu Arg Arg Pro Ile Arg Asn Leu Thr Phe Gln Asp
                85                  90                  95

Leu His Leu His His Gly Gly His Gln Ala Asn Ser Ser Gln Asp Leu
            100                 105                 110

Ala Gln Arg His Gly Leu Glu Ser Ala Ser Asp His His Gly Asn Phe
        115                 120                 125

Thr Ile Thr Met Arg Asn Leu Thr Leu Leu Asp Gly Gly Leu Tyr Cys
    130                 135                 140

Cys Leu Val Val Glu Ile Arg His Arg His Ser Glu Gln Arg Leu Tyr
145                 150                 155                 160

Gly Ala Met Glu Leu Gln Val Gln Arg Gly Glu Glu Ala Pro Ser Lys
                165                 170                 175

Cys Thr Val Tyr Pro Pro Ser Ser Lys Glu Ser Glu Ser Ile Thr Ala
            180                 185                 190

Ala Ala Leu Ala Thr Ser Ala Cys Ile Val Gly Ile Leu Cys Leu Pro
        195                 200                 205

Leu Ile Leu Leu Leu Val Tyr Lys Gln Arg Gln Val Ala Ser Asn Arg
    210                 215                 220

Arg Ala Gln Glu Leu Val Arg Met Asp Ser Asn Thr Gln Gly Ile Glu
225                 230                 235                 240

Asn Pro Gly Phe Glu Thr Ser Pro Pro Ser His Gly Met Pro Glu Thr
                245                 250                 255

Lys Pro Arg Gln Pro Leu Thr Tyr Met Ala Arg Arg Gln Pro Ser Glu
            260                 265                 270

Ser Gly Arg His Leu Leu Ser Glu Pro Asn Thr Pro Leu Ser Pro Pro
        275                 280                 285

Gly Pro Gly Asp Val Phe Phe Pro Ser Leu Asp Pro Val Pro Asp Ser
    290                 295                 300
```

```
Pro Asn Ser Glu Ala Ile
305                 310


<210> SEQ ID NO 20
<211> LENGTH: 288
<212> TYPE: PRT
<213> ORGANISM: Gallus gallus
<220> FEATURE:
<221> NAME/KEY: misc_feature
<222> LOCATION: (1)..(288)
<223> OTHER INFORMATION: VISTA orthlogue

<400> SEQUENCE: 20

Gly Gly Thr Ala Ala Phe Leu Val Thr Val Pro Tyr Thr Leu Cys Ile
1               5                   10                  15

Cys Pro Glu Gly Gln Asn Val Thr Leu Ser Cys Arg Val Ser Gly Pro
            20                  25                  30

Pro Ala Asp His His Asp Leu Ile Phe Lys Thr Trp Tyr Phe Ser Asn
        35                  40                  45

Asn Gly Asp Gln Ser Cys Ser Glu Lys Arg His Val Arg Asn Leu Thr
    50                  55                  60

Glu Lys Glu Leu Arg His Asp Pro Gly Arg His His Ser Thr Ala Ala
65                  70                  75                  80

Asn Ser Thr Ala Arg Ser Pro His Gly Ser Leu Ala Ser His His Gly
                85                  90                  95

Val Glu Phe Val Pro Asp His His Gly Ala Phe His Ile Val Val Met
            100                 105                 110

Asn Leu Thr Leu Gln Asp Ser Gly Asn Tyr Cys Cys Tyr Ala Met Glu
        115                 120                 125

Thr Arg Arg Asp His Gly Lys Ala His Thr Leu His Ile Ala His Gly
    130                 135                 140

Phe Val Glu Leu Gln Ile Gln Arg Gly Arg Gly Ser Leu Gln Asn Cys
145                 150                 155                 160

Thr Phe His Thr Ala Thr Ser Lys Asp Ile Thr Ala Ala Ala Leu Ala
                165                 170                 175

Thr Gly Ala Cys Ile Val Gly Ile Leu Cys Leu Pro Leu Ile Leu Leu
            180                 185                 190

Leu Ile Tyr Lys Gln Arg Gln Ala Val Ser His Arg Arg Ala His Glu
        195                 200                 205

Leu Val Arg Met Glu Ser Ser Ala Gln Gly Ile Glu Asn Pro Val Phe
    210                 215                 220

Glu Ala Leu Pro Ala Gly Ser Thr Glu Gln Arg Pro Arg Pro Gln Leu
225                 230                 235                 240

Ser Tyr Leu Gly Gly Arg Gln Leu Ser Glu Ser Gly Arg His Leu Leu
                245                 250                 255

Ser Glu Pro Asn Thr Pro Leu Ser Pro Pro Ala Pro Gly Glu Cys Phe
            260                 265                 270

Phe Pro Thr Leu Asp Pro Val Pro Asp Ser Pro Asn Ser Leu Lys Ala
        275                 280                 285


<210> SEQ ID NO 21
<211> LENGTH: 260
<212> TYPE: PRT
<213> ORGANISM: Xenopus
<220> FEATURE:
<221> NAME/KEY: misc_feature
<222> LOCATION: (1)..(260)
<223> OTHER INFORMATION: VISTA orthologue
```

<400> SEQUENCE: 21

```
Asp Ala Ile Thr Ala Phe Ser Val Ser Ala Leu Tyr Ser His Ile Thr
1               5                   10                  15

Cys Pro Glu Gly Gln Asn Val Asn Leu Thr Cys Thr Val Ser Gly His
            20                  25                  30

Val Ala Asp Lys His Asp Val Leu Phe Ser Leu Trp His Phe Ser Lys
        35                  40                  45

Asp Lys Asn Ser Asn Cys Leu Glu Arg Arg His Ile Gln Asn Thr Thr
    50                  55                  60

Glu Arg Asp His Leu His Lys Glu His Leu Ser His Ser Met His Asn
65                  70                  75                  80

Gly Ala Phe Gln Ile Thr Leu Thr Asn Val Ser Gln Gln Asp Ser Gly
                85                  90                  95

Gly Tyr Cys Cys Tyr Val Ile Glu Ala Ser Lys Lys His His Thr Arg
            100                 105                 110

His Tyr Ser Tyr Ile Glu Phe Gln Val Lys Thr Asp Asp Leu Asn Leu
        115                 120                 125

Tyr Thr Cys Met Phe His Ser Pro Thr Glu Gly Asp Asn Ser Ser Thr
    130                 135                 140

Ala Ala Ala Leu Ala Ile Val Ser Cys Val Ile Gly Ile Leu Cys Met
145                 150                 155                 160

Pro Leu Leu Leu Phe Leu Val Tyr Lys Gln Arg Arg Ala Leu Ser His
                165                 170                 175

Arg Arg Ser Tyr His Phe Val Phe Ile Asp Phe Ser Glu Ala Gln Gly
            180                 185                 190

Ile Glu Asn Pro Val Phe Asp Asp Pro Pro Pro Ala Asn Val Val Glu
        195                 200                 205

Gln Arg Pro Arg Leu Ala Phe Met Ala Ser Arg Gln Gln Ser Glu Ser
    210                 215                 220

Asp Arg His Leu Leu Ser Glu Pro Asn Thr Pro Leu Ser Pro Ser Cys
225                 230                 235                 240

Pro Asn Glu Cys Phe Phe Pro Ser Leu Pro Val Pro Asp Ser Pro Asp
                245                 250                 255

Pro Gly Asn Val
            260
```

<210> SEQ ID NO 22
<211> LENGTH: 315
<212> TYPE: PRT
<213> ORGANISM: Taeniopygia guttata
<220> FEATURE:
<221> NAME/KEY: misc_feature
<222> LOCATION: (1)..(315)
<223> OTHER INFORMATION: VISTA orthologue

<400> SEQUENCE: 22

```
Gly His Pro Ala Thr Met Gly Thr Ala Ser Pro Arg Pro Gly Leu Leu
1               5                   10                  15

Leu Ala Ala Leu Cys Leu Leu Ala Ser His Gly Gly Ala Asp Ala Phe
            20                  25                  30

Leu Ile Ser Thr Pro Tyr Ser Leu Cys Val Cys Pro Glu Gly Gln Asn
        35                  40                  45

Val Thr Leu Ser Cys Arg Ile Ser Gly Ala Leu Ala Glu Arg His Asp
    50                  55                  60

Leu Leu Tyr Lys Thr Trp Tyr Phe Ser Ser Thr Gly Asp Gln Ser Cys
65                  70                  75                  80
```

-continued

Ser Asp Lys Arg His Ile Arg Asn Val Thr Asp Lys Glu Leu Arg His
85 90 95

Asp Leu Gly Arg His His Glu Leu Pro Gly Asn Ala Ser Gln Lys Pro
100 105 110

Pro Phe Gly Trp Gln Ser Gly His His Gly Val Glu Leu Val Leu Asp
115 120 125

His His Gly Ala Phe His Leu Val Val Met Asn Leu Thr Leu Gln Asp
130 135 140

Ser Gly Asn Tyr Cys Cys Tyr Ala Val Glu Val Arg Arg Glu Gly His
145 150 155 160

Ser Lys Pro His Thr Val Gln Ala Ala His Gly Phe Val Glu Leu Gln
165 170 175

Ile Gln Arg Gly Glu Pro Cys Ser His Ala Arg Ala Gln Ser Gln Arg
180 185 190

Ala Ala Asp Asp Ile Thr Ala Ala Val Leu Ala Thr Gly Ala Cys Ile
195 200 205

Val Gly Ile Leu Cys Leu Pro Leu Ile Leu Leu Leu Ile Tyr Lys Gln
210 215 220

Arg Gln Ala Ala Ser Ser Arg Arg Ala His Glu Leu Val Arg Met Asp
225 230 235 240

Ser Gly Ala Gln Gly Ile Glu Asn Pro Val Phe Glu Ala Val Pro Ser
245 250 255

Ala Gly Ala Glu Pro Arg Pro Arg Ala Gln Leu Ser Tyr Val Ala Ser
260 265 270

Arg Leu Pro Ser Glu Ser Gly Arg His Leu Leu Ser Glu Pro Ser Thr
275 280 285

Pro Leu Ser Pro Pro Gly Pro Gly Asp Cys Phe Phe Pro Thr Leu Asp
290 295 300

Pro Val Pro Asp Ser Pro Asn Ser Leu Lys Ala
305 310 315

<210> SEQ ID NO 23
<211> LENGTH: 274
<212> TYPE: PRT
<213> ORGANISM: Danio rerio
<220> FEATURE:
<221> NAME/KEY: misc_feature
<222> LOCATION: (1)..(274)
<223> OTHER INFORMATION: VISTA orthologue

<400> SEQUENCE: 23

Met Asp Val Phe Arg Ala Val Leu Leu Cys Phe His Val Phe Thr Ala
1 5 10 15

Ile Gln Ala Ser Gly Asp His His Ser Leu Arg Val Ser Val Pro His
20 25 30

Arg Thr Tyr Glu Cys Pro Glu Gly Ala Asp Val Ile Leu Lys Cys Val
35 40 45

Pro Ser Gly Thr Lys Ala Tyr Pro Gln Asp Thr Phe Trp Thr Thr Trp
50 55 60

Leu Tyr Thr Pro Arg Ser Gln Asp His Cys Gln Lys Gly Ala His Pro
65 70 75 80

Arg Lys Ala Asn His Thr Asn Arg Ser Leu Gly Val Val Tyr Ser Ser
85 90 95

Gly Asp Lys Val Phe Ser Val Ser Leu Lys Asn Val Lys His Thr Asp
100 105 110

```
Gln Gly Lys Tyr Cys Cys Trp Leu Leu Asp Leu His Gly Arg His Lys
        115                 120                 125

Glu Gln Glu Ala His Asp Phe Met Tyr Leu Ser Val Met Pro Thr Pro
    130                 135                 140

Lys Asp Ala His Asn Gly Ser Leu Lys Cys Leu Glu Tyr Ser His Thr
145                 150                 155                 160

Ala Ser Asp Asp Val Ala Glu Gly Leu Ala Ile Ala Ala Cys Val Ala
                165                 170                 175

Phe Val Leu Cys Leu Pro Leu Ile Leu Met Leu Val Tyr Arg Gln Arg
            180                 185                 190

Gln Thr Val Glu Arg His Arg Arg Ala His Glu Leu Val Arg Met Asp
        195                 200                 205

Ser Glu Ala Gln Gly His Glu Asn Pro Val Phe Leu Gly Asp Ser Pro
    210                 215                 220

Glu Pro Lys Met Arg Thr Val Ser Gln Ile Met Met Arg Gln Pro Ser
225                 230                 235                 240

Glu Thr Gly His His Leu Leu Ser Glu Pro Gly Thr Pro Phe Ser Pro
                245                 250                 255

Asn Ile Gln Gly Glu Leu Phe Phe Ser Ala Gln Gly Leu Pro Glu Ser
            260                 265                 270

Asn Ile


<210> SEQ ID NO 24
<211> LENGTH: 293
<212> TYPE: PRT
<213> ORGANISM: Fugu
<220> FEATURE:
<221> NAME/KEY: misc_feature
<222> LOCATION: (1)..(293)
<223> OTHER INFORMATION: VISTA orthologue

<400> SEQUENCE: 24

Leu Glu Lys Phe Thr Ser Ala His His Thr Lys Gln Thr Leu Glu Lys
1               5                   10                  15

Gly Leu Asn Leu Leu Cys Leu Thr Lys Ser Asn Ala His His Gly His
            20                  25                  30

Pro Ala Met Ser Val Ser Ala Ser His Leu Tyr Tyr Thr Cys Pro Glu
        35                  40                  45

Gly Ala Asn Ala Thr Leu Val Cys Asn Gln Arg Gly Gly Ala Leu His
    50                  55                  60

Pro Asn Asp Ser Leu Trp Arg Leu Trp Phe Phe Thr Pro His Lys Asp
65                  70                  75                  80

Gln His Cys Thr Lys His Gly Pro Arg Asn Val Thr Phe Lys His Ser
                85                  90                  95

Lys Leu Ser Ser Gly Leu His Phe Gly Ala Thr Gln Glu Asn Phe Trp
            100                 105                 110

Val Gln Leu Gln Asn Val Thr His Ala Asp Gln Gly Arg Tyr Cys Cys
        115                 120                 125

Ala Ala Leu Glu Ile Glu Ser Ile His His Glu Ala Val Gln Arg Thr
    130                 135                 140

His Ser His Met Phe Leu Asn Ile Ile Pro Arg Gly Thr Gly Ser Pro
145                 150                 155                 160

Asn Cys Thr Val Ser Ala Pro Ser Ala Pro Glu Gly Asn Ala Thr Leu
                165                 170                 175

Cys Thr Val Pro Val Ala Leu Ala Met Gly Ala Cys Ile Leu Ala Leu
            180                 185                 190
```

```
Leu Ser Leu Pro Leu Ile Leu Leu Leu Val Tyr Arg Gln Arg Gln Ser
        195                 200                 205

Ala Gln Ser Arg Arg Arg Ala Gln Glu Leu Val Arg Met Asp Ser Glu
    210                 215                 220

Ala His Gly His Glu Asn Pro Val Phe Leu Gly Gly Ser Pro Gln Ile
225                 230                 235                 240

Lys Asn Arg Thr Val Ser Gln Ile Met Ala Arg Gln Ser Ser Glu Thr
                245                 250                 255

Gly Arg His Leu Leu Ser Glu Pro Gly Thr Pro Leu Ser Pro Pro Ala
            260                 265                 270

His Gly Asp Val Phe Phe Pro Ala Glu Asp Thr Ile Phe Glu Thr Pro
        275                 280                 285

Glu Leu Arg Gln Val
    290


<210> SEQ ID NO 25
<211> LENGTH: 159
<212> TYPE: PRT
<213> ORGANISM: Homo sapien
<220> FEATURE:
<221> NAME/KEY: DOMAIN
<222> LOCATION: (1)..(159)
<223> OTHER INFORMATION: Extracellular domain

<400> SEQUENCE: 25

Phe Lys Val Thr Thr Pro Tyr Ser Leu Tyr Val Cys Pro Glu Gly Gln
1               5                   10                  15

Asn Ala Thr Leu Thr Cys Arg Ile Leu Gly Pro Val Ser Lys Gly His
            20                  25                  30

Asp Val Thr Ile Tyr Lys Thr Trp Tyr Leu Ser Ser Arg Gly Glu Val
        35                  40                  45

Gln Met Cys Lys Glu His Arg Pro Ile Arg Asn Phe Thr Leu Gln His
    50                  55                  60

Leu Gln His His Gly Ser His Leu Lys Ala Asn Ala Ser His Asp Gln
65                  70                  75                  80

Pro Gln Lys His Gly Leu Glu Leu Ala Ser Asp His His Gly Asn Phe
                85                  90                  95

Ser Ile Thr Leu Arg Asn Val Thr Pro Arg Asp Ser Gly Leu Tyr Cys
            100                 105                 110

Cys Leu Val Ile Glu Leu Lys Asn His His Pro Glu Gln Arg Phe Tyr
        115                 120                 125

Gly Ser Met Glu Leu Gln Val Gln Ala Gly Lys Gly Ser Gly Ser Thr
    130                 135                 140

Cys Met Ala Ser Asn Glu Gln Asp Ser Asp Ser Ile Thr Ala Ala
145                 150                 155


<210> SEQ ID NO 26
<211> LENGTH: 221
<212> TYPE: PRT
<213> ORGANISM: Homo sapien
<220> FEATURE:
<221> NAME/KEY: DOMAIN
<222> LOCATION: (1)..(221)
<223> OTHER INFORMATION: Extracellular domain

<400> SEQUENCE: 26

Phe Thr Ile Thr Ala Pro Lys Asp Leu Tyr Val Val Glu Tyr Gly Ser
1               5                   10                  15
```

```
Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His
    210                 215                 220


<210> SEQ ID NO 27
<211> LENGTH: 202
<212> TYPE: PRT
<213> ORGANISM: Homo sapien
<220> FEATURE:
<221> NAME/KEY: DOMAIN
<222> LOCATION: (1)..(202)
<223> OTHER INFORMATION: Extracellular domain

<400> SEQUENCE: 27

Leu Phe Thr Val Thr Ala Pro Lys Glu Val Tyr Thr Val Asp Val Gly
1               5                   10                  15

Ser Ser Val Ser Leu Glu Cys Asp Phe Asp Arg Arg Glu Cys Thr Glu
            20                  25                  30

Leu Glu Gly Ile Arg Ala Ser Leu Gln Lys Val Glu Asn Asp Thr Ser
        35                  40                  45

Leu Gln Ser Glu Arg Ala Thr Leu Leu Glu Glu Gln Leu Pro Leu Gly
    50                  55                  60

Lys Ala Leu Phe His Ile Pro Ser Val Gln Val Arg Asp Ser Gly Gln
65                  70                  75                  80

Tyr Arg Cys Leu Val Ile Cys Gly Ala Ala Trp Asp Tyr Lys Tyr Leu
                85                  90                  95

Thr Val Lys Val Lys Ala Ser Tyr Met Arg Ile Asp Thr Arg Ile Leu
            100                 105                 110

Glu Val Pro Gly Thr Gly Glu Val Gln Leu Thr Cys Gln Ala Arg Gly
        115                 120                 125

Tyr Pro Leu Ala Glu Val Ser Trp Gln Asn Val Ser Val Pro Ala Asn
    130                 135                 140

Thr Ser His Ile Arg Thr Pro Glu Gly Leu Tyr Gln Val Thr Ser Val
```

```
145                 150                 155                 160

Leu Arg Leu Lys Pro Gln Pro Ser Arg Asn Phe Ser Cys Met Phe Trp
                165                 170                 175

Asn Ala His Met Lys Glu Leu Thr Ser Ala Ile Ile Asp Pro Leu Ser
            180                 185                 190

Arg Met Glu Pro Lys Val Pro Arg Thr Trp
        195                 200


<210> SEQ ID NO 28
<211> LENGTH: 220
<212> TYPE: PRT
<213> ORGANISM: Homo sapien
<220> FEATURE:
<221> NAME/KEY: DOMAIN
<222> LOCATION: (1)..(220)
<223> OTHER INFORMATION: Extracellular domain

<400> SEQUENCE: 28

Val Glu Val Gln Val Ser Glu Asp Pro Val Val Ala Leu Val Asp Thr
1               5                   10                  15

Asp Ala Thr Leu Phe Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Thr Glu Gly Arg Asp Gln Gly Ser Ala Tyr Ser Asn Arg
    50                  55                  60

Thr Ala Leu Phe Pro Asp Leu Leu Val Gln Gly Asn Ala Ser Leu Arg
65                  70                  75                  80

Leu Gln Arg Val Arg Val Thr Asp Glu Gly Ser Tyr Thr Cys Thr Val
                85                  90                  95

Ser Ile Gln Asp Phe Asp Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asn Met Val Thr Ile Thr Cys Ser Ser Tyr Gln Gly Tyr Pro
    130                 135                 140

Glu Ala Glu Val Phe Trp Lys Asp Gly Gln Gly Val Pro Leu Thr Gly
145                 150                 155                 160

Asn Val Thr Thr Ser Gln Met Ala Asn Glu Arg Gly Leu Phe Asp Val
                165                 170                 175

His Ser Val Leu Arg Val Val Leu Gly Ala Asn Gly Thr Tyr Ser Cys
            180                 185                 190

Leu Val Arg Asn Pro Val Leu Gln Gln Asp Ala His Gly Ser Val Thr
        195                 200                 205

Ile Thr Gly Gln Pro Leu Thr Phe Pro Pro Glu Ala
    210                 215                 220


<210> SEQ ID NO 29
<211> LENGTH: 233
<212> TYPE: PRT
<213> ORGANISM: Homo sapien
<220> FEATURE:
<221> NAME/KEY: DOMAIN
<222> LOCATION: (1)..(233)
<223> OTHER INFORMATION: Extracellular domain

<400> SEQUENCE: 29

Leu Ile Ile Gly Phe Gly Ile Ser Gly Lys His Phe Ile Thr Val Thr
1               5                   10                  15
```

```
Thr Phe Thr Ser Ala Gly Asn Ile Gly Glu Asp Gly Thr Leu Ser Cys
            20                  25                  30

Thr Phe Glu Pro Asp Ile Lys Leu Asn Gly Ile Val Ile Gln Trp Leu
        35                  40                  45

Lys Glu Gly Ile Lys Gly Leu Val His Glu Phe Lys Glu Gly Lys Asp
    50                  55                  60

Asp Leu Ser Gln Gln Met Glu Met Phe Ala Gly Arg Thr Ala Val Phe
65                  70                  75                  80

Ala Asp Gln Val Val Val Gly Asn Ala Ser Leu Arg Leu Lys Asn Val
                85                  90                  95

Gln Leu Thr Asp Ala Gly Thr Tyr Thr Cys Tyr Ile Arg Thr Ser Lys
            100                 105                 110

Gly Lys Gly Asn Ala Asn Leu Glu Tyr Lys Thr Gly Ala Phe Ser Met
        115                 120                 125

Pro Glu Ile Asn Val Asp Tyr Asn Ala Ser Ser Glu Ser Leu Arg Cys
    130                 135                 140

Glu Ala Pro Arg Trp Phe Pro Gln Pro Thr Val Ala Trp Ala Ser Gln
145                 150                 155                 160

Val Asp Gln Gly Ala Asn Phe Ser Glu Val Ser Asn Thr Ser Phe Glu
                165                 170                 175

Leu Asn Ser Glu Asn Val Thr Met Lys Val Val Ser Val Leu Tyr Asn
            180                 185                 190

Val Thr Ile Asn Asn Thr Tyr Ser Cys Met Ile Glu Asn Asp Ile Ala
        195                 200                 205

Lys Ala Thr Gly Asp Ile Lys Val Thr Asp Ser Glu Val Lys Arg Arg
    210                 215                 220

Ser Gln Leu Gln Leu Leu Asn Ser Gly
225                 230
```

<210> SEQ ID NO 30
<211> LENGTH: 159
<212> TYPE: PRT
<213> ORGANISM: Mus musculus
<220> FEATURE:
<221> NAME/KEY: DOMAIN
<222> LOCATION: (1)..(159)
<223> OTHER INFORMATION: Extracellular domain

<400> SEQUENCE: 30

```
Phe Lys Val Thr Thr Pro Tyr Ser Leu Tyr Val Cys Pro Glu Gly Gln
1               5                   10                  15

Asn Ala Thr Leu Thr Cys Arg Ile Leu Gly Pro Val Ser Lys Gly His
            20                  25                  30

Asp Val Thr Ile Tyr Lys Thr Trp Tyr Leu Ser Ser Arg Gly Glu Val
        35                  40                  45

Gln Met Cys Lys Glu His Arg Pro Ile Arg Asn Phe Thr Leu Gln His
    50                  55                  60

Leu Gln His His Gly Ser His Leu Lys Ala Asn Ala Ser His Asp Gln
65                  70                  75                  80

Pro Gln Lys His Gly Leu Glu Leu Ala Ser Asp His His Gly Asn Phe
                85                  90                  95

Ser Ile Thr Leu Arg Asn Val Thr Pro Arg Asp Ser Gly Leu Tyr Cys
            100                 105                 110

Cys Leu Val Ile Glu Leu Lys Asn His His Pro Glu Gln Arg Phe Tyr
        115                 120                 125
```

```
Gly Ser Met Glu Leu Gln Val Gln Ala Gly Lys Cys Ser Gly Ser Thr
    130                 135                 140

Cys Met Ala Ser Asn Glu Gln Asp Ser Asp Ser Ile Thr Ala Ala
145                 150                 155


<210> SEQ ID NO 31
<211> LENGTH: 149
<212> TYPE: PRT
<213> ORGANISM: Homo sapien
<220> FEATURE:
<221> NAME/KEY: Domain
<222> LOCATION: (1)..(149)
<223> OTHER INFORMATION: Extracellular domain

<400> SEQUENCE: 31

Ser Gly Trp Leu Leu Glu Val Pro Asn Gly Pro Trp Arg Ser Leu Thr
1               5                   10                  15

Phe Tyr Pro Ala Trp Leu Thr Val Ser Glu Gly Ala Asn Ala Thr Phe
            20                  25                  30

Thr Cys Ser Leu Ser Asn Trp Ser Glu Asp Leu Met Leu Asn Trp Asn
        35                  40                  45

Arg Leu Ser Pro Ser Asn Gln Thr Glu Lys Gln Ala Ala Phe Cys Asn
    50                  55                  60

Gly Leu Ser Gln Pro Val Gln Asp Ala Arg Phe Gln Ile Ile Gln Leu
65                  70                  75                  80

Pro Asn Arg His Asp Phe His Met Asn Ile Leu Asp Thr Arg Arg Asn
                85                  90                  95

Asp Ser Gly Ile Tyr Leu Cys Gly Ala Ile Ser Leu Met Pro Lys Ala
            100                 105                 110

Lys Ile Glu Glu Ser Pro Gly Ala Glu Leu Val Val Thr Glu Arg Ile
        115                 120                 125

Leu Glu Thr Ser Thr Arg Tyr Pro Ser Pro Ser Pro Lys Pro Glu Glu
    130                 135                 140

Arg Phe Gln Gly Met
145


<210> SEQ ID NO 32
<211> LENGTH: 126
<212> TYPE: PRT
<213> ORGANISM: Homo sapien
<220> FEATURE:
<221> NAME/KEY: Domain
<222> LOCATION: (1)..(126)
<223> OTHER INFORMATION: Extracellular domain

<400> SEQUENCE: 32

Glu Ala Ile Gln Val Thr Gln Pro Ser Val Val Leu Ala Ser Ser His
1               5                   10                  15

Gly Val Ala Ser Phe Pro Cys Glu Tyr Ser Pro Ser His Asn Thr Asp
            20                  25                  30

Glu Val Arg Val Thr Val Leu Arg Gln Thr Asn Asp Gln Met Thr Glu
        35                  40                  45

Val Cys Ala Thr Thr Phe Thr Glu Lys Asn Thr Val Gly Phe Leu Asp
    50                  55                  60

Tyr Pro Phe Cys Ser Gly Thr Phe Asn Glu Ser Arg Val Asn Leu Thr
65                  70                  75                  80

Ile Gln Gly Leu Arg Ala Val Asp Thr Gly Leu Tyr Leu Cys Lys Val
                85                  90                  95

Glu Leu Met Tyr Pro Pro Pro Tyr Phe Val Gly Met Gly Asn Gly Thr
```

```
            100                 105                 110

Gln Ile Tyr Val Ile Asp Pro Glu Pro Cys Pro Asp Ser Asp
        115                 120                 125


<210> SEQ ID NO 33
<211> LENGTH: 71
<212> TYPE: PRT
<213> ORGANISM: Homo sapien
<220> FEATURE:
<221> NAME/KEY: Domain
<222> LOCATION: (1)..(71)
<223> OTHER INFORMATION: Extracellular domain

<400> SEQUENCE: 33

Arg Ser Asn Ala Glu Phe Asn Cys Asp Gly Asp Phe Asp Asn Glu Thr
1               5                   10                  15

Val Thr Phe Arg Leu Trp Asn Leu His Val Asn His Thr Asp Ile Tyr
            20                  25                  30

Phe Cys Lys Ile Glu Phe Met Tyr Pro Pro Pro Tyr Leu Asp Asn Glu
        35                  40                  45

Arg Ser Asn Gly Thr Ile Thr His Ile Lys Glu Lys His Leu Cys His
    50                  55                  60

Thr Gln Ser Ser Pro Lys Leu
65                  70


<210> SEQ ID NO 34
<211> LENGTH: 154
<212> TYPE: PRT
<213> ORGANISM: Homo sapien
<220> FEATURE:
<221> NAME/KEY: domain
<222> LOCATION: (1)..(154)
<223> OTHER INFORMATION: Extracellular domain

<400> SEQUENCE: 34

Glu Lys Ala Thr Lys Arg Asn Asp Glu Glu Cys Pro Val Gln Leu Thr
1               5                   10                  15

Ile Thr Arg Asn Ser Lys Gln Ser Ala Arg Thr Gly Glu Leu Phe Lys
            20                  25                  30

Ile Gln Cys Pro Val Lys Tyr Cys Val His Arg Pro Asn Val Thr Trp
        35                  40                  45

Cys Lys His Asn Gly Thr Ile Cys Val Pro Leu Glu Val Ser Pro Gln
    50                  55                  60

Leu Tyr Thr Ser Trp Glu Glu Asn Gln Ser Val Pro Val Phe Val Leu
65                  70                  75                  80

His Phe Lys Pro Ile His Leu Ser Asp Asn Gly Ser Tyr Ser Cys Ser
                85                  90                  95

Thr Asn Phe Asn Ser Gln Val Ile Asn Ser His Ser Val Thr Ile His
            100                 105                 110

Val Arg Glu Arg Thr Gln Asn Ser Ser Glu His Pro Leu Ile Thr Val
        115                 120                 125

Ser Asp Ile Pro Asp Ala Thr Asn Ala Ser Gly Pro Ser Thr Met Glu
    130                 135                 140

Glu Arg Pro Gly Arg Thr Trp Leu Leu Tyr
145                 150


<210> SEQ ID NO 35
<211> LENGTH: 124
<212> TYPE: PRT
<213> ORGANISM: Homo sapien
```

```
<220> FEATURE:
<221> NAME/KEY: Domain
<222> LOCATION: (1)..(124)
<223> OTHER INFORMATION: Extracellar domain

<400> SEQUENCE: 35

Glu Ile Asn Gly Ser Ala Asp His Arg Met Phe Ser Phe His Asn Gly
1               5                   10                  15

Gly Val Gln Ile Ser Cys Lys Tyr Pro Glu Thr Val Gln Gln Leu Lys
            20                  25                  30

Met Arg Leu Phe Arg Glu Arg Glu Val Leu Cys Glu Leu Thr Lys Thr
        35                  40                  45

Lys Gly Ser Gly Asn Ala Val Ser Ile Lys Asn Pro Met Leu Cys Leu
    50                  55                  60

Tyr Met Leu Ser Asn Asn Ser Val Ser Phe Phe Leu Asn Asn Pro Asp
65                  70                  75                  80

Ser Ser Gln Gly Ser Tyr Tyr Phe Cys Ser Leu Ser Ile Phe Asp Pro
                85                  90                  95

Pro Pro Phe Gln Glu Arg Asn Leu Ser Gly Gly Tyr Leu His Ile Tyr
            100                 105                 110

Glu Ser Gln Leu Cys Cys Gln Leu Lys Leu Trp Leu
        115                 120


<210> SEQ ID NO 36
<211> LENGTH: 306
<212> TYPE: PRT
<213> ORGANISM: Mus musculus

<400> SEQUENCE: 36

Met Gly Val Pro Asn Val Pro Glu Ala Ser Ser Pro Arg Trp Gly Thr
1               5                   10                  15

Leu Ile Leu Ala Asp Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60

Asp Val Thr Ile Tyr Lys Thr Trp Tyr Leu Ser Ser Arg Gly Glu Val
65                  70                  75                  80

Gln Met Cys Lys Glu Glu Arg Pro Ile Arg Asn Phe Ile Leu Gln His
                85                  90                  95

Leu Gln His His Gly Ser His Leu Lys Ala Asn Ala Ser His Asp Gln
            100                 105                 110

Pro Gln Lys His Gly Leu Glu Thr Ala Ser Asp His His Gly Asn Phe
        115                 120                 125

Ser Ile Thr Leu Arg Asn Val Thr Pro Arg Asp Ser Gly Leu Tyr Cys
    130                 135                 140

Cys Leu Val Ile Glu Leu Lys Asn His His Pro Lys Gln Arg Phe Tyr
145                 150                 155                 160

Gly Ser Met Glu Leu Gln Val Gln Ala Gly Lys Gly Ser Gly Thr Asn
                165                 170                 175

Ala Ser Asn Glu Gln Asp Ser Asp Ser Ile Thr Ala Ala Ala Leu Ala
            180                 185                 190

Thr Gly Ala Cys Ile Val Gly Ile Leu Cys Leu Pro Leu Ile Leu Leu
        195                 200                 205

Leu Val Tyr Lys Gln Arg Gln Val Ala Ser His Arg Arg Ala Gln Glu
```

```
    210                 215                 220

Leu Val Arg Met Asp Ser Ser Asn Thr Gln Gly Ile Lys Asn Pro Gly
225                 230                 235                 240

Phe Glu Thr Thr Pro Pro Phe Gln Gly Met Pro Glu Ala Lys Thr Arg
                245                 250                 255

Pro Pro Leu Ser Tyr Val Ala Gln Arg Gln Pro Ser Glu Ser Gly Arg
            260                 265                 270

Tyr Leu Leu Ser Asp Pro Ser Thr Pro Leu Ser Pro Pro Gly Pro Gly
        275                 280                 285

Asp Val Phe Phe Pro Ser Leu Asp Pro Val Pro Asp Ser Asn Ser Glu
    290                 295                 300

Ala Ile
305


<210> SEQ ID NO 37
<211> LENGTH: 308
<212> TYPE: PRT
<213> ORGANISM: Homo sapien

<400> SEQUENCE: 37

Met Gly Val Pro Thr Ala Ile Glu Ala Ser Ser Trp Arg Trp Gly Ser
1               5                   10                  15

Leu Ile Phe Ala Leu Phe Leu Ala Ala Ser Leu Gly Pro Val Ala Ala
            20                  25                  30

Phe Lys Val Ala Thr Pro Tyr Ser Leu Val Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu Lys Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Asn Arg Asn Leu Thr Leu Leu Asp Ser Gly Leu Tyr
    130                 135                 140

Cys Cys Leu Val Val Glu Ile Arg His His His Ser Lys His Arg Val
145                 150                 155                 160

His Gly Ala Met Glu Leu Gln Val Gln Thr Gly Lys Asp Ala Pro Asn
                165                 170                 175

Val Val Tyr Pro Ser Ser Ser Gln Asp Ser Glu Asn Ile Thr Ala Ala
            180                 185                 190

Ala Leu Ala Thr Gly Ala Cys Ile Val Gly Ile Leu Cys Leu Pro Leu
        195                 200                 205

Ile Leu Leu Leu Val Tyr Lys Gln Arg Gln Ala Ala Ser Asn Arg Arg
    210                 215                 220

Ala Gln Glu Leu Val Arg Met Asp Ser Asn Ile Gln Gly Ile Lys Asn
225                 230                 235                 240

Pro Gly Phe Glu Ala Ser Pro Pro Ala Gln Gly Ile Pro Glu Ala Lys
                245                 250                 255

Val Arg His Pro Leu Ser Tyr Val Ala Gln Arg Gln Pro Ser Glu Ser
            260                 265                 270
```

```
Gly Arg His Leu Leu Ser Glu Pro Ser Thr Pro Leu Ser Pro Pro Gly
        275                 280                 285

Pro Gly Asp Val Phe Phe Pro Ser Leu Asp Pro Val Pro Asp Ser Asn
    290                 295                 300

Phe Glu Val Ile
305


<210> SEQ ID NO 38
<211> LENGTH: 25
<212> TYPE: DNA
<213> ORGANISM: Artificial Sequence
<220> FEATURE:
<223> OTHER INFORMATION: siRNA

<400> SEQUENCE: 38

gggcacgatg tgaccttcta caaga                                          25


<210> SEQ ID NO 39
<211> LENGTH: 25
<212> TYPE: DNA
<213> ORGANISM: Artificial Sequence
<220> FEATURE:
<223> OTHER INFORMATION: siRNA

<400> SEQUENCE: 39

cagatgccaa atgacttaca tctta                                          25


<210> SEQ ID NO 40
<211> LENGTH: 25
<212> TYPE: DNA
<213> ORGANISM: Artificial Sequence
<220> FEATURE:
<223> OTHER INFORMATION: siRNA

<400> SEQUENCE: 40

gagatggatt gtaagagcca gttta                                          25


<210> SEQ ID NO 41
<211> LENGTH: 25
<212> TYPE: DNA
<213> ORGANISM: Artificial Sequence
<220> FEATURE:
<223> OTHER INFORMATION: siRNA

<400> SEQUENCE: 41

gggctttgag gagagggtaa acata                                          25


<210> SEQ ID NO 42
<211> LENGTH: 25
<212> TYPE: DNA
<213> ORGANISM: Artificial Sequence
<220> FEATURE:
<223> OTHER INFORMATION: siRNA

<400> SEQUENCE: 42

cctatctcct gacattcaca gttta                                          25


<210> SEQ ID NO 43
<211> LENGTH: 25
<212> TYPE: DNA
<213> ORGANISM: Artificial Sequence
<220> FEATURE:
<223> OTHER INFORMATION: siRNA

<400> SEQUENCE: 43
```

cagtttaata gagacttcct gcctt 25

<210> SEQ ID NO 44
<211> LENGTH: 25
<212> TYPE: DNA
<213> ORGANISM: Artificial Sequence
<220> FEATURE:
<223> OTHER INFORMATION: siRNA

<400> SEQUENCE: 44
cagggagagg ctgaaggaat ggaat 25

<210> SEQ ID NO 45
<211> LENGTH: 25
<212> TYPE: DNA
<213> ORGANISM: Artificial Sequence
<220> FEATURE:
<223> OTHER INFORMATION: siRNA

<400> SEQUENCE: 45
ggaatgtgtt gagagggatt ctgaa 25

<210> SEQ ID NO 46
<211> LENGTH: 25
<212> TYPE: DNA
<213> ORGANISM: Artificial Sequence
<220> FEATURE:
<223> OTHER INFORMATION: siRNA

<400> SEQUENCE: 46
gagagggatt ctgaatgatc aatat 25

<210> SEQ ID NO 47
<211> LENGTH: 25
<212> TYPE: DNA
<213> ORGANISM: Artificial Sequence
<220> FEATURE:
<223> OTHER INFORMATION: siRNA

<400> SEQUENCE: 47
cacagagggc aatagaggtt ctgaa 25

<210> SEQ ID NO 48
<211> LENGTH: 25
<212> TYPE: DNA
<213> ORGANISM: Artificial Sequence
<220> FEATURE:
<223> OTHER INFORMATION: siRNA

<400> SEQUENCE: 48
cagatgccaa atgacttaca tctta 25

<210> SEQ ID NO 49
<211> LENGTH: 25
<212> TYPE: DNA
<213> ORGANISM: Artificial Sequence
<220> FEATURE:
<223> OTHER INFORMATION: siRNA

<400> SEQUENCE: 49
gagatggatt gtaagagcca gttta 25

<210> SEQ ID NO 50
<211> LENGTH: 25
<212> TYPE: DNA
<213> ORGANISM: Artificial Sequence
<220> FEATURE:
<223> OTHER INFORMATION: siRNA

<400> SEQUENCE: 50
ggtgagtcct ctgtggaatt gtgat 25

<210> SEQ ID NO 51
<211> LENGTH: 25
<212> TYPE: DNA
<213> ORGANISM: Artificial Sequence
<220> FEATURE:
<223> OTHER INFORMATION: siRNA

<400> SEQUENCE: 51
gggctttgag gagagggtaa acata 25

<210> SEQ ID NO 52
<211> LENGTH: 25
<212> TYPE: DNA
<213> ORGANISM: Artificial Sequence
<220> FEATURE:
<223> OTHER INFORMATION: siRNA

<400> SEQUENCE: 52
cctatctcct gacattcaca gttta 25

<210> SEQ ID NO 53
<211> LENGTH: 25
<212> TYPE: DNA
<213> ORGANISM: Artificial Sequence
<220> FEATURE:
<223> OTHER INFORMATION: siRNA

<400> SEQUENCE: 53
cagtttaata gagacttcct gcctt 25

<210> SEQ ID NO 54
<211> LENGTH: 25
<212> TYPE: DNA
<213> ORGANISM: Artificial Sequence
<220> FEATURE:
<223> OTHER INFORMATION: siRNA

<400> SEQUENCE: 54
cagggagagg ctgaaggaat ggaat 25

<210> SEQ ID NO 55
<211> LENGTH: 25
<212> TYPE: DNA
<213> ORGANISM: Artificial Sequence
<220> FEATURE:
<223> OTHER INFORMATION: siRNA

<400> SEQUENCE: 55
ggaatgtgtt gagagggatt ctgaa 25

<210> SEQ ID NO 56
<211> LENGTH: 25
<212> TYPE: DNA
<213> ORGANISM: Artificial Sequence
<220> FEATURE:
<223> OTHER INFORMATION: siRNA

<400> SEQUENCE: 56
gagagggatt ctgaatgatc aatat 25

<210> SEQ ID NO 57
<211> LENGTH: 25
<212> TYPE: DNA
<213> ORGANISM: Artificial Sequence
<220> FEATURE:
<223> OTHER INFORMATION: siRNA

<400> SEQUENCE: 57
cacagagggc aatagaggtt ctgaa 25

<210> SEQ ID NO 58
<211> LENGTH: 25
<212> TYPE: DNA
<213> ORGANISM: Artificial Sequence
<220> FEATURE:
<223> OTHER INFORMATION: siRNA

<400> SEQUENCE: 58
acaaagggca cgatgtgacc ttcta 25

<210> SEQ ID NO 59
<211> LENGTH: 25
<212> TYPE: DNA
<213> ORGANISM: Artificial Sequence
<220> FEATURE:
<223> OTHER INFORMATION: siRNA

<400> SEQUENCE: 59
gggcacgatg tgaccttcta caaga 25

<210> SEQ ID NO 60
<211> LENGTH: 25
<212> TYPE: DNA
<213> ORGANISM: Artificial Sequence
<220> FEATURE:
<223> OTHER INFORMATION: siRNA

<400> SEQUENCE: 60
gaccaccatg gcaacttctc catca 25

<210> SEQ ID NO 61
<211> LENGTH: 25
<212> TYPE: DNA
<213> ORGANISM: Artificial Sequence
<220> FEATURE:
<223> OTHER INFORMATION: siRNA

<400> SEQUENCE: 61
cagacaggca aagatgcacc atcca 25

<210> SEQ ID NO 62
<211> LENGTH: 25
<212> TYPE: DNA
<213> ORGANISM: Artificial Sequence
<220> FEATURE:
<223> OTHER INFORMATION: siRNA

<400> SEQUENCE: 62
ggcaaagatg caccatccaa ctgtg 25

<210> SEQ ID NO 63
<211> LENGTH: 25
<212> TYPE: DNA
<213> ORGANISM: Artificial Sequence
<220> FEATURE:
<223> OTHER INFORMATION: siRNA

<400> SEQUENCE: 63
ccatccaact gtgtggtgta cccat 25

<210> SEQ ID NO 64
<211> LENGTH: 25
<212> TYPE: DNA
<213> ORGANISM: Artificial Sequence
<220> FEATURE:
<223> OTHER INFORMATION: siRNA

<400> SEQUENCE: 64
ggatggacag caacattcaa gggat 25

<210> SEQ ID NO 65
<211> LENGTH: 25
<212> TYPE: DNA
<213> ORGANISM: Artificial Sequence
<220> FEATURE:
<223> OTHER INFORMATION: siRNA

<400> SEQUENCE: 65
gacagcaaca ttcaagggat tgaaa 25

<210> SEQ ID NO 66
<211> LENGTH: 25
<212> TYPE: DNA
<213> ORGANISM: Artificial Sequence
<220> FEATURE:
<223> OTHER INFORMATION: siRNA

<400> SEQUENCE: 66
ccctgtccct gactctccaa acttt 25

<210> SEQ ID NO 67
<211> LENGTH: 25
<212> TYPE: DNA
<213> ORGANISM: Artificial Sequence
<220> FEATURE:
<223> OTHER INFORMATION: siRNA

<400> SEQUENCE: 67
cctgactctc caaactttga ggtca 25

<210> SEQ ID NO 68
<211> LENGTH: 457
<212> TYPE: PRT
<213> ORGANISM: Artificial Sequence
<220> FEATURE:
<223> OTHER INFORMATION: Human VISTA - human IgG1 Fc fusion protein CDM8
<220> FEATURE:
<221> NAME/KEY: X
<222> LOCATION: (61)..(61)
<223> OTHER INFORMATION: unsure
<220> FEATURE:
<221> NAME/KEY: X
<222> LOCATION: (63)..(63)
<223> OTHER INFORMATION: unsure
<220> FEATURE:
<221> NAME/KEY: X
<222> LOCATION: (200)..(200)
<223> OTHER INFORMATION: unsure
<220> FEATURE:
<221> NAME/KEY: X
<222> LOCATION: (202)..(202)
<223> OTHER INFORMATION: unsure
<220> FEATURE:
<221> NAME/KEY: X
<222> LOCATION: (239)..(239)

<223> OTHER INFORMATION: unsure
<220> FEATURE:
<221> NAME/KEY: X
<222> LOCATION: (259)..(259)
<223> OTHER INFORMATION: unsure
<220> FEATURE:
<221> NAME/KEY: X
<222> LOCATION: (270)..(270)
<223> OTHER INFORMATION: unsure
<220> FEATURE:
<221> NAME/KEY: X
<222> LOCATION: (278)..(278)
<223> OTHER INFORMATION: unsure
<220> FEATURE:
<221> NAME/KEY: X
<222> LOCATION: (279)..(279)
<223> OTHER INFORMATION: unsure
<220> FEATURE:
<221> NAME/KEY: X
<222> LOCATION: (281)..(281)
<223> OTHER INFORMATION: unsure
<220> FEATURE:
<221> NAME/KEY: X
<222> LOCATION: (282)..(282)
<223> OTHER INFORMATION: unsure
<220> FEATURE:
<221> NAME/KEY: X
<222> LOCATION: (284)..(284)
<223> OTHER INFORMATION: unsure
<220> FEATURE:
<221> NAME/KEY: X
<222> LOCATION: (287)..(287)
<223> OTHER INFORMATION: unsure
<220> FEATURE:
<221> NAME/KEY: X
<222> LOCATION: (288)..(288)
<223> OTHER INFORMATION: unsure
<220> FEATURE:
<221> NAME/KEY: X
<222> LOCATION: (291)..(291)
<223> OTHER INFORMATION: unsure
<220> FEATURE:
<221> NAME/KEY: X
<222> LOCATION: (292)..(292)
<223> OTHER INFORMATION: unsure
<220> FEATURE:
<221> NAME/KEY: X
<222> LOCATION: (299)..(299)
<223> OTHER INFORMATION: unsure
<220> FEATURE:
<221> NAME/KEY: X
<222> LOCATION: (312)..(312)
<223> OTHER INFORMATION: unsure
<220> FEATURE:
<221> NAME/KEY: X
<222> LOCATION: (319)..(319)
<223> OTHER INFORMATION: unsure
<220> FEATURE:
<221> NAME/KEY: X
<222> LOCATION: (330)..(330)
<223> OTHER INFORMATION: unsure
<220> FEATURE:
<221> NAME/KEY: X
<222> LOCATION: (339)..(339)
<223> OTHER INFORMATION: unsure
<220> FEATURE:
<221> NAME/KEY: X
<222> LOCATION: (350)..(350)
<223> OTHER INFORMATION: unsure
<220> FEATURE:
<221> NAME/KEY: X
<222> LOCATION: (351)..(351)
<223> OTHER INFORMATION: unsure
<220> FEATURE:
<221> NAME/KEY: X
<222> LOCATION: (354)..(354)
<223> OTHER INFORMATION: unsure
<220> FEATURE:
<221> NAME/KEY: X
<222> LOCATION: (356)..(356)
<223> OTHER INFORMATION: unsure
<220> FEATURE:
<221> NAME/KEY: X
<222> LOCATION: (360)..(360)
<223> OTHER INFORMATION: unsure
<220> FEATURE:
<221> NAME/KEY: X
<222> LOCATION: (373)..(373)
<223> OTHER INFORMATION: unsure
<220> FEATURE:
<221> NAME/KEY: X
<222> LOCATION: (376)..(376)
<223> OTHER INFORMATION: unsure

<400> SEQUENCE: 68

```
Met Ser Leu Leu Phe Ala Leu Phe Leu Ala Ala Ser Leu Gly Pro Val
1               5                   10                  15

Ala Ala Phe Lys Val Ala Thr Pro Tyr Ser Leu Tyr Val Cys Pro Glu
            20                  25                  30

Gly Gln Asn Val Thr Leu Thr Cys Arg Leu Leu Gly Pro Val Asp Lys
        35                  40                  45

Gly His Asp Val Thr Phe Tyr Lys Thr Trp Tyr Arg Xaa Ser Xaa Gly
    50                  55                  60

Glu Val Gln Thr Cys Ser Glu Arg Arg Pro Ile Arg Asn Leu Thr Phe
65                  70                  75                  80

Gln Asp Leu His Leu His His Gly Gly His Gln Ala Ala Asn Thr Ser
                85                  90                  95

His Asp Leu Ala Gln Arg His Gly Leu Glu Ser Ala Ser Asp His His
            100                 105                 110

Gly Asn Phe Ser Ile Thr Met Arg Asn Leu Thr Leu Leu Asp Ser Gly
        115                 120                 125

Leu Tyr Cys Cys Leu Val Val Glu Ile Arg His His His Ser Glu His
    130                 135                 140

Arg Val His Gly Ala Met Glu Leu Gln Val Gln Thr Gly Lys Asp Ala
145                 150                 155                 160

Pro Ser Asn Cys Val Val Tyr Pro Ser Ser Ser Gln Glu Ser Glu Asn
                165                 170                 175

Ile Thr Ala Ala Asp Pro Gly Gly Gly Gly Gly Arg Leu Val Pro Arg
            180                 185                 190

Gly Phe Gly Thr Gly Asp Pro Xaa Pro Xaa Ser Ser Asp Lys Thr His
        195                 200                 205

Thr Cys Pro Pro Cys Pro Ala Pro Asp Ser Arg Val His Arg Gln Ser
    210                 215                 220

Ser Ser Ser Pro Lys Thr Lys Asp Thr Leu Met Ile Ser Arg Xaa Pro
225                 230                 235                 240

Glu Val Thr Cys Val Val Val Asp Val Ser Gln Glu Asp Pro Glu Val
                245                 250                 255

Lys Phe Xaa Trp Tyr Val Asp Gly Val Glu Met His Arg Xaa Lys Thr
            260                 265                 270

Lys Pro Arg Glu Glu Xaa Xaa Asn Xaa Xaa Leu Xaa Met Gly Xaa Xaa
        275                 280                 285

Leu Thr Xaa Xaa Gln Gln Asp Trp Leu Asn Xaa Lys Asp Tyr Lys Phe
    290                 295                 300

Lys Val Ser Asn Lys Lys Gln Xaa Asn Pro Phe Glu Lys Thr Xaa Ser
305                 310                 315                 320

Lys Ser Lys Arg Gln Thr Arg Glu Pro Xaa Val Tyr Asn Leu Pro Pro
                325                 330                 335
```

```
Ser Arg Xaa Glu Leu Thr Lys Ile Gln Val Ser Leu Thr Xaa Xaa Val
            340                 345                 350

Lys Xaa Phe Xaa Pro Ser Asp Xaa Ala Val Glu Trp Glu Ser Asn Gly
        355                 360                 365

Gln Pro Glu Asn Xaa Tyr Lys Xaa Thr Pro Pro Val Leu Asp Ser Asp
    370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
                405                 410                 415

Asn His Tyr Thr Gln Lys Ser Leu Ser Leu Ser Pro Gly Lys Gly Ser
            420                 425                 430

Ala Gly Gly Ser Gly Gly Leu Asn Asp Ile Phe Glu Ala Gln Lys Ile
        435                 440                 445

Glu Trp His Glu Ser Arg Gly Ser Leu
    450                 455


<210> SEQ ID NO 69
<211> LENGTH: 415
<212> TYPE: PRT
<213> ORGANISM: Artificial Sequence
<220> FEATURE:
<223> OTHER INFORMATION: Human VISTA - Human IgG1 Fc fusion protein
      pFUSE-hIgG1e3-Fc2

<400> SEQUENCE: 69

Met Tyr Arg Met Gln Leu Leu Ser Cys Ile Ala Leu Ser Leu Ala Leu
1               5                   10                  15

Val Thr Asn Ser Phe Lys Val Ala Thr Pro Tyr Ser Leu Tyr Val Cys
            20                  25                  30

Pro Glu Gly Gln Asn Val Thr Leu Thr Cys Arg Leu Leu Gly Pro Val
        35                  40                  45

Asp Lys Gly His Asp Val Thr Phe Tyr Lys Thr Trp Tyr Arg Ser Ser
    50                  55                  60

Arg Gly Glu Val Gln Thr Cys Ser Glu Arg Arg Pro Ile Arg Asn Leu
65                  70                  75                  80

Thr Phe Gln Asp Leu His Leu His His Gly Gly His Gln Ala Ala Asn
                85                  90                  95

Thr Ser His Asp Leu Ala Gln Arg His Gly Leu Glu Ser Ala Ser Asp
            100                 105                 110

His His Gly Asn Phe Ser Ile Thr Met Arg Asn Leu Thr Leu Leu Asp
        115                 120                 125

Ser Gly Leu Tyr Cys Cys Leu Val Val Glu Ile Arg His His His Ser
    130                 135                 140

Glu His Arg Val His Gly Ala Met Glu Leu Gln Val Gln Thr Gly Lys
145                 150                 155                 160

Asp Ala Pro Ser Asn Cys Val Val Tyr Pro Ser Ser Ser Gln Asp Ser
                165                 170                 175

Glu Asn Ile Thr Ala Ala Ala Arg Ser Ile Ser Ala Met Val Arg Ser
            180                 185                 190

Val Glu Cys Pro Pro Cys Pro Ala Pro Pro Val Ala Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
```

-continued

```
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Gly Leu Pro Ser Ser Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
        355                 360                 365

Asp Gly Ser Phe Phe Leu Tyr Ser Lys Leu Thr Val Asp Lys Ser Arg
    370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415


<210> SEQ ID NO 70
<211> LENGTH: 203
<212> TYPE: PRT
<213> ORGANISM: Artificial Sequence
<220> FEATURE:
<223> OTHER INFORMATION: VISTA Ig fusion protein Fc domain concensus
<220> FEATURE:
<221> NAME/KEY: X
<222> LOCATION: (3)..(3)
<223> OTHER INFORMATION: T or P
<220> FEATURE:
<221> NAME/KEY: X
<222> LOCATION: (12)..(12)
<223> OTHER INFORMATION: unsure
<220> FEATURE:
<221> NAME/KEY: X
<222> LOCATION: (24)..(24)
<223> OTHER INFORMATION: unsure
<220> FEATURE:
<221> NAME/KEY: X
<222> LOCATION: (32)..(32)
<223> OTHER INFORMATION: unsure
<220> FEATURE:
<221> NAME/KEY: X
<222> LOCATION: (40)..(40)
<223> OTHER INFORMATION: unsure
<220> FEATURE:
<221> NAME/KEY: X
<222> LOCATION: (42)..(42)
<223> OTHER INFORMATION: unsure
<220> FEATURE:
<221> NAME/KEY: X
<222> LOCATION: (43)..(43)
<223> OTHER INFORMATION: unsure
<220> FEATURE:
<221> NAME/KEY: X
<222> LOCATION: (51)..(52)
<223> OTHER INFORMATION: unsure
<220> FEATURE:
<221> NAME/KEY: X
<222> LOCATION: (54)..(55)
<223> OTHER INFORMATION: unsure
<220> FEATURE:
```

<221> NAME/KEY: X
<222> LOCATION: (56)..(56)
<223> OTHER INFORMATION: L or Y
<220> FEATURE:
<221> NAME/KEY: X
<222> LOCATION: (57)..(57)
<223> OTHER INFORMATION: unsure
<220> FEATURE:
<221> NAME/KEY: X
<222> LOCATION: (58)..(58)
<223> OTHER INFORMATION: M or V
<220> FEATURE:
<221> NAME/KEY: X
<222> LOCATION: (59)..(59)
<223> OTHER INFORMATION: G or V
<220> FEATURE:
<221> NAME/KEY: X
<222> LOCATION: (60)..(61)
<223> OTHER INFORMATION: unsure
<220> FEATURE:
<221> NAME/KEY: X
<222> LOCATION: (64)..(65)
<223> OTHER INFORMATION: unsure
<220> FEATURE:
<221> NAME/KEY: X
<222> LOCATION: (66)..(66)
<223> OTHER INFORMATION: Q or H
<220> FEATURE:
<221> NAME/KEY: X
<222> LOCATION: (72)..(72)
<223> OTHER INFORMATION: unsure
<220> FEATURE:
<221> NAME/KEY: X
<222> LOCATION: (74)..(74)
<223> OTHER INFORMATION: D or E
<220> FEATURE:
<221> NAME/KEY: X
<222> LOCATION: (77)..(77)
<223> OTHER INFORMATION: F or C
<220> FEATURE:
<221> NAME/KEY: X
<222> LOCATION: (83)..(83)
<223> OTHER INFORMATION: K or G
<220> FEATURE:
<221> NAME/KEY: X
<222> LOCATION: (84)..(84)
<223> OTHER INFORMATION: Q or L
<220> FEATURE:
<221> NAME/KEY: X
<222> LOCATION: (85)..(85)
<223> OTHER INFORMATION: unsure
<220> FEATURE:
<221> NAME/KEY: X
<222> LOCATION: (86)..(86)
<223> OTHER INFORMATION: N or S
<220> FEATURE:
<221> NAME/KEY: X
<222> LOCATION: (87)..(87)
<223> OTHER INFORMATION: P or S
<220> FEATURE:
<221> NAME/KEY: X
<222> LOCATION: (88)..(88)
<223> OTHER INFORMATION: F or I
<220> FEATURE:
<221> NAME/KEY: X
<222> LOCATION: (92)..(92)
<223> OTHER INFORMATION: unsure
<220> FEATURE:
<221> NAME/KEY: X
<222> LOCATION: (95)..(95)
<223> OTHER INFORMATION: S or A
<220> FEATURE:
<221> NAME/KEY: X
<222> LOCATION: (97)..(97)
<223> OTHER INFORMATION: R or G
<220> FEATURE:
<221> NAME/KEY: X
<222> LOCATION: (99)..(99)
<223> OTHER INFORMATION: T or P
<220> FEATURE:
<221> NAME/KEY: X
<222> LOCATION: (103)..(103)
<223> OTHER INFORMATION: unsure
<220> FEATURE:
<221> NAME/KEY: X
<222> LOCATION: (106)..(106)
<223> OTHER INFORMATION: N or T
<220> FEATURE:
<221> NAME/KEY: X
<222> LOCATION: (112)..(112)
<223> OTHER INFORMATION: unsure
<220> FEATURE:
<221> NAME/KEY: X
<222> LOCATION: (114)..(114)
<223> OTHER INFORMATION: L or M
<220> FEATURE:
<221> NAME/KEY: X
<222> LOCATION: (117)..(117)
<223> OTHER INFORMATION: I or N
<220> FEATURE:
<221> NAME/KEY: X
<222> LOCATION: (123)..(124)
<223> OTHER INFORMATION: unsure
<220> FEATURE:
<221> NAME/KEY: X
<222> LOCATION: (127)..(127)
<223> OTHER INFORMATION: unsure
<220> FEATURE:
<221> NAME/KEY: X
<222> LOCATION: (129)..(129)
<223> OTHER INFORMATION: unsure
<220> FEATURE:
<221> NAME/KEY: X
<222> LOCATION: (133)..(133)
<223> OTHER INFORMATION: unsure
<220> FEATURE:
<221> NAME/KEY: X
<222> LOCATION: (146)..(146)
<223> OTHER INFORMATION: unsure
<220> FEATURE:
<221> NAME/KEY: X
<222> LOCATION: (149)..(149)
<223> OTHER INFORMATION: unsure

<400> SEQUENCE: 70

```
Pro Lys Xaa Lys Asp Thr Leu Met Ile Ser Arg Xaa Pro Glu Val Thr
1               5                   10                  15

Cys Val Val Val Asp Val Ser Xaa Glu Asp Pro Glu Val Lys Phe Xaa
            20                  25                  30

Trp Tyr Val Asp Gly Val Glu Xaa His Xaa Xaa Lys Thr Lys Pro Arg
        35                  40                  45

Glu Glu Xaa Xaa Asn Xaa Xaa Xaa Xaa Xaa Xaa Xaa Xaa Leu Thr Xaa
    50                  55                  60

Xaa Xaa Gln Asp Trp Leu Asn Xaa Lys Xaa Tyr Lys Xaa Lys Val Ser
65                  70                  75                  80

Asn Lys Xaa Xaa Xaa Xaa Xaa Xaa Glu Lys Thr Xaa Ser Lys Xaa Lys
                85                  90                  95

Xaa Gln Xaa Arg Glu Pro Xaa Val Tyr Xaa Leu Pro Pro Ser Arg Xaa
            100                 105                 110

Glu Xaa Thr Lys Xaa Gln Val Ser Leu Thr Xaa Xaa Val Lys Xaa Phe
        115                 120                 125

Xaa Pro Ser Asp Xaa Ala Val Glu Trp Glu Ser Asn Gly Gln Pro Glu
    130                 135                 140

Asn Xaa Tyr Lys Xaa Thr Pro Pro Val Leu Asp Ser Asp Gly Ser Phe
145                 150                 155                 160

Phe Leu Tyr Ser Lys Leu Thr Val Asp Lys Ser Arg Trp Gln Gln Gly
                165                 170                 175
```

```
Asn Val Phe Ser Cys Ser Val Met His Glu Ala Leu His Asn His Tyr
            180                 185                 190

Thr Gln Lys Ser Leu Ser Leu Ser Pro Gly Lys
        195                 200


<210> SEQ ID NO 71
<211> LENGTH: 19
<212> TYPE: PRT
<213> ORGANISM: Artificial Sequence
<220> FEATURE:
<223> OTHER INFORMATION: Serine-glycine linker

<400> SEQUENCE: 71

Gly Thr Ser Gly Ser Ser Gly Ser Gly Ser Gly Gly Ser Gly Ser Gly
1               5                   10                  15

Gly Gly Gly


<210> SEQ ID NO 72
<211> LENGTH: 427
<212> TYPE: PRT
<213> ORGANISM: Artificial Sequence
<220> FEATURE:
<223> OTHER INFORMATION: VISTA Ig fusion protein with serine-glycine
      linker

<400> SEQUENCE: 72

Met Tyr Arg Met Gln Leu Leu Ser Cys Ile Ala Leu Ser Leu Ala Leu
1               5                   10                  15

Val Thr Asn Ser Phe Lys Val Ala Thr Pro Tyr Ser Leu Tyr Val Cys
            20                  25                  30

Pro Glu Gly Gln Asn Val Thr Leu Thr Cys Arg Leu Leu Gly Pro Val
        35                  40                  45

Asp Lys Gly His Asp Val Thr Phe Tyr Lys Thr Trp Tyr Arg Ser Ser
    50                  55                  60

Arg Gly Glu Val Gln Thr Cys Ser Glu Arg Arg Pro Ile Arg Asn Leu
65                  70                  75                  80

Thr Phe Gln Asp Leu His Leu His His Gly Gly His Gln Ala Ala Asn
                85                  90                  95

Thr Ser His Asp Leu Ala Gln Arg His Gly Leu Glu Ser Ala Ser Asp
            100                 105                 110

His His Gly Asn Phe Ser Ile Thr Met Arg Asn Leu Thr Leu Leu Asp
        115                 120                 125

Ser Gly Leu Tyr Cys Cys Leu Val Val Glu Ile Arg His His His Ser
    130                 135                 140

Glu His Arg Val His Gly Ala Met Glu Leu Gln Val Gln Thr Gly Lys
145                 150                 155                 160

Asp Ala Pro Ser Asn Cys Val Val Tyr Pro Ser Ser Ser Gln Asp Ser
                165                 170                 175

Glu Asn Ile Thr Ala Ala Ala Gly Thr Ser Gly Ser Ser Gly Ser Gly
            180                 185                 190

Ser Gly Gly Ser Gly Ser Gly Gly Gly Gly Arg Ser Val Glu Cys Pro
        195                 200                 205

Pro Cys Pro Ala Pro Pro Val Ala Gly Pro Ser Val Phe Leu Phe Pro
    210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
```

```
                245                 250                 255

Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
        275                 280                 285

Leu His Gln Asp Trp Leu Asn Gly Lys Glu Tyr Lys Cys Lys Val Ser
    290                 295                 300

Asn Lys Gly Leu Pro Ser Ser Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
        355                 360                 365

Asn Asn Tyr Lys Thr Thr Pro Pro Val Leu Asp Ser Asp Gly Ser Phe
    370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425
```

<210> SEQ ID NO 73
<211> LENGTH: 484
<212> TYPE: PRT
<213> ORGANISM: Artificial Sequence
<220> FEATURE:
<223> OTHER INFORMATION: VISTA-Ig fusion protein

<400> SEQUENCE: 73

```
Met Pro Met Gly Ser Leu Gln Pro Leu Ala Thr Leu Tyr Leu Leu Gly
1               5                   10                  15

Met Leu Val Ala Ser Cys Leu Gly Thr Ser Met Ser Leu Leu Phe Ala
            20                  25                  30

Leu Phe Leu Ala Ala Ser Leu Gly Pro Val Ala Ala Phe Lys Val Ala
        35                  40                  45

Thr Pro Tyr Ser Leu Tyr Val Cys Pro Glu Gly Gln Asn Val Thr Leu
    50                  55                  60

Thr Cys Arg Leu Leu Gly Pro Val Asp Lys Gly His Asp Val Thr Phe
65                  70                  75                  80

Tyr Lys Thr Trp Tyr Arg Ser Ser Arg Gly Glu Val Gln Thr Cys Ser
                85                  90                  95

Glu Arg Arg Pro Ile Arg Asn Leu Thr Phe Gln Asp Leu His Leu His
            100                 105                 110

His Gly Gly His Gln Ala Ala Asn Thr Ser His Asp Leu Ala Gln Arg
        115                 120                 125

His Gly Leu Glu Ser Ala Ser Asp His His Gly Asn Phe Ser Ile Thr
    130                 135                 140

Met Arg Asn Leu Thr Leu Leu Asp Ser Gly Leu Tyr Cys Cys Leu Val
145                 150                 155                 160

Val Asp Ile Arg His His His Ser Glu His Arg Val His Gly Ala Met
                165                 170                 175

Glu Leu Gln Val Gln Thr Gly Lys Asp Ala Pro Ser Asn Cys Val Val
```

```
            180                 185                 190

Tyr Pro Ser Ser Ser Gln Glu Ser Glu Asn Ile Thr Ala Ala Asp Pro
        195                 200                 205

Gly Gly Gly Gly Gly Arg Leu Val Pro Arg Gly Phe Gly Thr Gly Asp
    210                 215                 220

Pro Glu Pro Lys Ser Ser Asp Lys Thr His Thr Cys Pro Pro Cys Pro
225                 230                 235                 240

Ala Pro Glu Phe Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Thr Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys Gly Ser Ala Gly Gly Ser Gly
    450                 455                 460

Gly Leu Asn Asp Ile Phe Glu Ala Gln Lys Ile Glu Trp His Glu Ser
465                 470                 475                 480

Arg Gly Ser Leu
```

<210> SEQ ID NO 74
<211> LENGTH: 232
<212> TYPE: PRT
<213> ORGANISM: Artificial Sequence
<220> FEATURE:
<223> OTHER INFORMATION: Human IgG1 concensus sequence
<220> FEATURE:
<221> NAME/KEY: X
<222> LOCATION: (5)..(5)
<223> OTHER INFORMATION: S or C
<220> FEATURE:
<221> NAME/KEY: X
<222> LOCATION: (19)..(19)
<223> OTHER INFORMATION: F or L
<220> FEATURE:
<221> NAME/KEY: X
<222> LOCATION: (20)..(20)
<223> OTHER INFORMATION: E or L
<220> FEATURE:
<221> NAME/KEY: X
<222> LOCATION: (22)..(22)
<223> OTHER INFORMATION: A or G
<220> FEATURE:
<221> NAME/KEY: X
<222> LOCATION: (115)..(115)
<223> OTHER INFORMATION: T or A
<220> FEATURE:
<221> NAME/KEY: X
<222> LOCATION: (141)..(141)
<223> OTHER INFORMATION: D or E
<220> FEATURE:
<221> NAME/KEY: X
<222> LOCATION: (143)..(143)
<223> OTHER INFORMATION: L or M

<400> SEQUENCE: 74

Glu Pro Lys Ser Xaa Asp Lys Thr His Thr Cys Pro Pro Cys Pro Ala
1 5 10 15

Pro Glu Xaa Xaa Gly Xaa Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Xaa Pro Ile Glu Lys Thr Ile Ser Lys Ala Lys Gly Gln Pro
115 120 125

Arg Glu Pro Gln Val Tyr Thr Leu Pro Pro Ser Arg Xaa Glu Xaa Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 75
<211> LENGTH: 413
<212> TYPE: PRT
<213> ORGANISM: Artificial Sequence
<220> FEATURE:
<223> OTHER INFORMATION: Human VISTA Ig construct

<400> SEQUENCE: 75

Phe Lys Val Ala Thr Pro Tyr Ser Leu Tyr Val Cys Pro Glu Gly Gln
1 5 10 15

Asn Val Thr Leu Thr Cys Arg Leu Leu Gly Pro Val Asp Lys Gly His
20 25 30

Asp Val Thr Phe Tyr Lys Thr Trp Tyr Arg Ser Ser Arg Gly Glu Val

-continued

```
        35                  40                  45

Gln Thr Cys Ser Glu Arg Arg Pro Ile Arg Asn Leu Thr Phe Gln Asp
    50                  55                  60

Leu His Leu His His Gly Gly His Gln Ala Ala Asn Thr Ser His Asp
65                  70                  75                  80

Leu Ala Gln Arg His Gly Leu Glu Ser Ala Ser Asp His His Gly Asn
                85                  90                  95

Phe Ser Ile Thr Met Arg Asn Leu Thr Leu Leu Asp Ser Gly Leu Tyr
            100                 105                 110

Cys Cys Leu Val Val Asp Ile Arg His His His Ser Glu His Arg Val
        115                 120                 125

His Gly Ala Met Glu Leu Gln Val Gln Thr Gly Lys Asp Ala Pro Ser
    130                 135                 140

Asn Cys Val Val Tyr Pro Ser Ser Ser Gln Glu Ser Glu Asn Ile Thr
145                 150                 155                 160

Ala Ala Asp Pro Gly Gly Gly Gly Gly Arg Leu Val Pro Arg Gly Phe
                165                 170                 175

Gly Thr Gly Asp Pro Glu Pro Lys Ser Ser Asp Lys Thr His Thr Cys
            180                 185                 190

Pro Pro Cys Pro Ala Pro Glu Phe Glu Gly Ala Pro Ser Val Phe Leu
        195                 200                 205

Phe Pro Pro Lys Pro Lys Asp Thr Leu Met Ile Ser Arg Thr Pro Glu
    210                 215                 220

Val Thr Cys Val Val Val Asp Val Ser His Glu Asp Pro Glu Val Lys
225                 230                 235                 240

Phe Asn Trp Tyr Val Asp Gly Val Glu Val His Asn Ala Lys Thr Lys
                245                 250                 255

Pro Arg Glu Glu Gln Tyr Asn Ser Thr Tyr Arg Val Val Ser Val Leu
            260                 265                 270

Thr Val Leu His Gln Asp Trp Leu Asn Gly Lys Glu Tyr Lys Cys Lys
        275                 280                 285

Val Ser Asn Lys Ala Leu Pro Thr Pro Ile Glu Lys Thr Ile Ser Lys
    290                 295                 300

Ala Lys Gly Gln Pro Arg Glu Pro Gln Val Tyr Thr Leu Pro Pro Ser
305                 310                 315                 320

Arg Asp Glu Leu Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Val Leu Asp Ser Asp Gly
        355                 360                 365

Ser Phe Phe Leu Tyr Ser Lys Leu Thr Val Asp Lys Ser Arg Trp Gln
    370                 375                 380

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys
                405                 410
```

VISTA MODULATORS FOR DIAGNOSIS AND TREATMENT OF CANCER

RELATED APPLICATION DISCLOSURE

This application is a divisional application of U.S. Ser. No. 14/158,531, filed Jan. 17, 2014, and claims the benefit of U.S. Ser. No. 61/753,682, filed Jan. 17, 2013, entitled "VISTA MODULATORS FOR DIAGNOSIS AND TREATMENT OF CANCER", and also is a continuation-in-part of international application no. PCT/US13/58785, filed Sep. 9, 2013, entitled "VISTA MODULATORS FOR DIAGNOSIS AND TREATMENT OF CANCER" which claims the benefit of U.S. Ser. No. 61/698,003, filed Sep. 7, 2012 and is a continuation-in-part of international application no. PCT/US2013/047009, filed Jun. 21, 2013, entitled "NOVEL VISTA-IG CONSTRUCTS AND THE USE OF VISTA-IG FOR TREATMENT OF AUTOIMMUNE, ALLERGIC AND INFLAMMATORY DISORDERS" which claims the benefit of U.S. Provisional Application Ser. No. 61/663,431, filed Jun. 22, 2012, entitled "VISTA-IG FOR TREATMENT OF AUTOIMMUNE DISORDERS AND INFLAMMATORY DISORDERS", U.S. Provisional Application Ser. No. 61/663,969, filed Jun. 25, 2012, entitled "VISTA-IG FOR TREATMENT OF AUTOIMMUNE DISORDERS AND INFLAMMATORY DISORDERS", U.S. Provisional Application Ser. No. 61/735,799, filed Dec. 11, 2012, U.S. Provisional Application Ser. No. 61/776,234, filed Mar. 11, 2013, and U.S. Provisional Application Ser. No. 61/807,135, filed Apr. 1, 2013, each of which is hereby incorporated by reference in its entirety.

GOVERNMENT FUNDING

This invention was made with government support under Grant # AT005382 and Grant # AI098007 awarded by the National Institutes of Health. The government has certain rights in the invention.

SEQUENCE LISTING

The sequence listing in the filed named "43260.0702.txt" having a size of 112,868 bytes that was created Dec. 19, 2017 is hereby incorporated by reference in its entirety.

FIELD

The present disclosure relates to compositions and therapeutic methods for activating an immune response in a patient in need thereof. In a preferred embodiment, the subject methods and compositions are able to antagonize the activity of VISTA, a naturally occurring "checkpoint" protein which contributes to immune tolerance, optionally in combination with an antagonist of a second checkpoint pathway such as PD-1. For example, such methods and compositions may be suitable for preventing and treating colon cancer or another cancer. An exemplary VISTA antagonist, specifically, an anti-VISTA antibody, is demonstrated herein to activate an immune response against cancer cells in vitro and in vivo, thereby conferring protective anti-tumor immunity which decreased tumor burden. Additionally, an additive benefit was observed when a VISTA antagonist was used in combination with a second checkpoint protein antagonist, specifically, an antibody against PD-1 ligand (PD-L1).

In another aspect, the disclosure relates to diagnostic methods comprising measuring the level of expression of VISTA to diagnose disease mediated by immune tolerance. For example, detection of high levels of VISTA expression (e.g., VISTA protein or mRNA) in a patient sample may indicate the presence of a cancer. Additionally, these diagnostic tests may be used to assign a treatment to a patient, for example by administering a VISTA antagonist based upon the detection of a high level of VISTA expression in the patient's sample.

BACKGROUND

Immune responses against foreign pathogens and cancer are regulated by multiple checkpoints, including CTLA-4, PD-L1/PD-1 and B7-H4 pathways. They function as "effector molecules" on multiple immunosuppressive cells, including Tregs, myeloid-derived suppressors (MDSCs) and tolerogenic DCs, to disable tumour-specific T-cell responses.

CTLA-4 is induced on T cells upon activation, and constitutively expressed on Foxp3+CD4+CD25+ natural Tregs (nTreg). CTLA-4 critically regulates peripheral tolerance, suppresses T-cell responses, and contributes to Treg-mediated immune suppression (refs. 6-10). The critical role of CTLA-4 in suppressing tumour-specific immunity is demonstrated when antibody-mediated CTLA-4 blockade in combination with a cellular vaccine induced regression of established poorly immunogenic B16 melanoma (11). Ipilimumab, the human aCTLA-4 mAb, has been approved for treating advanced melanoma, although the survival response in metastatic melanoma is modest (12). It has also undergone early phase trials for other cancers (13). However, consistent with the severe autoimmune phenotypes in CTLA-4 knockout (KO) mice, aCTLA-4 therapy was associated with serious autoimmune toxicity in patients (14).

Programmed Death-1 (PD-1) and its ligand PD-L1 represent another immune checkpoint pathway (refs. 15, 16). PD-1 KO mice developed autoimmune disease (refs. 17, 18). In cancer, aberrant PD-L1 expression is seen on tumour cells, which correlates with poorer prognosis in cancer patients (refs. 19, 20). PD-L1/PD-1 axis downregulates tumour-specific immunity by inducing T-cell apoptosis, anergy, resistance to cytotoxic T-cell mediated lysis, functional exhaustion, and IL10 production (refs. 21-23). We and others previously demonstrated that PD-L1 expression on DCs promotes the induction of Foxp3+ adaptive Tregs (aTregs), and PD-L1 is a potent inducer of aTregs within the TME (2). Blocking the PD-L1/PD-1 pathway, in conjunction with other immune therapies such as CTLA-4 blockade, inhibits tumour progression (refs. 24-29). MDX-1106, the human aPD-1 mAb has entered clinical trials showing promising anti-tumour effect, and reduced toxicity compared to Ipilumimab (30).

B7-H4 is a newer member of the B7 inhibitory ligand family (ref. 31-33). B7-H4 expression is detected on many human cancers. In human ovarian cancer, B7-H4 expression is induced on tumour associated macrophages (TAM), and its blockade restored tumour-specific T-cell responses and contributed to tumour regression (34). Human Tregs also convey suppressive activity to APCs by upregulating B7-H4 expression through IL10 produced by APCs (35).

In summary, immune-checkpoint blockade improved both endogenous and vaccine-elicited anti-tumour immune responses, yet only produced limited responses in clinical trials.

Foxp3+CD4+CD25+ regulatory T cells (Tregs) are critical in maintaining peripheral tolerance under normal physiological conditions, as well as suppressing anti-tumour immune responses in cancer (36-38). In human ovarian cancer, large infiltration of Foxp3+ Tregs is associated with reduced survival (39). Systemic removal of Tregs or attenuation of their functions enhances natural and vaccine-induced antitumor T-cell responses, resulting in improved therapeutic efficacy (37, 40). Tregs activated by IDO+ plasmacytoid DCs upregulate B7-H1 expression on target DCs, and suppress T-cell responses in a PD-L1 dependent manner (41).

Monocytes are precursors for tissue macrophages and monocyte-derived DCs (mo-DC), which play critical roles for both innate and adaptive immunity (42-46). Murine monocytes are identified as CD115+CD11b+F4/80+ (47), consisting of two subsets LY6C+CX3CR1$^{int}$ and LY6C−CX3CR1$^{hi}$ (48, 49). The human counterparts are CD14+ CD16-CCR2+CX3CR1$^{int}$ and CD14loCD16+CX3CR1$^{hi}$ monocytes respectively. Murine Ly6C+ inflammatory monocytes (IMC) are recruited to inflammatory sites and differentiate to M1 macrophages and inflammatory mo-DCs, which produce high levels of TNF/iNOS (Tip DCs) and are critical for microbial clearance43, 50-53. In contrast, resident LY6C$^{neg}$ monocytes patrol blood vessels in the steady state, and differentiate into M2-like macrophages during infection and inflammation (46).

IMC critically influence the adaptive immune response. In man, TLR induces the differentiation of monocytes into macrophages and mo-DCs, which are required for optimal T-cell responses (54, 55). In mouse models, monocyte-derived M1 macrophages and mo-DCs are essential for the induction of T cell immunity against microbial infection or vaccination, via the production of inflammatory cytokines such as IL-12, and direct T-cell priming (56-58).

In tumour-bearing mice and cancer patients, IMCs expand aberrantly and contribute to the mononuclear subset of myeloid-derived suppressor cells (MDSC) (59-61). MDSCs are collectively marked as CD11b+Gr1+, consisting of the mononuclear (Ly6G+/−LY6C$^{-hi}$) and the granulocytic (Ly6G+LY6C$^{low}$) subset (62). MDSCs suppress T cells responses and impede the efficacy of cancer immunotherapies (60, 62-64). Strategies to eliminate MDSCs, or neutralize their activity, or induce their differentiation have shown efficacy in cancer immunotherapy (60, 63). The majority of tumour-associated DCs are monocyte-derived DCs. They are typically defective in antigen-presentation, lack costimulatory molecules, and upregulate inhibitory molecules such as PD-L1 (29, 65, 66). As such, these mo-DCs do not effectively prime T-cell responses, resulting in deletional tolerance, or the induction of functionally inert T cells, and even the expansion and induction of Tregs (40, 60, 62, 63, 67, 68). Therapeutic targeting of tumour DCs by PD-L1 blockade, CD40/TLR stimulation, or immunotoxin-mediated depletion significantly increased tumour-specific T-cell responses and enhanced survival (29, 69-74).

We have recently discovered a novel Immunoglobulin (Ig) family ligand, designated V-domain Immunoglobulin Suppressor of T cell Activation (VISTA) (Genbank: JN602184)75. Key features of VISTA include the following. VISTA bears limited homology to PD-L1, but does not belong to the B7 family due to its unique structure. VISTA is exclusively expressed within the hematopoietic compartment, with very high levels of expression on CD11b$^{high}$ myeloid cells, and lower expression levels on CD4+ and CD8+ T cells, and Tregs. A soluble VISTA-Ig fusion protein or VISTA expressed on APCs, acts as a ligand to suppress CD4+ and CD8+ T cell proliferation and cytokine production, via an unidentified receptor independent of PD-1. An anti-VISTA mAb (13F3) reversed VISTA-mediated T cell suppression in vitro and suppressed tumour growth in multiple murine tumour models by enhancing the anti-tumour T cell responses. VISTA over-expression on tumour cells impaired protective anti-tumour immunity in vaccinated hosts. VISTA KO mice develop an inflammatory phenotype, which points towards a loss of peripheral tolerance. See U.S. Pat. Nos. 8,236,304 and 8,231,872, Published International Applications WO/2011/120013 and WO/2006/116181, U.S. Published Application Nos. 2008/0287358, 2011/0027278, and 2012/0195894, and U.S. Provisional Patent Application Ser Nos. 60/674,567, filed Apr. 25, 2005, 61/663,431, filed Jun. 22, 2012, Ser. No. 61/663,969, filed Jun. 25, 2012, 61/390,434, filed Oct. 6, 2010, 61/436,379, filed Jan. 26, 2011, and 61/449,882, filed Mar. 7, 2011, each of which is hereby incorporated by reference in its entirety.

We therefore hypothesize that VISTA is a novel immune checkpoint protein ligand that critically regulates immune responses, and VISTA blockade will reverse the suppressive character of the tumour microenvironment (TME) and lead to the development of protective anti-tumour immunity.

The immune system is tightly controlled by co-stimulatory and co-inhibitory ligands and receptors. These molecules provide not only a second signal for T cell activation but also a balanced network of positive and negative signals to maximize immune responses against infection while limiting immunity to self.

Induction of an immune response requires T cell expansion, differentiation, contraction and establishment of T cell memory. T cells must encounter antigen presenting cells (APCs) and communicate via T cell receptor (TCR)/major histocompatibility complex (MHC) interactions on APCs. Once the TCR/MHC interaction is established, other sets of receptor-ligand contacts between the T cell and the APC are required, i.e. co-stimulation via CD154/CD40 and CD28/B7.1-B7.2. The synergy between these contacts results in a productive immune response capable of clearing pathogens and tumors, and may be capable of inducing autoimmunity.

Another level of control has been identified, namely regulatory T cells ($T_{reg}$). This specific subset of T cells is generated in the thymus, delivered into the periphery, and is capable of constant and inducible control of T cells responses. Sakaguchi (2000) Cell 101(5):455-8; Shevach (2000) *Annu. Rev. Immunol.* 18:423-49; Bluestone and Abbas (2003) *Nat. Rev. Immunol.* 3(3):253-7. $T_{reg}$ are represented by a CD4+CD25+ phenotype and also express high levels of cytotoxic T lymphocyte-associated antigen-4 (CTLA-4), OX-40, 4-1BB and the glucocorticoid inducible TNF receptor-associated protein (GITR). McHugh, et al. (2002) *Immunity* 16(2):311-23; Shimizu, et al. (2002) *Nat. Immun.* 3(2):135-42. Elimination of $T_{reg}$ cells by 5 day neonatal thymectomy or antibody depletion using anti-CD25, results in the induction of autoimmune pathology and exacerbation of T cells responses to foreign and self-antigens, including heightened anti-tumor responses. Sakaguchi, et al. (1985) *J. Exp. Med.* 161(1):72-87; Sakaguchi, et al. (1995) *J. Immunol.* 155(3):1151-64; Jones, et al. (2002) *Cancer Immun.* 2:1. In addition, $T_{reg}$ have also been involved in the induction and maintenance of transplantation tolerance, since depletion of $T_{reg}$ with anti-CD25 monoclonal antibodies results in ablation of transplantation tolerance and rapid graft rejection. Jarvinen, et al. (2003) *Transplantation* 76:1375-9. Among the receptors expressed by $T_{reg}$ GITR seems to be an important component since ligation of GITR on the surface of Treg with an agonistic monoclonal antibody results in rapid termination of $T_{reg}$ activity, resulting in autoimmune pathology and ablation of transplantation tolerance.

Costimulatory and co-inhibitory ligands and receptors not only provide a “second signal” for T cell activation, but also a balanced network of positive and negative signal to maximize immune responses against infection while limiting immunity to self. The best characterized costimulatory ligands are B7.1 and B7.2, which are expressed by professional APCs, and whose receptors are CD28 and CTLA-4. Greenwald, et al. (2005) *Annu Rev Immunol* 23, 515-548; Sharpe and Freeman (2002) *Nat Rev Immunol* 2, 116-126. CD28 is expressed by naïve and activated T cells and is critical for optimal T cell activation. In contrast, CTLA-4 is induced upon T cell activation and inhibits T cell activation by binding to B7.1/B7.2, thus impairing CD28-mediated costimulation. CTLA-4 also transduces negative signaling through its cytoplasmic ITIM motif. Teft, et al. (2006). *Annu Rev Immunol* 24, 65-97. B7.1/37.2 KO mice are impaired in adaptive immune response (Borriello, et al. (1997) *Immunity* 6, 303-313; Freeman, et al. (1993) *Science* 262, 907-909), whereas CTLA-4 KO mice can not adequately control inflammation and develop systemic autoimmune diseases. Chambers, et al. (1997) *Immunity* 7, 885-895; Tivol, et al. (1995) *Immunity* 3, 541-547; Waterhouse, et al. (1995) *Science* 270, 985-988. The B7 family ligands have expanded to include costimulatory B7-H2 (ICOS Ligand) and B7-H3, as well as co-inhibitory B7-H1 (PD-L1), B7-DC (PD-L2), B7-H4 (B7S1 or B7x), and B7-H6. See Brandt, et al. (2009) *J Exp Med* 206, 1495-1503; Greenwald, et al. (2005) *Annu Rev Immunol* 23: 515-548.

Inducible costimulatory (ICOS) molecule is expressed on activated T cells and binds to B7-H2. See Yoshinaga, et al. (1999) *Nature* 402, 827-832. ICOS is important for T cell activation, differentiation and function, as well as essential for T-helper-cell-induced B cell activation, Ig class switching, and germinal center (GC) formation. Dong, et al. (2001) *Nature* 409, 97-101; Tafuri, et al. (2001) *Nature* 409, 105-109; Yoshinaga, et al. (1999) *Nature* 402, 827-832. Programmed Death 1 (PD-1) on the other hand, negatively regulates T cell responses. PD-1 KO mice develop lupus-like autoimmune disease, or autoimmune dilated cardiomyopathy depending upon the genetic background. Nishimura, et al. (1999) *Immunity* 11, 141-151. Nishimura, et al. (2001) *Science* 291: 319-322. The autoimmunity most likely results from the loss of signaling by both ligands PD-L1 and PD-L2. Recently, CD80 was identified as a second receptor for PD-L1 that transduces inhibitory signals into T cells. Butte, et al. (2007) *Immunity* 27: 111-122. The receptor for B7-H3 and B7-H4 still remain unknown.

The best characterized co-stimulatory ligands are B7.1 and B7.2, which belong to the Ig superfamily and are expressed on professional APCs and whose receptors are CD28 and CTLA-4. Greenwald, et al. (2005) *Annu Rev. Immunol.* 23: 515-548. CD28 is expressed by naive and activated T cells and is critical for optimal T cell activation. In contrast, CTLA-4 is induced upon T cell activation and inhibits T cell activation by binding to B7.1/37.2, impairing CD28-mediated co-stimulation. B7.1 and B7.2 KO mice are impaired in adaptive immune response (Borriello, et al. (1997) *Immunity* 6: 303-313), whereas CTLA-4 KO mice cannot adequately control inflammation and develop systemic autoimmune diseases. Tivol, et al. (1995) *Immunity* 3: 541-547; Waterhouse, et al. (1995) *Science* 270: 985-988; Chambers, et al. (1997) *Immunity* 7: 885-895.

The B7 family ligands have expanded to include co-stimulatory B7-H2 (inducible T cell co-stimulator [ICOS] ligand) and B7-H3, as well as co-inhibitory B7-H1 (PD-L1), B7-DC (PD-L2), B7-H4 (B7S1 or B7x), and B7-H6. Greenwald, et al. (2005) *Annu Rev. Immunol.* 23: 515-548; Brandt, et al. (2009) *J. Exp. Med.* 206: 1495-1503. Accordingly, additional CD28 family receptors have been identified. ICOS is expressed on activated T cells and binds to B7-H2. ICOS is a positive coregulator, which is important for T cell activation, differentiation, and function. Yoshinaga, et al. (1999) *Nature* 402: 827-832; Dong, et al. (2001) *J. Mol. Med.* 81: 281-287. In contrast, PD-1 (programmed death 1) negatively regulates T cell responses. PD-1 KO mice developed lupus-like autoimmune disease or autoimmune dilated cardiomyopathy. Nishimura, et al. (1999) *Immunity* 11: 141-151; Nishimura, et al. (2001) *Science* 291: 319-322. The autoimmunity most likely results from the loss of signaling by both ligands PD-L1 and PD-L2. Recently, CD80 was identified as a second receptor for PD-L1 that transduces inhibitory signals into T cells. Butte, et al. (2007) *Immunity* 27: 111-122.

The two inhibitory B7 family ligands, PD-L1 and PD-L2, have distinct expression patterns. PD-L2 is inducibly expressed on DCs and macrophages, whereas PD-L1 is broadly expressed on both hematopoietic cells and nonhematopoietic cell types. Okazaki & Honjo (2006) *Trends Immunol.* 27(4): 195-201; Keir, et al. (2008) *Ann Rev Immunol.* 26: 677-704. Consistent with the immune-suppressive role of PD-1 receptor, a study using PD-$L1^{-/-}$ and PD-$L2^{-/-}$ mice has shown that both ligands have overlapping roles in inhibiting T cell proliferation and cytokine production. Keir, et al. (2006) *J Immunol.* 175(11): 7372-9. PD-L1 deficiency enhances disease progression in both the nonobese diabetic model of autoimmune diabetes and the mouse model of multiple sclerosis (experimental autoimmune encephalomyelitis [EAE]). Ansari, et al. (2003) *J. Exp. Med.* 198: 63-69; Salama, et al. (2003) *J. Exp. Med.* 198: 71-78; Latchman, et al. (2004) *Proc. Natl. Acad. Sci. USA.* 101: 10691-10696. PD-$L1^{-/-}$ T cells produce elevated levels of the proinflammatory cytokines in both disease models. In addition, BM chimera experiments have demonstrated that the tissue expression of PD-L1 (i.e., within pancreas) uniquely contributes to its capacity of regionally controlling inflammation. Keir, et al. (2006) *J. Exp. Med.* 203: 883-895; Keir, et al. (2007) *J. Immunol.* 179: 5064-5070; Grabie, et al. (2007) Circulation 116: 2062-2071. PD-L1 is also highly expressed on placental syncytiotrophoblasts, which critically control the maternal immune responses to allogeneic fetus. Guleria, et al. (2005) *J. Exp. Med.* 202: 231-237.

Consistent with its immune-suppressive role, PD-L1 potently suppresses antitumor immune responses and helps tumors evade immune surveillance. PD-L1 can induce apoptosis of infiltrating cytotoxic $CD8^+$ T cells, which express a high level of PD-1. Dong, et al. (2002) *Nat. Med.* 8: 793-800; Dong and Chen (2003) *J. Mol. Med.* 81: 281-287. Blocking the PD-L1-PD-1 signaling pathway, in conjunction with other immune therapies, prevents tumor progression by enhancing antitumor CTL activity and cytokine production. Iwai, et al. (2002) *Proc. Natl. Acad. Sci. USA* 99: 12293-12297; Blank, et al. (2004) *Cancer Res.* 64: 1140-1145; Blank, et al. (2005) *Cancer Immunol. Immunother.* 54: 307-314; Geng, et al. (2006) *Int. J. Cancer* 118: 2657-2664. PD-L1 expression on DCs promotes the induction of adaptive $Foxp3^+CD4^+$ regulatory T cells ($T_{reg}$ cells), and PD-L1 is a potent inducer of a $T_{reg}$ cells within the tumor microenvironment. Wang, et al. (2008) *Proc Natl. Acad. Sci. USA* 105: 9331-9336. Recent advances in targeting B7 family regulatory molecules show promise in treating immune-related diseases such as autoimmunity and cancer. Keir, et al. (2008) *Annu. Rev. Immunol.* 26: 677-704; Zou and Chen (2008) *Nat. Rev. Immunol.* 8: 467-477.

Autoimmune Disease

An autoimmune disorder is a condition that occurs when the immune system mistakenly attacks and destroys healthy body tissue. There are more than 80 different types of autoimmune disorders. Normally the immune system's white blood cells help protect the body from harmful substances, called antigens. Examples of antigens include bacteria, viruses, toxins, cancer cells, and blood or tissues from another person or species. The immune system produces antibodies that destroy these harmful substances. However, in patients with an autoimmune disorder, the immune system can not distinguish between self and non-self (e.g., healthy tissue and foreign antigens). The result is an immune response that destroys normal body tissues. This response is a hypersensitivity reaction similar to the response in allergic conditions. In allergies, the immune system reacts to an outside substance that it normally would ignore. With autoimmune disorders, the immune system reacts to normal body tissues that it would normally ignore, the cause of which is unknown.

An autoimmune disorder may result in the destruction of one or more types of body tissue, abnormal growth of an organ, and changes in organ function and may affect one or more organ or tissue types. Organs and tissues commonly affected by autoimmune disorders include blood vessels, connective tissues, endocrine glands (e.g., thyroid or pancreas), joints, muscles, red blood cells, and skin. A person may have more than one autoimmune disorder at the same time.

Symptoms of an autoimmune disease vary based on the disease and location of the abnormal immune response. Common symptoms that often occur with autoimmune diseases include fatigue, fever, and a general ill-feeling (malaise). Tests that may be done to diagnose an autoimmune disorder may include: antinuclear antibody tests, autoantibody tests, CBC, C-reactive protein (CRP), and erythrocyte sedimentation rate (ESR).

Medicines are often prescribed to control or reduce the immune system's response. They are often called immunosuppressive medicines. Such medicines may include corticosteroids (such as prednisone) and nonsteroid drugs such as azathioprine, cyclophosphamide, mycophenolate, sirolimus, or tacrolimus.

Complications are common and depend on the disease. Side effects of medications used to suppress the immune system can be severe, such as infections that can be hard to control. "Autoimmune disorders." MedlinePlus—U.S. National Library of Medicine (Apr. 19, 2012).

Inflammatory Conditions

Inflammation is part of the complex biological response of vascular tissues to harmful stimuli, such as pathogens, damaged cells, or irritants. Inflammation is a protective attempt by the organism to remove the injurious stimuli and to initiate the healing process. Without inflammation, wounds and infections would never heal. Similarly, progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma).

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. Kindt, et al. (2006) *Kuby Immunology* [$6^{th}$ Ed.]

T-cells are involved in the promulgation of inflammation. Differentiation of naïve T cells leads to the generation of T-cell subsets, each possessing distinct cytokine expression profiles for serving different immune functions. Through the activation of separate signaling pathways, this process results in both differentiated helper T (Th) cells, termed Th1, Th2 and Th17, and induced regulatory T cells, which suppress Th cells. These different cells are important for combating infectious diseases and cancers; however, when aberrant, they can be responsible for chronic inflammatory diseases. One such disease is inflammatory bowel disease (IBD), in which each T-cell subset can have a role in disease. Zenewicz, et al. (2009) Trends in Molecular Medicine 15(5): 199-207. Therefore, T cells are involved in both autoimmune disorders and inflammatory conditions and there is a need in the art for a novel molecule that can modulate the activity of T cells for the treatment of autoimmune disorders and inflammatory conditions.

SUMMARY

Cancer immunotherapies that target immune checkpoint proteins such as CTLA-4 and PD-1 have shown promising outcomes in clinical trials. This is especially promising considering the poor prognosis and treatment options for the patients involved. However, the overall response rate has been disappointingly low, with 6-21% patients in various ipilimumab (aCTLA-4) trials having objective responses 3-5. Therefore, identifying novel checkpoint proteins that play a non-redundant role and synergize with the known checkpoint pathways is critically needed. As a novel immune checkpoint pathway, VISTA provides a new target for immune intervention in cancer. VISTA blockade reverses the suppressive character of the TME, and leads to the development of protective antitumour immunity. The results described herein help show that VISTA blockade is an effective therapeutic strategy for targeting prominent immunosuppressive cells, including Tregs and MDSCs in cancer such as colorectal cancer (CRC).

In one aspect, the present disclosure provides a new paradigm in which a novel immune checkpoint pathway, VISTA, critically controls the anti-tumour immune responses. This paradigm builds a foundation for designing novel therapeutic strategies that target the VISTA pathway. The collaborative interaction between VISTA and another immune checkpoint pathway PD-L1/PD-1 argues against "redundancy", and emphasizes the necessity to target all of the immunosuppressive pathways for maximal impact. Base thereon, the application further provides novel combinatorial strategies and change the current regimes of targeting a single pathway in cancer immunotherapy. Moreover, the study of the role of VISTA during natural tumourigenesis will generate more clinically relevant information, and guide the development of better therapeutic strategies.

The invention provides an isolated VISTA fusion protein comprising a polypeptide with at least about 90% sequence identity to the extracellular domain of the polypeptide sequence of SEQ ID NO: 2, 4, 5, 16-25, 36, or 37 and an immunoglobulin (Ig) protein.

In one embodiment, the polypeptide may have at least about 95% sequence identity to the polypeptide sequence of SEQ ID NO: 2, 4, 5, 16-25, 36, or 37.

In one embodiment, the Ig protein may be IgG, IgG1, IgG2, IgG2a, IgM, IgE, or IgA. In one embodiment, the Ig protein may be the constant and hinge region of human IgG1.

In one embodiment, the extracellular domain of VISTA comprises amino acid residues 32-190 or the extracellular IgV domain of VISTA may comprise amino acids 16-194. In one embodiment, the fusion protein comprises at least two copies of a VISTA protein and IgG1, or IgG2a.

In one embodiment, the fusion protein comprises at least two copies of a VISTA protein and IgG1 Fc or non-FcR-binding IgG1. In one embodiment, the fusion protein comprises at least four copies of a VISTA protein and IgG1 or IgG2a. In one embodiment, the fusion protein comprises at least four copies of a VISTA protein and IgG1 Fc or non-FcR-binding IgG1.

In one embodiment, an isolated multimeric VISTA protein may comprise at least two copies of a polypeptide with at least about 90% sequence identical to the extracellular domain may comprise the polypeptide sequence of SEQ ID NO: 2, 4, or 25. In another embodiment, the polypeptide may have at least about 95% sequence identity to the polypeptide sequence of SEQ ID NO: 2, 4, 5, 16-25, 36, or 37. In another embodiment, the polypeptide may have at least about 90% sequence identity to a fragment of the extracellular domain of said VISTA polypeptide which may be at least 50 amino acids long.

In another embodiment, the fragment of the extracellular domain of said VISTA polypeptide may be at least about 75 amino acids long. In another embodiment, the fragment of the extracellular domain of said VISTA polypeptide may be at least about 100 amino acids long. In another embodiment, the fragment of the extracellular domain of said VISTA polypeptide may be at least about 125 amino acids long.

In another embodiment, the multimeric VISTA protein comprises at least three copies of said extracellular domain or fragment thereof. In another embodiment, the multimeric VISTA protein comprises at least four copies of said extracellular domain or fragment thereof. In another embodiment, the multimeric VISTA protein at least five copies of said extracellular domain or fragment thereof. In another embodiment, the multimeric VISTA protein at least six copies of said extracellular domain or fragment thereof.

In another embodiment, the extracellular domain or fragment may be attached to the N-terminus of an oligomerization domain. In another embodiment, the oligomerization domain may be GCN4, COMP, SNARE, CMP, MAT, LLR containing 1 NLRC, NOD2 nucleotide-binding NLRC2, LRR containing 1 NLRC NOD2 nucleotide-binding NLRC2, or PSORAS1.

In one embodiment, a composition may comprise the VISTA fusion protein. In one embodiment, a composition may comprise the multimeric VISTA protein. In another embodiment, the composition may be a pharmaceutical composition. In another embodiment, the pharmaceutical composition may comprise a pharmaceutically acceptable carrier, excipient, adjuvant, or solution. In another embodiment, the composition may further comprise at least one other immunosuppressive agent. In another embodiment, the immunosuppressive agent may be PD-1, PD-L1, PD-L2, CTLA4, ICOS proteins, or antibodies specific to any of the foregoing.

In one embodiment, a method of treating or preventing inflammation in a subject in need thereof may comprise administering an effective amount of a VISTA fusion protein, optionally a VISTA-Ig, or a multimeric VISTA protein.

In one embodiment, a composition for treating or preventing inflammation may comprise administering an effective amount of a VISTA fusion protein, optionally a VISTA-Ig, or a multimeric VISTA protein.

In another embodiment, the use of an effective amount of a VISTA fusion protein, optionally a VISTA-Ig, or a multimeric VISTA protein for the manufacture of a medicament for treating inflammation.

In another embodiment, the subject may have inflammatory condition.

In another embodiment, the inflammatory condition may be Acid Reflux/Heartburn, Acne, Acne Vulgaris, Allergies and Sensitivities, Alzheimer's Disease, Asthma, Atherosclerosis and Vascular Occlusive Disease, optionally Atherosclerosis, Ischaemic Heart Disease, Myocardial Infarction, Stroke, Peripheral Vascular Disease, or Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases, optionally Systemic Lupus Erythematosus, Systemic Sclerosis, Polymyositis, Dermatomyositis, or Sjogren's Syndrome, Corneal Disease, Crohn's Disease, Crystal Arthropathies, optionally Gout, Pseudogout, Calcium Pyrophosphate Deposition Disease, Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain, Arthritis, Rheumatoid Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases, optionally Rheumatoid Arthritis, Osteoarthritis, or Psoriatic Arthritis, Rheumatoid Arthritis, Sarcoidosis, Scleroderma, Sinusitis, Sjögren's Syndrome, Spastic Colon, Spondyloarthropathies, optionally Ankylosing Spondylitis, Reactive Arthritis, or Reiter's Syndrome, Systemic Candidiasis, Tendonitis, Transplant Rejection, UTI's, Vaginitis, Vascular Diseases including Atherosclerotic Vascular Disease, Vasculitides, optionally Polyarteritis Nodosa, Wegener's Granulomatosis, Churg-Strauss Syndrome, or vasculitis.

In one embodiment, a method of treating an autoimmune disease may comprise administering an effective amount of a VISTA fusion protein, optionally a VISTA-Ig, or a multimeric VISTA protein.

In one embodiment, a composition for treating an autoimmune disease may comprise administering an effective amount of a VISTA fusion protein, optionally a VISTA-Ig, or a multimeric VISTA protein.

In another embodiment, the use of an effective amount of a VISTA fusion protein, optionally a VISTA-Ig, or a multimeric VISTA protein for the manufacture of a medicament of the treatment of an autoimmune disease.

In another embodiment, the autoimmune disease may be a cell mediated autoimmune disease.

In another embodiment, the cell mediate autoimmune disease may be multiple sclerosis, diabetes type I, oophoritis, or thyroiditis.

In another embodiment, the autoimmune disease may be acquired immune deficiency syndrome (AIDS), acquired spenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, optionally, large vessel vasculitis, optionally, polymyalgia rheumatica and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis, optionally allergic alveolitis or fibrosing alveolitis, Alzheimer's disease, amyloidosis, amylotrophic lateral sclerosis (ALS; Lou Gehrig's disease), an eosinophil-related disorder, optionally eosinophilia, anaphylaxis, ankylosing spondylitis, antgiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis, optionally rheumatoid arthritis such as acute arthritis, or chronic rheumatoid arthritis, arthritis chronica progrediente, arthritis deformans, ascariasis, aspergilloma, granulomas containing eosinophils, aspergillosis, aspermiogenese, asthma, optionally asthma bronchiale, bronchial asthma, or auto-immune asthma, ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease, optionally autoimmune inner ear disease (AGED), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies, optionally epilepsy, channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy, optionally IgM polyneuropathies or IgM-mediated neuropathy, chronic obstructive airway disease, chronic pulmonary inflammatory disease, Chronic recurrent multifocal ostomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogans syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, optionally chronic cyclitis, heterochronic cyclitis, iridocyclitis, or Fuch's cyclitis, cystic fibrosis, cytokine-induced toxicity, deafness, degenerative arthritis, demyelinating diseases, optionally autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis, optionally allergic encephalomyelitis or encephalomyelitis allergica and experimental allergic encephalomyelitis (EAE), endarterial hyperplasia, endocarditis, endocrine ophthamopathy, endometriosis. endomyocardial fibrosis, endophthalmia phacoanaphylactica, endophthalmitis, enteritis allergica, eosinophilia-myalgia syndrome, eosinophilic faciitis, epidemic keratoconjunctivitis, epidermolisis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, flariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, haemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases, optionally anaphylaxis and allergic or atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes, optionally Lambert-Eaton myasthenic syndrome or Eaton-Lambert syndrome, parasitic diseases such as Lesihmania, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes, optionally autoimmune polyglandular syndromes (or polyglandular endocrinopathy syndromes), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis, optionally benign monoclonal gammopathy and monoclonal garnmopathy of undetermined significance, MGUS, primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyreoiditis, Raynauds phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma, optionally systemic scleroderma, sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes, cutaneous SLE, systemic necrotizing vasculitis, ANCA-associated vasculitis, optionally Churg-Strauss vasculitis or syndrome (CSS), tabes dorsalis, Takayasu's arteritis, telangiectasia, temporal arteritis/Giant cell arteritis, thromboangitis ubiterans, thrombocytopenia, including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria, optionally chronic allergic urticaria and chronic idiopathic urticaria, including chronic autoimmune urticaria, uveitis, anterior uveitis, uveoretinitis, valvulitis, vascular dysfunction, vasculitis, vertebral arthritis, vesiculobullous dermatosis, vitiligo, Wegener's granulomatosis (Granulomatosis with Polyangiitis (GPA)), Wiskott-Aldrich syndrome, or x-linked hyper IgM syndrome.

In a further embodiment, the method, use, or composition may further comprise the administration of another immune modulator and/or an antigen. In another embodiment, the immune modulator may be a TLR agonist (TLR1, TLR2, TLR3, TLR4, TLR5, TLR6, TLR7, TLR8, TLR9, TLR10, TLR11 agonist), may be a type 1 interferon, optionally alpha interferon or beta interferon, or a CD40 agonist.

In one embodiment, the method of treating an inflammatory disorder may comprise administering an effective amount of a VISTA fusion protein, optionally a VISTA-Ig, or a multimeric VISTA protein.

In one embodiment, the composition for treating an inflammatory disorder may comprise an effective amount of a VISTA fusion protein, optionally a VISTA-Ig, or a multimeric VISTA protein.

In one embodiment, the use of an effective amount of a VISTA fusion protein, optionally a VISTA-Ig, or a multimeric VISTA protein for the manufacture of a medicament for the treatment of an inflammatory disorder.

In one embodiment, the disorder treated may be selected from type 1 diabetes, multiple sclerosis, rheumatoid arthritis, psoriatic arthritis, systemic lupus erythematosis, rheumatic diseases, allergic disorders, asthma, allergic rhinitis, skin disorders, Crohn's disease, ulcerative colitis, transplant rejection, graft-versus-host disease, poststreptococcal and autoimmune renal failure, septic shock, systemic inflammatory response syndrome (SIRS), adult respiratory distress syndrome (ARDS) and envenomation; autoinflammatory diseases, osteoarthritis, crystal arthritis, capsulitis, arthropathies, tendonitis, ligamentitis or traumatic joint injury.

In one embodiment, the disorder treated may be multiple sclerosis or rheumatoid arthritis.

In one embodiment, the method of treating graft-versus-host-disease (GVHD) may comprise administration of an effective amount of an effective amount of a VISTA fusion protein, optionally a VISTA-Ig, or a multimeric VISTA protein.

In one embodiment, the composition for treating graft-versus-host-disease (GVHD) may comprise administration of an effective amount of an effective amount of a VISTA fusion protein, optionally a VISTA-Ig, or a multimeric VISTA protein.

In one embodiment, the use of an effective amount of an effective amount of a VISTA fusion protein, optionally a VISTA-Ig, or a multimeric VISTA protein in the manufacture of a medicament for the treatment of graft-versus-host-disease (GVHD).

In one embodiment, the graft-versus-host-disease may be acute graft-versus-host disease, chronic graft-versus-host disease, acute graft-versus-host disease associated with stem cell transplant, chronic graft-versus-host disease associated with stem cell transplant, acute graft-versus-host disease associated with bone marrow transplant, acute graft-versus-host disease associated with allogeneic hemapoetic stem cell transplant (HSCT), or chronic graft-versus-host disease associated with bone marrow transplant.

In one embodiment, the patient treated may have at least one symptom of graft-versus-host disease (GVHD), optionally wherein the patient exhibits acute GVHD includes but is not limited to abdominal pain, abdominal cramps, diarrhea, fever, jaundice, skin rash, vomiting, and weight loss. In one embodiment, the patient treated may have at least one symptom of chronic graft-versus-host disease (GVHD) includes but is not limited to dry eyes, dry mouth, hair loss, hepatisis, lung disorder, gastrointestinal tract disorders, skin rash, and skin thickening. In one embodiment, the patient has or is to receive allogeneic stem cell or bone marrow transplant.

In one embodiment, the patient may have or is to receive autologous stem cell or bone marrow transplant.

In one embodiment, the method of treating an individual with an allergic, inflammatory or autoimmune disorder may comprise administering an effective amount of a VISTA fusion protein, optionally a VISTA-Ig, or a multimeric VISTA protein.

In one embodiment, the composition for treating an individual with an allergic, inflammatory or autoimmune disorder may comprise administering an effective amount of a VISTA fusion protein, optionally a VISTA-Ig, or a multimeric VISTA protein.

In one embodiment, the use of an effective amount of a VISTA fusion protein, optionally a VISTA-Ig, or a multimeric VISTA protein for the manufacture of a medicament for the treatment of an allergic, inflammatory or autoimmune disorder.

In another embodiment, the allergic, inflammatory or autoimmune disorder may be selected from psoriasis, dermatitis, atopic dermatitis; systemic scleroderma, sclerosis; Crohn's disease, ulcerative colitis; respiratory distress syndrome, adult respiratory distress syndrome; ARDS); dermatitis; meningitis; encephalitis; uveitis; colitis; glomerulonephritis; eczema, asthma, atherosclerosis; leukocyte adhesion deficiency; rheumatoid arthritis; systemic lupus erythematosus (SLE); diabetes mellitus, optionally Type I diabetes mellitus or insulin dependent diabetes mellitis; multiple sclerosis; Reynaud's syndrome; autoimmune thyroiditis; allergic encephalomyelitis; Sjorgen's syndrome; juvenile onset diabetes; tuberculosis, sarcoidosis, polymyositis, granulomatosis and vasculitis; pernicious anemia (Addison's disease); graft rejection disease, GVHD, central nervous system (CNS) inflammatory disorder; multiple organ injury syndrome; hemolytic anemia, cryoglobinemia or Coombs positive anemia; myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) and autoimmune thrombocytopenia.

In another embodiment, the disease may be selected from arthritis, rheumatoid arthritis, acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma, systemic scleroderma, sclerosis, systemic sclerosis, multiple sclerosis (MS), spino-optical MS, primary progressive MS (PPMS), relapsing remitting MS (RRMS), progressive systemic sclerosis, atherosclerosis, arteriosclerosis, sclerosis disseminata, and ataxic sclerosis, inflammatory bowel disease (IBD), Crohn's disease, colitis, ulcerative colitis, colitis ulcerosa, microscopic colitis, collagenous colitis, colitis polyposa, necrotizing enterocolitis, transmural colitis, autoimmune inflammatory bowel disease, pyoderma gangrenosum, erythema nodosum, primary sclerosing cholangitis, episcleritis, respiratory distress syndrome, adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis, Rasmussen's encephalitis, limbic and/or brainstem encephalitis, uveitis, anterior uveitis, acute anterior uveitis, granulomatous uveitis, nongranulomatous uveitis, phacoantigenic uveitis, posterior uveitis, autoimmune uveitis, glomerulonephritis (GN), idiopathic membranous GN or idiopathic membranous nephropathy, membrano- or membranous proliferative GN (MPGN), rapidly progressive GN, allergic conditions, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis, lymphomatoid granulomatosis, Wegener's granulomatosis, agranulocytosis, vasculitides, including vasculitis, large vessel vasculitis, polymyalgia rheumatica, giant cell (Takayasu's) arteritis, medium vessel vasculitis, Kawasaki's disease, polyarteritis nodosa, microscopic polyarteritis, CNS vasculitis, necrotizing, cutaneous, hypersensitivity vasculitis, systemic necrotizing vasculitis, and ANCA-associated vasculitis, such as Churg-Strauss vasculitis or syndrome (CSS), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus, optionally pemphigus vulgaris, pemphigus foliaceus, pemphigus mucus-membrane pemphigoid, pemphigus erythematosus, autoimmune polyendocrinopathies, Reiter's disease or syndrome, immune complex nephritis, antibody-mediated nephritis, neuromyelitis optica, polyneuropathies, chronic neuropathy, IgM polyneuropathies, IgM-mediated neuropathy, thrombocytopenia, thrombotic thrombocytopenic purpura (TTP), idiopathic thrombocytopenic purpura (ITP), autoimmune orchitis and oophoritis, primary hypothyroidism, hypoparathyroidism, autoimmune thyroiditis, Hashimoto's disease, chronic thyroiditis (Hashimoto's thyroiditis); subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis, allergic encephalomyelitis, experimental allergic encephalomyelitis (EAE), myasthenia gravis, thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AGED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis, optionally benign monoclonal gammopathy or monoclonal garnmopathy of undetermined significance, MGUS, peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In one embodiment, a method of making antibodies may comprise immunizing an animal with a VISTA epitope, removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody.

In another embodiment, an anti-VISTA or antibody fragment thereof produced by the method comprising immunizing an animal with a VISTA epitope, removing said animal's spleen and prepare a single cell suspension, fusing a spleen cell with a myeloma cell, culturing post-fusion cells in hybridoma selection medium, culturing the resultant hybridomas, screening for specific antibody production, and selecting hybridomas which produce the desired antibody.

In another embodiment, the anti-VISTA or antibody fragment thereof may be a humanized, chimeric, or single chain variant.

In one embodiment, an isolated VISTA antagonist may be an antibody or an antibody fragment thereof, a peptide, a glycoalkoid, an antisense nucleic acid, a ribozyme, a retinoid, an avemir, a small molecule, or any combination thereof.

In one embodiment, a method of treating or preventing inflammation in a subject in need thereof may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a method of treating an autoimmune disease may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a method of treating an inflammatory disorder may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a method of treating graft-versus-host-disease (GVHD) may comprise administration of an effective amount of an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a method of treating an individual with an allergic, inflammatory or autoimmune disorder may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a composition for treating or preventing inflammation in a subject in need thereof may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a composition for treating an autoimmune disease may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a composition for treating an inflammatory disorder may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a composition for treating graft-versus-host-disease (GVHD) may comprise administration of an effective amount of an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, a composition for treating an individual with an allergic, inflammatory or autoimmune disorder may comprise administering an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof.

In one embodiment, the use of an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof, for the manufacture of a medicament for treating or preventing inflammation.

In one embodiment, the use of an effective amount of an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof, for the manufacture of a medicament for the treatment of an autoimmune disease.

In one embodiment, the use of an effective amount of an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof, for the manufacture of a medicament for the treatment of an inflammatory disorder.

In one embodiment, the use of an effective amount of an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof, for the manufacture of a medicament for the treatment of graft-versus-host-disease (GVHD).

In one embodiment, the use of an effective amount of an effective amount of an isolated VISTA antagonist, wherein said antagonist may be an antibody or an antibody fragment thereof, a peptide, a glycoalkoid, an antisense nucleic acid, a ribozyme, a retinoid, an avemir, a small molecule, or any combination thereof, for the manufacture of a medicament for the treatment of an allergic, inflammatory or autoimmune disorder.

In one embodiment, a method for detecting VISTA in a sample may comprise contacting a sample with an anti-VISTA antibody or antibody fragment and detecting the anti-VISTA antibody-VISTA conjugates. In another embodiment, the sample may be a biological sample. In another embodiment, the anti-VISTA antibody binds the amino acid sequence of SEQ ID NO: 2, 3, or 5.

In another embodiment, compositions for therapeutic, diagnostic or immune modulatory usage may comprise an isolated soluble VISTA (PD-L3) protein or VISTA fusion protein (e.g., a soluble VISTA-Ig fusion protein or a multimeric VISTA protein) may comprise an amino acid sequence that preferably may be at least 70-90% identical to the human or murine VISTA (PD-L3) polypeptide set forth in SEQ ID NO: 2, 4 or 5 or an ortholog, or fragment thereof encoded by a gene that specifically hybridizes to SEQ ID NO:1 or 3 that modulates VISTA in vivo and a pharmaceutically acceptable carrier. In some embodiments, the soluble or multimeric VISTA protein may be directly or indirectly linked to a heterologous (non-VISTA) protein or may be expressed by a viral vector or a cell containing (e.g., a transfected immune cell such as a T cell.)

In an embodiment, isolated or recombinant VISTA (PD-L3) polypeptides (e.g., proteins, polypeptides, peptides, or fragments or portions thereof). In one embodiment, an isolated VISTA (PD-L3) polypeptide or VISTA (PD-L3) fusion protein comprises at least one of the following domains: a signal peptide domain, an IgV domain, an extracellular domain, a transmembrane domain, or a cytoplasmic domain.

In an embodiment, a VISTA (PD-L3) polypeptide comprises at least one of the following domains: a signal peptide domain, an IgV domain, an extracellular domain, a transmembrane domain, or a cytoplasmic domain, and comprises an amino acid sequence at least about 71%, 75%, 80%, 85%, 90%, 91%, 92%, 93%, 94%, 95%, 96%, 97%, 98%, 99% identical to the amino acid sequence of SEQ ID NO: 2, 4, or 5. In another embodiment, a VISTA (PD-L3) polypeptide comprises at least one of the following domains: a signal peptide domain, an IgV domain, an extracellular domain, a transmembrane domain, or a cytoplasmic domain, and may have a VISTA (PD-L3) activity (as described herein).

In one embodiment, an isolated VISTA protein may comprise a polypeptide with at least about 90% sequence identity to the extracellular domain of the polypeptide sequence of SEQ ID NO: 2, 4, 5, 16-25, 36, or 37. In a further embodiment, the polypeptide may have at least about 95% sequence identity to the polypeptide sequence of SEQ ID NO: 2, 4, 5, 16-25, 36, or 37.

In another embodiment, a VISTA polypeptide comprises at least one of the following domains: a signal peptide domain, an IgV domain, an extracellular domain, a transmembrane domain, or a cytoplasmic domain, and may be encoded by a nucleic acid molecule having a nucleotide sequence which hybridizes under stringent hybridization conditions to a complement of a nucleic acid molecule may comprise the nucleotide sequence of SEQ ID NO: 1 or 3.

In another embodiment, fragments or portions of the polypeptide may comprise the amino acid sequence of SEQ ID NO: 2, 4, or 5, wherein the fragment comprises at least 15 amino acids (i.e., contiguous amino acids) of the amino acid sequence of SEQ ID NO: 2 or 4. In another embodiment, a VISTA (PD-L3) polypeptide comprises or consists of the amino acid sequence of SEQ ID NO: 2, 4 or 5. In another embodiment, a VISTA (PD-L3) polypeptide may be encoded by a nucleic acid molecule may comprise a nucleotide sequence at least about 70%, 75%, 80%, 85%, 90%, 91%, 92%, 93%, 94%, 95%, 96%, 97%, 98%, 99% identical to a nucleotide sequence of SEQ ID NO: 1 or 3, or a complement thereof. A VISTA (PD-L3) polypeptide which may be encoded by a nucleic acid molecule consisting of a nucleotide sequence which hybridizes under stringent hybridization conditions to a complement of a nucleic acid molecule may comprise the nucleotide sequence of SEQ ID NO: 1 or 3.

In one embodiment, the VISTA polypeptides may be agonists wherein they induce suppression. In another embodiment, the VISTA polypeptides may be antagonists wherein they interfere with suppression.

The polypeptides of the present invention or portions thereof, e.g., biologically active portions thereof, may be operatively linked to a non-VISTA (PD-L3) polypeptide (e.g., heterologous amino acid sequences) to form fusion polypeptides.

In one embodiment, expression vectors may comprise an isolated nucleic acid encoding a VISTA protein that may be at least about 70-99% identical to the human or murine VISTA amino acid sequence set forth in SEQ ID NO: 2, 4 or 5 or a fragment or ortholog thereof, which optionally may be fused to a sequence encoding another protein such as an Ig polypeptide (e.g., an Fc region) or a reporter molecule; and host cells containing said vectors.

In another embodiment, isolated nucleic acid molecules encoding VISTA polypeptides, preferably encoding soluble fusion proteins and multimeric VISTA proteins as well as nucleic acid fragments suitable as primers or hybridization probes for the detection of VISTA (PD-L3)-encoding nucleic acids. In one embodiment, a VISTA (PD-L3) nucleic acid molecule of the invention may be at least about 70%, 75%, 80%, 85%, 90%, 91%, 92%, 93%, 94%, 95%, 96%, 97%, 98%, 99% identical to the nucleotide sequence (e.g., to the entire length of the nucleotide sequence) encoding VISTA (PD-L3) in SEQ ID NO:1 or 3 or a complement thereof.

In another embodiment, a VISTA (PD-L3) nucleic acid molecule comprises a nucleotide sequence encoding a polypeptide having an amino acid sequence having a specific percent identity to the amino acid sequence of SEQ ID NO: 2, 4 or 5. In an embodiment, a VISTA (PD-L3) nucleic acid molecule comprises a nucleotide sequence encoding a polypeptide having an amino acid sequence at least about 71%, 75%, 80%, 85%, 90%, 95%, 96%, 97%, 98%, 99% identical to the entire length of the amino acid sequence of SEQ ID NO: 2, 4 or 5 or to the extracellular domain thereof.

In another embodiment, an isolated nucleic acid molecule encodes the amino acid sequence of human or murine or VISTA or a conserved region or functional domain therein. In yet another embodiment, the nucleic acid molecule comprises a nucleotide sequence encoding a polypeptide may comprise the amino acid sequence of SEQ ID NO: 2, 4 or 5. In yet another embodiment, the nucleic acid molecule may be at least about 50, 100, 150, 200, 250, 300, 350, 400, 450, 500, 550, 600, 650, 700, 750, 800, 850, 900, 950, 1000, 1050, 1100, 1150 nucleotides in length. In a further embodiment, the nucleic acid molecule may be at least about 50, 100, 150, 200, 250, 300, 350, 400, 450, 500, 550, 600, 650, 700, 750, 800, 850, 900, 950, 1000, 1050, 1100, 1150 nucleotides in length and encodes a polypeptide having a VISTA (PD-L3) activity or modulating VISTA (PD-L3) function.

Another embodiment features nucleic acid molecules, preferably VISTA (PD-L3) nucleic acid molecules, which specifically detect VISTA (PD-L3) nucleic acid molecules relative to nucleic acid molecules encoding non-VISTA (PD-L3) polypeptides. For example, in one embodiment, a nucleic acid molecule may be at least about 880, 900, 950, 1000, 1050, 1100, 1150 nucleotides in length and hybridizes under stringent conditions to a nucleic acid molecule encoding the polypeptide shown in SEQ ID NO: 2, 4 or 5, or a complement thereof. In another embodiment, a nucleic acid molecule may be at least 20, 30, 40, 50, 100, 150, 200, 250, 300 nucleotides in length and hybridizes under stringent conditions to a nucleic acid molecule encoding a fragment of VISTA (PD-L3), e.g., may comprise at least about 20, 30, 40, 50, 100, 150, 200, 250, 300, 350, 400, 450, 500, 550, 600, 650, 700, 750, 800, 850, 900, 950 nucleotides in length, comprises at least 15 (i.e., 15 contiguous) nucleotides of the disclosed nucleic acid sequence in SEQ ID NO:1 and 3 encoding the VISTA (PD-L3) polypeptides in SEQ ID NO: 2, 4 or 5, or a complement thereof, and hybridizes under stringent conditions to a nucleic acid molecule may comprise the nucleotide sequence shown in SEQ ID NO: 1 or 3 or a complement thereof.

In one embodiment, the nucleic acid molecule encodes a naturally occurring allelic variant of a polypeptide may comprise the amino acid sequence of SEQ ID NO: 2 or 4 or 5, wherein the nucleic acid molecule hybridizes to a complement of a nucleic acid molecule may comprise SEQ ID NO: 1 or 3, or a complement thereof, under stringent conditions.

Another embodiment of the invention provides an isolated antisense to a VISTA (PD-L3) nucleic acid molecule (e.g., antisense to the coding strand of a VISTA (PD-L3) nucleic acid molecule of SEQ ID NO: 1 or 3.)

Another aspect of the invention provides a vector may comprise a VISTA (PD-L3) nucleic acid molecule. In certain embodiments, the vector may be a recombinant expression vector.

In another embodiment, a host cell comprises a vector of the invention. In yet another embodiment, a host cell comprises a nucleic acid molecule of the invention. The invention also provides a method for producing a polypeptide, preferably a VISTA (PD-L3) polypeptide, by culturing in a suitable medium, a host cell, e.g., a mammalian host cell such as a non-human mammalian cell, of the invention containing a recombinant expression vector, such that the polypeptide may be produced.

In one embodiment, an siRNA molecule which targets VISTA mRNA transcribed from a VISTA DNA may comprise the nucleic acid sequence of SEQ ID NO: 1 or 3. In another embodiment, an siRNA molecule which targets VISTA mRNA transcribed from a VISTA DNA encoding the amino acid sequence set forth in SEQ ID NO: 2, 4 or 5. In a further embodiment, an siRNA molecule that targets VISTA may comprise the nucleic acid sequence of any one of SEQ ID NOs: 38-67. In another embodiment, an siRNA molecule that targets either the ORF or UTR region of VISTA may comprise the amino acid sequence of any one of SEQ ID NO: 38-47. In another embodiment, an siRNA molecule that targets the UTR region only of VISTA may comprise the amino acid sequence of any one of SEQ ID NO: 48-57. In another embodiment, an siRNA molecule that targets the ORF region only of VISTA may comprise the amino acid sequence of any one of SEQ ID NO: 58-67. In one embodiment, an siRNA molecule that targets VISTA may consist of the nucleic acid sequence of any one of SEQ ID NOs: 38-67. In one embodiment, an siRNA molecule that targets either the ORF or UTR region of VISTA may consist of the amino acid sequence of any one of SEQ ID NO: 38-47. In one embodiment, an siRNA molecule that targets the UTR region only of VISTA may consist the amino acid sequence of any one of SEQ ID NO: 48-57. In one embodiment, an siRNA molecule that targets the ORF region only of VISTA may consist the amino acid sequence of any one of SEQ ID NO: 58-67.

In a further embodiment, a composition may comprise an siRNA molecule comprising the nucleic acid sequence of any one of SEQ ID NOs: 38-67. In a further embodiment, a composition may comprise an siRNA molecule consisting of the nucleic acid sequence of any one of SEQ ID NOs: 38-67. In a further embodiment, a composition may be a pharmaceutical composition.

In one embodiment, a method for treating an autoimmune disorder may comprise administration of an siRNA molecule that targets VISTA comprising the nucleic acid sequence of any one of SEQ ID NOs: 38-67. In one embodiment, a method for treating an autoimmune disorder may comprise administration of an siRNA molecule that targets VISTA consisting of the nucleic acid sequence of any one of SEQ ID NOs: 38-67. In a further embodiment, a composition for treating an autoimmune disorder may comprise an siRNA molecule comprising the nucleic acid sequence of any one of SEQ ID NOs: 38-67. In a further embodiment, a composition for treating an autoimmune disorder may comprise an siRNA molecule consisting of the nucleic acid sequence of any one of SEQ ID NOs: 38-67. In a further embodiment, use of an siRNA molecule comprising any one of nucleic acid sequences of SEQ ID NOs: 38-67 for the manufacture of a medicament for the treatment of an autoimmune disease. In a further embodiment, use of an siRNA molecule consisting of any one of nucleic acid sequences of SEQ ID NOs: 38-67 for the manufacture of a medicament for the treatment of an autoimmune disease.

In one embodiment, a method for treating an inflammatory disorder may comprise administration of an siRNA molecule that targets VISTA comprising the nucleic acid sequence of any one of SEQ ID NOs: 38-67. In one embodiment, a method for treating an inflammatory disorder may comprise administration of an siRNA molecule that targets VISTA consisting of the nucleic acid sequence of any one of SEQ ID NOs: 38-67. In a further embodiment, a composition for treating an inflammatory disorder may comprise an siRNA molecule comprising the nucleic acid sequence of any one of SEQ ID NOs: 38-67. In a further embodiment, a composition for treating an inflammatory disorder an siRNA molecule may comprise an siRNA molecule consisting of the nucleic acid sequence of any one of SEQ ID NOs: 38-67. In a further embodiment, use of an siRNA molecule comprising any one of nucleic acid sequences of SEQ ID NOs: 38-67 for the manufacture of a medicament for the treatment of an inflammatory disease. In a further embodiment, use of an siRNA molecule consisting of any one of nucleic acid sequences of SEQ ID NOs: 38-67 for the manufacture of a medicament for the treatment of an inflammatory disease.

In one embodiment, a method for treating graft-versus-host disease may comprise administration of an siRNA molecule that targets VISTA comprising the nucleic acid sequence of any one of SEQ ID NOs: 38-67. In one embodiment, a method for treating graft-versus-host disease may comprise administration of an siRNA molecule that targets VISTA consisting of the nucleic acid sequence of any one of SEQ ID NOs: 38-67. In a further embodiment, a composition for treating graft-versus-host disease may comprise an siRNA molecule comprising the nucleic acid sequence of any one of SEQ ID NOs: 38-67. In a further embodiment, a composition for treating graft-versus-host disease an siRNA molecule may comprise an siRNA molecule consisting of the nucleic acid sequence of any one of SEQ ID NOs: 38-67. In a further embodiment, use of an siRNA molecule comprising any one of nucleic acid sequences of SEQ ID NOs: 38-67 for the manufacture of a medicament for the treatment of graft-versus-host disease. In a further embodiment, use of an siRNA molecule consisting of any one of nucleic acid sequences of SEQ ID NOs: 38-67 for the manufacture of a medicament for the treatment of graft-versus-host disease.

In one embodiment, an antagonist may specifically binds to a VISTA (PD-L3) protein may comprise the amino acid sequence set forth in SEQ ID NO:2, 4 or 5 or a variant, fragment, or ortholog thereof. In an embodiment, the binding agent modulates (agonizes or antagonizes) VISTA activity in vitro or in vivo.

In one embodiment, the VISTA antagonist may be a VISTA ligand. In another embodiment, the VISTA ligand may be a protein. In another embodiment, the VISTA antagonist may be an antibody or an antibody fragment ther7eof, a peptide, a glycoalkoid, an antisense nucleic acid, a ribozyme, a retinoid, an avemir, a small molecule, or any combination thereof.

In one embodiment, the VISTA antagonists may have functional properties including but not limited to modulating specific effects of VISTA (PD-L3) on immunity such as the suppressive effect of the protein on TCR activation, the suppressive effect of the protein on CD4 T cell proliferative responses to anti-CD3, suppression of antigen specific proliferative responses of cognate CD4 T cells, the suppressive effects of VISTA (PD-L3) on the expression of specific cytokines (e.g., IL-2 and γ interferon).

In one embodiment, an antagonist, optionally a proteinanceous antagonist, that specifically binds to a VISTA polypeptide, multimeric VISTA polypeptide, or VISTA fusion protein. In another embodiment, the antagonist, optionally a proteinanceous antagonist, may exhibit antitumor or antimetastatic activity. In another embodiment, the antagonist, optionally a proteinanceous antagonist, may specifically bind an epitope comprised in residues 1-20, 20-40, 30-50, 60-80, 70-90, 80-100, or 90-110. In another embodiment, the antagonist, optionally a proteinanceous antagonist, may bind an epitope comprised in the IgV, stalk region, cytoplasmic region or transmembrane region of said VISTA protein. In another embodiment, the antagonist, optionally a proteinanceous antagonist, may elicit at least one of the following activities: (a) upregulates cytokines; (b) induces expansion of T cells, (c) promotes antigenic specific T cell immunity; or (d) promotes CD4+ and/or CD8+ T cell activation.

In another embodiment, an isolated binding agent, preferably an antibody or antibody fragment, mayh specifically binds to a VISTA (PD-L3) protein may comprise the amino acid sequence set forth in SEQ ID NO:2, 4 or 5 or a variant, fragment or ortholog thereof. In an embodiment, the binding agent modulates (agonizes or antagonizes) VISTA activity in vitro or in vivo. In one embodiment, the binding agent may be an agonistic or antagonistic anti-VISTA antibody.

In one embodiment, the anti-VISTA (PD-L3) antibodies may have functional properties including but not limited to modulating specific effects of VISTA (PD-L3) on immunity such as the suppressive effect of the protein on TCR activation, the suppressive effect of the protein on CD4 T cell proliferative responses to anti-CD3, suppression of antigen specific proliferative responses of cognate CD4 T cells, the suppressive effects of VISTA (PD-L3) on the expression of specific cytokines (e.g., IL-2 and γ interferon).

In a further embodiment, antibodies, optionally monoclonal or polyclonal antibodies, may specifically bind VISTA (PD-L3) polypeptides including human VISTA polypeptides.

In one embodiment, an isolated antibody, or antibody fragment thereof, that specifically binds to a VISTA polypeptide, multimeric VISTA polypeptide, or VISTA fusion protein. In another embodiment, the antibody or antibody fragment thereof may exhibit antitumor or antimetastatic activity. In another embodiment, the antibody or antibody fragment thereof may specifically bind an epitope comprised in residues 1-20, 20-40, 30-50, 60-80, 70-90, 80-100, or 90-110. In another embodiment, the antibody or antibody fragment thereof may specifically bind an epitope comprised in the IgV, stalk region, cytoplasmic region or transmembrane region of said VISTA protein. In another embodiment, the antibody or antibody fragment thereof may elicit at least one of the following activities: (a) upregulates cytokines; (b) induces expansion of T cells, (c) promotes antigenic specific T cell immunity; or (d) promotes CD4+ and/or CD8+ T cell activation. In another embodiment, the antibody or fragment may be recombinant. In another embodiment, the antibody or fragment may have anti-tumor activity. In another embodiment, the antibody fragment may be a Fab, Fab', F(ab')2, Fv, CDR, paratope, or portion of an antibody that is capable of binding the antigen. In another embodiment, the antibody may be chimeric, humanized, anti-idiotypic, single-chain, bifunctional, or co-specific. In another embodiment, the antibody or fragment may be directly or indirectly conjugated to a label, cytotoxic agent, therapeutic agent, or an immunosuppressive agent. In a further embodiment, the may be a chemiluminescent label, paramagnetic label, an MRI contrast agent, fluorescent label, bioluminescent label, or radioactive label.

In one embodiment, the invention provides anti-VISTA antibodies and antibody fragments thereof. In one embodiment, the antibody fragment is a Fab, Fab', $F(ab')_2$, Fv and scFv fragment. In one embodiment, the antibody or antibody fragment thereof may comprise a Fab, Fab', $F(ab')_2$, Fv, single-chain variable fragment (scFv), IgNAR, SMIP, camelbody, or nanobody. In another embodiment, a recombinant protein may comprise the hypervariable region of an anti-VISTA antibody and selectively bind VISTA. In another embodiment, the antibody fragment may selective bind VISTA may comprise the amino acid sequence of SEQ ID NO:2, 4 or 5.

In addition, the VISTA (PD-L3) polypeptides (or biologically active portions thereof) or modulators of the VISTA (PD-L3) molecules (e.g., anti-VISTA antibodies) may be incorporated into pharmaceutical compositions, optionally may comprise a pharmaceutically acceptable carrier.

In another embodiment, the invention provides a vaccine may comprise an antigen and an agent that modulates (enhances or inhibits) VISTA (PD-L3) activity. In an embodiment, the vaccine inhibits the interaction between VISTA (PD-L3) and its natural binding partner(s). In another embodiment, a vaccine may comprise an antigen and an agent that inhibits the interaction between VISTA (PD-L3) and its natural binding partner(s). In another embodiment, a vaccine may comprise an antigen and an agent that promotes the interaction between VISTA (PD-L3) and its natural binding partner(s). In one embodiment, the vaccine comprises an excipient, adjuvant, or a carrier.

In one embodiment, a kit may comprise a VISTA fusion protein. In another embodiment, a kit may comprise a multimeric VISTA protein. In a further embodiment, the VISTA fusion protein or multimeric VISTA protein may be directly or indirectly fixed to a solid phase support. In a further embodiment, the solid phase support may be a bead, test tube, sheet, culture dish, or test strip. In another embodiment the solid phase support may be an array.

In another embodiment, immune cells may be activated may comprise contacting an immune cell with a VISTA polypeptide, VISTA-Ig fusion protein, or anti-VISTA antibody. In another embodiment, the immune cell may be a T cell, B cell, or an antigen-presenting cell. Immune cells activated in accordance with the method of the instant invention can subsequently be expanded ex vivo and used in the treatment and prevention of a variety of diseases; e.g., human T cells which have been cloned and expanded in vitro maintain their regulatory activity. Prior to expansion, a source of T cells may be obtained from a subject (e.g., a mammals such as a human, dog, cat, mouse, rat, or transgenic species thereof). T cells can be obtained from a number of sources, including peripheral blood mononuclear cells, bone marrow, lymph node tissue, cord blood, thymus tissue, tissue from a site of infection, spleen tissue, tumors or T cell lines. T cells may be obtained from a unit of blood collected from a subject using any number of techniques known to the skilled artisan, such as FICOLL® separation.

In another embodiment, a method for modulating VISTA (PD-L3) activity, may comprise contacting a cell capable of expressing VISTA (PD-L3) with an agent that modulates VISTA (PD-L3) activity, preferably an anti-VISTA (PD-L3) antibody such that VISTA (PD-L3) activity in the cell may be modulated. In one embodiment, the agent inhibits VISTA (PD-L3) activity. In another embodiment, the agent stimulates VISTA (PD-L3) activity. In a further embodiment, the agent interferes with or enhances the interaction between a VISTA (PD-L3) polypeptide and its natural binding partner (s). In one embodiment, the agent may be an antibody that specifically binds to a VISTA (PD-L3) polypeptide. In another embodiment, the agent may be a peptide, peptidomimetic, or other small molecule that binds to a VISTA (PD-L3) polypeptide.

In another embodiment, the agent modulates expression of VISTA (PD-L3) by modulating transcription of a VISTA (PD-L3) gene, translation of a VISTA (PD-L3) mRNA, or post-translational modification of a VISTA (PD-L3) polypeptide. In another embodiment, the agent may be a nucleic acid molecule having a nucleotide sequence that may be antisense to the coding strand of a VISTA (PD-L3) mRNA or a VISTA (PD-L3) gene. In a further embodiment, the agent may be an siRNA molecule that targets VISTA (PD-L3) mRNA.

In one embodiment, methods for treating autoimmune disorder or inflammatory condition may comprise administering an agent which may be a VISTA (PD-L3) modulator to the subject. In one embodiment, the VISTA (PD-L3) modulator may be a VISTA (PD-L3) polypeptide, preferably a soluble fusion protein or multimeric VISTA protein or anti-VISTA antibody as described infra. In another embodiment the VISTA (PD-L3) modulator may be a VISTA (PD-L3) nucleic acid molecule, e.g., in an adenoviral vector. In another embodiment, the invention further provides treating the subject with an additional agent that modulates an immune response.

In one embodiment, a method for modulating the interaction of VISTA (PD-L3) with its natural binding partner(s) on an immune cell may comprise contacting an antigen presenting cell which expresses VISTA (PD-L3) with an agent selected from the group consisting of a form of VISTA (PD-L3), or an agent that modulates the interaction of VISTA (PD-L3) and its natural binding partner(s) such that the interaction of VISTA (PD-L3) with it natural binding partner(s) on an immune cell may be modulated and assessing the interaction of VISTA with its natural binding partner(s). In an embodiment, an agent that modulates the interaction of VISTA (PD-L3) and its natural binding partner(s) may be an antibody that specifically binds to VISTA (PD-L3). In one embodiment, the interaction of VISTA (PD-L3) with its natural binding partner(s) may be upregulated. In another embodiment, the interaction of VISTA (PD-L3) with its natural binding partner(s) may be downregulated. In one embodiment, the method further comprises contacting the immune cell or the antigen presenting cell with an additional agent that modulates an immune response. In one embodiment, the step of contacting may be performed in vitro. In another embodiment, the step of contacting may be performed in vivo. In one embodiment, the immune cell may be selected from the group consisting of a T cell, a monocyte, a macrophage, a dendritic cell, a B cell, and a myeloid cell.

In one embodiment, a method for inhibiting activation in an immune cell may comprise inhibiting the activity or expression of VISTA (PD-L3) in a cell such that immune cell activation may be inhibited. In one embodiment, a method for increasing activation in an immune cell may comprise increasing the activity or expression of VISTA (PD-L3) in a cell such that immune cell activation may be increased.

In another embodiment, a method for upregulating an immune response may comprise administering an agent that inhibits the interaction between VISTA (PD-L3) and its natural binding partner(s) on immune cells. In one embodiment, the agent comprises a blocking antibody or a small molecule that binds to VISTA (PD-L3) and inhibits the interaction between VISTA (PD-L3) and its natural binding partner(s). In another embodiment, the method further comprises administering a second agent that upregulates an immune response to the subject. In another embodiment, a method for downregulating an immune response may comprise administering an agent that stimulates the interaction between VISTA (PD-L3) and its natural binding partner(s) on immune cells.

In one embodiment, a method for treating a condition selected from the group consisting of a tumor, a pathogenic infection, an inflammatory immune response or condition, preferably less pronounced inflammatory conditions, or an immunosuppressive disease may comprise administration of an effective amount of a VISTA polypeptide or VISTA-Ig fusion protein. Specific examples include multiple sclerosis, thyroiditis, rheumatoid arthritis, diabetes type II and type I and cancers, both advanced and early forms, including metastatic cancers (e.g., bladder cancer, ovarian cancer, melanoma, lung cancer), wherein VISTA suppresses an effective anti-tumor response. The subject may be administered cells or a viral vector that express a nucleic acid that encodes an anti-VISTA antibody or VISTA fusion protein.

In one embodiment, a method for treating a condition selected from the group consisting of transplant, an allergy, infectious disease, cancer, and inflammatory or autoimmune disorders (e.g., an inflammatory immune disorder) may comprise administration of an effective amount of a VISTA (PD-L3) proteins, binding agents or VISTA (PD-L3) antagonists or agonists. In another embodiment, type 1 diabetes, multiple sclerosis, rheumatoid arthritis, psoriatic arthritis, systemic lupus erythematosus, rheumatic diseases, allergic disorders, asthma, allergic rhinitis, skin disorders, gastrointestinal disorders such as Crohn's disease and ulcerative colitis, transplant rejection, poststreptococcal and autoimmune renal failure, septic shock, systemic inflammatory response syndrome (SIRS), adult respiratory distress syndrome (ARDS) and envenomation; autoinflammatory diseases as well as degenerative bone and joint diseases including osteoarthritis, crystal arthritis and capsulitis and other arthropathies may be treated may comprise administration of an effective amount of a VISTA (PD-L3) proteins, binding agents or VISTA (PD-L3) antagonists or agonists. Further, the methods and compositions may comprise an effective amount of a VISTA (PD-L3) proteins, binding agents or VISTA (PD-L3) antagonists or agonists may be used for treating tendonitis, ligamentitis and traumatic joint injury. In one embodiment, an agent comprises an antibody or a small molecule that stimulates the interaction between VISTA (PD-L3) and its natural binding partner(s). In another embodiment, the method further comprises administering a second agent that downregulates an immune response to the subject such as a PD-L1, PD-L2 or CTLA-4 fusion protein or antibody specific thereto.

In embodiments the subject VISTA (PD-L3) proteins, nucleic acids, and ligands specific to VISTA (PD-L3), preferably antibodies having desired effects on VISTA (PD-L3) functions may be used to treat conditions including but not limited to cancer, autoimmune diseases, allergy, inflammatory disorders or infection and more specifically immune system disorders such as severe combined immunodeficiency, multiple sclerosis, systemic lupus erythematosus, type I diabetes mellitus, lymphoproliferative syndrome, inflammatory bowel disease, allergies, asthma, graft-versus-host disease, and transplant rejection; immune responses to infectious pathogens such as bacteria and viruses; and immune system cancers such as lymphomas and leukemias. In one embodiment, an agent that modulates the activity of VISTA may relieve T cell exhaustion and enhance immunity to infectious disease.

In one embodiment, a method of treating a cancer in a patient in need thereof may comprise administering an effective amount of VISTA protein, multimeric VISTA protein, VISTA fusion protein, optionally a VISTA-Ig fusion protein, wherein said VISTA protein, multimeric VISTA protein, and/or VISTA fusion protein enhances antitumor immunity by suppressing the immunosuppressive activity of VISTA expressed by myeloid dendritic suppressor cells. In a further embodiment, the patient prior to treatment may be found to express elevated levels of VISTA protein on immune cells.

In one embodiment, a method of enhancing the efficacy of radiotherapy, chemotherapy or an anti-cancer biologic may comprise administering an effective amount of VISTA protein, multimeric VISTA protein, VISTA fusion protein, optionally a VISTA-Ig fusion protein, in a therapeutic regimen including the administration of radiotherapy, chemotherapy or an anti-cancer biologic. In a further embodiment, the patient prior to treatment may have a cancer that does not respond to said radiotherapy, chemotherapy or an anti-cancer biologic.

In one embodiment, a method of treating colorectal, bladder, ovarian, or melanoma cancer may comprise administering an effective amount of VISTA protein, multimeric VISTA protein, VISTA fusion protein, optionally a VISTA- Ig fusion protein, wherein said cancer is in early (non-metastatic) or metastatic form and the VISTA-Ig blocks interaction with its receptor.

In one embodiment, a method for modulating an immune cell response may comprise contacting an immune cell with an effective amount of a VISTA protein, multimeric VISTA protein, VISTA fusion protein, optionally a VISTA-Ig fusion protein in the presence of a primary signal so that a response of the immune cell is modulated.

In one embodiment, a method of modulating Treg cells in a subject in need thereof may comprise administering an effective amount of VISTA protein, multimeric VISTA protein, VISTA fusion protein, optionally a VISTA-Ig fusion protein.

In one embodiment, a method of releasing the suppressive effect of VISTA on immunity may comprise administering an effective amount of a VISTA protein, multimeric VISTA protein, VISTA fusion protein, optionally a VISTA-Ig fusion protein. In another embodiment, the treated patient may be found to express elevated levels of VISTA prior to treatment. In another embodiment, the VISTA levels may be monitored after treatment in order to assess that the immune response may have been enhanced.

In one embodiment, a method of enhancing cell mediated immunity in a subject in need thereof may comprise administering an effective amount of a VISTA protein, multimeric VISTA protein, VISTA fusion protein, optionally a VISTA-Ig fusion protein.

In one embodiment, a method for modulating an immune cell response may comprise contacting an immune cell with may comprise administering an effective amount of a VISTA fusion protein, optionally a VISTA-Ig fusion protein, or a multimeric VISTA protein in the presence of a primary signal so that a response of the immune cell is modulated. In another embodiment, the contacting may be performed in vitro, in vivo, or ex vivo.

In one embodiment, a method of regulating T cell responses during cognate interactions between T cells and myeloid derived APCs may comprise administering an effective amount of a VISTA fusion protein, optionally a VISTA-Ig fusion protein, or a multimeric VISTA protein.

In one embodiment, a method of eliciting immunosuppression in an individual in need thereof may comprise administering an effective amount of a VISTA fusion protein, optionally a VISTA-Ig fusion protein, or a multimeric VISTA protein.

In another embodiment, a method for decreasing immune cell activation may comprise administering an effective amount of a VISTA (PD-L3) polypeptide or VISTA-Ig fusion protein to a subject, wherein said VISTA (PD-L3) polypeptide or VISTA-Ig fusion protein acts as inhibitory signal for decreasing immune cell activation. In one embodiment, the immune cell activation is inhibited. In another embodiment, the immune cell activation is significantly decreased. In one embodiment, the inhibitory signal binds to an inhibitory receptor (e.g., CTLA-4 or PD-1) on an immune cell thereby antagonizing the primary signal which binds to an activating receptor (e.g., via a TCR, CD3, BCR, or Fc polypeptide). In one embodiment, the VISTA polypeptide or VISTA-Ig fusion protein inhibits second messenger generation; inhibits immune cell proliferation; inhibits effector function in the immune cell (e.g., reduced phagocytosis, reduced antibody production, reduced cellular cytotoxicity, the failure of the immune cell to produce mediators, (cytokines (e.g., IL-2) and/or mediators of allergic responses); or the development of anergy.)

In one embodiment, the primary signal may be a ligand (e.g., CD3 or anti-CD3) that binds TCR and initiates a primary stimulation signal. TCR ligands include but are not limited to anti-CD3 antibody OKT3 and anti-CD3 monoclonal antibody G19-4. In one embodiment, a primary signal may be delivered to a T cell through other mechanisms including a protein kinase C activator, such as a phorbol ester (e.g., phorbol myristate acetate), and a calcium ionophore (e.g., ionomycin, which raises cytoplasmic calcium concentrations). The use of such agents bypasses the TCR/CD3 complex but delivers a stimulatory signal to T cells. Other agents acting as primary signals may include natural and synthetic ligands. A natural ligand may comprise MHC with or without a peptide presented. Other ligands may include, but are not limited to, a peptide, polypeptide, growth factor, cytokine, chemokine, glycopeptide, soluble receptor, steroid, hormone, mitogen (e.g., PHA), or other superantigens, peptide-MHC tetramers and soluble MHC dimers.

In another embodiment, a method for detecting the presence of a VISTA (PD-L3) nucleic acid molecule, protein, or polypeptide in a biological sample comprises contacting the biological sample with an agent capable of detecting a VISTA (PD-L3) nucleic acid molecule, protein, or polypeptide, such that the presence of a VISTA (PD-L3) nucleic acid molecule, protein or polypeptide may be detected in the biological sample. This VISTA (PD-L3) expression may be used to detect certain disease sites such as inflammatory sites.

In another embodiment, a method for detecting the presence of VISTA (PD-L3) activity in a biological sample comprises contacting the biological sample with an agent capable of detecting an indicator of VISTA (PD-L3) activity, such that the presence of VISTA (PD-L3) activity may be detected in the biological sample. In a further embodiment, a method for detecting soluble VISTA in biological sample may comprise contacting the biological sample with an agent capable of detecting an indicator of VISTA (PD-L3) activity, such that the presence of VISTA (PD-L3) activity may be detected in the biological sample. In another embodiment, a method for detecting soluble VISTA in biological sample may comprise contacting the biological sample with an agent capable of binding VISTA (PD-L3), optionally an anti-VISTA antibody or antibody fragment, and detecting the presence of VISTA-antibody complexes. In a further embodiment, the measurement may be quantitative, optionally Western blot densitometry, colorimetric, or flourometic.

In another embodiment, diagnostic assays for identifying the presence or absence of a genetic alteration in a VISTA gene comprises obtaining a sample may comprise a nucleic acid and analyzing the sample, wherein said genetic alteration is characterized by at least one of (i) aberrant modification or mutation of a gene encoding a VISTA (PD-L3) polypeptide; (ii) misregulation of the gene; and (iii) aberrant post-translational modification of a VISTA (PD-L3) polypeptide, wherein a wild-type form of the gene encodes a polypeptide with a VISTA (PD-L3) activity. In one embodiment, the nucleic acid may be DNA or mRNA.

In one embodiment, a method of selecting for anti-VISTA antibodies for having potential use as a therapeutic or immune modulatory agent may comprise: (a) immunizing immune cells or a host with a VISTA protein, immunogenic fragment, or conjugate thereof; (b) selecting lymphoid cells which express antibodies that specifically bind to VISTA; (c) selecting anti-VISTA antibodies or antibody fragments thereof; (d) screening said anti-VISTA antibodies or antibody fragments thereof for the ability to inhibit or enhance at least one of the following activities of VISTA (PD-L3) or VISTA: (i) suppression of T cell activation or differentiation; (ii) suppression of CD4+ or CD8+ T cell proliferation, or suppression of cytokine production by T cells; (iii) wherein an antibody or antibody fragment thereof which has at least one of the activities in (d) has potential use as a therapeutic or immune modulatory agents.

In further embodiment, methods of selecting anti-VISTA (PD-L3) antibodies having desired functional properties may comprise screening panels of monoclonal antibodies produced against this protein or a VISTA (PD-L3)-Ig fusion protein based on desired functional properties including modulating specific effects of VISTA (PD-L3) on immunity such as the suppressive effect of the protein on TCR activation, the suppressive effect of the protein on CD4 T cell proliferative responses to anti-CD3, suppression of antigen specific proliferative responses of cognate CD4 T cells, the suppressive effects of VISTA (PD-L3) on the expression of specific cytokines (e.g., IL-2 and γ interferon) and selecting the desired antibody.

In another embodiment, methods for identifying a compound that binds to or modulates the activity of a VISTA (PD-L3) polypeptide may comprise providing an indicator composition may comprise a VISTA (PD-L3) polypeptide having VISTA (PD-L3) activity, contacting the indicator composition with a test compound, and determining the effect of the test compound on VISTA (PD-L3) activity in the indicator composition to identify a compound that modulates the activity of a VISTA (PD-L3) polypeptide.

In another embodiment, a cell-based assay for screening for compounds which modulate the activity of VISTA (PD-L3) may comprise contacting a cell expressing a VISTA (PD-L3) target molecule with a test compound and determining the ability of the test compound to modulate the activity of the VISTA (PD-L3) target molecule In another embodiment, a cell-free assay for screening for compounds which modulate the binding of VISTA (PD-L3) to a target molecule may comprise contacting a VISTA (PD-L3) polypeptide or biologically active portion thereof with a test compound and determining the ability of the test compound to bind to the VISTA (PD-L3) polypeptide or biologically active portion thereof.

In another embodiment, a method of identifying a compound, e.g. an anti-VISTA (PD-L3) antibody which modulates the effect of VISTA (PD-L3) on T cell activation or cytokine production at a first and second antigen concentration may comprise contacting a T cell expressing a VISTA (PD-L3) target molecule with a test compound at a first antigen concentration, determining the ability of the test compound to modulate T cell proliferation or cytokine production at the first antigen concentration, contacting a T cell expressing a VISTA (PD-L3) target molecule with the test compound at a second antigen concentration, and determining the ability of the test compound to modulate T cell proliferation or cytokine production at the second antigen concentration, thereby identifying a compound which modulates T cell activation or cytokine production at a first and second antigen concentration.

In other embodiments panels of anti-VISTA (PD-L3) antibodies and VISTA (PD-L3) proteins may be screened and selected on the basis of which anti-VISTA antibodies inhibit or promote the effects of VISTA (PD-L3) on CD4+ and CD8+ T cell differentiation, proliferation and/or cytokine production. In a further embodiment, a mouse that has been engineered to express human VISTA may be used to test the function of anti-human VISTA antibodies in regulating immunity.

In another embodiment, a method of treating graft-versus-host-disease (GVHD) may comprise administration of an effective amount of a VISTA fusion protein, optionally a VISTA-Ig fusion protein, or the multimeric VISTA protein. In another embodiment, a method for treating graft-versus-host disease (GVHD), acute graft-versus-host disease, chronic graft-versus-host disease, acute graft-versus-host disease associated with stem cell transplant, chronic graft-versus-host disease associated with stem cell transplant, acute graft-versus-host disease associated with bone marrow transplant, acute graft-versus-host disease associated with allogeneic hemapoetic stem cell transplant (HSCT), or chronic graft-versus-host disease associated with bone marrow transplant may comprise administering of an effective amount of a VISTA fusion protein, optionally a VISTA-Ig fusion protein, or the multimeric VISTA protein.

In one embodiment, the graft-versus-host disease (GVHD) may be graft-versus-host disease (GVHD), acute graft-versus-host disease, chronic graft-versus-host disease, acute graft-versus-host disease associated with stem cell transplant, chronic graft-versus-host disease associated with stem cell transplant, acute graft-versus-host disease associated with bone marrow transplant, acute graft-versus-host disease associated with allogeneic hemapoetic stem cell transplant (HSCT), or chronic graft-versus-host disease associated with bone marrow transplant. In another embodiment, the patient treated has at least one symptom of graft-versus-host disease (GVHD), optionally wherein the patient exhibits acute GVHD includes but is not limited to abdominal pain, abdominal cramps, diarrhea, fever, jaundice, skin rash, vomiting, and weight loss. In another embodiment, the patient treated has at least one symptom of chronic graft-versus-host disease (GVHD) includes but is not limited to dry eyes, dry mouth, hair loss, hepatisis, lung disorder, gastrointestinal tract disorders, skin rash, and skin thickening. In another embodiment, the patient has or is to receive allogeneic stem cell or bone marrow transplant. In another embodiment, the patient has or is to receive autologous stem cell or bone marrow transplant.

DETAILED DESCRIPTION OF THE DRAWINGS

FIGS. 1A-1E depicts sequence analysis. (A) Full length amino acid sequence of murine VISTA (PD-L3) (SEQ ID NO: 17). (B) Amino acid sequence alignment of extracellular Ig domains between murine VISTA (PD-L3) (SEQ ID NO: 25) and selected B7 family ligands, including B7-H1 (PD-L1) (SEQ ID NO: 26), B7-DC (PD-L2) (SEQ ID NO: 27), B7-H3 (CD276) (SEQ ID NO: 28), and B7-H4 (B7S1) (SEQ ID NO: 29). (C) Alignment of VISTA (PD-L3) (SEQ ID NO: 30) Ig domain with B7 family receptors, including PD-1 (SEQ ID NO: 31), CTLA-4 (SEQ ID NO: 32), CD28 (SEQ ID NO: 33), BTLA (SEQ ID NO: 34), and ICOS (SEQ ID NO: 35). Ig-v domain, " . . . "; Ig-c domain, "_". Alignment was performed using the MUSCLE algorithm (Multiple Sequence Comparison by Log-Expectation). (D) Sequence identity (%) of the Ig-V domains between VISTA (PD-L3) and other B7 family ligands and receptors is calculated using ClustalW2 program. (E) Sequence alignment to show sequence homology between human (SEQ ID NO: 37) and murine VISTA (PD-L3) (SEQ ID NO: 36). Identical residues are shaded in black. Highly conserved and semi-conserved residues are shaded in dark and light shade of gray respectively.

FIG. 2 depicts a hylogenic analysis of mouse VISTA (PD-L3) with other Immunoglobulin (Ig) superfamily members. Full-length sequence of mouse VISTA (PD-L3) and other Ig superfamily members, including CD28, CTLA-4, ICOS, BTLA, PD-1, B7-H1 (PD-L1), B7-DC (PD-L2), B7-H2, B7-H3, B7-H4, B7-1, B7-2, BTNL2, BTN3A3, BTN2A2, and BTN1A1, were analyzed using PhyML algorithm (Phylogenetic Maximum Likelihood). Branch distances were shown at tree branch joints.

FIGS. 3A-3G depict the tissue expression and hematopoietic cell expression patterns of VISTA (PD-L3) A. RT-PCR of full length VISTA (PD-L3) from mouse tissues. Lanes: (1) muscle (2) heart (3) eye (4) thymus (5) spleen (6) small intestine (7) kidney (8) liver (9) brain (10) mammary gland (11) lung (12) ovary (13) bone marrow. B. RT-PCR of full-length VISTA (PD-L3) from purified hematopoietic cell types. Lanes (1) peritoneal macrophages (2) splenic CD11b+ monocytes (3) splenic CD11c+ DCs (4) splenic CD4+ T cells (5) splenic CD8+ T cells (6) splenic B cells. C-E. Flow cytometry analysis of VISTA (PD-L3) expression on splenic CD4+ and CD8+ T cells from thymus and spleen (C), on CD11b+ monocytes (D), and on CD11c+ DC subsets from spleen and peritoneal cavity (E). (F) Splenic B cells, NK cells and granulocytes are also analyzed. (G) The differential expression of VISTA (PD-L3) on hematopoietic cells from different tissue sites, including mesenteric LN, peripheral LN, spleen, blood and peritoneal cavity. Representative data from at least 3 independent experiments are shown.

FIG. 4 depicts a VISTA, novel and structurally-distinct, Ig-superfamily inhibitory ligand, whose extracellular domain bears highest homology to the B7 family ligand PD-L1 as displayed on an Antigen Presenting Cell along with other CDs and B7 family members. VISTA has a 93 aa cytoplasmic domain with no obvious signal transducing motifs, except a possible protein kinase C binding site.

FIG. 5 depicts the specificity of VISTA (PD-L3) hamster monoclonal antibodies. Mouse EL4 cell lines over-expressing either PD-L1 or VISTA (PD-L3) fused to RFP were stained using the supernatants from hybridoma cultures and analyzed by flow cytometry. Two representative positive clones are shown, 8D8 AND 6E7.

FIG. 6 depicts a comparison of VISTA (PD-L3) expression with other B7 family ligands on in vitro cultured spleen cells. Expression of VISTA (PD-L3) and other B7 family ligands (i.e., PD-L1, PD-L2, B7-H3, and B7-H4) on hematopoietic cell types, including CD4+ T cells, CD11bhi monocytes, and CD11c+ DCs were compared. Cells were either freshly isolated, or in vitro cultured for 24 hrs, with and without activation. CD4+ T cells were activated with plate-bound αCD3 (5 μg/ml), CD11bhi monocytes and CD11c+ DCs were activated with IFNα (20 ng/ml) and LPS (200 ng/ml). Representative results from three independent experiments are shown.

FIGS. 7A-7B depict the comparison of in vivo expression patterns of VISTA (PD-L3) and other B7 family ligands during immunization. DO11.10 TCR transgenic mice were immunized with chicken ovalbumin (OVA) emulsified in complete Freund's adjuvant (CFA) on the flank. Draining and non-draining lymph node cells were collected 24 hr post immunization, and analyzed by flow cytometry for the expression of VISTA (PD-L3), PD-L1 and PD-L2. Shown are representative results from at least four independent experiments. (A) A population of CD11b+ cells expressing a high level of VISTA (PD-L3) was induced at 24 hr post immunization with CFA/OVA, but not with CFA alone within the draining lymph node. These cells are of mixed phenotype of F4/80+ macrophages and CD11C+ dendritic cells. (B) Expression of VISTA (PD-L3), PD-L1 and PD-L2 on CD1 bhi monocytes, CD11c+ DCs and CD4+ T cells were analyzed at 24 hr post immunization.

FIG. 8 depicts the loss of VISTA (PD-L3) expression on activated CD4+ T cells, $CD11b^+$ and $CD11c^+$ cells in response to immunization. DO11.10 mice were immunized with chicken ovalbumin (OVA) emulsified in complete Freund's adjuvant (CFA) on the flank. Draining and non-draining lymph node cells were collected 48 hr post immunization, and analyzed for VISTA (PD-L3) expression by flow cytometry. Shown are representative results from 2 independent experiments.

FIGS. 9A-9D depict that immobilized VISTA (PD-L3)-Ig fusion protein inhibited CD4+ and CD8+ T cell proliferation. (A) CFSE labeled CD4+ and CD8+ T cells were stimulated by plate-bound αCD3 with or without co-absorbed VISTA (PD-L3)-Ig. The percentage of CFSE-low cells was quantified and shown in (B). (C) CD4+ T cells from PD-1 ko mice were also suppressed by VISTA (PD-L3)-Ig. (D) VISTA (PD-L3)-Ig-mediated suppression is persistent and can act late. CD4+ T cells were activated in the presence of VISTA (PD-L3)-Ig or control-Ig for either 72 hrs (i), or for 24 hrs (ii, iii and iv). 24 hour-preactivated cells were harvested and re-stimulated under specified conditions for another 48 hours. Cell proliferation was analyzed at the end of the 72 hour culture. (ii) Pre-activation with VISTA (PD-L3)-Ig and re-stimulation with antiCD3; (iii) Pre-activation with antiCD3 and re-stimulation with VISTA (PD-L3)-Ig. (iv) Pre-activation with VISTA (PD-L3)-Ig and re-stimulation with VISTA (PD-L3)-Ig. Duplicated wells were analyzed for all conditions. Shown are representative results from four experiments.

FIG. 10 depicts the similar inhibitory effect of PD-L1-Ig and VISTA (PD-L3)-Ig fusion proteins on CD4+ T cell proliferation. Bulk purified CD4+ T cells were CFSE labeled and stimulated with plate-bound αCD3 together with titrated amount of PD-L1-Ig or VISTA (PD-L3)-Ig fusion proteins. CFSE dilution was analyzed at 72 hours and the percentage of CFSElow cells was quantified. Duplicated wells were analyzed for all conditions. Shown are representative results from 2 independent experiments.

FIGS. 11A-11B depict the suppressive impact of VISTA (PD-L3)-Ig on the proliferation of naïve and memory CD4+ T cells. (A) Naïve (CD25-CD44lowCD62Lhi) and memory (CD25-CD44hiCD62Llow) CD4+ T cell subsets were sorted, CFSE labeled, and stimulated with plate-bound anti-CD3 (2.5 μg/ml) together with VISTA (PD-L3)-Ig or control-Ig at indicated ratios. Cell proliferation was analyzed at 72 hours by examining the CFSE division profile. The percentage of proliferated cells, as determined by percentage of CFSElow cells, is calculated and shown in B. Duplicated wells were analyzed for all conditions. Shown are representative results from two independent experiments.

FIGS. 12A-12B depict VISTA (PD-L3)-Ig fusion protein suppressed early TCR activation and cell proliferation, but did not directly induce apoptosis. Bulk purified CD4+ T cells were stimulated with plate-bound anti-CD3 together with VISTA (PD-L3)-Ig or control-Ig at 1-2 ratio (2.5 μg/ml and 5 μg/ml respectively). Cells were analyzed at 24 hr and 48 hrs for the expression of CD69, CD62L, and CD44 by flow cytometry. Cells were also stained for early apoptosis marker annexin-V, and cell death marker 7-Aminoactinomycin D (7-AAD). Shown are representative results from two independent experiments.

FIG. 13A-13E depict VISTA-Ig inhibited cytokine production by CD4+ and CD8+ T cells. (A-B) Bulk purified CD4+ T cells were stimulated with plate-bound anti-CD3, and VISTA-Ig or control-Ig at stated ratios. Culture supernatants were collected after 24 hrs and 48 hrs. Levels of IL-2 and IFNγ were analyzed by ELISA. (C-D) CD4+ T cells were sorted into naïve (CD25-CD44lowCD62Lhi) and memory (CD25-CD44hiCD62Llow) cell populations. Cells were stimulated with plate-bound αCD3 and VISTA (PD-L3)-Ig or control-Ig at a ratio of 1:2. Culture supernatants were collected at 48 hrs and analyzed for the level of IL-2 and IFNγ by ELISA. (E) Bulk purified CD8+ T cells were stimulated with plate-bound αCD3, and VISTA (PD-L3)-Ig or control-Ig at indicated ratios. IFNγ in the culture supernatant was analyzed by ELISA. For all conditions, supernatant for six duplicated wells were pooled for ELISA analysis. Shown are representative results from three experiments.

FIGS. 14A-14D depict VISTA-Ig-mediated suppression may overcome a moderate level of costimulation provided by CD28, but was completely reversed by a high level of costimulation, as well as partially rescued by exogenous IL-2. A-B. Mouse CD4+ T cells were activated by plate-bound αCD3 together with either VISTA (PD-L3)-Ig or control-Ig at 1-1 ratio and 1-2 ratios. For cytokine rescue, soluble mIL-2, mIL7, mIL15 and mIL-23 (all at 40 ng/ml) were added to the cell culture (A). To examine the effects of costimulation, αCD28 (1 μg/ml) was immobilized together with αCD3 and Ig proteins at indicated ratios (B). Cell proliferation was analyzed at 72 hr by examining CFSE division profiles. C-D. To examine the suppressive activity of VISTA (PD-L3) in the presence of lower levels of costimulation, titrated amounts of αCD28 were coated together with anti-CD3 (2.5 μg/ml) and VISTA-Ig fusion proteins or control-Ig fusion protein (10 μg/ml) to stimulate mouse CD4+ T cell proliferation. Cell proliferation was analyzed at 72 hour. Percentages of proliferated CFSElow cells were quantified and shown in D. Duplicated wells were analyzed for all conditions. Representative CFSE profiles from three independent experiments are shown.

FIGS. 15A-15D depict that VISTA (PD-L3) expressed on antigen presenting cells suppressed CD4 T cell proliferation. A-C The CHO cell line that stably expresses MHCII molecule I-Ad and costimulation molecule B7-2 was used as the parent cell line. Cells were transduced with retrovirus expressing either VISTA-RFP or RFP control molecules. Transduced cells were sorted to achieve homogenous level of expression. To test their ability as antigen presenting cells, CHO-VISTA or CHO-RFP cells were mitomycin C treated and mixed with OVA-specific transgenic CD4+ T cells DO11.10, in the presence of titrated amount of OVA peptide. Proliferation of DO11 cells was analyzed at 72 hrs, either by CFSE division profiles (A-B), or by tritium incorporation (C). (D) bone marrow derived dendritic cells were transduced with RFP or B7B-H5-RFP retrovirus during 10-day culture period. Transduced CD11c+ RFP+ DCs and non-transduced CD11c+ RFP− DCs were sorted and used to stimulate OVA-specific transgenic CD4+ T cells OTII in the presence of titrated amount of OVA peptide. Cell proliferation was analyzed on day 3 by examining CFSE division. For all experiments, duplicated wells were analyzed for all conditions, and representative results from three independent experiments are shown.

FIG. 16 depicts the surface expression level of VISTA (PD-L3) in retrovirally transduced bone marrow derived DCs. Bone marrow derived DCs (BMDC) were cultured in the presence of GM-CSF (20 ng/ml) and transduced with either RFP or VISTA-RFP retrovirus as described herein. On day 10, surface expression level of VISTA were analyzed on cultured BMDCs, and compared to freshly-isolated peritoneal macrophages.

FIGS. 17A-17B shows that anti-PDL3monoclonal antibody exhibits efficacy in a passive transfer EAE model. In this adoptive transfer EAE model, donor SJL mice were immunized with CFA and PLP peptide. On day 10, total lymphocytes from draining LN were isolated, and cultured in vitro with PLP peptide, IL-23 (20 ng/ml) and anti-IFNg (10 μg/ml) for 4 days. Expanded CD4 T cells were then purified and adoptively transferred into naïve recipient mice. Disease progression was monitored and scored with: 0, no disease; 0.5 loss of tail tone; 1: limp tail; 2: limp tail+hind limb paresis; 2.5: 1 hind limb paralysis; 3: both hind limb paralysis; 3.5: forelimb weakness; 4: hind limb paralysis+ unilateral forelimb paralysis. Mice were sacrificed when disease score reached 4. *, mice were sacrificed.

FIG. 18 shows that VISTA expressed on antigen-presenting cells suppressed CD4+ T cell proliferation.

FIG. 19 shows that an anti-VISTA antibody inhibited tumor growth in mice transplanted with MB49 tumor cells.

FIG. 20A-20E show the antitumor effect of VISTA monoclonal antibodies in four different mouse anti-tumor models (A-D). FIG. 21E shows the expression of VISTA on different cells in the ID8 model. Very high expression on the myeloid dendritic cells in different anatomic locations. As can be seen, very high levels on myeloid dendritic cells in the ascites cells, the site where the tumor grows and leukocytes infiltrate.

Figure 21:
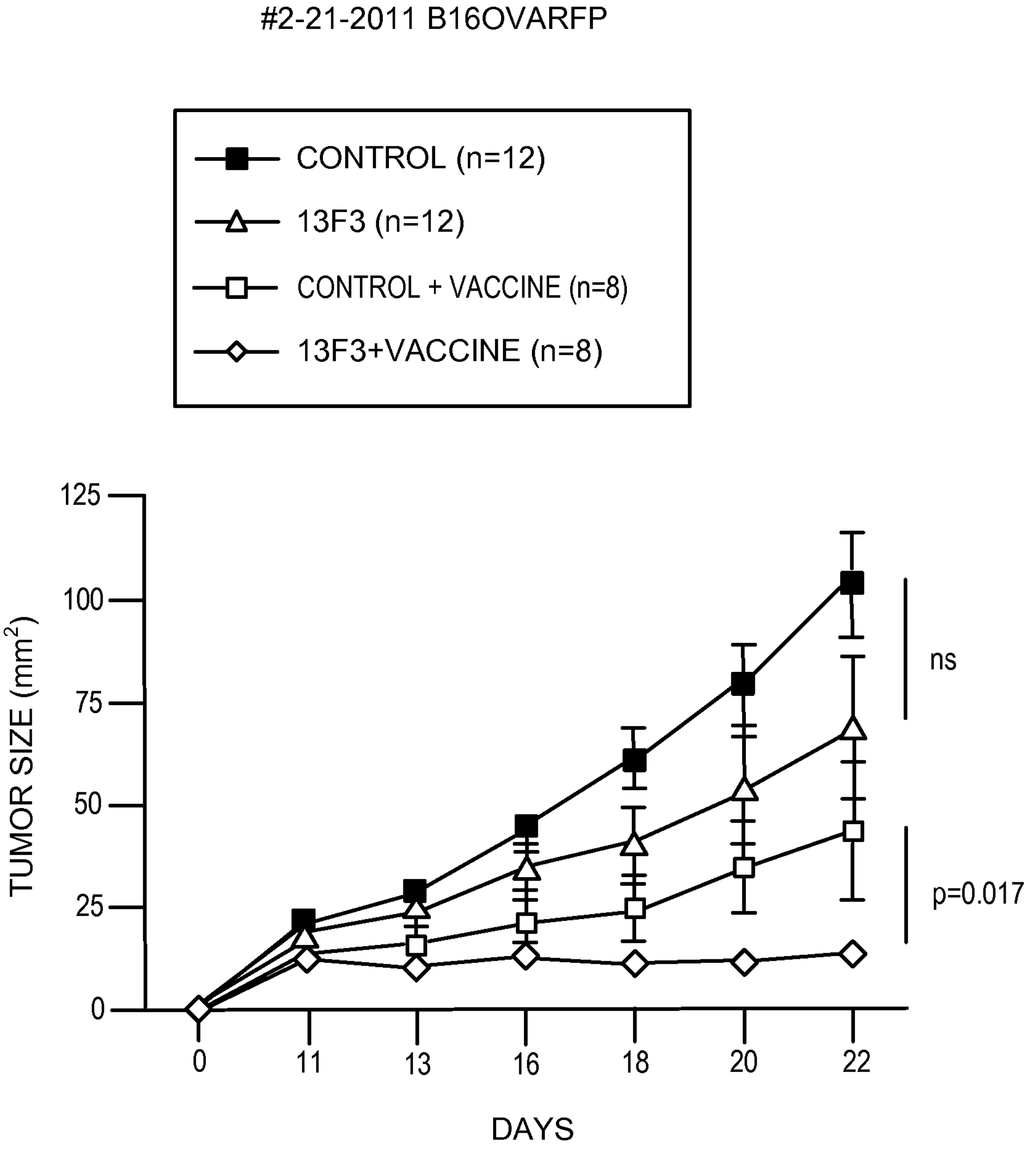

FIG. 21 shows the potentiating effect of VISTA monoclonal antibodies on the efficacy of a CD40/TLR agonist vaccine (consisting of using an agonistic αCD40 mab, TLR agonist and OVA peptide).

Figure 22:
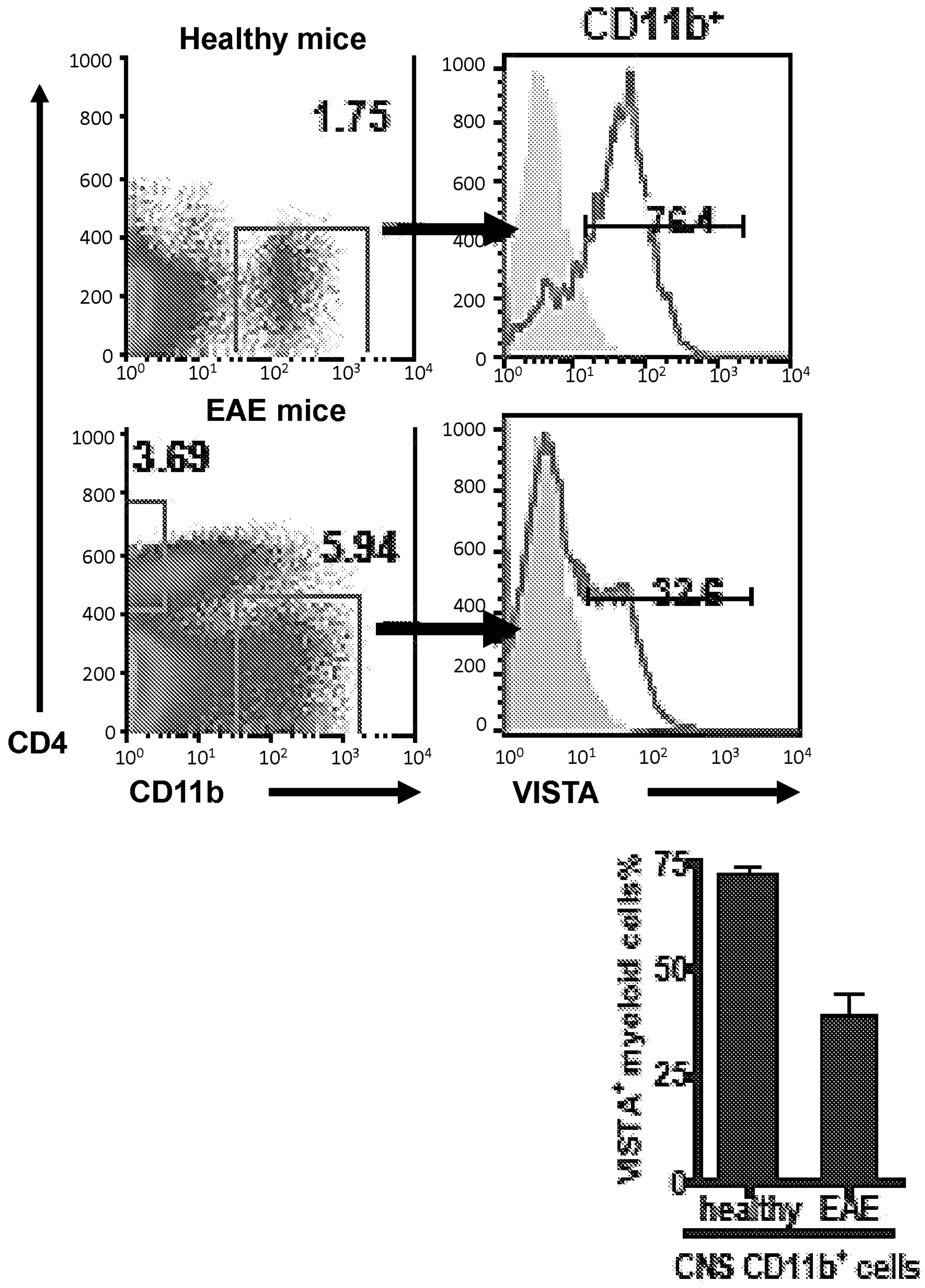

FIG. 22 shows VISTA expression on CNS cells in mice that are healthy or in mice that are developing EAE.

FIGS. 23A-23C depict a sequence and structural analysis of VISTA. (A) The primary amino acid sequence of mouse VISTA with the Ig-V domain, the stalk segment, and the transmembrane region highlighted in bold, italics, and Times New Roman, respectively. Cysteines in the ectodomain region are indicated by underlining. (B) Multiple sequence alignment of the Ig-V domains of several B7 family members and VISTA. The predicted secondary structure (using arrows, springs, and "T"s for strands, helices, and 1-turns, respectively) is marked above the alignment and is based on the VISTA structural model. VISTA (SEQ ID NO: 15), PD1L1 (SEQ ID NO: 11), PD1L2 (SEQ ID NO: 12), B7H4 (SEQ ID NO: 13), and B7H3 (SEQ ID NO: 14). (C) Multiple sequence alignment of VISTA orthologues. Invariant residues are represented by the red background, and physico-chemically conserved positions are represented by red letters. Conserved amino acids are marked by blue boxes. Conservation is calculated on the basis of 36 VISTA orthologous proteins, but only 9 representatives are shown. The canonical cysteine pair (within the "B" and "F" strands) that is conserved in almost all Ig superfamily members is highlighted by red circles, whereas cysteines that are specific to VISTA are marked by blue circles. The unique VISTA cysteine pattern is conserved in all orthologues from mouse (SEQ ID NO: 17), human (SEQ ID NO: 16), kangaroo (SEQ ID NO: 18), dolphin (SEQ ID NO: 19), chicken (SEQ ID NO: 20), xenopus (SEQ ID NO: 21), zebra finch (SEQ ID NO: 22), zebrafish, and fugu (SEQ ID NO: 23).

Figure 24A:
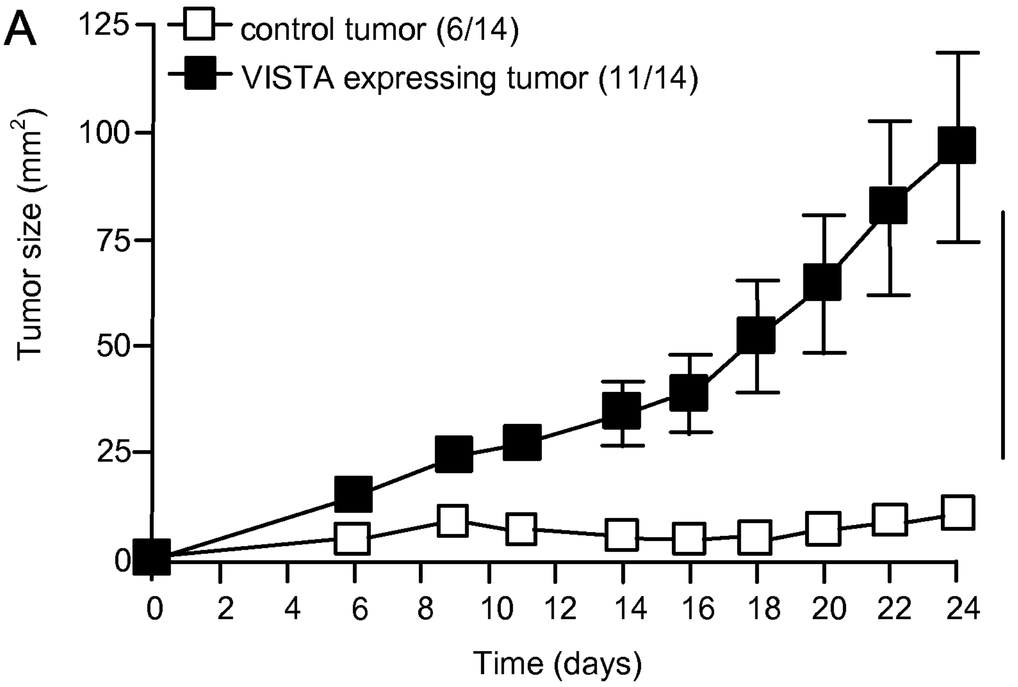
Figure 24B:
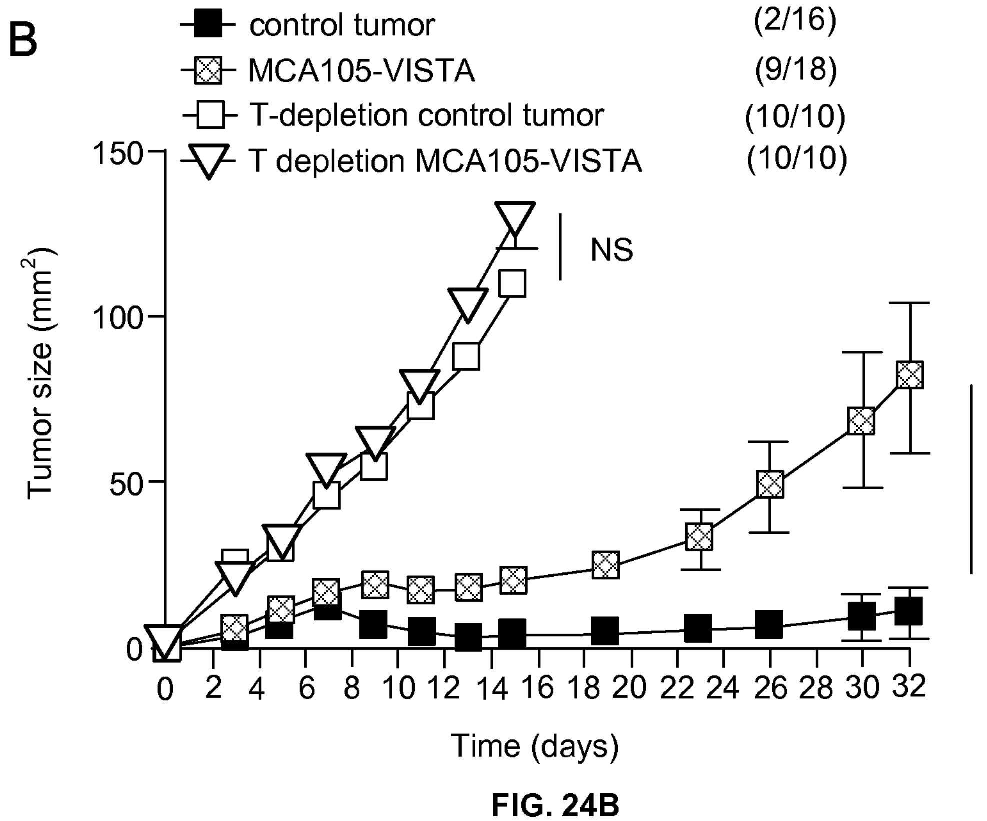

FIGS. 24A-24B depict that VISTA over expression on tumor cells overcomes protective antitumor immunity. MCA105 tumor cells over expressing VISTA or RFP control protein were generated by retroviral transduction and sorted to homogeneity. To generate protective immunity, naive mice were vaccinated with irradiated MCA105 tumor cells subcutaneously on the left flank. (A) Vaccinated mice were challenged 14 day later with live MCA105VISTA or MCA105RFP tumor cells subcutaneously on the right flank. Tumor growth was monitored every 2 d. Tumor size is shown as mean±SEM. Shown are representative results from three independent repeats. (B) Vaccinated mice were either untreated or depleted of both $CD4^+$ and $CD8^+$ T cells by monoclonal antibodies before live tumor challenge. Tumor size was monitored as in A and shown as mean±SEM. Shown are representative results from two independent repeats. For all experiments, ratios indicate the number of tumor-bearing mice among total number of mice per group. The statistical differences (p-values) were assessed with an unpaired Mann-Whitney test.

FIG. 25A-25D depict that VISTA blockade using a specific monoclonal antibody enhanced $CD4^+$ T cell response in vitro and in vivo. (A) A monoclonal antibody clone 13F3 neutralized VISTA-mediated suppression in vitro. A20-RFP and A20-VISTA cells were used to stimulate CFSE-labeled DO11.10 $CD4^+$ T cells in the presence of cognate OVA peptide. 20 μg/ml VISTA-specific monoclonal antibody 13F3 or control-Ig was added as indicated. CFSE dilution was analyzed after 72 h, and percentages of $CFSE^{low}$ cells are shown as mean±SEM. Duplicated wells were analyzed for all conditions. (B and C) Total $CD11b^{hi}$ myeloid cells (B) or CD11b-$CD11c^-$ monocytes (C) and $CD11b^{hi}CD11c^+$ myeloid DCs (D) sorted from naive splenocytes were irradiated and used to stimulate CFSE-labeled OT-II transgenic $CD4^+$ T cells in the presence of OVA peptide. Cell proliferation was measured by incorporation of tritiated thymidine during the last 8 h of a 72-h culture period and shown as mean±SEM. Triplicate wells were analyzed in all conditions.

Figure 26:
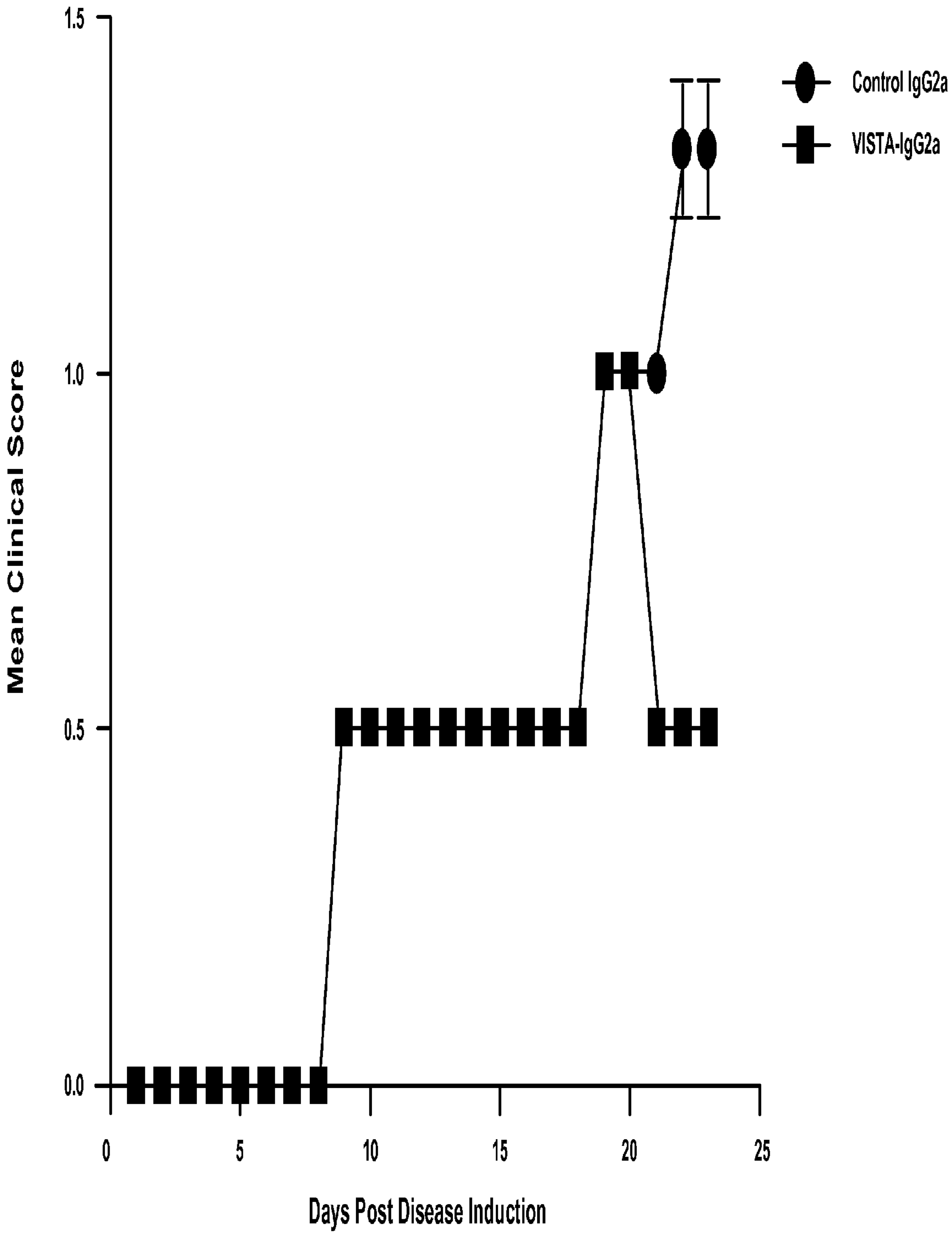

FIG. 26 depicts VISTA-IgG2a reduces Experimental Autoimmune Encephalomyelitis (EAE) (a model of multiple sclerosis) progression. Mice were immunized with 175 μg MOG/CFA and pertussis toxin (PT) 300 ng (day 0, 2) to induce active EAE. On day 14, 17, and 20, 150 μg VISTA-IgG 2a (n=8) or 150 μg control IgG2a (n=8) was administered. The data is shown as the mean±SEM.

Figure 27:
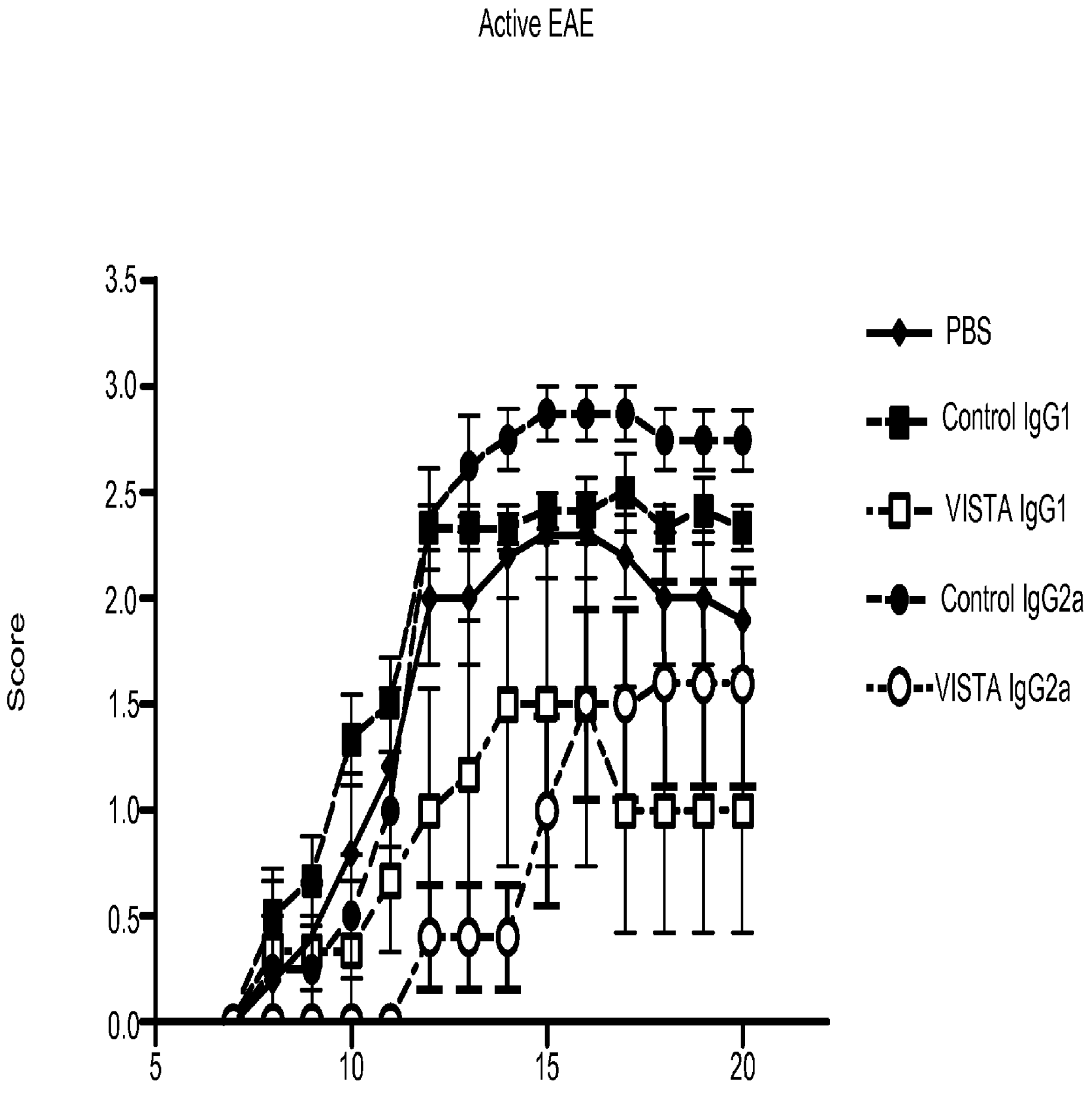

FIG. 27 depicts the therapeutic effect of VISTA-IgG1 and VISTA-IgG2a on Experimental Autoimmune Encephalomyelitis (EAE) progression. Mice were immunized with 175 μg MOG/CFA and pertussis toxin (PT) 300 ng (day 0, 2) to induce active EAE. On day 6, mice were treated with 3 doses per week of 150 μg control IgG1 (n=3), 150 μg control IgG2a (n=6), 150 μg mVISTA-IgG1 (n=3), or 150 μg mVISTA IgG2a (n=6) (two weeks in total). The data is shown as the mean±SEM.

Figure 28:
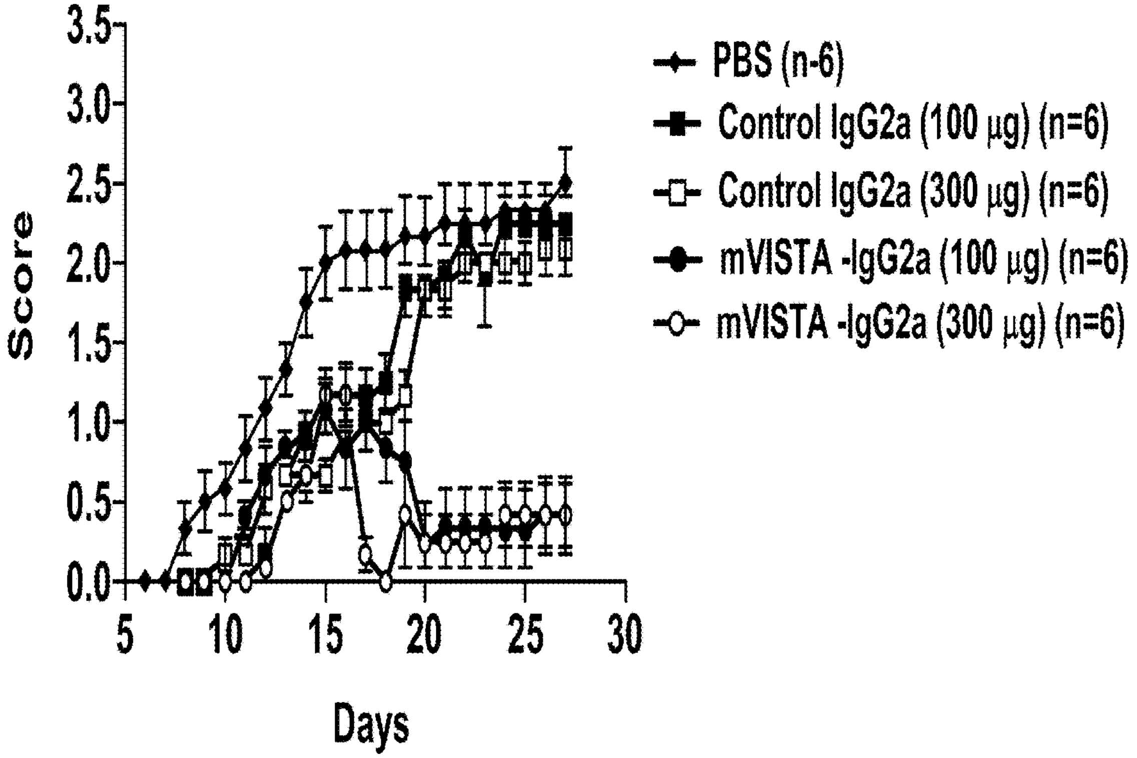

FIG. 28 depicts the therapeutic effect of VISTA-IgG2a fusion protein on Experimental Autoimmune Encephalomyelitis (EAE) progression. Mice were immunized with 175 μg MOG/CFA and pertussis toxin (PT) 300 ng (day 0, 2) to induce active EAE. On day 14, mice were treated with 3 doses per week of PBS (n=6), 100 μg control IgG2a (n=6), 300 μg control IgG2a (n=6), 100 μg VISTA-IgG2a (n=6), or 300 μg mVISTA IgG2a (n=6) (two weeks in total). The data is shown as the mean±SEM.

Figure 29:
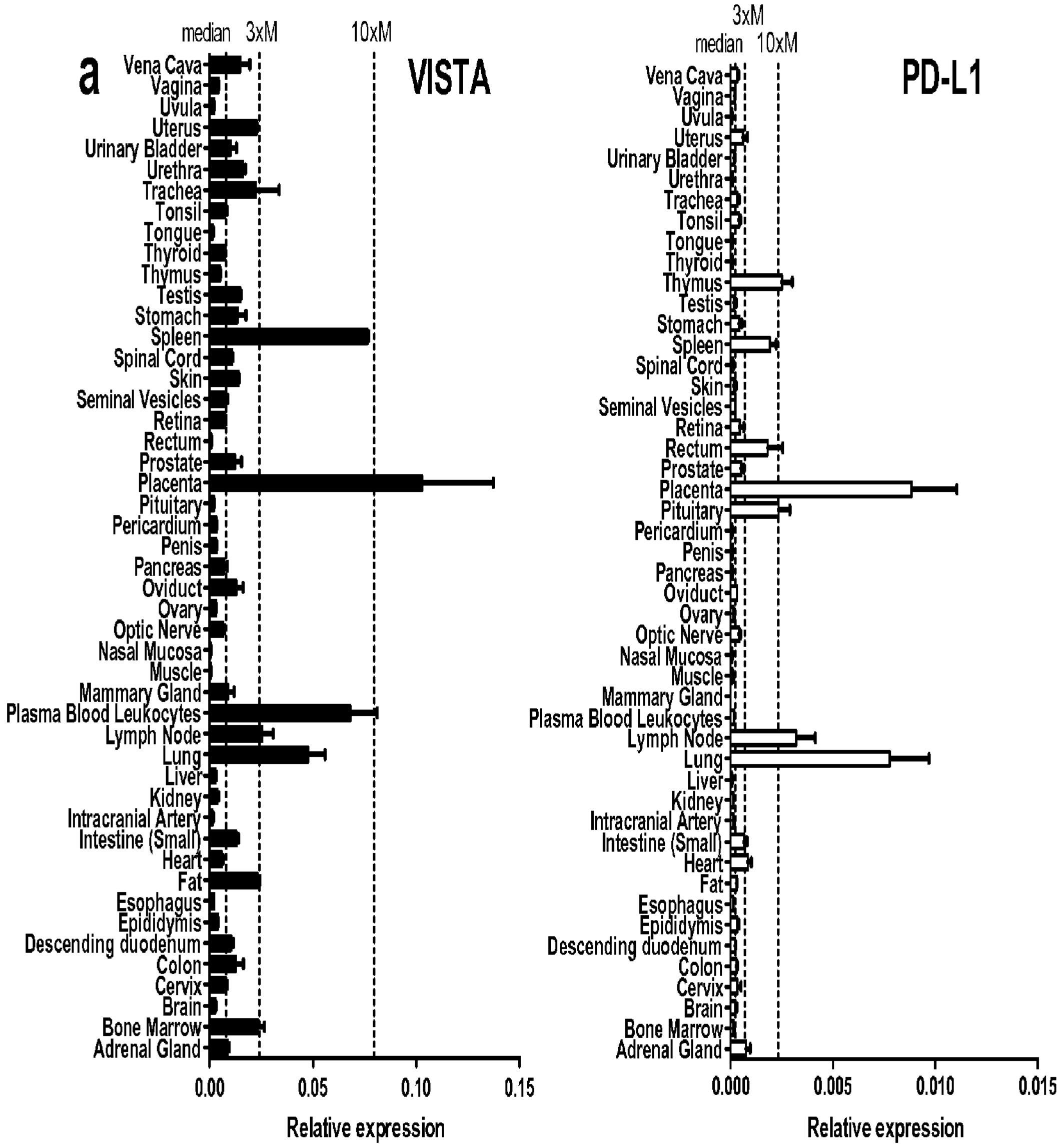

FIG. 29 depicts the expression of VISTA healthy human tissues was examined by real-time PCR analysis of a cDNA tissue panel (Origene). (A) VISTA was predominantly expressed in haematopoietic tissues or in tissues that contain significant numbers of haematopoietic tissues. This is consistent with importance of VISTA in immune related functions. (B) The expression pattern of expression was found to follow a similar trend to that of VISTA's closest homologue PD-L1.

Figure 30:
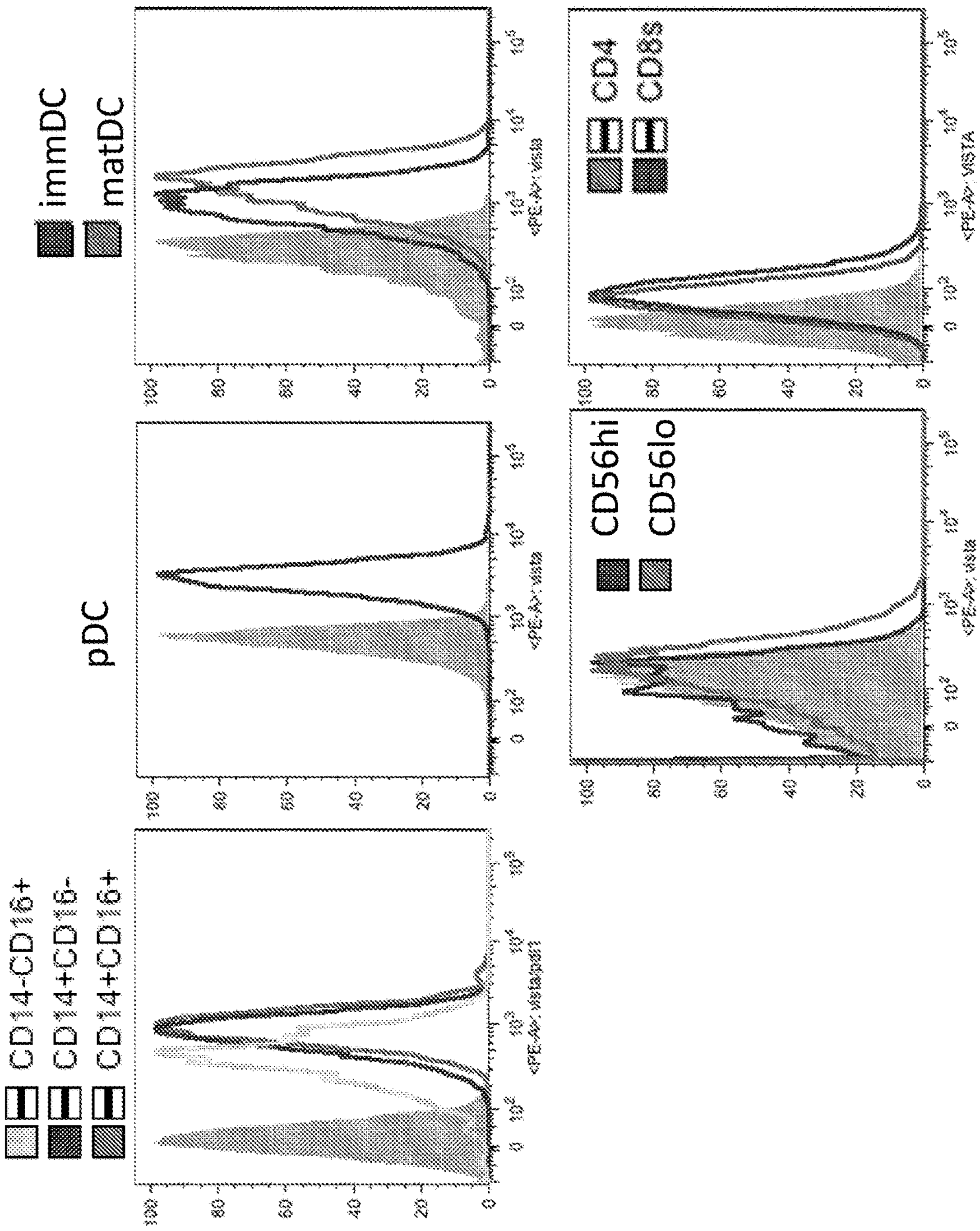
Figures 31A, 31B, 31C, 31D:
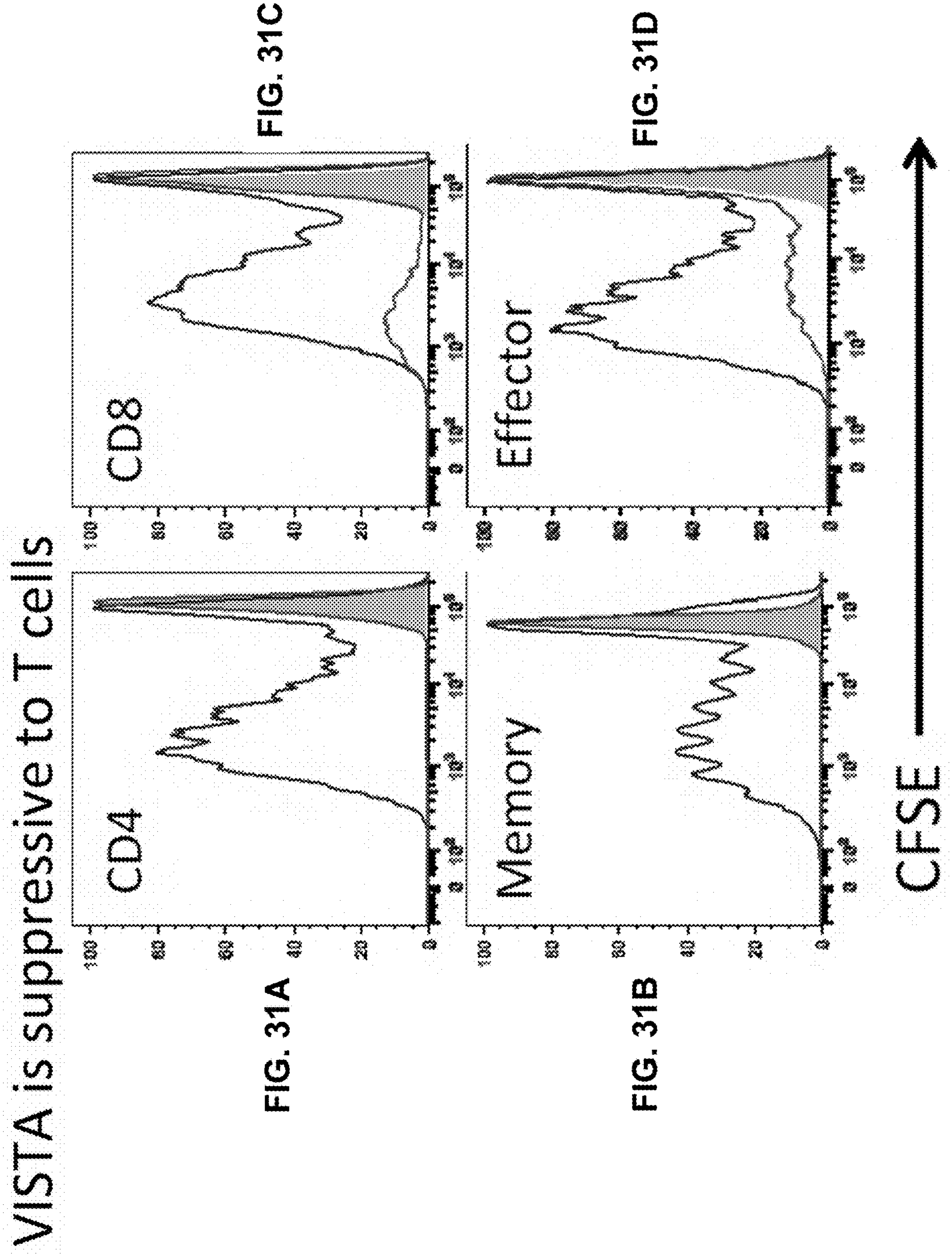

FIG. 30 depicts VISTA protein expression in monocytes, dendritic cells and by approximately 20% of CD4 and CD8 T cells (FIG. 30). VISTA expression was observed within both of the 'patrolling' ($CD14^{dim}CD16^+$) and 'inflammatory' ($CD14^+CD16^{+/-}$) subsets of blood monocytes, and within both lymphoid and myeloid subsets of dendritic cell.

FIGS. 31A-31D depict the suppression of CFSE dilution of bulk purified CD4 (FIG. 31A) and CD8 (FIG. 31B) T cells. An Ig fusion protein was created, consisting of the extracellular domain of VISTA and the Fc region of human IgG containing mutations for reduced Fc receptor binding. 10 μg/ml of VISTA-Ig or control Ig was immobilized on plates along with 2.5 μg/ml of anti-CD3 (OKT3) and then proliferation was measured by CFSE dilution.

Figure 32:
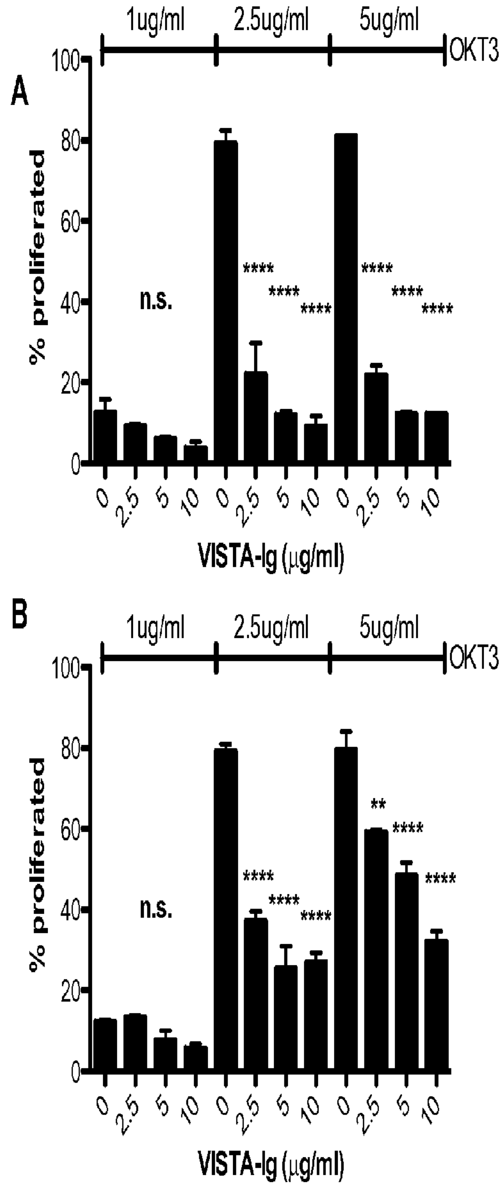

FIG. 32 depicts the titration of human VISTA-Ig and human VISTA-Ig over different concentrations of OKT3, showed that higher concentrations of OKT3 can be overcome by higher concentrations of VISTA (FIGS. 32A and 32B).

Figures 33A, 33B, 33C:
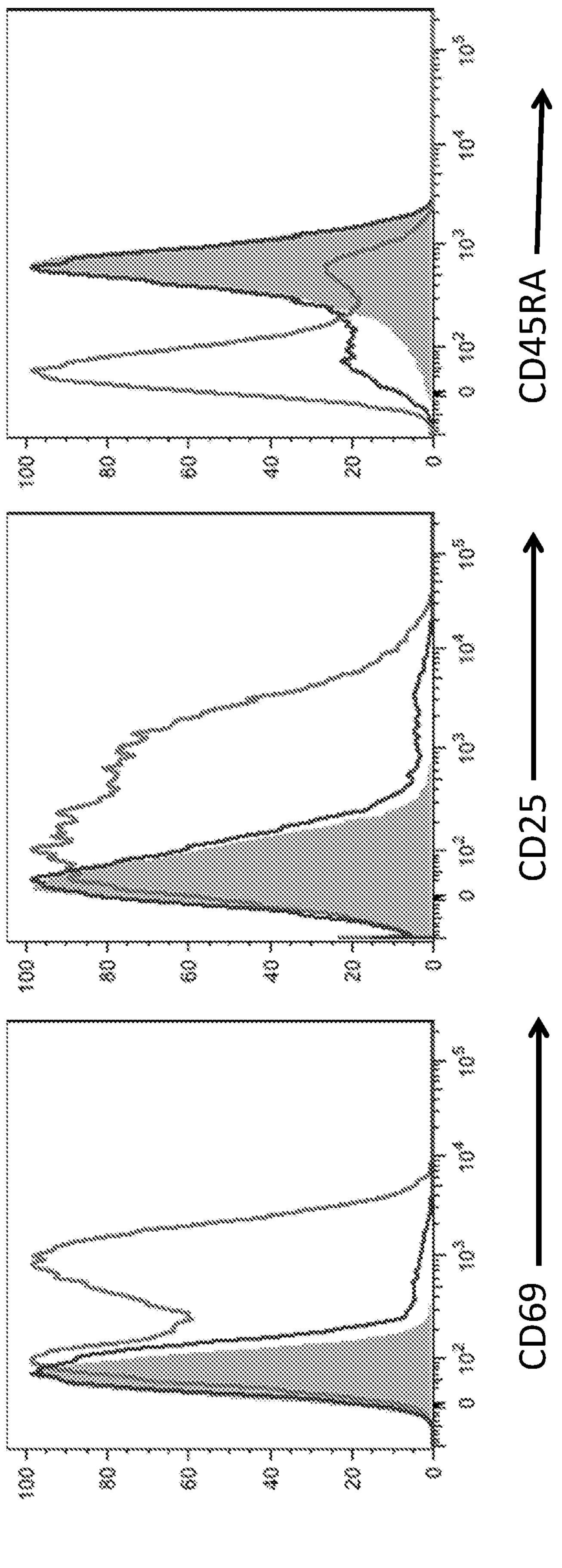
Figure 33D:
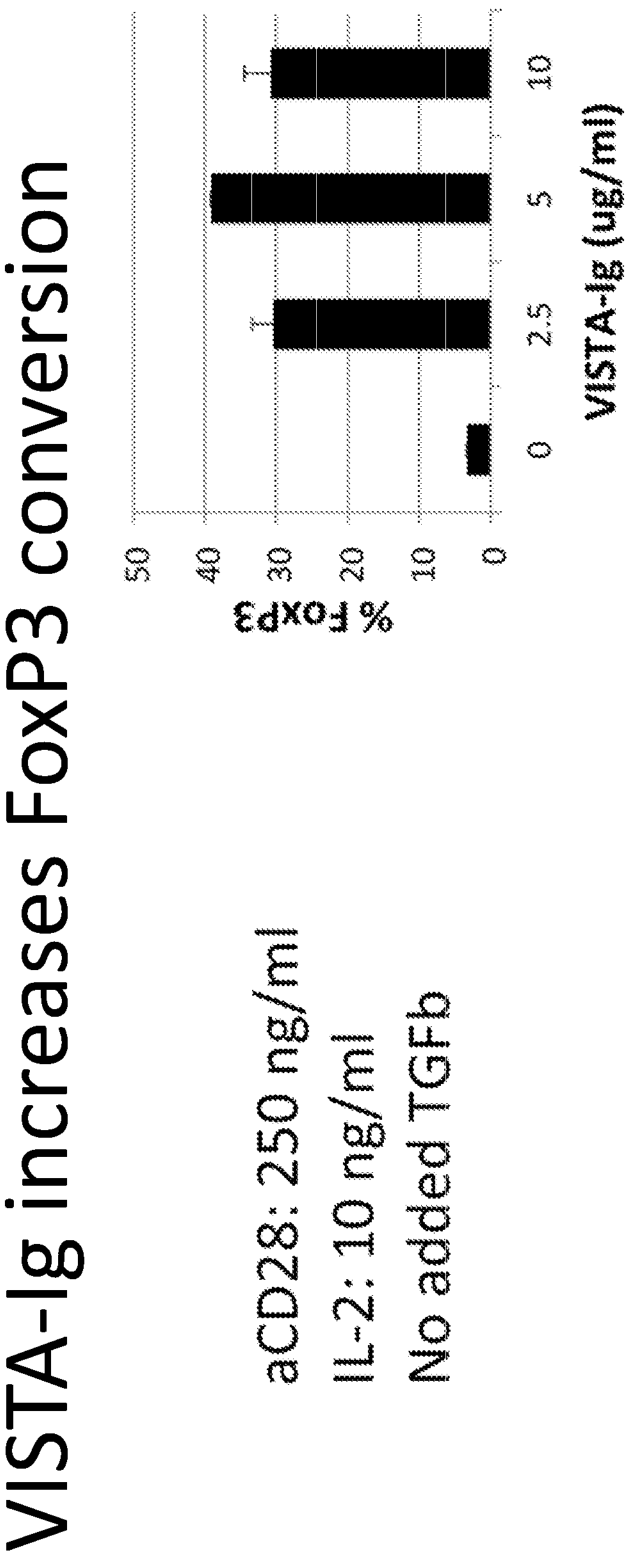

FIG. 33A-33D depicts the status of cells was examined following activation in the presence or absence of VISTA-Ig. During 2 days of culture, upregulation by anti-CD3 of the early activation markers CD25 and CD69 was blocked by VISTA-Ig (FIGS. 33A & 33B). Similarly, after 5 days of culture, the shift from expression of CD45RA to CD45RO, indicative of antigen-experience was prevented (FIG. 33C). VISTA had no affect on cell viability. FIG. 33D shows that VISTA-Ig increased FoxP3 conversion.

Figure 34:
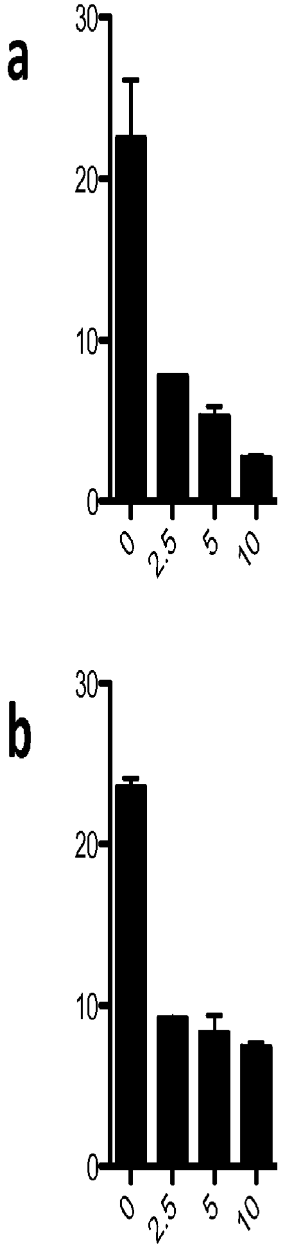

FIG. 34 depicts the suppression induced by VISTA where cells were cultured on anti-CD3 and VISTA-Ig for two days, and then moved onto anti-CD3 alone for 3 days. This further stimulation was unable to rescue suppression (FIGS. 34A and 34B.)

Figure 35:
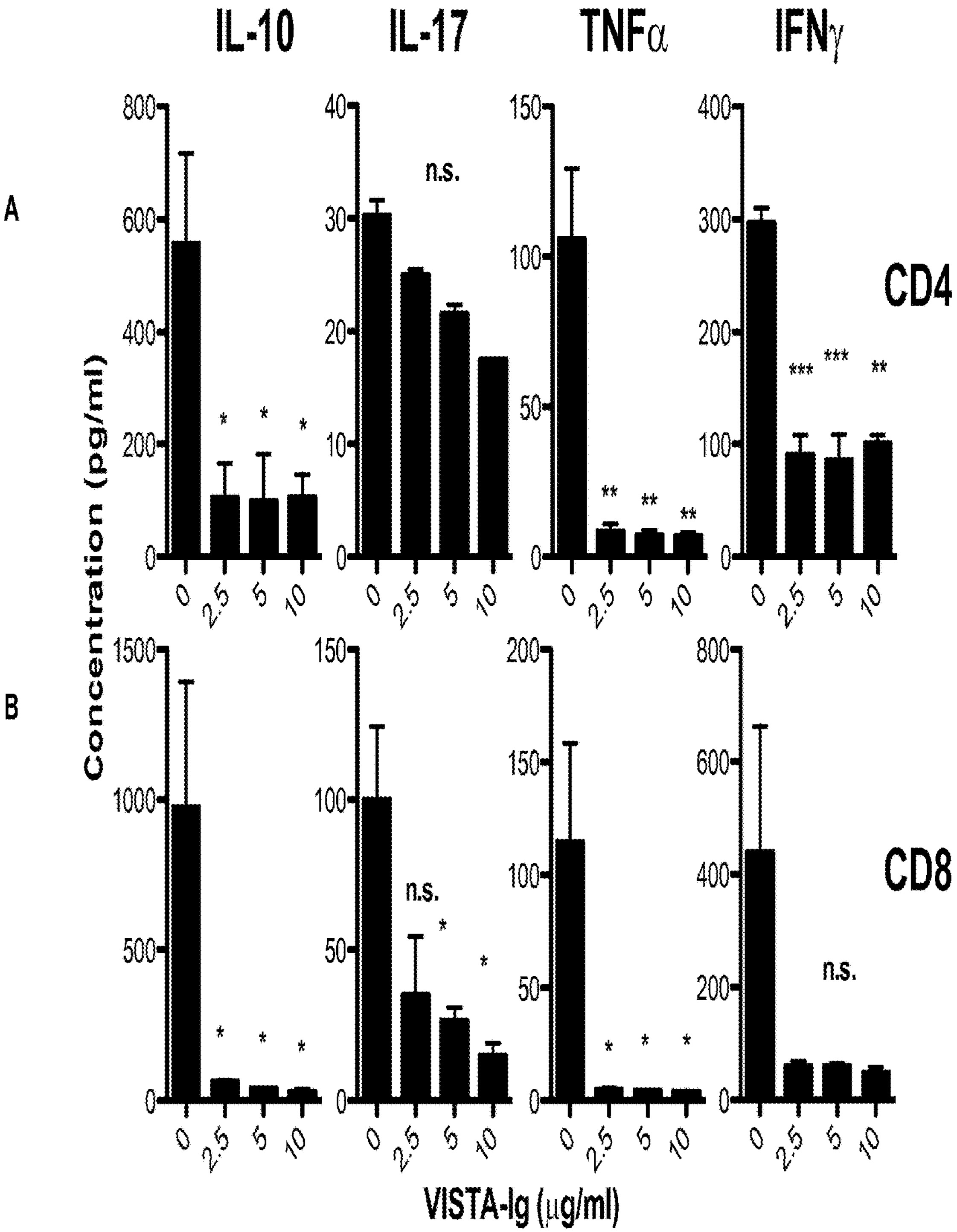

FIG. 35 shows that VISTA-Ig significantly reduced production of IL-10, TNFα and IFNγ by CD4 (FIG. 35A) and CD8 (FIG. 35B) T cells, and there was a trend towards a modest decrease in IL-17 production.

Figures 36A, 36B, 36C:
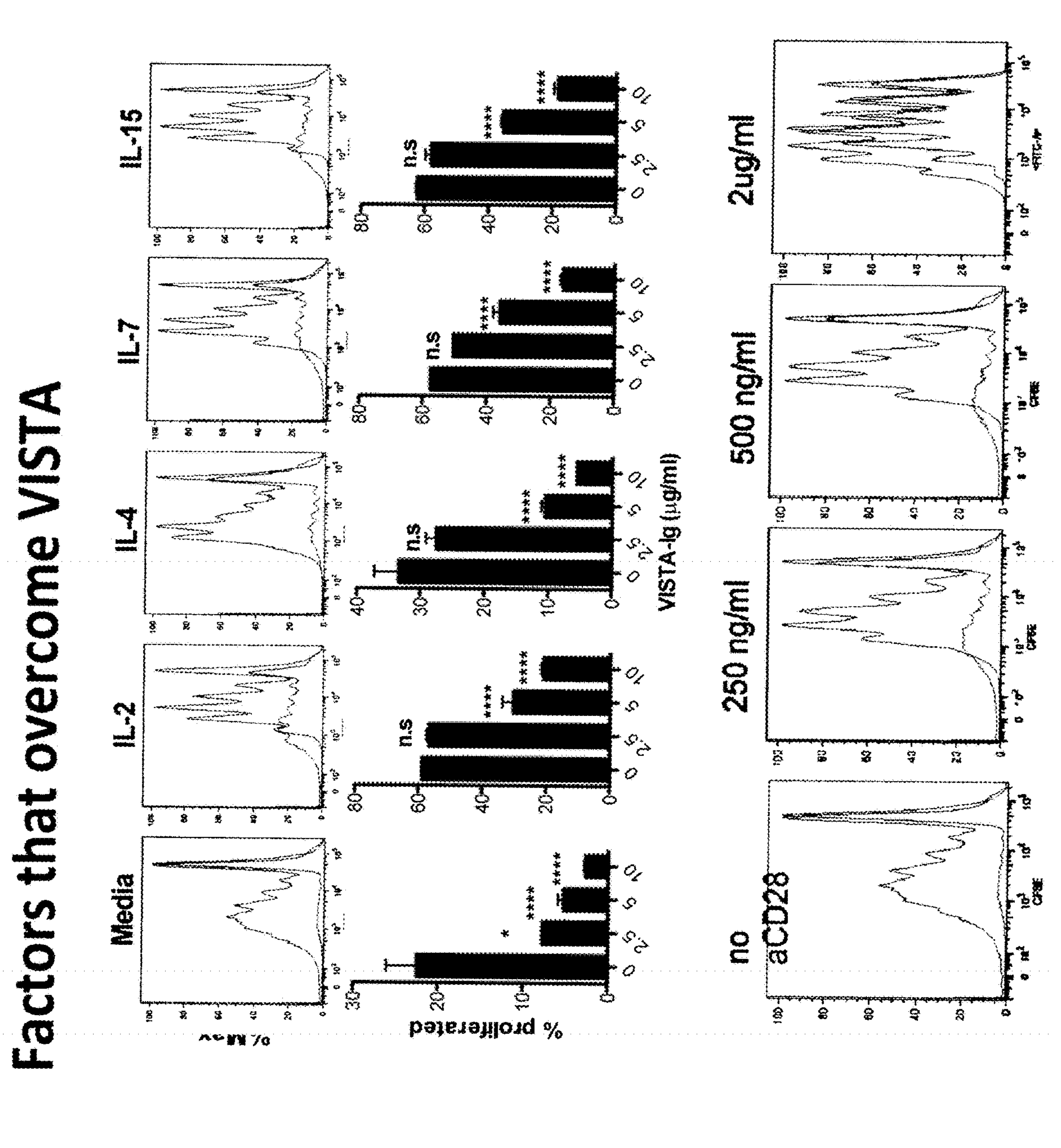

FIG. 36A-36C show that anti-CD28 agonistic antibody provides potent costimulation to T cells, and so titred into the cultures to challenge VISTA suppression (FIG. 36A-C).

Figure 37:
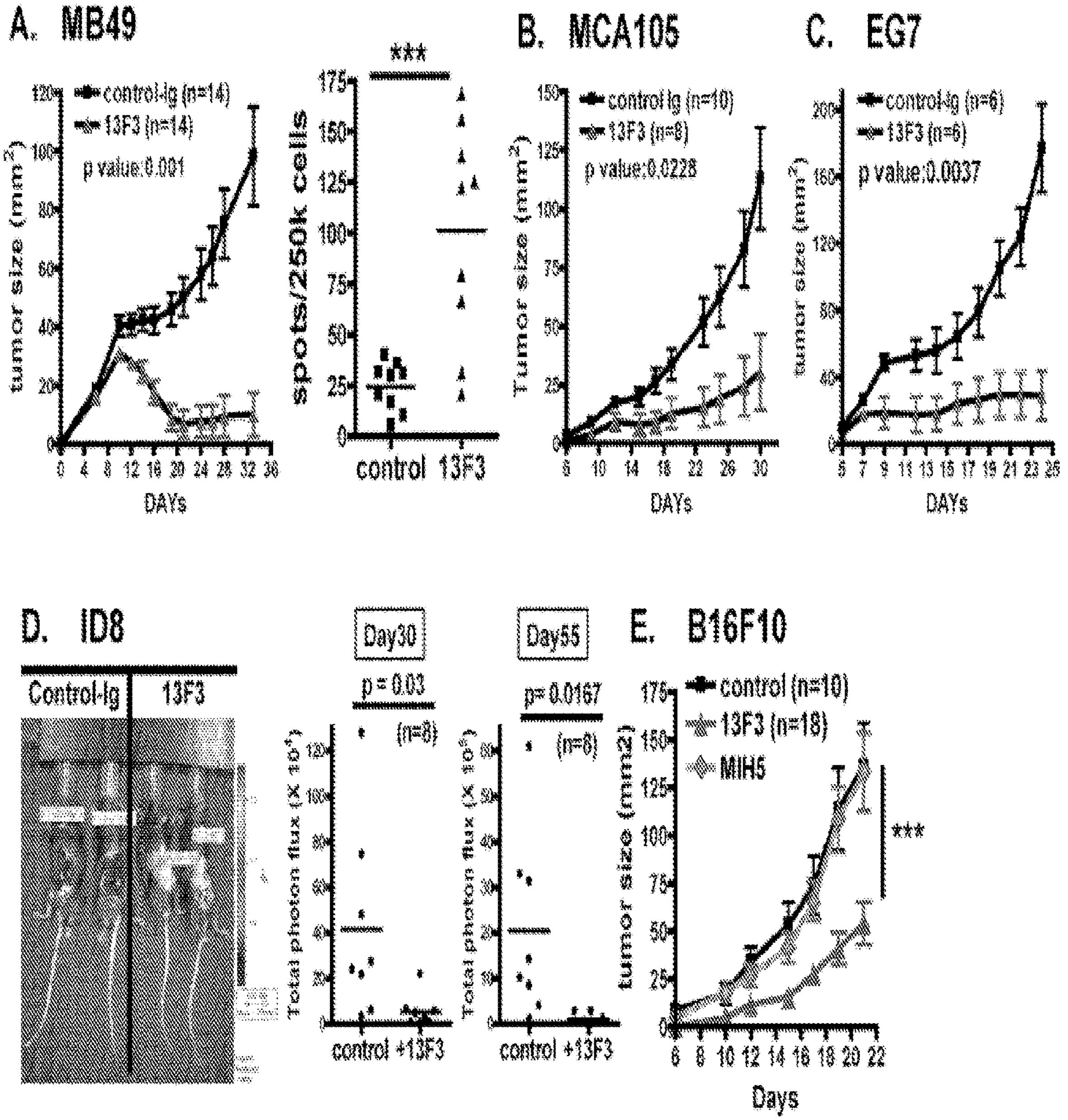

FIG. 37. VISTA mAb treatment reduced tumour growth. Mice were injected with A. MB49. B. MCA105. C. EG7 tumour cells, D. ID8-luciferase. E. B16F10. Mice were treated with VISTA mAb 13F3 every other day (300 μg) beginning on day 0 (A-D), or day-2 (E). PD-L1 mAb (MIH5) was also administered to B16F10. Subcutaneous tumour growth was monitored with calliper and recorded as $mm^2$. For intraperitoneal ID8-luciferase tumour, mice were imaged on day 30 and 55 using Xenogen IVIS. For MB49 ELISPOT analysis (A), tumour drain-LN cells were stimulated with irradiated tumour cells.

Figure 38:
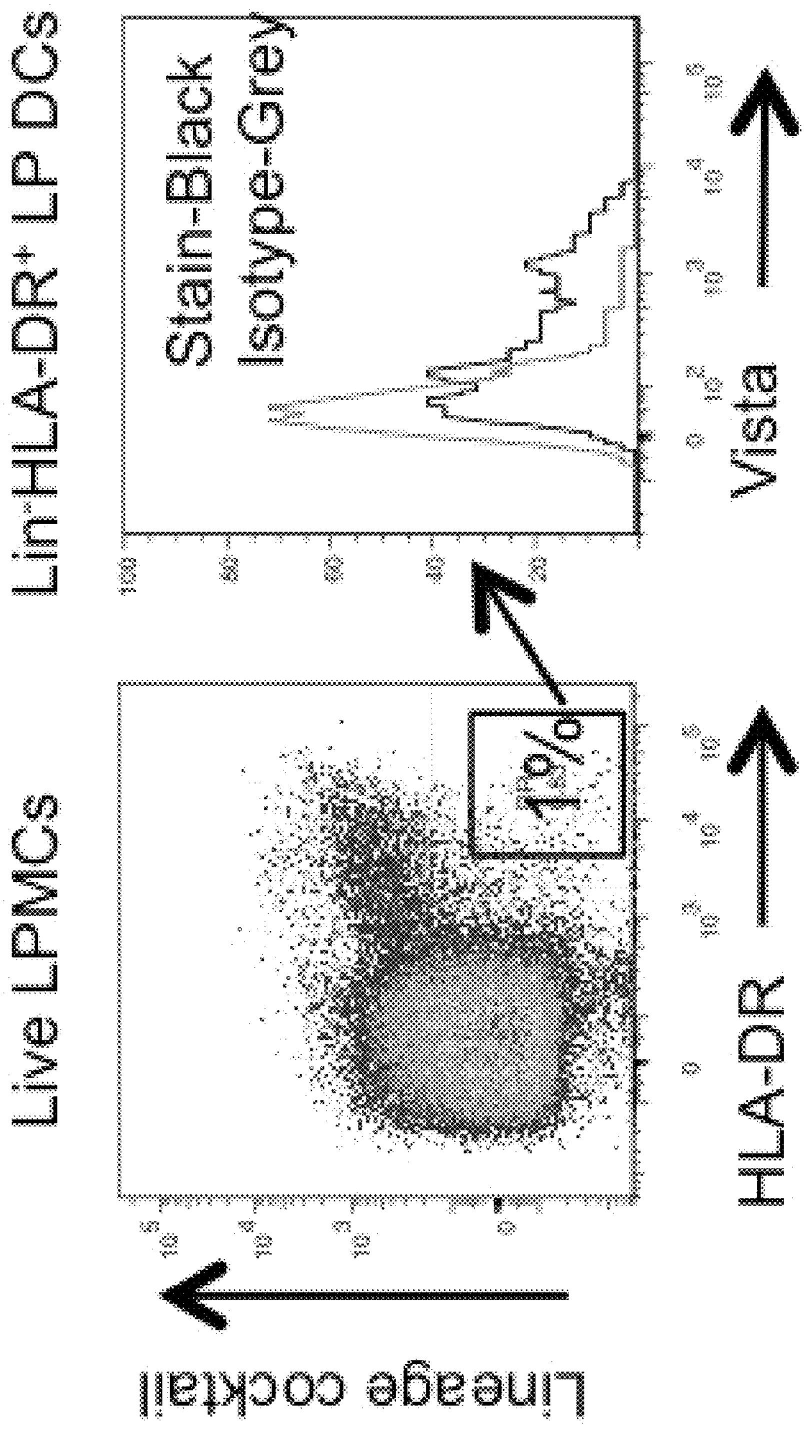

FIG. 38. Human lamina propria DCs express VISTAa. LMPCs isolated from healthy colon were stained with biotin-conjugated anti-human VISTA (antibody clone GA1) to identify VISTA expression in Lin-HLA-DR+ LP dendritic cells.

Figure 39B:
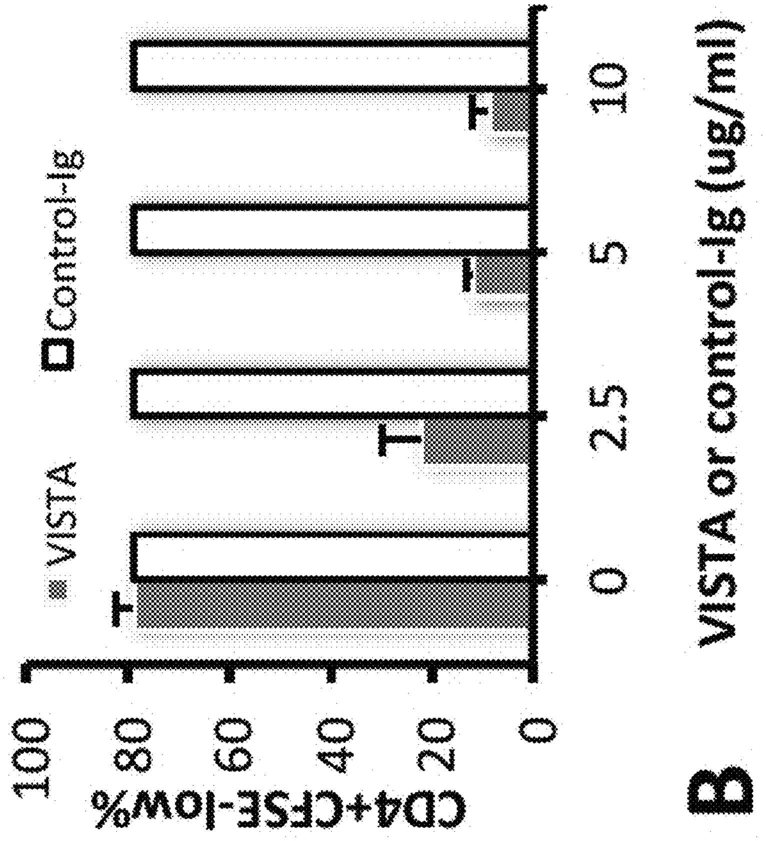
Figure 39A:
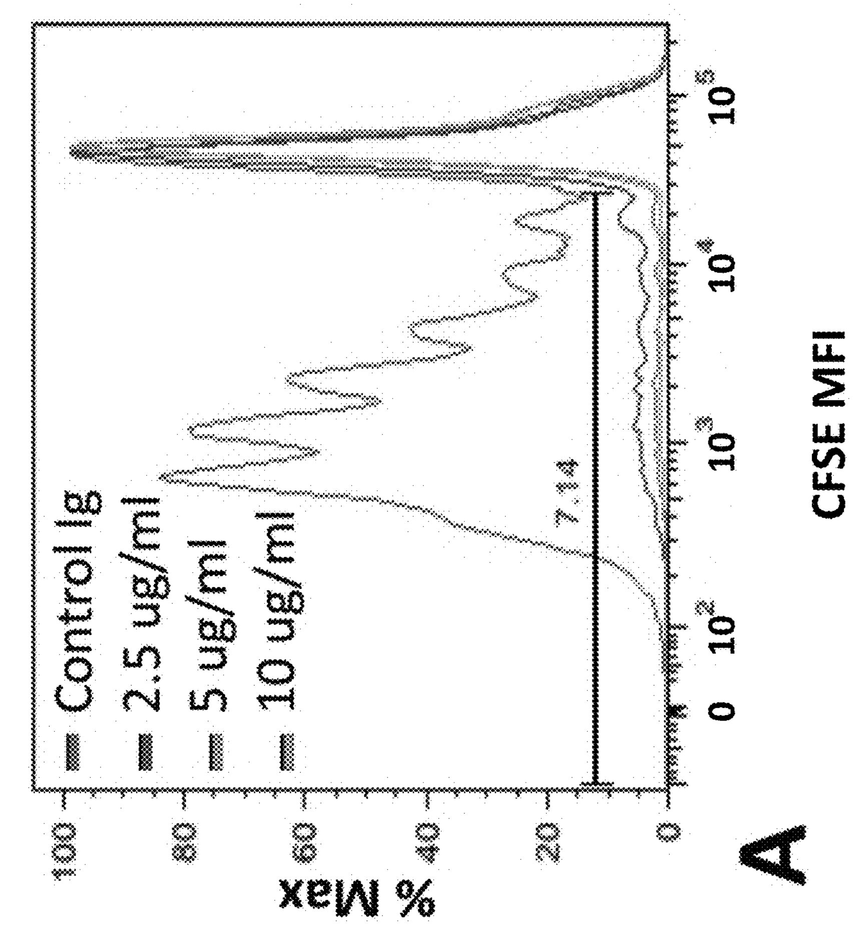

FIGS. 39A-39B Vista-Ig are suppressive to human D4 T cells. CFSE-labeled human CD4 T cells were stimulated with plate-bound anti-CD3 at 2.5 ug/ml and VISTA-Ig at the indicated concentrations. (A) Representative CFSE dilution profiles. (B) The percentage of CFSE-low cells was quantified and shown as mean+/−SEM.

FIGS. 40A-40C VISTA act in concert with the PD-L1/PD-1 pathway. A. Combinatorial treatment (Day+4) with αVISTA and aPD-L1 mAbs inhibited B16F10 tumour growth. B. Synergy in vitro: VISTA-Ig and PD-L1-Ig were immobilized together with αCD3/CD28 to stimulate CD4+ and CD8+ naïve T cells. Cell proliferation was assessed by CFSE dilution at 72 hrs. C. Differential expression pattern of PD-L1 and VISTA within the TME of B16F10 tumour. VISTA is expressed only on tumour-infiltrating leukocytes (TILs), whereas PD-L1 is expressed on both tumour cells and TILs.

Figure 41:
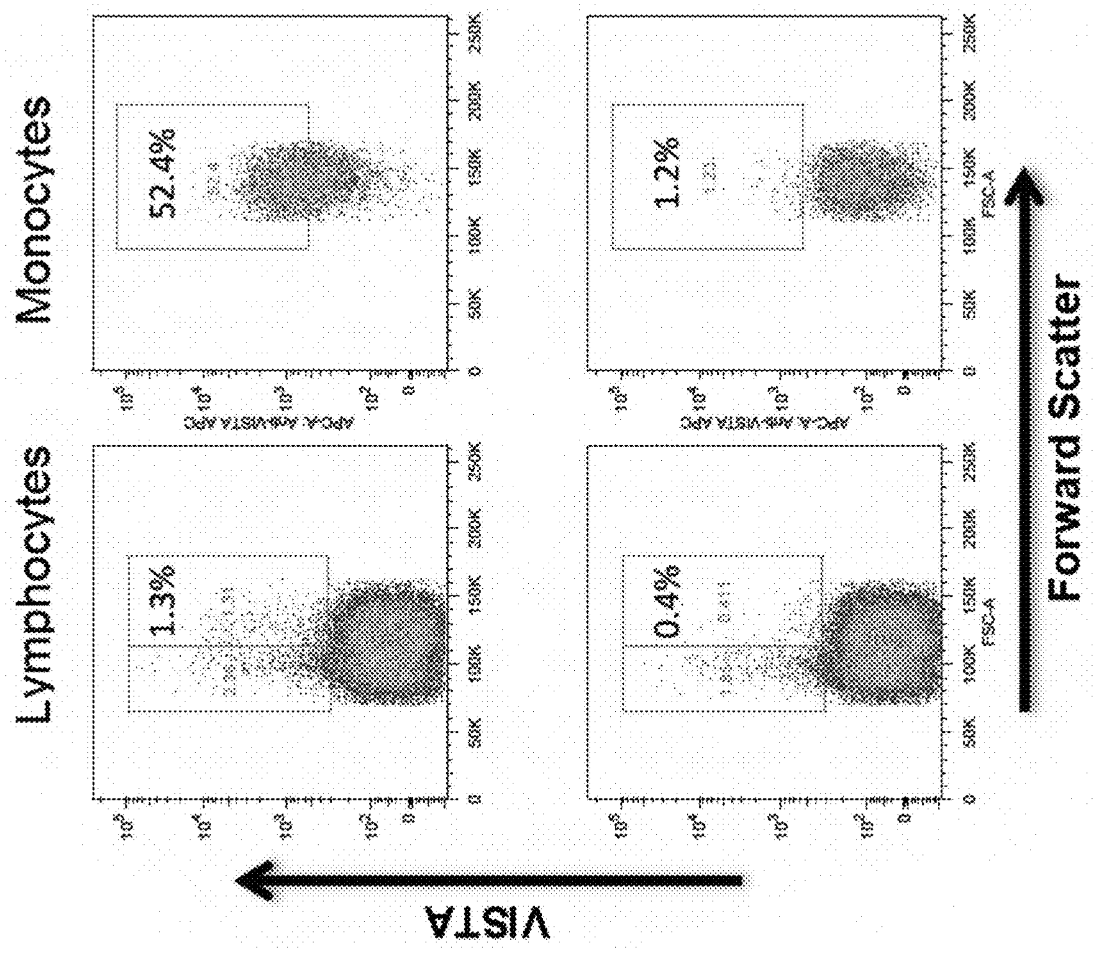

FIG. 41. Detection of VISTA on myeloid cells with ah VISTA mAb. PBL were stained in the absence (top) or presence of VISTA-Ig (bottom) to confirm specificity.

Figure 42:
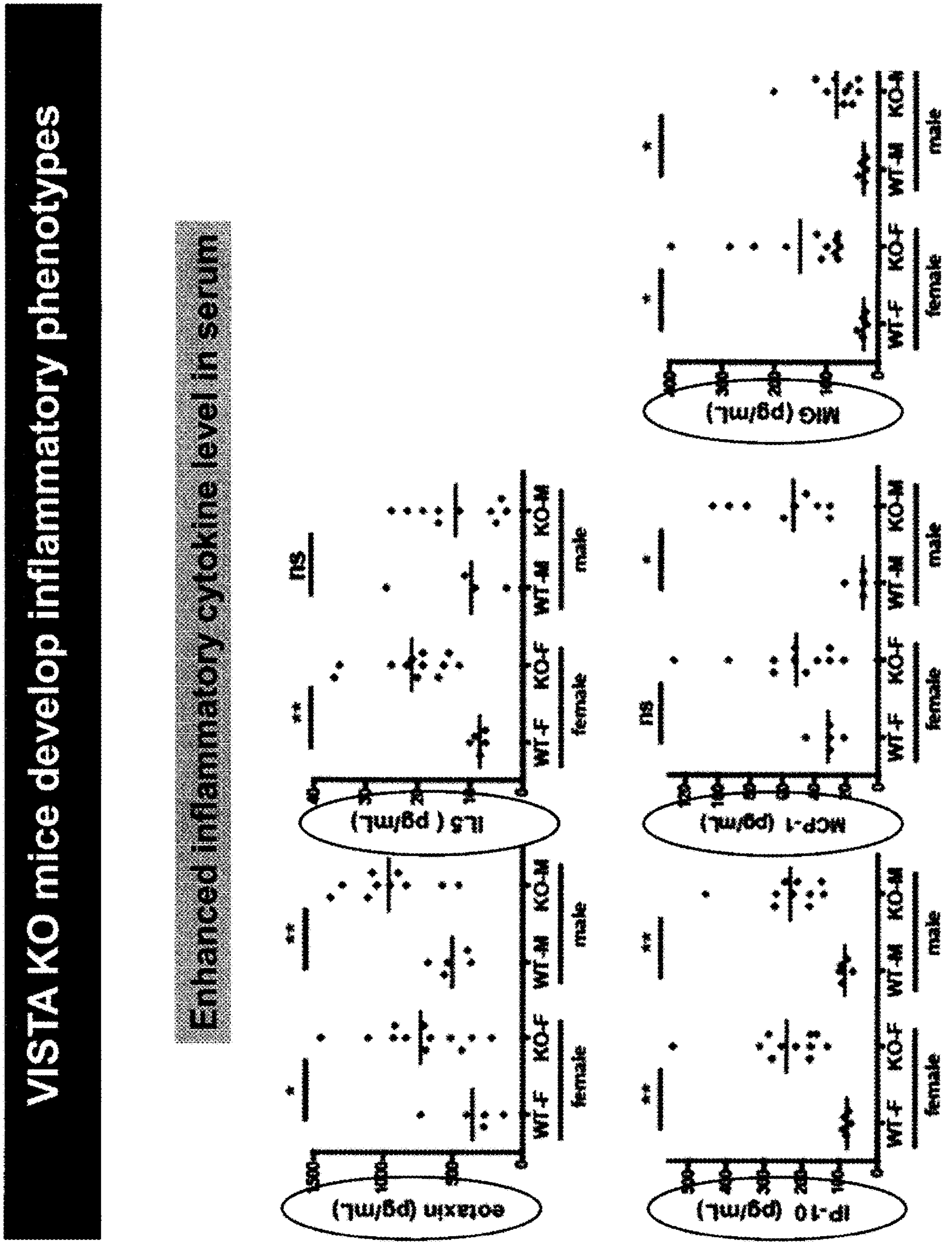

FIG. 42 shows that VISTA KO mice exhibit an inflammatory phenotypes characterized by enhanced inflammatory cytokine level in their serum.

Figure 43:
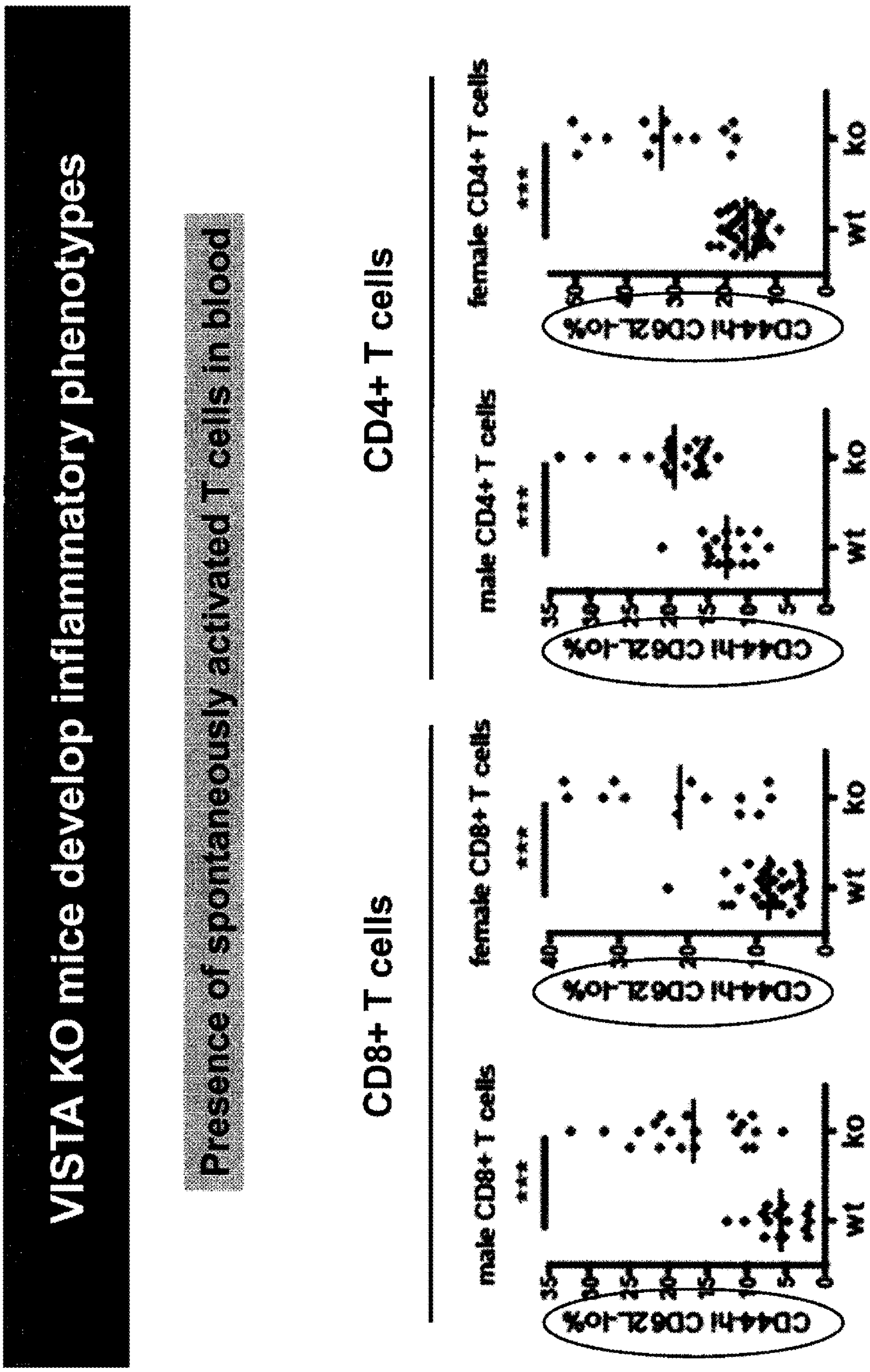

FIG. 43 shows that VISTA KO mice exhibit an inflammatory phenotypes characterized by the presence of spontaneously activated T cells in blood.

Figure 44:
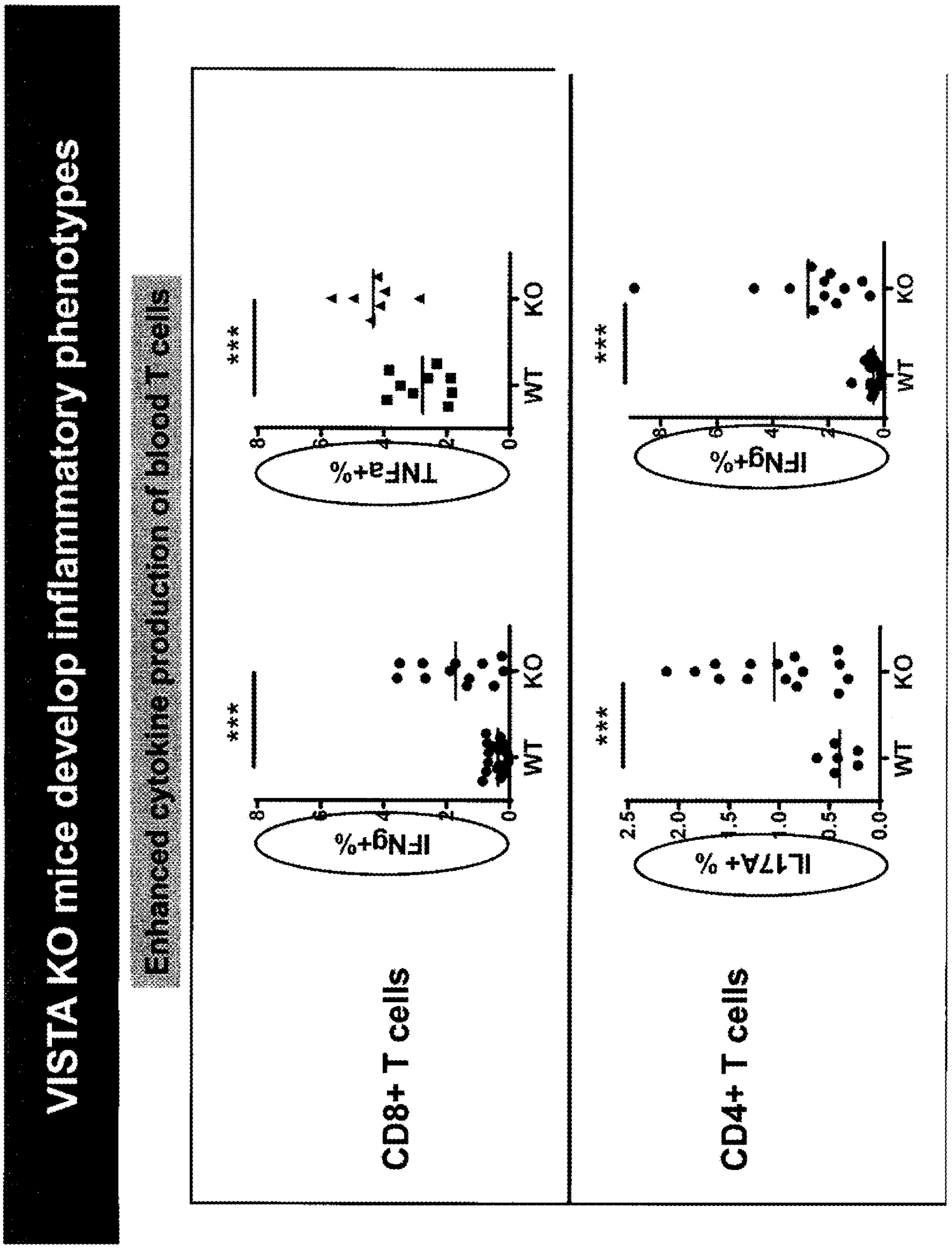

FIG. 44 shows that VISTA KO mice exhibit an inflammatory phenotypes characterized by enhanced cytokine production of blood T cells.

Figure 45:
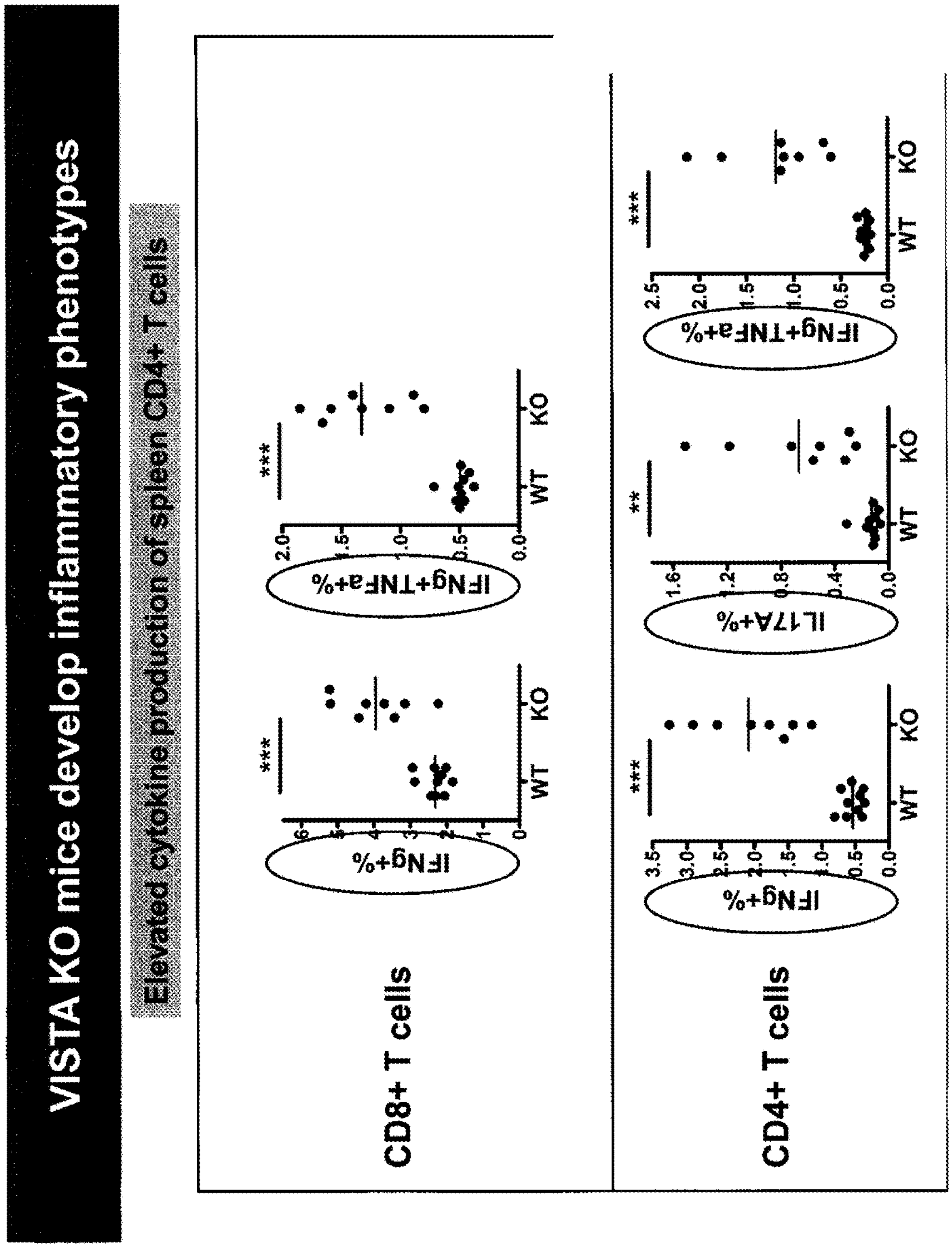

FIG. 45 shows that VISTA KO mice exhibit an inflammatory phenotypes characterized by enhanced cytokine production of spleen T cells.

DETAILED DESCRIPTION

We have discovered a novel inhibitory ligand, designated V-domain Ig Suppressor of T cell Activation (VISTA), that plays a key role in disrupting protective anti-tumour immunity in mice (1). VISTA bears limited homology to PDL1, and critically suppresses T cell activation via an unknown receptor, independent of PD-1. VISTA KO mice display inflammatory phenotypes, indicating an essential role for VISTA in maintaining peripheral tolerance. VISTA is highly expressed in the tumour microenvironment (TME) and directly impairs the generation of optimal anti-tumour immunity. VISTA mAb-mediated blockade significantly suppressed tumour growth in multiple mouse tumour models.

Based on these findings, we hypothesize that VISTA is expressed on tumour-infiltrating leukocytes, and that this expression is suppressive for T cell responses in the TME. This application extends our existing studies of VISTA in mouse models to human patients. Specifically, the application further describes examining VISTA expression in patient samples and testing how this influences T cell function. Based thereon, inhibition of VISTA may be used in the treatment of cancer (similar to the success with functionally related proteins CTLA-4 and PD-L1). In another aspect, the disclosure provides methods of identifying suitable blocking antibodies to be developed for this purpose.

In another aspect, the present invention relates to therapeutic methods that modulate the activity and/or which specifically bind or block the binding of a specific regulatory T cell protein to its counterreceptor. This protein, designated PD-L3 OR VISTA, is a novel and structurally-distinct, Ig-superfamily inhibitory ligand, whose extracellular domain bears homology to the B7 family ligand PD-L1. This molecule is referred to interchangeably herein as PD-L3 or VISTA or as V-domain Immunoglobulin Suppressor of T cell Activation (VISTA). VISTA is expressed primarily within the hematopoietic compartment and is highly regulated on myeloid APCs and T cells. Therapeutic intervention of the VISTA inhibitory pathway represents an exciting approach to modulate T cell-mediated immunity for the treatment of a wide variety of cancers.

The present invention in particular relates to the use of antibodies specific to VISTA or PD-L3 to treat specific cancers including colorectal cancer, bladder cancer, ovarian cancer, and melanoma.

As disclosed infra, the expression of VISTA appears to be exclusive to the hematopoietic compartment and this protein is highly expressed on mature myeloid cells ($CD11b^{bright}$), with lower levels of expression on $CD4^+$ T cells, $T^{reg}$ and $CD8^+$ T cells. Soluble VISTA proteins, e.g., soluble VISTA-Ig fusion protein, or VISTA expression on APCs, suppresses in vitro $CD4^+$ and $CD8^+$ T cell proliferation and cytokine production. It is also observed that anti-VISTA antibodies, e.g., an anti-VISTA mab (13F3) blocked VISTA-induced suppression of T cell responses by $VISTA^+$ APCs in vitro. Also, it has been discovered that an anti-VISTA mab exacerbated EAE and increased the frequency of encephalitogenic Th17s in vivo. Still further, as disclosed in detail infra, it has been found that an anti-VISTA mab induces tumor remission in multiple (4) murine tumor models. VISTA expression on myeloid derived suppressor cells (MDSC) in these models is extremely high, suggesting that $VISTA^+$ MDSC suppress tumor specific immunity. As shown herein, VISTA exerts immunosuppressive activities on T cells both in vitro and in vivo, in mouse and in human (in vitro only) and is an important mediator in controlling the development of autoimmunity and the immune responses to cancer. Specifically, the data show that:

(1) VISTA is a new member of the Ig superfamily and contains an Ig-V domain with distant sequence similarity to PD-L1. We disclose herein that when produced as an Ig fusion protein or when overexpressed on artificial APCs VISTA inhibits both mouse and human CD4+ and CD8+ T cell proliferation and cytokine production.

(2) VISTA expression on myeloid APCs is inhibitory for T cell responses in vitro.

(3) VISTA expression on MDSC in the tumor microenvironment is extremely high. Phenotypic and functional analysis of many cell surface molecules previously suggested to be involved in MDSC-mediated suppression of T cells: CD115, CD124, CD80, PD-L1, and PD-L2 were expressed by MDSC but with no differences in the levels of their expression or proportion of positive cells were found between MDSC and cells from tumor-free mice that lack immune suppressive activity. Therefore, we predict that VISTA will be the primary B7 negative regulator on MDSCs.

(4) Antibody-mediated VISTA blockade induces protective immunity to an autologous tumor.

Based thereon, VISTA appears to be a dominant, negative immune regulatory molecule on MDSCs that interferes with the development of protective anti-tumor immunity. Therefore, blocking the activity of this molecule with anti-VISTA antibodies will permit the development of protective anti-tumor immunity in humans and other mammals.

Therefore, the invention relates to methods of using soluble VISTA proteins, e.g., fusion proteins and multimeric VISTA proteins comprising multiple copies of the VISTA extravcelular domain or a fragment thereof, and VISTA binding agents, e.g., small molecules and antibodies or fragments thereof, which bind or modulate (agonize or antagonize) the activity of VISTA as immune modulators and for the treatment of different cancers, e.g., colorectal cancer, bladder, ovarian and lymphoma, autoimmune disease, allergy, infection and inflammatory conditions, e.g. multiple sclerosis and arthritis.

As described in detail infra, VISTA is a novel inhibitory ligand, which extracellular Ig-V domain bears homology to the two known B7 family ligands Programmed Death Ligand 1 and 2 (PD-L1 and PD-L2) and exhibits unique sequence features and distinctive expression patterns in vitro and in vivo on subsets of APCs and T cells, (which distinguishes PD-L3 or VISTA from other B7 family ligands). This protein has been shown to have a functional impact on $CD4^+$ and $CD8^+$ T cell proliferation and differentiation (suppresses $CD4^+$ and $CD8^+$ T cell proliferation, as well as cytokine production). Based on its expression pattern and inhibitory impact on T cells, PD-L3 OR VISTA apparently functions as a regulatory ligand that negatively regulates T cell responses during cognate interactions between T cells and myeloid derived APCs.

While PD-L3 OR VISTA appears to be a member of the B7 family of ligands, unlike other B7 family ligands, this molecule contains only an Ig-V domain without an Ig-C domain, and is phylogenically closer to the B7 family receptor Programmed Death-1 (PD-1). Based thereon, PD-L3 OR VISTA, and agonists or antagonists specific thereto can be used to regulate T cell activation and differentiation, and more broadly to modulate the regulatory network that controls immune responses. In particular PD-L3 or VISTA proteins and PD-L3 or VISTA agonists or antagonists, preferably antibodies specific to PD-L3 or VISTA are useful in modulating immune responses in autoimmunity, inflammatory responses and diseases, allergy, cancer, infectious disease and transplantation.

Therefore, the present invention in part relates to compositions e.g., for therapeutic, diagnostic or immune modulatory usage containing an isolated soluble PD-L3 OR VISTA protein or fusion protein, e.g., a soluble VISTA-Ig fusion protein or a multimeric VISTA protein, comprising an amino acid sequence that preferably is at least 70-90% identical to the human or murine PD-L3 OR VISTA polypeptide set forth in SEQ ID NO:2, 4 or 5 or an ortholog, or fragment thereof encoded by a gene that specifically hybridizes to SEQ ID NO:1 or 3 that modulates VISTA in vivo and a pharmaceutically acceptable carrier. In some embodiments, the soluble or multimeric VISTA protein may be directly or indirectly linked to a heterologous (non-VISTA) protein or may be expressed by a viral vector or a cell containing, e.g., a transfected immune cell such as a T cell.

The present invention also provides expression vectors comprising an isolated nucleic acid encoding a VISTA protein that is at least 70-90% identical to the human or murine VISTA amino acid sequence set forth in SEQ ID NO:2, 4 or 5 or a fragment or ortholog thereof, which optionally is fused to a sequence encoding another protein such as an Ig polypeptide, e.g., an Fc region or a reporter molecule; and host cells containing said vectors.

The present invention also specifically relates to an isolated binding agent, preferably an antibody or antibody fragment which specifically binds to a PD-L3 OR VISTA protein comprising the amino acid sequence set forth in SEQ ID NO:2, 4 or 5 or a variant, fragment or ortholog thereof. In a preferred embodiment, the binding agent modulates (agonizes or antagonizes) VISTA activity in vitro or in vivo. In most preferred embodiments, the binding agent is an agonistic or antagonistic antibody.

The present invention further provides methods for modulating an immune cell response by contacting an immune cell in vitro or in vivo with a VISTA protein, or binding agent specific thereto, in the presence of a primary signal so that a response of the immune cell is modulated. (Interaction of VISTA or a modulator thereof transmits a signal to immune cells, regulating immune responses. PD-L3 OR VISTA protein is expressed at high levels on myeloid antigen presenting cells, including myeloid dendritic cells (DCs) and macrophages, and at lower densities on CD4+ and CD8+ T cells. Upon immune activation, PD-L3 or VISTA expression is upregulated on myeloid APCs, but downregulated on CD4+ T cells). Therefore, the PD-L3 or VISTA nucleic acids and polypeptides of the present invention, and agonists or antagonists thereof are useful, e.g., in modulating the immune response.

In addition, the PD-L3 or VISTA polypeptides (or biologically active portions thereof) or modulators of the PD-L3 or VISTA molecules, i.e., antibodies such as selected using the foregoing methods can be incorporated into pharmaceutical compositions, which optionally include pharmaceutically acceptable carriers.

Immune cells activated in accordance with the method of the instant invention can subsequently be expanded ex vivo and used in the treatment and prevention of a variety of diseases; e.g., human T cells which have been cloned and expanded in vitro maintain their regulatory activity (Groux, et al. (1997) Nature 389(6652):737-42). Prior to expansion, a source of T cells is obtained from a subject (e.g., a mammals such as a human, dog, cat, mouse, rat, or transgenic species thereof). T cells can be obtained from a number of sources, including peripheral blood mononuclear cells, bone marrow, lymph node tissue, cord blood, thymus tissue, tissue from a site of infection, spleen tissue, tumors or T cell lines. T cells can be obtained from a unit of blood collected from a subject using any number of techniques known to the skilled artisan, such as Ficoll™ separation. In another aspect, the present invention provides a method for detecting the presence of a PD-L3 or VISTA nucleic acid molecule, protein, or polypeptide in a biological sample by contacting the biological sample with an agent capable of detecting a PD-L3 OR VISTA nucleic acid molecule, protein, or polypeptide, such that the presence of a PD-L3 OR VISTA nucleic acid molecule, protein or polypeptide is detected in the biological sample. This PD-L3 OR VISTA expression can be used to detect certain disease sites, including cancerous sites.

In another aspect, the invention provides a method for modulating PD-L3 OR VISTA activity, comprising contacting a cell capable of expressing PD-L3 OR VISTA with an agent that modulates PD-L3 OR VISTA activity, preferably an anti-PD-L3 OR VISTA antibody such that PD-L3 OR VISTA activity in the cell is modulated. In one embodiment, the agent inhibits PD-L3 OR VISTA activity. In another embodiment, the agent stimulates PD-L3 OR VISTA activity. In a further embodiment, the agent interferes with or enhances the interaction between a PD-L3 OR VISTA polypeptide and its natural binding partner(s). In one embodiment, the agent is an antibody that specifically binds to a PD-L3 OR VISTA polypeptide. In another embodiment, the agent is a peptide, peptidomimetic, or other small molecule that binds to a PD-L3 OR VISTA polypeptide.

In still another embodiment, the agent modulates expression of PD-L3 OR VISTA by modulating transcription of a PD-L3 OR VISTA gene, translation of a PD-L3 OR VISTA mRNA, or post-translational modification of a PD-L3 OR VISTA polypeptide. In another embodiment, the agent is a nucleic acid molecule having a nucleotide sequence that is antisense to the coding strand of a PD-L3 OR VISTA mRNA or a PD-L3 OR VISTA gene.

In one embodiment, the methods of the present invention are used to treat a subject having a disorder or condition characterized by aberrant, insufficient, or unwanted PD-L3 OR VISTA polypeptide or nucleic acid expression or activity by administering an agent which is a PD-L3 OR VISTA modulator to the subject. In one preferred embodiment, the PD-L3 OR VISTA modulator is a PD-L3 OR VISTA polypeptide, preferably a soluble fusion protein or multimeric VISTA protein or anti-VISTA antibody as described infra. In another embodiment the PD-L3 OR VISTA modulator is a PD-L3 OR VISTA nucleic acid molecule, e,g in an adenoviral vector. In another embodiment, the invention further provides treating the subject with an additional agent that modulates an immune response.

In still another embodiment, the invention provides a vaccine comprising an antigen and an agent that modulates (enhances or inhibits) PD-L3 OR VISTA activity. In a preferred embodiment, the vaccine inhibits the interaction between PD-L3 OR VISTA and its natural binding partner(s).

In another aspect the invention provides methods for identifying a compound that binds to or modulates the activity of a PD-L3 OR VISTA polypeptide, by providing an indicator composition comprising a PD-L3 OR VISTA polypeptide having PD-L3 OR VISTA activity, contacting the indicator composition with a test compound, and determining the effect of the test compound on PD-L3 OR VISTA activity in the indicator composition to identify a compound that modulates the activity of a PD-L3 OR VISTA polypeptide.

In one aspect, the invention features a method for modulating the interaction of PD-L3 OR VISTA with its natural binding partner(s) on an immune cell comprising contacting an antigen presenting cell which expresses PD-L3 OR VISTA with an agent selected from the group consisting of: a form of PD-L3 OR VISTA, or an agent that modulates the interaction of PD-L3 OR VISTA and its natural binding partner(s) such that the interaction of PD-L3 OR VISTA with it natural binding partner(s) on an immune cell is modulated. In a preferred embodiment, an agent that modulates the interaction of PD-L3 OR VISTA and its natural binding partner(s) is an antibody that specifically binds to PD-L3 OR VISTA. In one embodiment, the interaction of PD-L3 OR VISTA with its natural binding partner(s) is upregulated. In another embodiment, the interaction of PD-L3 OR VISTA with its natural binding partner(s) is downregulated. In one embodiment, the method further comprises contacting the immune cell or the antigen presenting cell with an additional agent that modulates an immune response.

In one embodiment, the step of contacting is performed in vitro. In another embodiment, the step of contacting is performed in vivo. In one embodiment, the immune cell is selected from the group consisting of: a T cell, a monocyte, a macrophage, a dendritic cell, a B cell, and a myeloid cell.

In another aspect, the invention pertains to a method for inhibiting or increasing activation in an immune cell comprising increasing or inhibiting the activity or expression of PD-L3 OR VISTA in a cell such that immune cell activation is inhibited or increased.

In yet another aspect, the invention pertains to a vaccine comprising an antigen and an agent that inhibits the interaction between PD-L3 OR VISTA and its natural binding partner(s).

In another aspect, the invention pertains to a method for treating a subject having a condition that would benefit from upregulation of an immune response comprising administering an agent that inhibits the interaction between PD-L3 OR VISTA and its natural binding partner(s) on immune cells of the subject such that a condition that would benefit from upregulation of an immune response is treated. In one preferred embodiment, the agent comprises a blocking antibody or a small molecule that binds to PD-L3 OR VISTA and inhibits the interaction between PD-L3 OR VISTA and its natural binding partner(s). In another embodiment, the method further comprises administering a second agent that upregulates an immune response to the subject. In another aspect, the invention pertains to a method for treating a subject having a condition that would benefit from downregulation of an immune response comprising administering an agent that stimulates the interaction between PD-L3 OR VISTA and its natural binding partner(s) on cells of the subject such that a condition that would benefit from downregulation of an immune response is treated.

For example the condition treated with the PD-L3 OR VISTA protein or binding agents is selected from the group consisting of: a tumor, a pathogenic infection, an inflammatory immune response or condition, preferably less pronounced inflammatory conditions, or an immunosuppressive disease. Specific examples include multiple sclerosis, thyroiditis, rheumatoid arthritis, diabetes type II and type I and cancers, both advanced and early forms, including metastatic cancers such as colorectal cancer, bladder cancer, ovarian cancer, melanoma, lung cancer, and other cancers wherein VISTA suppresses an effective anti-tumor response. In some case the individual may be administered cells or a viral vector that express a nucleic acid that encodes an anti-VISTA antibody or VISTA fusion protein.

Exemplary conditions treatable using PD-L3 OR VISTA proteins, binding agents or PD-L3 OR VISTA antagonists or agonists according to the invention include by way of example transplant, an allergy, infectious disease, cancer, and inflammatory or autoimmune disorders, e.g., an inflammatory immune disorder. Specific examples of the foregoing include type 1 diabetes, multiple sclerosis, rheumatoid arthritis, psoriatic arthritis, systemic lupus erythematosis, rheumatic diseases, allergic disorders, asthma, allergic rhinitis, skin disorders, gastrointestinal disorders such as Crohn's disease and ulcerative colitis, transplant rejection, poststreptococcal and autoimmune renal failure, septic shock, systemic inflammatory response syndrome (SIRS), adult respiratory distress syndrome (ARDS) and envenomation; autoinflammatory diseases as well as degenerative bone and joint diseases including osteoarthritis, crystal arthritis and capsulitis and other arthropathies. Further, the methods and compositions can be used for treating tendonitis, ligamentitis and traumatic joint injury.

In preferred embodiments the subject PD-L3 OR VISTA proteins, nuclei acids, and ligands specific to PD-L3 OR VISTA, preferably antibodies having desired effects on PD-L3 OR VISTA functions are used to treat conditions such a cancer, autoimmune diseases, allergy, inflammatory disorders or infection and more specifically immune system disorders such as severe combined immunodeficiency, multiple sclerosis, systemic lupus erythematosus, type I diabetes mellitus, lymphoproliferative syndrome, inflammatory bowel disease, allergies, asthma, graft-versus-host disease, and transplant rejection; immune responses to infectious pathogens such as bacteria and viruses; and immune system cancers such as lymphomas and leukemias)

In addition to the infectious and parasitic agents mentioned above, another area for desirable enhanced immunogenicity to a non-infectious agent is in the area of dysproliferative diseases, including but not limited to cancer, in which cells expressing cancer antigens are desirably eliminated from the body. Tumor antigens which can be used in the compositions and methods of the invention include, but are not limited to, prostate specific antigen (PSA), breast cancer antigens, bladder cancer antigens, ovarian cancer antigens, testicular cancer antigens, melanoma antigens, colorectal cancer antigens, telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells. It is contemplated by the invention that antigens from any type of tumor cell can be used in the compositions and methods described herein. The antigen may be a cancer cell, or immunogenic materials isolated from a cancer cell, such as membrane proteins. Included are survivin and telomerase universal antigens and the MAGE family of cancer testis antigens. Antigens which have been shown to be involved in autoimmunity and could be used in the methods of the present invention to induce tolerance include, but are not limited to, myelin basic protein, myelin oligodendrocyte glycoprotein and proteolipid protein of multiple sclerosis and CII collagen protein of rheumatoid arthritis.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; multiple myeloma and post-transplant lymphoproliferative disorder (PTLD).

Exemplary cancers amenable for treatment by the present invention include, but are not limited to, carcinoma, lymphoma, blastoma, sarcoma, and leukemia or lymphoid malignancies. More particular examples of such cancers include colorectal, bladder, ovarian, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of colorectal cancer, breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. In an exemplary embodiment the cancer is an early or advanced (including metastatic) bladder, ovarian or melanoma. In another embodiment the cancer is colorectal cancer. The cancerous conditions amenable for treatment of the invention include metastatic cancers wherein VISTA expression by myeloid derived suppressor cells suppress antitumor responses and anti-invasive immune responses. The method of the present invention is particularly suitable for the treatment of vascularized tumors.

The invention is also suitable for treating cancers in combination with chemotherapy or radiotherapy or other biologics and for enhancing the activity thereof, i.e., in individuals wherein VISTA expression by myeloid derived suppressor cells suppress antitumor responses and the efficacy of chemotherapy or radiotherapy or biologic efficacy. Any chemotherapeutic agent exhibiting anticancer activity can be used according to the present invention. Preferably, the chemotherapeutic agent is selected from the group consisting of alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. More preferably, the chemotherapeutic agent is selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the anti-VEGF antibody. One preferred combination chemotherapy is fluorouracil-based, comprising 5-FU and one or more other chemotherapeutic agent(s). Suitable dosing regimens of combination chemotherapies are known in the art and described in, for example, Saltz et al. (1999) *Proc ASCO* 18:233a and Douillard et al. (2000) Lancet 355:1041-7. The bilogic may be another immune potentiators such as antibodies to PD-L1, PD-L2, CTLA-4 and PD-L1, PD-L2, CTLA-4 fusion proteins as well as cytokines, growth factor antagonists and agonists, hormones and anti-cytokine antibodies.

"Activating receptor," as used herein, refers broadly to immune cell receptors that bind antigen, complexed antigen (e.g., in the context of MHC molecules), Ig-fusion proteins, ligands, or antibodies. Activating receptors but are not limited to T cell receptors (TCRs), B cell receptors (BCRs), cytokine receptors, LPS receptors, complement receptors, and Fc receptors. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g, protein phosphorylation, membrane lipid changes, ion fluxes, cyclic nucleotide alterations, RNA transcription changes, protein synthesis changes, and cell volume changes.

"Antigen presenting cell," as used herein, refers broadly to professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified (e.g., hydroxyproline, γ-carboxyglutamate, and O-phosphoserine.) Amino acid analogs refers to compounds that have the same basic chemical structure as a naturally occurring amino acid (i.e., an a carbon that is bound to a hydrogen, a carboxyl group, an amino group), and an R group (e.g., homoserine, norleucine, methionine sulfoxide, methionine methyl sulfonium.) Analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Anergy" or "tolerance," as used herein, refers broadly to refractivity to activating receptor-mediated stimulation. Refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134). Modulation of a costimulatory signal results in modulation of effector function of an immune cell. Thus, the term "PD-L3 OR VISTA activity" includes the ability of a PD-L3 OR VISTA polypeptide to bind its natural binding partner(s), the ability to modulate immune cell costimulatory or inhibitory signals, and the ability to modulate the immune response. Modulation of an inhibitory signal in an immune cell results in modulation of proliferation of and/or cytokine secretion by an immune cell.

"Antibody", as used herein, refers broadly to an "antigen-binding portion" of an antibody (also used interchangeably with "antibody portion," "antigen-binding fragment," "antibody fragment"), as well as whole antibody molecules. The term "antigen-binding portion", as used herein, refers to one or more fragments of an antibody that retain the ability to specifically bind to an antigen (e.g, VISTA (PD-L3)). The antigen-binding function of an antibody can be performed by fragments of a full-length antibody. Examples of antigen-binding fragments encompassed within the term "antigen-binding portion" of an antibody include (a) a Fab fragment, a monovalent fragment consisting of the VL, VH, CL and CH1 domains; (b) a F(ab')2 fragment, a bivalent fragment comprising two Fab fragments linked by a disulfide bridge at the hinge region; (c) a Fd fragment consisting of the VH and CH1 domains; (d) a Fv fragment consisting of the VL and VH domains of a single arm of an antibody; (e) a dAb fragment (Ward, et al. (1989) *Nature* 341: 544-546), which consists of a VH domain; and (f) an isolated complementarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv). See e.g., Bird, et al. (1988) *Science* 242: 423-426; Huston, et al. (1988) *Proc Natl. Acad. Sci. USA* 85: 5879-5883; and Osbourn, et al. (1998) *Nat. Biotechnol.* 16: 778. Single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and Vl can also be used in the generation of Fab, Fv, or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. See e.g., Holliger, et al. (1993) *Proc Natl. Acad. Sci. USA* 90: 6444-6448; Poljak, et al. (1994) *Structure* 2: 1121-1123.

Still further, an antibody or antigen-binding portion thereof (antigen-binding fragment, antibody fragment, antibody portion) may be part of a larger immunoadhesion molecules, formed by covalent or noncovalent association of the antibody or antibody portion with one or more other proteins or peptides. Examples of immunoadhesion molecules include use of the streptavidin core region to make a tetrameric scFv molecule (Kipriyanov, et al. (1995) *Hum. Antibodies Hybridomas* 6: 93-101) and use of a cysteine residue, a marker peptide and a C-terminal polyhistidine tag to make bivalent and biotinylated scFv molecules. Kipriyanov, et al. (1994) *Mol Immunol.* 31: 1047-1058. Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal, monoclonal, xenogeneic, allogeneic, syngeneic, or modified forms thereof, e.g., humanized, chimeric. Preferably, antibodies of the invention bind specifically or substantially specifically to VISTA (PD-L3) molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. In the case of a desired enhanced immune response to particular antigens of interest, antigens include, but are not limited to, infectious disease antigens for which a protective immune response may be elicited are exemplary.

"Allergic disease," as used herein, refers broadly to a disease involving allergic reactions. More specifically, an "allergic disease" is defined as a disease for which an allergen is identified, where there is a strong correlation between exposure to that allergen and the onset of pathological change, and where that pathological change has been proven to have an immunological mechanism. Herein, an immunological mechanism means that leukocytes show an immune response to allergen stimulation.

"Antisense nucleic acid molecule," as used herein, refers broadly to a nucleotide sequence which is complementary to a "sense" nucleic acid encoding a protein (e.g., complementary to the coding strand of a double-stranded cDNA molecule) complementary to an mRNA sequence or complementary to the coding strand of a gene. Accordingly, an antisense nucleic acid molecule can hydrogen bond to a sense nucleic acid molecule.

"Asthma," as used herein, refers broadly to a disorder of the respiratory system characterized by inflammation, narrowing of the airways and increased reactivity of the airways to inhaled agents. Asthma is frequently, although not exclusively, associated with atopic or allergic symptoms.

"Apoptosis," as used herein, refers broadly to programmed cell death which can be characterized using techniques which are known in the art. Apoptotic cell death can be characterized by cell shrinkage, membrane blebbing, and chromatin condensation culminating in cell fragmentation. Cells undergoing apoptosis also display a characteristic pattern of internucleosomal DNA cleavage.

"Autoimmunity" or "autoimmune disease or condition," as used herein, refers broadly to a disease or disorder arising from and directed against an individual's own tissues or a co-segregate or manifestation thereof or resulting condition therefrom.

"B cell receptor" (BCR)," as used herein, refers broadly to the complex between membrane Ig (mIg) and other transmembrane polypeptides (e.g., Ig $\alpha$ and Ig $\beta$) found on B cells. The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

"Cancer," as used herein, refers broadly to any neoplastic disease (whether invasive or metastatic) characterized by abnormal and uncontrolled cell division causing malignant growth or tumor (e.g., unregulated cell growth.)

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, the variable region or a portion thereof, is altered, replaced or exchanged with a variable region having a different or altered antigen specificity.

"Coding region," as used herein, refers broadly to regions of a nucleotide sequence comprising codons which are translated into amino acid residues, whereas the term "non-coding region" refers to regions of a nucleotide sequence that are not translated into amino acids (e.g., 5' and 3' untranslated regions).

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. "Silent variations" are one species of conservatively modified nucleic acid variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "*Sequences of Proteins of Immunological Interest*" National Institutes of Health, Bethesda, Md. These expressions include the hypervariable regions as defined by Kabat, et al. (1983) "*Sequences of Proteins of Immunological Interest*" U.S. Dept. of Health and Human Services or the hypervariable loops in 3-dimensional structures of antibodies. Chothia and Lesk (1987) J Mol. Biol. 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) *Methods* 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Costimulatory receptor," as used herein, refers broadly to receptors which transmit a costimulatory signal to an immune cell, e.g., CD28 or ICOS. As used herein, the term "inhibitory receptors" includes receptors which transmit a negative signal to an immune cell.

"Costimulate," as used herein, refers broadly to the ability of a costimulatory molecule to provide a second, non-activating, receptor-mediated signal (a "costimulatory signal") that induces proliferation or effector function. For example, a costimulatory signal can result in cytokine secretion (e.g., in a T cell that has received a T cell-receptor-mediated signal.) Immune cells that have received a cell receptor-mediated signal (e.g., via an activating receptor) may be referred to herein as "activated immune cells."

"Cytoplasmic domain," as used herein, refers broadly to the portion of a protein which extends into the cytoplasm of a cell.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Extracellular domain," as used herein refers broadly to the portion of a protein that extend from the surface of a cell.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Family," as used herein, refers broadly to the polypeptide and nucleic acid molecules of the invention is intended to mean two or more polypeptide or nucleic acid molecules having a common structural domain or motif and having sufficient amino acid or nucleotide sequence homology as defined herein. Family members can be naturally or non-naturally occurring and can be from either the same or different species. For example, a family can contain a first polypeptide of human origin, as well as other, distinct polypeptides of human origin or alternatively, can contain homologues of non-human origin (e.g., monkey polypeptides.) Members of a family may also have common functional characteristics.

"Fc receptor" (FcRs) as used herein, refers broadly to cell surface receptors for the Fc portion of immunoglobulin molecules (Igs). Fc receptors are found on many cells which participate in immune responses. Among the human FcRs that have been identified so far are those which recognize IgG (designated FcγR), IgE (FcεR1), IgA (FcαR), and polymerized IgM/A (FcμαR). FcRs are found in the following cell types: FcεRI (mast cells), Fcε RII (many leukocytes), FcαR (neutrophils), and FcμαR (glandular epithelium, hepatocytes). Hogg (1988) *Immunol. Today* 9: 185-86. The widely studied FcγRs are central in cellular immune defenses, and are responsible for stimulating the release of mediators of inflammation and hydrolytic enzymes involved in the pathogenesis of autoimmune disease. Unkeless (1988) *Annu. Rev. Immunol.* 6: 251-87. The FcγRs provide a crucial link between effector cells and the lymphocytes that secrete Ig, since the macrophage/monocyte, polymorphonuclear leukocyte, and natural killer (NK) cell Fc gamma Rs confer an element of specific recognition mediated by IgG. Human leukocytes have at least three different receptors for IgG: hFcγRI (found on monocytes/macrophages), hFcγRII (on monocytes, neutrophils, eosinophils, platelets, possibly B cells, and the K562 cell line), and FcγIII (on NK cells, neutrophils, eosinophils, and macrophages).

With respect to T cells, transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

"Framework region" or "FR," as used herein, refers broadly to one or more of the framework regions within the variable regions of the light and heavy chains of an antibody. See Kabat, et al. (1987) "*Sequences of Proteins of Immunological Interest*" National Institutes of Health, Bethesda, Md. These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid (e.g., a promoter from one source and a coding region from another source.) Similarly, a heterologous protein indicates that the protein comprises two or more subsequences that are not found in the same relationship to each other in nature (e.g., a fusion protein).

"High affinity," as used herein, refers broadly to an antibody having a KD of at least $10^{-8}$ M, more preferably at least $10^{-9}$ M and even more preferably at least $10^{-10}$ M for a target antigen. However, "high affinity" binding can vary for other antibody isotypes. For example, "high affinity" binding for an IgM isotype refers to an antibody having a KD of at least $10^{-7}$ M, more preferably at least $10^{-8}$ M.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to refer to a cell into which a nucleic acid molecule of the invention, such as a recombinant expression vector of the invention, has been introduced. Host cells may be prokaryotic cells (e.g., *E. coli*), or eukaryotic cells such as yeast, insect (e.g., SF9), amphibian, or mammalian cells such as CHO, HeLa, HEK-293, e.g., cultured cells, explants, and cells in vivo. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, progeny may not, in fact, be identical to the parent cell, but are still included within the scope of the term as used herein.

"Humanized antibody," as used herein, refers broadly to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

"Hybridization," as used herein, refers broadly to the physical interaction of complementary (including partially complementary) polynucleotide strands by the formation of hydrogen bonds between complementary nucleotides when the strands are arranged antiparallel to each other.

"IgV domain" and "IgC domain" as used herein, refer broadly to Ig superfamily member domains. These domains correspond to structural units that have distinct folding patterns called Ig folds. Ig folds are comprised of a sandwich of two beta sheets, each consisting of antiparallel beta strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of beta strands.

"Immune cell," as used herein, refers broadly to cells that are of hematopoietic origin and that play a role in the immune response. Immune cells include lymphocytes, such as B cells and T cells; natural killer cells; and myeloid cells, such as monocytes, macrophages, eosinophils, mast cells, basophils, and granulocytes.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Immune response," as used herein, refers broadly to T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "downmodulation" with reference to the immune response includes a diminution in any one or more immune responses, while the term "upmodulation" with reference to the immune response includes an increase in any one or more immune responses. It will be understood that upmodulation of one type of immune response may lead to a corresponding downmodulation in another type of immune response. For example, upmodulation of the production of certain cytokines (e.g., IL-10) can lead to downmodulation of cellular immune responses.

"Inflammatory conditions or inflammatory disease," as used herein, refers broadly to chronic or acute inflammatory diseases.

"Inhibitory signal," as used herein, refers broadly to a signal transmitted via an inhibitory receptor molecule on an immune cell. A signal antagonizes a signal via an activating receptor (e.g., via a TCR, CD3, BCR, or Fc molecule) and can result, e.g., in inhibition of: second messenger generation; proliferation; or effector function in the immune cell, e.g., reduced phagocytosis, antibody production, or cellular cytotoxicity, or the failure of the immune cell to produce mediators (e.g., cytokines (e.g., IL-2) and/or mediators of allergic responses); or the development of anergy.

"Isolated," as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody"). For example, "isolated" or "purified," as used herein, refers broadly to a protein, DNA, antibody, RNA, or biologically active portion thereof, that is substantially free of cellular material or other contaminating proteins from the cell or tissue source from which the biological substance is derived, or substantially free from chemical precursors or other chemicals when chemically synthesized. The language "substantially free of cellular material" includes preparations of VISTA (PD-L3) protein in which the protein is separated from cellular components of the cells from which it is isolated or recombinantly produced.

An "isolated antibody", as used herein, is intended to refer to an antibody that is substantially free of other antibodies having different antigenic specificities (e.g., an isolated antibody that specifically binds PD-L3 OR VISTA is substantially free of antibodies that specifically bind antigens other than PD-L3 OR VISTA). Moreover, an isolated antibody may be substantially free of other cellular material and/or chemicals.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) Short Protocols in Molecular Biology ($5^{th}$ Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, tapirs, and voles. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Naturally-occurring nucleic acid molecule," as used herein, refers broadly to refers to an RNA or DNA molecule having a nucleotide sequence that occurs in nature (e.g., encodes a natural protein).

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Oligomerization domain", as used herein, refers broadly to a domain that when attached to a VISTA extracellular domain or fragment thereof, facilitates oligomerization. Said oligomerization domains comprise self-associating α-helices, for example, leucine zippers, that can be further stabilized by additional disulfide bonds. The domains are designed to be compatible with vectorial folding across a membrane, a process thought to facilitate in vivo folding of the polypeptide into a functional binding protein. Examples thereof are known in the art and include by way of example coiled GCN4, and COMP.

The α-helical coiled coil is probably the most widespread subunit oligomerization motif found in proteins. Accordingly, coiled coils fulfill a variety of different functions. In several families of transcriptional activators, for example, short leucine zippers play an important role in positioning the DNA-binding regions on the DNA. Ellenberger, et al. (1992) Cell 71: 1223-1237. Coiled coils are also used to form oligomers of intermediate filament proteins. Coiled-coil proteins furthermore appear to play an important role in both vesicle and viral membrane fusion. Skehel and Wiley (1998) Cell 95: 871-874. In both cases hydrophobic sequences, embedded in the membranes to be fused, are located at the same end of the rod-shaped complex composed of a bundle of long α-helices. This molecular arrangement is believed to cause close membrane apposition as the complexes are assembled for membrane fusion. The coiled coil is often used to control oligomerization. It is found in many types of proteins, including transcription factors include, but not limited to GCN4, viral fusion peptides, SNARE complexes and certain tRNA synthetases, among others. Very long coiled coils are found in proteins such as tropomyosin, intermediate filaments and spindle-pole-body components. Coiled coils involve a number of α-helices that are supercoiled around each other in a highly organized manner that associate in a parallel or an antiparallel orientation. Although dimers and trimers are the most common. The helices may be from the same or from different proteins. The coiled-coil is formed by component helices coming together to bury their hydrophobic seams. As the hydrophobic seams twist around each helix, so the helices also twist to coil around each other, burying the hydrophobic seams and forming a supercoil. It is the characteristic interdigitation of side chains between neighbouring helices, known as knobs-into-holes packing, that defines the structure as a coiled coil. The helices do not have to run in the same direction for this type of interaction to occur, although parallel conformation is more common. Antiparallel conformation is very rare in trimers and unknown in pentamers, but more common in intramolecular dimers, where the two helices are often connected by a short loop. In the extracellular space, the heterotrimeric coiled-coil protein laminin plays an important role in the formation of basement membranes. Other examples are the thrombospondins and cartilage oligomeric matrix protein (COMP) in which three (thrombospondins 1 and 2) or five (thrombospondins 3, 4 and COMP) chains are connected. The molecules have a flower bouquet-like appearance, and the reason for their oligomeric structure is probably the multivalent interaction of the C-terminal domains with cellular receptors. The yeast transcriptional activator GCN4 is 1 of over 30 identified eukaryotic proteins containing the basic region leucine zipper (bZIP) DNA-binding motif. Ellenberger, et al. (1992) Cell 71: 1223-1237. The bZIP dimer is a pair of continuous alpha helices that form a parallel coiled-coil over their carboxy-terminal 34 residues and gradually diverge toward their amino termini to pass through the major groove of the DNA binding site. The coiled-coil dimerization interface is oriented almost perpendicular to the DNA axis, giving the complex the appearance of the letter T. bZIP contains a 4-3 heptad repeat of hydrophobic and nonpolar residues that pack together in a parallel alpha-helical coiled-coil. Ellenberger, et al. (1992) Cell 71: 1223-1237. The stability of the dimer results from the side-by-side packing of leucines and nonpolar residues in positions a and d of the heptad repeat, as well as a limited number of intra- and interhelical salt bridges, shown in a crystal structure of the GCN4 leucine zipper peptide. Ellenberger, et al. (1992) Cell 71: 1223-1237. Another example is CMP (matrilin-1) isolated from bovine tracheal cartilage as a homotrimer of subunits of Mr 52,000 (Paulsson & Heinegard (1981) Biochem J. 197: 367-375), where each subunit consists of a vWFA1 module, a single EGF domain, a vWFA2 module and a coiled coil domain spanning five heptads. Kiss, et al. (1989) J. Biol. Chem. 264:8126-8134; Hauser and Paulsson (1994) J. Biol. Chem. 269: 25747-25753. Electron microscopy of purified CMP showed a bouquet-like trimer structure in which each subunit forms an ellipsoid emerging from a common point corresponding to the coiled coil. Hauser and Paulsson (1994) J. Biol. Chem. 269: 25747-25753. The coiled coil domain in matrilin-1 has been extensively studied. The trimeric structure is retained after complete reduction of interchain disulfide bonds under non-denaturing conditions. Hauser and Paulsson (1994) J. Biol. Chem. 269: 25747-25753. Yet another example is Cartilage Oligomeric Matrix Protein (COMP). A non-collagenous glycoprotein, COMP, was first identified in cartilage. Hedbom, et al. (1992) J. Biol. Chem. 267:6132-6136. The protein is a 524 kDa homopentamer of five subunits which consists of an N-terminal heptad repeat region (cc) followed by four epidermal growth factor (EGF)-like domains (EF), seven calcium-binding domains (T3) and a C-terminal globular domain (TC). According to this domain organization, COMP belongs to the family of thrombospondins. Heptad repeats $(abcdefg)_n$ with preferentially hydrophobic residues at positions a and d form-helical coiled-coil domains. Cohen and Parry (1994) *Science* 263: 488-489. Recently, the recombinant five-stranded coiled-coil domain of COMP (COMPcc) was crystallized and its structure was solved at 0.2 nm resolution. Malashkevich, et al. (1996) *Science* 274: 761-765.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. Antigens (Chapter 3) Immunology ($5^{th}$ Ed.) New York: W.H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient."

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Signal sequence" or "signal peptide," as used herein, refers broadly to a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., Valine, Leucine, Isoleucine or Phenylalanine). A "signal sequence," also referred to in the art as a "signal peptide," serves to direct a polypeptide containing such a sequence to a lipid bilayer, and is cleaved in secreted and membrane bound polypeptides.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (1987) CSH Symp. Quant. Biol. LII: 123-33; Frier, et al. (1986) PNAS 83: 9373-77; Turner, et al. (1987) J. Am. Chem. Soc. 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Subjects" as used herein, refers broadly to anyone suitable to be treated according to the present invention include, but are not limited to, avian and mammalian subjects, and are preferably mammalian. Any mammalian subject in need of being treated according to the present invention is suitable. Human subjects of both genders and at any stage of development (i.e., neonate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

"Substantially free of chemical precursors or other chemicals," as used herein, refers broadly to preparations of VISTA protein in which the protein is separated from chemical precursors or other chemicals which are involved in the synthesis of the protein. In one embodiment, the language "substantially free of chemical precursors or other chemicals" includes preparations of VISTA protein having less than about 30% (by dry weight) of chemical precursors or non-VISTA chemicals, more preferably less than about 20% chemical precursors or non-VISTA chemicals, still more preferably less than about 10% chemical precursors or non-VISTA chemicals, and most preferably less than about 5% chemical precursors or non-VISTA (PD-L3) chemicals.

"Symptoms" of disease as used herein, refers broadly to any morbid phenomenon or departure from the normal in structure, function, or sensation, experienced by the patient and indicative of disease.

"T cell," as used herein, refers broadly to CD4+ T cells and CD8+ T cells. The term T cell also includes both T helper 1 type T cells and T helper 2 type T cells.

"Treg cell" (sometimes also referred to as suppressor T cells) as used herein refers to a subpopulation of T cells which modulate the immune system and maintain tolerance to self-antigens and can abrogate autoimmune diseases. Foxp3+CD4+CD25+ regulatory T cells (Tregs) are critical in maintaining peripheral tolerance under normal physiological conditions, and suppress anti-tumour immune responses in cancer.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., inflammation, pain).

"Transmembrane domain," as used herein, refers broadly to an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In an embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, et al. (1996) Annu. Rev. Neurosci. 19:235-263.

"Transgenic animal," as used herein, refers broadly to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

"Tumor," as used herein, refers broadly to at least one cell or cell mass in the form of a tissue neoformation, in particular in the form of a spontaneous, autonomous and irreversible excess growth, which is more or less disinhibited, of endogenous tissue, which growth is as a rule associated with the more or less pronounced loss of specific cell and tissue functions. This cell or cell mass is not effectively inhibited, in regard to its growth, by itself or by the regulatory mechanisms of the host organism, e.g., colorectal cancer, melanoma or carcinoma. Tumor antigens not only include antigens present in or on the malignant cells themselves, but also include antigens present on the stromal supporting tissue of tumors including endothelial cells and other blood vessel components.

"Unresponsiveness," as used herein, refers broadly to refractivity of immune cells to stimulation, e.g., stimulation via an activating receptor or a cytokine. Unresponsiveness can occur, e.g., because of exposure to immunosuppressants or high doses of antigen.

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. The techniques and procedures are generally performed according to conventional methods well known in the art and as described in various general and more specific references that are cited and discussed throughout the present specification. See, e.g., Sambrook, et al. (2001) Molec. Cloning: Lab. Manual [$3^{rd}$ Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein.

The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

VISTA

This application relates to a novel, structurally-distinct, Ig-superfamily inhibitory ligand designated as V-region Immunoglobulin-containing Suppressor of T cell Activation (VISTA) or PD-L3 that is selectively expressed on hematopoietic cells. The extracellular domain bears homology to the B7 family ligand PD-L1, and like PD-L1, VISTA has a profound impact on immunity. However, unlike PD-L1, VISTA is selectively expressed within the hematopoietic compartment. Expression is most prominent on myeloid antigen-presenting cells (APCs), although expression on CD4+ T cells, $CD8^+$ T cells and higher expression on a subset of Foxp3+ regulatory T cells (Treg) is also of significant interest. A soluble VISTA-Ig fusion protein, or VISTA expression on APCs, potently inhibits in vitro T cell proliferation, cytokine production and induces Foxp3 expression in T cells. Conversely, a newly developed anti- VISTA monoclonal antibody interfered with VISTA-induced immune suppression of T cell responses by VISTA+ APCs in vitro. Furthermore, in vivo anti-VISTA intensified the development of the T cell mediated autoimmune disease experimental allergic encephalomyelitis (EAE), and facilitated the development of a protective, tumor-specific immune response with subsequent tumor remission. Initial studies of VISTA−/− mice are revealing early indications of spontaneous inflammatory disease, and their ultimate pathologic fate will be determined. Unlike all other PD-Ligand-related molecules (e.g., B7-H3, H4, H6), VISTA is selectively expressed in hematopoietic cells, together with its profound suppressive activities and unique structural features, illustrates that VISTA is a novel, functionally nonredundant, central negative regulator of immunity, whose expression is primarily T cell and myeloid-restricted. See WO 2011/120013.

The best characterized costimulatory ligands are B7.1 and B7.2 and they belong to the Ig superfamily which consists of many critical immune regulators, such as the B7 family ligands and receptors. Ig superfamily members are expressed on professional antigen-presenting cells (APCs), and their receptors are CD28 and CTLA-4. CD28 is expressed by naïve and activated T cells and is critical for optimal T-cell activation. In contrast, CTLA-4 is induced following T-cell activation and inhibits T-cell activation by binding to B7.1/B7.2, impairing CD28-mediated costimulation. B7.1 and B7.2 knockout (KO) mice are impaired in adaptive immune response, whereas CTLA-4 KO mice cannot adequately control inflammation and develop systemic autoimmune diseases. Over time the B7 family ligands have expanded to include costimulatory ligands such as B7-H2 (ICOS Ligand) and B7-H3, and coinhibitory ligands such as B7-H1 (PD-L1), B7-DC (PD-L2), B7-H4 (B7S1 or B7x), and B7-H6. Accordingly, additional CD28 family receptors have been identified. ICOS is expressed on activated T cells and binds to B7-H2. ICOS is a positive co-regulator, important for T-cell activation, differentiation and function. On the other hand, Programmed Death 1 (PD-1) negatively regulates T cell responses. PD-1 KO mice developed lupus-like autoimmune disease, or T dilated cardiomyopathy. In contrast to VISTA, the two inhibitory B7 family ligands, PD-L1 and PD-L2, have distinct expression patterns. PD-L2 is inducibly expressed on DCs and macrophages, whereas PD-L1 is broadly expressed on both hematopoietic cells and nonhematopoietic cell types. Consistent with the immune-suppressive role of PD-1 receptor, studies using PD-L1−/− and PD-L2−/− mice have shown that both ligands have overlapping roles in inhibiting T-cell proliferation and cytokine production. PD-L1 deficiency enhances disease progression in both the nonobese diabetic (NOD) model of autoimmune diabetes and the murine model of multiple sclerosis (experimental autoimmune encephalomyelitis (EAE). PD-L1−/− T cells produce elevated levels of the proinflammatory cytokines in both disease models. In addition, studies in NOD mice have demonstrated that the tissue expression of PD-L1 (i.e., within pancreas) uniquely contributes to its capacity of regionally controlling inflammation. PD-L1 is also highly expressed on placental syncytiotrophoblasts, which critically control the maternal immune responses to allogeneic fetus.

Anti-CTLA-4 antibodies show an enhanced therapeutic benefit in murine models and clinical trials of melanoma. Mice vaccinated with B16-GM-CSF (Gvax) promote the rejection of B16 melanomas when combined with antibody blockade of CTLA-4. Antibodies to PD-1 as well as PD-L1 also document enhanced anti-tumor immunity and host survival in a wide range of murine tumor models. Finally, although CTLA-4 and PD-1 belong to the same family of co-inhibitory molecules, evidence suggests they use distinct nonredundant mechanisms to inhibit T-cell activation, and there is synergy in the ability of anti-CTLA-4 and anti-PD-1/L1 to enhance host survival in murine melanoma when used in combination.

The immunoglobulin (Ig) superfamily consists of many critical immune regulators, including the B7 family ligands and receptors. VISTA is a novel and structurally distinct Ig superfamily inhibitory ligand, whose extracellular domain bears homology to the B7 family ligand PD-L1. This molecule is designated V-domain Ig suppressor of T cell activation (VISTA). VISTA is primarily expressed on hematopoietic cells, and VISTA expression is highly regulated on myeloid antigen-presenting cells (APCs) and T cells. A soluble VISTA-Ig fusion protein or VISTA expression on APCs inhibits T cell proliferation and cytokine production in vitro. A VISTA-specific monoclonal antibody interferes with VISTA-induced suppression of T cell responses by VISTA-expressing APCs in vitro. Furthermore, anti-VISTA treatment exacerbates the development of the T cell-mediated autoimmune disease experimental autoimmune encephalomyelitis in mice. Finally, VISTA over expression on tumor cells interferes with protective antitumor immunity in vivo in mice. These findings show that VISTA, a novel immunoregulatory molecule, has functional activities that are nonredundant with other Ig superfamily members and may play a role in the development of autoimmunity and immune surveillance in cancer. See Wang, et al. (2011) The Journal of Experimental Medicine 208(3): 577-92.

Human VISTA (PD-L3) or VISTA was identified as an upregulated molecule in a T cell transcriptional profiling screen. Our characterization of an identical 930 bp gene product recovered from a murine $CD4^+$ T-cell cDNA library confirmed the size and sequence. Silico-sequence and structural analysis predicts a type I transmembrane protein of 309 amino acids upon maturation. Its extracellular domain contains a single extracellular Ig-V domain of 136 amino acids, which is linked to a 23-amino acid stalk region, a 21-residue transmembrane segment, and a 97-amino acid cytoplasmic domain. The cytoplasmic tail of VISTA does not contain any signaling domains. A BLAST sequence search with the VISTA Ig-V domain identified PD-L1 of the B7 family as the closest evolutionarily related protein with a borderline significant e-value score. A structure based sequence alignment of VISTA with the B7 family members PD-L1, PD-L2, B7-H3, and B7-H4 highlights several amino acids that are systematically conserved in all Ig-V domain proteins.

The expression of VISTA appears to be selectively expressed in the hematopoietic compartment and this protein is highly expressed on mature myeloid cells ($CD11b^{bright}$), with lower levels of expression on $CD4^+$ T cells, $T^{reg}$ and $CD8^+$ T cells. Soluble VISTA proteins, e.g., soluble VISTA-Ig fusion protein, or VISTA expression on APCs, suppresses in vitro $CD4^+$ and $CD8^+$ T cell proliferation and cytokine production. It is also observed that anti-VISTA antibodies, e.g., an anti-VISTA monoclonal antibody (13F3) blocked VISTA-induced suppression of T cell responses by $VISTA^+$ APCs in vitro. Also, it has been discovered that an anti-VISTA monoclonal antibody exacerbated EAE and increased the frequency of encephalitogenic Th17s in vivo. Still further, the inventors suprisingly discovered that an anti-VISTA monoclonal antibody induces tumor remission in multiple murine tumor models. VISTA expression on myeloid derived suppressor cells (MDSC) in these models is extremely high, suggesting that VISTA-MDSC suppress tumor specific immunity. VISTA exerts immunosuppressive activities on T cells both in vitro and in vivo, in mouse and in human (in vitro only) and is an important mediator in controlling the development of autoimmunity and the immune responses to cancer. Specifically, the data show that VISTA is a new member of the Ig superfamily and contains an Ig-V domain with distant sequence similarity to PD-L1. A VISTA-Ig fusion protein or when over expressed on artificial APCs VISTA inhibits both mouse and human CD4+ and CD8+ T cell proliferation and cytokine production. Further, VISTA expression on myeloid APCs is inhibitory for T cell responses in vitro.

VISTA expression on MDSC in the tumor microenvironment is extremely high. Phenotypic and functional analysis of many cell surface molecules previously suggested to be involved in MDSC-mediated suppression of T cells: CD115, CD124, CD80, PD-L1, and PD-L2 were expressed by MDSC but with no differences in the levels of their expression or proportion of positive cells were found between MDSC and cells from tumor-free mice that lack immune suppressive activity. Therefore, VISTA is the primary B7 negative regulator on MDSCs.

Antibody-Mediated VISTA Blockade Induces Protective Immunity to an Autologous Tumor.

VISTA is a dominant, negative immune regulatory molecule on MDSCs that interferes with the development of protective anti-tumor immunity. Therefore, blocking the activity of this molecule with anti-VISTA antibodies may be used to induce protective anti-tumor immunity in mammals (e.g., humans).

Methods of using soluble VISTA proteins, e.g., fusion proteins and multimeric VISTA proteins comprising multiple copies of the VISTA extracellular domain or a fragment thereof, and VISTA binding agents, e.g., small molecules and antibodies or fragments thereof, which bind or modulate (agonize or antagonize) the activity of VISTA as immune modulators and for the treatment of different cancers, e.g., bladder, ovarian and lymphoma, autoimmune disease, allergy, infection and inflammatory conditions, e.g. multiple sclerosis and arthritis.

VISTA is a novel inhibitory ligand, which extracellular Ig-V domain bears homology to the two known B7 family ligands Programmed Death Ligand 1 and 2 (PD-L1 and PD-L2) and exhibits unique sequence features and distinctive expression patterns in vitro and in vivo on subsets of APCs and T cells, (which distinguishes PD-L3 or VISTA from other B7 family ligands). VISTA has a functional impact on $CD4^+$ and $CD8^+$ T cell proliferation and differentiation (suppresses $CD4^+$ and $CD8^+$ T cell proliferation, as well as cytokine production). Based on its expression pattern and inhibitory impact on T cells, PD-L3 or VISTA apparently functions as a regulatory ligand that negatively regulates T cell responses during cognate interactions between T cells and myeloid derived APCs.

Although VISTA (PD-L3) appears to be a member of the B7 family of ligands, unlike other B7 family ligands, this molecule contains only an Ig-V domain without an Ig-C domain, and is phylogenically closer to the B7 family receptor Programmed Death-1 (PD-1). Based thereon, VISTA (PD-L3), and agonists or antagonists specific thereto can be used to regulate T cell activation and differentiation, and more broadly to modulate the regulatory network that controls immune responses. In particular VISTA (PD-L3) proteins and VISTA (PD-L3) agonists or antagonists, preferably antibodies specific to VISTA (PD-L3) are useful in modulating immune responses in autoimmunity, inflammatory responses and diseases, allergy, cancer, infectious disease and transplantation.

Anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer. Kang, et al. (1992) *Science* 257: 1134.

A VISTA (PD-L3) molecule of the present invention is identified based on the presence of a "extracellular domain" in the polypeptide or corresponding nucleic acid molecule. In another embodiment, a VISTA (PD-L3) molecule of the present invention is identified based on the presence of a "cytoplasmic domain" in the polypeptide or corresponding nucleic acid molecule.

Methods for modulating an immune cell response by contacting an immune cell in vitro or in vivo with a VISTA protein, or binding agent specific thereto, in the presence of a primary signal so that a response of the immune cell is modulated. (Interaction of VISTA or a modulator thereof transmits a signal to immune cells, regulating immune responses. VISTA (PD-L3) protein is expressed at high levels on myeloid antigen presenting cells, including myeloid dendritic cells (DCs) and macrophages, and at lower densities on CD4+ and CD8+ T cells. Upon immune activation, VISTA (PD-L3) expression is upregulated on myeloid APCs, but downregulated on CD4+ T cells). Therefore, the VISTA (PD-L3) nucleic acids and polypeptides of the present invention, and agonists or antagonists thereof are useful, e.g., in modulating the immune response.

As used interchangeably herein, "VISTA (PD-L3) activity", "biological activity of VISTA (PD-L3)" or "functional activity of VISTA (PD-L3)", refers to an activity exerted by a VISTA (PD-L3) protein, polypeptide or nucleic acid molecule on a VISTA (PD-L3)-responsive cell or tissue, or on a VISTA (PD-L3) polypeptide binding partner, as determined in vivo, or in vitro, according to standard techniques. These activities include modulating CD4+ and CD8+ T cell proliferation and cytokine production. In another embodiment, a VISTA (PD-L3) activity is a direct activity, such as an association with a VISTA (PD-L3) binding partner. As used herein, a "target molecule" or "binding partner" is a molecule with which a VISTA (PD-L3) polypeptide binds or interacts in nature, i.e., expressed on a T cell, such that VISTA (PD-L3)-mediated function is achieved. Alternatively, a VISTA (PD-L3) activity is an indirect activity, such as a cellular signaling activity mediated by the VISTA (PD-L3) polypeptide. The biological activities of VISTA (PD-L3) are described herein. For example, the VISTA (PD-L3) polypeptides and VISTA (PD-L3) agonists or antagonists of the present invention can have one or more of the following activities: (1) suppresses or promotes CD4+ and CD8+ T cell proliferation, (2) suppresses or promotes cytokine production (3) functions as a regulatory ligand that negatively regulates T cell responses during cognate interactions between T cells and myeloid derived APCs (4) negatively regulates CD4+ T cell responses by suppressing early TCR activation and arresting cell division, but with minimum direct impact on apoptosis, (5) suppresses or promotes antigen-specific T cell activation during cognate interactions between APCs and T cells and/or (6) suppresses or promotes T cell-mediated immune responses; (7) modulate activation of immune cells, e.g., T lymphocytes, and (8) modulate the immune response, e.g., inflammatory immune response of an organism, e.g., a mouse or human organism.

Isolated VISTA (PD-L3) proteins and polypeptides that modulate one or more VISTA (PD-L3) activities. These polypeptides will include VISTA (PD-L3) polypeptides having one or more of the following domains: a signal peptide domain, an IgV domain, an extracellular domain, a transmembrane domain, and a cytoplasmic domain, and, preferably, a VISTA (PD-L3) activity.

Modulation of a costimulatory signal may result in modulation of effector function of an immune cell. Thus, the term "VISTA activity" includes the ability of a VISTA polypeptide to bind its natural binding partner(s), the ability to modulate immune cell costimulatory or inhibitory signals, and the ability to modulate the immune response.

Modulation of an inhibitory signal in an immune cell results in modulation of proliferation of and/or cytokine secretion by an immune cell. For example, the family of VISTA (PD-L3) polypeptides of the present invention preferably comprises least one "signal peptide domain". As described infra a signal sequence was identified in the amino acid sequence of native human VISTA (PD-L3) and was also identified in the amino acid sequence of native mouse VISTA (PD-L3).

Stimulation of VISTA (PD-L3) activity is desirable in situations in which VISTA (PD-L3) is abnormally downregulated and/or in which increased VISTA (PD-L3) activity is likely to have a beneficial effect. Likewise, inhibition of VISTA (PD-L3) activity is desirable in situations in which VISTA (PD-L3) is abnormally upregulated and/or in which decreased VISTA (PD-L3) activity is likely to have a beneficial effect. Exemplary agents for use in downmodulating VISTA (PD-L3) (i.e., VISTA (PD-L3) antagonists) include, e.g., antisense nucleic acid molecules, antibodies that recognize and block VISTA (PD-L3), combinations of antibodies that recognize and block VISTA (PD-L3) and antibodies that recognize and block VISTA (PD-L3) counter receptors, and compounds that block the interaction of VISTA (PD-L3) with its naturally occurring binding partner(s) on an immune cell (e.g., soluble, monovalent VISTA (PD-L3) molecules; soluble forms of VISTA (PD-L3) molecules that do not bind Fc receptors on antigen presenting cells; soluble forms of VISTA (PD-L3) binding partners; and compounds identified in the subject screening assays). Exemplary agents for use in upmodulating VISTA (PD-L3) (i.e., VISTA (PD-L3) agonists) include, e.g., nucleic acid molecules encoding VISTA (PD-L3) polypeptides, multivalent forms of VISTA (PD-L3), compounds that increase the expression of VISTA (PD-L3), compounds that enhance the interaction of VISTA (PD-L3) with its naturally occurring binding partners and cells that express VISTA (PD-L3).

Depending upon the form of the VISTA (PD-L3) molecule that binds to a receptor, a signal can be either transmitted (e.g., form of a VISTA (PD-L3) molecule that results in crosslinking of the receptor or by a soluble form of VISTA (PD-L3) that binds to Fc receptors on antigen presenting cells) or inhibited (e.g., by a soluble, monovalent form of a VISTA (PD-L3) molecule or a soluble form of VISTA (PD-L3) that is altered using methods known in the art such that it does not bind to Fc receptors on antigen presenting cells), e.g., by competing with activating forms of VISTA (PD-L3) molecules for binding to the receptor. However, there are instances in which a soluble molecule can be stimulatory. The effects of the various modulatory agents can be easily demonstrated using routine screening assays as described herein.

Downregulation of Immune Responses

Upregulating the inhibitory function of a VISTA (PD-L3) polypeptide may be used to downregulate immune responses. Downregulation can be in the form of inhibiting or blocking an immune response already in progress, or may involve preventing the induction of an immune response. The functions of activated immune cells can be inhibited by downregulating immune cell responses or by inducing specific anergy in immune cells, or both. For example, VISTA (PD-L3) may bind to an inhibitory receptor, forms of VISTA (PD-L3) that bind to the inhibitory receptor, e.g., multivalent VISTA (PD-L3) on a cell surface, can be used to downmodulate the immune response. An activating antibody may be used to stimulate VISTA (PD-L3) activity is a bispecific antibody. For example, such an antibody can comprise a VISTA (PD-L3) binding site and another binding site which targets a cell surface receptor on an immune cell, e.g., a T cell, a B cell, or a myeloid cell. Such an antibody, in addition to comprising a VISTA (PD-L3) binding site, can further comprise a binding site which binds to a B cell antigen receptor, a T cell antigen receptor, or an Fc receptor, in order to target the molecule to a specific cell population. Selection of this second antigen for the bispecific antibody provides flexibility in selection of cell population to be targeted for inhibition. Agents that promote a VISTA (PD-L3) activity or which enhance the interaction of VISTA (PD-L3) with its natural binding partners (e.g., VISTA (PD-L3) activating antibodies or VISTA (PD-L3) activating small molecules) can be identified by their ability to inhibit immune cell proliferation and/or effector function, or to induce anergy when added to an in vitro assay. For example, cells can be cultured in the presence of an agent that stimulates signal transduction via an activating receptor. A number of art-recognized readouts of cell activation can be employed to measure, e.g., cell proliferation or effector function (e.g., antibody production, cytokine production, phagocytosis) in the presence of the activating agent. The ability of a test agent to block this activation can be readily determined by measuring the ability of the agent to effect a decrease in proliferation or effector function being measured. In one embodiment, at low antigen concentrations, VISTA (PD-L3) immune cell interactions inhibit strong B7-CD28 signals. In another embodiment, at high antigen concentrations, VISTA (PD-L3) immune cell interactions may reduce cytokine production but not inhibit T cell proliferation. Accordingly, the ability of a test compound to block activation can be determined by measuring cytokine production and/or proliferation at different concentrations of antigen.

Tolerance may be induced against specific antigens by co-administering an antigen with a VISTA (PD-L3) agonist. For example, tolerance may be induced to specific polypeptides. Immune responses to allergens or foreign polypeptides to which an immune response is undesirable can be inhibited. For example, patients that receive Factor VIII frequently generate antibodies against this clotting factor. Co-administration of an agent that stimulates VISTA (PD-L3) activity or interaction with its natural binding partner, with recombinant factor VIII (or physically linking VISTA (PD-L3) to Factor VIII, e.g., by cross-linking) can result in immune response downmodulation.

A VISTA (PD-L3) agonist and another agent that can block activity of costimulatory receptors on an immune cell can be used to downmodulate immune responses. Exemplary molecules include: agonists forms of other PD ligands, soluble forms of CTLA-4, anti-B7-1 antibodies, anti-B7-2 antibodies, or combinations thereof. Alternatively, two separate peptides (for example, a VISTA (PD-L3) polypeptide with blocking forms of B7-2 and/or B7-1 polypeptides), or a combination of antibodies (e.g., activating antibodies against a VISTA (PD-L3) polypeptide with blocking anti-B7-2 and/or anti-B7-1 monoclonal antibodies) can be combined as a single composition or administered separately (simultaneously or sequentially) to downregulate immune cell mediated immune responses in a subject. Furthermore, a therapeutically active amount of one or more peptides having a VISTA (PD-L3) polypeptide activity, along with one or more polypeptides having B7-1 and/or B7-1 activity, can be used in conjunction with other downmodulating reagents to influence immune responses. Examples of other immunomodulating reagents include antibodies that block a costimulatory signal (e.g., against CD28 or ICOS), antibodies that activate an inhibitory signal via CTLA4, and/or antibodies against other immune cell markers (e.g., against CD40, CD40 ligand, or cytokines), fusion proteins (e.g., CTLA4-Fc or PD-1-Fc), and immunosuppressive drugs (e.g., rapamycin, cyclosporine A, or FK506). The VISTA (PD-L3) polypeptides may also be useful in the construction of therapeutic agents which block immune cell function by destruction of cells. For example, portions of a VISTA (PD-L3) polypeptide can be linked to a toxin to make a cytotoxic agent capable of triggering the destruction of cells to which it binds.

Infusion of one or a combination of such cytotoxic agents (e.g., VISTA (PD-L3) ricin (alone or in combination with PD-L1-ricin), into a patient may result in the death of immune cells, particularly in light of the fact that activated immune cells that express higher amounts of VISTA (PD-L3) binding partners. For example, because PD-1 is induced on the surface of activated lymphocytes, a VISTA (PD-L3) polypeptide can be used to target the depletion of these specific cells by Fc-R dependent mechanisms or by ablation by conjugating a cytotoxic drug (e.g., ricin, saporin, or calicheamicin) to the VISTA (PD-L3) polypeptide to kill cells that express a receptor for VISTA. A toxin can be conjugated to an anti-VISTA (PD-L3) antibody in order to target for death VISTA (PD-L3)-expressing antigen-presenting cell. In a further embodiment, the VISTA (PD-L3)-antibody-toxin can be a bispecific antibody. Such bispecific antibodies are useful for targeting a specific cell population, e.g., using a marker found only on a certain type of cell, e.g., B lymphocytes, monocytes, dendritic cells, or Langerhans cells. Downregulating immune responses by activating VISTA (PD-L3) activity or the VISTA (PD-L3)-immune cell interaction (and thus stimulating the negative signaling function of VISTA (PD-L3)) is useful in downmodulating the immune response, e.g., in situations of tissue, skin and organ transplantation, in graft-versus-host disease (GVHD), or allergies, or in autoimmune diseases such as systemic lupus erythematosus and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a molecule which promotes the activity of VISTA (PD-L3) or the interaction of VISTA (PD-L3) with its natural binding partner(s), on immune cells (such as a soluble, multimeric form of a VISTA (PD-L3) polypeptide) alone or in conjunction with another downmodulatory agent prior to or at the time of transplantation can inhibit the generation of a costimulatory signal. Moreover, promotion of VISTA (PD-L3) activity may also be sufficient to anergize the immune cells, thereby inducing tolerance in a subject.

To achieve sufficient immunosuppression or tolerance in a subject, it may also be desirable to block the costimulatory function of other molecules. For example, it may be desirable to block the function of B7-1 and B7-2 by administering a soluble form of a combination of peptides having an activity of each of these antigens or blocking antibodies against these antigens (separately or together in a single composition) prior to or at the time of transplantation. Alternatively, it may be desirable to promote inhibitory activity of VISTA (PD-L3) and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers, or soluble forms of other receptor ligand pairs (e.g., agents that disrupt the interaction between CD40 and CD40 ligand (e.g., anti CD40 ligand antibodies)), antibodies against cytokines, or immunosuppressive drugs. For example, activating VISTA (PD-L3) activity or the interaction of VISTA (PD-L3) with its natural binding partner(s), is useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of agents that promote activity of VISTA (PD-L3) (PD-L3) or VISTA interaction with its natural binding partner(s), may induce antigen-specific tolerance of autoreactive immune cells which could lead to long-term relief from the disease. Additionally, co-administration of agents which block costimulation of immune cells by disrupting receptor-ligand interactions of B7 molecules with costimulatory receptors may be useful in inhibiting immune cell activation to prevent production of autoantibodies or cytokines which may be involved in the disease process. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis. See Paul ed., *Fundamental Immunology*, Raven Press, New York, 1989, pages 840-856.

Inhibition of immune cell activation is useful therapeutically in the treatment of allergies and allergic reactions, e.g., by inhibiting IgE production. An agent that promotes VISTA (PD-L3) activity or VISTA (PD-L3) interaction with its natural binding partner(s) can be administered to an allergic subject to inhibit immune cell-mediated allergic responses in the subject. Stimulation VISTA (PD-L3) activity or interaction with its natural binding partner(s), can be accompanied by exposure to allergen in conjunction with appropriate MHC molecules. Allergic reactions can be systemic or local in nature, depending on the route of entry of the allergen and the pattern of deposition of IgE on mast cells or basophils. Thus, immune cell-mediated allergic responses can be inhibited locally or systemically by administration of an agent that promotes VISTA (PD-L3) activity or VISTA (PD-L3)-immune cell interactions.

Downregulation of an immune response via stimulation of VISTA (PD-L3) activity or VISTA (PD-L3) interaction with its natural binding partner(s), may also be useful in treating an autoimmune attack of autologous tissues. Thus, conditions that are caused or exacerbated by autoimmune attack (e.g., heart disease, myocardial infarction or atherosclerosis) may be ameliorated or improved by increasing VISTA (PD-L3) activity or VISTA (PD-L3) biding to its natural binding partner. It is therefore within the scope of the invention to modulate conditions exacerbated by autoimmune attack, such as autoimmune disorders (as well as conditions such as heart disease, myocardial infarction, and atherosclerosis) by stimulating VISTA (PD-L3) activity or VISTA (PD-L3) interaction with its counter receptor.

Upregulation of Immune Responses

Inhibition of VISTA (PD-L3) activity or VISTA (PD-L3) interaction with its natural binding partner(s), as a means of upregulating immune responses is also useful in therapy. Upregulation of immune responses can be in the form of enhancing an existing immune response or eliciting an initial immune response. For example, enhancing an immune response through inhibition of VISTA (PD-L3) activity is useful in cases of infections with microbes, e.g., bacteria, viruses, or parasites, or in cases of immunosuppression. For example, an agent that inhibits VISTA (PD-L3) activity, e.g., a non-activating antibody (i.e., a blocking antibody) against VISTA (PD-L3), or a soluble form of VISTA (PD-L3), is therapeutically useful in situations where upregulation of antibody and cell-mediated responses, resulting in more rapid or thorough clearance of a virus, bacterium, or parasite, would be beneficial. These conditions include viral skin diseases such as Herpes or shingles, in which case such an agent can be delivered topically to the skin. In addition, systemic viral diseases such as influenza, the common cold, and encephalitis might be alleviated by the administration of such agents systemically. In certain instances, it may be desirable to further administer other agents that upregulate immune responses, for example, forms of B7 family members that transduce signals via costimulatory receptors, in order further augment the immune response.

Immune responses may be enhanced in an infected patient by removing immune cells from the patient, contacting immune cells in vitro with an agent that inhibits the VISTA (PD-L3) activity or VISTA (PD-L3) interaction with its natural binding partner(s), and reintroducing the in vitro-stimulated immune cells into the patient. In another embodiment, a method of enhancing immune responses involves isolating infected cells from a patient, e.g., virally infected cells, transfecting them with a nucleic acid molecule encoding a form of VISTA (PD-L3) that cannot bind its natural binding partner(s), such that the cells express all or a portion of the VISTA (PD-L3) molecule on their surface, and reintroducing the transfected cells into the patient. The transfected cells may be capable of preventing an inhibitory signal to, and thereby activating, immune cells in vivo.

A agent that inhibits VISTA (PD-L3) activity or VISTA (PD-L3) interaction with its natural binding partner(s), can be used prophylactically in vaccines against various polypeptides, e.g., polypeptides derived from pathogens. Immunity against a pathogen, e.g., a virus, can be induced by vaccinating with a viral polypeptide along with an agent that inhibits VISTA (PD-L3) activity, in an appropriate adjuvant. Alternately, a vector comprising genes which encode for both a pathogenic antigen and a form of VISTA (PD-L3) that blocks VISTA (PD-L3) interaction with immune cells can be used for vaccination. Nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin. Haynes, et al. (1996) J. Biotechnol. 44:37. Alternatively, nucleic acid vaccines can be administered by non-invasive means. For example, pure or lipid-formulated DNA can be delivered to the respiratory system or targeted elsewhere, e.g., Peyers patches by oral delivery of DNA. Schubbert (1997) *Proc Natl. Acad. Sci. USA* 94: 961. Attenuated microorganisms can be used for delivery to mucosal surfaces. Sizemore et al. (1995) *Science* 270:29.

The antigen in the vaccine may be a self-antigen. Such a vaccine is useful in the modulation of tolerance in an organism. Immunization with a self antigen and an agent that blocks VISTA (PD-L3) activity or VISTA (PD-L3) interaction with its natural binding partner can break tolerance (i.e., interfere with tolerance of a self antigen). Such a vaccine may also include adjuvants such as alum or cytokines (e.g., GM-CSF, IL-12, B7-1, or B7-2). In one embodiment, an agent which inhibits VISTA (PD-L3) activity or VISTA (PD-L3) interaction with its natural binding partner(s), can be administered with class I MHC polypeptides by, for example, a cell transfected to coexpress a VISTA (PD-L3) polypeptide or blocking antibody and MHC class I ac chain polypeptide and 132 microglobulin to result in activation of T cells and provide immunity from infection. For example, viral pathogens for which vaccines are useful include: hepatitis B, hepatitis C, Epstein-Barr virus, cytomegalovirus, HIV-1, HIV-2, tuberculosis, malaria and schistosomiasis.

Inhibition of VISTA (PD-L3) activity or VISTA (PD-L3) interaction with its natural binding partner(s), can be useful in the treatment of tumor immunity. Tumor cells (e.g., colorectal cancer, sarcoma, melanoma, lymphoma, leukemia, neuroblastoma, or carcinoma) can be transfected with a nucleic acid molecule that inhibits VISTA (PD-L3) activity. These molecules can be, e.g., nucleic acid molecules which are antisense to VISTA (PD-L3), or can encode non-activating anti-VISTA (PD-L3) antibodies. These molecules can also be the variable region of an anti-VISTA (PD-L3) antibody. If desired, the tumor cells can also be transfected with other polypeptides which activate costimulation (e.g., B7-1 or B7-2). The transfected tumor cells are returned to the patient, which results in inhibition (e.g., local inhibition) of VISTA (PD-L3) activity Alternatively, gene therapy techniques can be used to target a tumor cell for transfection in vivo.

Stimulation of an immune response to tumor cells can also be achieved by inhibiting VISTA (PD-L3) activity or VISTA (PD-L3) interaction with its natural binding partner(s), by treating a patient with an agent that inhibits VISTA (PD-L3) activity or VISTA (PD-L3) interaction with its natural binding partner(s). Preferred examples of such agents include, e.g., antisense nucleic acid molecules, antibodies that recognize and block VISTA (PD-L3), and compounds that block the interaction of VISTA (PD-L3) with its naturally occurring binding partner(s) on an immune cell (e.g., soluble, monovalent VISTA (PD-L3) molecules; soluble forms of VISTA (PD-L3) molecules that do not bind to Fc receptors on antigen presenting cells; soluble forms of VISTA (PD-L3) binding partner(s); and compounds identified in the subject screening assays). In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I α chain polypeptide and beta2 microglobulin polypeptide or an MHC class II α chain polypeptide and an MHC class II β chain polypeptide to thereby express MHC class I or MHC class II polypeptides on the cell surface. Expression of the appropriate class I or class II MHC in conjunction with an VISTA (PD-L3) inhibiting polypeptide or antisense nucleic acid induces a T cell mediated immune response against the transfected tumor cell. Optionally, a gene encoding an antisense construct which blocks expression of an MHC class II-associated polypeptide, such as the invariant chain, can also be cotransfected with a DNA encoding a VISTA (PD-L3) inhibiting polypeptide or antisense nucleic acid to promote presentation of tumor associated antigens and induce tumor specific immunity. Expression of B7-1 by B7-negative murine tumor cells has been shown to induce T cell mediated specific immunity accompanied by tumor rejection and prolonged protection to tumor challenge in mice. Chen, et al. (1992) *Cell* 71: 1093-1102; Townsend & Allison (1993) *Science* 259: 368-370; Baskar, et al. (1993) *Proc Natl. Acad. Sci.* 90: 5687-5690. Thus, the induction of an immune cell-mediated immune response in a human subject can be sufficient to overcome tumor-specific tolerance in the subject. In another embodiment, the immune response can be stimulated by the inhibition of VISTA (PD-L3) activity or VISTA (PD-L3) interaction with its natural binding partner(s), such that preexisting tolerance is overcome. For example, immune responses against antigens to which a subject cannot mount a significant immune response, e.g., tumor-specific antigens, can be induced by administering an agent that inhibits the activity of VISTA (PD-L3) activity or the ability of VISTA (PD-L3) to bind to its natural binding partner, can be used as adjuvants to boost responses to foreign antigens in the process of active immunization.

Immune cells may be obtained from a subject and cultured ex vivo in the presence of an agent that that inhibits VISTA (PD-L3) activity or VISTA (PD-L3) interaction with its natural binding partner(s), to expand the population of immune cells. In a further embodiment the immune cells are then administered to a subject. Immune cells can be stimulated to proliferate in vitro by, for example, providing the immune cells with a primary activation signal and a costimulatory signal, as is known in the art. Various forms of VISTA (PD-L3) polypeptides or agents that inhibit VISTA (PD-L3) activity can also be used to costimulate proliferation of immune cells. In one embodiment, immune cells are cultured ex vivo according to the methods described in WO 94/29436. The costimulatory molecule can be soluble, attached to a cell membrane or attached to a solid surface, such as a bead.

In performing any of the methods described herein, it is within the scope of the invention to upregulate an immune response by administering one or more additional agents. For example, the use of other agents known to stimulate the immune response, such as cytokines, adjuvants, or stimulatory forms of costimulatory molecules or their ligands can be used in conjunction with an agent that inhibits VISTA (PD-L3) activity or VISTA (PD-L3) interaction with its natural binding partner(s).

Identification of Cytokines Modulated by Modulation of VISTA (PD-L3) Activity or VISTA (PD-L3)-Interactions with its Counter Receptor on T Cells The VISTA (PD-L3) molecules described herein may be used to identify cytokines which are produced by or whose production is enhanced or inhibited in immune cells in response to modulation of VISTA (PD-L3) activity or VISTA (PD-L3) interaction with its natural binding partner(s), Immune cells may be suboptimally stimulated in vitro with a primary activation signal, for example, T cells can be stimulated with phorbol ester, anti-CD3 antibody or preferably, antigen, in association with an MHC class II molecule, and given a costimulatory signal, e.g., by a stimulatory form of B7 family antigen, for instance by a cell transfected with nucleic acid encoding a B7 polypeptide and expressing the peptide on its surface, or by a soluble, stimulatory form of the peptide. The cells can then be contacted with cells expressing VISTA (PD-L3) (e.g., antibodies against VISTA (PD-L3) Known cytokines released into the media can be identified by ELISA or by the ability of an antibody which blocks the cytokine to inhibit immune cell proliferation or proliferation of other cell types that are induced by the cytokine. For example, an IL-4 ELISA kit is available from Genzyme (Cambridge, Mass.), as is an IL-7 blocking antibody. Blocking antibodies against IL-9 and IL-12 are available from Genetics Institute (Cambridge, Mass.). The effect of stimulating or blocking VISTA (PD-L3) activity or the interaction of VISTA (PD-L3) and its binding partner(s) on the cytokine profile can then be determined. As noted supra and shown in the examples VISTA (PD-L3) apparently suppresses the expression of IL-2 and gamma interferon by immune cells.

An in vitro immune cell costimulation assay as described above can also be used in a method for identifying novel cytokines which can be modulated by modulation of VISTA (PD-L3) activity. For example, where stimulation of the CD28/CTLA4 pathway seems to enhance IL-2 secretion, stimulation of the ICOS pathway seems to enhance IL-10 secretion. Hutloff, et al. (1999) Nature 397: 263. If a particular activity induced upon costimulation, e.g., immune cell proliferation, cannot be inhibited by addition of blocking antibodies to known cytokines, the activity may result from the action of an unknown cytokine. Following costimulation, this cytokine can be purified from the media by conventional methods and its activity measured by its ability to induce immune cell proliferation.

To identify cytokines which may play a role the induction of tolerance, an in vitro T cell costimulation assay as described above can be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a cytokine blocking antibody to a subject along with an agent that promotes VISTA (PD-L3) activity or VISTA (PD-L3) interaction with a binding partner.

Thus, to summarize a novel member of the Programmed Death Ligand (PDL) family has now been identified which is expressed by Treg cells. This novel protein has been designated VISTA (PD-L3). The receptors of this PD-L family are type I transmembrane proteins containing a single IgV domain, while the ligands are type I transmembrane proteins expressing both an IgV and an IgC extracellular domains. Like other members of the PDL family, VISTA (PD-L3) co-stimulates αCD3 proliferation of T cells in vitro. In addition, the expression of VISTA (PD-L3) is increased in αCD3 activated Treg and reduced in the presence of αGITR.

A second, TNF-like, protein has also been identified as being upregulated upon αCD3/αGITR stimulation. This protein has been designated Treg-sTNF. These proteins may be involved in contact-dependent and paracrine suppression of immunity and therefore are useful for modulating (e.g., inhibiting or stimulating) an immune response and in the treatment of diseases and conditions involving Treg signaling. For example, the VISTA (PD-L3) protein can be used as a co-stimulatory signal for stimulating or enhancing immune cell activation. VISTA (PD-L3) proteins and VISTA (PD-L3) binding agents and VISTA (PD-L3) agonists and antagonists are especially useful in treating immune conditions wherein regulation of T cell immunity is desired, e.g., modulation of T cell activation, differentiation and proliferation, and in particular modulation of CD4+ and CD8+ T cell proliferation, cytokine production, and T cell responses during cognate interactions between T cells and myeloid derived APCs.

VISTA and VISTA Conjugate Polypeptides

The invention provides VISTA and VISTA conjugate polypeptides. The inventors surprisingly discovered that VISTA and VISTA conjugate polypeptides act as negative immune modulators. Exemplary VISTA polypeptides are provided in SEQ ID NO: 2, 4, and 5. VISTA (PD-L3) molecules of the invention include at least one or more of the following domains: a signal peptide domain, an IgV domain, an extracellular domain, a transmembrane domain, or a cytoplasmic domain. Isolated polypeptides of the present invention, preferably VISTA (PD-L3) polypeptides, may comprise an amino acid sequence sufficiently identical to the amino acid sequence of SEQ ID NO: 2 or 4, or 5 or are encoded by a nucleotide sequence sufficiently identical to SEQ ID NO: 1 or 3 or fragment or complement thereof. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% homology and share a common functional activity are defined herein as sufficiently identical. An extracellular domain of the VISTA polypeptide may comprise an IgV domain and may include a signal peptide domain. See FIGS. 1 and 23.

VISTA (PD-L3) polypeptides may have at least one extracellular domain, and one or more of a signal peptide domain, an IgV domain, an transmembrane domain, and a cytoplasmic domain, and are, preferably, encoded by a nucleic acid molecule having a nucleotide sequence which hybridizes under stringent hybridization conditions to a nucleic acid molecule comprising a complement of the nucleotide sequence of SEQ ID NO: 1 or 3 herein. The nucleotide and amino acid sequences sequence of the exemplified isolated human and murine VISTA (PD-L3) cDNA and the predicted amino acid sequence of the human VISTA (PD-L3) polypeptide are contained in the sequence listing herein.

A VISTA (PD-L3) polypeptide of the present invention may be identified based on the presence of a "transmembrane domain". The transmembrane domain region of PDL3 are identified herein. See e.g., FIGS. 1 and 23. A VISTA (PD-L3) molecule of the present invention may be identified based on the absence of an "IgC domain" and the presence of an "IgV domain" in the polypeptide or corresponding nucleic acid molecule. The amino acid residues of the native human and murine VISTA (PD-L3) polypeptide, constituting the IgV domain can be seen in FIGS. 1 and 23. The presence of an IgV domain is likely required for binding of VISTA (PD-L3) to its natural binding partner(s).

Nucleic acids encoding VISTA polypeptides may be modified using standard molecular biological techniques that result in variants polypeptides comprising at least one VISTA and VISTA conjugate including but not limited to deletions, additions and substitutions in the amino acid sequence, that retain the specific antigenicity of the VISTA and VISTA conjugate (e.g., the VISTA polypeptides is bound by an anti-VISTA antibody). Additionally, variant polypeptides comprising at least one VISTA polypeptide may also retain the antigenicity of the VISTA polypeptide (e.g., raise a specific immune response against the VISTA polypeptide and variant VISTA polypeptide, respectively, upon immunization in a subject). The VISTA and VISTA conjugate polypeptides may be formulated with a pharmaceutical carrier to manufacture an antigen composition useful as a "cancer vaccine" (e.g., a pharmaceutical composition that elicits a specific immune response against the VISTA and VISTA conjugate, that produces anti-tumor antibodies after immunization in a subject). The VISTA polypeptides and VISTA conjugates described herein may be used to treat autoimmune disorders and inflammatory diseases.

Polypeptide Derivatives and Analogs

It will be appreciated that polypeptides described herein may be degradation products, synthetic peptides or recombinant peptides as well as peptidomimetics, synthetic peptides, peptoids, and semipeptoids (e.g., peptide analogs, which may have, for example, modifications rendering the peptides more stable while in a body or more capable of penetrating into cells.) Modifications of the VISTA and VISTA conjugate polypeptides described herein include, but are not limited to N-terminus modification, C-terminus modification, peptide bond modification (e.g., $CH_2$—NH, $CH_2$—S, $CH_2$—S═O, O═C—NH, $CH_2$—O, $CH_2$—$CH_2$, S═C—NH, CH═CH or CF═CH), backbone modifications, and residue modification. Methods for preparing peptidomimetic compounds are well known in the art. Martin, (2010) Quantitative Drug Design: A Critical Introduction [$2^{nd}$ Ed.] CRC Press.

Peptide bonds (—CO—NH—) within the peptide may be substituted, for example, by N-methylated bonds (—N($CH_3$)—CO—), ester bonds (—C(R)H—C—O—O—C (R)—N—), ketomethylen bonds (—CO—CH2-), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH═CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted by synthetic non-natural acid such as phenylglycine, TIC, naphthylelanine (Nol), ring-methylated derivatives of phenylalanine, halogenated derivatives of phenylalanine or o-methyl-tyrosine. In addition to the above, the polypeptides of the present invention may also include one or more modified amino acids or one or more non-amino acid monomers (e.g. fatty acids, complex carbohydrates), for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Since the polypeptides of the present invention are preferably utilized in therapeutics which requires the peptides to be in soluble form, the polypeptides of the present invention may comprise one or more non-natural or natural polar amino acids, including but not limited to serine and threonine which are capable of increasing peptide solubility due to their hydroxyl-containing side chain.

The polypeptides of the present invention may be in a linear form, although it will be appreciated that in cases may also be utilized.

The VISTA and VISTA conjugate polypeptides described herein may be purified from cells that have been altered to express it (e.g., recombinant). DNA sequences encoding the VISTA and VISTA conjugate polypeptides may be inserted into an expression vector and then transformed (or transfected) in an appropriate host cell and/or expressed in a transgenic animal. The VISTA and VISTA conjugate polypeptides so expressed may then be isolated by methods known in the art. See, e.g., Maniatis, et al. (2001) Molecular Cloning: A Laboratory Manual [$3^{rd}$ Ed.] Cold Spring Harbor Laboratory Press.

The polypeptides of the present invention may be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry. Solid phase peptide synthesis procedures are well known in the art and further described by Stewart (1984) Solid Phase Peptide Syntheses [$2^{nd}$ Ed.] Pierce Chemical Company and Benoiton (2005) Chemistry of Peptide Synthesis CRC Press. Synthetic peptides may be purified by preparative high performance liquid chromatography and the composition of which may be confirmed via amino acid sequencing. See Creighton (1992) [$2^{nd}$ Ed.] Proteins, Structures and Molecular Principles W.H. Freeman and Company; Aguilar (2004) [Ed.] HPLC of Peptides and Proteins: Methods and Protocols Humana Press; Simpson (2002) Protein Sequencing Protocols [$2^{nd}$ Ed.] Humana Press.

In cases where large amounts of the polypeptides of the present invention are desired, the polypeptides of the present invention may be generated using recombinant techniques such as described by Invitrogen (2002) "Guide to Baculovirus Expression Vector Systems (BEVs) and Insect Culture Techniques" Instruction Manual; Hatti-Kaul and Mattiasson (2003) [Eds] Isolation and Purification of Proteins; Ahmed (2004) Principles and Reactions of Protein Extraction, Purification and Characterization CRC Press. Further recombinant techniques such as described by, for example, Bitter, et al. (1987) Methods in Enzymol. 153: 516-544, Studier, et al. (1990) Methods in Enzymol. 185: 60-89, Brisson, et al. (1984) Nature 310: 511-514, Takamatsu, et al. (1987) EMBO J. 6: 307-311, Coruzzi, et al. (1984) EMBO J. 3: 1671-1680 and Brogli, et al. (1984) *Science* 224: 838-843, Gurley, et al. (1986) Mol. Cell. Biol. 6: 559-565 and Weissbach & Weissbach (1988) Methods for Plant Molecular Biology, Academic Press, NY, Section VIII, pages 421-463.

Polypeptide Sequence Variants

For any VISTA and VISTA conjugate sequence described herein, further characterization or optimization may be achieved by systematically either adding or removing amino acid residues to generate longer or shorter peptides, and testing those and sequences generated by walking a window of the longer or shorter size up or down the antigen from that point. Coupling this approach to generating new candidate targets with testing for effectiveness of antigenic molecules based on those sequences in an immunogenicity assay, as known in the art or as described herein, may lead to further manipulation of the antigen. Further still, such optimized sequences may be adjusted by, e.g., the addition, deletions, or other mutations as known in the art and/or discussed herein to further optimize the VISTA and VISTA conjugate (e.g., increasing serum stability or circulating half-life, increasing thermal stability, enhancing delivery, enhance immunogenicity, increasing solubility, targeting to a particular in vivo location or cell type).

The VISTA and VISTA conjugate polypeptides described herein may comprise conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

VISTA and VISTA conjugate polypeptide sequences may have at least about 60, 65, 70, 75, 80, 81, 82, 83, 84, 85, 86, 87, 88, 89, 90, 91, 92, 93, 94, 95, 96, 97, 98, 99, or 100% sequence homology to any one or more of the polypeptide sequences of SEQ ID NO: 2, 4, or 5. More preferably, the invention contemplates polypeptide sequences having at least about 95% sequence homology, even more preferably at least about 98% sequence homology, and still more preferably at least about 99% sequence homology to any one or more of the polypeptide sequences of VISTA and VISTA conjugate polypeptide sequences of SEQ ID NO: 2, 4, or 5. Methods for determining homology between amino acid sequences, as well as nucleic acid sequences, are well known to those of ordinary skill in the art. See, e.g., Nedelkov & Nelson (2006) New and Emerging Proteomic Techniques Humana Press.

Thus, a VISTA and VISTA conjugate polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with a polypeptide sequence. For example, a VISTA and VISTA conjugate polypeptide may have at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence homology with SEQ ID NO: 2, 4, or 5.

The term homology, or identity, is understood as meaning the number of agreeing amino acids (identity) with other proteins, expressed in percent. The identity is preferably determined by comparing a given sequence with other proteins with the aid of computer programs. If sequences which are compared with each other are different in length, the identity is to be determined in such a way that the number of amino acids which the short sequence shares with the longer sequence determines the percentage identity. The identity can be determined routinely by means of known computer programs which are publicly available such as, for example, ClustalW. Thompson, et al. (1994) Nucleic Acids Research 22: 4673-4680. ClustalW is publicly available from the European Molecular Biology Laboratory and may be downloaded from various internet pages, inter alia the IGBMC (Institut de Génétique et de Biologie Moleculaire et Cellulaire) and the EBI and all mirrored EBI internet pages (European Bioinformatics Institute). If the ClustalW computer program Version 1.8 is used to determine the identity between, for example, the reference protein of the present application and other proteins, the following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS (OFF), NOPGAP, NOHGAP. See also European Bioinformatics Institute (EBI) toolbox available on-line and Smith (2002) Protein Sequencing Protocols [$2^{nd}$ Ed.] Humana Press.

One possibility of finding similar sequences is to carry out sequence database researches. Here, one or more sequences may be entered as what is known as a query. This query sequence is then compared with sequences present in the selected databases using statistical computer programs. Such database queries (blast searches) are known to the skilled worker and may be carried out at different suppliers. If, for example, such a database query is carried out at the NCBI (National Center for Biotechnology Information), the standard settings for the respective comparison query should be used. For protein sequence comparisons (blastp), these settings are: Limit entrez=not activated; Filter=low complexity activated; Expect value=10; word size=3; Matrix=BLOSUM62; Gap costs: Existence=11, Extension=1. The result of such a query is, among other parameters, the degree of identity between the query sequence and the similar sequences found in the databases.

VISTA and VISTA conjugates include functional fragments of said polypeptides. A "functional fragment" of said polypeptide includes a fragment of the gene or cDNA encoding said VISTA and VISTA conjugate, which fragment is capable of eliciting an immune response (e.g., humoral or cellular immune response.) Thus, for example, fragments of the VISTA and VISTA conjugate according to the invention which correspond to amino acid residues that contribute to the immunogenicity of the antigen and which fragments may serve to function as antigens to elicit an immune response (e.g., humoral or cellular immune response.) This aspect of the invention also includes differentially spliced isoforms and transcriptional starts of the polypeptides according to the invention. The polypeptides according to the invention also may comprise fragments, derivatives and allelic variants of the VISTA and VISTA conjugates. Methods and materials for making fragments of VISTA and VISTA conjugate polypeptides are well known in the art. See, e.g., Maniatis, et al. (2001) Molecular Cloning: A Laboratory Manual [$3^{rd}$ Ed.] Cold Spring Harbor Laboratory Press.

Variant VISTA and VISTA conjugate polypeptides may retain their antigenic specificity to bind their respective antibodies (e.g., a variant VISTA polypeptide will be bound by an anti-VISTA antibody.) Fully antigenic variants may contain only conservative variations or variations in non-critical residues or in non-critical regions. Antigenic variants may also contain substitution of similar amino acids that result in no change or an insignificant change in antigenicity. Alternatively, such substitutions may positively or negatively affect antigenicity to some degree. Non-antigenic variants typically contain one or more non-conservative amino acid substitutions, deletions, insertions, inversions, or truncation or a substitution, insertion, inversion, or deletion in a critical residue or critical region of an epitope. Molecular biology and biochemistry techniques for modifying VISTA and VISTA conjugate polypeptides while preserving specific antigenicity of the polypeptides for their respective antibodies are well known in the art. See, e.g., Ho, et al. (1989) Gene 77(1): 51-59; Landt, et al. (1990) Gene 96(1): 125-128; Hopp & Woods (1991) *Proc. Natl. Acad. Sci. USA* 78(6): 3824-3828; Kolaskar & Tongaonkar (1990) *FEBS Letters* 276(1-2): 172-174; and Welling, et al. (1985) *FEBS Letters* 188(2): 215-218.

Variants of the VISTA polypeptides which function as either VISTA agonists (mimetics) or as VISTA antagonists. Variants of the VISTA polypeptides can be generated by mutagenesis, e.g., discrete point mutation or truncation of a VISTA polypeptide. An agonist of the VISTA polypeptides can retain substantially the same, or a subset, of the biological activities of the naturally occurring form of a VISTA polypeptide. An antagonist of a VISTA polypeptide can inhibit one or more of the activities of the naturally occurring form of the VISTA polypeptide by, for example, competitively modulating a VISTA-mediated activity of a VISTA polypeptide. Thus, specific biological effects can be elicited by treatment with a variant of limited function. For example, a subject may be treated with a variant having a subset of the biological activities of the naturally occurring form of the polypeptide has fewer side effects in a subject relative to treatment with the naturally occurring form of the VISTA polypeptide.

Variants of a VISTA polypeptide which function as either VISTA agonists (mimetics) or as VISTA antagonists may be identified by screening combinatorial libraries of mutants, e.g., truncation mutants, of a VISTA polypeptide for VISTA polypeptide agonist or antagonist activity. Diseases treatable with the subject VISTA (PD-L3) binding agents are identified previously and include various inflammatory, autoimmune, cancer, allergic and infectious disorders. A particularly preferred indication is multiple sclerosis.

Peptidomimetics

In addition to VISTA polypeptides consisting only of naturally-occurring amino acids, VISTA peptidomimetics are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere (1986) Adv. Drug Res. 15: 29; Advances in Amino Acid Mimetics and Peptidomimetics (Volume 2) Andrew Abell (Ed.) (1999) JAI Press, Inc. and Evans et al. (1987) J. Med. Chem 30: 1229) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i e., a polypeptide that has a biological or pharmacological activity), such as human or mouse VISTA, but have one or more peptide linkages optionally replaced by a linkage selected from the group consisting of —$CH_2NH$—, —$CH_2S$—, —$CH_2$—$CH_2$—, —CH═CH— (cis and trans), —$COCH_2$—, —CH(OH)$CH_2$—, and —$CH_2SO$—, by methods known in the art and further described in the following references: Spatola in Chemistry and Biochemistry of Amino Acids, Peptides, and Proteins Weinstein, B., ed., Marcel Dekker, New York, p. 267 (1983); Spatola, Vega Data (March 1983), Vol. 1, Issue 3, "Peptide Backbone Modifications"; Morley (1980) Trends. Pharm. Sci. pp. 463-468; Hudson, et al. (1979) Int. J. Pept. Prot. Res. 14:177-185 (—$H_2NH$—, $CH_2CH_2$—); Spatola, et al. (1986) Life. Sci. 38:1243-1249 (—CH2-S); Hann, (1982) J. Chem. SoC Perkin. Trans. I 307-314 (—CH—H—, cis and trans); Almquist, et al. (1980) J. Med. Chem. 23:1392-1398 (—$COCH_2$—); Jennings-White, et al. (1982) Tetrahedron Lett. 23:2533 (—$COCH_2$—); (—CH(OH)$CH_2$—); Holladay, et al. (1983) Tetrahedron. Lett. 24:4401-4404 (—C (OH)$CH_2$—); and Hruby (1982) Life Sci. 31:189-199 (—$CH_2$—S—). A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of a VISTA amino acid sequence with a D-amino acid of the same type (e.g., D-lysine in place of L-lysine) can be used to generate more stable peptides. In addition, constrained peptides comprising a VISTA amino acid sequence or a substantially identical sequence variation can be generated by methods known in the art (Rizo and Gierasch (1992) Annu. Rev. Biochem. 61:387); for example, by adding internal cysteine residues capable of forming intramolecular disulfide bridges which cyclize the peptide. The amino acid sequences of the VISTA polypeptides identified herein will enable those of skill in the art to produce polypeptides corresponding to VISTA peptide sequences and sequence variants thereof. Such polypeptides can be produced in prokaryotic or eukaryotic host cells by expression of polynucleotides encoding a VISTA peptide sequence, frequently as part of a larger polypeptide. Alternatively, such peptides can be synthesized by chemical methods. Methods for expression of heterologous polypeptides in recombinant hosts, chemical synthesis of polypeptides, and in vitro translation are well known in the art. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides can be used therapeutically to treat disease, e.g., by altering costimulation in a patient.

Amino acids that are essential for function may be identified by methods known in the art, such as site-directed mutagenesis or alanine-scanning mutagenesis. Cunningham, et al. (1989) Sci. 244: 1081-85. The latter procedure introduces single alanine mutations at every residue in the molecule. The resulting mutant molecules are then tested for biological activity such as epitope binding or in vitro ADCC activity. Sites that are critical for ligand-receptor binding may also be determined by structural analysis such as crystallography, nuclear magnetic resonance, or photoaffinity labeling. Smith, et al. (1992) J. Mol. Biol. 224: 899-904; de Vos, et al. (1992) Sci. 255: 306-12.

For example, one class of substitutions is conserved amino acid substitutions. Such substitutions are those that substitute a given amino acid in a VISTA and VISTA conjugate polypeptide with another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr. Guidance concerning which amino acid changes are likely to be phenotypically silent is found in, for example, Bowie, et al. (1990) Sci. 247: 1306-10. Hence, one of ordinary skill in the art appreciates that the inventors possess peptide variants without delineation of all the specific variants. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. See, e.g., Creighton (1992) Proteins: Structures and Molecular Properties [$2^{nd}$ d Ed.] W.H. Freeman.

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, g-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See Creighton (1992) Proteins: Structure and Molecular Properties [$2^{nd}$ Ed.] and Lundblad (1995) Techniques in Protein Modification [$1^{st}$ Ed.] Many detailed reviews are available on this subject.

See, e.g., Wold (1983) Posttranslational Covalent Modification of Proteins Acad. Press, NY; Seifter, et al. (1990) Meth. Enzymol. 182: 626-46; and Rattan, et al. (1992) Ann. NY Acad. Sci. 663: 48-62.

Fragments

A biologically active portion of a VISTA polypeptide includes a fragment of a VISTA polypeptide which participates in an interaction between a VISTA molecule and a non-VISTA molecule, e.g., a natural ligand of VISTA. Biologically active portions of a VISTA polypeptide include peptides comprising amino acid sequences sufficiently identical to or derived from the amino acid sequence of the VISTA polypeptide, e.g., the amino acid sequence shown in SEQ ID NO: 2, 4 or 5, which include fewer amino acids than the full length VISTA polypeptides, and exhibit at least one activity of a VISTA polypeptide. Typically, biologically active portions comprise a domain or motif with at least one activity of the VISTA polypeptide, e.g., modulating (suppressing) CD4 T cell proliferative responses to anti-CD3, suppression of the proliferative response of cognate CD4 T cells in an antigen specific manner, effects on the expression of specific cytokines. A biologically active portion of a VISTA polypeptide can be a polypeptide which is, for example, 25, 50, 75, 100, 125, 150, 175, 200, 225 or more amino acids in length. Biologically active portions of a VISTA polypeptide can be used as targets for developing agents which modulate a VISTA-mediated activity, e.g., immune cell activation.

A biologically active portion of a VISTA polypeptide may comprise at least a portion of an extracellular domain. A biologically active portion of a VISTA polypeptide may contain at least a portion of an extracellular domain (e.g., comprising an IgV), and one or more of the following domains: a signal peptide domain, a transmembrane domain, or a cytoplasmic domain. Moreover, other biologically active portions, in which other regions of the polypeptide are deleted, can be prepared by recombinant techniques and evaluated for one or more of the functional activities of a native VISTA polypeptide.

The VISTA polypeptide may have the amino acid sequence shown in SEQ ID NO: 2, 4 or 5. The VISTA polypeptide may be substantially identical to SEQ ID NO: 2, 4 or 5, and retains the functional activity of the polypeptide of SEQ ID NO: 2, 4 or 5, yet differs in amino acid sequence due to natural allelic variation or mutagenesis, as described herein.

Fusion Proteins

Fusions comprising the VISTA and VISTA conjugate polypeptides are also within the scope of the present invention. For example, the fusion protein may be linked to a GST fusion protein in which the VISTA and VISTA conjugate polypeptide sequences are fused to the C-terminus of the GST sequences. Such fusion proteins may facilitate the purification of the recombinant VISTA and VISTA conjugate polypeptides. Alternatively, VISTA and VISTA conjugate polypeptides may be fused with a protein that binds B-cell follicles, thus initiating both a humoral immune response and activation of T cells. Berney, et al. (1999) *J. Exp. Med.* 190: 851-60. Alternatively, for example, the VISTA and VISTA conjugate polypeptides may be genetically coupled with and anti-dendritic cell antibody to deliver the antigen to the immune system and stimulate a cellular immune response. He, et al. (2004) Clin. *Cancer Res.* 10: 1920-27. A chimeric or fusion protein of the invention may be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene may be synthesized by conventional techniques including automated DNA synthesizers.

Fusion proteins may include C-terminal or N-terminal translocation sequences. Further, fusion proteins can comprise additional elements, e.g., for protein detection, purification, or other applications. Detection and purification facilitating domains including but not limited to metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAG extension/affinity purification system (Immunex Corp, Seattle Wash.)

A fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. See, e.g., U.S. Patent Application Publication No. 2006/0034852. The term "Fc chain" also optionally comprises any type of Fc fragment. Several of the specific amino acid residues that are involved in antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect. See McCafferty, et al. (2002) Antibody Engineering: A Practical Approach (Eds.) Oxford University Press.

The inclusion of a cleavable linker sequences such as Factor Xa (See, e.g., Ottavi, (1998) Biochimie 80: 289-93), subtilisin protease recognition motif (See, e.g., Polyak (1997) Protein Eng. 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (See, e.g., Williams (1995) Biochemistry 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) DNA Cell. Biol. 12: 441-53.

A fusion protein may be a GST-VISTA fusion protein in which the VISTA sequences are fused to the C-terminus of the GST sequences. Such fusion proteins can facilitate the purification of recombinant VISTA. In another embodiment, the fusion protein is a VISTA polypeptide containing a heterologous signal sequence at its N-terminus. In certain host cells (e.g., mammalian host cells), expression and/or secretion of VISTA can be increased through use of a heterologous signal sequence. In an embodiment, the fusion protein is an Ig-VISTA fusion protein in which the VISTA sequences are fused to a portion of an Ig molecule. The Ig portion of the fusion protein can include and immunoglobulin constant region, e.g., a human Cγ1 domain or a Cγ4 domain (e.g., the hinge, CH2, and CH3 regions of human IgCγ1 or human IgCγ4 (see, e.g., U.S. Pat. Nos. 5,116,964; 5,580,756; 5,844,095). A resulting fusion protein may have altered VISTA solubility, binding affinity, stability and/or valency (i.e., the number of binding sites per molecule) and may increase the efficiency of protein purification.

Particularly preferred VISTA Ig fusion proteins include an extracellular domain portion of VISTA coupled to an immunoglobulin constant region (e.g, the Fc region). The immunoglobulin constant region may contain genetic modifications which reduce or eliminate effector activity inherent in the immunoglobulin structure. For example, DNA encoding an extracellular portion of a VISTA polypeptide can be joined to DNA encoding the hinge, CH2, and CH3 regions of human IgGγ1 and/or IgGγ4 modified by site-directed mutagenesis, e.g., as taught in WO 97/28267. The VISTA fusion proteins of the invention can be incorporated into pharmaceutical compositions and administered to a subject in vivo. The VISTA fusion proteins can be used to affect the bioavailability of a VISTA binding partner. Use of VISTA fusion proteins may be useful therapeutically for the treatment of conditions or disorders that would benefit from modulation of the immune response. Moreover, the VISTA-fusion proteins of the invention can be used as immunogens to produce anti-VISTA antibodies in a subject, to purify VISTA-binding proteins, and in screening assays to identify molecules which inhibit the interaction of VISTA with its natural binding partner.

Conjugates

The VISTA and VISTA conjugate, antibodies that bind the VISTA and VISTA conjugate and fragments thereof, may be conjugated to other moieties. Such conjugates are often used in the preparation of vaccines. The VISTA and VISTA conjugate polypeptide may be conjugated to a carbohydrate (e.g., mannose, fucose, glucose, GlcNAs, maltose), which is recognized by the mannose receptor present on dendritic cells and macrophages. The ensuing binding, aggregation, and receptor-mediated endocytosis and phagocytosis functions provide enhanced innate and adaptive immunity. See Mahnke, et al. (2000) J. Cell Biol. 151: 673-84; Dong, et al. (1999) J. Immonol. 163: 5427-34.

Other moieties suitable for conjugation to elicit an immune response includes but not limited to Keyhole Limpit Hemocyannin (KLH), diphtheria toxoid, cholera toxoid, *Pseudomonas* exoprotein A, and microbial outer membrane proteins (OMPS).

Polypeptide Isolation

The present invention also provides methods for isolation of the VISTA and VISTA conjugate polypeptides. For example, relevant cell lines or tumor samples may be obtained from a cancer patient. After homogenization and solubilization in a detergent, the antigen is chromatographically purified. Size-exclusion or affinity chromatography may be used for this, and may be used in conjunction with anti-VISTA and anti-VISTA-Ig conjugate antibodies. For example, anti-VISTA or anti-VISTA-Ig conjugate antibody may be immobilized on a solid support (e.g., coupled to resins, magnetic beads) for simple antigen adsorption, washing, and elution from the solid support. The eluted protein is then studied further for antigen presence, characterization, and identification. See Walker (2002) Protein Protocols Handbook [$2^{nd}$ Ed.] Humana Press and Culture (2003) [Ed.] Protein Purification Protocols Humana Press.

The antigen isolated in this way may be used for preparing a pharmaceutical using the conventional pharmaceutical excipient and carrier substance. For example, in-vivo administration of the purified antigen in a physiological NaCl solution.

Additionally, the VISTA and VISTA conjugate polypeptides according to the invention may serve as an antigen in the identification of activities as part of a high-throughput screening. High-throughput screening methods are known to persons skilled in the art. Wells (2002) High Throughout Bioanalytical Sample Preparation Elsevier Health Sciences.

Polynucleotides Encoding VISTA and VISTA Conjugate

The present invention also provides nucleotides which encode VISTA and VISTA conjugates. The present invention also provides polynucleotides comprising the nucleic acid sequences of SEQ ID NOs: 1 and 3 which encode VISTA polypeptides. The present invention also provides for fragments, sequences hybridizable with, and sequences homologous to the polynucleotide sequences described herein which are at least about 80%, 81%, 82%, 83%, 84%, 85%, 86%, 87%, 88%, 89%, 90%, 91%, 92%, 93%, 94%, 95%, 96%, 97%, 98%, 99%, or 100%.

The invention also provides polynucleotides comprising at least one VISTA and VISTA conjugate sequence encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (e.g., which form a part of a polynucleotide sequence of the present invention), which include sequence regions unique to the polynucleotides of the present invention.

The present invention also encompasses nucleic acids encoding homologues of VISTA and VISTA conjugate polypeptides, such homologues can be at least about 80%, 81%, 82%, 83%, 84%, 85%, 86%, 87%, 88%, 89%, 90%, 91%, 92%, 93%, 94%, 95%, 96%, 97%, 98%, 99%, or 100% identical homologous to the amino acid sequences set forth herein, as may be determined using BlastP software of the National Center of Biotechnology Information (NCBI) using default parameters. The present invention also encompasses fragments of the above described polynucleotides and polypeptides having mutations, such as deletions, insertions or substitutions of one or more nucleic acids, either naturally occurring or man induced, either randomly or in a targeted fashion.

Nucleic acid molecules may encode a VISTA and VISTA conjugate, or a functional fragment of said nucleic acid molecule. A "functional fragment" of said nucleic acid includes a fragment of the gene or cDNA encoding said VISTA and VISTA conjugate, which fragment is capable of being expressed to produce a VISTA and VISTA conjugate capable of eliciting an immune response (e.g., antibodies which selectively bind the VISTA and VISTA conjugate) Thus, for example, fragments of the VISTA and VISTA conjugate according to the invention which correspond to amino acid residues that contribute to the immunogenicity of the antigen and which fragments may serve to function as antigens to elicit an immune response (e.g., humoral or cellular immune response.) This aspect of the invention also includes differentially spliced isoforms and transcriptional starts of the nucleic acids according to the invention. The nucleic acid molecules according to the invention also comprise fragments, derivatives and allelic variants of the nucleic acid molecules described above that encodes a VISTA and VISTA conjugate according to the invention. Methods and materials for making nucleic acids encoding fragments of VISTA and VISTA conjugate are well known in the art. See, e.g., Maniatis, et al. (2001) Molecular Cloning: A Laboratory Manual [3rd Ed.] Cold Spring Harbor Laboratory Press.

A nucleic acid molecule encompassing all or a portion of SEQ ID NO: 1, 3, or an ortholog or variant can be isolated by the polymerase chain reaction (PCR) using synthetic oligonucleotide primers designed based upon the sequence of SEQ ID NO: 1, 2, 3, 4 or 5.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to VISTA (PD-L3) nucleotide sequences can be prepared by standard synthetic techniques, e.g., using an automated DNA synthesizer.

In an embodiment, an isolated VISTA encoding nucleic acid molecule of the invention comprises the nucleotide sequence shown in SEQ ID NO: 1 or 3, or a fragment thereof. In another embodiment the nucleic acid molecule of the invention comprises a nucleic acid molecule which is a complement of the nucleotide sequence shown in SEQ ID NO: 1 or 3, or a portion of any of these nucleotide sequences. A nucleic acid molecule which is complementary to the nucleotide sequence shown in SEQ ID NO: 1 or 3, is one which is sufficiently complementary to the nucleotide sequence shown in SEQ ID NO: 1 or 3 such that it can hybridize to the nucleotide sequence shown in SEQ ID NO: 1 or 3 respectively, thereby forming a stable duplex.

In another embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99%, or 99.5% identical to the entire length of the nucleotide sequence shown in SEQ ID NO: 1 or 3, or a portion of any of these nucleotide sequences.

Moreover, the nucleic acid molecule of the invention can comprise only a portion of the nucleic acid sequence of SEQ ID NO: 1 or 3, for example, a fragment which can be used as a probe or primer or a fragment which encodes a portion of a VISTA polypeptide, e.g., a biologically active portion of a VISTA-polypeptide. The nucleotide sequences determined from the cloning of the human PD-L2 gene allow for the generation of probes and primers designed for use in identifying and/or cloning other PD-L2 family members, as well as VISTA homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1 or 3; of an anti-sense sequence of SEQ ID NO: 1, 3, or a naturally occurring allelic variant or mutant of SEQ ID NO: 1 or 3.

In one embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, or more nucleotides in length and hybridizes under stringent hybridization conditions to a nucleic acid molecule of SEQ ID NO: 1 or 3, or the complement thereof. In a further embodiment, a nucleic acid molecule of the present invention comprises a nucleotide sequence which is greater than about 880-900, 900-950, 950-1000, 1000-1050, 1050-1100, 1100-1150, or more nucleotides in length and hybridizes under stringent hybridization conditions to a nucleic acid molecule of SEQ ID NO: 1 or 3, or the complement thereof. In yet another embodiment, a nucleic acid molecule of the present invention comprises a nucleotide sequence which is greater than 50-100, 100-150, 150-200, 200-250, 250-300 or more nucleotides in length and hybridizes under stringent hybridization conditions to a nucleic acid molecule comprising the coding region in SEQ ID NO: 1 or 3, or a complement thereof. In yet a further embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 850-900, 900-950, or more nucleotides in length, includes at least about 15 (i.e., 15 contiguous) nucleotides of the sequence comprising the coding region of SEQ ID NO: 1 or 3, or a complement thereof, and hybridizes under stringent conditions to a nucleic acid molecule comprising the nucleotide sequence shown in SEQ ID NO: 1 or 3 a complement thereof.

Probes based on the VISTA nucleotide sequences can be used to detect transcripts or genomic sequences encoding the same or homologous polypeptides. In embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a VISTA polypeptide, such as by measuring a level of a VISTA-encoding nucleic acid in a sample of cells from a subject, e.g., detecting VISTA mRNA levels or determining whether a genomic VISTA gene has been mutated or deleted.

In addition to the VISTA nucleotide sequences of SEQ ID NO: 1 and 3, it will be appreciated by those skilled in the art that DNA sequence polymorphisms that lead to changes in the amino acid sequences of the VISTA polypeptides may exist within a population (e.g., the human population). Such genetic polymorphism in the VISTA genes may exist among individuals within a population due to natural allelic variation. As used herein, the terms "gene" and "recombinant gene" refer to nucleic acid molecules which include an open reading frame encoding a VISTA polypeptide, preferably a mammalian VISTA polypeptide, and can further include non-coding regulatory sequences, and introns.

Allelic variants of human or mouse VISTA include both functional and non-functional VISTA polypeptides. Functional allelic variants are naturally occurring amino acid sequence variants of the human or mouse VISTA polypeptide that maintain the ability to bind natural VISTA binding partner(s) and/or modulate CD4+ and CD8+ T cell proliferation and cytokine production and lymphocyte activation. Functional allelic variants will typically contain only conservative substitution of one or more amino acids of SEQ ID NO: 2, 4 or 5, or substitution, deletion or insertion of non-critical residues in non-critical regions of the polypeptide.

Non-functional allelic variants are naturally occurring amino acid sequence variants of the human or mouse VISTA polypeptide that do not have the ability to either bind natural VISTA binding partners, and/or modulate any of the VISTA activities described herein. Non-functional allelic variants will typically contain a non-conservative substitution, deletion, or insertion or premature truncation of the amino acid sequence of SEQ ID NO: 2, 4 or 5, or a substitution, insertion or deletion in critical residues or critical regions of the polypeptide, e.g., in an IgV domain.

The present invention further provides non-human, non-mouse orthologs of the human or mouse VISTA polypeptide. Orthologs of the human or mouse VISTA polypeptide are polypeptides that are isolated from non-human, non-mouse organisms and possess the same binding activity and/or lymphocyte activation-modulating activity, and ability to modulate CD4+ and CD8+ T cell proliferation and cytokine production as the human and murine VISTA polypeptides disclosed herein. Orthologs of the human or mouse PD-L3 polypeptide can readily be identified as comprising an amino acid sequence that is substantially identical to SEQ ID NO: 2, 4 or 5.

A mutant VISTA polypeptide may be assayed for the ability to bind to and/or modulate the activity of a natural VISTA binding partner, to modulate intra- or intercellular signaling, modulate activation of T lymphocytes, and/or modulate the immune response of an organism.

Isolated nucleic acid molecules encoding a VISTA or VISTA fusion proteins. Such nucleic acid molecules, comprising at least a first nucleotide sequence encoding a VISTA or VISTA protein, polypeptide or peptide operatively linked to a second nucleotide sequence encoding a non-VISTA protein, polypeptide or peptide, can be prepared by standard recombinant DNA techniques.

Furthermore, identity refers broadly to the that functional and/or structural equivalence that exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations may occur naturally, for example they may be sequences from other species, or they may be mutants, wherein these mutants may have occurred in a natural manner or have been introduced by objective mutagenesis. The variations may also be synthetically manufactured sequences. The allelic variants may be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

Included also within the scope of the invention is any nucleotide sequence that encodes the amino acid sequence of VISTA and VISTA conjugate thereof. Because the genetic code is degenerate, more than one codon may be used to encode a particular amino acid. Using the genetic code, one or more different nucleotides may be identified, each of which would be capable of encoding the amino acid. The probability that a particular nucleotide will, in fact, constitute the actual codon encoding sequence may be estimated by considering abnormal base pairing relationships and the frequency with which a particular codon is actually used (to encode a particular amino acid) in eukaryotic or prokaryotic cells expressing a VISTA and VISTA conjugate thereof. Such “codon usage rules” are disclosed by Lathe, et al. (1985) J. Molec. Biol. 183: 1-12.

Modified VISTA and VISTA Conjugate Polynucleotides

The nucleotides of the present invention may be modified polynucleotides. Unmodified nucleotide are often less optimal in some applications, e.g., prone to degradation by cellular nucleases. Chemical modifications to one or more of the subunits of oligonucleotide may confer improved properties, e.g., may render polynucleotides more stable to nucleases. Typical oligonucleotide modifications are well-known in the art and may include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the modification or replacement of the 2' hydroxyl on the ribose sugar; (iii) wholesale replacement of the phosphate moiety; (iv) modification or replacement of a naturally occurring base with a non-natural base; (v) replacement or modification of the ribose-phosphate backbone, e.g. with peptide nucleic acid (PNA); (vi) modification of the 3' end or 5' end of the oligonucelotide; and (vii) modification of the sugar, e.g., six membered rings. Polynucleotides used in accordance with this invention may be synthesized by any number of means well-known in the art, or purchased from a variety of commercial vendors (LC Sciences, Houston, Tex.; Promega, Madison, Wis.; Invitrogen, Carlsbad, Calif.).

Antisense

In addition to the nucleic acid molecules encoding VISTA polypeptides described above, another embodiment of the invention pertains to isolated nucleic acid molecules which are antisense thereto. An “antisense” nucleic acid comprises a nucleotide sequence which is complementary to a “sense” nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire VISTA coding strand, or to only a portion thereof. In one embodiment, an antisense nucleic acid molecule is antisense to a “coding region” of the coding strand of a nucleotide sequence encoding a VISTA. The term “coding region” refers to the region of the nucleotide sequence comprising codons which are translated into amino acid residues. In another embodiment, the antisense nucleic acid molecule is antisense to a “noncoding region” of the coding strand of a nucleotide sequence encoding PD-L. The term “noncoding region” refers to 5' and 3' sequences which flank the coding region that are not translated into amino acids (also referred to as 5' and 3' untranslated regions). Given the coding strand sequences encoding human or mouse VISTA or VISTA disclosed herein, antisense nucleic acids of the invention can be designed according to the rules of Watson and Crick base pairing. The antisense nucleic acid molecule can be complementary to the entire coding region of VISTA mRNA, but more preferably is an oligonucleotide which is antisense to only a portion of the coding or noncoding region of VISTA mRNA. For example, the antisense oligonucleotide can be complementary to the region surrounding the translation start site of VISTA or VISTA mRNA. An antisense oligonucleotide can be, for example, about 5, 10, 15, 20, 25, 30, 35, 40, 45 or 50 nucleotides in length. An antisense nucleic acid molecule of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridin-e, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiour-acil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a VISTA or VISTA polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

The VISTA antisense nucleic acid molecule may be an α-anomeric nucleic acid molecule. An α-anomeric nucleic acid molecule forms specific double-stranded hybrids with complementary RNA in which, contrary to the usual β-units, the strands run parallel to each other. Gaultier, et al. (1987) Nucleic Acids Res. 15: 6625-6641. The antisense nucleic acid molecule can also comprise a 2'-O-methylribonucleotide (Inoue, et al. (1987) Nucleic Acids Res. 15: 6131-6148) or a chimeric RNA-DNA analogue (Inoue, et al. (1987) FEBS Lett. 215: 327-330).

A VISTA antisense nucleic acid may be a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) Nature 334:585-591)) can be used to catalytically cleave VISTA mRNA transcripts to thereby inhibit translation of VISTA mRNA. A ribozyme having specificity for a VISTA-encoding nucleic acid can be designed based upon the nucleotide sequence of a VISTA cDNA disclosed herein (i.e., SEQ ID NO: 1 or 3). For example, a derivative of a Tetrahymena L-19 IVS RNA can be constructed in which the nucleotide sequence of the active site is complementary to the nucleotide sequence to be cleaved in a VISTA-encoding mRNA. See, e.g., U.S. Pat. Nos. 4,987,071 and 5,116,742. Alternatively, VISTA mRNA can be used to select a catalytic RNA having a specific ribonuclease activity from a pool of RNA molecules. See, e.g., Bartel and Szostak (1993) *Science* 261:1411-1418.

Alternatively, VISTA gene expression can be inhibited by targeting nucleotide sequences complementary to the regulatory region of the VISTA (e.g., the VISTA promoter and/or enhancers; to form triple helical structures that prevent transcription of the PD-L3 gene in target cells. See generally, Helene (1991) Anticancer Drug Des. 6(6):569-84; Helene, et al. (1992) Ann. N.Y. Acad. Sci. 660:27-36; and Maher, L. J. (1992) Bioessays 14(12):807-15.

Peptide Nucleic Acid

In yet another embodiment, the VISTA nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids. See Hyrup and Nielsen (1996) Bioorg. Med. Chem. 4(1): 5-23. As used herein, the terms "peptide nucleic acids" or "PNAs" refer to nucleic acid mimics, e.g, DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc Natl. Acad. Sci. USA* 93:14670-675.

PNAs of VISTA nucleic acid molecules can be used in therapeutic and diagnostic applications. For example, PNA scan be used as antisense or antigene agents for sequence-specific modulation of gene expression by, for example, inducing transcription or translation arrest or inhibiting replication. PNAs of VISTA nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

PNAs of VISTA can be modified (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of VISTA nucleic acid molecules can be generated which may combine the advantageous properties of PNA and DNA. Such chimeras allow DNA recognition enzymes (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) Nucleic Acids Res. 24 (17):3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a bridge between the PNA and the 5' end of DNA (Mag, M. et al. (1989) Nucleic Acids Res. 17:5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, et al. (1975) Bioorganic Med. Chem. Lett. 5:1119-11124).

Oligonucleotide

The oligonucleotide may include other appended groups such as peptides (e.g., for targeting host cell receptors in vivo), or agents facilitating transport across the cell membrane (See, e.g., Letsinger et al. (1989) *Proc Natl. Acad. Sci. USA* 86:6553-6556; Lemaitre et al. (1987) *Proc Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) Biotechniques 6:958-976) or intercalating agents (See, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

siRNA

Small interfering RNA (siRNA) are a class of double-stranded RNA molecules usually about 20-25 nucleotides in length that bind to a specific mRNA and direct it to mRNA degradation, thus suppressing the transcrioption (e.g., expression) of the gene. See Hamilton & Baulcombe (1999) Science 286(5441): 950-2 and Elbashir, et al. (2001) Nature 411(6836): 494-8. It is also possible to take advantage of ribozyme or RNA interference (siRNA) technology, which prevents a gene from producing a functional protein by destroying the messenger RNA. An siRNA molecule may bind to VISTA mRNA transcribed from a VISTA DNA comprising the nucleic acid sequence of SEQ ID NO: 1 or 3. An siRNA molecule may bind to VISTA mRNA transcribed from a VISTA DNA encoding the amino acid sequence set forth in SEQ ID NO:2, 4 or 5.

An siRNA molecule which targets VISTA mRNA transcribed from a VISTA DNA may comprise the nucleic acid sequence of SEQ ID NO: 1 or 3. An siRNA molecule which targets VISTA mRNA transcribed from a VISTA DNA encoding the amino acid sequence set forth in SEQ ID NO:2, 4 or 5. The siRNA molecule that targets VISTA may comprise the nucleic acid sequence of any one of SEQ ID NOs: 38-67. An siRNA molecule that targets either the ORF or UTR region of VISTA may comprise the amino acid sequence of any one of SEQ ID NO: 38-47. An siRNA molecule that targets the UTR region only of VISTA may comprise the amino acid sequence of any one of SEQ ID NO: 48-57. An siRNA molecule that targets the ORF region only of VISTA may comprise the amino acid sequence of any one of SEQ ID NO: 58-67. An siRNA molecule that targets VISTA may consist of the nucleic acid sequence of any one of SEQ ID NOs: 38-67. An siRNA molecule that targets either the ORF or UTR region of VISTA may consist of the amino acid sequence of any one of SEQ ID NO: 38-47. An siRNA molecule that targets the UTR region only of VISTA may consist the amino acid sequence of any one of SEQ ID NO: 48-57. An siRNA molecule that targets the ORF region only of VISTA may consist the amino acid sequence of any one of SEQ ID NO: 58-67.

TABLE 1 siRNA for human VISTA

| siRNA sequence | Target region of VISTA | SEQ ID NO: |
|---|---|---|
| GGGCACGATGTGACCTTCTACAAGA | ORF | 38 |
| CAGATGCCAAATGACTTACATCTTA | UTR3 | 39 |
| GAGATGGATTGTAAGAGCCAGTTTA | UTR3 | 40 |
| GGGCTTTGAGGAGAGGGTAAACATA | UTR3 | 41 |
| CCTATCTCCTGACATTCACAGTTTA | UTR3 | 42 |
| CAGTTTAATAGAGACTTCCTGCCTT | UTR3 | 43 |
| CAGGGAGAGGCTGAAGGAATGGAAT | UTR3 | 44 |
| GGAATGTGTTGAGAGGGATTCTGAA | UTR3 | 45 |
| GAGAGGGATTCTGAATGATCAATAT | UTR3 | 46 |
| CACAGAGGGCAATAGAGGTTCTGAA | UTR3 | 47 |
| CAGATGCCAAATGACTTACATCTTA | UTR3 | 48 |
| GAGATGGATTGTAAGAGCCAGTTTA | UTR3 | 49 |
| GGTGAGTCCTCTGTGGAATTGTGAT | UTR3 | 50 |
| GGGCTTTGAGGAGAGGGTAAACATA | UTR3 | 51 |
| CCTATCTCCTGACATTCACAGTTTA | UTR3 | 52 |
| CAGTTTAATAGAGACTTCCTGCCTT | UTR3 | 53 |
| CAGGGAGAGGCTGAAGGAATGGAAT | UTR3 | 54 |
| GGAATGTGTTGAGAGGGATTCTGAA | UTR3 | 55 |
| GAGAGGGATTCTGAATGATCAATAT | UTR3 | 56 |
| CACAGAGGGCAATAGAGGTTCTGAA | UTR3 | 57 |
| ACAAAGGGCACGATGTGACCTTCTA | ORF | 58 |
| GGGCACGATGTGACCTTCTACAAGA | ORF | 59 |
| GACCACCATGGCAACTTCTCCATCA | ORF | 60 |
| CAGACAGGCAAAGATGCACCATCCA | ORF | 61 |
| GGCAAAGATGCACCATCCAACTGTG | ORF | 62 |
| CCATCCAACTGTGTGGTGTACCCAT | ORF | 63 |
| GGATGGACAGCAACATTCAAGGGAT | ORF | 64 |

TABLE 1-continued siRNA for human VISTA

| siRNA sequence | Target region of VISTA | SEQ ID NO: |
|---|---|---|
| GACAGCAACATTCAAGGGATTGAAA | ORF | 65 |
| CCCTGTCCCTGACTCTCCAAACTTT | ORF | 66 |
| CCTGACTCTCCAAACTTTGAGGTCA | ORF | 67 |

Expression

Isolation and expression of the VISTA and VISTA conjugate of the invention may be effected by well-established cloning procedures using probes or primers constructed based on the VISTA and VISTA conjugate nucleic acids sequences disclosed in the application. Related VISTA and VISTA conjugate sequences may also be identified from human or other species genomic databases using the sequences disclosed herein and known computer-based search technologies, e.g., BLAST sequence searching. The pseudogenes disclosed herein may be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers) within the vectors of the invention. Any of the known methods described for increasing or decreasing expression or activity can be used.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) *Adv. Immunol.* 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) *Cell* 33:741-748), neuron-specific promoters (e.g., the neurofilament promoter; Byrne and Ruddle (1989) *Proc Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) *Science* 249:374-379) and the α-fetoprotein promoter (Campes and Tilghman (1989) Genes Dev. 3: 537-546).

The polynucleotide sequences provided herein may be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art. See, e.g., Maniatis, et al. (2001) Molecular Cloning: A Laboratory Manual [$3^{rd}$ Ed.] Cold Spring Harbor Laboratory Press; Swamy (2008) Laboratory Manual on Biotechnology Rastogi Publications; Herdewijn (2005) [Ed.] Methods in Molecular Biolog: Oligonucleotide Synthesis: Methods and Applications Volume 288 Humana Press; and Rapley (2000) [Ed.] The Nucleic Acid Protocols Handbook Humana Press. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization are well described in the scientific and patent literature. See, e.g., Sambrook, et al. (2001) (Eds.) Molecular Cloning: A Laboratory Manual ($3^{rd}$ Ed.) Cold Spring Harbor Laboratory; Ausubel, et al. (2011) Ed., Current Protocols in Molecular Biology, John Wiley & Sons, Inc., New York; Tijssen (1993) [Ed.] Laboratory Techniques in Biochemistry and Molecular Biology: Hybridization With Nucleic Acid Probes, Part I, Theory and Nucleic Acid Preparation, Elsevier, N.Y.

Hybridization and the strength of hybridization (e.g., the strength of the association between polynucleotides) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid. Techniques of nucleic acid hybridization are disclosed by Sambrook, et al. (2001) (Eds.) Molecular Cloning: A Laboratory Manual [$3^{rd}$ Ed.] Cold Spring Harbor Laboratory, and by Haymes, et al. (1985) in NUCLEIC ACID HYBRIDIZATION, A PRACTICAL APPROACH (IRL Press, DC). Hybridization wash conditions may include wash solution of 0.2×SSC/0.1% SDS and incubation with rotation for 10 minutes at room temperature, (low stringency wash), wash solution of prewarmed (42° C.) 0.2×SSC/0.1% SDS and incubation with rotation for 15 minutes at 42° C. (medium stringency wash) and wash solution of prewarmed (68° C.) 0.1×SSC/0.1% SDS and incubation with rotation for 15 minutes at 68° C. (high stringency wash). See Ausubel, et al. (2011) [Ed.] Current Protocols in Molecular Biology John Wiley & Sons, Inc.

Oligonucleotide primers may be used to amplify nucleic acids encoding a VISTA and VISTA conjugate. The nucleic acids described herein can also be cloned or measured quantitatively using amplification techniques. Amplification methods are also well known in the art, and include, e.g., polymerase chain reaction (PCR) (Innis (1990) [Ed.] PCR Protocols, a Guide to Methods and Applications, Academic Press, NY.; Innis (1995) [Ed.] PCR Strategies, Academic Press, Inc., NY.); ligase chain reaction (LCR) (Wu (1989) Genomics 4: 560; Landegren (1988) *Science* 241: 1077; Barringer (1990) Gene 89: 117); transcription amplification (Kwoh (1989) PNAS 86: 1173); self-sustained sequence replication (Guatelli (1990) PNAS 87: 1874); Q Beta replicase amplification (Smith (1997) J. Clin. Microbiol. 35: 1477-91)); automated Q-beta replicase amplification assay (Burg (1996) Mol. Cell. Probes 10: 257-71); and other RNA polymerase mediated techniques (e.g., NASBA, Cangene, Mississauga, Ontario). See, also, Berger (1987) Methods Enzymol. 152: 307-16; Sambrook, et al. (2001) (Eds.) Molecular Cloning: A Laboratory Manual ($3^{rd}$ Ed.) Cold Spring Harbor Laboratory; Ausubel, et al. (2011) [Ed.] Current Protocols in Molecular Biology, John Wiley & Sons, Inc., New York; Maniatis, et al. (2001) Molecular Cloning: A Laboratory Manual [$3^{rd}$ Ed.] Cold Spring Harbor Laboratory Press; U.S. Pat. Nos. 4,683,195 and 4,683,202; Sooknanan (1995) Biotechnology 13: 563-64.

Paradigms to design degenerate primer pairs are well known in the art. For example, a COnsensus-DEgenerate Hybrid Oligonucleotide Primer (CODEHOP) strategy computer program is readily accessible and is directly linked from the BlockMaker multiple sequence alignment site for hybrid primer prediction beginning with a set of related protein sequences, such as the VISTA and VISTA conjugate sequences provided herein. See, e.g., Rose (1998) Nucleic Acids Res. 26: 1628-35; Singh (1998) Biotechniques 24: 318-19.

Polymorphic variants, alleles, and interspecies homologs that are substantially identical to VISTA and VISTA conjugate disclosed herein may be isolated using the nucleic acid probes described above. Alternatively, expression libraries can be used to clone VISTA and VISTA conjugates and polymorphic variants, alleles, and interspecies homologs thereof, by detecting expressed homologs immunologically with antisera or purified antibodies made against a VISTA and VISTA conjugate, which also recognize and selectively bind to the VISTA or VISTA conjugate homolog.

Nucleic acids that encode VISTA and VISTA conjugate may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from VISTA or VISTA conjugate expressing cells. Methods for expression of heterologous sequences in host cells are well known in the art. See, e.g., Maniatis, et al. (2001) Molecular Cloning: A Laboratory Manual [$3^{rd}$ Ed.] Cold Spring Harbor Laboratory Press.

Fusion Proteins Comprising a VISTA and VISTA Conjugate

Hybrid protein-coding sequences comprising nucleic acids encoding VISTA and VISTA conjugate fused to a translocation sequences may be constructed. Also provided are hybrid VISTA and VISTA conjugate comprising the motifs and antigenic regions. These nucleic acid sequences may be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

Fusion proteins may comprise C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.)

The inclusion of a cleavable linker sequences such as Factor Xa (see, e.g., Ottavi, (1998) Biochimie 80: 289-93), subtilisin protease recognition motif (see, e.g., Polyak (1997) Protein Eng. 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams (1995) Biochemistry 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) DNA Cell. Biol. 12: 441-53.

Systems for Recombinant Expression of the VISTA and VISTA Conjugate

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Sambrook, et al. (2001) [Eds.] Molecular Cloning: A Laboratory Manual ($3^{rd}$ Ed.) Cold Spring Harbor Laboratory; Ausubel, et al. (2011) [Ed.] Current Protocols in Molecular Biology John Wiley & Sons, Inc.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences. See, e.g., Ausubel, et al. (2011) [Ed.] Current Protocols in Molecular Biology John Wiley & Sons, Inc.; and Walker & Papley (2009) Molecular Biology and Biotechnology [$5^{th}$ Ed.] Royal Society of Chemistry. Because selectable marker genes conferring resistance to substrates like neomycin or hygromycin can only be utilized in tissue culture, chemoresistance genes are also used as selectable markers in vitro and in vivo.

To enable cellular expression of the polynucleotides of the present invention, a nucleic acid construct according to the present invention may be used, which includes at least a coding region of one of the above nucleic acid sequences, and further includes at least one cis acting regulatory element. Preferably, the promoter utilized by the nucleic acid construct of the present invention is active in the specific cell population transformed. Examples of cell type-specific and/or tissue-specific promoters are well-known in the art. See Bernardi (2003) [Ed.] Gene Transfer and Expression in Mammalian Cells Volume 38 Elsevier Science B.V. The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (Carlsbad, Calif.) Examples of retroviral vector and packaging systems are those sold by Clontech (San Diego, Calif.), including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5' LTR promoter.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel (1990) Gene Expression Technology: Methods in Enzymology 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired. The expression vectors of the invention can be introduced into host cells to thereby produce proteins or peptides, including fusion proteins or peptides, encoded by nucleic acids as described herein.

The recombinant expression vectors of the invention may be designed for production of variant proteins in prokaryotic or eukaryotic cells. For example, proteins of the invention can be expressed in bacterial cells such as *Escherichia coli*, insect cells (e.g., using baculovirus expression vectors), yeast cells, or mammalian cells. Suitable host cells are discussed further in Goeddel (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson (1988) Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

The recombinant mammalian expression vector is capable of directing expression of the nucleic acid may be in a particular cell type (e.g., tissue-specific regulatory elements are used to express the nucleic acid). Tissue-specific regulatory elements are known in the art. For efficient production of the protein, it is preferable to place the nucleotide sequences encoding the protein of the invention under the control of expression control sequences optimized for expression in a desired host. For example, the sequences may include optimized transcriptional and/or translational regulatory sequences (e.g., altered Kozak sequences).

One strategy to maximize recombinant protein expression in *E. coli* is to express the protein in a host bacterium with an impaired capacity to proteolytically cleave the recombinant protein. See, e.g., Gottesman (1990) Gene Expression Technology: Methods in Enzymology Academic Press, San Diego, Calif. 185: 119-128. Another strategy is to alter the nucleic acid sequence of the nucleic acid to be inserted into an expression vector so that the individual codons for each amino acid are those preferentially utilized in *E. coli*. See, e.g., Wada, et al. (1992) Nucl. Acids Res. 20: 2111-2118. Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

The expression vector encoding for the protein of the invention may be a yeast expression vector. Examples of vectors for expression in yeast *Saccharomyces cerevisiae* include pYepSec1 (Baldari, et al. (1987) EMBO J. 6: 229-234), pMFa (Kurjan and Herskowitz (1982) Cell 30: 933-943), pJRY88 (Schultz, et al. (1987) Gene 54: 113-123), pYES2 (Invitrogen Corporation, San Diego, Calif.), and picZ (Invitrogen Corp, San Diego, Calif.)

Alternatively, polypeptides of the present invention can be produced in insect cells using baculovirus expression vectors. Baculovirus vectors available for expression of proteins in cultured insect cells (e.g., SF9 cells) include the pAc series (Smith, et al. (1983) Mol. Cell. Biol. 3: 2156-2165) and the pVL series (Lucklow and Summers (1989) Virology 170: 31-39). In yet another embodiment, a nucleic acid of the invention is expressed in mammalian cells using a mammalian expression vector. Examples of mammalian expression vectors include pCDM8 (Seed (1987) Nature 329: 840) and pMT2PC (Kaufman, et al. (1987) EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Sambrook, et al. (2001) (Eds.) Molecular Cloning: A Laboratory Manual ($3^{rd}$ Ed.) Cold Spring Harbor Laboratory.

A host cell can be any prokaryotic or eukaryotic cell. For example, protein of the invention can be produced in bacterial cells such as *E. coli*, insect cells, yeast, plant or mammalian cells (e.g., Chinese hamster ovary cells (CHO), COS, HEK293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001) [Eds.] Molecular Cloning: A Laboratory Manual ($3^{rd}$ Ed.) Cold Spring Harbor Laboratory and other laboratory manuals.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. See, e.g., Sambrook, et al. (2001) (Eds.) Molecular Cloning: A Laboratory Manual ($3^{rd}$ Ed.) Cold Spring Harbor Laboratory and Walker & Papley (2009) Molecular Biology and Biotechnology [$5^{th}$ Ed.] Royal Society of Chemistry. It is only necessary that the particular genetic engineering procedure used be capable of successfully introducing at least one nucleic acid molecule into the host cell capable of expressing the VISTA and VISTA conjugate, fragment, or variant of interest.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593.

Antibodies which Bind VISTA or VISTA Conjugates

The present invention also provides antibodies which selectively bind the VISTA and VISTA conjugate including but not limited monoclonal and humanized monoclonal antibodies. The antibodies which selectively bind the VISTA and VISTA conjugate may be admixed in compositions with pharmaceutical carriers and additional antibodies (e.g., anti-PD-L1, PD-L2 or CTLA-4 antibodies).

An isolated VISTA polypeptide, or a portion or fragment thereof, can be used as an immunogen to generate antibodies that bind VISTA using standard techniques for polyclonal and monoclonal antibody preparation. A full-length VISTA polypeptide can be used or, alternatively, the invention provides antigenic peptide fragments of VISTA for use as immunogens. In one embodiment, an antigenic peptide of VISTA comprises at least 8 amino acid residues of the amino acid sequence shown in SEQ ID NO: 2, 4 or 5 and encompasses an epitope of VISTA such that an antibody raised against the peptide forms a specific immune complex with the VISTA polypeptide. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of VISTA that are located in the extracellular domain of the polypeptide, e.g., hydrophilic regions, as well as regions with high antigenicity.

A VISTA immunogen typically is used to prepare antibodies by immunizing a suitable subject (e.g., rabbit, goat, mouse, or other mammal) with the immunogen. An appropriate immunogenic preparation can contain, for example, recombinantly expressed VISTA polypeptide or a chemically synthesized VISTA polypeptide. The preparation can further include an adjuvant, such as Freund's complete or incomplete adjuvant, or similar immunostimulatory agent. Immunization of a suitable subject with an immunogenic VISTA preparation induces a polyclonal anti-VISTA antibody response.

Antibodies may comprise of two identical light polypeptide chains of molecular weight approximately 23,000 daltons ("light chain"), and two identical heavy chains of molecular weight 53,000-70,000 ("heavy chain"). See Edelman (1971) Ann. NY. Acad. Sci. 190: 5. The four chains are joined by disulfide bonds in a "Y" configuration wherein the light chains bracket the heavy chains starting at the mouth of the "Y" configuration. The "branch" portion of the "Y" configuration is designated the $F_b$ region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is about 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (e.g., IgG, IgM, IgA, IgD, and IgE corresponding to γ, μ, α, δ, and ε heavy chain constant regions). The constant region or class determines subsequent effector function of the antibody, including activation of complement (Kabat (1976) *Structural Concepts in Immunology and Immunochemistry* [2$^{nd}$ Ed.] pages 413-436; Holt, Rinehart, Winston) and other cellular responses (Andrews, et al. (1980) Clinical Immunobiology 1-18; Kohl, et al. (1983) *Immunology* 48: 187) while the variable region determines the antigen with which it will react. Light chains are classified as either κ (kappa) or λ. (lambda). Each heavy chain class may be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein. See, e.g., Harlow & Lane (1998) USING ANTIBODIES: A LABORATORY MANUAL Cold Spring Harbor Laboratory, for a description of immunoassay formats and conditions that can be used to determine specific immunoreactivity. Typically a specific or selective reaction will be at least twice background signal or noise and more typically more than about 10 to 100 times background.

Antibodies may be screened to identify those that bind to specific epitopes of VISTA, e.g. in the IgV domain or other specific domains and/or to select antibodies possessing high affinity and avidity to VISTA protein. In addition these antibodies are screened to identify those of which modulate specific functions and effects of VISTA on immunity and immune cells in vitro and in vivo. For example assays can be conducted to ascertain the modulatory effect, if any, of a particular anti-VISTA antibody on immune functions negatively regulated by VISTA including cytokine production by CD4+ or CD8+ T cells, CD28 costimulation, CD4+ T cell proliferation, and the proliferation of naïve and memory CD4+ T cells, et al. In an embodiment assays are conducted to identify potential therapeutic anti-VISTA antibodies which in vitro, when the presence of VISTA-Ig enhance the suppression by VISTA-Ig as these anti-VISTA antibodies behave oppositely in vivo, i.e., they are immunosuppressive. The invention encompasses anti-VISTA antibodies and use thereof that specifically bind to the 136 amino acid extracellular domain, e.g., to amino acids 1-50, 50-100, 100-136, antibodies that specifically bind the IgV, antibodies that specifically bind the stalk region, antibodies that specifically bind the transmembrane region and antibodies that specifically bind the cytoplasmic region of VISTA. These specific regions are identified in the application.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) *Adv. Immunol.* 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) *Proc Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) *Science* 249:374-379) and the α-fetoprotein promoter (Campes and Tilghman (1989) Genes Dev. 3: 537-546).

Polyclonal Antibody

Polyclonal antibodies are heterogeneous populations of antibody molecules derived from the sera of animals immunized with an antigen. Polyclonal antibodies which selectively bind the VISTA and VISTA conjugate may be made by methods well-known in the art. See, e.g., Howard & Kaser (2007) Making and Using Antibodies: A Practical Handbook CRC Press.

Monoclonal Antibody

A monoclonal antibody contains a substantially homogeneous population of antibodies specific to antigens, which population contains substantially similar epitope binding sites. Monoclonal antibodies may be obtained by methods known to those skilled in the art. See, e.g. Kohler and Milstein (1975) Nature 256: 495-497; U.S. Pat. No. 4,376,110; Ausubel, et al. [Eds.] (2011) CURRENT PROTOCOLS IN MOLECULAR BIOLOGY, Greene Publishing Assoc. and Wiley Interscience, NY.; and Harlow & Lane (1998) USING ANTIBODIES: A LABORATORY MANUAL Cold Spring Harbor Laboratory; Colligan, et al. (2005) [Eds.] Current Protocols in Immunology Greene Publishing Assoc. and Wiley Interscience, NY. Such antibodies may be of any immunoglobulin class including IgG, IgM, IgE, IgA, GILD and any subclass thereof. A hybridoma producing an antibody of the present invention may be cultivated in vitro, in situ, or in vivo.

Chimeric Antibody

Chimeric antibodies are molecules different portions of which are derived from different animal species, such as those having variable region derived from a murine antibody and a human immunoglobulin constant region, which are primarily used to reduce immunogenicity in application and to increase yields in production, for example, where murine monoclonal antibodies have higher yields from hybridomas but higher immunogenicity in humans, such that human murine chimeric monoclonal antibodies are used. Chimeric antibodies and methods for their production are known in the art. See Cabilly, et al. (1984) *Proc. Natl. Acad. Sci. USA* 81: 3273-3277; Morrison, et al. (1994) *Proc. Natl. Acad. Sci. USA* 81: 6851-6855, Boulianne, et al. (1984) Nature 312: 643-646; Neuberger, et al. (1985) Nature 314: 268-270; European Patent Application 173494 (1986); WO 86/01533 (1986); European Patent Application 184187 (1986); European Patent Application 73494 (1986); Sahagan, et al. (1986) J. Immunol. 137: 1066-1074; Liu, et al. (1987) *Proc. Natl. Acad. Sci. USA* 84: 3439-3443; Sun, et al. (1987) *Proc. Natl. Acad. Sci. USA* 84: 214-218; Better, et al. (1988)

*Science* 240: 1041-1043; and Harlow & Lane (1998) USING ANTIBODIES: A LABORATORY MANUAL Cold Spring Harbor Laboratory; U.S. Pat. No. 5,624,659.

Humanized Antibody

Humanized antibodies are engineered to contain even more human-like immunoglobulin domains, and incorporate only the complementarity-determining regions of the animal-derived antibody. This may be accomplished by examining the sequence of the hyper-variable loops of the variable regions of the monoclonal antibody, and fitting them to the structure of the human antibody chains. See, e.g., U.S. Pat. No. 6,187,287. Likewise, other methods of producing humanized antibodies are now well known in the art. See, e.g., U.S. Pat. Nos. 5,225,539; 5,530,101; 5,585,089; 5,693,762; 6,054,297; 6,180,370; 6,407,213; 6,548,640; 6,632,927; and 6,639,055; Jones, et al. (1986) Nature 321: 522-525; Reichmann, et al. (1988) Nature 332: 323-327; Verhoeyen, et al. (1988) *Science* 239: 1534-36; and Zhiqiang An (2009) [Ed.] Therapeutic Monoclonal Antibodies: From Bench to Clinic John Wiley & Sons, Inc.

Antibody Fragments

In addition to entire immunoglobulins (or their recombinant counterparts), immunoglobulin fragments comprising the epitope binding site (e.g., Fab', $F(ab')_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. Antigen-binding fragments of immunoglobulins include but are not limited to SMIPs (small molecule immunopharmaceuticals), camelbodies, nanobodies, and IgNAR.

Anti-Idiotypic Antibody

An anti-idiotypic (anti-Id) antibody is an antibody which recognizes unique determinants generally associated with the antigen-binding site of an antibody. An Id antibody may be prepared by immunizing an animal of the same species and genetic type (e.g., mouse strain) as the source of the antibody with the antibody to which an anti-Id is being prepared. The immunized animal will recognize and respond to the idiotypic determinants of the immunizing antibody by producing an antibody to these idiotypic determinants (the anti-Id antibody). See e.g., U.S. Pat. No. 4,699,880. The anti-Id antibody may also be used as an "immunogen" to induce an immune response in yet another animal, producing a so-called anti-anti-Id antibody. The anti-anti-Id may be epitopically identical to the original antibody which induced the anti-Id. Thus, by using antibodies to the idiotypic determinants of an antibody it is possible to identify other clones expressing antibodies of identical specificity.

Engineered and Modified Antibodies

An antibody of the invention further may be prepared using an antibody having one or more of the VH and/or VL sequences derived from an antibody starting material to engineer a modified antibody, which modified antibody may have altered properties from the starting antibody. An antibody may be engineered by modifying one or more residues within one or both variable regions (i.e., VH and/or VL), for example within one or more CDR regions and/or within one or more framework regions. Additionally or alternatively, an antibody may be engineered by modifying residues within the constant region(s), for example to alter the effector function(s) of the antibody.

One type of variable region engineering that may be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. See, e.g., Riechmann, et al. (1998) *Nature* 332: 323-327; Jones, et al. (1986) *Nature* 321: 522-525; Queen, et al. (1989) *Proc. Natl. Acad. U.S.A.* 86: 10029-10033; U.S. Pat. Nos. 5,225,539; 5,530,101; 5,585,089; 5,693,762; and 6,180,370.

Suitable framework sequences may be obtained from public DNA databases or published references that include germline antibody gene sequences. For example, germline DNA sequences for human heavy and light chain variable region genes may be found in the "VBase" human germline sequence database (available on the Internet), as well as in Kabat, E. A., et al. (1991) *Sequences of Proteins of Immunological Interest* [5th Ed.]U.S. Department of Health and Human Services, NIH Publication No. 91-3242; Tomlinson, et al. (1992) "The Repertoire of Human Germline VH Sequences Reveals about Fifty Groups of VH Segments with Different Hypervariable Loops" J. Mol. Biol. 227: 776-798; and Cox, et al. (1994) *Eur. J Immunol.* 24: 827-836.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis may be performed to introduce the mutation(s) and the effect on antibody binding, or other functional property of interest, may be evaluated in appropriate in vitro or in vivo assays. Preferably conservative modifications (as discussed herein) may be introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues may be identified by comparing the antibody framework sequences to the germline sequences from which the antibody is derived.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties may be attached to the antibody) or be modified to alter its glycosylation, again to alter one or more functional properties of the antibody. Such embodiments are described further below. The numbering of residues in the Fc region is that of the EU index of Kabat.

The hinge region of CH1 may be modified such that the number of cysteine residues in the hinge region is altered, e.g., increased or decreased. See U.S. Pat. No. 5,677,425. The number of cysteine residues in the hinge region of CH1 may be altered to, for example, facilitate assembly of the light and heavy chains or to increase or decrease the stability of the antibody.

The Fc hinge region of an antibody may be mutated to decrease the biological half life of the antibody. More specifically, one or more amino acid mutations may be introduced into the CH2-CH3 domain interface region of the Fc-hinge fragment such that the antibody has impaired Staphylococcyl protein A (SpA) binding relative to native Fc-hinge domain SpA binding. See, e.g., U.S. Pat. No. 6,165,745.

The antibody may be modified to increase its biological half life. Various approaches are possible. For example, one or more of the following mutations may be introduced: T252L, T254S, T256F. See U.S. Pat. No. 6,277,375. Alternatively, to increase the biological half life, the antibody may be altered within the CH1 or CL region to contain a salvage receptor binding epitope taken from two loops of a CH2 domain of an Fc region of an IgG. See U.S. Pat. Nos. 5,869,046 and 6,121,022.

The Fc region may be altered by replacing at least one amino acid residue with a different amino acid residue to alter the effector function(s) of the antibody. For example, one or more amino acids selected from amino acid residues 234, 235, 236, 237, 297, 318, 320 and 322 may be replaced with a different amino acid residue such that the antibody has an altered affinity for an effector ligand but retains the antigen-binding ability of the parent antibody. The effector ligand to which affinity may be altered may be, for example, an Fc receptor or the C1 component of complement. See U.S. Pat. Nos. 5,624,821 and 5,648,260.

The glycosylation of an antibody may be modified. For example, an aglycoslated antibody may be made (i.e., the antibody lacks glycosylation). Glycosylation may be altered to, for example, increase the affinity of the antibody for antigen. Such carbohydrate modifications may be accomplished by, for example, altering one or more sites of glycosylation within the antibody sequence. For example, one or more amino acid substitutions may be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody may be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications may be accomplished by, for example, expressing the antibody in a host cell with altered glycosylation machinery. Cells with altered glycosylation machinery have been described in the art and may be used as host cells in which to express recombinant antibodies of the invention to thereby produce an antibody with altered glycosylation. See U.S. Patent Application Publication No. 2004/0110704 and Yamane-Ohnuki, et al. (2004) Biotechnol Bioeng. 87: 614-22; EP 1,176,195; WO 2003/035835; Shields, et al. (2002) J. Biol. Chem. 277: 26733-26740; WO 99/54342; Umana, et al. (1999) Nat. Biotech. 17: 176-180; and Tarentino, et al. (1975) Biochem. 14: 5516-23.

An antibody may be Pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer).

The invention also provides variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

Antibody Conjugates

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Methods of Engineering Antibodies

Antibodies having VH and VL sequences disclosed herein may be used to create new variant antibodies by modifying the VH and/or VL sequences, or the constant region(s) attached thereto. Thus, the structural features of an variant antibody of the invention, are used to create structurally related variant antibodies that retain at least one functional property of the antibodies of the invention, such as binding to VISTA and VISTA conjugate. For example, one or more CDR regions of one Anti-VISTA variant antibody or anti-VISTA conjugate variant antibody, or mutations thereof, may be combined recombinantly with known framework regions and/or other CDRs to create additional, recombinantly-engineered, anti-VISTA or anti-VISTA conjugate antibodies (e.g., antibodies which bind the VISTA and VISTA conjugate) of the invention, as discussed herein. The starting material for the engineering method may be one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein. Standard molecular biology techniques may be used to prepare and express altered antibody sequence.

The antibody encoded by the altered antibody sequence(s) may retain one, some or all of the functional properties of the anti-VISTA or anti-VISTA conjugate antibodies produced by methods and with sequences provided herein, which functional properties include binding to variant VISTA or variant VISTA conjugate with a specific KD level or less and/or modulating immune cell activity, and/or selectively binding to desired target cells such as, for example, colorectal carcinoma, lung cancer, prostate cancer, pancreas cancer, ovarian cancer, gastric cancer, and liver cancer. The functional properties of the altered antibodies may be assessed using standard assays available in the art and/or described herein.

Mutations may be introduced randomly or selectively along all or part of an anti-VISTA or anti-VISTA conjugate antibody coding sequence and the resulting modified anti-VISTA or anti-VISTA conjugate antibodies may be screened for binding activity and/or other desired functional properties. See WO 2011/120013.

Nucleic Acids Encoding Antibodies that Selectively Bind VISTA or VISTA Conjugate Another embodiment of the invention pertains to nucleic acid molecules that encode the antibodies of the invention which bind the VISTA and VISTA conjugate. The nucleic acids may be present in whole cells, in a cell lysate, or in a partially purified or substantially pure form. A nucleic acid may be isolated by purification away from other cellular components or other contaminants (e.g., other cellular nucleic acids or proteins) by standard techniques, including alkaline/SDS treatment, CsCl banding, column chromatography, agarose gel electrophoresis and others well known in the art. See Ausubel, et al. (2011) Current Protocols in Molecular Biology John Wiley & Sons, Inc. A nucleic acid of the invention may be, for example, DNA or RNA and may or may not contain intronic sequences. The nucleic acid may be a cDNA molecule.

Nucleic acids of the invention may be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma may be obtained by standard PCR amplification or cDNA cloning techniques. For antibodies obtained from an immunoglobulin gene library (e.g., using phage display techniques), nucleic acid encoding the antibody may be recovered from the library.

Specifically, degenerate codon substitutions may be achieved by generating, e.g., sequences in which the third position of one or more selected codons is substituted with mixed-base and/or deoxyinosine residues. Batzer, et al. (1991) Nucleic Acid Res. 19: 5081; Ohtsuka, et al. (1985) J. Biol. Chem. 260: 2605-08; Rossolini, et al. (1994) Mol. Cell. Probes 8: 91-98.

Once DNA fragments encoding VH and VL segments are obtained, these DNA fragments may be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The isolated DNA encoding the VH region may be converted to a full-length heavy chain gene by operatively linking the VH-encoding DNA to another DNA molecule encoding heavy chain constant regions (CH1, CH2 and CH3). The sequences of human heavy chain constant region genes are known in the art (see, e.g., Kabat, et al. (1991) Sequences of Proteins of Immunological Interest, Fifth Edition, U.S. Department of Health and Human Services, NIH Publication No. 91-3242) and DNA fragments encompassing these regions may be obtained by standard PCR amplification. The heavy chain constant region may be an IgG1, IgG2, IgG3, IgG4, IgA, IgE, IgM, or IgD constant region, but most preferably is an IgG1 or IgG4 constant region. For a Fab fragment heavy chain gene, the VH-encoding DNA may be operatively linked to another DNA molecule encoding only the heavy chain CH1 constant region.

The isolated DNA encoding the VL region may be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, et al. (1991) Sequences of Proteins of Immunological Interest Fifth Edition, U.S. Department of Health and Human Services, NIH Publication No. 91-3242) and DNA fragments encompassing these regions may be obtained by standard PCR amplification. The light chain constant region may be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly4-Ser)_3$, such that the VH and VL sequences may be expressed as a contiguous single-chain protein, with the VL and VH regions joined by the flexible linker. See, e.g., Bird, et al. (1988) *Science* 242: 423-426; Huston, et al. (1988) *Proc. Natl. Acad. Sci. USA* 85: 5879-5883; McCafferty, et al. (1990) *Nature* 348: 552-554.

Methods of Producing Antibodies and Fragments Thereof

The present invention also provides methods for producing antibodies and fragments thereof. Methods of producing antibodies are well known to those of ordinary skill in the art. For example, methods of producing chimeric antibodies are now well known in the art. See, e.g., U.S. Pat. No. 4,816,567; Morrison, et al. (1984) PNAS USA 81: 8651-55; Neuberger, et al. (1985) Nature 314: 268-270; Boulianne, et al. (1984) Nature 312: 643-46.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that may be detected by screening with the antigen or immunogen.

Antibodies, and fragments thereof, of the invention may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, while the DNA sequence encoding the remaining parts of the antibody chain is derived from a human cell source. Furthermore, the invention relates to vectors, especially plasmids, cosmids, viruses, bacteriophages and other vectors common in genetic engineering, which contain the above-mentioned nucleic acid molecules of the invention. The nucleic acid molecules contained in the vectors may be linked to regulatory elements that ensure the transcription in prokaryotic and eukaryotic cells.

Vectors contain elements that facilitate manipulation for the expression of a foreign protein within the target host cell. Conveniently, manipulation of sequences and production of DNA for transformation is first performed in a bacterial host (e.g., *E. coli*) and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that confer resistance to antibiotics or other toxins, complement auxotrophic deficiencies, or supply critical nutrients not available from complex media. Exemplary vectors and methods for transformation of yeast are described in the art. See, e.g., Burke, et al. (2000) Methods in Yeast Genetics Cold Spring Harbor Laboratory Press.

The polypeptide coding sequence of interest may be operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included (e.g., a signal sequence).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" refers broadly to contiguous linked DNA sequences, and, in the case of a secretory leader, contiguous and in reading frame. However, enhancers do not have to be contiguous.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (e.g., that increase levels of transcription in response to absence of a repressor). Inducible promoters may initiate increased levels of transcription from DNA under their control in response to some change in culture conditions (e.g., the presence or absence of a nutrient or a change in temperature.)

A second expression vector may be produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibodies, and fragments thereof, may be either a bacterial cell such as *E. coli*, or a eukaryotic cell. A mammalian cell of a well-defined type for this purpose, such as a myeloma cell, a Chinese hamster ovary (CHO), a NSO, or a HEK293 cell line may be used.

The general methods by which the vectors may be constructed, transfection methods required to produce the host cell and culturing methods required to produce the antibodies, and fragments thereof, from said host cells all include conventional techniques. Although preferably the cell line used to produce the antibody is a mammalian cell line, any other suitable cell line, such as a bacterial cell line such as an *E. coli*-derived bacterial strain, or a yeast cell line, may be used.

Similarly, once produced the antibodies may be purified according to standard procedures in the art, such as for example cross-flow filtration, ammonium sulphate precipitation, and affinity column chromatography.

Generation of Antibodies that Bind a VISTA or VISTA Conjugate Using Animals

The antibodies of the invention that selectively bind the VISTA and VISTA conjugate may be human monoclonal antibodies. Such human monoclonal antibodies directed against a VISTA and VISTA conjugate may be generated using transgenic or transchromosomic mice carrying parts of the human immune system rather than the mouse system. These transgenic and transchromosomic mice include mice referred to herein as the HuMAb Mouse® and KM Mouse® respectively, and are collectively referred to herein as "human Ig mice." The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci. See, e.g., Lonberg, et al. (1994) Nature 368(6474): 856-859. Accordingly, the mice exhibit reduced expression of mouse IgM or K, and in response to immunization, the introduced human heavy and light chain transgenes undergo class switching and somatic mutation to generate high affinity human IgGK monoclonal. Lonberg (1994) Handbook of Experimental Pharmacology 113: 49-101; Lonberg and Huszar (1995) *Intern. Rev. Immunol.* 13: 65-93, and Harding and Lonberg (1995) Ann. NY. Acad. Sci. 764: 536-546. The preparation and use of the HuMab Mouse®, and the genomic modifications carried by such mice, is further described in Taylor, et al. (1992) *Nucleic Acids Research* 20: 6287-6295; Chen, et al. (1993) *International Immunology* 5: 647-656; Tuaillon, et al. (1993) *Proc. Natl. Acad. Sci. USA* 90: 3720-3724; Choi, et al. (1993) Nature Genetics 4: 117-123; Chen, et al. (1993) *EMBO J.* 12: 821-830; Tuaillon, et al. (1994) *J. Immunol.* 152: 2912-2920; Taylor, et al. (1994) *International Immunology* 6: 579-591; and Fishwild, et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; WO 92/03918, WO 93/12227, WO 94/25585; WO 97/13852; WO 98/24884; WO 99/45962; and WO 01/14424.

Human anti-VISTA and anti-VISTA-Ig conjugate antibodies (e.g., antibodies which selectively bind the VISTA and VISTA conjugate) of the invention may be raised using a mouse that carries human immunoglobulin sequences on transgenes and transchromosomes, such as a mouse that carries a human heavy chain transgene and a human light chain transchromosome. Such mice, referred to herein as "KM Mice®", are described in detail in WO 02/43478.

Still further, alternative transgenic animal systems expressing human immunoglobulin genes are available in the art and may be used to raise anti-VISTA and anti-VISTA-Ig conjugate antibodies of the invention. For example, an alternative transgenic system referred to as the Xenomouse (Abgenix, Inc.) may be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and may be used to raise anti-VISTA and anti-VISTA-Ig conjugate antibodies of the invention. For example, mice carrying both a human heavy chain transchromosome and a human light chain transchromosome, referred to as "TC mice" may be used. See Tomizuka, et al. (2000) *Proc. Natl. Acad. Sci. USA* 97: 722-727. Furthermore, cows carrying human heavy and light chain transchromosomes have been described in the art (Kuroiwa, et al. (2002) Nature Biotechnology 20: 889-894) and may be used to raise anti-VISTA and anti-VISTA-Ig conjugate antibodies of the invention.

Human monoclonal antibodies of the invention may also be prepared using phage display methods for screening libraries of human immunoglobulin genes. Such phage display methods for isolating human antibodies are established in the art. See, for example, U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915 and 6,593,081.

Human monoclonal antibodies of the invention may also be prepared using SCID mice into which human immune cells have been reconstituted such that a human antibody response may be generated upon immunization. See, e.g., U.S. Pat. Nos. 5,476,996 and 5,698,767.

When human Ig mice are used to raise human antibodies of the invention, such mice may be immunized with a purified or enriched preparation of VISTA and VISTA conjugate polypeptide, as described by Lonberg, et al. (1994) Nature 368(6474): 856-859; Fishwild, et al. (1996) Nature Biotechnology 14: 845-851; WO 98/24884 and WO 01/14424. Preferably, the mice will be 6-16 weeks of age upon the first infusion. For example, a purified or recombinant preparation (5-50 μg) of VISTA and VISTA conjugate may be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response may be monitored over the course of the immunization protocol with plasma samples being obtained by retroorbital bleeds. The plasma may be screened by ELISA (as described below), and mice with sufficient titers of anti-VISTA or anti-VISTA-Ig human immunoglobulin may be used for fusions. Mice may be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene may be bred together into a single mouse having two different human heavy chain transgenes (HCo7/HCo12). Alternatively or additionally, the KM Mouse® strain may be used.

Generation of Hybridomas Producing Human Monoclonal Antibodies of the Invention

To generate hybridomas producing human monoclonal antibodies of the invention, splenocytes and/or lymph node cells from immunized mice may be isolated and fused to an appropriate immortalized cell line, such as a mouse myeloma cell line. The resulting hybridomas may be screened for the production of antigen-specific antibodies. For example, single cell suspensions of splenic lymphocytes from immunized mice may be fused to one-sixth the number of P3X63-Ag8.653 nonsecreting mouse myeloma cells (ATCC, CRL 1580) with 50% PEG. Cells may be plated at approximately $2\times10^{-5}$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells may be cultured in medium in which the HAT is replaced with HT. Individual wells may then be screened by ELISA for human monoclonal IgM and IgG antibodies. Once extensive hybridoma growth occurs, medium may be observed usually after 10-14 days. The antibody secreting hybridomas may be replated, screened again, and if still positive for human IgG, the monoclonal antibodies may be subcloned at least twice by limiting dilution. The stable subclones may then be cultured in vitro to generate small amounts of antibody in tissue culture medium for characterization.

To purify human monoclonal antibodies, selected hybridomas may be grown in two-liter spinner-flasks for monoclonal antibody purification. Supernatants may be filtered and concentrated before affinity chromatography with protein A-Sepharose (Pharmacia, Piscataway, N.J.) Eluted IgG may be checked by gel electrophoresis and high performance liquid chromatography to ensure purity. The buffer solution may be exchanged into PBS, and the concentration may be determined by OD280 using 1.43 extinction coefficient. The monoclonal antibodies may be aliquoted and stored at −80° C.

Transgenic Animals

The host cells of the invention can also be used to produce non-human transgenic animals. For example, in one embodiment, a host cell of the invention is a fertilized oocyte or an embryonic stem cell into which VISTA-coding sequences have been introduced. Such host cells can then be used to create non-human transgenic animals in which exogenous VISTA sequences have been introduced into their genome or homologous recombinant animals in which endogenous VISTA sequences have been altered. Such animals are useful for studying the function and/or activity of a VISTA and for identifying and/or evaluating modulators of VISTA activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous VISTA gene has been altered by homologous recombination between the endogenous gene and an exogenous DNA molecule introduced into a cell of the animal, e.g., an embryonic cell of the animal, prior to development of the animal. A transgenic animal of the invention can be created by introducing a VISTA-encoding nucleic acid into the male pronuclei of a fertilized oocyte, e.g., by microinjection, retroviral infection, and allowing the oocyte to develop in a pseudopregnant female foster animal. The VISTA cDNA sequence of SEQ ID NO: 1 or 4 can be introduced as a transgene into the genome of a non-human animal. Alternatively, a nonhuman homologue of a human VISTA gene, such as a monkey or rat VISTA gene, can be used as a transgene. Alternatively, a VISTA gene homologue, such as another VISTA family member, can be isolated based on hybridization to the VISTA cDNA sequences of SEQ ID NO: 1 or 3 and used as a transgene. Intronic sequences and polyadenylation signals can also be included in the transgene to increase the efficiency of expression of the transgene. A tissue-specific regulatory sequence(s) can be operably linked to a VISTA transgene to direct expression of a VISTA polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder, et al. U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a VISTA transgene in its genome and/or expression of VISTA mRNA in tissues or cells of the animals. A transgenic founder animal can then be used to breed additional animals carrying the transgene. Moreover, transgenic animals carrying a transgene encoding a VISTA polypeptide can further be bred to other transgenic animals carrying other transgenes.

To create a homologous recombinant animal, a vector is prepared which contains at least a portion of a VISTA gene into which a deletion, addition or substitution has been introduced to thereby alter, e.g., functionally disrupt, the VISTA gene. The VISTA gene can be a human or murine gene (e.g., the cDNA of SEQ ID NO: 1 or 3)

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc Natl. Acad. Sci. USA* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected polypeptide are required. Such animals can be provided through the construction of "double" transgenic animals, e.g., by mating two transgenic animals, one containing a transgene encoding a selected polypeptide and the other containing a transgene encoding a recombinase.

Clones of the non-human transgenic animals described herein can also be produced according to the methods described in Wilmut, et al. (1997) Nature 385: 810-813; WO 97/07668; and WO 97/07669. In brief, a cell, e.g., a somatic cell, from the transgenic animal can be isolated and induced to exit the growth cycle and enter GO phase. The quiescent cell can then be fused, e.g., through the use of electrical pulses, to an enucleated oocyte from an animal of the same species from which the quiescent cell is isolated. The reconstructed oocyte is then cultured such that it develops to the morula or blastocyst stage and then transferred to pseudopregnant female foster animal. The offspring borne of this female foster animal will be a clone of the animal from which the cell, e.g., the somatic cell, is isolated.

Labels

The polypeptides, conjugates, and antibodies described herein may be modified post-translationally to add effector moieties such as chemical linkers, detectable moieties such as for example fluorescent dyes, enzymes, substrates, bioluminescent materials, radioactive materials, chemiluminescent moieties, a cytotoxic agent, radioactive materials, or functional moieties.

A wide variety of entities, e.g., ligands, may be coupled to the oligonucleotides as known in the art. Ligands may include naturally occurring molecules, or recombinant or synthetic molecules. Exemplary ligands include, but are not limited to, avadin, biotin, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, immunoglobulins (e.g., antibodies), insulin, transferrin, albumin, sugar, lipophilic molecules (e.g., steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. See, e.g., U.S. Pat. Nos. 6,153,737;

6,172,208; 6,300,319; 6,335,434; 6,335,437; 6,395,437; 6,444,806; 6,486,308; 6,525,031; 6,528,631; and 6,559,279.

Additionally, moieties may be added to the antigen or epitope to increase half-life in vivo (e.g., by lengthening the time to clearance from the blood stream. Such techniques include, for example, adding PEG moieties (also termed pegilation), and are well-known in the art. See U.S. Patent Application Publication No. 2003/0031671.

An antigen, antibody or antigen binding fragment thereof, described herein may be "attached" to a substrate when it is associated with the solid label through a non-random chemical or physical interaction. The attachment may be through a covalent bond. However, attachments need not be covalent or permanent. Materials may be attached to a label through a "spacer molecule" or "linker group." Such spacer molecules are molecules that have a first portion that attaches to the biological material and a second portion that attaches to the label. Thus, when attached to the label, the spacer molecule separates the label and the biological materials, but is attached to both. Methods of attaching biological material (e.g., label) to a label are well known in the art, and include but are not limited to chemical coupling.

Detectable Labels

The VISTA and VISTA conjugate described herein may be modified post-translationally to add effector labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, β-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin, luciferase, and aequorin. Further exemplary radioactive materials include, but are not limited to, bismuth-213 ($^{213}Bs$), carbon-14 ($^{14}C$), carbon-11 ($^{11}C$), chlorine-18 ($Cl^{18}$), chromium-51 ($^{51}Cr$), cobalt-57 ($^{57}Co$), cobalt-60 ($^{60}Co$), copper-64 ($^{64}Cu$), copper-67 ($^{67}Cu$), dysprosium-165 ($^{165}Dy$), erbium-169 ($^{169}Er$), fluorine-18 ($^{18}F$), gallium-67 ($^{67}Ga$), gallium-68 ($^{68}Ga$), germanium-68 ($^{68}Ge$), holmium-166 ($^{166}Ho$), indium-111 ($^{111}In$), iodine-125 ($^{125}I$), iodine-123 ($^{124}I$), iodine-124 ($^{124}I$), iodine-131 ($^{131}I$), iridium-192 ($^{192}Ir$), iron-59 ($^{59}Fe$), krypton-81 ($^{81}Kr$), lead-212 ($^{212}Pb$), lutetium-177 ($^{177}Lu$), molybdenum-99 ($^{99}Mo$), nitrogen-13 ($^{13}N$), oxygen-15 ($^{15}O$), palladium-103 ($^{103}Pd$), phosphorus-32 ($^{32}P$), potassium-42 ($^{42}K$), rhenium-186 ($^{186}Re$), rhenium-188 ($^{18}Re$), rubidium-81 ($^{81}Rb$), rubidium-82 ($^{82}Rb$), samarium-153 ($^{153}Sm$), selenium-75 ($^{75}Se$), sodium-24 ($^{24}Na$), strontium-82 ($^{82}Sr$), strontium-89 ($^{89}Sr$), sulfur 35 ($^{35}S$), technetium-99m ($^{99}Tc$), thallium-201 ($^{201}Tl$), tritium ($^{3}H$), xenon-133 ($^{133}Xe$), ytterbium-169 ($^{169}Yb$), ytterbium-177 ($^{177}Yb$), and yttrium-90 ($^{90}Y$).

Cytotoxic Agents

For making cytotoxic agents, VISTA polypeptides and VISTA conjugates of the invention may be linked, or operatively attached, to toxins using techniques that are known in the art. A wide variety of toxins are known that may be conjugated to polypeptides or antibodies of the invention. Examples include: numerous useful plant-, fungus- or even bacteria-derived toxins, which, by way of example, include: various A chain toxins, particularly ricin A chain; ribosome inactivating proteins such as saporin or gelonin; alpha-sarcin; aspergillin; restrictocin; and ribonucleases such as placental ribonuclease, angiogenic, diphtheria toxin, or *pseudomonas* exotoxin. A preferred toxin moiety for use in connection with the invention is toxin A chain which has been treated to modify or remove carbohydrate residues, deglycosylated A chain. U.S. Pat. No. 5,776,427.

The VISTA and VISTA conjugates described herein may be conjugated to cytotoxic agents including, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (TAXOL®), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g., IL-12 or IL-2), IL-12R antagonists, Toxin conjugated monoclonal antibodies, tumor antigen specific monoclonal antibodies, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or binding fragments thereof, to generate cell-type-specific-killing reagents. Youle, et al. (1980) *Proc. Nat'l Acad. Sci. USA* 77: 5483; Gilliland, et al. (1980) *Proc. Nat'l Acad. Sci. USA* 77: 4539; Krolick, et al. (1980) *Proc. Nat'l Acad. Sci. USA* 77: 5419. Other cytotoxic agents include cytotoxic ribonucleases. See U.S. Pat. No. 6,653,104.

The VISTA protein described herein may be conjugated to a radionuclide that emits alpha or beta particles (e.g., radioimmunoconjuagtes). Such radioactive isotopes include but are not limited to beta-emitters such as phosphorus-32 ($^{32}P$), scandium-47 ($^{47}Sc$), copper-67 ($^{67}Cu$), gallium-67 ($^{67}Ga$), yttrium-88 ($^{88}Y$), yttrium-90 ($^{90}Y$), iodine-125 ($^{125}I$), iodine-131 ($^{131}I$), samarium-153 ($^{153}Sm$), lutetium-177 ($^{1}77Lu$), rhenium-186 ($^{186}Re$), rhenium-188 ($^{188}Re$), and alpha-emitters such as astatine-211 ($^{211}At$), lead-212 ($^{212}Pb$), bismuth-212 ($^{212}Bi$), bismuth-213 ($^{213}Bi$) or actinium-225 ($^{225}Ac$).

Methods are known in the art for conjugating a VISTA and VISTA conjugate described herein to a label, such as those methods described by Hunter, et al (1962) Nature 144: 945; David, et al. (1974) Biochemistry 13: 1014; Pain, et al. (1981) *J. Immunol. Meth.* 40: 219; and Nygren (1982) Histochem and Cytochem, 30: 407.

Substrates

The VISTA and VISTA conjugate described herein may be attached to a substrate. A number of substrates (e.g., solid supports) known in the art are suitable for use with the VISTA and VISTA conjugate described herein. The substrate may be modified to contain channels or other configurations. See Fung (2004) [Ed.] Protein Arrays: Methods and Protocols Humana Press and Kambhampati (2004) [Ed.] Protein Microarray Technology John Wiley & Sons.

Substrate materials include, but are not limited to acrylics, agarose, borosilicate glass, carbon (e.g., carbon nanofiber sheets or pellets), cellulose acetate, cellulose, ceramics, gels, glass (e.g., inorganic, controlled-pore, modified, soda-lime, or functionalized glass), latex, magnetic beads, membranes, metal, metalloids, nitrocellulose, NYLON®, optical fiber bundles, organic polymers, paper, plastics, polyacryloylmorpholide, poly(4-methylbutene), poly(ethylene terephthalate), poly(vinyl butyrate), polyacrylamide, polybutylene, polycarbonate, polyethylene, polyethyleneglycol terephthalate, polyformaldehyde, polymethacrylate, polymethylmethacrylate, polypropylene, polysaccharides, polystyrene, polyurethanes, polyvinylacetate, polyvinylchloride, polyvinylidene difluoride (PVDF), polyvinylpyrrolidinone, rayon, resins, rubbers, semiconductor materials, SEPHAROSE®, silica, silicon, styrene copolymers, TEFLON®, and variety of other polymers.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate may be a singular discrete body (e.g., a single tube, a single bead), any number of a plurality of substrate bodies (e.g, a rack of 10 tubes, several beads), or combinations thereof (e.g., a tray comprises a plurality of microtiter plates, a column filled with beads, a microtiter plate filed with beads).

An VISTA and VISTA conjugate may be "attached" to a substrate when it is associated with the solid substrate through a non-random chemical or physical interaction. The attachment may be through a covalent bond. However, attachments need not be covalent or permanent. Materials may be attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., label) to a substrate are well known in the art, and include but are not limited to chemical coupling.

Plates, such as microtiter plates, which support and contain the solid-phase for solid-phase synthetic reactions may be used. Microtiter plates may house beads that are used as the solid-phase. By "particle" or "microparticle" or "nanoparticle" or "bead" or "microbead" or "microsphere" herein is meant microparticulate matter having any of a variety of shapes or sizes. The shape may be generally spherical but need not be spherical, being, for example, cylindrical or polyhedral. As will be appreciated by those in the art, the particles may comprise a wide variety of materials depending on their use, including, but not limited to, cross-linked starch, dextrans, cellulose, proteins, organic polymers including styrene polymers such as polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON®. See e.g., "Microsphere Detection Guide" from Bangs Laboratories, Fishers, Ind.

The VISTA and VISTA conjugate described herein may be attached to on any of the forms of substrates described herein (e.g., bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads may be a component of a gelling material or may be separate components such as latex beads made of a variety of synthetic plastics (e.g., polystyrene). The label (e.g., streptavidin) may be bound to a substrate (e.g., bead).

Pharmaceutical Compositions

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration may occur by means of injection, powder, liquid, gel, drops, or other means of administration.

As noted such compositions may additionally comprise a desired antigen, e.g., a tumor antigen or another immune modulatory compounds such as Toll like receptor agonists, type 1 interferon such as alpha and beta interferons and CD40 agonists such as agonistic CD40 antibodies and antibody fragments, preferably anti-human CD40 agonistic antibodies and antibody fragments or other immune enhancers or suppressors such as PD-L1, PD-L2, CTLA4 fusion proteins and antibodies specific thereto.

In one embodiment, the antigen may be a cancer antigen or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, am11, Prostate Specific Antigen (PSA) and its antigenic epitopes PSA-1, PSA-2, and PSA-3, prostate-specific membrane antigen (PSMA), T-cell receptor/CD3-.zeta. chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, ε-cadherin, α-catenin, β-catenin, γ-catenin, p120ctn, gp10.sup.Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, PIA, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, α-catenin, β-catenin, γ-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100.sup.Pmel117), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations may be found, for example, in Grennaro (2005) [Ed.] Remington: The Science and Practice of Pharmacy [$21^{st}$ Ed.]

Pharmaceutical compositions typically must be sterile and stable under the conditions of manufacture and storage. The invention contemplates that the pharmaceutical composition is present in lyophilized form. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

The polypeptides, conjugates, and antibodies described herein may be formulated into pharmaceutical compositions of various dosage forms. To prepare the pharmaceutical compositions of the invention, at least one VISTA and VISTA conjugate as the active ingredient may be intimately mixed with appropriate carriers and additives according to techniques well known to those skilled in the art of pharmaceutical formulations. See Grennaro (2005) [Ed.] Remington: The Science and Practice of Pharmacy [$21^{st}$ Ed.] For example, the antibodies described herein may be formulated in phosphate buffered saline pH 7.2 and supplied as a 5.0 mg/mL clear colorless liquid solution.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, arachis oil or sesame oil, with other additives for aiding solubility or preservation may also be included. In the case of a solution, it may be lyophilized to a powder and then reconstituted immediately prior to use. For dispersions and suspensions, appropriate carriers and additives include aqueous gums, celluloses, silicates, or oils.

For each of the recited embodiments, the VISTA and VISTA conjugate may be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In many cases, it will be preferable to include isotonic agents, e.g., sugars, polyalcohols such as mannitol, sorbitol, or sodium chloride in the composition. Prolonged absorption of the injectable compositions may be brought about by including in the composition an agent which delays absorption, e.g., monostearate salts and gelatin. Moreover, the compounds described herein may be formulated in a time release formulation, e.g. in a composition that includes a slow release polymer. The VISTA and VISTA conjugate may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Supplementary active compounds can also be incorporated into the compositions.

For example, compositions may further comprise a desired antigen, e.g., a tumor antigen or another immune modulatory compounds such as Toll like receptor agonists, type 1 interferon such as alpha and beta interferons and CD40 agonists such as agonistic CD40 antibodies and antibody fragments, preferably anti-human CD40 agonistic antibodies and antibody fragments or other immune enhancers or suppressors such as PD-L1, PD-L2, CTLA4 fusion proteins and antibodies specific thereto.

Compositions comprising VISTA may further comprise an antigen or other immune agonist. The antigen may be administered in an amount that, in combination with the other components of the combination, is effective to generate an immune response against the antigen. For example, the antigen may be administered in an amount from about 100 μg/kg to about 100 mg/kg. In some embodiments, the antigen may be administered in an amount from about 10 μg/kg to about 10 mg/kg. In some embodiments, the antigen may be administered in an amount from about 1 mg/kg to about 5 mg/kg. The particular amount of antigen that constitutes an amount effective to generate an immune response, however, depends to some extent upon certain factors such as, for example, the particular antigen being administered; the particular agonist being administered and the amount thereof; the particular agonist being administered and the amount thereof; the state of the immune system; the method and order of administration of the agonist and the antigen; the species to which the formulation is being administered; and the desired therapeutic result. Accordingly, it is not practical to set forth generally the amount that constitutes an effective amount of the antigen. Those of ordinary skill in the art, however, can readily determine the appropriate amount with due consideration of such factors.

The antigen can be any material capable of raising a Th1 immune response, which may include one or more of, for example, a CD8+ T cell response, an NK T cell response, a γ/δ T cell response, or a Th1 antibody response. Suitable antigens include but are not limited to peptides; polypeptides; lipids; glycolipids; polysaccharides; carbohydrates; polynucleotides; prions; live or inactivated bacteria, viruses or fungi; and bacterial, viral, fungal, protozoal, tumor-derived, or organism-derived antigens, toxins or toxoids.

Furthermore, certain currently experimental antigens, especially materials such as recombinant proteins, glycoproteins, and peptides that do not raise a strong immune response, can be used in connection with adjuvant combinations of the invention. Exemplary experimental subunit antigens include those related to viral disease such as adenovirus, AIDS, chicken pox, cytomegalovirus, dengue, feline leukemia, fowl plague, hepatitis A, hepatitis B, HSV-1, HSV-2, hog cholera, influenza A, influenza B, Japanese encephalitis, measles, parainfluenza, rabies, respiratory syncytial virus, rotavirus, wart, and yellow fever.

The antigen may be a cancer antigen or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, am11, Prostate Specific Antigen (PSA) and its antigenic epitopes PSA-1, PSA-2, and PSA-3, prostate-specific membrane antigen (PSMA), T-cell receptor/CD3-ζ chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, ε-cadherin, α-catenin, β-catenin, γ-catenin, p120ctn, gp10.sup.Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, PIA, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, am11, cyclophilin b), B cell lymphoma (Ig-idiotype), glioma (E-cadherin, α-catenin, β-catenin, γ-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100.sup.Pmel117), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

A person of skill in the art would be able to determine an effective dosage and frequency of administration through routine experimentation, for example guided by the disclosure herein and the teachings in Goodman, et al. (2011) Goodman & Gilman's The Pharmacological Basis of Therapeutics [12$^{th}$ Ed.]; Howland, et al. (2005) Lippincott's Illustrated Reviews: Pharmacology [2$^{nd}$ Ed.]; and Golan, (2008) Principles of Pharmacology: The Pathophysiologic Basis of Drug Therapy [2$^{nd}$ Ed.] See, also, Grennaro (2005) [Ed.] Remington: The Science and Practice of Pharmacy [21$^{st}$ Ed.]

Routes of Administration

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are intravenous injection or infusion. The administration can be local, where the composition is administered directly, close to, in the locality, near, at, about, or in the vicinity of, the site(s) of disease, e.g., tumor, or systemic, wherein the composition is given to the patient and passes through the body widely, thereby reaching the site(s) of disease. Local administration (e.g., injection) may be accomplished by administration to the cell, tissue, organ, and/or organ system, which encompasses and/or is affected by the disease, and/or where the disease signs and/or symptoms are active or are likely to occur (e.g., tumor site). Administration can be topical with a local effect, composition is applied directly where its action is desired (e.g., tumor site).

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

In further embodiments, the present invention provides kits including one or more containers comprising pharmaceutical dosage units comprising an effective amount of one or more antibodies and fragments thereof of the present invention. Kits may include instructions, directions, labels, marketing information, warnings, or information pamphlets.

Dosages

The amount of VISTA or VISTA conjugate in a therapeutic composition according to any embodiments of this invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of antibodies, and fragments thereof, calculated to produce the desired therapeutic effect in association with the required pharmaceutical carrier. The specification for the dosage unit forms of the invention are dictated by and directly dependent on the unique characteristics of the antibodies, and fragments thereof, and the particular therapeutic effect to be achieved, and the limitations inherent in the art of compounding such an antibodies, and fragments thereof, for the treatment of sensitivity in individuals. In therapeutic use for treatment of conditions in mammals (e.g., humans) for which the antibodies and fragments thereof of the present invention or an appropriate pharmaceutical composition thereof are effective, the antibodies and fragments thereof of the present invention may be administered in an effective amount. The dosages as suitable for this invention may be a composition, a pharmaceutical composition or any other compositions described herein.

The dosage may be administered as a single dose, a double dose, a triple dose, a quadruple dose, and/or a quintuple dose. The dosages may be administered singularly, simultaneously, and sequentially.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof, and are known in the art.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

It will be appreciated that the pharmacological activity of the compositions may be monitored using standard pharmacological models that are known in the art. Furthermore, it will be appreciated that the compositions comprising a VISTA and VISTA conjugate, antibody or antigen-binding fragment thereof, may be incorporated or encapsulated in a suitable polymer matrix or membrane for site-specific delivery, or may be functionalized with specific targeting agents capable of effecting site specific delivery. These techniques, as well as other drug delivery techniques are well known in the art. Determination of optimal dosages for a particular situation is within the capabilities of those skilled in the art. See, e.g., Grennaro (2005) [Ed.] Remington: The Science and Practice of Pharmacy [$21^{st}$ Ed.]

Methods of Treatment

The VISTA and VISTA conjugates described herein may be used in methods for treating inflammatory disorders, autoimmune diseases, suppress $CD4^+$ T cell proliferation, suppress $CD8^+$ T cell proliferation, suppress $CD4^+$ T cell cytokine production, and suppress $CD8^+$ T cell cytokine production comprising administering an effective amount of a VISTA and VISTA conjugate to a subject in need thereof. Further, the VISTA and VISTA conjugates described herein may be used to manufacture medicaments for use in treating autoimmune diseases, suppress $CD4^+$ T cell proliferation, suppress $CD8^+$ T cell proliferation, suppress $CD4^+$ T cell cytokine production, and suppress $CD8^+$ T cell cytokine production comprising an effective amount of a VISTA and VISTA conjugate described herein. The VISTA and VISTA conjugates described herein may be admixed with a pharmaceutically acceptable carrier to manufacture a composition for treating autoimmune diseases, suppress $CD4^+$ T cell proliferation, suppress $CD8^+$ T cell proliferation, suppress $CD4^+$ T cell cytokine production, and suppress $CD8^+$ T cell cytokine production comprising an effective amount of a VISTA or VISTA conjugate described herein.

The therapeutic methods described herein may comprise administration of PD-L3 or VISTA, is a novel and structurally-distinct, Ig-superfamily inhibitory ligand, whose extracellular domain bears homology to the B7 family ligand PD-L1. This molecule is referred to interchangeably herein as PD-L3 or VISTA or as V-domain Immunoglobulin Suppressor of T cell Activation (VISTA). VISTA is expressed primarily within the hematopoietic compartment and is highly regulated on myeloid APCs and T cells. Therapeutic intervention of the VISTA inhibitory pathway represents a novel approach to modulate T cell-mediated immunity for the treatment of a wide variety of cancers. VISTA polypeptides, conjugates, nucleic acids, ligands, and modulators thereof, may be useful in regulating immunity, especially T cell immunity, for the treatment of autoimmune disorders and inflammatory disorders.

The use of VISTA, VISTA-conjugates (e.g., VISTA-Ig), and anti-VISTA antibodies to treat cancers including but not limited to colorectal cancer, bladder cancer, ovarian cancer, and melanoma, autoimmune disorders, and inflammatory disorders. In addition, the present invention in particular relates to the use of VISTA proteins, especially multimeric VISTA proteins and viral vectors (e.g., adenoviral) that express same to treat conditions wherein immunosupression is therapeutically desired such as allergy, autoimmune disorders, and inflammatory conditions.

The patient may express symptoms of an autoimmune disease or a patient without symptoms. The methods described herein may be used on cells, e.g., human cells, in vitro or ex vivo. Alternatively, the method may be performed on cells present in a subject as part of an in vivo (e.g., therapeutic) protocol.

The present invention provides for both prophylactic and therapeutic methods of treating a subject at risk of (or susceptible to) a disorder characterized by insufficient or excessive production of VISTA (PD-L3) protein or production of VISTA (PD-L3) protein forms which have decreased or aberrant activity compared to VISTA (PD-L3) wild type protein. Moreover, the anti-VISTA (PD-L3) antibodies of the invention can be used to detect and isolate VISTA (PD-L3) proteins, regulate the bioavailability of VISTA (PD-L3) proteins, and modulate VISTA (PD-L3) activity, e.g., by modulating the interaction of VISTA (PD-L3) with its counter receptor.

Uses and Methods of the Invention

The VISTA molecules, e.g., the VISTA nucleic acid molecules, polypeptides, polypeptide homologues, and antibodies and antibody fragments described herein can be used in one or more of the following methods: a) screening assays; b) predictive medicine (e.g., diagnostic assays, prognostic assays, and monitoring clinical trials); and c) methods of treatment (e.g., therapeutic and prophylactic, e.g., by up- or down-modulating the immune response). As described herein, a VISTA (PD-L3) polypeptide of the invention has one or more of the following activities: 1) binds to and/or modulates the activity of its natural binding partner(s), 2) modulates intra- or intercellular signaling, 3) modulates activation of T lymphocytes, 4) modulates the immune response of an organism, e.g., a mammalian organism, such as a mouse or human. The isolated nucleic acid molecules of the invention can be used, for example, to express VISTA (PD-L3) polypeptide (e.g., via a recombinant expression vector in a host cell in gene therapy applications), to detect VISTA (PD-L3) mRNA (e.g., in a biological sample) or a genetic alteration in a VISTA (PD-L3) gene, and to modulate VISTA (PD-L3) activity, as described further below. The VISTA (PD-L3) polypeptides can be used to treat conditions or disorders characterized by insufficient or excessive production of a VISTA (PD-L3) polypeptide or production of VISTA (PD-L3) inhibitors. In addition, the VISTA (PD-L3) polypeptides can be used to screen for naturally occurring VISTA (PD-L3) binding partner(s), to screen for drugs or compounds which modulate VISTA (PD-L3) activity, as well as to treat conditions or disorders characterized by insufficient or excessive production of VISTA (PD-L3)

polypeptide or production of VISTA (PD-L3) polypeptide forms which have decreased, aberrant or unwanted activity compared to VISTA (PD-L3) wild-type polypeptide (e.g., immune system disorders such as severe combined immunodeficiency, multiple sclerosis, systemic lupus erythematosus, type I diabetes mellitus, lymphoproliferative syndrome, inflammatory bowel disease, allergies, asthma, graft-versus-host disease, and transplant rejection; immune responses to infectious pathogens such as bacteria and viruses; and immune system cancers such as lymphomas and leukemias). Moreover, the anti-VISTA (PD-L3) antibodies of the invention can be used to detect and isolate VISTA (PD-L3) polypeptides, regulate the bioavailability of VISTA (PD-L3) polypeptides, and modulate VISTA (PD-L3) activity, e.g., by modulating the interaction between VISTA (PD-L3) and its natural binding partner(s).

Anti-VISTA (PD-L3) antibodies for use as therapeutics may be selected based on the fact that in the presence of soluble VISTA (PD-L3)-proteins (e.g., VISTA (PD-L3)-Ig fusion protein), the anti-VISTA antibodies enhance the suppressive effects of VISTA (PD-L3) on VISTA (PD-L3) related immune functions. This is quite unexpected as these anti-VISTA antibodies behave in vivo opposite to what would be expected from their in vitro effect on immunity (i.e., these anti-VISTA monoclonal antibodies are immunosuppressive.)

An important aspect of the invention pertains to methods of modulating VISTA (PD-L3) expression or activity or interaction with its natural binding partners, Relevant to therapy VISTA (PD-L3) has been demonstrated to inhibit CD28 costimulation, to inhibit TCR activation of immune cells, to inhibit proliferation of activated immune cells (CD4+ and CD8+ T cells), to inhibit cytokine production by T cells (IL-2, gamma interferon) and to transmit an inhibitory signal to immune cells. Accordingly, the activity and/or expression of VISTA (PD-L3), as well as the interaction between VISTA (PD-L3) and its binding partners) on T cells can be modulated in order to modulate the immune response. Because VISTA (PD-L3) binds to inhibitory receptors (on T cells), upregulation of VISTA (PD-L3) activity should result in downregulation of immune responses, whereas downregulation of VISTA (PD-L3) activity should results in upregulation of immune responses. In an embodiment, VISTA (PD-L3) binds to inhibitory receptors. As noted previously, counterintuitively VISTA (PD-L3) specific antibodies produced by Applicant which in vitro (in the presence of VISTA (PD-L3)-Ig) enhance the suppressive activities of VISTA (PD-L3)-Ig fusion proteins (i.e., these antibodies enhance the suppression of VISTA (PD-L3) related activities such as effects of VISTA (PD-L3) on cytokine production, T cell proliferation, differentiation or activation and other functions noted previously), behave oppositely to what would be expected in vivo, i.e., these antibodies have been found to be immunosuppressive in vivo.

Modulatory methods of the invention involve contacting a cell with a VISTA (PD-L3) polypeptide or agent that modulates one or more of the activities of VISTA (PD-L3) polypeptide activity associated with the cell, e.g., an agent that modulates expression or activity of VISTA (PD-L3) and/or modulates the interaction of VISTA (PD-L3) and its natural binding partner(s). An agent that modulates VISTA (PD-L3) polypeptide activity can be an agent as described herein, such as a nucleic acid or a polypeptide, a naturally-occurring binding partner of a VISTA (PD-L3) polypeptide a VISTA (PD-L3) antibody, a VISTA (PD-L3) agonist or antagonist, a peptidomimetic of a VISTA (PD-L3) agonist or antagonist, a VISTA (PD-L3) peptidomimetic, or other small molecule. Soluble forms of VISTA (PD-L3) may also be used to interfere with the binding of VISTA (PD-L3) to any of its natural binding partner(s) or ligands.

An agent that modulates the expression of VISTA (PD-L3) is, e.g., an antisense nucleic acid molecule, triplex oligonucleotide, ribozyme, or recombinant vector for expression of a VISTA (PD-L3) polypeptide. For example, an oligonucleotide complementary to the area around a VISTA (PD-L3) polypeptide translation initiation site can be synthesized. One or more antisense oligonucleotides can be added to cell media, typically at 200 μg/ml, or administered to a patient to prevent the synthesis of a VISTA (PD-L3) polypeptide. The antisense oligonucleotide is taken up by cells and hybridizes to a VISTA (PD-L3) mRNA to prevent translation. Alternatively, an oligonucleotide which binds double-stranded DNA to form a triplex construct to prevent DNA unwinding and transcription can be used. As a result of either, synthesis of VISTA (PD-L3) polypeptide is blocked. When VISTA (PD-L3) expression is modulated, preferably, such modulation occurs by a means other than by knocking out the VISTA (PD-L3) gene.

Agents which modulate expression, by virtue of the fact that they control the amount of VISTA (PD-L3) in a cell, also modulate the total amount of VISTA (PD-L3) activity in a cell. In one embodiment, the agent the modulates VISTA (PD-L3) stimulates one or more VISTA (PD-L3) activities. Examples of such stimulatory agents include active VISTA (PD-L3) polypeptide and a nucleic acid molecule encoding VISTA (PD-L3) that has been introduced into the cell. In another embodiment, the agent inhibits one or more VISTA (PD-L3) activities. Examples of such inhibitory agents include antisense VISTA (PD-L3) nucleic acid molecules, anti-VISTA (PD-L3) antibodies, VISTA (PD-L3) inhibitors, and compounds identified in the subject screening assays. In a further embodiment, an inhibitory agent is a combination of an anti-VISTA (PD-L3) antibody and an anti-PD-L1 or anti-PD-L2 antibody. These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of a VISTA (PD-L3) polypeptide, e.g., a disorder characterized by unwanted, insufficient, or aberrant expression or activity of a VISTA (PD-L3) polypeptide or nucleic acid molecule. In one embodiment, the method involves administering an agent (e.g., an agent identified by a screening assay described herein), or combination of agents that modulates (e.g., upregulates or downregulates) VISTA (PD-L3) expression or activity. In another embodiment, the method involves administering a VISTA (PD-L3) polypeptide or nucleic acid molecule as therapy to compensate for reduced, aberrant, or unwanted VISTA (PD-L3) expression or activity.

The invention provides a method for preventing in a subject, a disease or condition associated with an aberrant or unwanted VISTA (PD-L3) expression or activity, by administering to the subject a VISTA (PD-L3) polypeptide or an agent which modulates VISTA (PD-L3) expression or at least one VISTA (PD-L3) activity. Subjects at risk for a disease or disorder which is caused or contributed to by aberrant or unwanted VISTA (PD-L3) expression or activity can be identified by, for example, any or a combination of diagnostic or prognostic assays as described herein. Administration of a prophylactic agent can occur prior to the manifestation of symptoms characteristic of the VISTA (PD-L3) aberrancy, such that a disease or disorder is prevented or, alternatively, delayed in its progression. Depending on the type of VISTA (PD-L3) aberrancy, for example, a VISTA (PD-L3) polypeptide, VISTA (PD-L3) agonist or VISTA (PD-L3) antagonist (e.g., an anti-VISTA (PD-L3) antibody) agent can be used for treating the subject. The appropriate agent can be determined based on screening assays described herein.

The VISTA and VISTA conjugate, may be admixed with additional chemotherapeutic agents, cytotoxic agent, antibodies (e.g., anti-PD-L1, PD-L2 or CTLA-4 antibodies), lymphokine, or hematopoietic growth factor. The VISTA and VISTA conjugate, may also be administered in combination with another antibody, a lymphokine, cytotoxic agent (e.g., a moiety that inhibits DNA, RNA, or protein synthesis, a radionuclide, or ribosomal inhibiting protein, e.g., $^{212}$Bi, $^{131}$I, $^{188}$Re, $^{90}$Y, vindesine, methotrexate, adriamycin, cisplatin, pokeweed antiviral protein, *Pseudomonas* exotoxin A, ricin, diphtheria toxin, ricin A chain, or cytotoxic phospholipase enzyme), immunosuppressive agent (e.g., cyclosporine, leflunomide, methotrexate, azothiprine, mercaptopurine, dactinomycin, tacrolimus, or sirolimus) or a hematopoietic growth factor. The VISTA and VISTA conjugate, may be label with a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label. In the methods described herein, the second agent may be administered simultaneously or sequentially with the antibody. For example, the second agent may be an agent that downregulates an immune response (e.g., PD-L1, PD-L2 or CTLA-4 fusion protein or antibody specific thereto.)

In one embodiment, methods of treating a subject with an autoimmune disease comprising administering a VISTA and VISTA conjugate, to a subject who may be receiving secondary therapy. Examples of secondary therapy include chemotherapy, radiotherapy, immunotherapy, phototherapy, cryotherapy, toxin therapy, hormonal therapy, or surgery. Thus, the invention contemplates use of the methods and compositions in conjunction with standard anti-cancer therapies. The patient to be treated may be of any age. One of skill in the art will recognize the presence and development of other anticancer therapies which may be used in conjugation with the VISTA or VISTA conjugate. Determination of dose is within the level of ordinary skill in the art. The VISTA and VISTA conjugate, may be administered for acute treatment, over one week or less, often over a period of one to three days or may be used in chronic treatment, over several months or years. In general, a therapeutically effective amount of the VISTA and VISTA conjugate is an amount sufficient to produce a clinically significant change in the autoimmune disease.

An inhibitory signal as transduced by an inhibitory receptor can occur even if a costimulatory receptor (e.g., CD28 or ICOS) in not present on the immune cell and, thus, is not simply a function of competition between inhibitory receptors and costimulatory receptors for binding of costimulatory molecules (Fallarino, et al. (1998) *J. Exp. Med.* 188: 205). Transmission of an inhibitory signal to an immune cell can result in unresponsiveness, anergy or programmed cell death in the immune cell. Preferably, transmission of an inhibitory signal operates through a mechanism that does not involve apoptosis.

Autoimmune Diseases

The VISTA polypeptides, multimeric VISTA polypeptides, VISTA fusion proteins (e.g., VISTA-Ig), and anti-VISTA antibodies described herein may be used in compositions, uses, and methods for the treatment of autoimmune diseases.

V-domain Immunoglobulin containing Suppressor of T cell Activation (VISTA) is a member of a family related to the Immunoglobulin (Ig) superfamily, which exerts profound impact on the immune system. The Ig superfamily consists of many critical immune regulators, such as the B7 family ligands and receptors. The best characterized costimulatory ligands are B7.1 and B7.2 that belong to the Ig superfamily and are expressed on professional APCs and whose receptors are CD28 and CTLA-4.

The B7 family ligands have expanded to include co-stimulatory B7-H2 (ICOS Ligand) and B7-H3, as well as co-inhibitory B7-H1 (PD-L1), B7-DC (PD-L2), B7-H4 (B7S1 or B7x), and B7-H6. Brandt, et al. (2009) *J Exp Med* 206, 1495-1503; Greenwald, et al. (2005) *Annu Rev Immunol* 23: 515-548. Accordingly, additional CD28 family receptors have been identified. ICOS is expressed on activated T cells and binds to B7-H2. ICOS is a positive co-regulator, important for T-cell activation, differentiation and function. Dong, et al. (2001) Nature 409, 97-101. On the other hand, programmed death 1 (PD-1) negatively regulates T cell responses. PD-1−/− mice develop lupus-like autoimmune disease, or autoimmune dilated cardiomyopathy. Nishimura, et al. (2001) *Science* 291: 319-322. Recently, CD80 was identified as a second receptor for PD-L1 that transduces inhibitory signals into T cells. Butte, et al. (2007) *Immunity* 27, 111-122. The two inhibitory B7 family ligands, PD-L1 and PD-L2, have distinct expression patterns. PD-L2 is expressed inducibly on DCs and macrophages, whereas PD-L1 is broadly expressed on both hematopoietic cells and non-hematopoietic cell types. Consistent with the immune-suppressive role of PD-1 receptor, studies using PD-L1$^{-/-}$ and PD-L2$^{-/-}$ mice have shown that both ligands have overlapping roles in inhibiting T-cell proliferation and cytokine production. At this time, VISTA appears to be selectively expressed hematopoietic cells, which distinguishes it from PD-L1 in distribution, and likely plays a critical role in negatively regulating the development of autoimmune disease.

Figure 4:
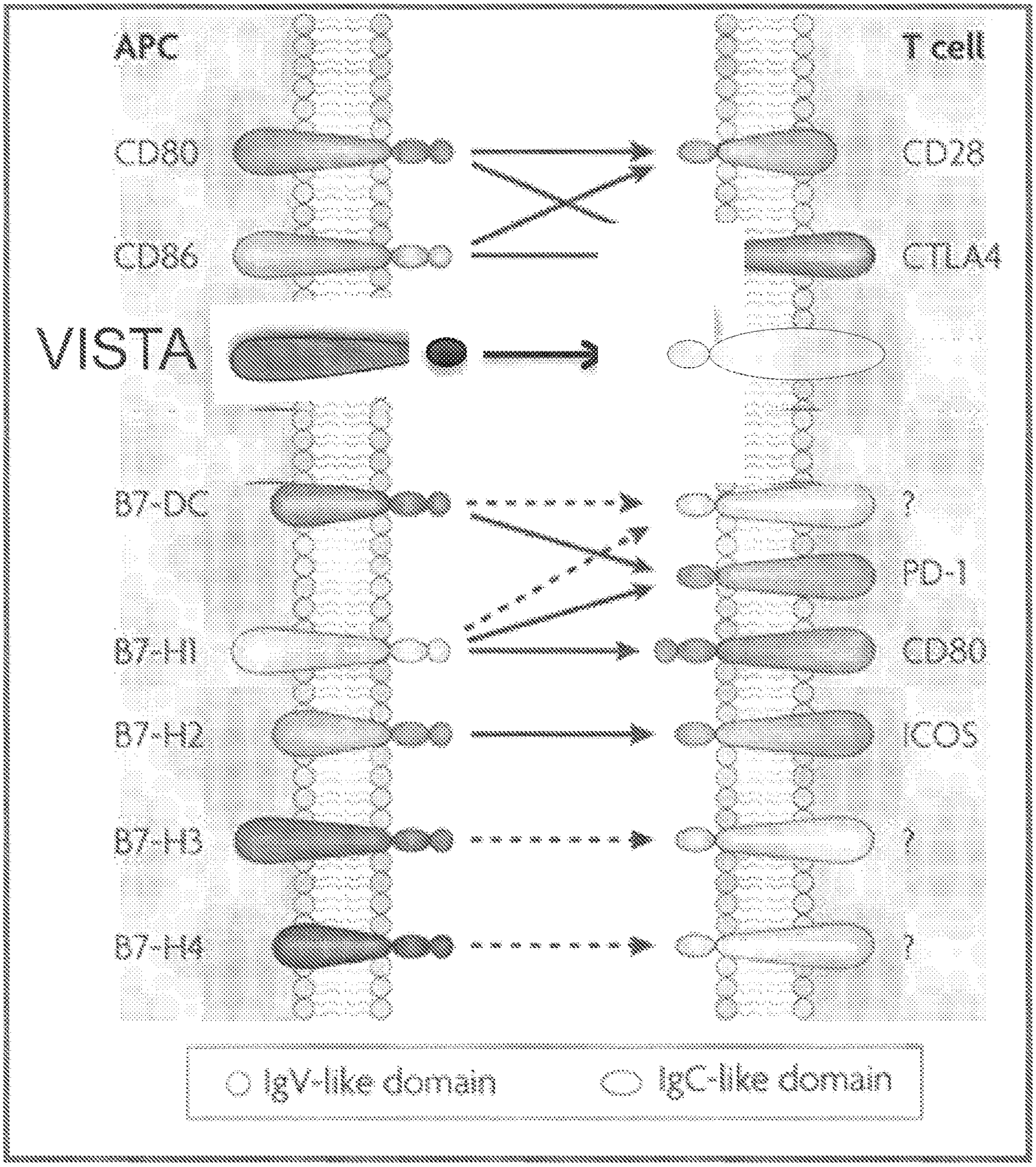

A novel and structurally-distinct, Ig-superfamily inhibitory ligand, whose extracellular domain bears highest homology to the B7 family ligand PD-L1. Although its closest relative phylogenetically is PD-L1, it was not designated a PD-L name due to its modest level of similarity (20%). It has a 93 aa cytoplasmic domain with no obvious signal transducing motifs, except a possible protein kinase C binding site. See FIG. 4. VISTA is a negative, regulatory ligand and that is based on the following facts:

A soluble VISTA-Ig fusion protein suppresses in vitro CD4$^+$ and CD8$^+$ T cell proliferation and cytokine production. Suppression is observed with PD-1$^{-/-}$ T cells indicating that PD-1 is not the VISTA receptor.

Overexpression of VISTA on APCs suppresses in vitro CD4$^+$ and CD8$^+$ T cell proliferation.

VISTA over-expression on tumor cells impaired protective anti-tumor immunity in tumor-vaccinated hosts.

VISTA$^{-/-}$ mice develop an inflammatory phenotype, establishing that VISTA has an immunosuppressive function. VISTA$^{-/-}$ DC stimulate more T cell proliferation then WT DCs.

Anti-VISTA monoclonal antibody (13F3) blocked VISTA-induced suppression of T cell responses by VISTA$^+$ APCs in vitro to enhance T cell activation.

Anti-VISTA monoclonal antibody exacerbated EAE and increased the frequency of encephalitogenic Th17s in vivo.

Anti-VISTA monoclonal antibody induces tumor remission in multiple (6) murine tumor models and VISTA expression on myeloid derived suppressor cells (MDSC) in these models is extremely high, suggesting that $VISTA^+$ MDSC suppress tumor specific immunity.

The VISTA polypeptides, multimeric VISTA polypeptides, VISTA fusion proteins (e.g., VISTA-Ig), siRNA molecules consisting of any one of the nucleic acid sequences SEQ ID NO: 38-67, and anti-VISTA antibodies described herein may be used in compositions, uses, and methods for the treatment of autoimmune diseases or disorders. Examples of autoimmune diseases or disorders include, but are not limited to acquired immune deficiency syndrome (AIDS), acquired spenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis (including large vessel vasculitis (including polymyalgia rheumatica and giant cell (Takayasu's) arthritis), allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis (e.g., allergic alveolitis and fibrosing alveolitis), Alzheimer's disease, amyloidosis, amylotrophic lateral sclerosis (ALS; Lou Gehrig's disease), an eosinophil-related disorder (e.g., eosinophilia), anaphylaxis, ankylosing spondylitis, antgiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis (e.g., rheumatoid arthritis such as acute arthritis, chronic rheumatoid arthritis), arthritis chronica progrediente, arthritis deformans, ascariasis, aspergilloma (or granulomas containing eosinophils), aspergillosis, aspermiogenese, asthma (e.g., asthma bronchiale, bronchial asthma, and auto-immune asthma), ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease (e.g., autoimmune inner ear disease (AGED)), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies (e.g., epilepsy), channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy (e.g., IgM polyneuropathies or IgM-mediated neuropathy), chronic obstructive airway disease, chronic pulmonary inflammatory disease, Chronic recurrent multifocal ostomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogans syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis (e.g., chronic cyclitis, heterochronic cyclitis, iridocyclitis, or Fuch's cyclitis), cystic fibrosis, cytokine-induced toxicity, deafness, degenerative arthritis, demyelinating diseases (e.g., autoimmune demyelinating diseases), demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis (e.g., allergic encephalomyelitis or encephalomyelitis allergica and experimental allergic encephalomyelitis (EAE)), endarterial hyperplasia, endocarditis, endocrine ophthamopathy, endometriosis. endomyocardial fibrosis, endophthalmia phacoanaphylactica, endophthalmitis, enteritis allergica, eosinophilia-myalgia syndrome, eosinophilic faciitis, epidemic keratoconjunctivitis, epidermolisis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, flariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, haemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases (e.g., anaphylaxis and allergic and atopic rhinitis), IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antobodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes (e.g., Lambert-Eaton myasthenic syndrome or Eaton-Lambert syndrome), parasitic diseases such as Lesihmania, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes (e.g., autoimmune polyglandular syndromes (or polyglandular endocrinopathy syndromes)), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis (e.g., benign monoclonal gammopathy and monoclonal garnmopathy of undetermined significance, MGUS), primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyreoiditis, Raynauds phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma (including systemic scleroderma), sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes (e.g., cutaneous SLE), systemic necrotizing vasculitis, and ANCA-associated vasculitis, such as Churg-Strauss vasculitis or syndrome (CSS)), tabes dorsalis, Takayasu's arteritis, telangiectasia, temporal arteritis/Giant cell arteritis, thromboangitis ubiterans, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria (e.g., chronic allergic urticaria and chronic idiopathic urticaria, including chronic autoimmune urticaria), uveitis (e.g., anterior uveitis), uveoretinitis, valvulitis, vascular dysfunction, vasculitis, vertebral arthritis, vesiculobullous dermatosis, vitiligo, Wegener's granulomatosis (now termed Granulomatosis with Polyangiitis (GPA), Wiskott-Aldrich syndrome, and x-linked hyper IgM syndrome.

Treatment of Cancer

The VISTA polypeptides, multimeric VISTA polypeptides, VISTA fusion proteins (e.g., VISTA-Ig), siRNA molecules consisting of any one of the nucleic acid sequences of SEQ ID NO: 38-67, and anti-VISTA antibodies described herein may be used in compositions, uses, and methods for the treatment of cancer (e.g., tumors).

Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; multiple myeloma and post-transplant lymphoproliferative disorder (PTLD).

The term cancer amenable for treatment by the present invention include, but not limited to, colorectal cancer, carcinoma, lymphoma, blastoma, sarcoma, and leukemia or lymphoid malignancies. More particular examples of such cancers include bladder, ovarian, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of colorectal cancer, breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. The cancer may be an early advanced (including metastatic) colorectal cancer, bladder cancer, ovarian cancer or melanoma. The cancer may be colorectal cancer. The cancerous conditions amenable for treatment of the invention include metastatic cancers wherein VISTA expression by myeloid derived suppressor cells suppress antitumor responses and anti-invasive immune responses. The method of the present invention is particularly suitable for the treatment of vascularized tumors.

The invention is also suitable for treating cancers in combination with chemotherapy or radiotherapy or other biologics and for enhancing the activity thereof, i.e., in individuals wherein VISTA expression by myeloid derived suppressor cells suppress antitumor responses and the efficacy of chemotherapy or radiotherapy or biologic efficacy. Any chemotherapeutic agent exhibiting anticancer activity can be used according to the present invention. Preferably, the chemotherapeutic agent may be selected from the group consisting of alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. More preferably, the chemotherapeutic agent may be selected from the group consisting of 5-fluorouracil (5-FU), leucovorin (LV), irenotecan, oxaliplatin, capecitabine, paclitaxel and doxetaxel. Two or more chemotherapeutic agents can be used in a cocktail to be administered in combination with administration of the anti-VEGF antibody. One preferred combination chemotherapy is fluorouracil-based, comprising 5-FU and one or more other chemotherapeutic agent(s). Suitable dosing regimens of combination chemotherapies are known in the art and described in, for example, Saltz, et al. (1999) *Proc ASCO* 18:233a and Douillard, et al. (2000) Lancet 355: 1041-7. The biologic may be another immune potentiators such as antibodies to PD-L1, PD-L2, CTLA-4 and PD-L1, PD-L2, CTLA-4 fusion proteins as well as cytokines, growth factor antagonists and agonists, hormones and anti-cytokine antibodies.

Allergies

The VISTA polypeptides, multimeric VISTA polypeptides, VISTA fusion proteins (e.g., VISTA-Ig), and anti-VISTA antibodies described herein may be used in compositions, uses, and methods for the treatment of allergies (e.g., allergic reactions to allergens).

Examples of allergens include mite antigens and pollen antigens.

Representative allergic diseases include bronchial asthma, allergic rhinitis, atopic dermatitis, and pollen and insect allergies. Allergic diathesis is a genetic factor that can be inherited by the children of allergic parents. Familial allergic diseases are also called atopic diseases, and the causative, genetically transmitted factor is atopic diathesis. "Atopic dermatitis" is a general term for an atopic disease, especially diseases accompanied by dermatitis symptoms. Preferred examples include allergic condition is selected from the group consisting of eczema, allergic rhinitis, hay fever, urticaria, and food allergies. Allergic conditions include eczema, allergic rhinitis or coryza, hay fever, bronchial asthma, urticaria (hives) and food allergies, and other atopic conditions.

Inflammatory Conditions and Inflammatory Diseases

The VISTA polypeptides, multimeric VISTA polypeptides, VISTA fusion proteins (e.g., VISTA-Ig), siRNA molecules consisting of any one of the nucleic acid sequences of SEQ ID NO: 38-67, and anti-VISTA antibodies described herein may be used in compositions, uses, and methods for the treatment of inflammatory conditions and inflammatory disease.

Inflammatory conditions and inflammatory diseases, include but are not limited to rheumatic diseases (e.g., rheumatoid arthritis, osteoarthritis, psoriatic arthritis) spondyloarthropathies (e.g., ankylosing spondylitis, reactive arthritis, Reiter's syndrome), crystal arthropathies (e.g., gout, pseudogout, calcium pyrophosphate deposition disease), multiple sclerosis, Lyme disease, polymyalgia rheumatica; connective tissue diseases (e.g., systemic lupus erythematosus, systemic sclerosis, polymyositis, dermatomyositis, Sjogren's syndrome); vasculitides (e.g., polyarteritis nodosa, Wegener's granulomatosis, Churg-Strauss syndrome); inflammatory conditions including consequences of trauma or ischaemia, sarcoidosis; vascular diseases including atherosclerotic vascular disease, atherosclerosis, and vascular occlusive disease (e.g., atherosclerosis, ischaemic heart disease, myocardial infarction, stroke, peripheral vascular disease), and vascular stent restenosis; ocular diseases including uveitis, corneal disease, iritis, iridocyclitis, and cataracts.

Inflammatory conditions also include, but are not limited to acid Reflux/Heartburn, Acne, Acne Vulgaris, Allergies and Sensitivities, Alzheimer's Disease, Asthma, Atherosclerosis and Vascular Occlusive Disease (e.g., Atherosclerosis, Ischaemic Heart Disease, Myocardial Infarction, Stroke, Peripheral Vascular Disease) and Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases (e.g., Systemic Lupus Erythematosus, Systemic Sclerosis, Polymyositis, Dermatomyositis, Sjogren's Syndrome), Corneal Disease, Crohn's Disease, Crystal Arthropathies (e.g., Gout, Pseudogout, Calcium Pyrophosphate Deposition Disease), Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain/Arthritis/Rheumatoid Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases (e.g., Rheumatoid Arthritis, Osteoarthritis, Psoriatic Arthritis), Rheumatoid Arthritis, Sarcoidosis, Scleroderma, Sinusitis, Sjögren's Syndrome, Spastic Colon, Spondyloarthropathies (e.g., Ankylosing Spondylitis, Reactive Arthritis, Reiter's Syndrome), Systemic Candidiasis, Tendonitis, Transplant Rejection, UTI's, Vaginitis, Vascular Diseases including Atherosclerotic Vascular Disease, Vasculitides (e.g., Polyarteritis Nodosa, Wegener's Granulomatosis, Churg-Strauss Syndrome), and Vasculitis.

Graft Versus Host Disease

The VISTA polypeptides, multimeric VISTA polypeptides, VISTA fusion proteins (e.g., VISTA-Ig), siRNA molecules consisting of any one of the nucleic acid sequences of SEQ ID NO: 38-67, and anti-VISTA antibodies described herein may be used in compositions, uses, and methods for the treatment of graft-versus-host disease (GVHD).

The invention also provides a method of treating graft-versus-host-disease (GVHD) comprising administration of an effective amount of a VISTA fusion protein, optionally a VISTA-Ig fusion protein, or the multimeric VISTA protein. A method for treating graft-versus-host disease (GVHD), acute graft-versus-host disease, chronic graft-versus-host disease, acute graft-versus-host disease associated with stem cell transplant, chronic graft-versus-host disease associated with stem cell transplant, acute graft-versus-host disease associated with bone marrow transplant, acute graft-versus-host disease associated with allogeneic hemapoetic stem cell transplant (HSCT), or chronic graft-versus-host disease associated with bone marrow transplant may comprise administering of an effective amount of a VISTA fusion protein, optionally a VISTA-Ig fusion protein, or the multimeric VISTA protein.

The graft-versus-host disease (GVHD) may be graft-versus-host disease (GVHD), acute graft-versus-host disease, chronic graft-versus-host disease, acute graft-versus-host disease associated with stem cell transplant, chronic graft-versus-host disease associated with stem cell transplant, acute graft-versus-host disease associated with bone marrow transplant, acute graft-versus-host disease associated with allogeneic hemapoetic stem cell transplant (HSCT), or chronic graft-versus-host disease associated with bone marrow transplant. The patient treated to be treated may have at least one symptom of graft-versus-host disease (GVHD), optionally wherein the patient exhibits acute GVHD includes but is not limited to abdominal pain, abdominal cramps, diarrhea, fever, jaundice, skin rash, vomiting, and weight loss. The patient may have at least one symptom of chronic graft-versus-host disease (GVHD) includes but is not limited to dry eyes, dry mouth, hair loss, hepatisis, lung disorder, gastrointestinal tract disorders, skin rash, and skin thickening. The patient may have or may be to receive allogeneic stem cell or bone marrow transplant. The patient may have or may be to receive autologous stem cell or bone marrow transplant.

Diagnostic Methods

The anti-VISTA and anti-VISTA conjugate antibodies which selectively bind the VISTA and VISTA conjugate, siRNA molecules consisting of any one of the nucleic acid sequences of SEQ ID NO: 38-67, and antigen-binding fragments thereof, may be used in diagnostic methods for detecting the presence or absence of an VISTA and VISTA conjugate. Anti-VISTA and anti-VISTA conjugate antibodies may be used in methods comprising (a) contacting a test sample with an antibody, or fragment thereof, that binds a VISTA or VISTA conjugate, and (b) assaying for antibody-epitope complexes. The antibody-epitope complex may be detected by Western blot, radioimmunoassay, ELISA (enzyme linked immunosorbent assay), "sandwich" immunoassay, immunoprecipitation assay, precipitation reaction, gel diffusion precipitation reaction, immunodiffusion assay, agglutination assay, complement-fixation assay, immunohistochemical assay, fluorescent immunoassay, and protein A immunoassay. The sample may be sample is a tissue biopsy, lymph, urine, cerebrospinal fluid, amniotic fluid, inflammatory exudate, blood, serum, stool, or liquid collected from the colorectal tract.

The antibodies which selectively bind a VISTA and VISTA conjugate may be recombinant. The fragments of antibodies which selectively bind a VISTA and VISTA conjugate may be a Fab, Fab', F(ab')2, Fv, CDR, paratope, or portion of an antibody that is capable of binding the antigen. The antibodies which selectively bind a VISTA and VISTA conjugate may be chimeric, humanized, anti-idiotypic, single-chain, bifunctional, or co-specific. The antibodies which selectively bind a VISTA and VISTA conjugate may be or fragment is conjugated to a label, including but not limited to a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label.

Additionally, VISTA and VISTA conjugate, antibody which selectively bind a VISTA and VISTA conjugate, and antigen-binding fragments thereof, may be attached to a solid support (e.g., bead, test tube, sheet, culture dish, or test strip) such as an array.

The method may comprise imaging a VISTA polypeptide or VISTA conjugate by positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

Screening Assays

The invention provides a method for identifying modulators ("screening assay"), i.e., candidate or test compounds or agents (e.g., peptides, peptidomimetics, small molecules or other drugs) which bind to VISTA polypeptides, have a stimulatory or inhibitory effect on, for example, VISTA expression or VISTA activity, or have a stimulatory or inhibitory effect on the interaction between VISTA and its natural binding partner(s).

Assays for screening candidate or test compounds which bind to the VISTA polypeptide or biologically active portion thereof, e.g., modulate the ability of the VISTA polypeptide to interact with its natural binding partner(s) may comprise contacting a candidate compound with a VISTA polypeptide and testing for the modulating of the ability of the VISTA polypeptide to interact with its natural binding partner. Assays for screening candidate or test compounds which bind to or modulate the activity of a VISTA protein or polypeptide or biologically active portion thereof may comprise contacting a VISTA polypeptide and testing for binding between the VISTA polypeptide and the candidate agent. Assays for screening candidate or test compounds which have a stimulatory or inhibitory effect on immune functions negatively regulated by VISTA such as are identified herein or based on its effect on the interaction of between VISTA and its natural binding partner(s). These VISTA related functions include by way of example inhibiting cytokine production (e.g., Il-2, gamma interferon by T cells, suppressing moderate CD28 costimulation, inhibiting CD4+ and CD8+ T cell proliferation, suppressing proliferation of naïve and memory CD4+ T cells, and suppressing TCR activation without inducing apoptosis.) The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. Lam (1997) Anticancer Drug Des. 12: 145.

An assay may be a cell-based assay in which a cell which expresses a VISTA polypeptide or biologically active portion thereof comprising contacting a VISTA polypeptide or biologically active portion thereof with a test compound, and determining the ability of the test compound to modulate VISTA activity. Determining the ability of the test compound to modulate VISTA activity can be accomplished by monitoring, for example, the ability of VISTA to bind to its natural binding partner(s), and modulate immune cell activity. The immune cell can be a T cell, a B cell, or a myeloid cell. Determining the ability of the test compound to modulate VISTA binding to its counter-receptor can be accomplished, for example, by coupling VISTA with a radioisotope or enzymatic label to monitor the ability of a test compound to modulate VISTA binding to T cells which express the VISTA counter-receptor. Determining the ability of the test compound to bind VISTA can be accomplished, for example, by coupling the compound with a radioisotope or enzymatic label such that binding of the compound to VISTA can be determined by detecting the labeled VISTA compound in a complex.

Assays may be used to determine the ability of a compound to interact with VISTA without the labeling of any of the interactants. For example, a microphysiometer can be used to detect the interaction of a compound with VISTA without the labeling of either the compound or the VISTA. McConnell, H. M. et al. (1992) *Science* 257:1906-1912. A microphysiometer (e.g., Cytosensor) is an analytical instrument that measures the rate at which a cell acidifies its environment using a light-addressable potentiometric sensor (LAPS). Changes in this acidification rate can be used as an indicator of the interaction between a compound and VISTA.

An assay may be a cell-based assay comprising contacting a T cell expressing a VISTA binding partner with a test compound and determining the ability of the test compound to modulate (e.g., stimulate or inhibit) the activity of the VISTA binding partner. Determining the ability of the test compound to modulate the activity of a VISTA binding partner can be accomplished, for example, by determining the ability of the VISTA polypeptide to bind to or interact with the VISTA binding partner.

Determining the ability of the VISTA polypeptide, or a biologically active fragment thereof, to bind to or interact with a VISTA binding partner, can be accomplished by one of the methods described above for determining direct binding. In an embodiment, determining the ability of the VISTA polypeptide to bind to or interact with a VISTA binding partner can be accomplished by determining the activity of the binding partner. For example, the activity of the binding partner can be determined by detecting induction of a cellular second messenger (e.g., tyrosine kinase or phosphatase activity), detecting catalytic/enzymatic activity of an appropriate substrate, detecting the induction of a reporter gene (comprising a target-responsive regulatory element operatively linked to a nucleic acid encoding a detectable marker, e.g., luciferase), or detecting a target-regulated cellular response. For example, determining the ability of the VISTA polypeptide to bind to or interact with a natural VISTA binding partner, can be accomplished by measuring the ability of a compound to modulate immune cell costimulation or inhibition in a proliferation assay, or by interfering with the ability of a VISTA polypeptide to bind to antibodies that recognize a portion of the VISTA polypeptide. In one embodiment, compounds that modulate T cell activation can be identified by determining the ability of a compound to modulate T cell proliferation or cytokine production. In an embodiment, compounds that modulate T cell activation can be identified by determining the ability of a compound to modulate T cell proliferation or cytokine production at more than one antigen concentration.

An assay may be a cell-free assay in which a VISTA polypeptide or biologically active portion thereof is contacted with a test compound and the ability of the test compound to bind to the VISTA polypeptide or biologically active portion thereof is determined. Preferred biologically active portions of the VISTA polypeptides to be used in assays of the present invention include fragments which participate in interactions with non-VISTA molecules, e.g., at least a portion of an extracellular domain which binds to a VISTA binding partner. Binding of the test compound to the VISTA polypeptide can be determined either directly or indirectly as described above.

The assay may be a cell-free assay in which a VISTA polypeptide or biologically active portion thereof is contacted with a test compound and the ability of the test compound to modulate (e.g., stimulate or inhibit) the activity of the VISTA polypeptide or biologically active portion thereof is determined. Determining the ability of the test compound to modulate the activity of a VISTA polypeptide can be accomplished, for example, by determining the ability of the VISTA polypeptide to bind to a VISTA binding partner by one of the methods described above for determining direct binding. The cell-free assays of the present invention are amenable to use of both soluble and/or membrane-bound forms of polypeptides (e.g., VISTA polypeptides or biologically active portions thereof, or binding partners to which VISTA binds). In the case of cell-free assays in which a membrane-bound form a polypeptide is used (e.g., a cell-surface VISTA), it may be desirable to utilize a solubilizing agent such that the membrane-bound form of the polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit, Isotridecypoly(ethylene glycol ether)n, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl.dbd.N,N-dimethyl-3-ammonio-1-propane sulfonate.

In assay methods, it may be desirable to immobilize either VISTA or its binding partner to facilitate separation of complexed from uncomplexed forms of one or both of the polypeptides, as well as to accommodate automation of the assay. Binding of a test compound to a VISTA polypeptide, or interaction of a VISTA polypeptide with its binding partner in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the polypeptides to be bound to a matrix. For example, glutathione-S-transferase/VISTA fusion proteins or glutathione-S-transferase/binding partner fusion proteins can be adsorbed onto glutathione SEPHAROSE® beads (Sigma Chemical, St. Louis, Mo.) or glutathione derivatized microtitre plates, which are then combined with the test compound or the test compound and either the non-adsorbed binding partner polypeptide or VISTA polypeptide, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of VISTA binding or activity determined using standard techniques. Other techniques for immobilizing polypeptides on matrices can also be used in the screening assays of the invention. Determining the ability of the test compound to modulate the activity of a VISTA polypeptide may be accomplished by determining the ability of the test compound to modulate the activity of a molecule that functions downstream of VISTA, e.g., by interacting with the cytoplasmic domain of a VISTA binding partner. For example, levels of second messengers, the activity of the interacting molecule on an appropriate target, or the binding of the interactor to an appropriate target can be determined as previously described.

Modulators of VISTA expression may be identified in a method wherein a cell is contacted with a candidate compound and the expression of VISTA mRNA or polypeptide in the cell is determined. The level of expression of VISTA mRNA or polypeptide in the presence of the candidate compound is compared to the level of expression of VISTA mRNA or polypeptide in the absence of the candidate compound. The candidate compound can then be identified as a modulator of VISTA expression based on this comparison if the change is statistically significant.

The VISTA polypeptides may be used as "bait proteins" in a two-hybrid assay or three-hybrid assay (See, e.g., U.S. Pat. No. 5,283,317; Zervos, et al. (1993) Cell 72:223-232; Madura, et al. (1993) J. Biol. Chem. 268:12046-12054; Bartel, et al. (1993) Biotechniques 14:920-924; Iwabuchi, et al. (1993) Oncogene 8:1693-1696; and WO 94/10300), to identify other polypeptides which bind to or interact with VISTA ("VISTA-binding proteins", "VISTA binding partners", or "VISTA-bp") and are involved in VISTA activity. Such VISTA-binding proteins are also likely to be involved in the propagation of signals by the VISTA polypeptides or VISTA targets as, for example, downstream elements of a VISTA-mediated signaling pathway. Alternatively, such VISTA-binding polypeptides may be VISTA inhibitors. The two-hybrid system is based on the modular nature of most transcription factors, which consist of separable DNA-binding and activation domains. Briefly, the assay utilizes two different DNA constructs. In one construct, the gene that codes for a VISTA polypeptide is fused to a gene encoding the DNA binding domain of a known transcription factor (e.g, GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a VISTA-dependent complex, the DNA-binding and activation domains of the transcription factor are brought into close proximity. This proximity allows transcription of a reporter gene (e.g, LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the VISTA polypeptide.

A combination of two or more of the assays described herein. For example, a modulating agent may be identified using a cell-based or a cell-free assay, and the ability of the agent to modulate the activity of a VISTA polypeptide can be confirmed in vivo, e.g., in an animal such as an animal model for cellular transformation and/or tumorigenesis.

This invention further pertains to novel agents identified by the above-described screening assays. An agent as identified in the methods described herein in an appropriate animal model. For example, an agent identified as described herein (e.g., a VISTA modulating agent, an antisense VISTA nucleic acid molecule, a VISTA-specific antibody, or a VISTA binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the VISTA nucleotide sequences, described herein, can be used to map the location of the VISTA genes on a chromosome. The mapping of the VISTA sequences to chromosomes is an important first step in correlating these sequences with genes associated with disease. Briefly, VISTA genes can be mapped to chromosomes by preparing PCR primers (preferably 15-25 bp in length) from the VISTA nucleotide sequences. Computer analysis of the VISTA sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the VISTA sequences will yield an amplified fragment. Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. D'Eustachio, et al. (1983) *Science* 220: 919-924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the VISTA nucleotide sequences to design oligonucleotide primers, sublocalization can be achieved with panels of fragments from specific chromosomes. Other mapping strategies which can similarly be used to map a VISTA sequence to its chromosome include in situ hybridization (described in Fan, et al. (1990) *Proc Natl. Acad. Sci. USA* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, see Verma, et al. Human Chromosomes: A Manual of basic Techniques (Pergamon Press, New York 1988). Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data Ultimately, complete sequencing of genes from several individuals can be performed to confirm the presence of a mutation and to distinguish mutations from polymorphisms.

Tissue Typing

The VISTA sequences of the present invention can also be used to identify individuals from minute biological samples. Furthermore, the sequences of the present invention can be used to provide an alternative technique which determines the actual base-by-base DNA sequence of selected portions of an individual's genome. Thus, the VISTA nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The VISTA nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1 or 4 can comfortably provide positive individual identification with a panel of perhaps 10 to 1,000 primers which each yield a noncoding amplified sequence of 100 bases. If predicted coding sequences, such as those in SEQ ID NO: 3 or 6 are used, a more appropriate number of primers for positive individual identification would be 500-2000.

If a panel of reagents from VISTA nucleotide sequences described herein is used to generate a unique identification database for an individual, those same reagents can later be used to identify tissue from that individual. Using the unique identification database, positive identification of the individual, living or dead, can be made from extremely small tissue samples.

Use of VISTA Sequences in Forensic Biology

DNA-based identification techniques can also be used in forensic biology. The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1 or 3 are particularly appropriate for this use as greater numbers of polymorphisms occur in the noncoding regions, making it easier to differentiate individuals using this technique. Examples of polynucleotide reagents include the VISTA nucleotide sequences or portions thereof, e.g., fragments derived from the noncoding regions of SEQ ID NO: 1 or 3 having a length of at least 20 bases, preferably at least 30 bases. The VISTA nucleotide sequences described herein can further be used to provide polynucleotide reagents, e.g., labeled or labelable probes which can be used in, for example, an in situ hybridization technique, to identify a specific tissue, e.g., lymphocytes. This can be very useful in cases where a forensic pathologist is presented with a tissue of unknown origin. Panels of such VISTA probes can be used to identify tissue by species and/or by organ type. In a similar fashion, these reagents, e.g., VISTA primers or probes can be used to screen tissue culture for contamination (i.e., screen for the presence of a mixture of different types of cells in a culture).

Diagnostic Assays

An exemplary method for detecting the presence or absence of VISTA polypeptide or nucleic acid in a biological sample involves obtaining a biological sample from a test subject and contacting the biological sample with a compound or an agent capable of detecting VISTA polypeptide or nucleic acid (e.g., mRNA or genomic DNA) that encodes VISTA polypeptide such that the presence of VISTA polypeptide or nucleic acid is detected in the biological sample. A preferred agent for detecting VISTA mRNA or genomic DNA is a labeled nucleic acid probe capable of hybridizing to VISTA mRNA or genomic DNA. The nucleic acid probe can be, for example, the VISTA nucleic acid set forth in SEQ ID NO: 1 or 3, or a portion thereof, such as an oligonucleotide of at least 15, 30, 50, 100, 250 or 500 nucleotides in length and sufficient to specifically hybridize under stringent conditions to VISTA mRNA or genomic DNA. Other suitable probes for use in the diagnostic assays of the invention are described herein. A preferred agent for detecting VISTA polypeptide is an antibody capable of binding to VISTA polypeptide, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect VISTA mRNA, polypeptide, or genomic DNA in a biological sample in vitro as well as in vivo. For example, in vitro techniques for detection of PD-L2 mRNA include Northern hybridizations and in situ hybridizations. in vitro techniques for detection of VISTA polypeptide include enzyme linked immunosorbent assays (ELISAs), Western blots, immunoprecipitations and immunofluorescence. in vitro techniques for detection of VISTA genomic DNA include Southern hybridizations. Furthermore, in vivo techniques for detection of VISTA polypeptide include introducing into a subject a labeled anti-VISTA antibody. For example, the antibody can be labeled with a radioactive marker whose presence and location in a subject can be detected by standard imaging techniques. In one embodiment, the biological sample contains polypeptide molecules from the test subject. Alternatively, the biological sample can contain mRNA molecules from the test subject or genomic DNA molecules from the test subject. A preferred biological sample is a serum sample isolated by conventional means from a subject. In another embodiment, the methods further involve obtaining a control biological sample from a control subject, contacting the control sample with a compound or agent capable of detecting VISTA polypeptide, mRNA, or genomic DNA, such that the presence of VISTA polypeptide, mRNA or genomic DNA is detected in the biological sample, and comparing the presence of VISTA polypeptide, mRNA or genomic DNA in the control sample with the presence of VISTA polypeptide, mRNA or genomic DNA in the test sample.

The invention also encompasses kits for detecting the presence of VISTA in a biological sample. For example, the kit can comprise a labeled compound or agent capable of detecting VISTA polypeptide or mRNA in a biological sample; means for determining the amount of VISTA in the sample; and means for comparing the amount of VISTA in the sample with a standard. The compound or agent can be packaged in a suitable container. The kit can further comprise instructions for using the kit to detect VISTA polypeptide or nucleic acid.

Prognostic Assays

The diagnostic methods described herein can furthermore be utilized to identify subjects having or at risk of developing a disease or disorder associated with aberrant or unwanted VISTA expression or activity. As used herein, the term “aberrant” includes a VISTA expression or activity which deviates from the wild type VISTA expression or activity. Aberrant expression or activity includes increased or decreased expression or activity, as well as expression or activity which does not follow the wild type developmental pattern of expression or the subcellular pattern of expression. For example, aberrant VISTA expression or activity is intended to include the cases in which a mutation in the VISTA gene causes the VISTA gene to be under-expressed or over-expressed and situations in which such mutations result in a non-functional VISTA polypeptide or a polypeptide which does not function in a wild-type fashion, e.g., a polypeptide which does not interact with a VISTA binding partner, or one which interacts with a non-VISTA binding partner. As used herein, the term “unwanted” includes an unwanted phenomenon involved in a biological response such as immune cell activation. For example, the term unwanted includes a VISTA expression or activity which is undesirable in a subject.

The assays described herein, such as the preceding diagnostic assays or the following assays, can be utilized to identify a subject having or at risk of developing a disorder associated with a misregulation in VISTA polypeptide activity or nucleic acid expression, such as an autoimmune disorder, an immunodeficiency disorder, an immune system disorder such as autoimmunity, allergic or inflammatory disorder or cancer. Thus, the present invention provides a method for identifying a disease or disorder associated with aberrant or unwanted VISTA expression or activity in which a test sample is obtained from a subject and VISTA polypeptide or nucleic acid (e.g., mRNA or genomic DNA) is detected, wherein the presence of VISTA polypeptide or nucleic acid is diagnostic for a subject having or at risk of developing a disease or disorder associated with aberrant or unwanted VISTA expression or activity. As used herein, a “test sample” refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant or unwanted VISTA expression or activity. For example, such methods can be used to determine whether a subject can be effectively treated with an agent for an autoimmune disorder, immunodeficiency disorder, immune system cancer, or allergic or inflammatory disorder. Thus, the present invention provides methods for determining whether a subject can be effectively treated with an agent for a disorder associated with aberrant or unwanted VISTA expression or activity in which a test sample is obtained and VISTA polypeptide or nucleic acid expression or activity is detected (e.g., wherein the abundance of VISTA polypeptide or nucleic acid expression or activity is diagnostic for a subject that can be administered the agent to treat a disorder associated with aberrant or unwanted VISTA expression or activity). The methods of the invention can also be used to detect genetic alterations in a VISTA gene, thereby determining if a subject with the altered gene is at risk for a disorder characterized by misregulation in VISTA polypeptide activity or nucleic acid expression, such as an autoimmune disorder, an immunodeficiency disorder, an immune system cancer, an allergic disorder, or an inflammatory disorder. The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a VISTA gene. Furthermore, any cell type or tissue in which VISTA is expressed may be utilized in the prognostic assays described herein.

Immunoassays

The VISTA and VISTA conjugate, antibodies and antigen-binding fragments that bind the VISTA and VISTA conjugate, may be used in immunoassays to qualitatively or quantitatively detect and analyze markers in a sample. This method comprises providing an antibody specifically binds to a VISTA or VISTA conjugate; contacting a sample with the antibody; and detecting the presence of a complex of the antibody bound to the marker in the sample.

VISTA and VISTA conjugate may be detected and/or quantified using any of a number of well recognized immunological binding assays. Useful assays include, for example, an enzyme immune assay (EIA) such as enzyme-linked immunosorbent assay (ELISA), a radioimmunoassay (RIA), a Western blot assay, or a slot blot assay. See, e.g., U.S. Pat. Nos. 4,366,241; 4,376,110; 4,517,288; and 4,837,168. Generally, a sample obtained from a subject can be contacted with the antibody specifically binds the VISTA or VISTA conjugate.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies may be attached to a solid support.

After incubating the sample with antibodies, the mixture is washed and the antibody-marker complex formed may be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations. Usually the assays will be carried out at ambient temperature, although they can be conducted over a range of temperatures (e.g., 10° C.-40° C.).

The immunoassay can be used to determine a test amount of a marker in a sample from a subject. First, a test amount of a marker in a sample may be detected using the immunoassay methods described above. If a marker is present in the sample, it will form an antibody-marker complex with an antibody specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal. Several immunoassays are known in the art and the VISTA polypeptide or VISTA conjugate described herein may used in such immunoassays including but not limited to radio-immunoassay (RIA), enzyme linked immunosorbent assay (ELISA), magnetic immunoassay, immunoblot, Western blot, immunoprecipitation assays, immunohistochemical analysis, and fluorescence activated cell sorting (FACS). See Wild, (2008) [Ed.] The Immunoassay Handbook [3rd Ed.] Elsevier.

Radio-Imaging Methods

The VISTA and VISTA conjugate may be used in radioimaging methods to diagnosis cancer including pancreatic and colorectal cancer, or monitor the progression of tumors. These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. SPECT may optionally be used with two labels simultaneously. See U.S. Pat. No. 6,696,686.

Commercial Applications and Methods

The present invention further provides for the production of VISTA and VISTA conjugate to reach commercial quantities. The VISTA and VISTA conjugate may be produced on a large scale, stored if necessary, and supplied to hospitals, clinicians or other healthcare facilities.

Methods of production, storage, and distribution of VISTA and VISTA conjugate may be produced by the methods disclosed herein. Following production, the VISTA and VISTA conjugate may be harvested, purified, and optionally stored prior to a patient's treatment. For example, once a patient presents with an indication such as, for example, cancer, autoimmune disease, or inflammatory condition, VISTA and VISTA conjugate may be ordered and provided in a timely manner. Accordingly, the present invention relates to methods of producing VISTA and VISTA conjugate to attain antibodies on a commercial scale, pharmaceutical compositions comprising antibodies and antigen binding fragments thereof which selectively bind to VISTA and VISTA conjugate, as well as methods of providing (i.e., producing, optionally storing, and selling) the VISTA and VISTA conjugate to hospitals and clinicians. The production of VISTA and VISTA conjugate may be scaled up for commercial use.

The present invention also provides for methods of conducting a pharmaceutical business comprising establishing a distribution system for distributing the preparation for sale or may include establishing a sales group for marketing the pharmaceutical preparation.

Library of Nucleic Acids

A variegated library of VISTA (PD-L3) variants may be generated by combinatorial mutagenesis at the nucleic acid level and is encoded by a variegated gene library. A variegated library of VISTA (PD-L3) variants may be produced by, for example, enzymatically ligating a mixture of synthetic oligonucleotides into gene sequences such that a degenerate set of potential VISTA (PD-L3) sequences expressible as individual polypeptides, or alternatively, as a set of larger fusion proteins (e.g., for phage display) containing the set of VISTA (PD-L3) sequences therein. There are a variety of methods which can be used to produce libraries of potential VISTA (PD-L3) variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential VISTA (PD-L3) sequences. Methods for synthesizing degenerate oligonucleotides are known in the art. See, e.g., Narang (1983) Tetrahedron 39:3; Itakura, et al. (1984) Annu. Rev. Biochem. 53:323; Itakura, et al. (1984) *Science* 198:1056; Ike, et al. (1983) Nucleic Acids Res. 11:477.

In addition, libraries of fragments of a VISTA (PD-L3) polypeptide coding sequence may be used to generate a variegated population of VISTA (PD-L3) fragments for screening and subsequent selection of variants of a VISTA (PD-L3) polypeptide. A library of coding sequence fragments can be generated by treating a double stranded PCR fragment of a VISTA (PD-L3) coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the VISTA (PD-L3) polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of VISTA (PD-L3) polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify VISTA (PD-L3) variants. Arkin and Youvan (1992) *Proc Natl. Acad. Sci. USA* 89:7811-7815; Delagrave et al. (1993) Protein Eng. 6(3):327-331.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining VISTA polypeptide and/or nucleic acid expression as well as VISTA activity, in the context of a biological sample (e.g., blood, serum, cells, or tissue) to thereby determine whether an individual is afflicted with a disease or disorder, or is at risk of developing a disorder, associated with aberrant or unwanted VISTA expression or activity. The invention also provides for prognostic (or predictive) assays for determining whether an individual is at risk of developing a disorder associated with VISTA polypeptide, nucleic acid expression or activity. For example, mutations in a VISTA gene can be assayed in a biological sample. Such assays can be used for prognostic or predictive purpose to thereby prophylactically treat an individual prior to the onset of a disorder characterized by or associated with VISTA polypeptide, nucleic acid expression or activity.

Another embodiment of the invention pertains to monitoring the influence of agents (e.g., drugs, compounds) on the expression or activity of VISTA in clinical trials. These and other agents are described in further detail in the following sections.

Monitoring of Effects During Clinical Trials

Monitoring the influence of agents (e.g., drugs) on the expression or activity of a VISTA polypeptide (e.g., the modulation of cell proliferation and/or migration) can be applied not only in basic drug screening, but also in clinical trials. For example, the effectiveness of an agent determined by a screening assay as described herein to increase VISTA gene expression, polypeptide levels, or upregulate VISTA activity, can be monitored in clinical trials of subjects exhibiting decreased VISTA gene expression, polypeptide levels, or downregulated VISTA activity. Alternatively, the effectiveness of an agent determined by a screening assay to decrease VISTA gene expression, polypeptide levels, or downregulate VISTA activity, can be monitored in clinical trials of subjects exhibiting increased VISTA gene expression, polypeptide levels, or VISTA activity. As noted VISTA is expressed on many hematopoietic cell types including APCs (macrophages and myeloid dendritic cells), and CD4+ T cells, and more specifically is expressed on $CD11c^+$ DCs, $CD4^+$ T cells (including both $Foxp3^-$ effector T cells and $Foxp3^+$ nTregs), $CD8^+$ T cells, and $Gr1^+$ granulocytes, and expressed at low levels on B cells and NK cells In such clinical trials, the expression or activity of a VISTA gene, and preferably, other genes that have been implicated in, for example, a VISTA-associated disorder can be used as a "read out" or marker of the phenotype of a particular cell.

For example, and not by way of limitation, genes, including VISTA, that are modulated in cells by treatment with an agent (e.g., compound, drug or small molecule) which modulates VISTA activity (e.g., identified in a screening assay as described herein) can be identified. Thus, to study the effect of agents on VISTA-associated disorders, for example, in a clinical trial, cells can be isolated and RNA prepared and analyzed for the levels of expression of VISTA and other genes implicated in the VISTA-associated disorder, respectively. The levels of gene expression (e.g., a gene expression pattern) can be quantified by Northern blot analysis or RT-PCR, as described herein, or alternatively by measuring the amount of polypeptide produced, by one of the methods as described herein, or by measuring the levels of activity of VISTA or other genes. In this way, the gene expression pattern can serve as a marker, indicative of the physiological response of the cells to the agent. Accordingly, this response state may be determined before, and at various points during treatment of the individual with the agent. In an embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression of a VISTA polypeptide, mRNA, or genomic DNA in the preadministration sample; (iii) obtaining one or more post-administration samples from the subject; (iv) detecting the level of expression or activity of the VISTA polypeptide, mRNA, or genomic DNA in the post-administration samples; (v) comparing the level of expression or activity of the VISTA polypeptide, mRNA, or genomic DNA in the pre-administration sample with the VISTA polypeptide, mRNA, or genomic DNA in the post administration sample or samples; and (vi) altering the administration of the agent to the subject accordingly. For example, increased administration of the agent may be desirable to increase the expression or activity of VISTA to higher levels than detected, i.e., to increase the effectiveness of the agent. Alternatively, decreased administration of the agent may be desirable to decrease expression or activity of VISTA to lower levels than detected, i.e., to decrease the effectiveness of the agent. According to such an embodiment, VISTA expression or activity may be used as an indicator of the effectiveness of an agent, even in the absence of an observable phenotypic response.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

In order that the invention herein described may be fully understood, the foregoing detailed description is set forth. Various embodiments of the invention are described in detail and may be further illustrated by the provided examples.

EXAMPLES

The invention now being generally described, it will be more readily understood by reference to the following examples, which are included merely for purposes of illustration of certain aspects and embodiments of the present invention, and are not intended to limit the invention.

Example 1

Cloning and Sequence Analysis of VISTA (PD-L3)

VISTA (PD-L3) and Treg-sTNF were identified by global transcriptional profiling of resting Treg, Treg activated with αCD3, and Treg activated with αCD3/αGITR. αGITR was selected for this analysis as triggering of GITR on Treg has been shown to extinguish their contact-dependent suppressive activity (Shimizu, et al. (2002) supra). VISTA (PD-L3) and Treg-sTNF were identified on AFFIMETRIX® DNA arrays based on their unique expression patterns (Table 2). VISTA (PD-L3) exhibited an increase in expression in αCD3 activated Treg and reduced expression in the presence of αGITR; and Treg-sTNF exhibited a αCD3/αGITR-dependent increase in expression.

Purified CD4+CD25+ T cells were stimulated in culture overnight with none, αCD3, or αCD3/αGITR, and RNA isolated for real-time PCR analysis. Expression listed is relative to actin.

TABLE 2

| | Relative Expression | | |
|---|---|---|---|
| mRNA | None | αCD3 | αCD3/αGITR |
| VISTA (PD-L3) | 6 | 10 | 7 |
| $T^{reg}$-sTNF | 0.2 | 0.3 | 1.5 |

AFFIMETRIX® analysis of activated vs. resting CD25+ CD4+ nTregs revealed the expression of a gene product (RIKEN cDNA 4632428N05, or 4632428N05Rik) with unknown function but with sequence homology to the Ig superfamily.

More specifically, a 930 bp gene product was cloned from the CD4+ T cell cDNA library, which matched the predicted size and sequence. Silico-sequence and structural analysis predicts a transmembrane protein of 309 amino acids upon maturation, with an extracellular domain of 159 amino acids, a transmembrane domain of 22 amino acids and a cytoplasmic tail of 95 amino acids (FIG. 1A). Amino acid sequence alignment reveals an extracellular Immunoglobulin (Ig)-V like domain homologous to B7 family ligands such as PD-L1, PD-L2, B7-H3 and B7-H4, as well as to the B7 family receptors (i.e., PD-1, CTLA-4, CD28, BTLA, ICOS) (FIG. 1B-C). Although the sequence identity of the Ig-V domains between B7 family ligands and receptors in general is not very high (<40%), the Ig-V domain of 4632428N05Rik bears the highest homology with B7 family ligands PD-L1 and PD-L2. Sequence alignment also reveals several highly conserved cysteines (FIG. 1B) that are important for intra-chain disulfide bond formation, which is characteristic of the B7 family ligands. See also FIG. 23; Sica, et al. (2003) Immunity 18: 849-861.

The extracellular domain of 4632428N05Rik contains only the Ig-V domain but lacks the Ig-C domain (FIG. 1B-C). This unique feature is characteristic of the B7 family receptors, and distinguishes 4632428N05Rik from all other B7 family ligands, which contain both Ig-V and Ig-C domains. Freeman (2008) *Proc Natl Acad Sci USA* 105: 10275-10276; Lazar-Molnar, et al. (2008) *Proc Natl Acad Sci USA* 105: 10483-10488; Lin, et al. (2008) *Proc Natl Acad Sci USA* 105: 3011-3016; Schwartz, et al. (2001) Nature 410: 604-608; Stamper, et al. (2001) Nature 410: 608-61. Consistently, the phylogenic analysis using PhyML algorithm (Phylogenetic Maximum Likelihood) placed 4632428N05Rik in a closer evolutionary distance with B7 family receptors, in particular with PD-1, than the B7 family ligands (FIG. 2). Guindon & Gascuel (2003) Syst Biol 52: 696-704. However, the cytoplasmic tail of VISTA (PD-L3) does not contain any signaling domains (e.g. ITIM, ITAM or ITSM), which are the signature domains of B7 family receptors. Sharpe & Freeman (2002) *Nat Rev Immunol.* 2: 116-126. Despite its close evolutionary relationship with the inhibitory receptor PD-1, 4632428N05Rik represents a novel member of the B7 ligand family. Based on these structural and phylogenic characteristics, this molecule was named PD-1-eXpressed as Ligand (VISTA (PD-L3)). VISTA (PD-L3) is also highly conserved between the mouse and human orthologs, sharing 77% sequence identity (FIG. 1D).

The nucleic acid sequence encoding mouse VISTA (PD-L3) is set forth herein as SEQ ID NO:1 and the mouse VISTA (PD-L3) protein sequence is set forth as SEQ ID NO:2.

The human homolog of VISTA (PD-L3) is located on chromosome 10 (72.9 Mb) and composed of 6 exons thereby generating a transcript of 4689 bases in length coding for a 311 residue protein. The human homolog mRNA coding sequence is provided in GENBANK accession number NM_022153 and protein sequence give as NP_071436. The nucleic acid sequence encoding human VISTA (PD-L3) is set forth herein as SEQ ID NO: 3 and the human VISTA (PD-L3) protein sequence is set forth as SEQ ID NO:4. Mouse and human genes share 74% homology and are 68% identical at the protein level. Homologs were also identified in *Rattus norvegicus* on chromosome 20 (27.7 Mb; GENBANK accession number BC098723), as well as *Fugu rubripes* and *Danio rerio*. In one embodiment, VISTA (PD-L3) proteins of the present share the common amino acid sequence set forth in SEQ ID NO: 5. Additional orthologues of VISTA have been identified and are shown in FIG. 23D, e.g., (SEQ ID NO: 17), human (SEQ ID NO: 16), kangaroo (SEQ ID NO: 18), dolphin (SEQ ID NO: 19), chicken (SEQ ID NO: 20), *xenopus* (SEQ ID NO: 21), zebra finch (SEQ ID NO: 22), zebrafish, and fugu (SEQ ID NO: 23).

Example 2

Expression Studies of VISTA (PD-L3) by RT-PCR Analysis and Flow Cytometry

Figure 3A:
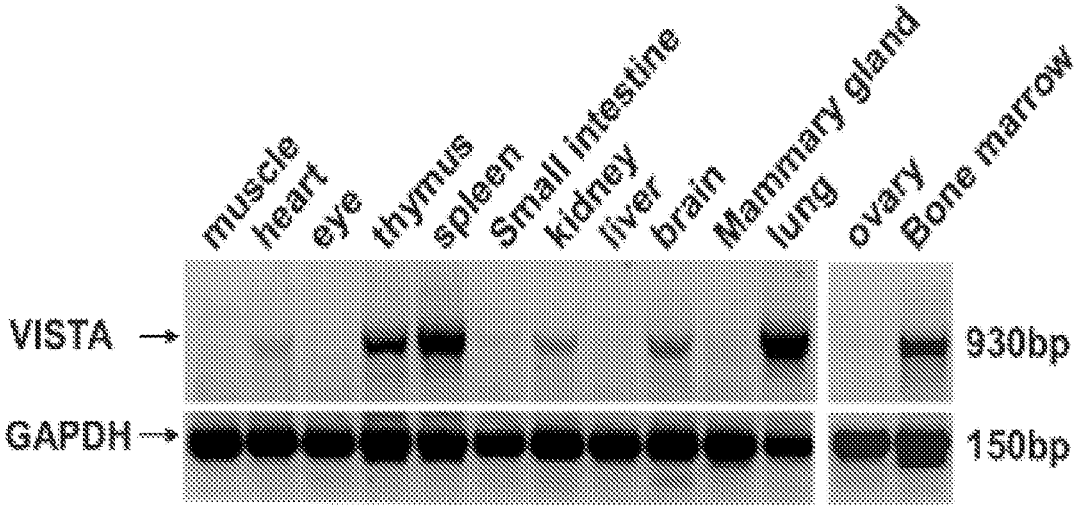
Figure 3B:
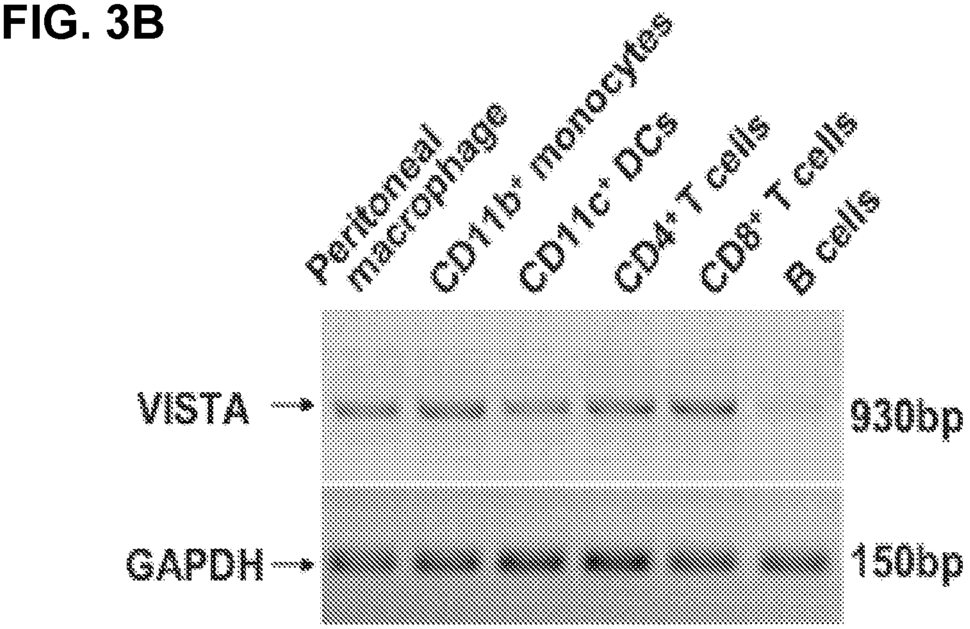

RT-PCR analysis was used to determine the mRNA expression pattern of VISTA (PD-L3) in mouse tissues (FIG. 3A). VISTA (PD-L3) is mostly expressed on hematopoietic tissues (spleen, thymus, bone marrow), or tissues with ample infiltration of leukocytes (i.e. lung). Weak expression was also detected in non-hematopoietic tissues (i.e. heart, kidney, brain, and ovary). Analysis of several hematopoietic cell types reveals expression of VISTA (PD-L3) on peritoneal macrophages, splenic CD11b+ monocytes, CD11c+ DCs, CD4+ T cells and CD8+ T cells, but lower expression level on B cells (FIG. 3B). This expression pattern is also largely consistent with the GNF (Genomics Institute of Novartis Research Foundation) gene array database, as well as NCBI GEO (gene expression omnibus) database (FIG. 4A-D). See Su, et al. (2002) *Proc Natl Acad Sci USA* 99: 4465-4470.

Figure 5:
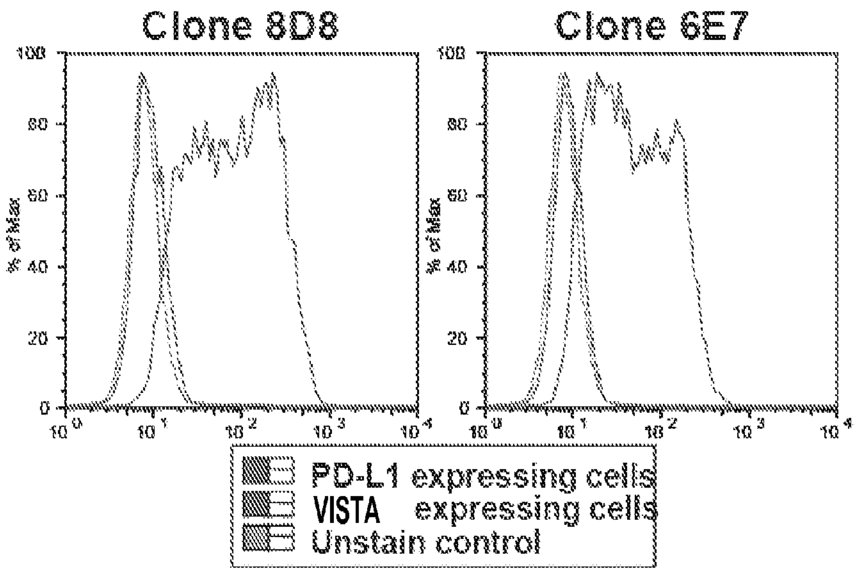

In order to study the protein expression, VISTA (PD-L3) specific hamster 8D8 and 6E7 monoclonal antibodies were produced. The specificity is demonstrated by positive staining on VISTA (PD-L3)-overexpressing murine EL4 T cells, but negative staining on PD-L1-overexpressing EL4 cells (FIG. 5).

Both polyclonal and monoclonal antibodies were raised against VISTA (PD-L3). Using a rabbit anti-VISTA (PD-L3) antibody, VISTA (PD-L3) protein was localized to lymphoid organs and prominently found in brain tissue. Of the monoclonal antibodies identified, the specificity of αVISTA (PD-L3) clone 8D8 was further evaluated. In this analysis, clone 8D8 was tested for binding against a panel of PD-L like-Ig fusion protein molecules including CTLA-4, PD-1, PD-L1, PD-L2, B7-1, B7-2, VISTA (PD-L3) and hIg. The results of this analysis indicated that 8D8 αPDL-3 was highly specific for VISTA (PD-L3).

Figure 3C:
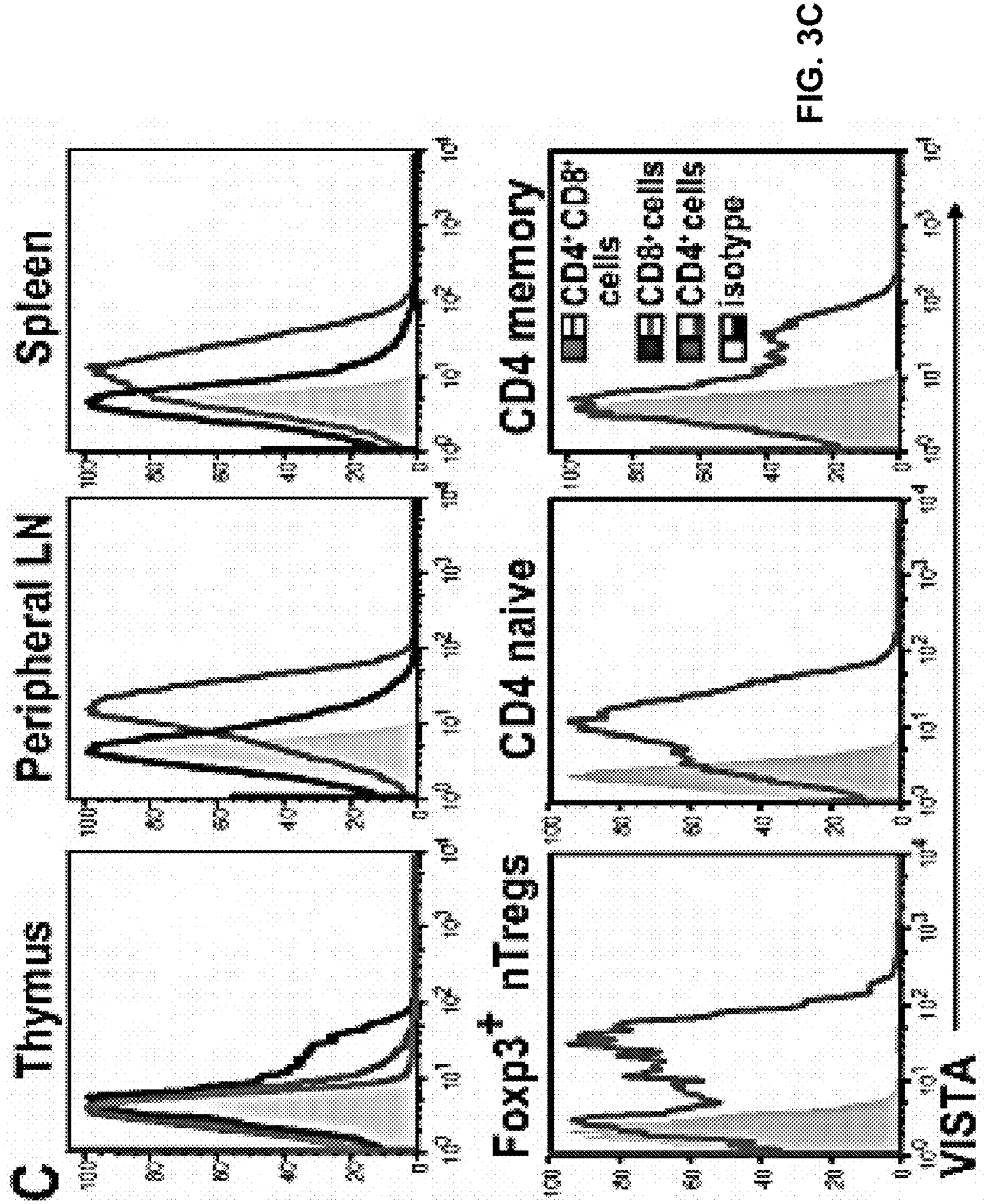
Figure 3D:
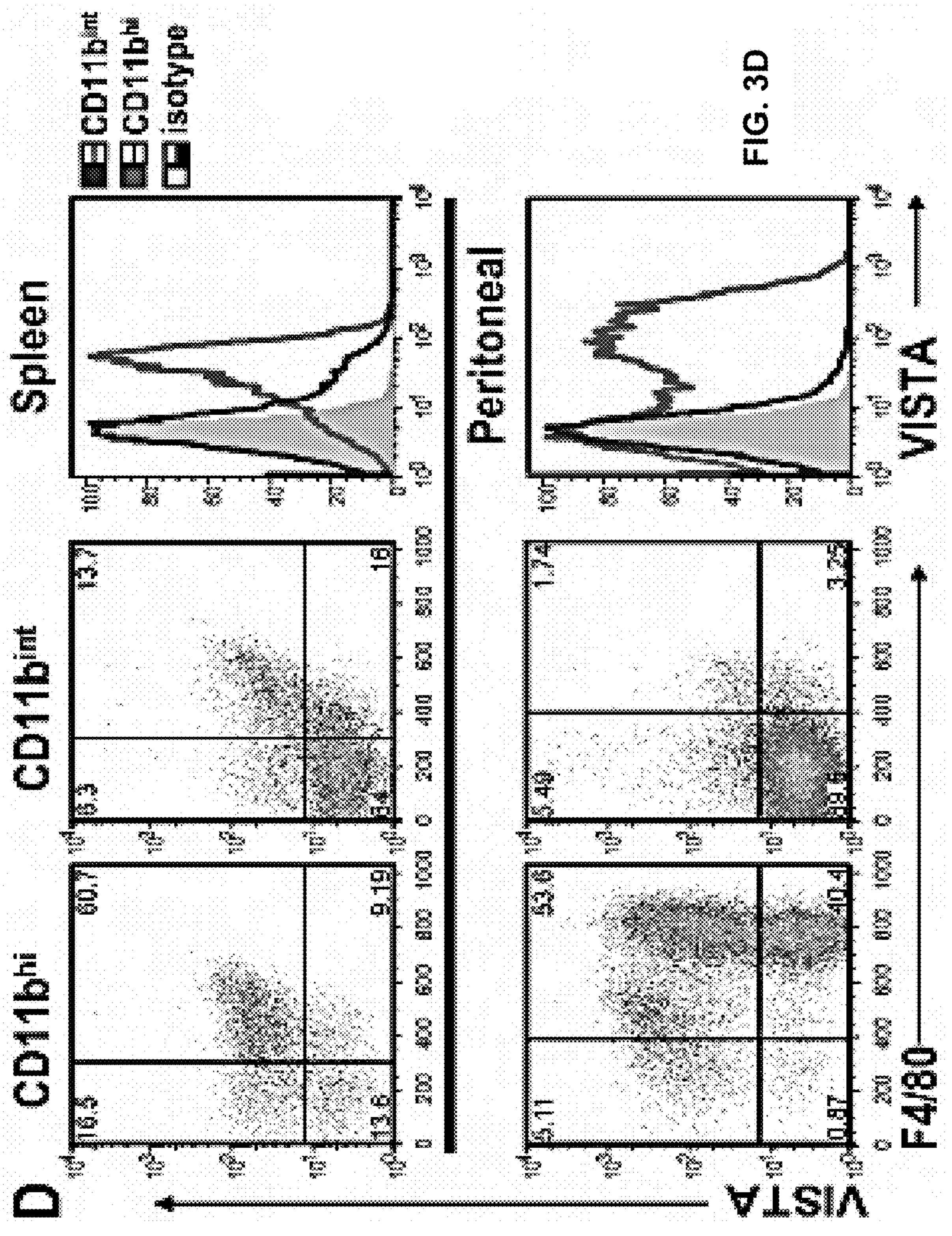
Figure 3E:
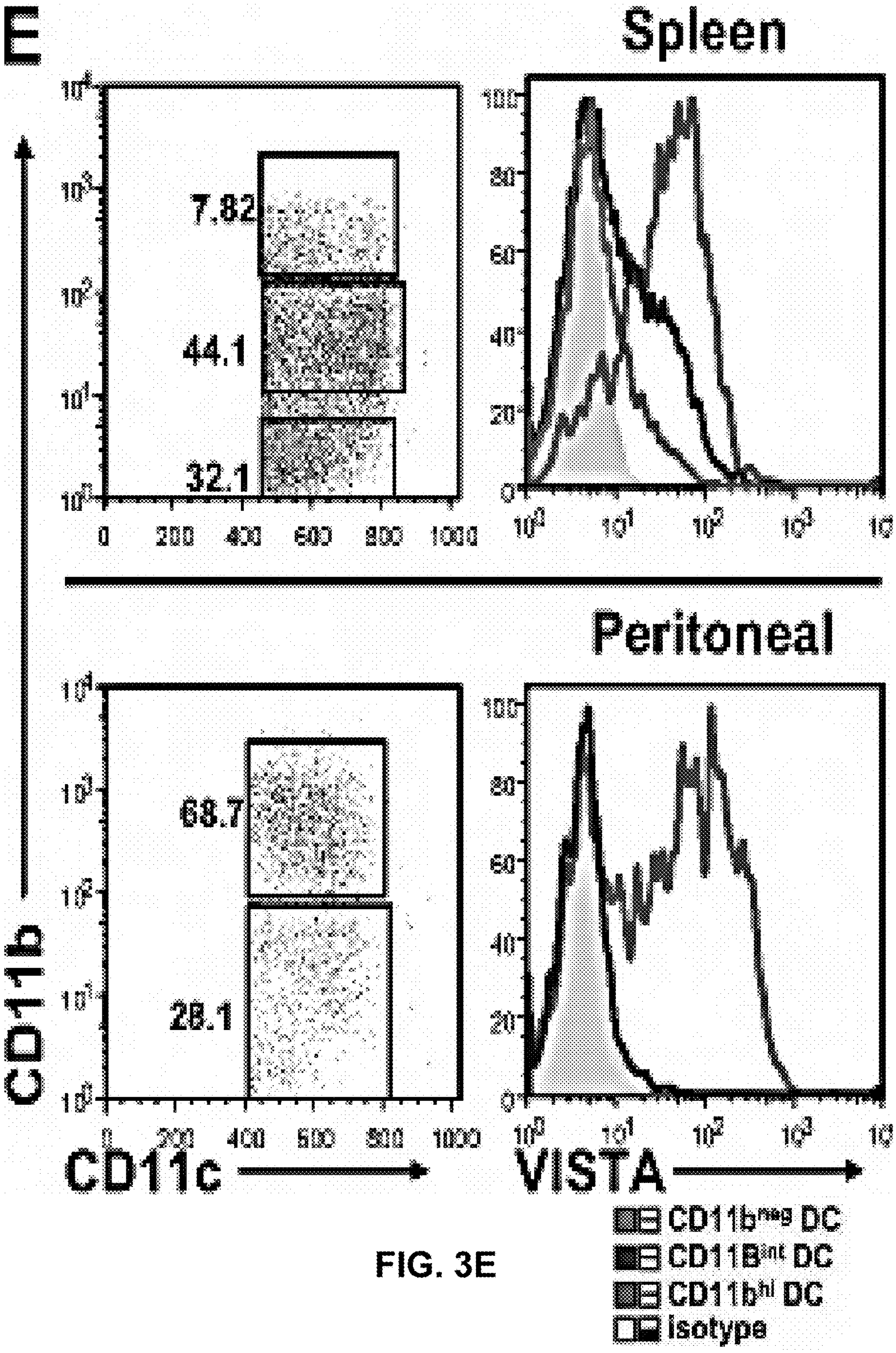
Figure 3F:
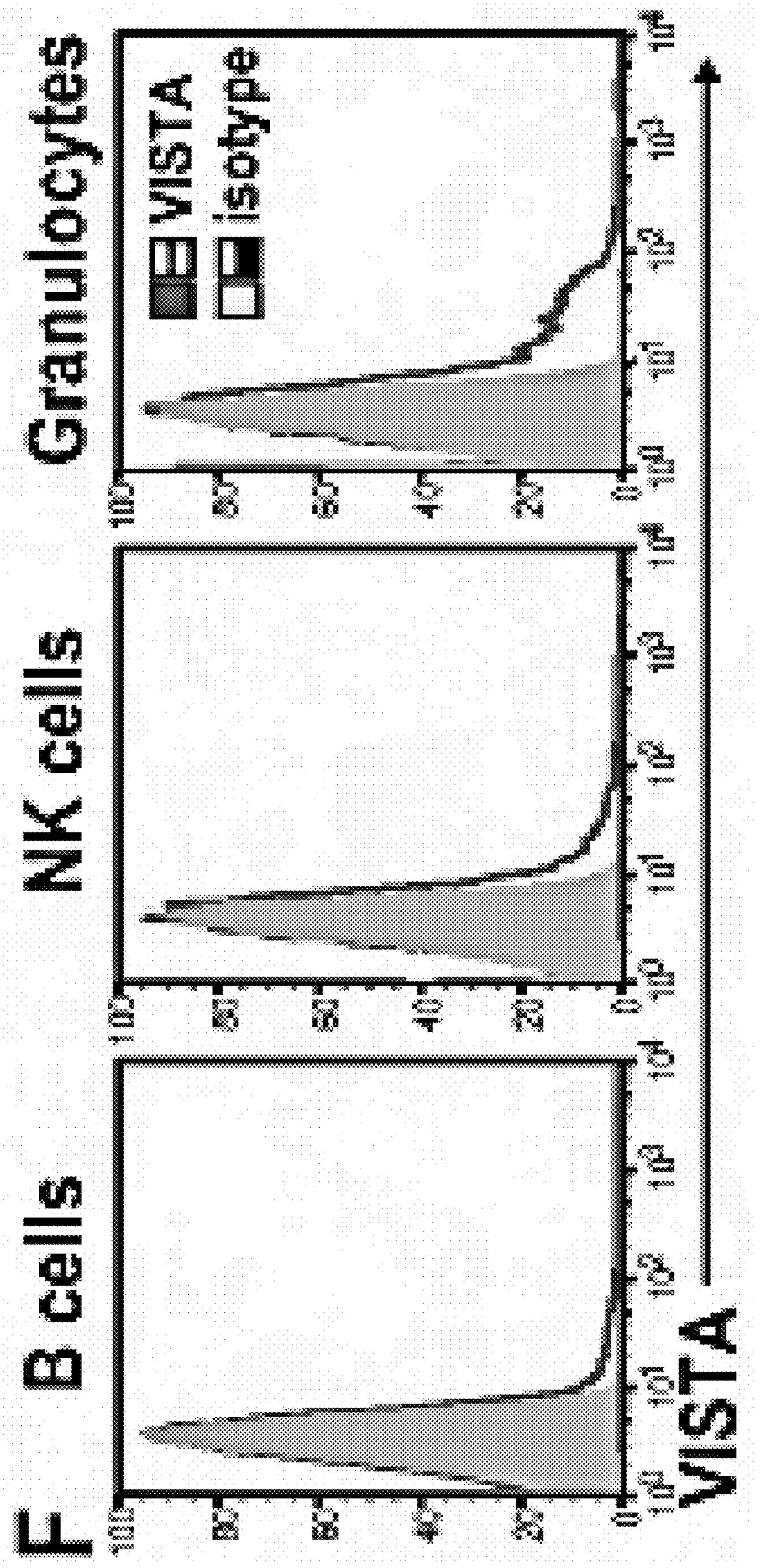

Specifically, using the anti-VISTA (PD-L3) monoclonal antibody clone 8D8, VISTA (PD-L3) expression was analyzed on hematopoietic cells by flow cytometry. Foxp3GFP knock-in reporter mice were used to distinguish CD4+ nTregs. In peripheral lymphoid organs (spleen and lymph nodes), significant expression is seen on all CD4+ T cell subsets (see total CD4+ T cells, or Foxp3− naïve T cells and Foxp3+ nTreg cells, and memory CD4+ T cells), whereas CD8+ T cells express markedly lower amount of surface VISTA (PD-L3) (FIG. 3C). In thymus, VISTA (PD-L3) expression is negative on CD4+CD8+ double positive thymocytes, low on CD4 single positive cells, and detectable on CD8 single positive cells. Next, a strong correlation of high VISTA (PD-L3) expression with CD11b marker can be seen for both splenic and peritoneal cells, including both F4/80 macrophages and myeloid CD11c+ DCs (FIG. 3D-E). On the other hand, B cells and NK cells are mostly negative for VISTA (PD-L3) expression. A small percentage of Gr-1+ granulocytes also express VISTA (PD-L3) (FIG. 3F).

Figure 3G:
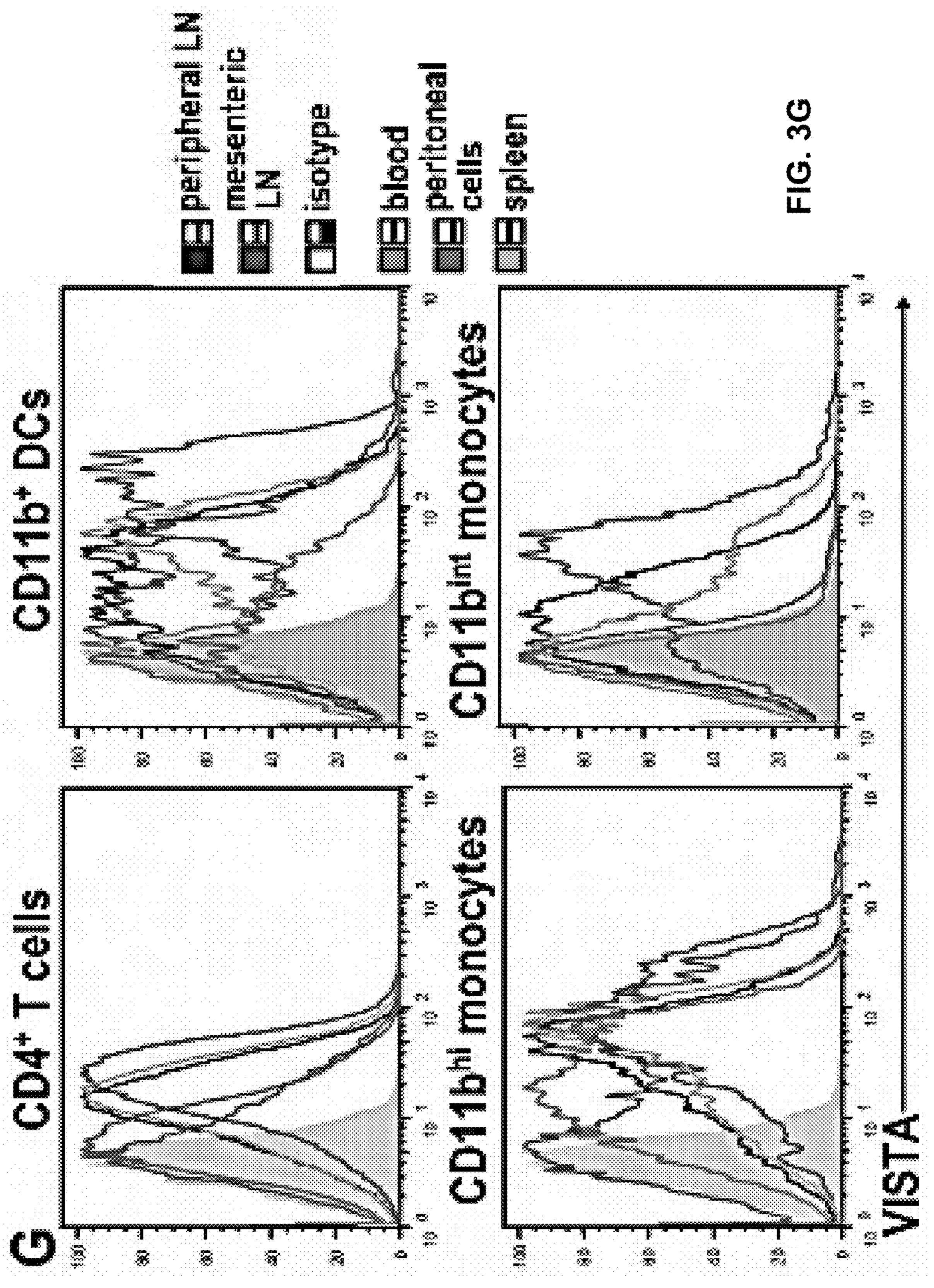

A differential expression pattern is shown on the same lineage of cells from different lymphoid organs (FIG. 3G). For CD4+ T cells and CD11b intermediate monocytes, the expression level follows the pattern of mesenteric lymph node>peripheral LN and spleen>peritoneal cavity and blood. This pattern is less pronounced for CD11bhi cells. This data suggests that VISTA (PD-L3) expression on certain cell types might be regulated by cell maturity and/or tissue microenvironment.

Figure 6:
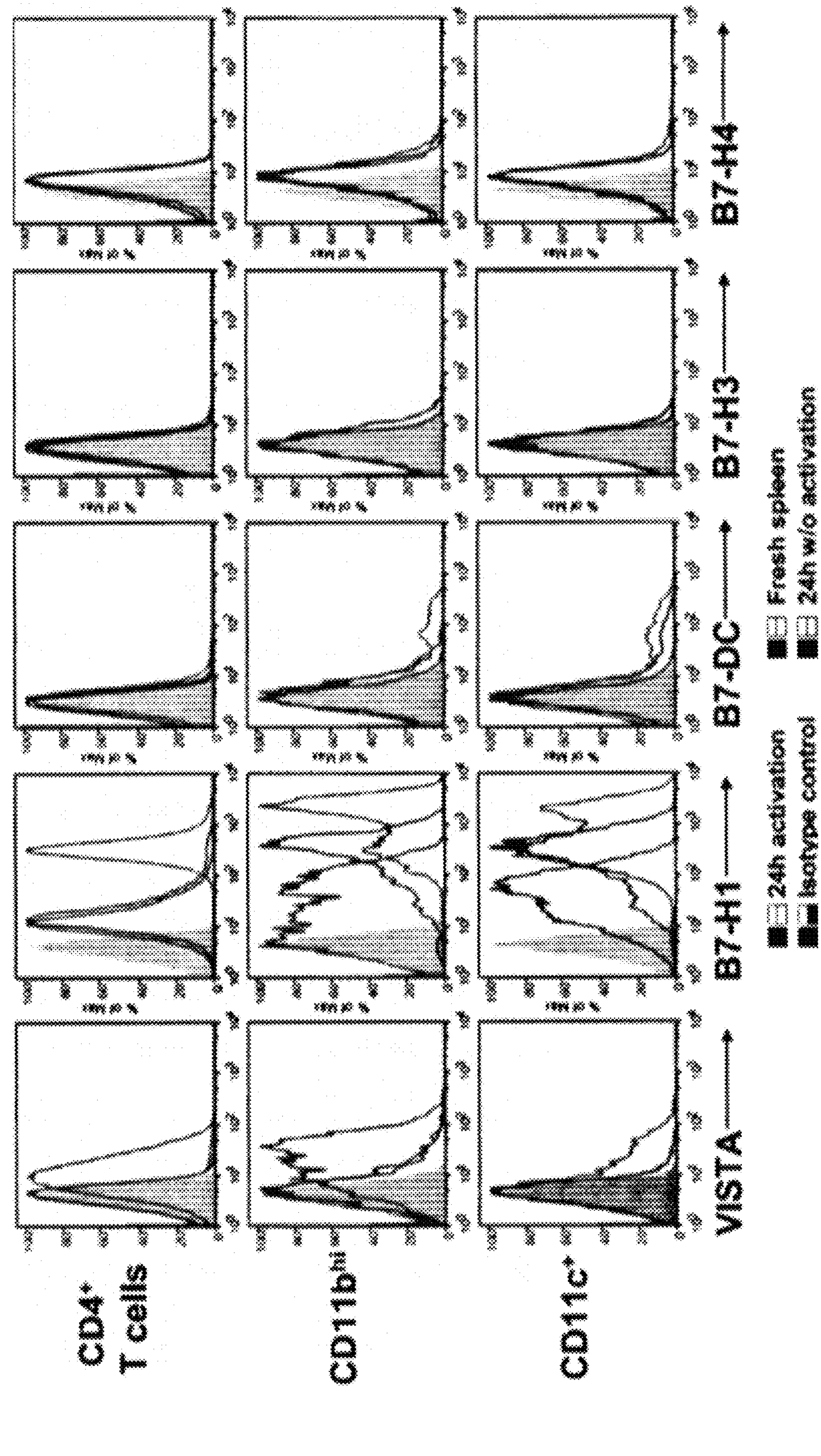

In addition to freshly isolated cells, VISTA (PD-L3) expression was analyzed on splenic CD4+ T cells, CD11bhi monocytes and CD11c+ DCs upon in vitro culture with and without activation (FIG. 6). Spleen cells were either cultured with medium, or with anti-CD3 (for activating T cells), or with IFNγ and LPS (for activating monocytes and DCs) for 24 hrs before being analyzed for the expression of VISTA (PD-L3) and other B7 family ligands (e.g. PD-L1, PD-L2, B7-H3 and B7-H4). This comparison revealed distinctive expression patterns between these molecules. VISTA (PD-L3) expression is quickly lost on all cell types upon in vitro culture, regardless of the activation status. In contrast, PD-L1 expression is upregulated on CD4+ T cells upon stimulation, or on CD11bhi monocytes and CD11c+ DCs upon culture in medium alone, and further enhanced in the face of stimulation. The expression of PD-L2, B7-H3 and B7-H4 are not prominent under the culture conditions used. The loss of VISTA (PD-L3) expression in vitro is unique when compared to other B7 family ligands, but might reflect non-optimal culture conditions that fail to mimic the tissue microenvironment.

Figure 7A:
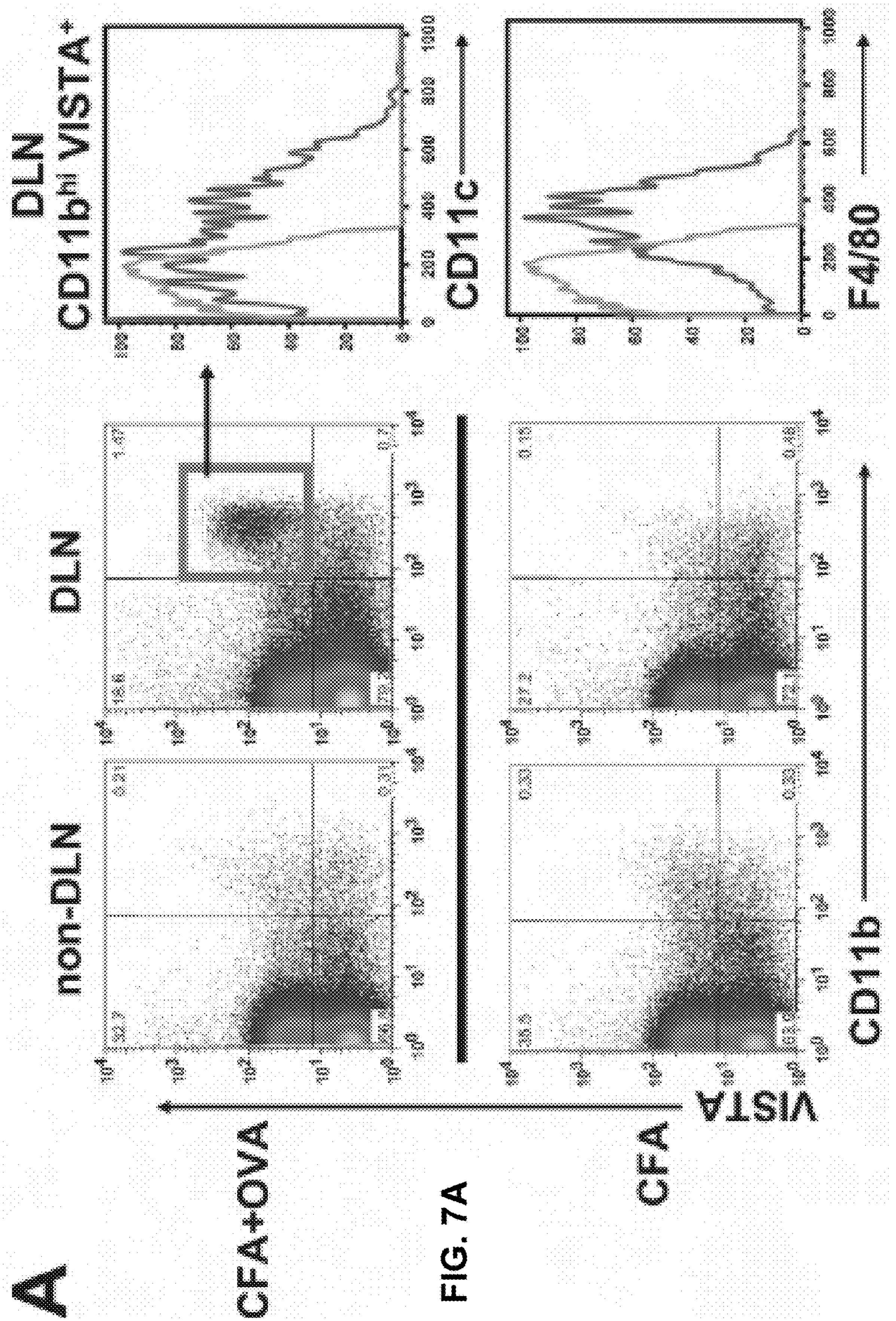
Figure 7B:
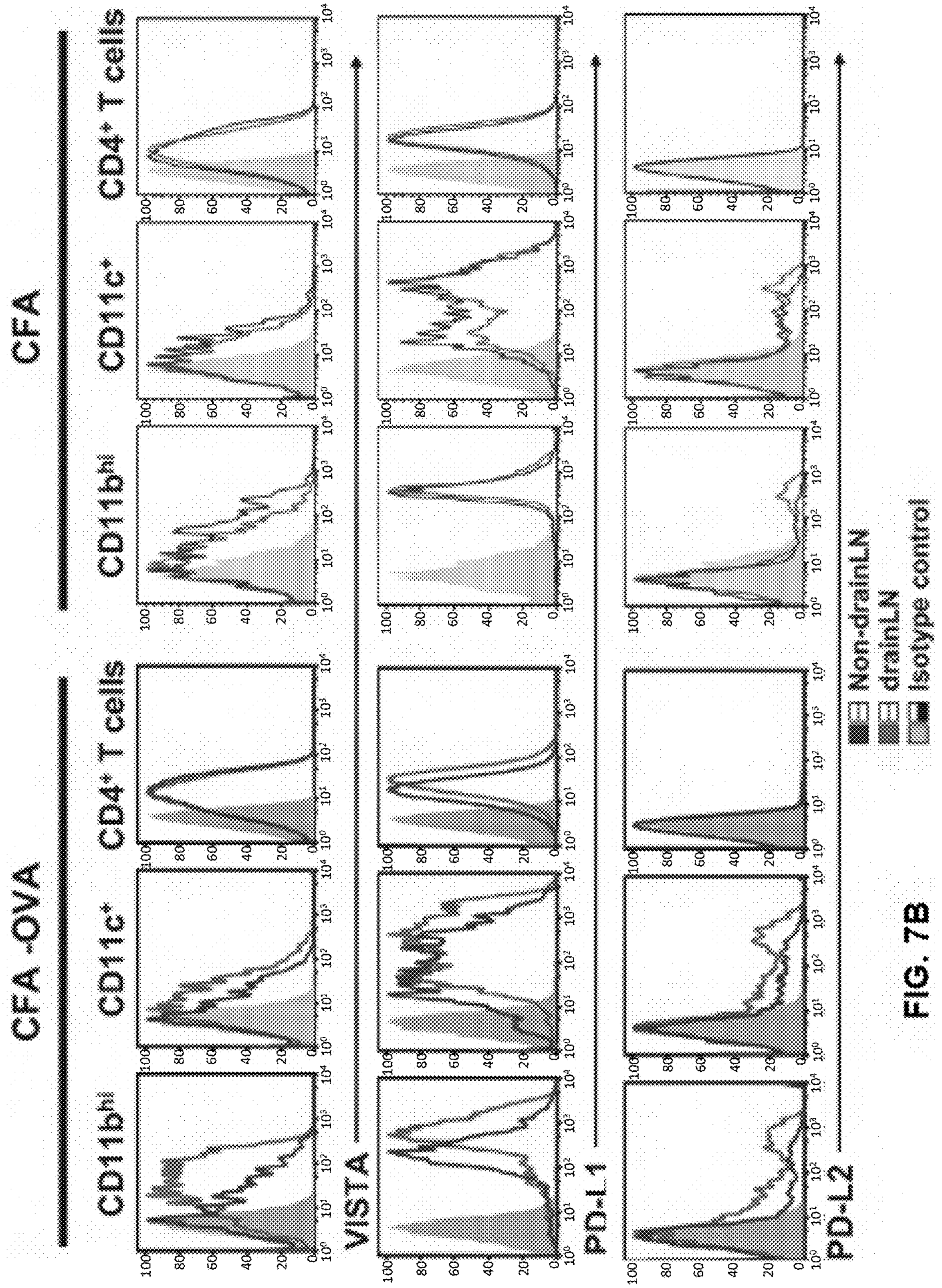

To address how VISTA (PD-L3) expression might be regulated in vivo, CD4 TCR transgenic mice DO11.10 were immunized with the cognate antigen chicken ovalbumin (OVA) emulsified in complete Freund's adjuvant (CFA). At 24 hrs after immunization, cells from the draining lymph node were analyzed for VISTA (PD-L3) expression (FIG. 7A). Immunization with antigen (CFA/OVA) but not the adjuvant alone drastically increased the CD11b+ VISTA (PD-L3)+ myeloid cell population, which contained a mixed population of F4/80+ macrophages and CD11c+ DCs. Further comparison with PD-L1 and PD-L2 reveals that even though PD-L1 has the highest constitutive expression level, VISTA (PD-L3) is the most highly upregulated during such an inflammatory immune response (FIG. 7B). Collectively, these data strongly suggest that the expression of VISTA (PD-L3) on myeloid APCs is tightly regulated by the immune system, which might contribute to its role in controlling immune responses and regulating T cell immunity.

Figure 8:
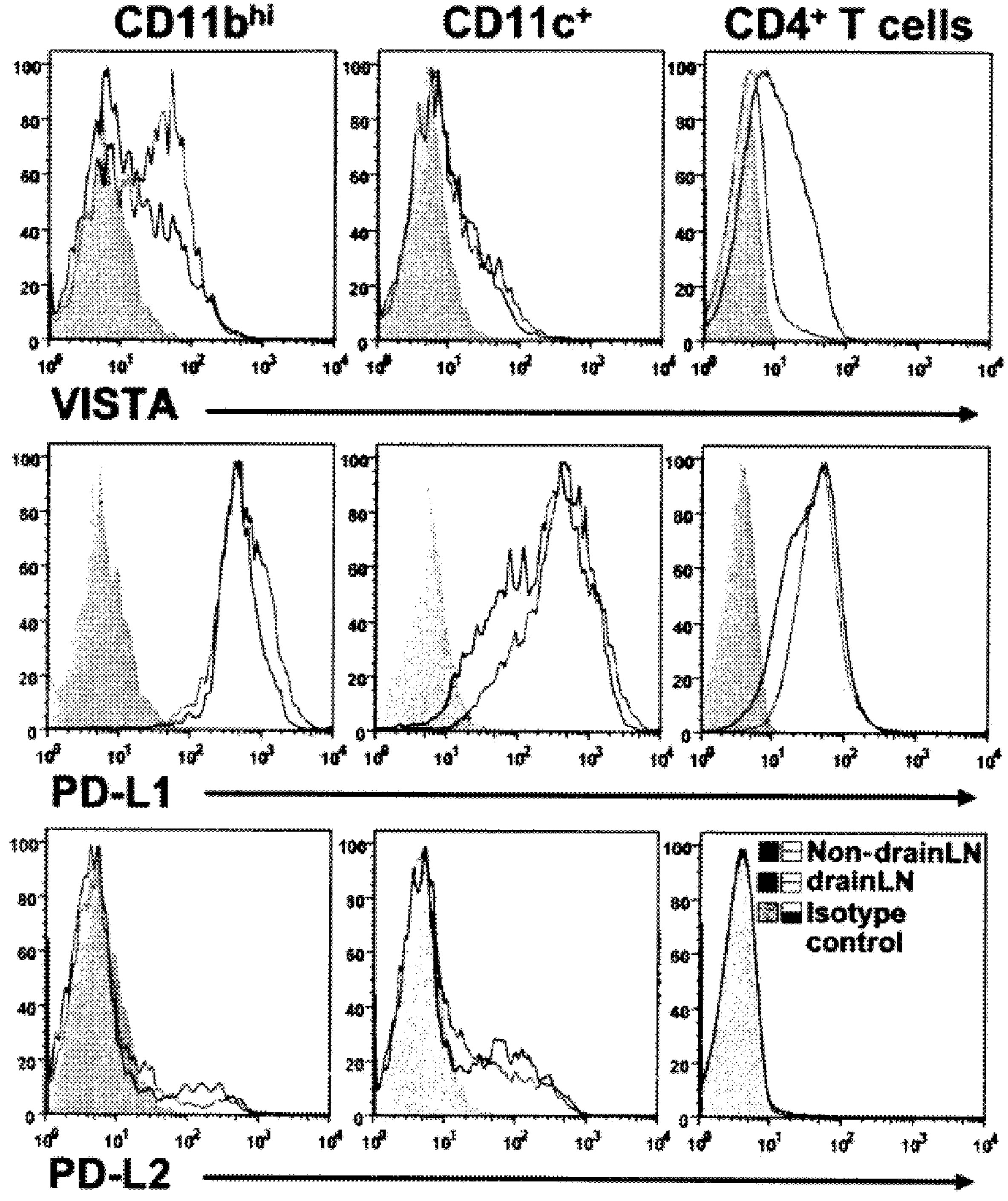

In contrast to its increased expression on APCs, VISTA (PD-L3) expression is diminished on activated DO11.10 CD4+ T cells at a later time point upon immunization (i.e. at 48 hr but not at 24 hr) (FIG. 8). This result suggests that VISTA (PD-L3) expression on CD4 T cells in vivo may be regulated by its activation status and cytokine microenvironment during an active immune response.

Example 3

Functional Impact of VISTA (PD-L3) Signaling on CD4+ and CD8+ T Cell Responses

Figure 9A:
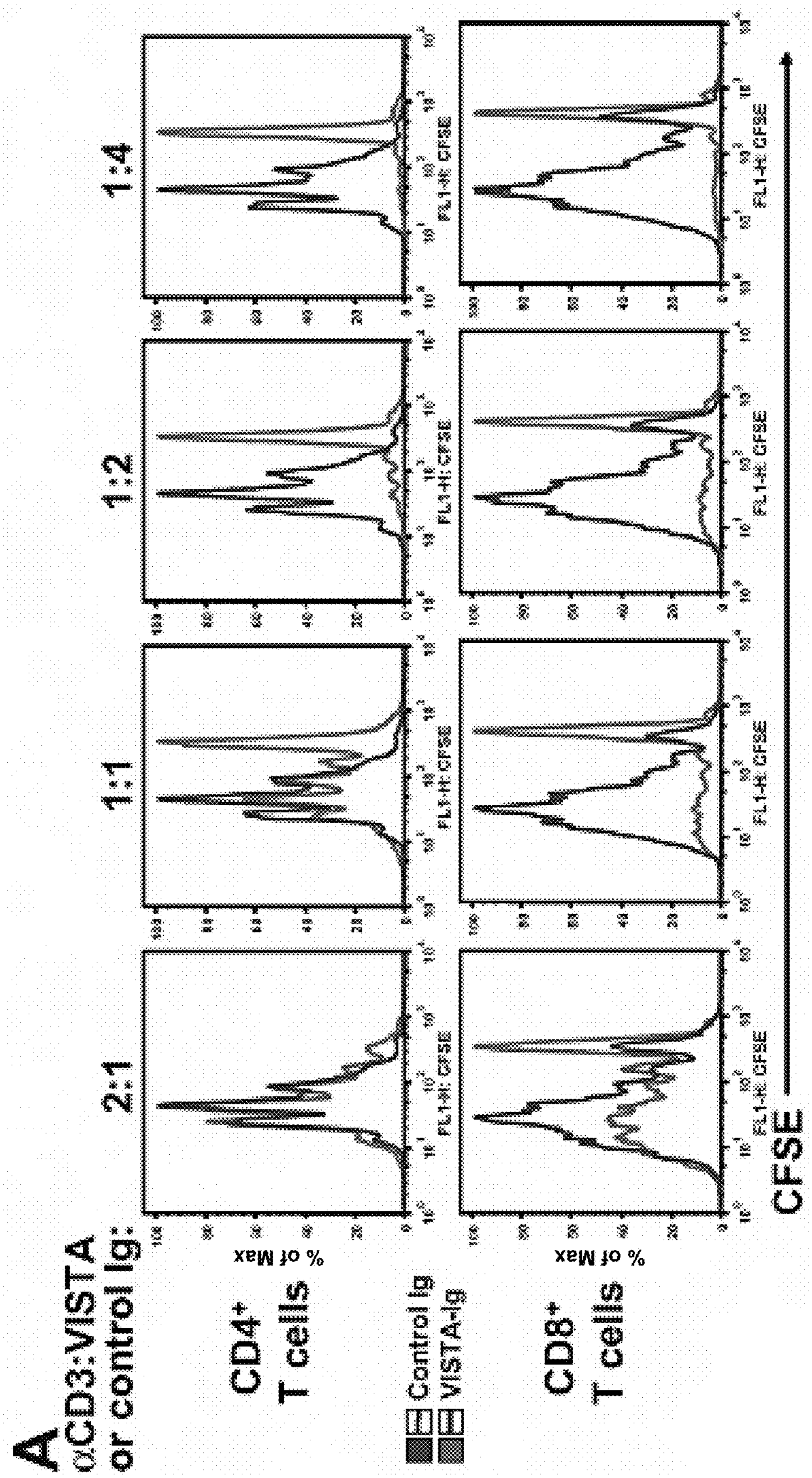
Figure 9B:
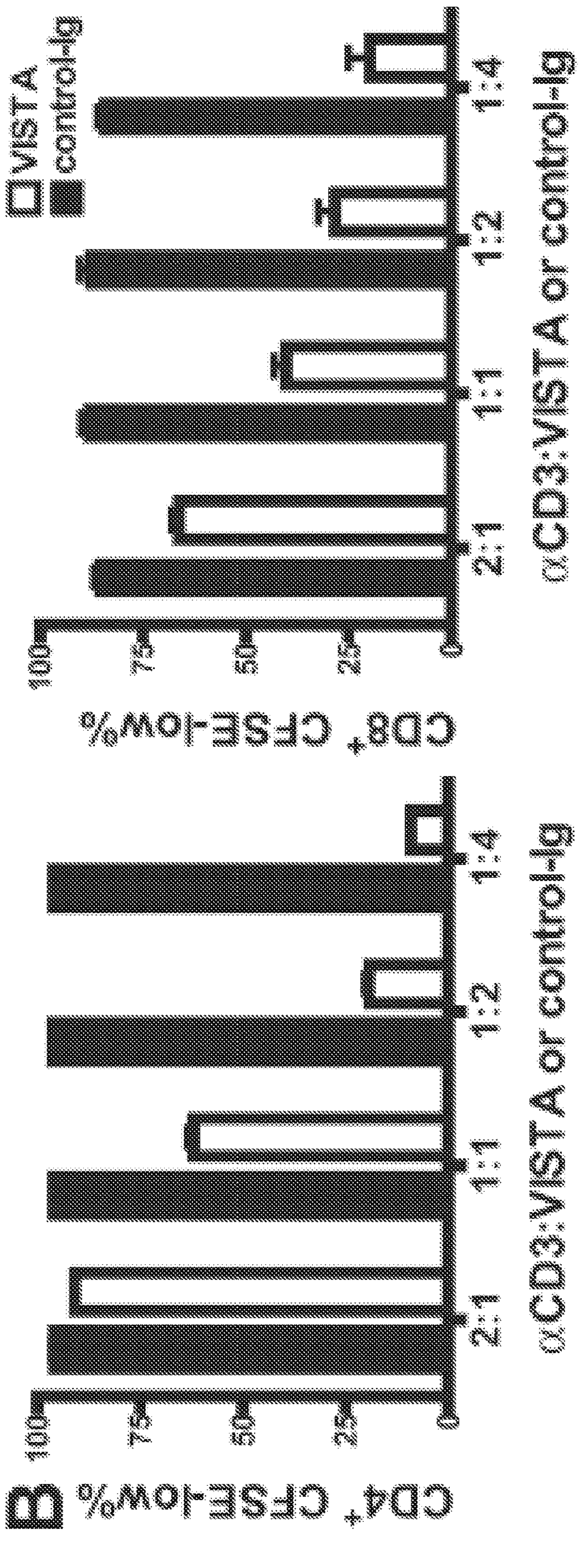
Figure 9C:
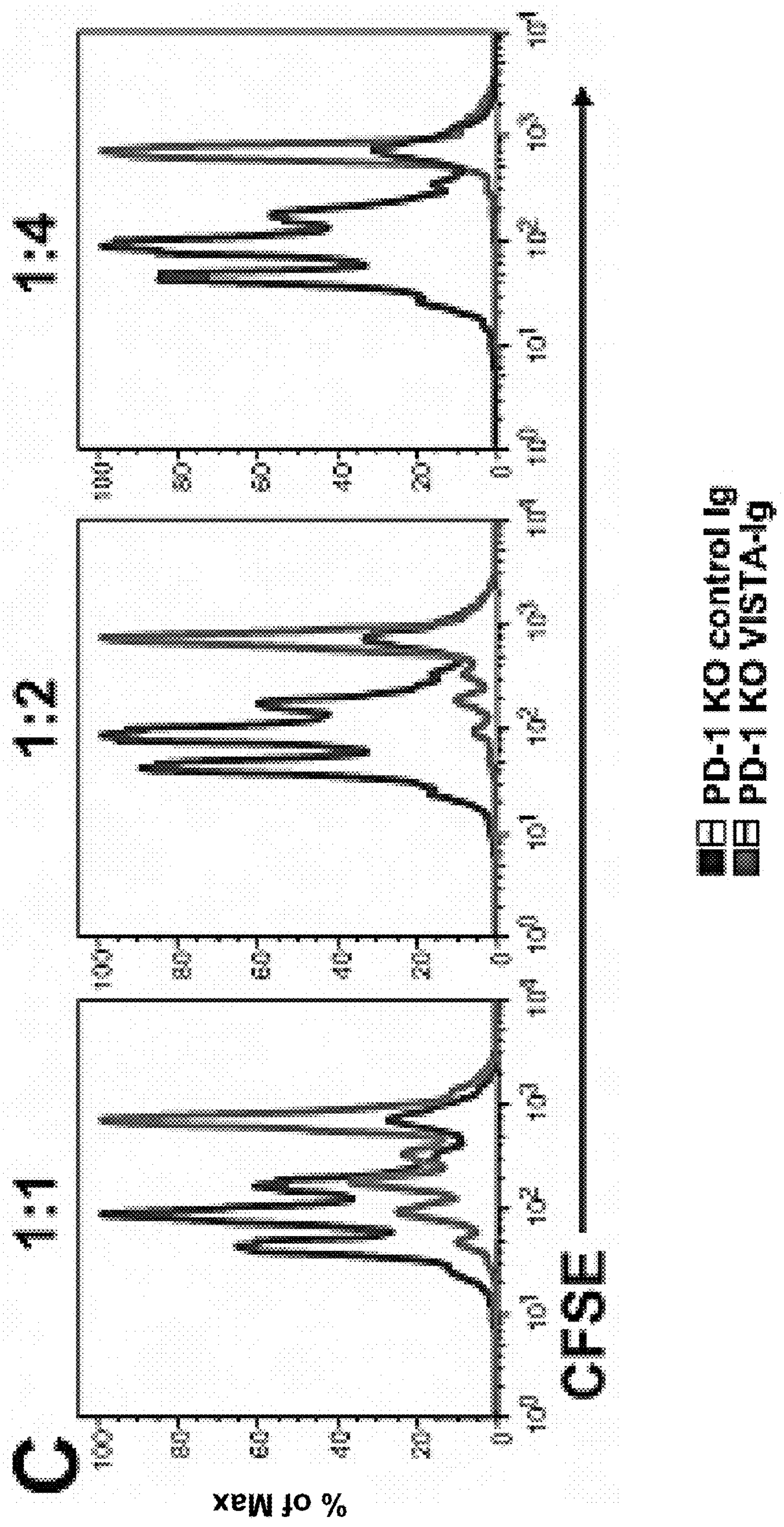
Figure 10:
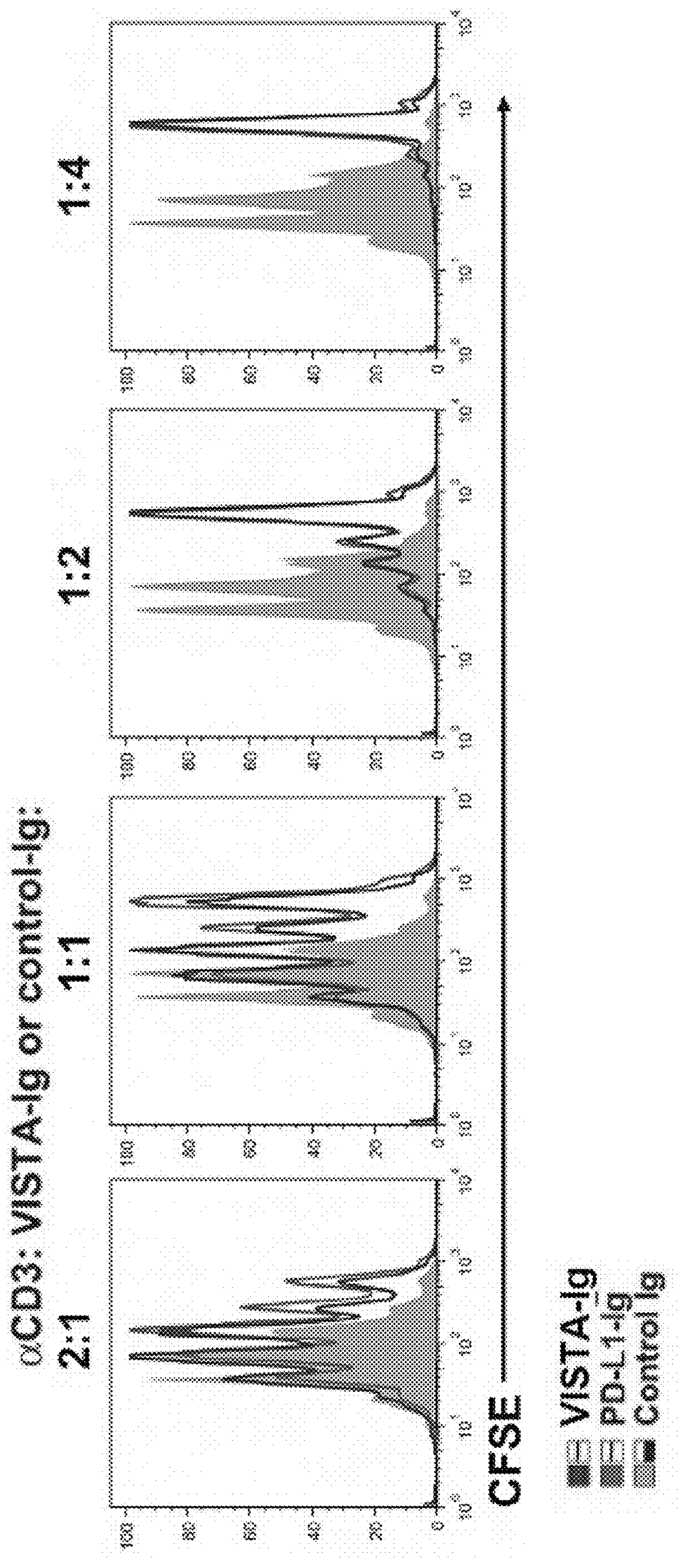

A VISTA (PD-L3)-Ig fusion proteins were was produced to examine the regulatory roles of VISTA (PD-L3) on CD4+ T cell responses. The VISTA (PD-L3)-Ig fusion protein contains the extracellular domain of VISTA (PD-L3) fused to the human IgG1 Fc region. When immobilized on the microplate, VISTA (PD-L3)-Ig but not control Ig suppressed the proliferation of bulk purified CD4+ and CD8+ T cells in response to plate-bound anti-CD3 stimulation, as determined by arrested cell division (FIG. 9A-B). The VISTA (PD-L3) Ig fusion protein did not affect the absorption of anti-CD3 antibody to the plastic wells, as determined by ELISA, thus excluding the possibility of non-specific inhibitory effects. PD-1 KO CD4+ T cells were also suppressed (FIG. 9C), indicating that PD-1 is not the receptor for VISTA (PD-L3). The inhibitory effect of PD-L1-Ig and VISTA (PD-L3)-Ig was also directly compared (FIG. 10). When titrated amounts of Ig fusion proteins were absorbed to the microplates together with αCD3 to stimulate CD4+ T cells, VISTA (PD-L3)-Ig showed similar inhibitory efficacy as PD-L1-Ig fusion protein.

Figure 11A:
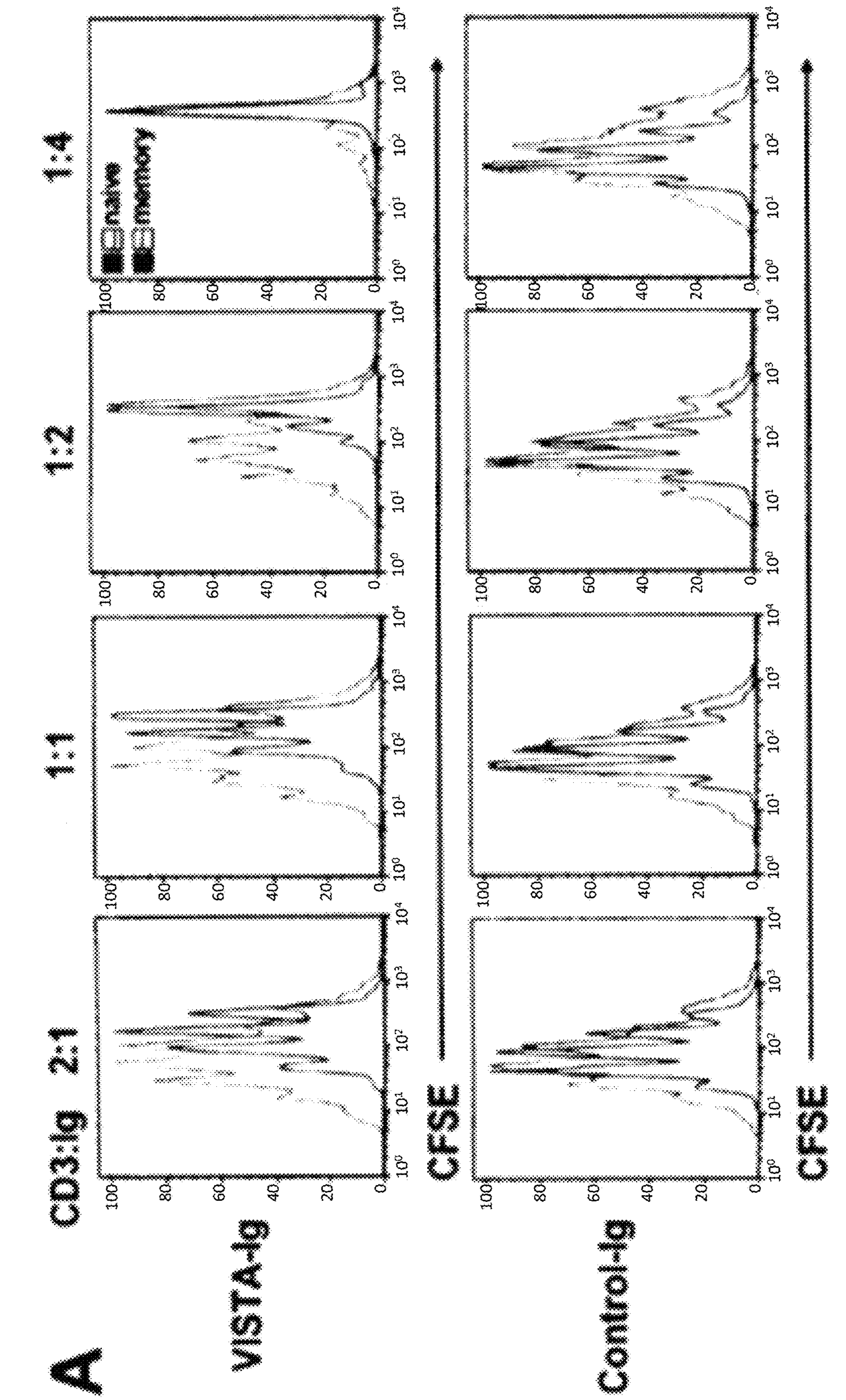
Figure 11B:
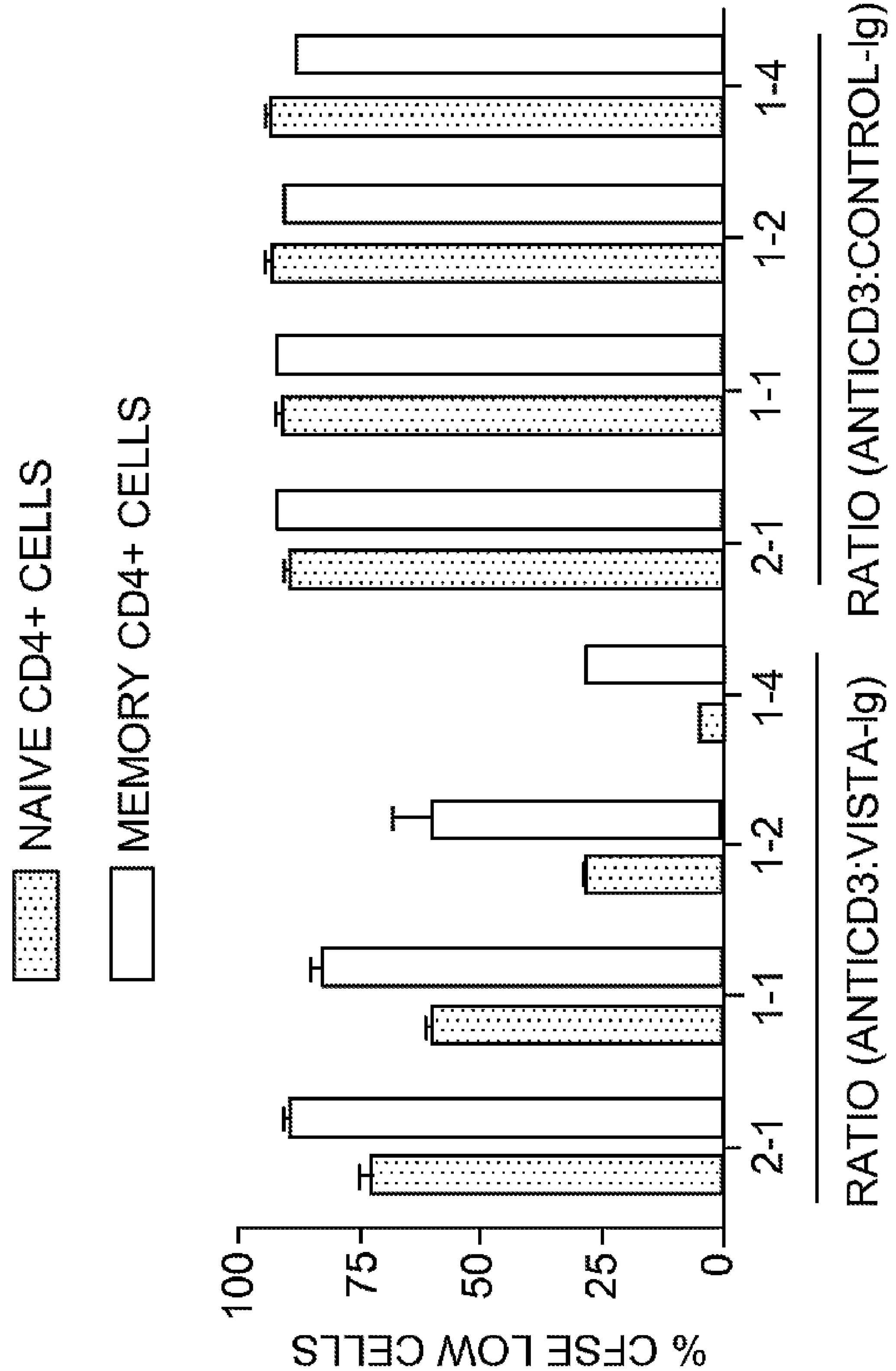

Since bulk purified CD4+ T cells contain various subsets, the impact of VISTA (PD-L3)-Ig on sorted naïve (CD25-CD44lowCD62Lhi) and memory (CD25-CD44hiCD62Llow) CD4+ T cell subsets was evaluated (FIG. 11). VISTA (PD-L3) can suppresses the proliferation of both subsets, albeit with much less efficacy on the memory cells.

Figure 12A:
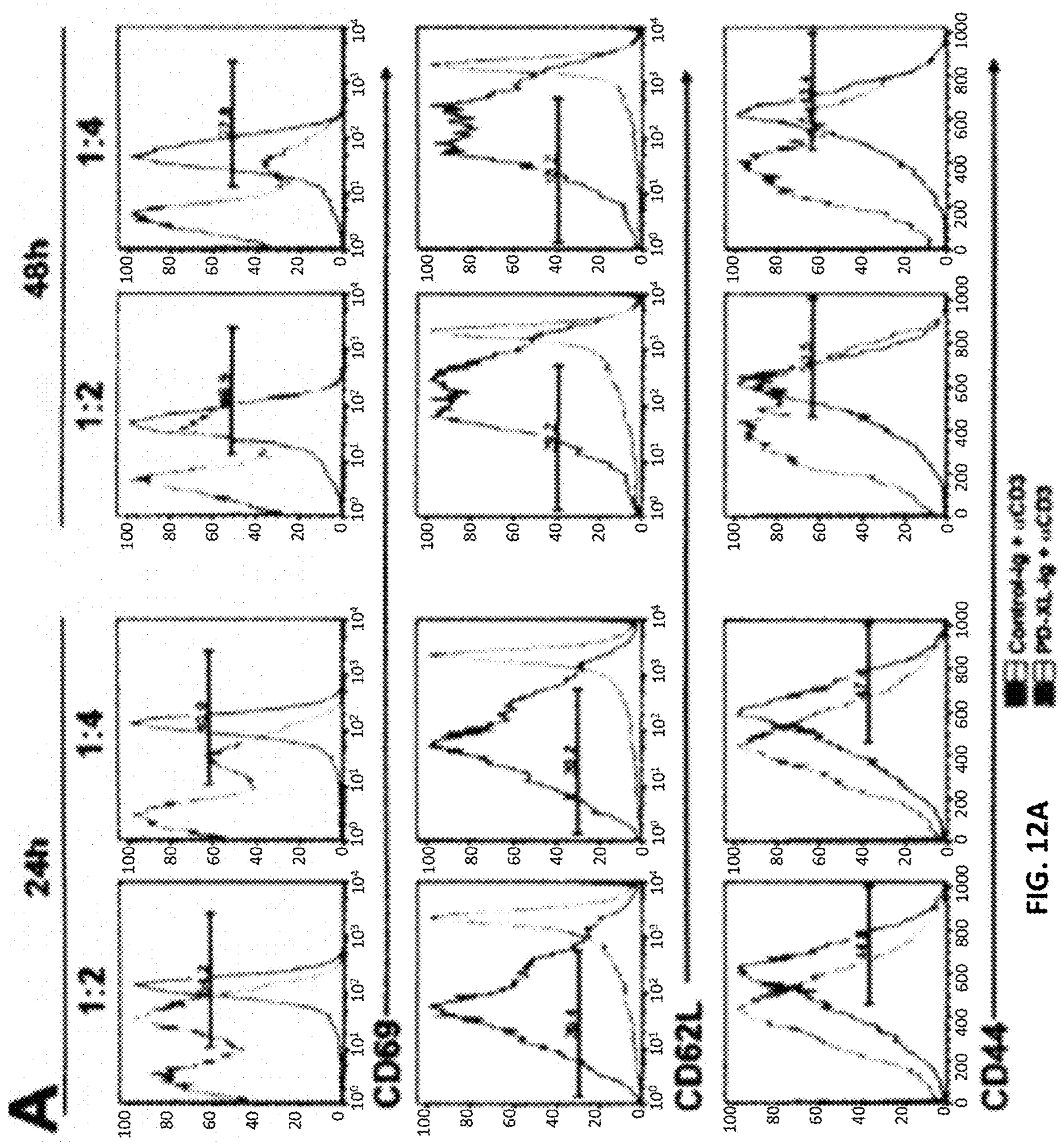
Figure 12B:
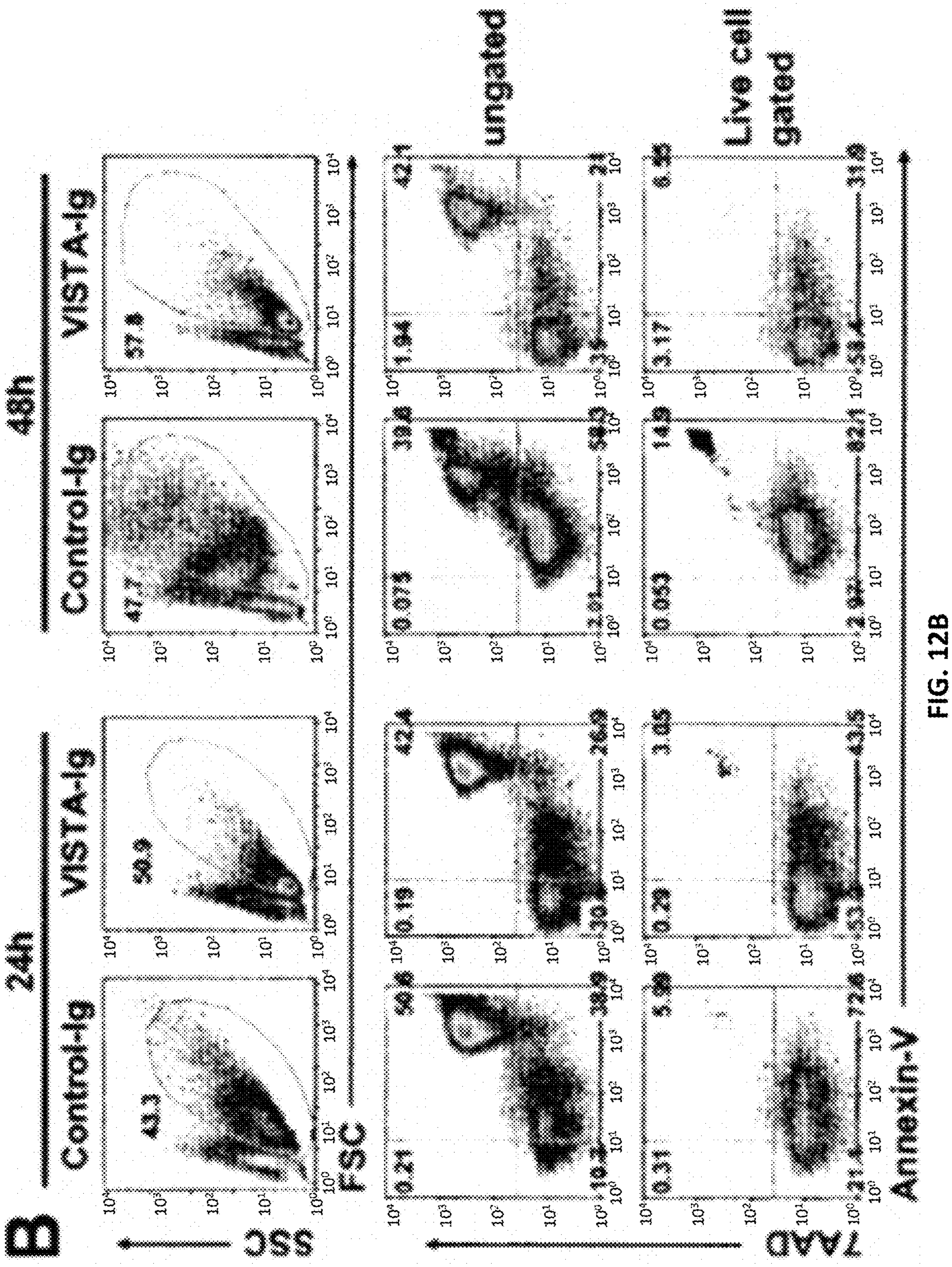

To further understand the mechanism of VISTA (PD-L3)-mediated suppression, the expression of early TCR activation markers and apoptosis were measured following T cell activation in the presence or absence of VISTA (PD-L3)-Ig. Consistent with the negative impact on cell proliferation, there is a global suppression on the expression of the early activation markers CD69, CD44, and CD62L (supplemental FIG. 12A). On the other hand, the VISTA (PD-L3)-Ig fusion protein did not induce apoptosis. On the contrary, less apoptosis (as determined by the percentage of annexin V+ 7AAD− cells) was seen in the presence of VISTA (PD-L3) or VISTA-Ig than the control-Ig, at both early (24 hr) and later stage (48 hr) of TCR activation (FIG. 12B). For example, at 24 hr time point, on total "ungated' population, ~27% cells were apoptotic in the presence of VISTA (PD-L3) or VISTA-Ig, but ~39% control cells were apoptotiC When examining the cells within the live cell R1 gate, it is apparent that VISTA (PD-L3) or VISTA-Ig strongly inhibited activation-induced-cell-death (ACID), because about 72.6% control cells became apoptotic whereas only 43.5% cells were apoptotic when treated with VISTA (PD-L3) or VISTA-Ig. Similar results were seen for the 48 hr time point. Therefore, it appears that VISTA (PD-L3) or VISTA negatively regulates CD4+ T cell responses by suppressing early TCR activation and arresting cell division, but with minimum direct impact on apoptosis. This mechanism of suppression is similar to that of B7-H4. Sica, et al. (2003) Immunity 18: 849-861.

Figure 9D:
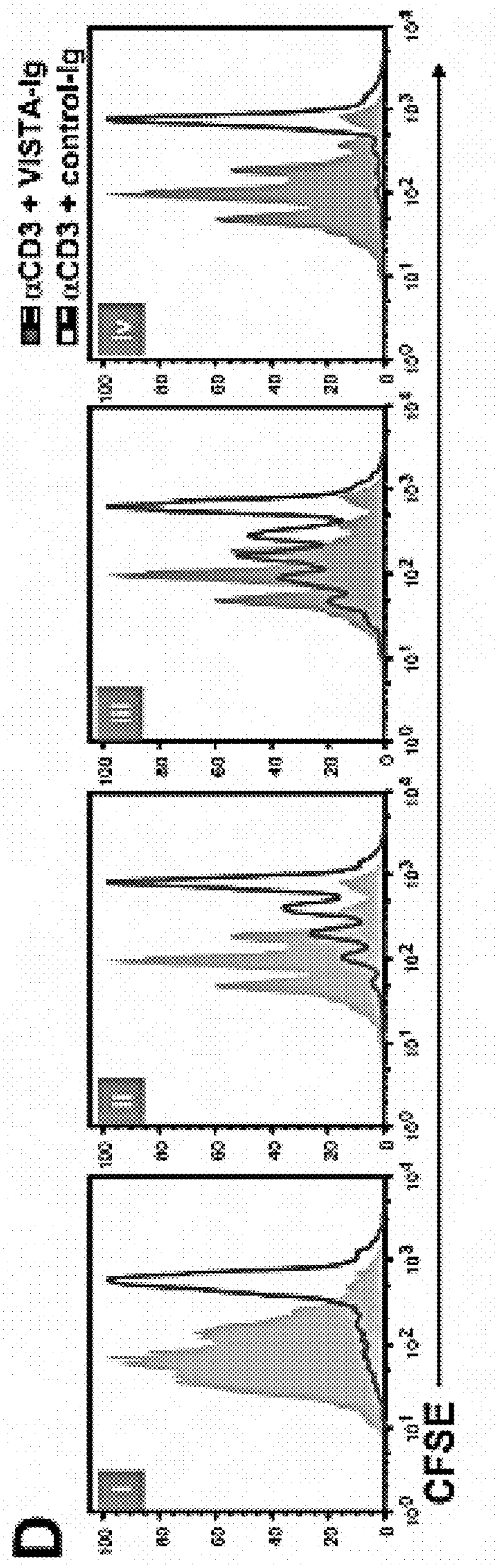

A 2-step assay was developed to determine whether VISTA (PD-L3) or VISTA-Ig can suppress pre-activated CD4 T cells, and how persistent its suppressive effect is. It is shown that the suppressive effect of VISTA (PD-L3) or VISTA-Ig fusion protein persists after its removal at 24 hr post activation (FIG. 9D). In addition, both naïve and pre-activated CD4+ T cells could be suppressed by VISTA (PD-L3) or VISTA-Ig. See FIGS. 9D(i), 9D(iii), and 9D(iv).

Figure 13A:
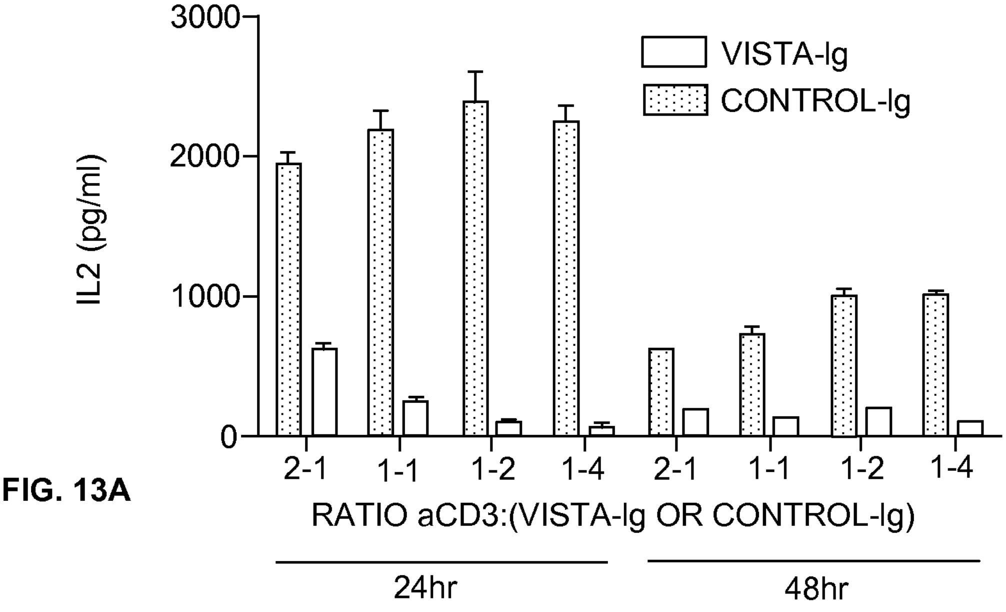
Figure 13B:
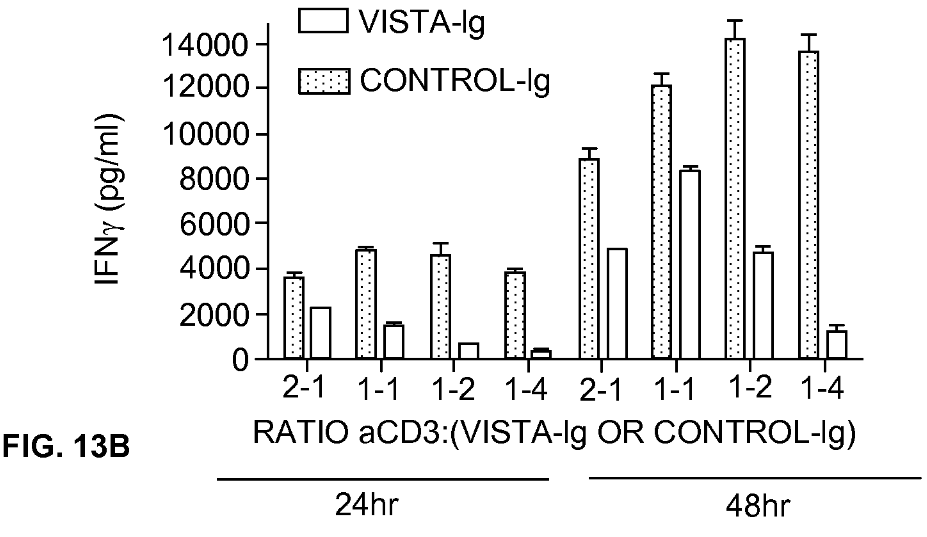
Figure 13C:
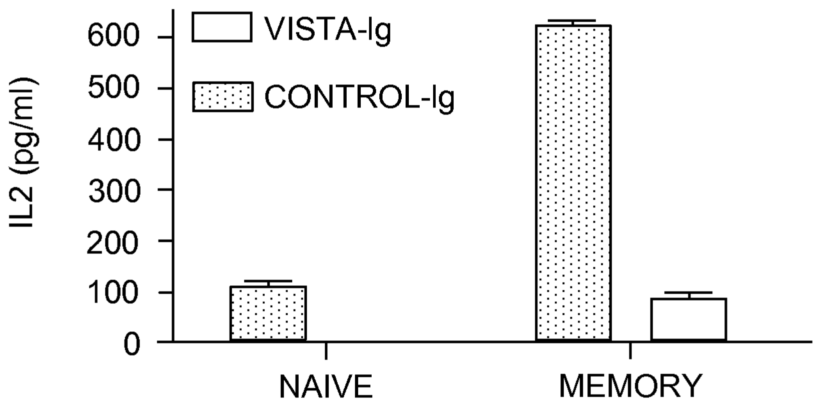
Figure 13D:
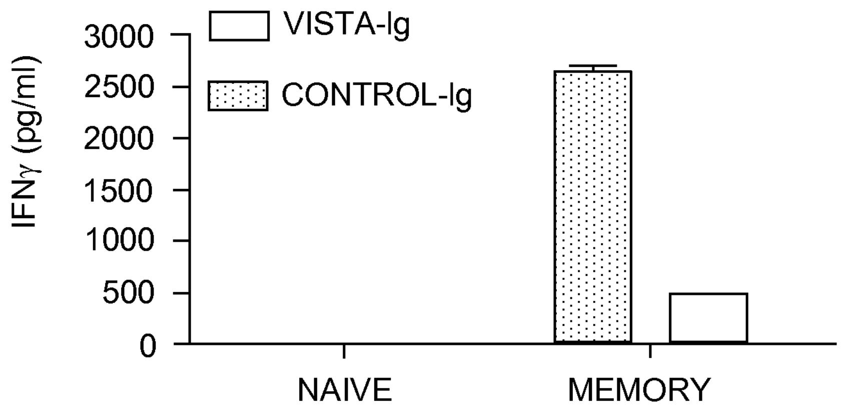
Figure 13E:
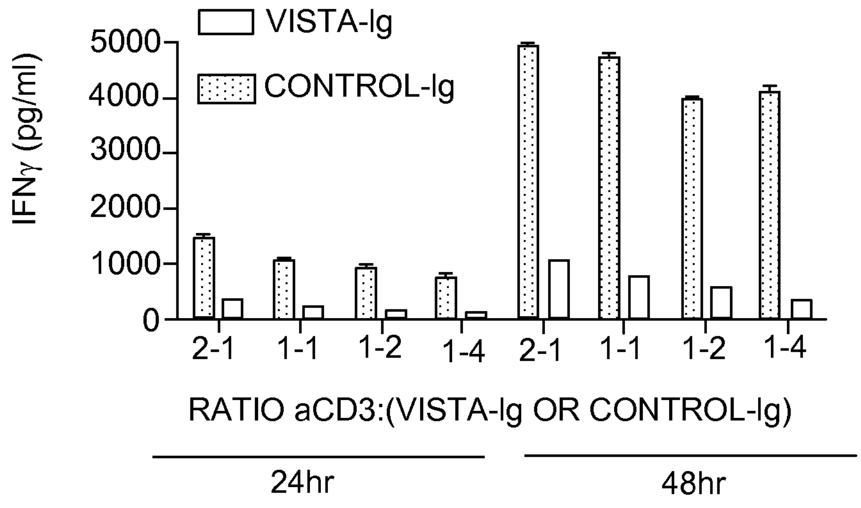

Next, the impact of VISTA (PD-L3) or VISTA-Ig on CD4+ T cell cytokine production was analyzed. VISTA (PD-L3) or VISTA-Ig suppressed the production of Th1 cytokines IL-2 and IFNα from bulk purified CD4+ T cell culture (FIG. 13A-B). The impact of VISTA (PD-L3) or VISTA was further tested on separate naïve (CD25-CD44lowCD62Lhi) and memory (CD25-CD44hiCD62Llow) CD4+ T cell populations. It is shown that memory CD4+ T cells are the major source for cytokine production within the CD4+ T cell compartment, and VISTA (PD-L3) or VISTA can suppress this production (FIG. 13C-D). Similar inhibitory effect of VISTA (PD-L3) or VISTA on IFNα production from CD8+ T cells was also shown (FIG. 13E). This inhibitory effect of VISTA (PD-L3) or VISTA on cytokine production by CD4+ and CD8+ T cells is consistent with the hypothesis that VISTA (PD-L3) or VISTA is an inhibitory ligand that down-regulates immune responses.

Figure 14A:
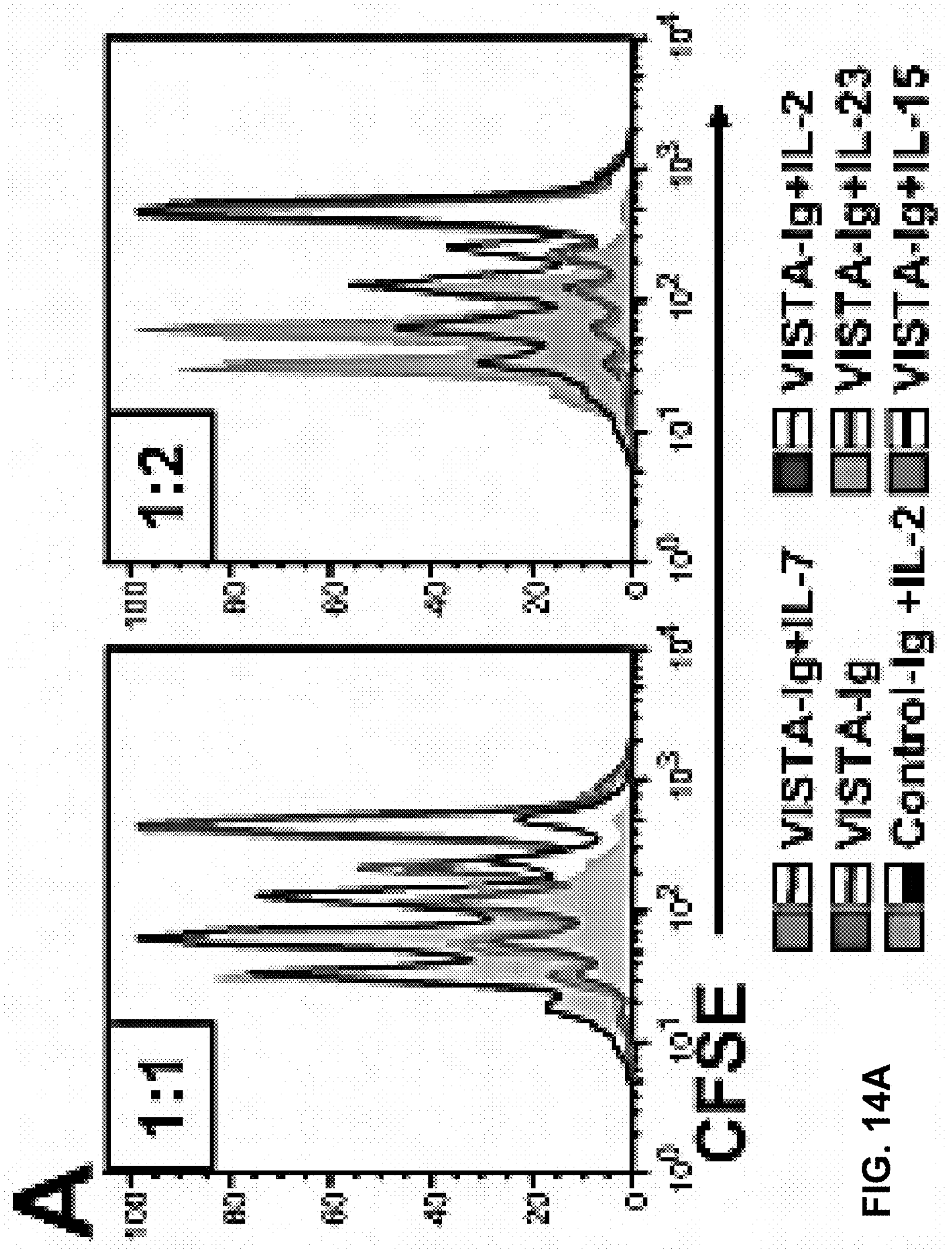
Figure 14B:
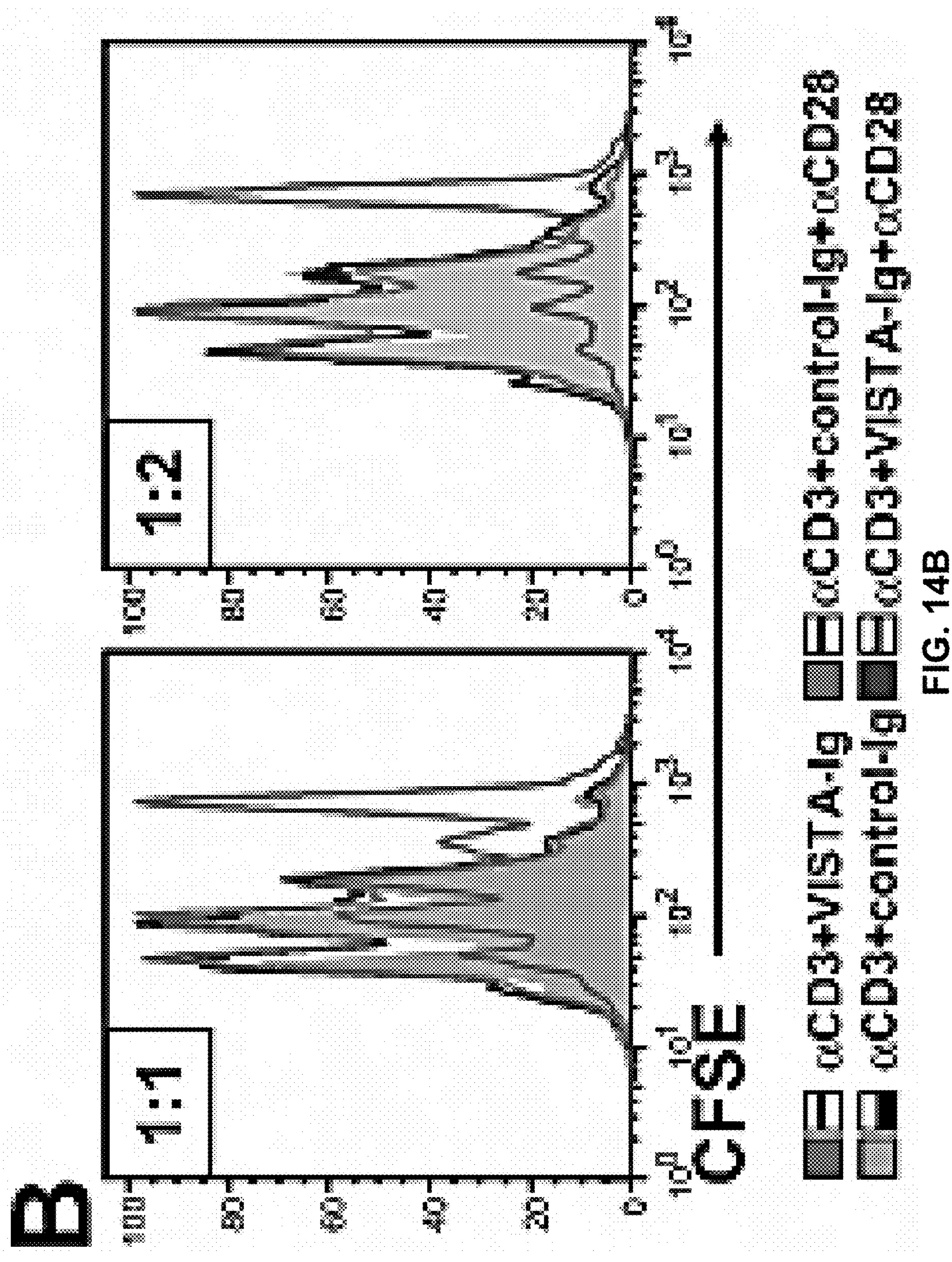
Figure 14C:
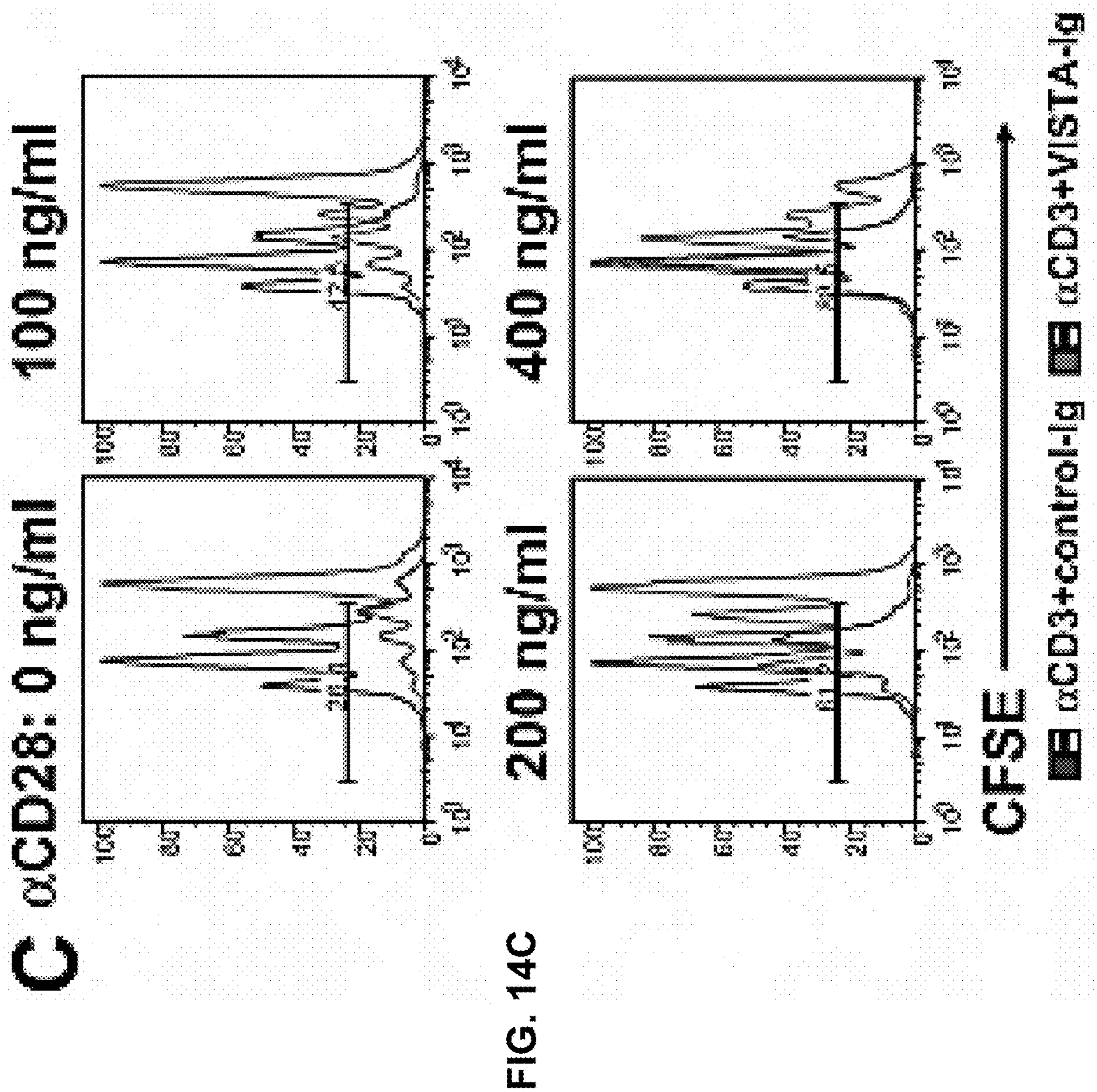
Figure 14D:
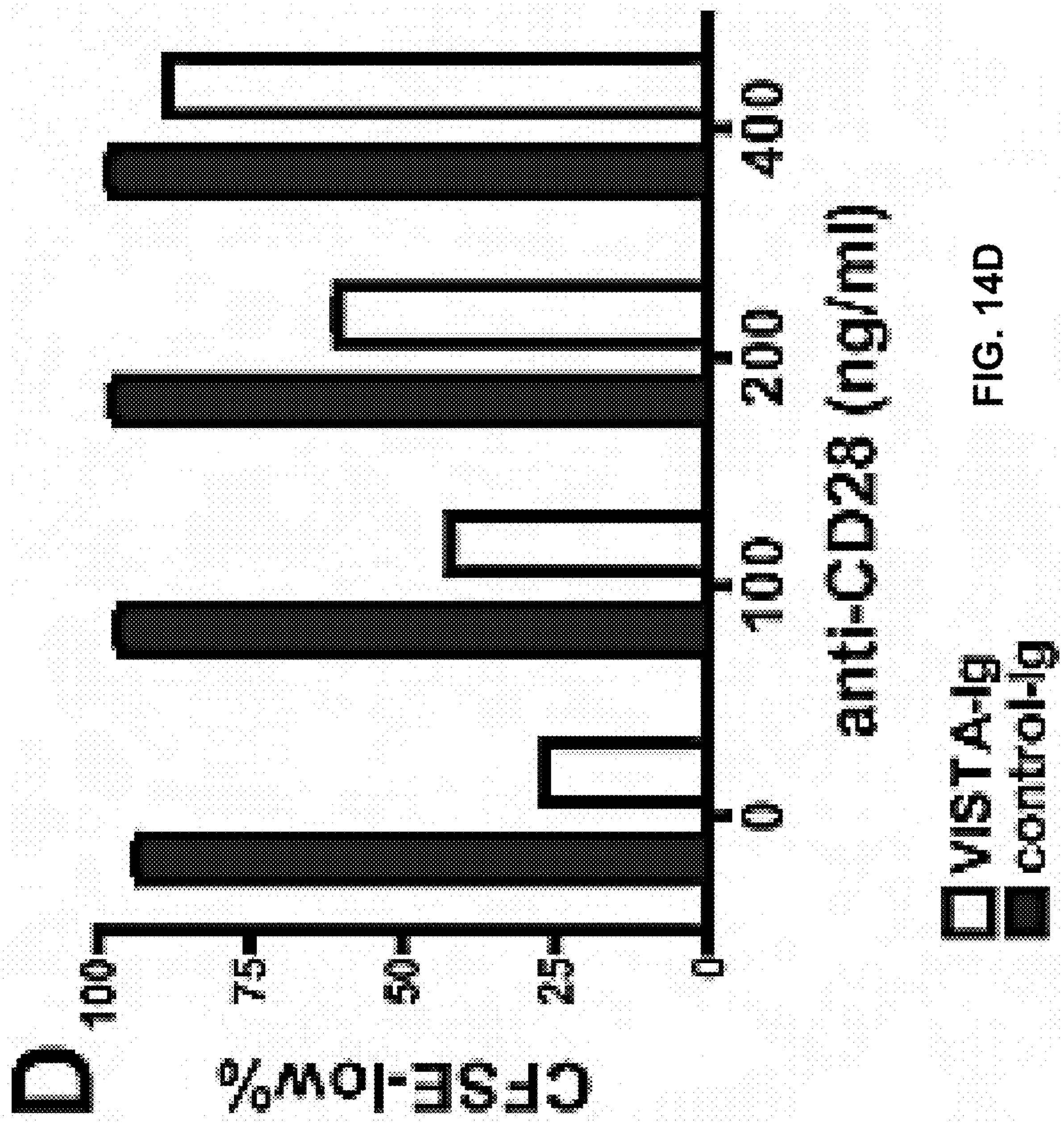

Next, studies were designed to determine the factors that are able to overcome the inhibitory effect of VISTA (PD-L3) or VISTA. Given that VISTA (PD-L3) or VISTA suppressed IL-2 production, and IL-2 is critical for T cell survival and proliferation, IL-2 might circumvent the inhibitory activity of VISTA (PD-L3) or VISTA. As shown in FIG. 14A, exogenous IL-2, but not IL-15, IL-7, or IL-23, partially reversed the suppressive effect of VISTA (PD-L3) or VISTA-Ig on cell proliferation. The incomplete rescue by high levels of IL-2 indicates that VISTA (PD-L3) or VISTA signaling targets broader T cell activation pathways than simply IL-2 production. On the other hand, potent co-stimulation signal provided by anti-CD28 agonistic antibody completely reversed VISTA (PD-L3) or VISTA-Ig mediated suppression (FIG. 14B), whereas intermediate levels of costimulation is still suppressed by VISTA (PD-L3) or VISTA signaling (FIG. 14C). This result suggests that VISTA (PD-L3) or VISTA-mediated immune suppression would be more effective under less inflammatory conditions, but will be inevitably overwhelmed by strong positive costimulatory signals. In this regard, VISTA (PD-L3) or VISTA shares this feature with other suppressive B7 family ligands such as PD-L1 and B7-H4. Sica, et al. (2003) *Immunity* 18: 849-861; Carter, et al. (2002) *Eur J Immunol.* 32: 634-643.

In addition to VISTA (PD-L3) or VISTA-Ig fusion protein, it is necessary to confirm that VISTA (PD-L3) or VISTA expressed on APCs can suppress antigen-specific T cell activation during cognate interactions between APCs and T cells. For this purpose, VISTA (PD-L3) or VISTA-RFP or RFP control protein was over-expressed via retroviral transduction in an artificial antigen presenting cell line (CHO-APC) that stably expresses MHCII and B7-2 molecules Latchman, et al. (2001) *Nat Immunol* 2: 261-268. One problem in expressing VISTA (PD-L3) or VISTA in CHO is that the majority of VISTA (PD-L3) or VISTA failed to localize to the cell surface, perhaps due to the alien environment that lacks support for VISTA (PD-L3) or VISTA surface localization. Although there are no clear motifs present on the cytoplasmic tail of VISTA (PD-L3) or VISTA to suggest the mode of regulation, the tail might play a role for its intracellular localization. Consequently, a tail-less VISTA (PD-L3) or VISTA mutant was designed and was found to successfully localize to CHO cell surface.

Figure 15A:
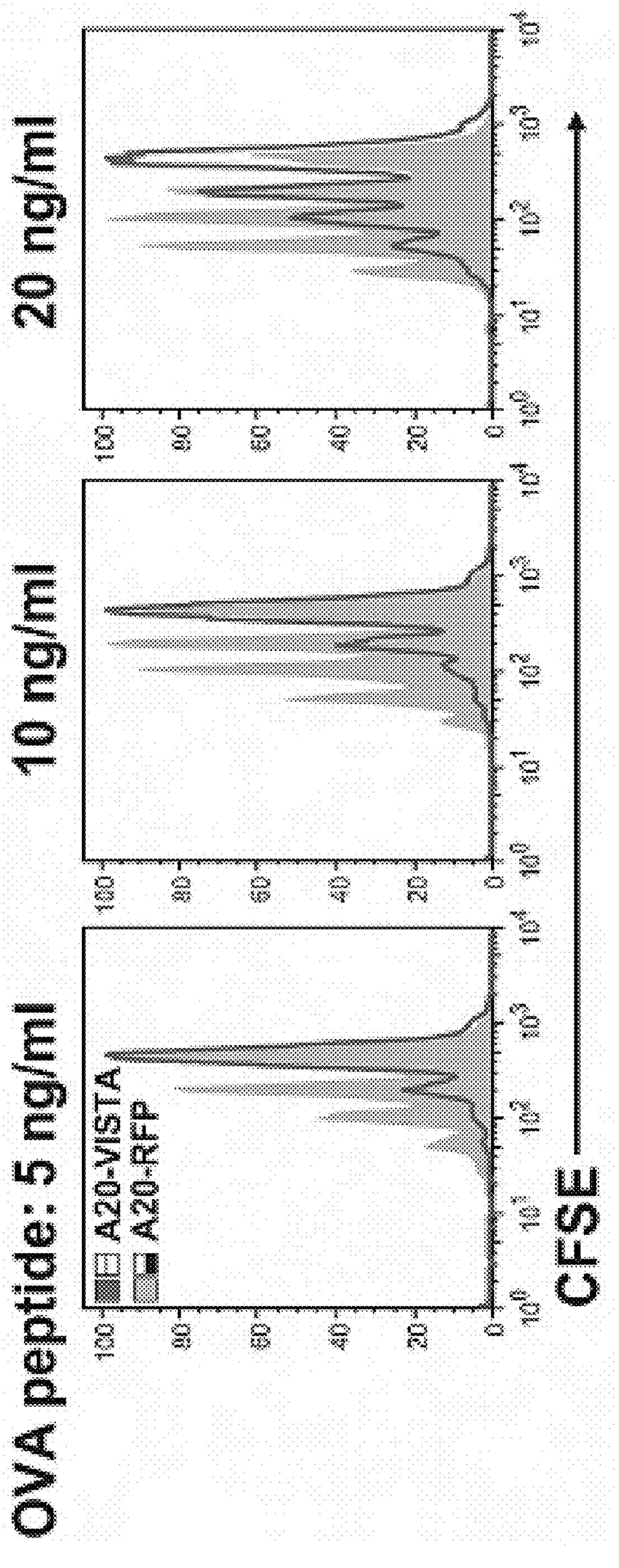
Figure 15B:
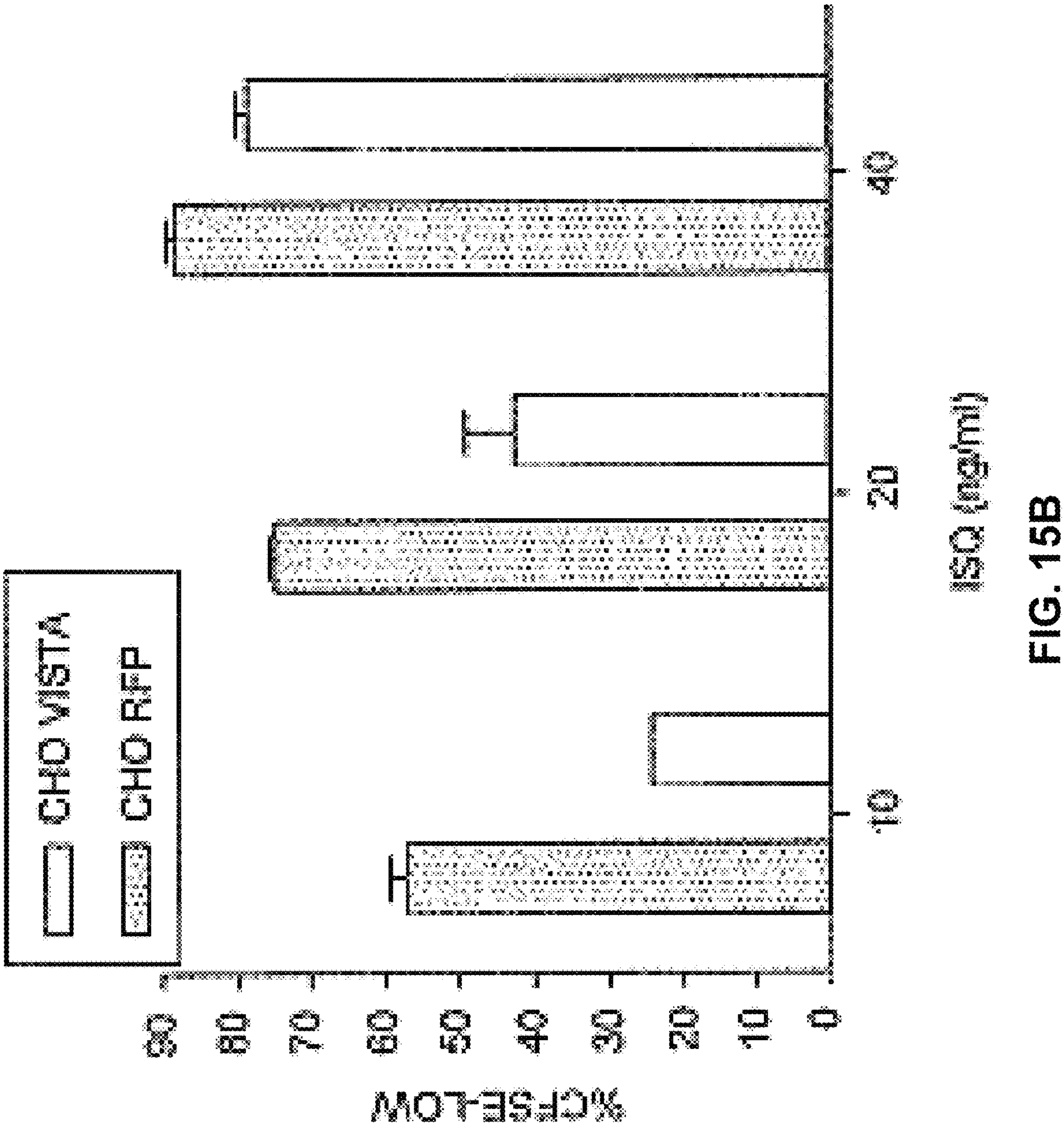
Figure 15C:
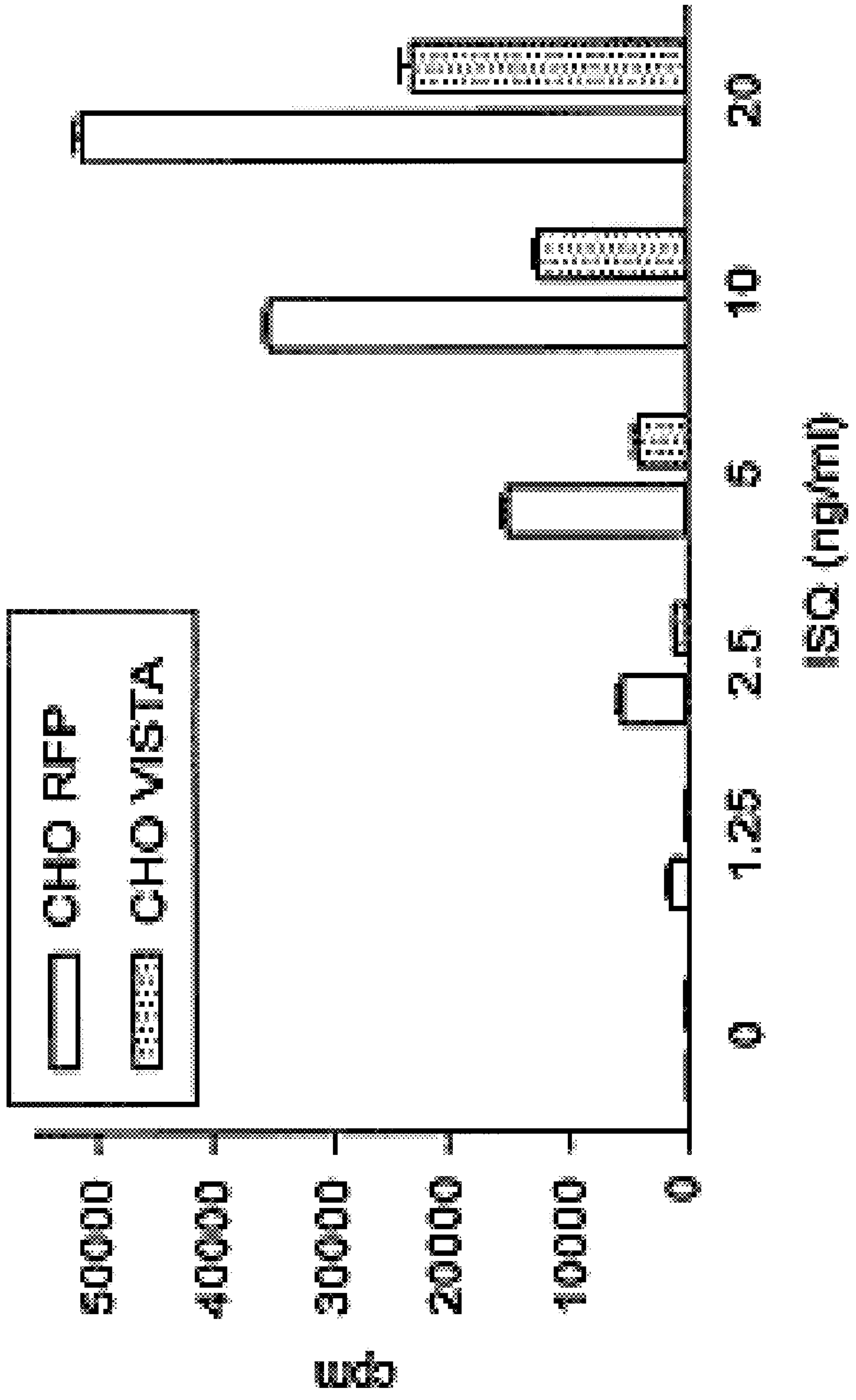
Figure 15D:
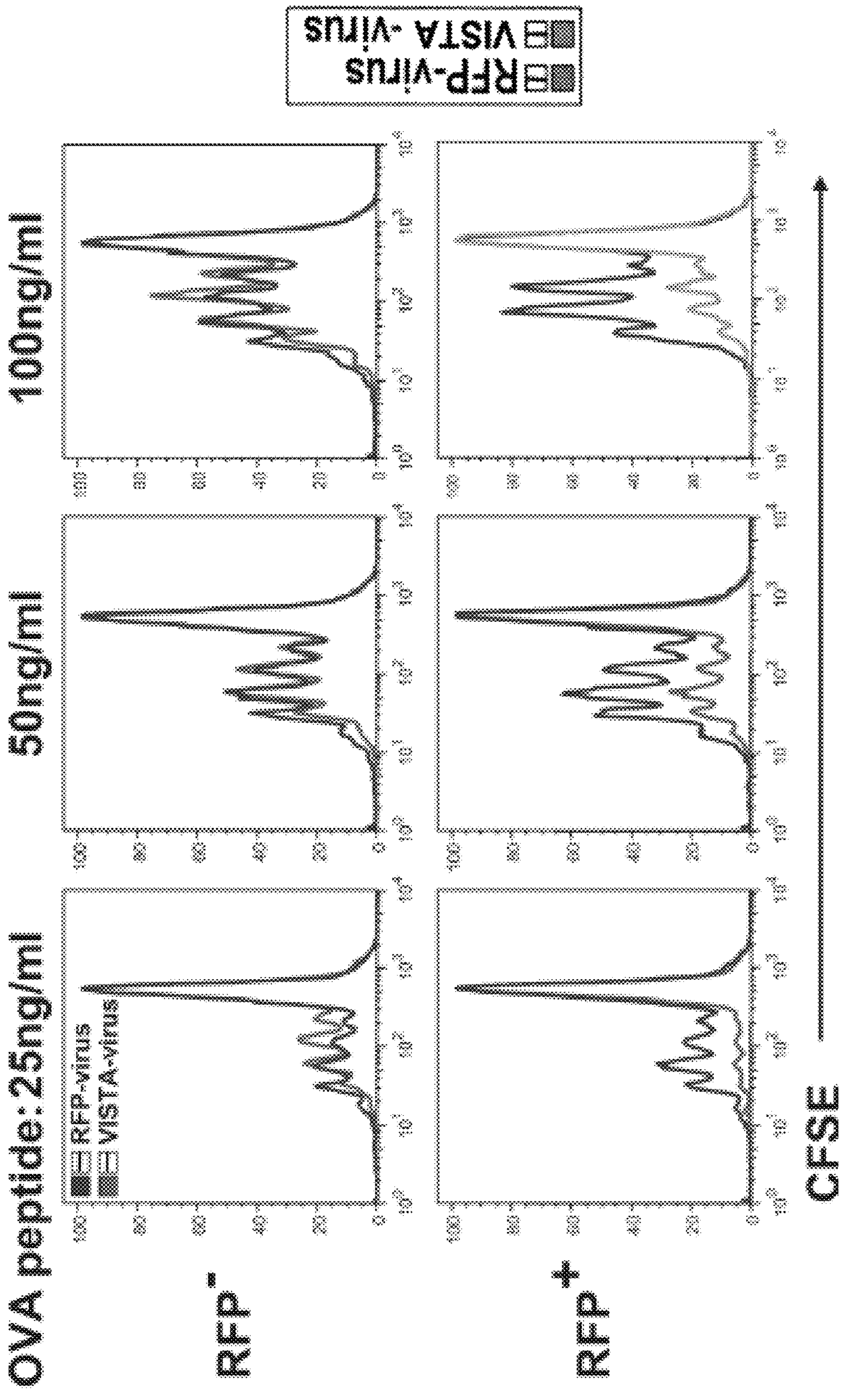
Figure 16:
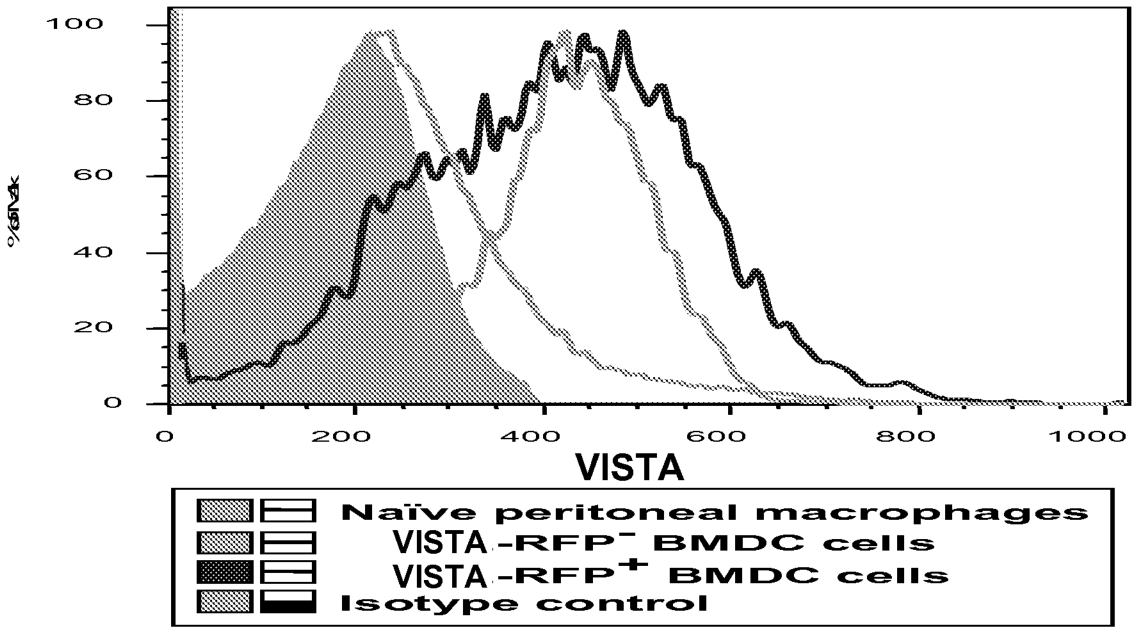

To stimulate T cell response, CHO-VISTA (PD-L3) or VISTA or CHO-RFP cells were incubated together with DO11.10 CD4+ T cells in the presence of antigenic OVA peptide. As shown in FIG. 15A-C, CHO-VISTA (PD-L3) or VISTA induced less proliferation of DO11.10 cells than CHO-RFP cells. This suppressive effect is more pronounced at lower peptide concentrations, consistent with the notion that a stronger stimulatory signal would overcome the suppressive impact of VISTA (PD-L3) or VISTA. In addition, the inhibitory effect of full-length VISTA (PD-L3) or VISTA on natural APCs was confirmed. in vitro cultured bone marrow derived dendritic cells (BMDC) do not express high level of VISTA (PD-L3) or VISTA (FIG. 16). VISTA (PD-L3) or VISTA-RFP or RFP was expressed in BMDCs by retroviral transduction during the 10 day culture period. Transduced cells were sorted to homogeneity based on RFP expression. The expression level of VISTA (PD-L3) or VISTA on transduced DCs was estimated by staining with anti-VISTA (PD-L3) or VISTA monoclonal antibody, and found to be similar to the level on freshly isolated peritoneal macrophages, thus within the physiological expression range (FIG. 16). Sorted BMDCs were then used to stimulate OVA-specific transgenic CD4+ T cells (OTII) in the presence of OVA peptide (FIG. 15D). Expression of VISTA (PD-L3) or VISTA on BMDCs suppressed the cognate CD4+ T cell proliferative responses. This result is consistent with previous data using VISTA (PD-L3) or VISTA-Ig fusion protein and CHO-APC cells, suggesting that VISTA (PD-L3) or VISTA can suppress T cell-mediated immune responses.

Example 4

Evaluation of Anti-VISTA (PD-L3) or VISTA Antibodies in Multiple Sclerosis Animal Model (EAE)

Figure 17A:
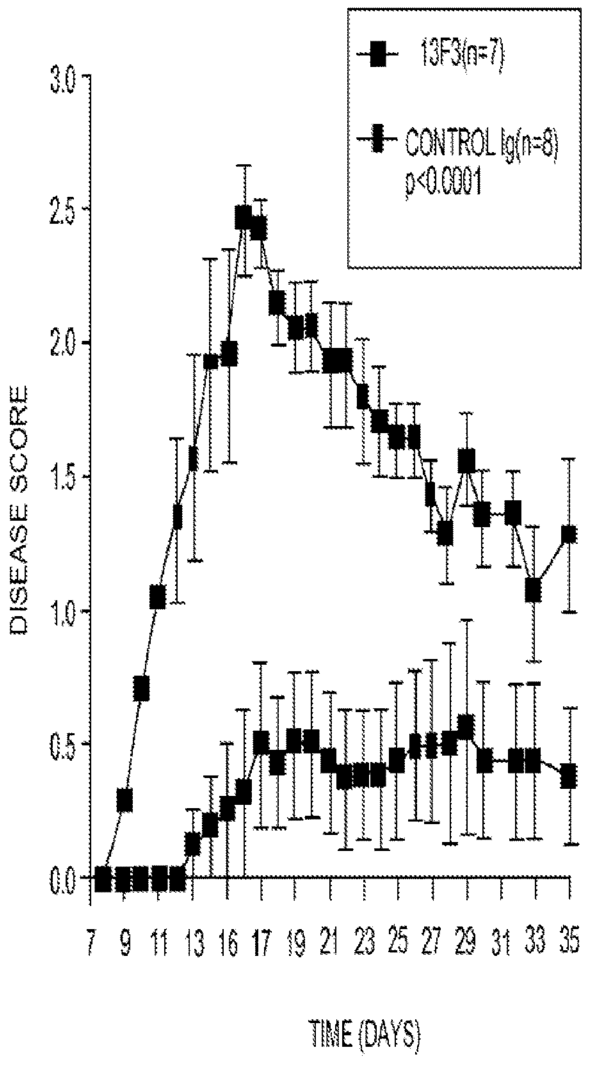
Figure 17B:
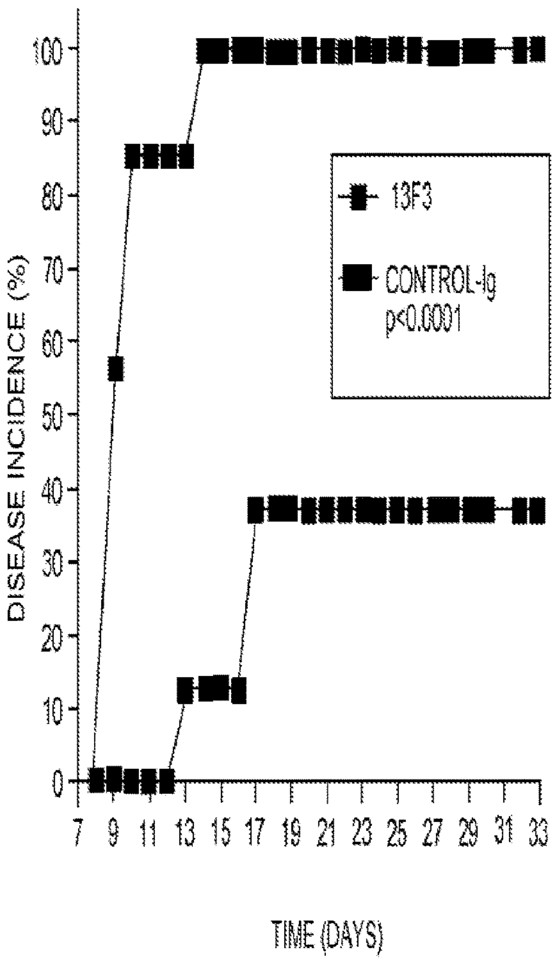
Figure 20A:
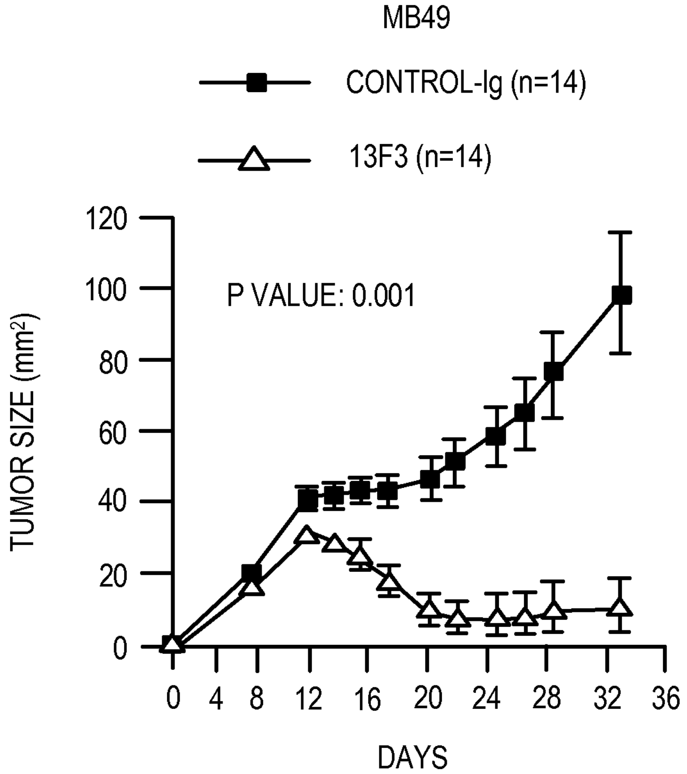
Figure 20B:
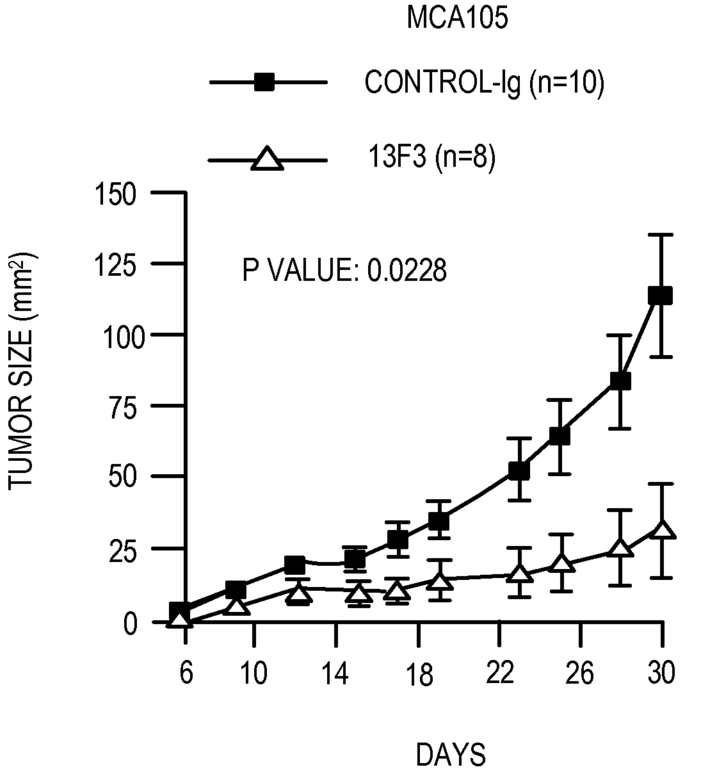
Figure 20C:
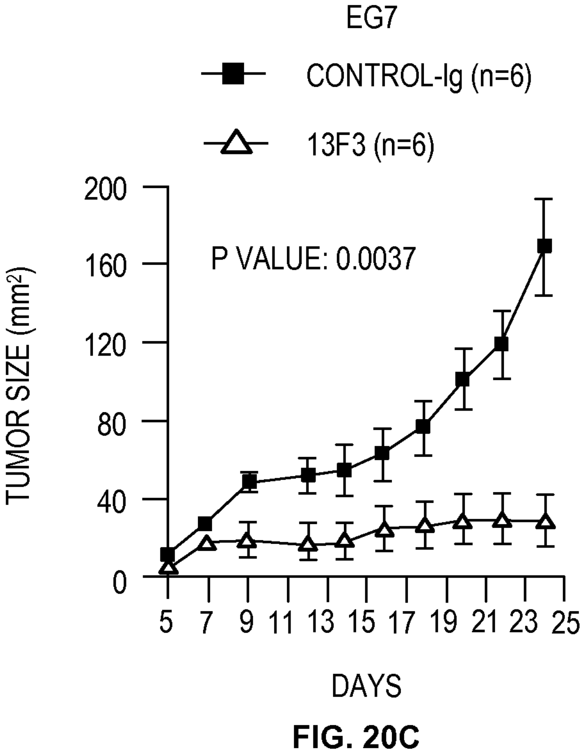
Figure 20D:
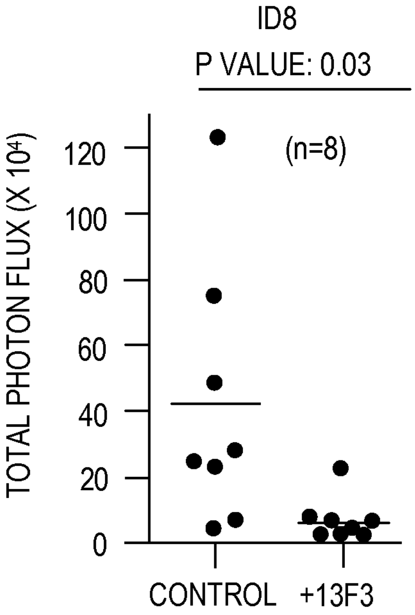
Figure 20E:
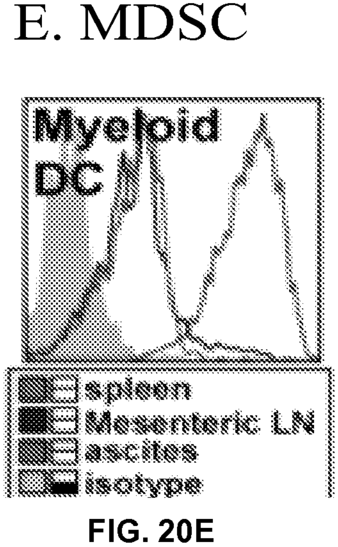

Because the αVISTA (PD-L3) or VISTA monoclonal antibodies in vivo appeared to suppress T cell responses, αVISTA (PD-L3) or VISTA was tested to evaluate if it can inhibit a T cell-mediated autoimmune disease. Using the Experimental Allergic Encephalomyelitis (EAE) model, the functional impact of αPDL-L3 monoclonal antibodies on inflammatory diseases was determined. EAE is a widely used murine model of the human autoimmune disease multiple sclerosis. EAE can be induced by either immunization with myelin antigens in adjuvant or by adoptive transfer of myelin-specific T cells, which results in inflammatory infiltrates of various effector T cells and B cells, and macrophages, and demyelination of central nervous systems.

αPDL-L3 monoclonal antibody was tested in the passive EAE model to avoid induction of anaphylaxis due to the injection of large amount of monoclonal antibody as foreign antigen. In this adoptive transfer EAE model, donor SJL mice were immunized with CFA and PLP peptide. On day 10, total lymphocytes from draining LN were isolated, and cultured in vitro with PLP peptide, IL-23 (20 ng/ml) and anti-IFNγ (10 μg/ml) for 4 days. Expanded CD4 T cells were then purified and adoptively transferred into naïve recipient mice. This analysis indicated that αPDL-L3 monoclonal antibody delayed disease onset, as well as reduced disease severity, thereby shifting the disease progression curve significantly (FIG. 17). In addition, it reduced severity in a large percentage of the mice and greatly increased survival from around 22% to over 75%. This demonstrated activity of αPDL-L3 monoclonal antibody in EAE is consistent with the in vitro data, and demonstrates the use of this reagent as a novel immunoregulatory reagent in various inflammatory diseases.

Example 5

Expression of VISTA in the CNS

The expression of VISTA in the CNS was also effected. These assays revealed that in mice with disease, VISTA expression is markedly reduced (from 76%→33%) on the CD11b+ cells (FIG. 22), consistent with the hypothesis that the loss of VISTA may be permissive for enhanced inflammation. This is interesting, and likely functionally important when we contrast inflammatory myeloid cells herein, with the MDSC in tumors that express extremely high levels of VISTA. It has been reported that EAE mice have elevated numbers of myeloid derived suppressor cells (CD11b+Ly-6Chigh MDSC) in the spleen which are potently suppressive for T cell activation and may temper disease32. Our data strongly suggest that VISTA may play a role in myeloid-mediated suppression in EAE.

Example 6

The Impact of VISTA on the Fate and Function of T Cells in EAE

We also conducted experiments assaying the effect of VISTA on the fate and function of T cells in EAE. We wanted to assess if VISTA alters the development of pathogenic, encephalitogenic T cells, clonal T cell expansion, T cell polarity, longevity, and conversion of Teff→Treg. We studied the impact of VISTA blockade on T cell fate in EAE. Consistent with the higher disease score, analysis of CNS at the end of disease course confirmed significantly more IL17A-producing CD4+ T cell infiltration (from 0.66→11%) in 13F3 (αVISTA) treated group.

Example 7

VISTA (PD-L3) or VISTA Transgenic and Knock-Out Mice

Using Lentiviral infection of embryos, four transgenic mice ubiquitously expressing VISTA (PD-L3) or VISTA have been produced. These mice express full-length VISTA (PD-L3) or VISTA under the control of the human elongation factor 1 promoter. These mice were generated using lentiviral vector pWPT. Similar to other PD-L1 family members (Appay, et al. (2002) *J. Immunol.* 168: 5954-8), it is contemplated that VISTA (PD-L3) or VISTA will function as a negative regulator in vivo while functioning to co-stimulate αCD3 T cell proliferation in vitro. In this respect, these mice are expected to spontaneously develop autoimmunity and in vivo immune responses in the VISTA (PD-L3) or VISTA transgenic mice (i.e., humoral immune responses, T cell priming) are evaluated to assess systemic autoimmune disease development.

For knock-out mice, VISTA (PD-L3) or VISTA is inactivated by homologous recombination. A BAC clone containing full-length VISTA (PD-L3) or VISTA sequence was purchased from INVITROGEN® (Carlsbad, Calif.). A VISTA (PD-L3) or VISTA targeting vector was generated by inserting a 1.6 kb fragment located at the 5' side of the second exon of VISTA (PD-L3) or VISTA gene upstream the neomycin gene and the 5 kb fragment located at the 3' side of the third exon of VISTA (PD-L3) or VISTA gene downstream the neomycin gene. B6-derived embryonic stem (ES) cells are electroporated with VISTA (PD-L3) or VISTA targeting vector and recombined clones are selected. Selected clones are then injected into C57BL/6 blastocysts and the resulting chimeric male offspring are mated to FLP-deleter mice to remove the neomycin cassette. Transmission of the targeted allele in the offspring is determined by PCR from genomic DNA. The second and the third exon contain the VISTA (PD-L3) or VISTA domain, therefore, the resulting mice have only the inactivated form of the VISTA (PD-L3) or VISTA molecule.

The overall immune capacity of VISTA (PD-L3) or VISTA deficient mice is determined as with other PD-L−/− mice, including assessment of T cell responses to antigen, humoral immune responses, overt autoimmunity (e.g., Systemic Lupus Erythematosus, inflammatory bowel disease), and increased susceptibility to induced autoimmune disease (experimental autoimmune encephalomyelitis) (Chen (2004) supra).

Example 8

VISTA (PD-L3) or VISTA Specific Antibodies Tested in Collagen-Induced Arthritis Animal Model Male DBA/1J mice were immunized at the base of their tail with 100 μl of emulsion containing 100 μg chick type-II collagen (C-II) in CFA (*Mycobacterium tuberculosis* 3.5 mg/ml) and boosted IP with 100 μg aqueous C-II on day 21 post-immunization. Mice of each treatment group (n=6) were either untreated (NT-black circles), injected with 300 μg hamster IgG (Ham Ig-black squares) or injected with 300 μg of monoclonal-antibody "7c9" (red triangle) or "13F3" (green triangle), as indicated. Injections were given every 2 days. Arthritic swelling was scored on a scale of 0-4 for each paw of each mouse on the days indicated. The arthritis score shown is the total score of all paws of mice in each treatment group divided by the number of mice in the group.

Example 9

VISTA Blockade by a Specific VISTA Monoclonal Antibody Enhances T Cell Responses In Vitro A VISTA-specific monoclonal antibody (13F3) was identified which neutralizes VISTA-mediated suppression (FIG. 18). $CD11b^{hi}$ myeloid APCs were purified from naïve mice to stimulate OT-II transgenic $CD4^+$ T cells in the presence or absence of 13F3. Consistent with its neutralizing effect, 13F3 enhanced T cell proliferation stimulated by $CD11b^{hi}$ myeloid cells, which were shown to express high levels of VISTA.

Example 10

Anti-VISTA Enhances Anti-Tumor Immunity

Because of the capacity of anti-VISTA to enhance T cell activation, whether anti-VISTA would enhance the protective immune response to an immunogenic tumor was assessed. A model in which we have a great deal of experience is the bladder carcinoma, MB49. MB49 expresses male antigen, and thus it is modestly immunogenic in female mice, although, it will grow and kill female mice if there is no immune intervention. To test the efficacy of αVISTA therapy, female mice were administered MB49 tumor cells subcutaneously (sq) and treated with αVISTA. Days thereafter, the size of the tumor was measured until the mice had to be euthanized. FIG. 19 shows that anti-VISTA therapy greatly impairs tumor growth. This is due to the ability of anti-VISTA to intensify cell-mediated immune (CMI) responses.

Example 11

Effect of AVISTA on Tumor Regression in 4 Murine Tumor Models

Experiments in the immunogenic bladder carcinoma tumor MB49 have shown that neutralization of VISTA using monoclonal antibody 13F3 and protects host from tumor growth. The data indicates that VISTA has a considerable negative immunoregulatory role in the microenvironment of a tumor because of its extremely high expression of MDSCs. Studies examining the effect of anti-mouse VISTA on the growth of immunogenic (MB49) and highly non-immunogenic (B16) tumor models will further confirm the efficacy of αVISTA therapy, shed light on the mechanism of action, and provide the basis for selecting the optimal dose and timing. The rationale for each tumor model is detailed below.

TABLE 3

| Tumor Name | Tumor Type | Host | Groups | ASSAYS |
|---|---|---|---|---|
| MB49 | Bladder Carcinoma | B6 Female | αVISTA Control Ig | Tumor growth |
| MB49 | Bladder Carcinoma | B6 Male | | Survival Immune/ |
| B16.F10 | Melanoma | B6 Male or female | | Autoimmune |
| ID8 | Ovarian Cancer | B6 Female | | Assays |

MB49 in female mice: Efficacy in this murine model has been demonstrated. MDSCs in this model also express elevated levels of VISTA. In this model, due to the presence of H-Y antigen, the MB49 tumor is modestly immunogenic. Since we know anti-VISTA therapy is effective, this model will serve as a “positive” control to determine dosing (1-100 μg/mouse; and timing (day of tumor inoculation, or 4, 7, 10 days after tumor; therapeutic intervention) of anti-VISTA therapy.

MB49 in male mice: Using doses and timing effective in female mice, the efficacy of anti-VISTA therapy in male mice (in which the tumor is less immunogenic) is determined.

B16 melanoma: Anti-CTLA-4 monoclonal antibody was shown highly effective in this model, and represents a non-immunogenic tumor where the mouse model has been valuable for predicting success in humans. Dosing regimes and timing will be similar to those shown to be effective in the MB49 model.

ID8 Ovarian carcinoma: It is in this model, that VISTA expression has been shown to be extremely high on MDSCs. Mice bearing ID8 tumor are treated with αVISTA at the time of tumor inoculum or at day 5, 15, 25 post inoculation.

Methods. B6 WT mice are used to determine the optimal dose and timing of anti-VISTA treatment for the remission of all murine tumor models noted. The models to be used are listed in the Table 3.

The readout for this dose and timing assay are tumor growth kinetics. For MB49 and B16 studies, all tumor studies are done via intradermal (i.d.) inoculation and therefore tumor size can be readily measured. Tumor measurements is collected every 2-3 days using a caliper. In each of these models, the impact of anti-VISTA or control antibody will be tested for its ability to slow tumor growth or facilitate tumor regression. Growth of ID8 will be followed using a luciferase transduced ID8 and whole body imaging using an IVIS Workstation. In addition, host survival will also be determined.

Data on tumor growth is expressed as mean tumor volume±SEM and differences between groups will be analyzed by two-tailed ANOVA. Probability (p) values less than 0.05 is considered statistically significant. Survival data is analyzed using the Kaplan-Meier method with the Wilcoxon rank test and the log-rank test used to verify the significance of the difference in survival between groups. In the B16 models, frequencies of mice that develop vitiligo is determined.

Using these methods slowed tumor growth and/or tumor regression in mice treated with anti-VISTA monoclonal antibody is obtained as compared with mice treated with control ab in several of the non-immunogenic tumor models. It has already been shown that anti-VISTA treatment delays tumor growth in an immunogenic tumor model. As each of these tumor models have their own specific growth kinetics and, anticipated dependency on VISTA to confer tumor growth and suppress immunity, mice will be administered monoclonal antibody either at the time of tumor inoculum or at times thereafter. Additionally, at least 3 different concentrations of anti-VISTA monoclonal antibodies are tested to determine the optimal dose for therapeutic benefit.

As shown in FIG. 20A-E, VISTA monoclonal antibody treatment reduced tumor growth in all 4 of these tumor models wherein mice were inoculated either subcutaneously (sq) with (A) MB49, (B) MCA105, (C) EG7 tumor cells, or (D) intraperitoneal (ip) with ID8-luciferase tumor cells, and treated with VISTA monoclonal antibody 13F3 every other day (300 μg) beginning on day +1. Subcutaneous tumor growth was monitored. For ID8-luciferase tumor, mice were imaged on day 30 using Xenogen IVIS. (E) VISTA expression on myeloid leukocytes in tumor-bearing mice was also determined. Draining LN and tumor tissues (ascites) were analyzed for VISTA expression. These findings show that VISTA expressed on MDSC is a major suppressive molecule that interferes with the development of protective anti-tumor immunity, and αVISTA relieves this suppressive activity allowing immune intervention and slowing growth of tumor. These findings also support the conclusion that VISTA on myeloid cells in autoimmune disease plays a pivotal function in regulating the extent of inflammation.

Example 12

Synthesis of Oligomeric VISTA and VISTA Fusion Proteins Useful for the Treatment of Autoimmunity Soluble VISTA-Ig in vitro is not suppressive nor can its binding to cells be readily detected. By contrast, this molecule bound to plastic is profoundly suppressive. In addition, studies using VISTA-Ig in vivo did not show overt activity. With respect to these studies the VISTA-Ig that was created has mutations in the CH2-CH3 domain precluding FcR binding, and therefore is not cytophilic in vivo. Recent studies have shown that tetrameric PD-L1 bound 100× higher ($K_d$ 6×10$^{-8}$ M) than monomeric PD-L126 to PD-1, and that binding to cells was readily detectable. Tetrameric PD-L1 was not tested in vivo, but in vitro it was shown to block the functional suppression by native PD-L1. Using similar methods oligomers are made that will target the VISTA pathway and elicit potent immunosuppressive activity in vitro ad in vivo.

Such oligomers are constructed using the monomeric extracellular domain of VISTA or a fragment thereof, e.g., at least 50, 75, 100, 125, 150, 175 or 200 amino acids long which extracellular domain or a portion thereof is used as the building blocks for oligomer. In these methods the inventors take advantage of the well-established MHC tetramer technologies. In these methods the VISTA ectodomain construct or a fragment is linked to the N-terminus of a variety of oligomerization domains (identified herein) in order to generate a series of VISTA complexes with valencies that span from divalent to heptavalent.

Thereby, a series of non-covalent oligomers is created based on high affinity coiled-coil domains that direct the stable formation of dimeric, trimeric, tetrameric, pentameric and heptameric assemblie. These oligomeric constructs are expressed in a host cell (e.g., *E. coli*). When expression is effected in *E coli* the expressed oligomers are then refolded and purified from inclusion bodies using standard laboratory protocols. This approach has routinely produced high quality material for biological and structural analysis, including MHC-peptide complexes and trimeric GITRL66. The isolated oligomeric proteins are then assessed by SDS-PAGE, analytical gel filtration, analytical ultracentrifugation and mass spectrometry. These quality control measures ensure the availability of homogeneous, well-characterized materials for in vitro and in vivo studies. The parallel organization of these constructs results in molecules in which the valency is equal to the oligomeric state since each individual VISTA complex is positioned to productively interact with cell surface bound VISTA receptor. The above constructs possess extreme stability and homogeneitiy of oligomeric state. (Non-covalent coiled-coil oligomerization domains typically exhibit melting temperatures that exceed 100° C., except for the heptamer sequence which exhibits a melting temperature of 95° C.

In addition dimeric VISTA-Ig is tetramerized that is either cytophilic or not cytophilic. The Fc fusion constructs of VISTA in frame with the IgG1 Fc (both wild-type IgG1 and the existing non-FcR-binding IgG1) are modified with an N-terminal BirA site for enzymatic biotinylation and cloned into the pIRES2-EGFP vector. Enzymatic biotinylation will allow specific, single residue modification and orientation upon avidin multimerization. This approach has been used for the generation of numerous Ig-fusion proteins, including B7-1, PD-L1, PD-L2 and TIM-3. The expressed proteins are then enzymatically biotinylated in vitro, purified by size exclusion HPLC, and tetramerized using PE-Avidin. The resulting tetramers which are cytophilic or not, are assessed in vivo.

These engineered multimeric VISTA proteins are useful in treating autoimmunity and other conditions wherein intervention in the VISTA pathway and immunosuppression is therapeutically warranted.

Example 13

VISTA Adenoviral Vectors for Inducing Immune Suppression

Gene transfer using recombinant adeno-associated virus (AAV) has seen great technological development in gene therapy Specifically, AAV-mediated gene delivery of PD-L1 gene, or CTLA4-Ig and CD40-Ig has achieved therapeutic efficacy in autoimmune disease models of lupus (Kyttaris et al., 2005) and cardiac transplantation. These methods will be used to deliver either full length VISTA, or oligomeric VISTA ectodomains, and their therapeutic effects are assessed in the EAE model. Recombinant adenovirus vector expressing either full-length murine VISTA, or oligomeric VISTA ectodomain, is created using the Adeno-XTM Expression System (Clontech) according to the manufacturer's instructions. Briefly, VISTA is cloned into an E1 and E3-deleted, pAdDEST-based expression vector, under the control of the human cytomegalovirus (CMV) promoter. VISTA and control lacZ expressing adenovirus are then purified from cell lysates. For systemic overexpression of VISTA, adenovirusis administered to mice by intravenous tail vein injection ($1\times10^9$ plaque-forming units [Pfu]) either prior to or shortly after disease induction via immunization, or after disease onset. The control mice will receive 100 μl PBS. Disease development and alterations are monitored in both SJL mice and C57BL/6 mice, which exhibit different disease progression pattern, and which represent two distinct forms of clinical manifestation of human MS patients.

Example 14

Functional Studies with Engineered Proteins and Adenoviral Vectors

Mice are also administered (5-100 μg of protein/mouse×3 weekly) with engineered VISTA and/or adenoviral vectors. Following administration, T cell expansion, differentiation, as well as EAE development is determined.

Example 15

Structural Studies on VISTA and Determining Molecular Determinants of VISTA Function Affinity, specificity, oligomeric state, and the formation and localization of organized signaling complexes are critical contributors to immune function. All of these features impact signaling and immune regulation, as the organization of the receptor-ligand ectodomains directly controls the recruitment, organization and function of non-covalently associated cytoplasmic signaling and scaffolding molecules. The high resolution crystal structure of VISTA is determined using techniques including bacterial, insect and mammalian expression systems, as well as high-throughput crystallization and structure determination approaches. To validate the crystallographically-observed disulfide bonding pattern, high resolution mass spectrometry using approaches that successfully supported studies of TIM-3 and human DcR359 will be used. Based on these structural results, a series of mutants with altered oligomeric properties is designed, as well as mutants in the vicinity of any perturbed regions of the VISTA IgV domain. These mutant proteins will provide additional direct mechanistic insight into VISTA function and should be useful in therapeutics wherein immunosuppression is desired such as the autoimmune, allergic and inflammatory diseases identified herein. These mutants, especially oligomers are tested in in vitro systems and are assessed in animal autoimmune and inflammatory disease models in order to assess the immunosuppressive effect on disease progression, disease remission or in protecting the animal from developing the autoimmune or inflammatory condition.

These oligomeric VISTA proteins will activate the VISTA pathway and function as a target of immune intervention in autoimmunity. This intervention will suppress immunity and exert a therapeutic benefit on autoimmune disease and other conditions wherein autoimmune suppression is desired. This is accomplished by administering the oligomerized VISTA proteins in different autoimmune and inflammatory models such as the EAE and collagen-induced arthritis animal models. In addition, as discussed above, adenoviral vectors that over-express full-length VISTA or VISTA oligomers are constructed and tested in vivo. These studies will confirm the immunosuppressive effects of VISTA oligomers.

Example 16

Experiments Using Conditional Over-Expressing VISTA Transgenic Mouse Strain (VISTA Transgenic Mouse Strain: R26StopFLVISTA (VISTA)

A targeting construct containing the full-length cDNA of VISTA preceded by a loxP-flanked STOP cassette, has been targeted into the ubiquitously expressed ROSA26 locus. Multiple correctly targeted R26StopFL/-VISTA pups were born, and bred onto the CMV-Cre deleter strain60. Preliminary data in the VISTA×CMV-cre confirm GFP and heightened VISTA expression. Studies on the immune status of these mice (T cell responses to antigen, antibody titers) will confirm a suppressed phenotype. The VISTA strain will be interbred with CD4-cre, CD11c-cre, and Lys-Cre to determine if the lineage location of VISTA expression influences suppression. The phenotype and function of the T cells is also determined and it is determined if over-expression of VISTA results in the generation of aTreg. In these studies Tregs from OVA-immune cre×VISTA strain are adoptively transferred into WT hosts, to see if antigen immunization in the presence of over-expressed VISTA induces antigen-specific Tregs. This should verify that VISTA impacts Treg differentiation.

In addition, studies are effected in the EAE model whereby the impact of VISTA proteins on different lineages (by interbreeding with CD4-, CD11c-, Lys-cre) with respect to disease development is assessed. Assuming that disease can be suppressed by lineage restricted overexpression of VISTA mutants or in the CMV×VISTA mutant□ the temporal control of disease development is also using Cre-ERT2×VISTAη. Through the administration of tamoxifen we can induce overexpression of VISTA prior to, or at disease initiation or at peak disease to determine if VISTA can impact on the induction and/or effector phases of immunity. Using BM chimeric mice, temporally-restricted overexpression of VISTA can be restricted to the hematopoietic compartment. For an appreciation of controlling the window of time VISTA is overexpressed, VISTA is genetically turned on, then serologically turned off with the administration of anti-VISTA monoclonal antibody. These studies will determine where and when VISTA has to act to control the development and progression of autoimmune disease.

Example 17

Effect of Anti-VISTA Antibodies CD40/TLR Agonist Vaccine

As shown in FIG. 21, experiments were conducted that assayed the effect of anti-VISTA antibodies on vaccine efficacy. These results show that anti-VISTA enhances the therapeutic efficacy of a CD40/TLR vaccine. C57BL/6 mice were challenged with 1×105 metastatic B16.F10 melanoma cells s.q. Four days later, mice were vaccinated with 100 μg of the tumor associated antigen ΔV, 100 μg αCD40 FGK45 (CD40 agonistic antibody) and 100 μg S-27609(TLR7 agonist) with or without anti-VISTA (200 μg×3/week). Growth of tumor was monitored by caliper measurements.

Example 18

Expression Profiling

To facilitate comparisons with established expression profiles of Treg cells, standard growth and activation conditions were employed (McHugh, et al. (2002) supra). Briefly, fresh isolated Treg cells (~96% positive) were inoculated at 106/mL into complete RPMI medium supplemented with 10% fetal bovine serum and 100 units IL-2 in a 24-well plate precoated with anti-CD3 with or without anti-GITR (DTA-1)(Shimizu, et al. (2002) supra). The cells were cultured at 37° C. for 0 and 12 hours, RNA was purified and subsequently analyzed using an AFFYMETRIX® mouse genome A430 oligonucleotide array.

By comparing the data from resting or activated CD4+ CD25+ T cell groups, gene expression patterns were found to be similar to those established in the art (Gavin, et al. (2002) supra; McHugh, et al. (2002) supra). To identify genes regulated by GITR signaling, gene expression profiles were compared between the different cell populations with or without anti-GITR treatment. A list of known as well as unknown genes were compiled including the previously uncharacterized VISTA and Treg-sTNF.

Example 19

Molecular Cloning of VISTA, Retrovirus Production and Retroviral Transduction of Cells Full length VISTA was cloned from purified murine CD4+ T cells. Total RNA was isolated from CD4+ T cells using Qiagen RNAmini kit. cDNA was generated using Bio-Rad iScript™ cDNA synthesis kit. Full-length VISTA was amplified and cloned into the ECorI-XhoI site of a retroviral vector pMSCV-IRES-GFP (Zhang & Ren (1998) Blood 92: 3829-3840) in which the IRES-GFP fragment was replaced by RFP, thus resulting in a fusion protein of VISTA fused to the N-terminus of RFP. Helper free retroviruses were generated in HEK293T cells by transient transfection of the VISTA-RFP retroviral vector together with an ecotrophic packaging vector pCL-Eco (IMGENEX Corp.) Retroviral transduction of murine T cell line EL4 cells, or bone marrow derived DCs were carried out by spin infection at 2000 rpm at RT for 45 min in the presence of 8 μg/ml polybrene (Sigma).

Example 20

Production of VISTA-Ig Fusion Protein

The extracellular domain of VISTA (amino acid 32-190) was amplified and cloned into the SpeI-BamHI sites of the parental vector CDM7B. Hollenbaugh, et al. (1995) *J Immunol Methods* 188: 1-7. This vector contains the mutant form of constant and hinge regions of human IgG1, which has much reduced binding to Fc receptors. The resulting vector CDM7B-VISTA was co-transfected with a DHFR expression vector pSV-dhfr (McIvor & Simonsen (1990) Nucleic Acids Res 18: 7025-7032) into the CHO (dhfr-) cell line (ATCC # CRL-9096). Stable CHO cell clones that express VISTA-Ig were selected in medium MEM-alpha without nucleotides (INVITROGEN®). Further amplification with 0.5-1 μM methotrexate (SIGMA® M9929) yielded clones expressing high levels of soluble VISTA-Ig fusion protein. The fusion protein was further purified from culture supernatant using standard protein-G column affinity chromatography.

Example 21

Generation of VISTA Monoclonal Antibodies

Armenian hamsters were immunized 4× times with EL4 cells over-expressing VISTA-RFP weekly, then boosted with VISTA-Ig fusion protein emulsified in CFA. Four weeks after the boost, hamsters were boosted again with soluble VISTA-Ig fusion protein. Four days after the last boost, hamster spleen cells were harvested and fused to the myeloma cell line SP2/0-Ag14 (ATCC # CRL-1581) using standard hybridoma fusion techniques Shulman, et al. (1978) Nature 276: 269-270. Hybridoma clones that secret VISTA specific antibodies were selected after limiting dilution and screened by both ELISA and flow cytometric methods.

Example 22

Inhibitory Activity of VISTA

The inhibitory activity of PD-L1 was revealed by using antigen presenting cells over-expressing PD-L1 in vitro with CD4+ and CD8+ T cell antigen receptor transgenic T cells and antigen stimulation (Carter, et al. (2002) *Eur. J. Immunol.* 32:634-43). Similarly, the lentivector disclosed herein, which expresses the full-length VISTA, is transduced into cell lines expressing class II major histocompatibility complex (MHC) and class I MHC. The response of TEa Tg or the 2C transgenic T cells to antigen presented by empty vector-transduced or VISTA-transduced antigen presenting cells is determined according to established methods.

Example 23

Monoclonal Antibody Production

VISTA was overexpressed in the murine B cell line A20, and the recombinant cell line was used to immunize Armenian hamsters. After 5× cell immunization, hamsters were boosted with purified VISTA-Ig fusion protein emulsified in CFA. Four weeks later, a final boost was provided with soluble VISTA-Ig. Subsequently, fusions of hamster splenocytes with SP2/0 cells were performed on day 4. Sixteen different clones were identified that recognized VISTA-Ig fusion protein by ELISA, as well as stained VISTA but not PD-L1 overexpressed on the murine T cell line EL4. Eleven of the clones were successfully subcloned and prepared for evaluation of their ability to stain endogenous VISTA on cells and tissues, and to block VISTA functions.

Example 24

VISTA-Ig Conjugates Negatively Regulates T Cell Responses

The immunoglobulin (Ig) superfamily consists of many critical immune regulators, including the B7 family ligands and receptors. VISTA, a novel and structurally distinct Ig superfamily inhibitory ligand, whose extracellular domain bears homology to the B7 family ligand PD-L1. This molecule is designated V-domain Ig suppressor of T cell activation (VISTA). VISTA is primarily expressed on hematopoietic cells, and VISTA expression is highly regulated on myeloid antigen-presenting cells (APCs) and T cells. A soluble VISTA-Ig fusion protein or VISTA expression on APCs inhibits T cell proliferation and cytokine production in vitro. A VISTA-specific monoclonal antibody interferes with VISTA-induced suppression of T cell responses by VISTA-expressing APCs in vitro. Furthermore, anti-VISTA treatment exacerbates the development of the T cell-mediated autoimmune disease experimental autoimmune encephalomyelitis in mice. Finally, VISTA overexpression on tumor cells interferes with protective antitumor immunity in vivo in mice. These findings show that VISTA, a novel immunoregulatory molecule, has functional activities that are nonredundant with other Ig superfamily members and may play a role in the development of autoimmunity and immune surveillance in cancer. See Wang, et al. (2011) The Journal of Experimental Medicine 208(3): 577-592. In this Example, VISTA may also be referred to as "PD-XL."

Materials and Methods

Mice. C57BL/6 mice, OT-II CD4 transgenic mice, and SJL/J mice were purchased from the Jackson Laboratory. FoxP3-GFP reporter mice were as previously described (Fontenot, et al. 2005) and were provided by A. Rudensky (University of Washington School of Medicine, Seattle, Wash.). PD-1 KO mice were provided by T. Honjo (Kyoto University, Kyoto, Japan; Nishimura, et al. 1999, 2001). All animals were maintained in a pathogen-free facility at Dartmouth Medical School. All animal protocols were approved by the Institutional Animal Care and Use Committee of Dartmouth College.

Antibodies, Cell Lines, and Reagents.

Antibodies α-CD3 (2C11), α-CD28 (PV-1), α-CD4 (GK1.5), α-CD8 (53-6.7), α-CD11b (M1/70), α-F4/80 (BM8), α-CD11c (N418), α-NK1.1 (PK136), α-Gr1 (RB6-8C5), α-PD-L1 (MIN5), α-PD-L2 (TY25), α-B7-H3 (M3.2D7), and α-B7-H4 (188) were purchased from eBioscience. LPS (Sigma-Aldrich), recombinant mouse IFN-γ (PeproTech), human IL-2 (PeproTech), and soluble PD-L1-Ig fusion protein (R&D Systems) were used at the indicated concentrations. CFA and chicken OVA were purchased from Sigma-Aldrich. The B cell lymphoma cell line A20 (BALB/c origin) was obtained from the American Type Culture Collection.

Molecular Cloning of VISTA, Retrovirus Production, and Retroviral Transduction of Cells.

Full-length VISTA was cloned from purified mouse CD4+ T cells. Total RNA was isolated from CD4+ T cells using an RNAmini kit (QIAGEN). cDNA was generated using an iScript cDNA synthesis kit (Bio-Rad Laboratories). Full-length VISTA was amplified and cloned into the ECORI-XhoI site of a retroviral vector pMSCV-IRES-GFP (Zhang and Ren, 1998), in which the IRES-GFP fragment was replaced by RFP, thus resulting in a fusion protein of VISTA fused to the N terminus of RFP. Helper free retroviruses were generated in HEK293T cells by transient transfection of the VISTA-RFP retroviral vector together with an ecotrophic packaging vector pCL-Eco (Imgenex Corp.). Retroviral transduction of mouse T cell line EL4 cells or BMDCs was performed by spin infection at 2,000 rpm at room temperature for 45 min in the presence of 8 μg/ml polybrene (Sigma-Aldrich).

Bioinformatics Analysis of VISTA.

Proteins that are evolutionarily related to the VISTA Ig-V sequence were identified by the BLAST algorithm (Altschul, et al. 1990). The most suitable structural templates from the Protein Data Bank (Berman, et al. 2000) were identified with the mGenTHREADER algorithm (Lobley, et al. 2009). PD-L1 (Protein Data Bank accession no. 3BIS), one of the top scoring hits, was selected as the template for comparative protein structure modeling. The structural model of VISTA was constructed with the MMM server using the optimal combination of two alignment methods, MUSCLE and HHalign (Rai and Fiser, 2006; Rai, et al. 2006). 36 VISTA orthologous proteins were collected from the ENSEMBL database (Flicek, et al. 2008). Structure and sequence alignments were calculated with DALI (Holm and Park, 2000) and Clustalw (Larkin, et al. 2007), respectively, and were presented using the ESPript 2.2 server (Gouet, et al. 1999). The BLAST pairwise comparison network was constructed as described previously (Atkinson, et al. 2009) and analyzed using Cytoscape (Shannon, et al. 2003).

Production of VISTA-Ig Fusion Protein.

The extracellular domain of VISTA (aa 32-190) was amplified and cloned into the SpeI-BamHI sites of the parental vector CDM7B (Hollenbaugh, et al. 1995). This vector contains the mutant form of constant and hinge regions of human IgG1, which has much reduced binding to Fc receptors. The resulting vector CDM7B-VISTA was cotransfected with a dihydrofolate reductase expression vector pSV-dhfr (McIvor and Simonsen, 1990) into the Chinese hamster ovary (dhfr) cell line (# CRL-9096; American Type Culture Collection). Stable Chinese hamster ovary cell clones that express VISTA-Ig were selected in medium MEM-α without nucleotides (Invitrogen). Further amplification with 0.5-1 μM methotrexate (M9929; Sigma-Aldrich) yielded clones expressing high levels of soluble VISTA-Ig fusion protein. The fusion protein was further purified from culture supernatant using standard protein G column affinity chromatography.

Generation of VISTA Monoclonal Antibodies (mAb).

Armenian hamsters were immunized with EL4 cells overexpressing VISTA-RFP and then boosted with VISTA-Ig fusion protein emulsified in CFA. 4 wk after the boost, hamsters were boosted again with soluble VISTA-Ig fusion protein. 4 d after the last boost, hamster spleen cells were harvested and fused to the myeloma cell line SP2/0-Ag14 (# CRL-1581; American Type Culture Collection) using standard hybridoma fusion techniques (Shulman, et al. 1978). Hybridoma clones that secret VISTA-specific antibodies were selected after limiting dilution and screened by both ELISA and flow cytometry methods.

RNA and RT-PCR.

Total RNA from various mouse tissue samples or purified hematopoietic cell types were collected by using TRIZOL® (Invitrogen) according to the company's instructions. cDNAs were prepared by using the iScript cDNA synthesis kit (Bio-Rad Laboratories). Equal amounts of tissue cDNAs (10 ng) were used for RT-PCR reactions to amplify full-length VISTA. PCR products were viewed after running through a 1% agarose gel.

Flow Cytometry and Analysis.

Flow cytometry analysis was performed on FACScan using CellQuest software (BD). Data analysis was performed using FlowJo software (Tree Star, Inc.). To quantify cell proliferation, the histogram profile of CFSE divisions was analyzed, and the percentage of proliferative $CFSE^{low}$ cells was graphed using Prism 4 (GraphPad Software, Inc.).

Cell Preparation.

Total $CD4^+$ T cells were isolated from naive mice using a total $CD4^+$ T cell isolation kit (Miltenyi Biotec). When indicated, enriched $CD4^+$ T cells were flow sorted into naive ($CD44^{low}CD25^-CD62L^{hi}$) and memory ($CD44^{hi}CD25^-$ $CD62^{low}$) populations. For in vitro proliferation assays, $CD4^+$ T cells were labeled with 5 μM CFSE (Invitrogen) for 10 min at 37° C. and washed twice before being stimulated.

For A20 assay, A20-RFP or A20-PD-XL cells (20,000) were pretreated with 100 μg/ml mitomycin C (1 h) and then incubated with CFSE-labeled DO11.10 $CD4^+$ T cells (100,000) in the presence of OVA peptide. Control-Ig or 13F3 monoclonal antibody was added as indicated. Cell proliferation was analyzed at 72 h by CFSE dilution. For sorting $CD11b^{hi}$ myeloid APCs, $CD11b^+$ monocytes were enriched from naive splenocytes using CD11b magnetic beads (Miltenyi Biotec). Total $CD11b^{hi}$ myeloid APCs, or $CD11b^{hi}CD11c^-$ monocytes and $CD11b^{hi}CD11c^+$ myeloid DCs were sorted, irradiated (2,500 rad), and used to stimulate OT-II transgenic $CD4^+$ T cells in the presence of OVA peptide. Control-Ig or 13F3 monoclonal antibody was added as indicated. Cell proliferation was measured by tritium incorporation during the last 8 h of a 72-hour assay.

In Vitro Plate-Bound T Cell Activation Assay.

Purified $CD4^+$ T cells (100,000 cells per well) were cultured in 96-well flat-bottom plates in the presence of anti-CD3 (clone 2C11) and either VISTA-Ig or control-Ig at the indicated concentration ratios. For example, for a full-range titration, the 96-well plates were coated with 2.5 μg/ml of α-CD3 mixed together with 1.25 μg/ml (ratio 2:1), 2.5 μg/ml (ratio 1:1), 5 μg/ml (ratio 1:2), or 10 μg/ml (ratio 1:4) VISTA-Ig or control-Ig protein in PBS at 4° C. overnight. Wells were washed three times with PBS before adding $CD4^+$ T cells. Replicate cultures were in complete RPMI 1640 medium supplemented with 10% FBS, 10 mM Hepes, 50 μM β-ME, and penicillin/streptomycin/L-glutamine. When indicated, either 100 U/ml human IL-2 (PeproTech) or a titrated amount of α-CD28 (clone PV-1; Bio X Cell) was coated together with α-CD3 to rescue the inhibitory effects of VISTA-Ig. Cultures were analyzed on day 3 for CFSE profiles or according to a time course as indicated.

Culture of BMDCs, Retroviral Transduction, and Stimulation of Transgenic $CD4^+$ T Cells.

BMDCs were generated as described previously (Lutz, et al. 1999; Son, et al. 2002), with some modifications. In brief, on day 0, BM cells were isolated from tibia and femur by flushing with a 27-gauge needle. After red blood cell lysis, $1\text{-}2\times10^6$ BM cells were resuspended in 1 ml complete RPMI 1640 medium containing 20 ng/ml GM-CSF (PeproTech). Cells were infected with RFP or VISTA-RFP retrovirus in the presence of 8 μg/ml Polybrene (Sigma-Aldrich). Infection was performed by spinning the plate at 2,000 rpm for 45 min at room temperature. Cells were then cultured for another 2 h before fresh medium was added. Similar infection procedure was repeated on days 1, 3, and 5. Loosely adherent cells (90% were $CD11c^+$) were collected on day 10, and $CD11c^+RFP^+$-double positive cells were sorted and used to stimulate OT-II transgenic $CD4^+$ T cells. For OT-II T cell proliferation assays, 100,000 CFSE-labeled OT-II $CD4^+$ T cells were cultured in 96-well round-bottom plates with 30,000 sorted $RFP^+$ or VISTA-$RFP^+$ BMDCs, with a titrated amount of synthetic $OVA_{323\text{-}339}$ peptide (AnaSpec). Proliferation of OT-II T cells was analyzed at 72 h by examining CFSE profiles.

Tumor Experiment.

Parent MCA105 tumor cells were retrovirally transduced with VISTA-RFP or RFP control and sorted to homogeneity based on RFP expression. For tumor vaccination, naive C57BL/6 mice were immunized with 1,000,000 irradiated MCA105 (10,000 rad) cells that were inoculated subcutaneously into the left flank. On day 14, vaccinated mice were challenged with live MCA105 tumor cells that were inoculated subcutaneously into the right flank. Tumor growth was monitored every 2 d. Mice were euthanized when tumor size reached 150 $mm^2$. For T cell depletion, vaccinated mice were pretreated intraperitoneally (250 μg) with monoclonal antibody specific for $CD4^+$ T cells (clone GK1.5) and $CD8^+$ T cells (clone 53.6.72) 2 d before live tumor cell challenge, and the treatment was repeated every 3-4 d until the end of the experiment. Mice were euthanized when tumor size reached 160 $mm^2$.

Passive Induction of EAE and Characterization of Central Nervous System-Infiltrating $CD4^+$ T Cells.

For passive transfer EAE, female SJL mice (6 wk old) were immunized subcutaneously with 200 μl of emulsion containing 400 μg *Mycobacterium tuberculosis* H37Ra and 100 μg PLP peptide. Draining LN cells were harvested on day 10 for in vitro stimulation. Red blood cells were lysed. Single cell suspensions (10,000,000 per microliter) were cultured in complete IMDM medium with 10% FBS, 50 μM 2-ME, 1 mM glutamine, 1% penicillin/streptavidin, 1 mM nonessential amino acids, 20 ng/ml IL-23, 10 ng/ml IL-6, 10 ng/ml IL-13, 20 μg/ml anti-IFN-γ, and 20 μg/ml PLP peptide. On day 4, cells were harvested, and live CD4 T cells were purified using CD4 magnetic beads (Miltenyi Biotec). 1,500,000-2,000,000 purified live CD4 T cells were adoptively transferred into naive SJL mice to induce EAE. Mice were treated with either nonspecific hamster control-Ig or 400 μg VISTA-specific monoclonal antibody every 3 days. Disease was scored as the following: 0, no disease; 1, hind limb weakness or loss of tail tone; 2, flaccid tail and hind limb paresis; 2.5, one hind limb paralysis; 3, both hind limb paralysis; 4, front limb weakness; 5, moribund. Mice were euthanized at a score of 4.

Cloning and Sequence and Structural Analysis of VISTA

Affymetrix® analysis of activated versus resting mouse $CD25^+CD4^+$ natural $T_{reg}$ cells ($nT_{reg}$ cells) revealed the expression of a gene product (RIKEN cDNA 4632428N05 or 4632428N05Rik) with unknown function but with sequence homology to the Ig superfamily. A 930-bp gene product was cloned from the mouse $CD4^+$ T cell cDNA library, which matched the predicted size and sequence. Silico sequence and structural analysis predicts a type I transmembrane protein of 309 aa upon maturation. Its extracellular domain contains a single extracellular Ig-V domain of 136 aa, which is linked to a 23-aa stalk region, a 21-residue transmembrane segment, and a 97-aa cytoplasmic domain (FIG. 23A). The cytoplasmic tail of 4632428N05Rik does not contain any signaling domains. Based on the structural feature of the Ig-V domain and its immune-suppressive function that is shown herein, this molecule was named VISTA.

A BLAST (Altschul, et al. 1990) sequence search with the VISTA Ig-V domain identified PD-L1 of the B7 family as the closest evolutionarily related protein with a borderline significant e-value score of $10^{-4}$ and with a sequence identity of 24%.

A structure-based sequence alignment of VISTA with the B7 family members PD-L1, PD-L2, B7-H3, and B7-H4 highlights several amino acids that are known to be systematically conserved in all Ig-V domain proteins and are thought to be important for the stability of the Ig-V fold (FIG. 23C). Examples include the two cysteines in the B and the F B strands that form a disulfide bond between the two B sheets, which is a hallmark feature of Ig superfamily proteins (FIG. 23C). This multiple sequence alignment also reveals additional sequence features that are unique to VISTA.

Expression experiments of VISTA by RT-PCR analysis and flow cytometry. RT-PCR analysis was used to determine the messenger RNA expression pattern of VISTA in mouse tissues (FIG. 3A). VISTA is mostly expressed on hematopoietic tissues (spleen, thymus, and BM) or tissues with ample infiltration of leukocytes (i.e., lung). Weak expression was also detected in nonhematopoietic tissues (i.e., heart, kidney, brain, and ovary). Analysis of several hematopoietic cell types revealed expression of VISTA on peritoneal macrophages, splenic $CD11b^+$ monocytes, $CD11c^+$ DCs, $CD4^+$ T cells, and $CD8^+$ T cells but a lower expression level on B cells (FIG. 3B). This expression pattern is also largely consistent with the GNF (Genomics Institute of the Novartis Research Foundation) gene array database (symbol 4632428N05Rik; Su, et al. 2002), as well as the National Center for Biotechnology Information GEO (Gene Expression Omnibus) database (Accession No. GDS868).

To study the protein expression, VISTA-specific hamster monoclonal antibodies were produced. The specificity is demonstrated by positive staining on VISTA-overexpressing mouse EL4 T cells but negative staining on PD-L1-overexpressing EL4 cells.

Using an α-VISTA monoclonal antibody clone 8D8, VISTA expression was analyzed on hematopoietic cells by flow cytometry. Foxp3-GFP knockin reporter mice were used to distinguish $CD4^+$ $nT_{reg}$ cells (Fontenot, et al. 2005). In peripheral lymphoid organs (spleen and LNs), significant expression was seen on all $CD4^+$ T cell subsets (see total $CD4^+$ T cells or $Foxp3^-$ naive T cells and $Foxp3^+$ $nT_{reg}$ cells and memory $CD4^+$ T cells), whereas $CD8^+$ T cells expressed a markedly lower amount of surface VISTA (FIG. 3C). In thymus, VISTA expression was negative on $CD4^+CD8^+$-double positive thymocytes, low on CD4-single positive cells, and detectable on CD8-single positive cells. Next, a strong correlation of high VISTA expression with CD11b marker was seen for both splenic and peritoneal cells, including both F4/80 macrophages and myeloid $CD11c^+$ DCs (FIGS. 3D and 3E). In contrast, B cells and NK cells were mostly negative for VISTA expression. A small percentage of $Gr\text{-}1^+$ granulocytes also expressed VISTA (FIG. 3F).

A differential expression pattern was shown on the same lineage of cells from different lymphoid organs (FIG. 3G). For $CD4^+$ T cells and $CD11b^{intermediate}$ monocytes, the expression level followed the pattern of mesenteric LN>peripheral LN and spleen>peritoneal cavity and blood. This pattern was less pronounced for $CD11^{hi}$ cells. These data suggest that VISTA expression on certain cell types might be regulated by cell maturity and/or tissue microenvironment.

In addition to freshly isolated cells, VISTA expression was analyzed on splenic $CD4^+$ T cells, $CD11b^{hi}$ monocytes, and $CD11c^+$ DCs upon in vitro culture with and without activation (FIG. 6). Spleen cells were cultured with medium, with α-CD3 (for activating T cells), or with IFN-γ and LPS (for activating monocytes and DCs) for 24 h before expression analysis of VISTA and other B7 family ligands (e.g., PD-L1, PD-L2, B7-H3, and B7-H4). This comparison revealed distinctive expression patterns between these molecules. VISTA expression was quickly lost on all cell types upon in vitro culture, regardless of the activation status. In contrast, PD-L1 expression was up-regulated on activated $CD4^+$ T cells or on $CD11b^{hi}$ monocytes and $CD11c^+$ DCs after culture in medium alone and further enhanced upon stimulation. The expression of PD-L2, B7-H3, and B7-H4 was not prominent under the culture conditions used. The loss of VISTA expression in vitro is unique when compared with other B7 family ligands but might reflect nonoptimal culture conditions that fail to mimic the tissue microenvironment.

To address how VISTA expression might be regulated in vivo, CD4 TCR transgenic mice DO11.10 were immunized with the cognate antigen chicken OVA emulsified in CFA. At 24 h after immunization, cells from the draining LN were analyzed for VISTA expression (FIG. 7A). Immunization with antigen (CFA/OVA) but not the adjuvant alone drastically increased the $CD11b^+$ $VISTA^+$ myeloid cell population, which contained a mixed population of $F4/80^+$ macrophages and $CD11c^+$ DCs. Further comparison with PD-L1 and PD-L2 revealed that even though PD-L1 had the highest constitutive expression level, VISTA was the most highly up-regulated during such an inflammatory immune response (FIG. 7B). Collectively, these data strongly suggest that the expression of VISTA on myeloid APCs is tightly regulated by the immune system, which might contribute to its role in controlling immune responses. In contrast to its increased expression on APCs, VISTA expression was diminished on activated DO11.10 $CD4^+$ T cells at a later time point upon immunization (i.e., at 48 h but not at 24 h).

Functional impact of VISTA signaling on $CD4^+$ and $CD8^+$ T cell responses in vitro. A VISTA Ig fusion protein (VISTA-Ig) was produced to examine the regulatory roles of VISTA on $CD4^+$ T cell responses. VISTA-Ig contained the extracellular domain of VISTA fused to the human $IgG_1$ Fc region. When immobilized on the microplate, VISTA-Ig but not control-Ig suppressed the proliferation of bulk purified $CD4^+$ and $CD8^+$ T cells in response to α-CD3 stimulation (FIGS. 9A and 9B). The VISTA-Ig did not affect the absorption of anti-CD3 antibody to the plastic wells, as determined by ELISA, thus excluding the possibility of nonspecific inhibitory effects. The inhibitory effect of PD-L1-Ig and VISTA-Ig was directly compared. When titrated amounts of Ig fusion proteins were absorbed to the microplates together with α-CD3 to stimulate $CD4^+$ T cells, VISTA-Ig showed potent inhibitory efficacy similar to the PD-L1-Ig fusion protein. PD-1 KO $CD4^+$ T cells were also suppressed (FIG. 9C), indicating that PD-1 is not the receptor for VISTA.

Because bulk purified $CD4^+$ T cells contain various subsets, the impact of VISTA-Ig on sorted naive (CD25-$CD44^{low}CD62L^{hi}$) and memory (CD25-$CD44^{hi}CD62^{low}$) $CD4^+$ T cell subsets was evaluated. VISTA suppressed the proliferation of both subsets, albeit with less efficacy on the memory cells.

To further understand the mechanism of VISTA-mediated suppression, the expression of early TCR activation markers and apoptosis were measured after T cell activation. Consistent with the negative effect on cell proliferation, there was a global suppression on the expression of the early activation markers CD69, CD44, and CD62L (FIG. 12A). In contrast, VISTA-Ig did not induce apoptosis. Less apoptosis (as determined by the percentage of annexin $V^+$ $7AAD^-$ cells) was seen in the presence of VISTA-Ig than the control-Ig at both early (24 hours) and later (48 hours) stages of TCR activation (FIG. 12B). For example, at 24 h, of the total ungated population, ~27% of cells were apoptotic in the presence of VISTA-Ig, but ~39% of cells were apoptotic in the presence of control-Ig. Similarly, of the cells within the live cell R1 gate, ~72.6% cells became apoptotic in the presence of control-Ig, whereas only ~43.5% cells were apoptotic in the presence of VISTA-Ig. Similar results were seen at the 48-h time point. Therefore, it appears that VISTA negatively regulates $CD4^+$ T cell responses by suppressing early TCR activation and arresting cell division but with minimum direct impact on apoptosis. This mechanism of suppression is similar to that of B7-H4 (Sica, et al. 2003).

A two-step assay was developed to determine whether VISTA-Ig can suppress preactivated CD4 T cells and how persistent its suppressive effect is. The suppressive effect of VISTA-Ig fusion protein persisted after its removal at 24 hours after activation (FIG. 9D, ii). In addition, both naive and preactivated $CD4^+$ T cells were suppressed by VISTA-Ig (FIG. 9D, i, iii, and iv).

Next, the effect of VISTA-Ig on $CD4^+$ T cell cytokine production was analyzed. VISTA-Ig suppressed the production of Th1 cytokines IL-2 and IFN-γ from bulk purified $CD4^+$ T cell culture (FIGS. 13A and 13B). The impact of VISTA was further tested on separate naive ($CD25^-$ $CD44^{low}$CD62Lhi) and memory (CD25-$CD44^{hi}CD62^{low}$) $CD4^+$ T cell populations. Memory $CD4^+$ T cells were the major source for cytokine production within the $CD4^+$ T cell compartment, and VISTA suppressed this production (FIGS. 13C and 13D). IFN-γ production from $CD8^+$ T cells was also inhibited by VISTA-Ig (FIG. 13E). This inhibitory effect of VISTA on cytokine production by $CD4^+$ and $CD8^+$ T cells is consistent with the hypothesis that VISTA is an inhibitory ligand that down-regulates T cell-mediated immune responses.

Further experiments were designed to determine the factors that are able to overcome the inhibitory effect of VISTA. Given that VISTA suppressed IL-2 production and IL-2 is critical for T cell survival and proliferation, we hypothesized that IL-2 might circumvent the inhibitory activity of VISTA. As shown in FIG. 14A, exogenous IL-2 but not IL-15, IL-7, or IL-23 partially reversed the suppressive effect of VISTA-Ig on cell proliferation. The incomplete rescue by high levels of IL-2 indicates that VISTA signaling targets broader T cell activation pathways than simply IL-2 production. In contrast, potent co-stimulatory signals provided by α-CD28 agonistic antibody completely reversed VISTA-Ig-mediated suppression (FIG. 14B), whereas intermediate levels of co-stimulation continued to be suppressed by VISTA signaling (FIG. 14C). In this regard, VISTA shares this feature with other suppressive B7 family ligands such as PD-L1 and B7-H4 (Carter, et al. 2002; Sica, et al. 2003).

In addition to the VISTA-Ig fusion protein, it was necessary to confirm that VISTA expressed on APCs can suppress antigen-specific T cell activation during cognate interactions between APCs and T cells. We have used two independent cell systems to address this question. First, VISTA-RFP or RFP control protein was overexpressed via retroviral transduction in a B cell line A20. The correct cells surface localization of VISTA-RFP fusion protein was confirmed by fluorescence microscopy. To stimulate T cell response, A20-VISTA or A20-RFP cells were incubated together with DO11.10 $CD4^+$ T cells in the presence of antigenic OVA peptide. As shown in FIGS. 15A and C), A20-VISTA induced less proliferation of DO11.10 cells than A20-RFP cells. This suppressive effect is more pronounced at lower peptide concentrations, which is consistent with the notion that a stronger stimulatory signal would overcome the suppressive impact of VISTA.

Second, the inhibitory effect of full-length VISTA on natural APCs was confirmed. in vitro cultured BM-derived DCs (BMDCs) did not express high levels of VISTA (FIG. 16). VISTA-RFP or RFP was expressed in BMDCs by retroviral transduction during the 10-day culture period. Transduced cells were sorted to homogeneity based on RFP expression. The expression level of VISTA on transduced DCs was estimated by staining with α-VISTA monoclonal antibody and found to be similar to the level on freshly isolated peritoneal macrophages, thus within the physiological expression range (FIG. 16). Sorted BMDCs were then used to stimulate OVA-specific transgenic $CD4^+$ T cells (OT-II) in the presence of OVA peptide. The expression of VISTA on BMDCs suppressed the cognate $CD4^+$ T cell proliferation (FIG. 15D). This result is consistent with data (FIG. 5) using VISTA-Ig fusion protein or VISTA-expressing A20 cells, suggesting that VISTA expressed on APCs can suppress T cell-mediated immune responses.

To validate the impact of VISTA expression in vivo, whether VISTA overexpression on tumor cells could impair the antitumor immune response was examined. MCA105 (methylcholanthrene 105) fibrosarcoma does not express VISTA. Two MCA105 tumor lines were established by retroviral transduction with either VISTA-RFP or RFP control virus. Because MCA105 tumor is immunogenic and can be readily controlled in hosts preimmunized with irradiated MCA105 cells (Mackey, et al. 1997), we examined the effect of tumor VISTA expression on such protective immunity. As shown in FIG. 26A, VISTA-expressing MCA105 grew vigorously in vaccinated hosts, whereas the control tumors failed to thrive. To confirm that there is no intrinsic difference in tumor growth rate in the absence of T cell-mediated antitumor immunity, tumors were inoculated in vaccinated animals in which both $CD4^+$ and $CD8^+$ T cells were depleted using monoclonal antibodies. As shown in FIG. 26B, upon T cell depletion, both MCA105RFP and MCA105VISTA tumors grew at an equivalent rate and much more rapidly than non-T-depleted hosts. Together, these data indicate that VISTA expression on tumor cells can interfere with the protective antitumor immunity in the host.

VISTA Blockade by a Specific Monoclonal Antibody Enhanced T Cell Responses In Vitro and In Vivo.

Figure 25A:
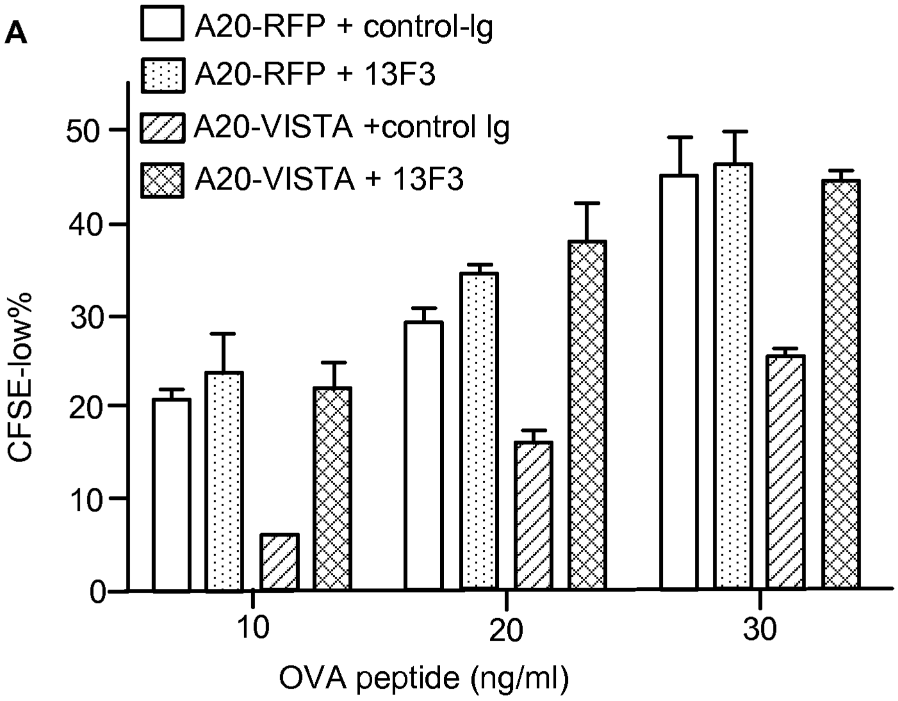
Figure 25B:
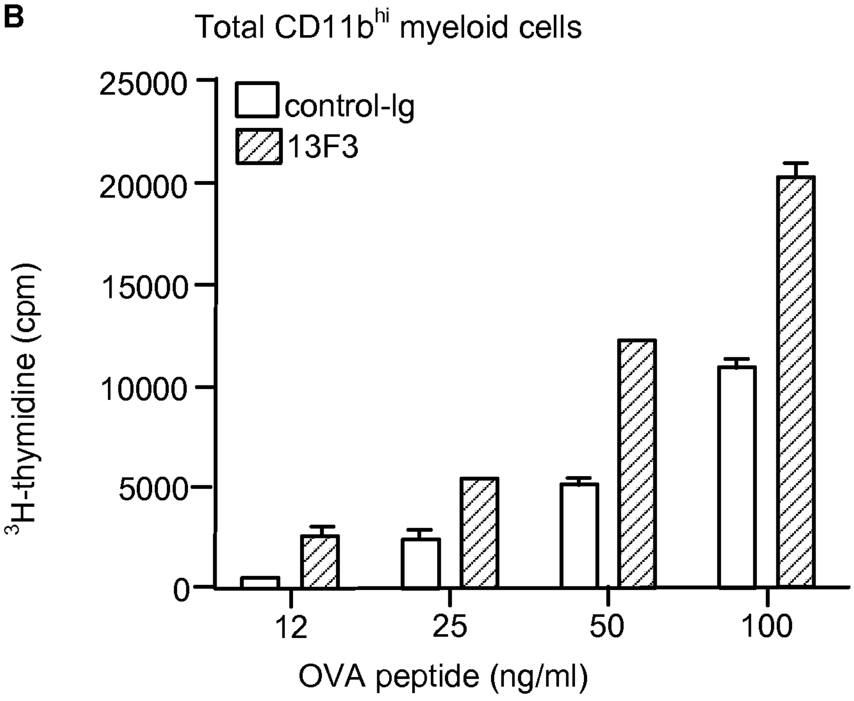
Figure 25C:
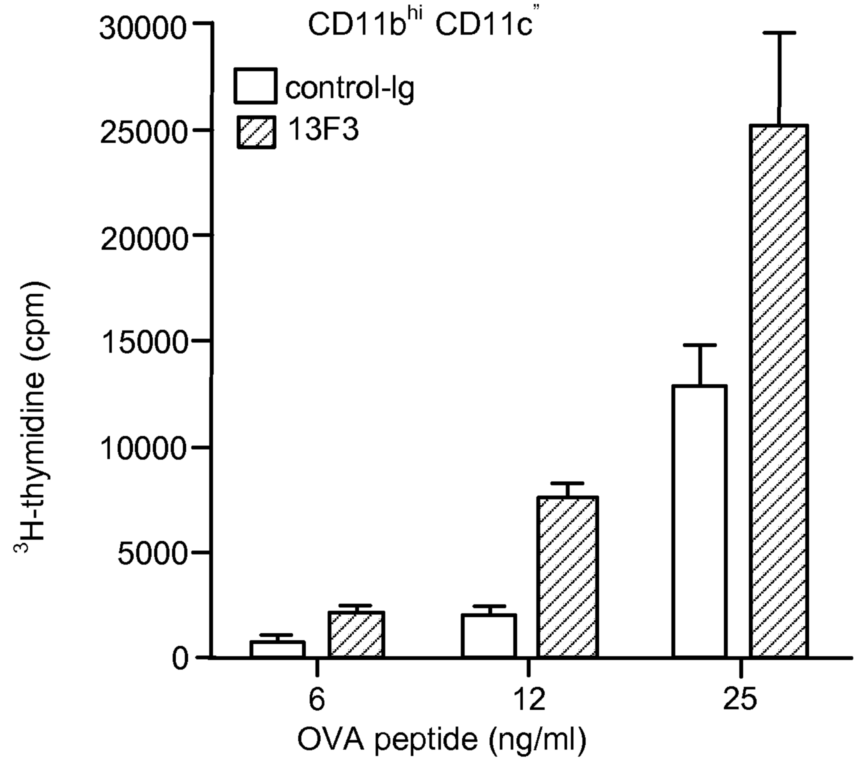
Figure 25D:
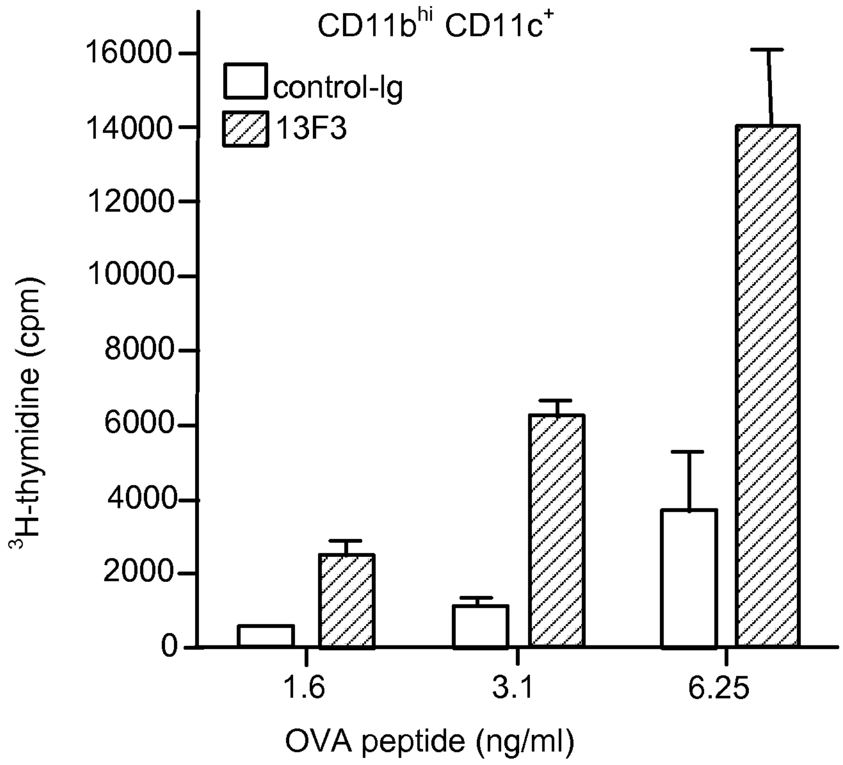

A VISTA-specific monoclonal antibody (13F3) was identified to neutralize VISTA-mediated suppression in the A20-DO11.10 assay system (FIG. 25A). To further confirm the impact of 13F3 on T cell responses, $CD11b^{hi}$ myeloid APCs were purified from naive mice to stimulate OT-II transgenic $CD4^+$ T cells in the presence or absence of 13F3 (FIG. 25B). Consistent with its neutralizing effect, 13F3 enhanced T cell proliferation stimulated by $CD11b^{hi}$ myeloid cells, which were shown to express high levels of VISTA (FIG. 3). A similar effect of 13F3 could be seen on both $CD11b^{hi}CD11c^+$ myeloid DCs and $CD11b^{hi}CD11c^-$ monocytes (FIG. 25C-D).

Next, the impact of VISTA blockade by monoclonal antibody was examined in a passive transfer model of EAE, which is a mouse autoimmune inflammatory disease model for human multiple sclerosis (Stromnes and Goverman, 2006). Encephalitogenic $CD4^+$ T cells were primed in the donor mice by active immunization with proteolipid protein (PLP) peptide and adoptively transferred into naive mice. So as to carefully evaluate the ability of α-VISTA to exacerbate disease, tittered numbers of activated encephalitogenic T cells were passively transferred into naive hosts treated with α-VISTA or control-Ig, and the development of EAE was monitored. 13F3 was found to significantly accelerate disease onset, as well as exacerbate disease severity under the suboptimal T cell transfer dosage. The 13F3-treated group reached 100% disease incidence by day 14, whereas those mice treated with control antibody did not reach 100% disease incidence during the experimental duration. The mean disease score was significantly higher in the 13F3-treated group than the control group throughout the disease course. Consistent with the higher disease score, analysis of the central nervous system at the end of disease course confirmed significantly more IL-17A-producing $CD4^+$ T cell infiltration in the 13F3-treated group.

Example 25

VISTA KO Mice

Experiments were conducted where the expression of VISTA was knocked out in mice in order to further assess the effects of VISTA in vivo. It is known to assess the effects of immunoregulatory molecules in vivo by knocking out the expression of such molecule and assessing its effect in the knock-out animal versus wild-type mice. For example, CTLA4 KO mice show dramatic loss of peripheral tolerance, massive lympho-proliferative phenotype, which results in early death, with this being explained by different mechanisms of action including the direct suppression of effector T cell activation, and CTLA4' involvement in the suppressive function of Foxp3+ CD4+ Tregs and de novo induction of adaptive Tregs.

In addition, PD-1 KO mice have been produced in order to assess the in vivo effects of PD-1. It has been observed that PD1 KO mice develop milder autoimmune phenotypes, which vary depending upon genetic background and are generally late-onset.

TABLE 1

Autoimmune phenotypes of $Pdcd1^{-/-}$ mice

| Genotype | Phenotype | Age at onset | Penetrance | Refs |
|---|---|---|---|---|
| C57BL/6-$Pdcd1^{-/-}$ | SLE-like | >6 months | ~50% | [29] |
| BALB/c-$Pdcd1^{-/-}$ | DCM | 5-25 weeks | 10-60%[a] | [30, 49] |
| | Gastritis | 10-20 weeks | ~80% | [49] |
| NOD-$Pdcd1^{-/-}$ | Diabetes | 4-10 weeks | 100% | [33] |
| BALB/c-$Fcgr2b^{-/-}$ $Pdcd1^{-/-}$ | Hydronephrosis | 10-20 weeks | 35% | [49] |
| 2C-$Pdcd1^{-/-}$ H-$2^{bid}$ | GVH-like | 5-10 weeks | 26-100%[b] | [29] |

[a]The penetrance of dilated cardiomyopathy (DCM) is variable among the different colonies of mice examined ([49] and our unpublished observations).
[b]The penetrance of GVH-like disease is variable depending on the genetic background (our unpublished observations).

In addition, PD-L1 KO mice have been made. These mice exhibit no apparent pathological phenotypes in aged mice; exhibit enhanced adaptive immune response upon immune challenge (i.e. model antigen immunization, infection etc); and the knockout of this protein results in the promotion of autoimmune disease development in disease-prone background Accordingly, a critical function of PD-L1 is in mediating peripheral tolerance at tissue sites due to the tissue expression of PD-L1 on non-hematopoietic cell types.

As noted previously, VISTA bears homology to PD-L1. Similarly, within the hematopoietic compartment, VISTA is highly expressed on CD11bhigh myeloid cells under normal conditions and myeloid-derived suppressor cells (MDSC) in tumor-bearing hosts. VISTA is also expressed on CD4+ and CD8+ T cells, and Tregs. Moreover, as the human homologue shares 90% homology with murine VISTA and similar expression patterns, the in vivo effects of human and murine VISTA should be functionally equivalent.

As shown in FIG. 42, VISTA-KO mice develop inflammatory phenotypes, including the enhanced amounts of serum inflammatory cytokines including IP-10, MCP-1, MIG, IL-5 and eotoxin. Also, as shown in FIG. 43 these same mice exhibit an increase in spontaneously activated CD4+ and CD8+ T cells within their serum. Also, as shown in FIG. 44, the blood T cells of these VISTA-KO mice express increased amounts of inflammatory cytokines, i.e., the CD4+ T cells express increased amounts of gamma interferon and IL17A and the CD8+ T cells express increased amounts of gamma interferon and TNFalpha. Further, as shown in FIG. 45, the spleen T cells similarly express inflammatory cytokines, i.e., the spleen CD4+ T cells express increased amounts of gamma interferon, TNF-alpha and IL17A and the spleen CD8+ T cells express increased amounts of gamma interferon and TNFalpha.

After 1 year, the VISTA KO mice also exhibit evidence of organ specific immune cell infiltration in different organs including the pancreas, lung, stomach. However, the KO mice do not otherwise exhibit any overt organ-specific autoimmune pathology.

Accordingly, the results herein show that soluble VISTA-Ig fusion protein, or VISTA expressed on APCs, acts as a ligand to suppress CD4+ and CD8+ T cell proliferation and cytokine production, via a cognate receptor independent of PD-1. Moreover, the results herein indicate that VISTA functions as a novel immune checkpoint protein ligand: by controlling inflammation and autoimmunity and by impairing the generation of anti-tumor immunity.

Related thereto, the results herein indicate that VISTA-Ig fusion protein may be used as a negative regulator of inflammation because it may significantly reduce production of IL-10, TNFalpha and IFNgamma by CD4+ and CD8+ T cells. This should result in a therapeutic downregulation of the immune response and provide relief from autoimmune or inflammatory disorders.

DISCUSSION

VISTA is as a novel member of the Ig superfamily network, which exerts immunosuppressive activities on T cells both in vitro and in vivo and is an important mediator in controlling the development of autoimmunity and the immune responses to cancer. The data presented suggests that (a) VISTA is a new member of the Ig superfamily that contains an Ig-V domain with distant sequence similarity to PD-L1, (b) when produced as an Ig fusion protein or overexpressed on artificial APCs, it inhibits both CD4 and $CD8^+$ T cell proliferation and cytokine production, (c) VISTA expression on myeloid APCs is inhibitory for T cell responses in vitro, (d) overexpression on tumor cells impairs protective antitumor immunity in vaccinated mice, and (e) antibody-mediated VISTA blockade exacerbates the development of a T cell-mediated autoimmune disease, EAE.

Bioinformatics analysis of the VISTA Ig-V domain suggests that the B7-butyrophilin family members PD-L1, PD-L2, and MOG, as well as the non-B7 family CAR and VCBP3 are the closest evolutionary relatives of VISTA (FIG. 23). However, close examination of primary sequence signatures suggests that all VISTA orthologues share unique and conserved sequence motifs and that VISTA possibly represents a structurally and functionally novel member of the Ig superfamily. Specifically, the presence of four invariant cysteines that are unique to the VISTA ectodomain (three in the Ig-V domain and one in the stalk) may contribute to novel structural features that impact its function. Given their strict invariance, it is plausible that all four VISTA-specific cysteines participate in disulfide bonds. This observation suggests several possibilities, including that the four cysteines (a) form two intramolecular disulfide bonds, (b) form four intermolecular disulfide bonds at a dimer interface, and (c) form one intramolecular and two intermolecular disulfide bonds. Any of these scenarios would represent a novel disulfide bonding pattern and would lead to unique tertiary and/or quaternary structures relative to typical Ig superfamily members. In addition, a global sequence comparison suggests that VISTA is not a member of any known functional groups within the Ig superfamily.

The expression pattern of VISTA further distinguishes VISTA from other B7 family ligands. This data has contrasted mostly with PD-L1 and PD-L2 because of the higher sequence homology between these two ligands and VISTA and their similar inhibitory function on T cell activation. The steady-state expression of VISTA is selectively expressed on hematopoietic cells and most highly expressed on both APCs (macrophages and myeloid DCs) and $CD4^+$ T lymphocytes. In this context, PD-L1 has broad expression on both hematopoietic and nonhematopoietic cells, whereas PD-L2 is restricted on DCs and macrophages (Keir, et al. 2006, 2008). Although both PD-L1 and PD-L2 are up-regulated on APCs upon in vitro culture and upon activation (Yamazaki, et al. 2002; Liang, et al. 2003; Keir, et al. 2008), VISTA expression on myeloid cells and T cells is lost after short-term in vitro culture, regardless of whether any stimuli were present (FIG. 6). Such loss might reflect the necessary role of lymphoid tissue microenvironment to maintain or regulate VISTA expression in vivo. Consistent with this hypothesis, even at steady-state, VISTA is differentially expressed at different tissue sites (i.e., higher at mesenteric LN than peripheral lymphoid tissues and lowest in blood). We speculate that such different expression levels might reflect the differential suppressive function of VISTA at particular tissue sites.

VISTA expression in vivo is highly regulated during active immune response. Immunization with adjuvant plus antigen (OVA/CFA) but not adjuvant alone (CFA) in TCR transgenic mice induced a population of $VISTA^{hi}$ myeloid APCs within the draining LN (FIG. 7). The need for antigen suggests that VISTA up-regulation on APCs might be a result of T cell activation. Compared with VISTA, PD-L1 and PD-L2 were also up-regulated on myeloid APCs in response to immunization but to a much lesser degree. We speculate that the induction of $VISTA^+$ myeloid APCs constitutes a self-regulatory mechanism to curtail an ongoing immune response. Consistent with this hypothesis, a neutralizing VISTAmonoclonal antibody enhanced T cell proliferative response in vitro when stimulated by VISTA-expressing myeloid APCs (FIG. 25).

In contrast to the expression pattern on myeloid cells, VISTA expression is diminished on in vivo activated $CD4^+$ T cells. This result suggests that VISTA expression on CD4 T cells in vivo may be regulated by its activation status and cytokine microenvironment during an active immune response. Such down-regulation is unique and has not been seen for other inhibitory B7 family ligands such as PD-L1, PD-L2, and B7-H4. Although the functional significance of VISTA expression on $CD4^+$ T cells is currently unknown, the possibility of reverse signaling from T cells to APCs during their cognate interaction will be investigated in future studies.

The inhibitory ligand function of VISTA was delineated by using the VISTA-Ig fusion protein, APCs expressing VISTA, and tumors overexpressing VISTA, as well as the neutralizing monoclonal antibody both in vitro and in vivo. VISTA-overexpressing tumor could overcome a potent protective immunity in vaccinated hosts. The strong enhancing effect of VISTAmonoclonal antibody in the EAE model further validates the hypothesis that VISTA is an inhibitory ligand in vivo. Similar approaches have been used to characterize the functions of other B7 family ligands (Sica, et al. 2003; Keir, et al. 2008). It is important to note that VISTA exerts its suppressive function by engaging a different receptor than PD-1 (FIG. 9). The fact that blockade of the VISTA pathway exacerbates EAE confirms that its function is not redundant with PD-L1 or PD-L2. On the contrary, we speculate that VISTA controls immune response in a manner that is reflected by its unique structural features, expression pattern, and dynamics. Identification of its unknown receptor will further shed light on the mechanisms of VISTA-mediated suppression.

In summary, VISTA was identified as a novel immune-suppressive ligand. Expression of VISTA on APCs suppresses T cell responses by engaging its yet to be identified counter-receptor on T cells during cognate interactions between T cells and APCs. VISTA blockade enhanced T cell-mediated immunity in an autoimmune disease model, suggesting its unique and nonredundant role in controlling autoimmunity when compared with other inhibitory B7 family ligands such as PD-L1 and PD-L2. Its highly regulated expression pattern at early stages of immune activation might also indicate a feedback control pathway to downregulate T cell immunity and attenuate inflammatory responses. In this regard, therapeutic intervention of the VISTA inhibitory pathway represents a novel approach to modulate T cell-mediated immunity for treating diseases such as viral infection and cancer.

Example 25

The VISTA Pathway as a Target of Immune Intervention in Autoimmunity

The purpose of these studies is to determine if soluble VISTA-Ig proteins can suppress immune responses in vivo. Studies using a murine VISTA-mIGg2a in vivo showed that therapeutic treatment as late as day 14 had a beneficial effect on Clinical Disease Score in EAE. These ongoing, experiments look very exciting in that we may have identified a new axis in autoimmune disease intervention (FIG. 26). With this success we have extended our studies using murine VISTA on a murine IgG1 or IgG2a backbone to exploit their cytophilic capacity. The Fc fusion constructs of VISTA in frame with the IgG1 Fc (both wild-type IgG1 and the existing non-FcR-binding IgG1) have been produced. Each of these soluble VISTA molecules was tested to determine if they can suppress EAE and it is shown that both VISTA-IgG1 and VISTA-IgG2a suppress the development and progression of EAE (FIG. 27). While these early results suggest that a dimeric, cytophilic VISTA will have activity in vivo, we will also be prepared to tetramerize using site specific biotinylation and complexing with avidin for multimerization. The proposed studies leverage this expertise for the systematic generation and analysis of a set of multivalent reagents to modulate T cell function in vitro and, in particular, in the context of EAE. Finally, we believe that the efforts described in this proposal hold substantial promise for the development of new therapeutic strategies and will be of considerable benefit to the entire community interested in autoimmunity and T cell function in general.

Example 26

VISTA-Ig Conjugate Reduces EAE Progression

Experimental Autoimmune Encephalomyelitis (EAE) is a model of multiple sclerosis. EAE was induced by immunizing mice with 175 μg MOG/CFA and pertussis toxin (PT) 300 ng (day 0, 2). On day 14, 17, and 20, 150 μg VISTA-IgG 2a (n=8) or 150 μg control IgG2a (n=8) was administered. The data is shown in FIG. 26 as the mean±SEM. In another experiment, on day 6, mice were treated with 3 doses per week of 150 μg control IgG1 (n=3), 150 μg control IgG2a (n=6), 150 μg mVISTA-IgG1 (n=3), or 150 μg mVISTA IgG2a (n=6) (two weeks in total). The data is shown in FIG. 27 as the mean±SEM. In another experiment, on day 14, mice were treated with 3 doses per week of PBS (n=6), 100 μg control IgG2a (n=6), 300 μg control IgG2a (n=6), 100 μgVISTA-IgG2a (n=6), or 300 μg mVISTA IgG2a (n=6) (two weeks in total). The data is shown in FIG. 28 as the mean±SEM. Thus, a VISTA-Ig fusion protein has a therapeutic effect on an inflammatory condition, e.g., multiple sclerosis.

Example 27

Analysis of VISTA Expression in Human Cells and Suppression by VISTA-Ig

The expression pattern of VISTA and its suppression by administration of a VISTA-Ig fusion protein was examined in human cell samples.

Materials and Methods

Production of VISTA-Ig Fusion Protein—

A fusion protein was created consisting of amino acids 16-194 from the extracellular IgV domain of human VISTA and a form of human IgG1 mutated for low binding of Fc receptors. The VISTA sequence was cloned into the SpeI-BamHI sites of the vector CDM7B. Protein was produced by transient transfection of Freestyle CHO cells using Freestyle transfection reagent and protein-free Freestyle Expression Media according to manufacturer instructions (Invitrogen). Supernatant was harvested after 5 days of growth and purified by protein G affinity columns. Protein was concentrated using 10K MWCO spin columns (Amicon).

Cell Preparation—

Human apheresis samples were obtained from unidentified healthy human donors. For culture experiments, blood was layered onto Lymphoprep (PAA) and isolated by density-gradient centrifugation. Interface cells were washed twice in PBS, then once in MACS buffer before undergoing magnetic bead selection with Miltenyi CD4 Negative selection kit II, CD8 Negative Selection Kit, or the CD4 Memory T cell selection kit according to manufacturer instructions. For effector cell isolation, CD4 T cells were subsequently depleted of $CD27^+$ cell types with Miltenyi CD27 positive selection beads.

Culture—

T cells were plated at $2\times10^5$ cells per well in 96-well flat-bottom plates coated with anti-CD3 (clone OKT3, BioXCell) and either VISTA-Ig or control-Ig (ZZ, R&D biosystems). Unless otherwise indicated, anti-CD3 was coated at 2.5 μg/ml mixed together with 10 μg/ml (ratio 1:4) VISTA-Ig or control-Ig protein in PBS at 4° C. overnight. Wells were washed twice with complete media before adding cells. When indicated, a titrated amount of anti-CD28 (Miltenyi Biotech) was included in the coating mix, or 50 ng/ml of IL-2, IL-4, IL-7 or IL-15 (Peprotech) was added to the culture media. Cultures were analyzed on day 2 for early activation markers, and on day 5 for late activation markers or CFSE profiles.

Flow Cytometry—

For staining following culture, cells were harvested and transferred into V-bottomed 96-well plates. Cells were washed and stained in HBSS/5% BCS staining buffer containing antibodies (CD4, CD8, CD25, CD69, CD45RA; BD biosciences) and near-infrared fixable live-dead dye (Invitrogen). Cells were washed and fixed with BD fixation buffer before analysis.

For staining for VISTA expression, whole blood was washed and stained with PBA buffer (PBS/0.1% BSA/0.1% sodium azide) containing antibodies for extracellular markers. Antibodies against CD4, CD8, CD3, CD45RA, CD56, CD11b, CD11c, CD123, HLA-DR, CD14 and CD16 were purchased from BD biosciences and anti-VISTA was produced as described herein. To stain FoxP3 intracellularly, Foxp3 Fixation/Permeabilization Concentrate and Diluent kit from eBiosciences and anti-FoxP3 antibody from BD biosciences were used. See FIG. 33D.

Samples were acquired on a LSRII Fortessa (Becton & Dickinson, San Jose, Calif., USA) with FACSDiva software v6.1.2 (Becton & Dickinson) and analysed with FlowJo software (Tree Star, Inc.). Graphs were created using graphed using Prism 5 (GraphPad Software, Inc.)

Results

The Human VISTA Protein—

A BLAST of the mouse VISTA sequence against the human genome identifies chromosome 10 open reading frame 54 (C10orf54 or platelet receptor Gi24 precursor, GENE ID: 64115) with an e-value of 8e-165 and 77% identity. Common with mouse VISTA, this protein is predicted to encode a type I transmembrane protein with a single extracellular IgV domain. Human VISTA is a 311 amino acid (aa) long, consisting of a 32-aa signal peptide, a 130-aa extracellular IgV domain, 33-aa stalk region, 20-aa transmembrane domain and a long 96-aa cytoplasmic tail. See amino acid sequence of SEQ ID NO: 16.

VISTA Expression Analysis—

The expression of VISTA healthy human tissues was examined by real-time PCR analysis of a cDNA tissue panel (Origene) FIG. 29A). Similar to mouse tissues, VISTA was predominantly expressed in haematopoietic tissues or in tissues that contain significant numbers of haematopoietic tissues. This is consistent with importance of VISTA in immune related functions. Interestingly, expression of VISTA was particularly high in human placenta, which may be indicative of a functional role for VISTA in maintenance of tolerance to the allogeneic environment of pregnancy. This pattern of expression was found to follow a similar trend to that of VISTA's closest homologue PD-L1 (FIG. 29B).

Next, VISTA protein expression was examined within the haematopoietic compartment by flow cytometry. PBMCs were isolated from peripheral blood and stained with the anti-VISTA monoclonal antibody GA1. VISTA was highly expressed by the majority of monocytes, dendritic cells and by approximately 20% of CD4 and CD8 T cells (FIG. 30). VISTA expression was observed within both of the 'patrolling' ($CD14^{dim}CD16^{+}$) and 'inflammatory' ($CD14^{+}$ $CD16^{+/-}$) subsets of blood monocytes, and within both lymphoid and myeloid subsets of dendritic cell.

Functional Effect of VISTA on T Cell Function—

VISTA has previously been demonstrated to have a negative impact on mouse T cell immune responses (Wang, et al. (2011) *J. Exp. Med.* pages 1-16). Whether VISTA had the same role in the human cell-mediated immune response was examined. An Ig fusion protein was created, consisting of the extracellular domain of VISTA and the Fc region of human IgG containing mutations for reduced Fc receptor binding. 10 μg/ml of VISTA-Ig or control Ig was immobilized on plates along with 2.5 μg/ml of anti-CD3 (OKT3) and then proliferation was measured by CFSE dilution. VISTA was found to suppress CFSE dilution of bulk purified CD4 (FIG. 31A) and CD8 (FIG. 31B) T cells. The suppression by VISTA is comparable to that induced by PD-L1-Ig (R&D biosystems). Additionally, VISTA-Ig was effective at suppression of memory ($CD45RO^{+}$, FIG. 31C) and effector ($CD27^{-}$, FIG. 31D) subsets. Comparison of mouse VISTA and human VISTA on human CD4 T cells demonstrated that VISTA is cross-reactive across species. Titration of human VISTA-Ig and human VISTA-Ig over different concentrations of OKT3, showed that higher concentrations of OKT3 can be overcome by higher concentrations of VISTA (FIGS. 32A and 32B).

To gain some insight into the mechanism of suppression, the status of cells was examined following activation in the presence or absence of VISTA-Ig. During 2 days of culture, upregulation by anti-CD3 of the early activation markers CD25 and CD69 was blocked by VISTA-Ig (FIGS. 33A & 33B). Similarly, after 5 days of culture, the shift from expression of CD45RA to CD45RO, indicative of antigen-experience was prevented (FIG. 33C). VISTA had no affect on cell viability. Consistent with a block in proliferation, cells treated with VISTA-Ig had forward and side-scatter profiles similar to unstimulated cells rather than blasting cells seen with OKT3 alone. To determine if the suppression induced by VISTA is stable, cells were cultured on anti-CD3 and VISTA-Ig for two days, and then moved onto anti-CD3 alone for 3 days. This further stimulation was unable to rescue suppression as shown in FIGS. 34A and 34B.

Next, the effect of VISTA-Ig on cytokine production was examined. Cells were stimulated with plate-bound OKT3 for 5 days in the presence of increasing amounts of VISTA-Ig, and then the concentration of various cytokines was measured in culture supernatants by cytometric bead array. Only trace levels of IL-2, IL-4 or IL-6 were detected (<5 μg/ml) and no differences were observed. However, VISTA-Ig significantly reduced production of IL-10, TNFα and IFNγ by CD4 (FIG. 35A) and CD8 (FIG. 35B) T cells, and there was a trend towards a modest decrease in IL-17 production.

Factors that were able to overcome the VISTA-induced suppression of T cells were also examined. Anti-CD28 agonistic antibody provides potent costimulation to T cells, and so titred into the cultures to challenge VISTA suppression (FIG. 36A-C). Although lower amounts of anti-CD28 were unable to overcome VISTA, when anti-CD28 was included at a coating concentration of 1 μg/ml VISTA was unable to block proliferation. Similarly, while low concentrations of VISTA could be overcome by the addition of cytokines such as IL-2, IL-7 and IL-15, higher concentrations of VISTA were still suppressive even with a physiologically high concentration of cytokine at 50 ng/ml. Thus, VISTA-Ig fusion protein may be used as a negative regulator of inflammation because it may significantly reduce production of IL-10, TNFα and IFNγ by CD4 and CD8 T cells. This, in turn, may lead to a therapeutic downregulation of the immune response and provide relief from autoimmune or inflammatory disorders.

Example 28

VISTA Expression on Tumour Infiltrating Leukocytes (TILs) in Human Colorectal Carcinoma and Relationship to Disease Stage and Prognosis We previously demonstrated that murine TILs express very high levels of VISTA, and blocking antibody to VISTA reduces tumour growth (2). We have also demonstrated VISTA expression in both peripheral blood mononuclear cells (PBMCs) and healthy colonic lamina propria mononuclear cells (LPMCs) in humans and hypothesize that VISTA is expressed on tumour-infiltrating leukocytes in human colorectal carcinoma (CRC). This example describes characterization of VISTA expression in CRC, adjacent "healthy" mucosa and paired peripheral blood by immunofluorescence microscopy and flow cytometry. Tissue sections give valuable information about the architecture of VISTA expression within the TME. Flow cytometry allows more extensive characterization of VISTA-expressing and non-expressing cells, including the frequency and activation status of TILs such as myeloid-derived suppressor cells (MDSCs), tumour-associated macrophages (TAMs), dendritic cells (DCs) and regulatory T cells (Tregs). VISTA expression in CRC is also related to clinical and pathological data to demonstrate the association between VISTA expression and prognostic markers, such as tumour stage.

Antibody-Mediated VISTA Blockade Inhibits Tumour Growth:

Previous studies in the lab have established that VISTA is a potent immune suppressive ligand that binds to an unknown receptor on T cells independently of PD-1 (1). VISTA suppresses T-cell proliferation and cytokine production when expressed on APCs. VISTA overexpression on tumour cells impaired protective anti-tumour immunity in vaccinated hosts. Anti-VISTA clone 13F3 functionally blocked the suppressive activity of VISTA in vitro, and exacerbated disease progression of Experimental Autoimmune Encephalomyelitis (EAE) (75). Furthermore, 13F3 administration significantly reduced tumour growth in multiple transplantable tumour systems including a bladder tumour MB49, a Methylcholanthrene (MCA)-105 fibrosarcoma, a thymoma EG7, an ovarian tumour ID8 (FIG. 37), and B16F10 melanoma. In addition, we have confirmed that αVISTA-mediated tumour rejection is correlated with enhanced regional anti-tumour T-cell response, as measured by IFNg ELISPOT from MB49 tumour-draining lymph node (LN) lymphocytes.

To further demonstrate the direct translational relevance of the above murine data to the pathogenesis of cancer in man, our group has initiated a multi-site, NIHR-funded, CLRN-registered observational study investigating defects in mucosal immunology in inflammatory bowel disease and CRC (REC 10/H0804/65, NIHR CRN 9929). Next, we perfected the extraction of LPMCs from intestinal resection specimens, for use in multi-colour flow cytometry and functional assays. Using anti-VISTA clones GA1 and HCl (APS Biotech Ltd), we subsequently identified VISTA expression in human peripheral blood and lamina propria monocytes and Lin-HLA-DR+ DCs and monocytes, which has not previously been described (FIG. 38). Consequently, in addition to being expressed in healthy LPMCs, we hypothesise that VISTA is expressed in TILs in adjacent CRC.

We have optimised 8-10 colour Fluorescence Assisted Cell Sorting (FACS) antibody panels to determine the frequency and activation status of immune cells, in addition to cytokine and transcription factor expression, and applied these panels to PBMCs and LPMCs. FACS is then used to distinguish populations of TILs in the colon tumour samples based on population-specific surface markers. For example human MDSCs are found to be CD11b+, CD33+, HLA-DR- and are further divided into CD14+ and CD14− subsets. The VISTA positive and negative sub-populations of these are further distinguished with the help of the 2 antibody clones our lab has previously developed for the molecule (FIG. 41; GA1 and HCl). Activation markers like CD69 on the T cells, CD64, CD62L on tumour associated macrophages, etc. are compared between the VISTA positive and negative sub-populations. These can then be further studied, as in Example 29, in in vitro conditions.

Sections of tumour samples are frozen in OCT, then analysed for VISTA expression. These are be stained by immunofluorescence, or by immunohistochemistry with haematoxylin counterstain. Immunofluorescence staining will use anti-VISTA antibodies along with antibodies specific for other cells in the TME (e.g. epithelial cells, MDSCs, tolerogenic DCs, T cells, B cells and other immune cells. This demonstrates the micro-anatomical localisation of VISTA-expressing cells and their spatial interaction with other cells in the TME. Immunohistochemistry with a haematoxylin counterstain elucidates the pathology and morphology of the tumour, and how VISTA is associated with different pathology (e.g. inflamed or necrotic regions).

Further, VISTA expression is compared to clinical and pathological data such as Duke's stage, pathological TNM staging and histological features such as neural invasion and degree of differentiation, to determine how VISTA expression relates to proxies for clinical outcome. Using the paradigm of COX-2 expression in CRC ("High" COX-2 expression in Duke's A 66% vs. Duke's D 100%), a sample size of 80 (n=20 in each Duke's staging group) has an 84% power ($\alpha$=0.05) to detect a 33% difference between any two groups (76).

By classifying the samples in a globally and clinically accepted manner, the study provides clinically relatable data. Characterization of the TILs in patient samples will outline which cells express VISTA in humans and how expression within each subset changes with each stage of cancer development and is associated with outcome. For example, it has been found that in human ovarian cancer, large infiltration of FoxP3+ Tregs is associated with a poorer prognosis. This aim will also drive further in vitro studies, as in Example 29.

Example 29

The Functional Role of VISTA Expression on Tumour Infiltrating Leukocytes (TIL)

Our murine data suggest that VISTA-positive Tregs are more suppressive than VISTA-negative Tregs. Consequently, we hypothesized that VISTA-expressing TILs will be more suppressive on effector immune responses than VISTA-negative TILs. This hypothesis is tested using two complementary methods. First, TAMs, MDSCs, DCs and Tregs from colonic cancer and healthy control samples are sorted for VISTA positive versus negative subsets. The suppressive or stimulatory nature of these cells towards T cells is determined in vitro, followed by further mechanistic experiments. Second, VISTA expression is knocked down by retroviral RNAi to determine how this influences the suppressive nature of different TIL cell types in vitro. This approach helps further our understanding of how potential treatments may impact the TME.

We have demonstrated that VISTA profoundly suppresses CD4+ and CD8+ T cell responses (FIG. 39). Specifically, FIG. 3 shows the proliferation suppression in an in vitro assay using plate-bound VISTA-Ig in an αCD3 proliferation assay. This example further examines how VISTA influences the function of different cell types within the TME. Understanding the functional role of VISTA in colon cancer further provides the basis for anticancer treatment made possible by the use of anti-VISTA antibodies.

Fluorescence Assisted Cell Sorting is used to obtain individual populations of myeloid or lymphoid derived TILs (tumour associated macrophages, myeloid derived suppressor cells, T cells, B cells, and DC's) from tumour samples based on cell-specific and activation markers. They are then transfected with lentiviruses expressing iRNA to knock-down VISTA or PD-L1 expression, or retroviruses expressing high-level VISTA, PD-L1 or 'empty'. PD-L1 will be used as a positive control and to give data context within the B7-CD28 family. Constructs for four unique 29mer shRNAs for hVISTA and a control non-functional 29mer scrambled shRNA in a retroviral vector are commercially available (Origene, Rockville, Md.). These are guaranteed to achieve greater than 70% knockdown. Following transfection, TILs are tested for suppressive/stimulatory ability in standard mixed lymphocyte reaction (MLR) cultures with CFSE labelled responder T cells. Cytokine production is also measured to determine how VISTA impacts differentiation.

Example 30

Screening a Panel of Anti-VISTA Antibodies and Comparing Activity with Existing Anti-PD-L1 mAb and Identification of VISTA Blocking Antibodies Anti-VISTA antibodies previously produced in our lab have proved to be effective in diminishing tumour growth in mice, and closest homologue to VISTA, PD-L1 is already performing well in clinical trials for treatment of melanoma. This example describes testing a panel of anti-VISTA antibodies for efficacy in enhancing T cell proliferation in vitro, compared to the efficacy of either anti-PD-L1 alone, or the combination of VISTA and PD-L1 blockade.

The role of immune checkpoint pathways such as PD-L1/PD-1 and CTLA-4 has been well documented in human patients, and CTLA-4 blockade (Ipilumimab) the first immunological treatment with any efficacy against late-stage melanoma (77). The use of anti-VISTA treatment in combination with blockade of another immunological checkpoint protein may enhance anti-tumour responses still further. Our lab tested this theory using the cell line B16F10 in C57BL/6 mice. Due to its poor immunogenicity, B16F10 also represents a very challenging murine tumour system for immune-interventions against cancer. Prophylactic treatment (day−2) with αVISTA halted B16F10 tumour progression significantly, whereas blockade of another immune checkpoint protein, PD-L1, failed to have any impact (FIG. 40). When αVISTA was administered therapeutically (day+4), efficacy as a single reagent was not detected. However, an additive impact on tumour growth was seen when VISTA blockade was combined with PD-L1 blockade (FIG. 40). Greater synergistic effect was observed in vitro when VISTA-Ig and PD-L1-Ig were used together to suppress T cell activation.

Our results lead us to the belief that VISTA synergizes with PD-L1 to maximally suppress T-cell responses. In this example, we test a panel of anti-VISTA antibodies for efficacy in enhancing T cell proliferation in vitro, and contrast this with either anti-PD-L1 alone, or the combination of VISTA and PD-L1 blockade.

We have previously generated clones of anti-VISTA, GA1 and HCl. Staining with GA1 mAb is shown in FIG. 41. GA1 was selected by its ability to bind hVISTA-Ig but not Ig in an ELISA and then selected by specific staining of GFP-VISTA transduced cells but not control transduced cells. As shown (FIG. 41) using mAb supernatant, GA1 binds over 50% of monocytes in peripheral blood and a small percentage of lymphocytes, all which are blocked by VISTA-Ig. A more extensive panel of anti-human VISTA antibodies is generated and tested for efficacy in blocking the VISTA pathway. To generate further antibodies, we will mice with an irradiated VISTA-expressing EL4 cell line, followed by monthly boosts with VISTA-Ig. Titres are confirmed by ELISA using VISTA-Ig against human IgG to control for responses against the Fc region. Spleens are then used to generate myelomas. Supernatants are then screened for binders using human PBMCs and also VISTA-expressing cell lines. Positive clones are subcloned and cryopreserved. Based on initial data, from each fusion, we expect 5-10 candidate binders, and will therefore immunize 10 mice in the first instance.

Antibodies are tested for efficacy in blocking T cell responses induced by VISTA expressing APCs. Human apheresis leukocyte-enriched cones (e.g., available from King's College Hospital). From each sample, we typically can obtain about $10^9$ PBMCs. Large numbers of CD4 T cells, and from mismatched donors CD14+ monocytes, are both isolated by Miltenyi bead selection and cryopreserved. This gives a relatively consistent cell population to screen antibodies with in mixed lymphocyte reactions. Human blood monocytes express high levels of VISTA (FIG. 41), and therefore are a suitable stimulatory population to use. Proliferative responses of T cells are measured by CFSE dilution in the presence of anti-vista antibodies relative to control Ig. Additionally, anti-PD-L1 antibody is also used, as it is a well-characterized agent useful as a positive control and for comparison. We also test the effect of using both reagents together for synergy, and envision using the two reagents together as treatment.

Using similar methods, anti-VISTA antibodies are tested for efficacy in blocking T cell responses induced by the VISTA-expressing APC cell lines such as K-562.

Additionally, anti-VISTA antibodies are tested for the ability to block VISTA-Ig suppression of anti-CD3 stimulation. As described in Example 3 above, VISTA (PD-L3)-Ig suppressed the proliferation of bulk purified CD4+ and CD8+ T cells in response to plate-bound anti-CD3 stimulation, as determined by arrested cell division (see FIG. 9A-B).

VISTA-inhibitory antibodies identified in these assays are further tested in vivo for promoting anti-tumor responses in animal models of cancer, e.g., as further described in the preceding examples. Additionally, antibodies that show efficacy may be humanized and further developed for potential therapeutic use.

All publications, patents and patent applications are herein incorporated by reference in their entirety to the same extent as if each individual publication, patent or patent application was specifically and individually indicated to be incorporated by reference in its entirety.

Those skilled in the art will recognize, or be able to ascertain using no more than routine experimentation, many equivalents to the specific embodiments of the invention described herein. Such equivalents are intended to be encompassed by the following claims.

REFERENCES

1. Wang, L., et al., VISTA, a novel Ig-superfamily ligand that negatively regulates T cell responses. J. Exp. Med., 2011. 208(3): p. 577-92.

2. Wang, L., et al., Programmed death 1 ligand signaling regulates the generation of adaptive Foxp3+CD4+ regulatory T cells. Proc Natl Acad Sci USA, 2008. 105(27): p. 9331-6.
3. Hodi, F. S., Overcoming immunological tolerance to melanoma: Targeting CTLA-4. Asia Pac J Clin Oncol, 2010. 6 Suppl 1: p. S16-23.
4. Tarhini, A., E. Lo, and D. R. Minor, Releasing the brake on the immune system: ipilimumab in melanoma and other tumors. Cancer Biother Radiopharm, 2010. 25(6): p. 601-13.
5. Kaehler, K. C., et al., Update on immunologic therapy with anti-CTLA-4 antibodies in melanoma: identification of clinical and biological response patterns, immune-related adverse events, and their management. Semin Oncol, 2010. 37(5): p. 485-98.
6. Wing, K., et al., CTLA-4 control over Foxp3+ regulatory T cell function. Science, 2008. 322(5899): p. 271-5.
7. Chambers, C. A., T. J. Sullivan, and J. P. Allison, Lymphoproliferation in CTLA-4-deficient mice is mediated by costimulation-dependent activation of CD4+ T cells. Immunity, 1997. 7(6): p. 885-95.
8. Waterhouse, P., et al., Lymphoproliferative disorders with early lethality in mice deficient in Ctla-4. Science, 1995. 270(5238): p. 985-8.
9. Tivol, E. A., et al., Loss of CTLA-4 leads to massive lymphoproliferation and fatal multiorgan tissue destruction, revealing a critical negative regulatory role of CTLA-4. Immunity, 1995. 3(5): p. 541-7.
10. Zheng, S. G., et al., TGF-beta requires CTLA-4 early after T cell activation to induce FoxP3 and generate adaptive CD4+CD25+ regulatory cells. J Immunol, 2006. 176(6): p. 3321-9.
11. van Elsas, A., A. A. Hurwitz, and J. P. Allison, Combination immunotherapy of B16 melanoma using anticytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med, 1999. 190(3): p. 355-66.
12. Hoos, A., et al., Development of ipilimumab: contribution to a new paradigm for cancer immunotherapy. Semin Oncol, 2010. 37(5): p. 533-46.
13. Calabro, L., et al., Clinical studies with anti-CTLA-4 antibodies in non-melanoma indications. Semin Oncol, 2010. 37(5): p. 460-7.
14. Attia, P., et al., Autoimmunity correlates with tumor regression in patients with metastatic melanoma treated with anti-cytotoxic T-lymphocyte antigen-4. J Clin Oncol, 2005. 23(25): p. 6043-53.
15. Freeman, G. J., et al., Engagement of the PD-1 immunoinhibitory receptor by a novel B7 family member leads to negative regulation of lymphocyte activation. J Exp Med, 2000. 192(7): p. 1027-34.
16. Butte, M. J., et al., Programmed death-1 ligand 1 interacts specifically with the b7-1 costimulatory molecule to inhibit T cell responses. Immunity, 2007. 27(1): p. 111-22.
17. Nishimura, H., et al., Development of lupus-like autoimmune diseases by disruption of the PD-1 gene encoding an ITIM motif-carrying immunoreceptor. Immunity, 1999. 11(2): p. 141-51.
18. Nishimura, H., et al., Autoimmune dilated cardiomyopathy in PD-1 receptor-deficient mice. Science, 2001. 291 (5502): p. 319-22.
19. Keir, M. E., et al., PD-1 and its ligands in tolerance and immunity. Annu Rev Immunol, 2008. 26: p. 677-704.
20. Gao, Q., et al., Overexpression of PD-L1 significantly associates with tumor aggressiveness and postoperative recurrence in human hepatocellular carcinoma. Clin Cancer Res, 2009. 15(3): p. 971-9.
21. Dong, H. and L. Chen, B7-H1 pathway and its role in the evasion of tumor immunity. J Mol Med, 2003. 81(5): p. 281-7.
22. Zou, W. and L. Chen, Inhibitory B7-family molecules in the tumour microenvironment. Nat Rev Immunol, 2008. 8(6): p. 467-77.
23. Dong, H., et al., Tumor-associated B7-H1 promotes T-cell apoptosis: a potential mechanism of immune evasion. Nat Med, 2002. 8(8): p. 793-800.
24. Blank, C., et al., PD-L1/B7H-1 inhibits the effector phase of tumor rejection by T cell receptor (TCR) transgenic CD8+ T cells. Cancer Res, 2004. 64(3): p. 1140-5.
25. Blank, C., T. F. Gajewski, and A. Mackensen, Interaction of PD-L1 on tumor cells with PD-1 on tumorspecific T cells as a mechanism of immune evasion: implications for tumor immunotherapy. Cancer Immunol Immunother, 2005. 54(4): p. 307-14.
26. Iwai, Y., et al., Involvement of PD-L1 on tumor cells in the escape from host immune system and tumor immunotherapy by PD-L1 blockade. Proc Natl Acad Sci USA, 2002. 99(19): p. 12293-7.
27. Geng, H., et al., HSP70 vaccine in combination with gene therapy with plasmid DNA encoding sPD-1 overcomes immune resistance and suppresses the progression of pulmonary metastatic melanoma. Int J Cancer, 2006. 118(11): p. 2657-64.
28. Hirano, F., et al., Blockade of B7-H1 and PD-1 by monoclonal antibodies potentiates cancer therapeutic immunity. Cancer Res, 2005. 65(3): p. 1089-96.
29. Curiel, T. J., et al., Blockade of B7-H1 improves myeloid dendritic cell-mediated antitumor immunity. Nat Med, 2003. 9(5): p. 562-7.
30. Brahmer, J. R., et al., Phase I study of single-agent anti-programmed death-1 (MDX-1106) in refractory solid tumors: safety, clinical activity, pharmacodynamics, and immunologic correlates. J Clin Oncol, 2010. 28(19): p. 3167-75.
31. Sica, G. L., et al., B7-H4, a molecule of the B7 family, negatively regulates T cell immunity. Immunity, 2003. 18(6): p. 849-61.
32. Prasad, D. V., et al., B7S1, a novel B7 family member that negatively regulates T cell activation. Immunity, 2003. 18(6): p. 863-73.
33. Yi, K. H. and L. Chen, Fine tuning the immune response through B7-H3 and B7-H4. Immunol Rev, 2009. 229(1): p. 145-51.
34. Kryczek, I., et al., B7-H4 expression identifies a novel suppressive macrophage population in human ovarian carcinoma. J Exp Med, 2006. 203(4): p. 871-81.
35. Kryczek, I., et al., Cutting edge: induction of B7-H4 on APCs through IL-10: novel suppressive mode for regulatory T cells. J Immunol, 2006. 177(1): p. 40-4.
36. Shevach, E. M., CD4+CD25+ suppressor T cells: more questions than answers. Nat Rev Immunol, 2002. 2(6): p. 389-400.
37. Nishikawa, H. and S. Sakaguchi, Regulatory T cells in tumor immunity. Int J Cancer, 2010. 127(4): p. 759-67.
38. Yamaguchi, T. and S. Sakaguchi, Regulatory T cells in immune surveillance and treatment of cancer. Semin Cancer Biol, 2006. 16(2): p. 115-23.
39. Curiel, T. J., et al., Specific recruitment of regulatory T cells in ovarian carcinoma fosters immune privilege and predicts reduced survival. Nat Med, 2004. 10(9): p. 942-9.

40. Zou, W., Regulatory T cells, tumour immunity and immunotherapy. Nat Rev Immunol, 2006. 6(4): p. 295-307.
41. Sharma, M. D., et al., Plasmacytoid dendritic cells from mouse tumor-draining lymph nodes directly activate mature Tregs via indoleamine 2,3-dioxygenase. J Clin Invest, 2007. 117(9): p. 2570-82.
42. Tacke, F. and G. J. Randolph, Migratory fate and differentiation of blood monocyte subsets. Immunobiology, 2006. 211(6-8): p. 609-18.
43. Shortman, K. and S. H. Naik, Steady-state and inflammatory dendritic-cell development. Nat Rev Immunol, 2007. 7(1): p. 19-30.
44. Leon, B. and C. Ardavin, Monocyte-derived dendritic cells in innate and adaptive immunity. Immunol Cell Biol, 2008. 86(4): p. 320-4.
45. Auffray, C., M. H. Sieweke, and F. Geissmann, Blood monocytes: development, heterogeneity, and relationship with dendritic cells. Annu Rev Immunol, 2009. 27: p. 669-92.
46. Geissmann, F., et al., Development of monocytes, macrophages, and dendritic cells. Science, 2010. 327(5966): p. 656-61.
47. Qu, C., et al., Role of CCR8 and other chemokine pathways in the migration of monocyte-derived dendritic cells to lymph nodes. J Exp Med, 2004. 200(10): p. 1231-41.
48. Geissmann, F., S. Jung, and D. R. Littman, Blood monocytes consist of two principal subsets with distinct migratory properties. Immunity, 2003. 19(1): p. 71-82.
49. Sunderkotter, C., et al., Subpopulations of mouse blood monocytes differ in maturation stage and inflammatory response. J Immunol, 2004. 172(7): p. 4410-7.
50. Randolph, G. J., et al., Differentiation of phagocytic monocytes into lymph node dendritic cells in vivo. Immunity, 1999. 11(6): p. 753-61.
51. Robben, P. M., et al., Recruitment of Gr-1+ monocytes is essential for control of acute toxoplasmosis. J Exp Med, 2005. 201(11): p. 1761-9.
52. Serbina, N. V., et al., TNF/iNOS-producing dendritic cells mediate innate immune defense against bacterial infection. Immunity, 2003. 19(1): p. 59-70.
53. Copin, R., et al., MyD88-dependent activation of B220-CD11b+LY-6C+ dendritic cells during *Brucella melitensis* infection. J Immunol, 2007. 178(8): p. 5182-91.
54. Geissmann, F., et al., Blood monocytes: distinct subsets, how they relate to dendritic cells, and their possible roles in the regulation of T-cell responses. Immunol Cell Biol, 2008. 86(5): p. 398-408.
55. Krutzik, S. R., et al., TLR activation triggers the rapid differentiation of monocytes into macrophages and dendritic cells. Nat Med, 2005. 11(6): p. 653-60.
56. Leon, B., M. Lopez-Bravo, and C. Ardavin, Monocyte-derived dendritic cells formed at the infection site control the induction of protective T helper 1 responses against *Leishmania*. Immunity, 2007. 26(4): p. 519-31.
57. Le Borgne, M., et al., Dendritic cells rapidly recruited into epithelial tissues via CCR6/CCL20 are responsible for CD8+ T cell crosspriming in vivo. Immunity, 2006. 24(2): p. 191-201.
58. Nakano, H., et al., Blood-derived inflammatory dendritic cells in lymph nodes stimulate acute T helper type 1 immune responses. Nat Immunol, 2009. 10(4): p. 394-402.
59. Rabinovich, G. A., D. Gabrilovich, and E. M. Sotomayor, Immunosuppressive strategies that are mediated by tumor cells. Annu Rev Immunol, 2007. 25: p. 267-96.
60. Gabrilovich, D. I. and S. Nagaraj, Myeloid-derived suppressor cells as regulators of the immune system. Nat Rev Immunol, 2009. 9(3): p. 162-74.
61. Wilcox, R. A., Cancer-associated myeloproliferation: old association, new therapeutic target. Mayo Clin Proc, 2010. 85(7): p. 656-63.
62. Ostrand-Rosenberg, S. and P. Sinha, Myeloid-derived suppressor cells: linking inflammation and cancer. J Immunol, 2009. 182(8): p. 4499-506.
63. Marigo, I., et al., Tumor-induced tolerance and immune suppression by myeloid derived suppressor cells. Immunol Rev, 2008. 222: p. 162-79.
64. Corzo, C. A., et al., HIF-1alpha regulates function and differentiation of myeloid-derived suppressor cells in the tumor microenvironment. J Exp Med, 2010. 207(11): p. 2439-53.
65. Gabrilovich, D., Mechanisms and functional significance of tumour-induced dendritic-cell defects. Nat Rev Immunol, 2004. 4(12): p. 941-52.
66. Melief, C. J., Cancer immunotherapy by dendritic cells. Immunity, 2008. 29(3): p. 372-83.
67. Steinman, R. M., D. Hawiger, and M. C. Nussenzweig, Tolerogenic dendritic cells. Annu Rev Immunol, 2003. 21: p. 685-711.
68. Ghiringhelli, F., et al., Tumor cells convert immature myeloid dendritic cells into TGF-beta-secreting cells inducing CD4+CD25+ regulatory T cell proliferation. J Exp Med, 2005. 202(7): p. 919-29.
69. Conejo-Garcia, J. R., et al., Tumor-infiltrating dendritic cell precursors recruited by a beta-defensin contribute to vasculogenesis under the influence of Vegf-A. Nat Med, 2004. 10(9): p. 950-8.
70. Huarte, E., et al., Depletion of dendritic cells delays ovarian cancer progression by boosting antitumor immunity. Cancer Res, 2008. 68(18): p. 7684-91.
71. Cubillos-Ruiz, J. R., et al., Polyethylenimine-based siRNA nanocomplexes reprogram tumor-associated dendritic cells via TLR5 to elicit therapeutic antitumor immunity. J Clin Invest, 2009. 119(8): p. 2231-44.
72. Bak, S. P., et al., Murine ovarian cancer vascular leukocytes require arginase-1 activity for T cell suppression. Mol Immunol, 2008. 46(2): p. 258-68.
73. Scarlett, U. K., et al., In situ stimulation of CD40 and Toll-like receptor 3 transforms ovarian cancerinfiltrating dendritic cells from immunosuppressive to immunostimulatory cells. Cancer Res, 2009. 69(18): p. 7329-37.
74. Nesbeth, Y. C., et al., CD4+ T cells elicit host immune responses to MHC class II-negative ovarian cancer through CCL5 secretion and CD40-mediated licensing of dendritic cells. J Immunol, 2010. 184(10): p. 5654-62.
75. Wang, L., et al., VISTA, a novel mouse Ig-superfamily ligand that negatively regulates T cell responses. J Exp Med, 2010.
76. Sheehan, K., K. Sheehan, and D. O'Donoghue, The relationship between cyclooxygenase-2 expression and colorectal cancer. JAMA, 1999. 282: p. 1254-7.
77. Weber, J., Immune checkpoint proteins: a new therapeutic paradigm for cancer—preclinical background: CTLA-4 and PD-1 blockade. Semin Oncol, 2010. 37(5): p. 430-9.

What is claimed is:

1. A method for treating a subject having a cancer condition that would benefit from upregulation of an immune response comprising: removing T-lymphocytes from the subject, transfecting said T-lymphocytes in vitro with at least one siRNA that downregulates VISTA expression and at least one siRNA that downregulates PD-1 and/or PD-L1 expression, and reintroducing said transfected T-lymphocytes into said subject.

2. The method of claim 1, wherein said T-lymphocytes comprise $CD^+$ T cells and/or $CD8^+$ T cells.

3. The method of claim 1, wherein said T-lymphocytes are expanded in vitro.

4. The method of claim 1, wherein said siRNA molecule that downregulates the expression of VISTA comprises one or more of SEQ ID NOs: 38-67 and/or said siRNA molecule targets the ORF or UTR region of VISTA.

5. The method of claim 1, wherein the cancer is colorectal cancer, sarcoma, melanoma, lymphoma, leukemia, neuroblastoma, or carcinoma.

6. The method of claim 1, which further comprises administering an anti-VISTA antibody, anti-PD-1 antibody, an anti-PD-L1 antibody, an anti-CTLA-4 antibody, or an anti-B7-H4 antibody.

7. The method of claim 1, further comprising determining the level of expression of VISTA in a sample from said subject, wherein said sample from said subject comprises one or more of the cells of said cancer, the tumor microenvironment, or peripheral blood and/or comprises one or more of Tregs, MDSCs, and/or tolerogenic DCs.

8. The method of claim 1, wherein said T-lymphocytes are expanded in vitro before and/or after transfection.

9. The method of claim 2, wherein said $CD4^+$ T cells and/or $CD8^+$ T cells are expanded in vitro before and/or after transfection.

10. The method of claim 7, wherein cells in the sample of the subject are determined to express VISTA.

* * * * *